United States Patent
Rao et al.

(10) Patent No.: US 9,453,014 B2
(45) Date of Patent: Sep. 27, 2016

(54) CYCLIC AMIDE DERIVATIVES AS INHIBITORS OF 11-β-HYDROXYSTEROID DEHYDROGENASE AND USES THEREOF

(71) Applicant: CONNEXIOS LIFE SCIENCES PVT. LTD., Bangalore (IN)

(72) Inventors: Jagannath Madanahalli Ranganath Rao, Bangalore (IN); Uppala Venkatesham, Bangalore (IN); Jenson George, Bangalore (IN); George Fernand, Bangalore (IN); Sivanageswara Rao Doppalapudi, Bangalore (IN); G R Madhavan, Bangalore (IN); Nagarajan Arumugam, Bangalore (IN); Mohammed Ansari, Bangalore (IN); K Murugavel, Bangalore (IN); Jidugu Pradeep, Bangalore (IN); Sulthan Allavuddeen, Bangalore (IN); K Vijayaramalingam, Bangalore (IN); Hampelingaiah Shiva Prasad, Bangalore (IN); Augustine Michael Raj, Bangalore (IN); S Gnanavel, Bangalore (IN); Ramamoorthy Kottamalai, Bangalore (IN); Naresh M P S Babu, Bangalore (IN); Bommegowda Yadaganahalli Kenchegowda, Bangalore (IN)

(73) Assignee: Connexios Life Sciences Pvt. Ltd., Bangalore (IN)

( * ) Notice: Subject to any disclaimer, the term of this patent is extended or adjusted under 35 U.S.C. 154(b) by 0 days.

(21) Appl. No.: 14/367,614

(22) PCT Filed: Dec. 21, 2012

(86) PCT No.: PCT/IN2012/000841
§ 371 (c)(1),
(2) Date: Jun. 20, 2014

(87) PCT Pub. No.: WO2013/128465
PCT Pub. Date: Sep. 6, 2013

(65) Prior Publication Data
US 2015/0158860 A1    Jun. 11, 2015

(30) Foreign Application Priority Data

Dec. 22, 2011    (IN) .......................... 4527/CHE/2011

(51) Int. Cl.
*C07D 471/04*    (2006.01)
*C07D 401/06*    (2006.01)
(Continued)

(52) U.S. Cl.
CPC ........... *C07D 471/04* (2013.01); *C07D 209/44* (2013.01); *C07D 401/06* (2013.01); *C07D 401/12* (2013.01); *C07D 403/06* (2013.01); *C07D 405/06* (2013.01);
(Continued)

(58) Field of Classification Search
CPC    C07D 471/04; C07D 401/06; C07D 401/12; C07D 403/06; C07D 417/12; C07D 417/06
USPC ........................ 546/135, 146; 514/314, 307
See application file for complete search history.

(56) References Cited

U.S. PATENT DOCUMENTS 5,631,279 A    5/1997    Crespo et al.

FOREIGN PATENT DOCUMENTS

DE    2903966 A1    8/1980
EP    336356 A2 *    10/1989
(Continued)

OTHER PUBLICATIONS

Cecil Textbook of Medicine (20th Edition, vol. 2, 1996, pp. 1739-1747).*

(Continued)

*Primary Examiner* — Kahsay Habte
(74) *Attorney, Agent, or Firm* — Hauptman Ham, LLP

(57) ABSTRACT

The present invention relates amide compounds of formula (I):

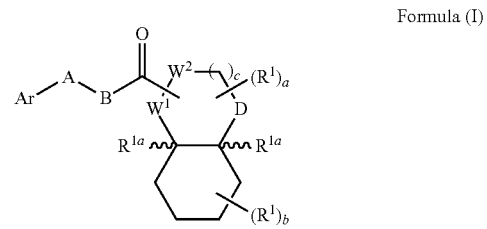

Formula (I)

wherein $R^1$, $R^{1a}$, Ar, A, B, $W^1$, $W^2$, D, a, b, and c are defined herein, and pharmaceutical acceptable salts thereof. These compounds have the ability to inhibit 11-β-hydroxysteroid dehydrogenase type 1 (11β-HSD-1) and which are therefore useful in the treatment of certain disorders that can be prevented or treated by inhibition of this enzyme. In addition the invention relates to the compounds, methods for their preparation, pharmaceutical compositions containing the compounds and the uses of these compounds in the treatment of certain disorders. It is expected that the compounds of the invention will find application in the treatment of conditions such as non-insulin dependent type 2 diabetes mellitus (NIDDM), insulin resistance, obesity, impaired fasting glucose, impaired glucose tolerance, lipid disorders such as dyslipidemia, hypertension and as well as other diseases and conditions.

18 Claims, No Drawings

(51) Int. Cl.
*C07D 401/12* (2006.01)
*C07D 403/06* (2006.01)
*C07D 417/12* (2006.01)
*C07D 417/06* (2006.01)
*C07D 209/44* (2006.01)
*C07D 405/06* (2006.01)
*C07D 405/14* (2006.01)
*C07D 409/14* (2006.01)
*C07D 413/06* (2006.01)

(52) U.S. Cl.
CPC ......... *C07D 405/14* (2013.01); *C07D 409/14* (2013.01); *C07D 413/06* (2013.01); *C07D 417/06* (2013.01); *C07D 417/12* (2013.01)

(56) References Cited

FOREIGN PATENT DOCUMENTS

| | | |
|---|---|---|
| EP | 1340749 A1 | 9/2003 |
| WO | 99/52876 A1 | 10/1999 |
| WO | 2005/073199 A1 | 8/2005 |
| WO | 2005/075471 A2 | 8/2005 |
| WO | 2006/012504 A2 | 2/2006 |
| WO | 2009/126675 A1 | 10/2009 |
| WO | 2010/139827 A1 | 12/2010 |

OTHER PUBLICATIONS

International Search Report for PCT/IN2014/000841 published on WIPO website on Sep. 6, 2013.

* cited by examiner

CYCLIC AMIDE DERIVATIVES AS INHIBITORS OF 11-β-HYDROXYSTEROID DEHYDROGENASE AND USES THEREOF

FIELD OF THE INVENTION

The present invention relates to bicyclic heterocyclic amide derivatives that have the ability to inhibit 11-β-hydroxysteroid dehydrogenase type 1 (11β-HSD-1) and which are therefore useful in the treatment of certain disorders that can be prevented or treated by inhibition of this enzyme. In addition the invention relates to the compounds, methods for their preparation, pharmaceutical compositions containing the compounds and the uses of these compounds in the treatment of certain disorders. It is expected that the compounds of the invention will find application in the treatment of conditions such as non-insulin dependent type 2 diabetes mellitus (NIDDM), insulin resistance, obesity, impaired fasting glucose, impaired glucose tolerance, lipid disorders such as dyslipidemia, hypertension and as well as other diseases and conditions.

BACKGROUND OF THE INVENTION

Glucocorticoids are stress hormones with regulatory effects on carbohydrate, protein and lipid metabolism. Cortisol (or hydrocortisone in rodent) is the most important human glucocorticoid. 11-beta hydroxyl steroid dehydrogenase or 11 beta-HSD1 (11β-HSD-1) is a member of the short chain dehydrogenase super-family of enzymes which converts functionally inert cortisone to active cortisol locally, in a pre-receptor manner. Given that the enzyme is abundantly expressed in metabolically important tissues, such as adipose, muscle, and liver, that become resistant to insulin action in Type 2 Diabetes, inhibition of 11β-HSD-1 offers the potential to restore the glucose lowering action of insulin in these tissues without impacting the central HPA. Another important 11-beta hydroxyl steroid dehydrogenase, namely Type 2 11-beta-HSD (11β-HSD-2), which converts cortisol into cortisone, is a unidirectional dehydrogenase mainly located in kidney and protects mineralocorticoid receptors from illicit activation by glucocorticoids.

Multiple lines of evidence indicate that 11β-HSD-1-mediated intracellular cortisol production May have a pathogenic role in Obesity, Type 2 Diabetes and its co-morbidities.

In humans, treatment with non-specific inhibitor carbenoxolone improves insulin sensitivity in lean healthy volunteers and people with type 2 diabetes (Walker B R et al (1995)). Likewise, 11β-HSD-1 activity was decreased in liver and increased in the adipose tissue of obese individuals. Similarly 11β-HSD-1 mRNA was found to be increased in both visceral and subcutaneous adipose tissue of obese patients (Desbriere R et al (2006)) and was positively related to BMI and central obesity in Pima Indians, Caucasians and Chinese youth (Lindsay R S et al (2003), Lee Z S et al (1999)). Adipose tissue 11β-HSD-1 and Hexose-6-Phosphate Dehydrogenase gene expressions have also been shown to increase in patients with type 2 diabetes mellitus (Uckaya G et al (2008)). In human skeletal muscle 11β-HSD-1 expression was found to be positively associated with insulin resistance (Whorwood C B et al (2002)). Increased 11β-HSD-1 expression was also seen in diabetic myotubes (Abdallah B M et al (2005)).

Various studies have been conducted in rodent models to substantiate the role of 11β-HSD-1 in diabetes and obesity. For example, over-expression of 11β-HSD-1 specifically in adipose tissue causes development of metabolic syndrome (glucose intolerance, obesity, dyslipidemia and hypertension) in mice (Masuzaki H et al (2001)). Conversely, when 11β-HSD-1 gene was knocked out, the resulting mice showed resistance to diet induced obesity and improvement of the accompanying dysregulation of glucose and lipid metabolism (Kotelevtsev Y et al (1997), Morton N M et al (2001), Morton N M et al (2004)). In addition, treatment of diabetic mouse models with specific inhibitors of 11β-HSD-1 caused a decrease in glucose output from the liver and overall increase in insulin sensitivity (Alberts P et al (2003)).

The results of the preclinical and early clinical studies suggest that the treatment with a selective and potent inhibitor of 11β-HSD-1 will be an efficacious therapy for type 2 diabetes, obesity and metabolic syndrome.

The role of 11β-HSD-1 as an important regulator of liver glucocorticoid level and thus of hepatic glucose production is well substantiated. Hepatic insulin sensitivity was improved in healthy human volunteers treated with the non-specific 11β-HSD-1 inhibitor carbenoxolone (Walker B R (1995)). Many in vitro and in vivo (animal model) studies showed that the mRNA levels and activities of two key enzymes (PEPCK and G6PC) in gluconeogenesis and glycogenolysis were reduced by reducing 11β-HSD-1 activity. Data from these models also confirm that inhibition of 11β-HSD-1 will not cause hypoglycemia, as predicted since the basal levels of PEPCK and G6Pase are regulated independently of glucocorticoids (Kotelevtsev Y (1997)).

In the pancreas cortisol is shown to inhibit glucose induced insulin secretion as well as increase stress induced beta cell apoptosis. Inhibition of 11β-HSD-1 by carbenoxolone in isolated murine pancreatic beta-cells improves glucose-stimulated insulin secretion (Davani B et al (2000)). Recently, it was shown that 11β-HSD-1 within alpha cells regulates glucagon secretion and in addition may act in a paracrine manner to limit insulin secretion from beta cells (Swali A et al (2008)). Levels of 11β-HSD-1 in islets from ob/ob mice were shown to be positively regulated by glucocorticoids and were lowered by a selective 11β-HSD-1 inhibitor and a glucocorticoid receptor antagonist. Increased levels of 11β-HSD-1 were associated with impaired GSIS (Ortsater H et al (2005)). In Zuker diabetic rats, troglitazone treatment improved metabolic abnormalities with a 40% decline in expression of 11β-HSD-1 in the islets (Duplomb L et al (2004)). Cortisol inhibition may lead to an increase in the insulin gene transcription and a normalization of first phase insulin secretion (Shinozuka Y et al (2001)).

In human skeletal muscle 11β-HSD-1 expression is positively associated insulin resistance and increased expression of 11β-HSD-1 was also reported in type 2 diabetic myotubes (Abdallah B M et al (2005)). Recently the contribution of cortisol in muscle pathology is being considered for modulating its action. Very recently it has been demonstrated that targeted reduction or pharmacological inhibition of 11β-HSD-1 in primary human skeletal muscle prevents the effect of cortisone on glucose metabolism and palmitate oxidation (Salehzadeh F et al (2009)). Over activity of cortisol in muscle leads to muscle atrophy, fibre type switch and poor utilization of glucose due to insulin resistance. Cortisol might have a direct role in reducing muscle glucose uptake.

Obesity is an important factor in Metabolic syndrome as well as in the majority (>80%) of type 2 diabetics, and omental (visceral) fat appears to be of central importance. 11β-HSD-1 activity is increased in the both visceral and subcutaneous adipose tissue of obese individual (Lindsay R S et al (2003)). Cortisol activity in adipose is known to increase the adipogenic program. Inhibition of 11β-HSD-1 activity in pre-adipocytes has been shown to decrease the rate of differentiation into adipocytes (Bader T et al (2002)). This is predicted to result in diminished expansion (possibly reduction) of the omental fat depot, i.e., reduced central obesity (Bujalska I J et al (1997) and (2006)). Intra-adipose cortisol levels have been associated with adipose hypertrophy, independent of obesity (Michailidou Z et al (2006)).

Cortisol in coordination with adrenergic signalling is also known to increase lipolysis which leads to increase in plasma free fatty acid concentrations which, in turn, is the primary cause of many deleterious effects of obesity (Tomlinson J W et al (2007)).

Adrenalectomy attenuates the effect of fasting to increase both food intake and hypothalamic neuropeptide Y expression. This supports the role of glucocorticoids in promoting food intake and suggests that inhibition of 11β-HSD-1 in the brain might increase satiety and therefore reduce food intake (Woods S C (1998)). Inhibition of 11β-HSD-1 by a small molecule inhibitor also decreased food intake and weight gain in diet induced obese mice (Wang S J Y et al (2006)).

The effects discussed above therefore suggest that an effective 11β-NSD-1 inhibitor would have activity as an anti-obesity agent.

Cortisol in excess can also trigger triglyceride formation and VLDL secretion in liver, which can contribute to hyperlipidemia and associated dyslipidemia. It has been shown that 11β-HSD-1-/- transgenic mice have markedly lower plasma triglyceride levels and increased HDL cholesterol levels indicating a potential atheroprotective phenotype (Morton N M et al (2001)). In a diet-induced obese mouse model, a non-selective inhibitor of 11β-HSD-1 reduced plasma free fatty acid as well as triacylglycerol (Wang S J et al (2006)). Over-expression of 11β-HSD-1 in liver increased liver triglyceride and serum free fatty acids with the up regulation of hepatic lipogenic genes (Paterson J M et al (2004). It has been illustrated that inhibition of 11β-HSD-1 improves triglyceridemia by reducing hepatic VLDL-TG secretion, with a shift in the pattern of TG-derived fatty acid uptake toward oxidative tissues, in which lipid accumulation is prevented by increased lipid oxidation (Berthiaume M et al (2007)).

Atherosclerotic mouse model (APOE -/-) which are susceptible to atheroma when fed high fat diet, are protected against development of atherosclerosis when treated with 11β-HSD-1 inhibitors (Hermanowski-Vostaka A et al, (2005)).

Inhibition of 11β-HSD-1 in mature adipocytes is expected to attenuate secretion of the plasminogen activator inhibitor 1 (PAI-1)—an independent cardiovascular risk factor (Halleux C M et al (1999)). Furthermore, there is a clear correlation between glucocorticoid activity and cardiovascular risk factor suggesting that a reduction of the glucocorticoid effects would be beneficial (Walker B R et al (1998), Fraser R et al (1999)).

The association between hypertension and insulin resistance might be explained by increased activity of cortisol. Recent data show that the intensity of dermal vasoconstriction after topical application of glucocorticoids is increased in patients with essential hypertension (Walker B R et al (1998)). Glucocorticoid was shown to increase the expression of angiotensin receptor in vascular cell and thus potentiating the renin-angiotensin pathway (Ullian M E et al (1996)), (Sato A et al (1994)). Role of cortisol in NO signalling and hence vasoconstriction has been proved recently (Liu Y et al (2009)). These findings render 11β-HSD-1 a potential target for controlling hypertension and improving blood-flow in target tissues.

In the past decade, concern on glucocorticoid-induced osteoporosis has increased with the widespread use of exogenous glucocorticoids (GC). GC-induced osteoporosis is the most common and serious side-effect for patients receiving GC. Loss of bone mineral density (BMD) is greatest in the first few months of GC use. Mature bone-forming cells (osteoblasts) are considered to be the principal site of action of GC in the skeleton. The whole differentiation of mesenchymal stem cell toward the osteoblast lineage has been proven to be sensitive to GC as well as collagen synthesis (Kim C H et al (1999)). The effects of GC on this process are different according to the stage of differentiation of bone cell precursors. The presence of intact GC signalling is crucial for normal bone development and physiology, as opposed to the detrimental effect of high dose exposure (Pierotti S et al (2008), Cooper M S et al (2000)). Other data suggest a role of 11β-HSD-1 in providing sufficiently high levels of active glucocorticoid in osteoclasts, and thus in augmenting bone resorption (Cooper M S et al (2000)). The negative effect on bone nodule formation could be blocked by the non-specific inhibitor carbenoxolone suggesting an important role of 11β-HSD-1 in the glucocorticoid effect (Bellows C G et al (1998)).

Stress and glucocorticoids influence cognitive function (de Quervain D J et al (1998)). The enzyme 11β-HSD-1 controls the level of glucocorticoid action in the brain also known to contributes to neurotoxicity (Rajan V et al (1996)). It has been also suggested that inhibiting 11β-HSD-1 in the brain may result in reduced anxiety (Tronche F et al (1999)). Thus, taken together, the hypothesis is that inhibition of 11β-HSD-1 in the human brain would prevent reactivation of cortisone into cortisol and protect against deleterious glucocorticoid-mediated effects on neuronal survival and other aspects of neuronal function, including cognitive impairment, depression, and increased appetite.

Recent data suggest that the levels of the glucocorticoid target receptors and the 11β-HSD-1 enzymes determine the susceptibility to glaucoma (Stokes, J. et al. (2000)). Ingestion of carbenoxolone, a non-specific inhibitor of 11β-HSD-1, was shown to reduce the intraocular pressure by 20% in normal subjects. There are evidences that 11β-HSD-1 isozyme may modulate steroid-regulated sodium transport across the NPE, thereby influencing intra ocular pressure (IOP). 11β-HSD-1 is suggested to have a role in aqueous production, rather than drainage, but it is presently unknown if this is by interfering with activation of the glucocorticoid or the mineralocorticoid receptor, or both (Rauz S et al (2001; 2003)).

The multitude of glucocorticoid action is exemplified in patients with prolonged increase in plasma glucocorticoids, so called "Cushing's syndrome". These patients have prolonged increase in plasma glucocorticoids and exhibit impaired glucose tolerance, type 2 diabetes, central obesity, and osteoporosis. These patients also have impaired wound healing and brittle skin. Administration of glucocorticoid receptor agonist (RU38486) in Cushing's syndrome patients reverses the features of metabolic syndrome (Neiman L K et al (1985)).

Glucocorticoids have been shown to increase risk of infection and delay healing of open wounds. Patients treated with glucocorticoids have 2-5-fold increased risk of complications when undergoing surgery. Glucocorticoids influence wound healing by interfering with production or action of cytokines and growth factors like IGF, TGF-beta, EGF, KGF and PDGF (Beer H D et al (2000)). TGF-beta reverses the glucocorticoid-induced wound-healing deficit in rats by PDGF regulation in macrophages (Pierce G F et al (1989)). It has also been shown that glucocorticoids decrease collagen synthesis in rat and mouse skin in vivo and in rat and human fibroblasts (Oishi Y et al, 2002).

Glucocorticoids have also been implicated in conditions as diverse aspolycystic Ovaries Syndrome, infertility, memory dysfunction, sleep disorders, myopathy (Endocrinology. 2011 January; 152(1):93-102. Epub 2010 Nov. 24.PMID: 21106871) and muscular dystrophy. As such the ability to target enzymes that have an impact on glucocorticoid levels is expected to provide promise for the treatment of these conditions:

Based on patent literature and company press releases, there are many compound tested for 11β-HSD-1 inhibition in the different stages of drug discovery pipeline.

Incyte Corporation's INCB13739 has proceeded furthest to phase IIb stage of clinical trial. The results of phase IIa trial for type 2 diabetes (28-days, placebo-controlled, two-step hyperinsulinemic clamp studies) showed that it was safe and well tolerated without any serious side effects and hypoglycemia.

Though this molecule significantly improved hepatic insulin sensitivity there was no appreciable improvement in plasma glucose levels. The molecule appeared to be having positive effects on risk factors for cardiovascular disease including reduction of LDL, total cholesterol and triglycerides as well as more modest increases in HDL. INCB13739 is currently being studied in a dose ranging phase II b trials in T2D patients whose glucose levels are not controlled by metformin monotherapy.

In the pre-clinical stage, Incyte's lead inhibitor INCB13739 was tested in rhesus monkey and was shown to inhibit adipose 11β-HSD-1 (INCB013739, a selective inhibitor of 11β-Hydroxysteroid Dehydrogenase Type 1 (11βHSD1) improves insulin sensitivity and lowers plasma cholesterol over 28 days in patients with type 2 diabetes mellitus.

The evidence therefore strongly suggests that compounds that are inhibitors of 11β-Hydroxysteroid Dehydrogenase would be useful in the treatment of a number of clinical conditions associated with the expression of this enzyme. In addition it would be desirable if the inhibitors were selective inhibitors so as not to interfere with the functioning of closely related enzymes such as 11β-HSD-2 which is known to provide a protective effect in the body.

OBJECTS OF INVENTION

The principal object of the invention is to provide compounds that are inhibitors of 11β-Hydroxysteroid Dehydrogenase. These compounds would be expected to be useful in the treatment of 11β-Hydroxysteroid Dehydrogenase related conditions as discussed above.

A further object is to provide a pharmaceutical composition containing a compound that is an inhibitor of 11β-Hydroxysteroid Dehydrogenase and a pharmaceutically acceptable excipient, diluent or carrier.

A further object is to provide a method of prevention or treatment of a condition associated with 11β-Hydroxysteroid Dehydrogenase activity in a mammal.

STATEMENT OF INVENTION

The present invention provides compounds of Formula (I):

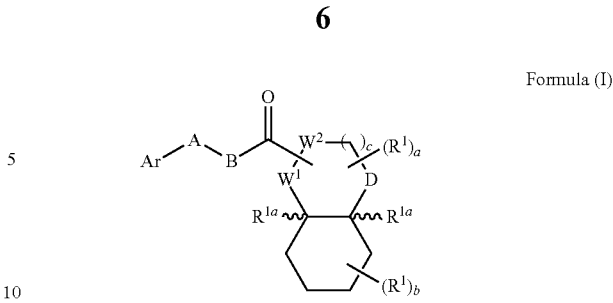

Formula (I)

wherein:
each $R^1$ and $R^{1a}$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^2$, $SO_3H$, $SO_2NR^2R^3$, $SO_2R^2$, $SONR^2R^3$, $SOR^2$, $COR^2$, COOH, $COOR^2$, $CONR^2R^3$, $NR^2COR^3$, $NR^2COOR^3$, $NR^2SO_2R^3$, $NR^2CONR^2R^3$, $NR^2R^3$, and acyl, or any two $R^1$ on adjacent carbon atoms may be joined to form a cyclic moiety, or any two $R^1$ on the same carbon when taken together may form a group of the formula $=O$ or $=NR^5$, and the two $R^{1a}$ may be joined to form a double bond;

Ar is an optionally substituted $C_1$-$C_{18}$ heteroaryl group;

A is selected from the group consisting of S, SO, $SO_2$, O, and —$CR^aR^b$—;

B is a group of the formula —$(CR^cR^d)_n$—;

wherein each $R^a$, $R^b$, $R^c$ and $R^d$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_2$-$C_{10}$heteroalkyl, optionally substituted $C_1$-$C_{12}$haloalkyl, optionally substituted $C_3$-$C_{12}$cycloalkyl, optionally substituted $C_6$-$C_{18}$aryl, optionally substituted $C_1$-$C_{18}$heteroaryl; $SR^2$, $SO_3H$, $SO_2NR^2R^3$, $SO_2R^2$, $SONR^2R^3$, $SOR^2$, $COR^2$, COOH, $COOR^2$, $CONR^2R^3$, $NR^2COR^3$, $NR^2COOR^3$, $NR^2SO_2R^3$, $NR^2CONR^2R^3$, $NR^2R^3$, and acyl, or any two $R^a$, $R^b$, $R^c$ and $R^d$ on the same carbon atom when taken together may form a cycloalkyl group or a substituent of the formula:

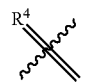

wherein each $R^2$ and $R^3$ is independently selected from the group consisting of H, optionally substituted $C_1$-$C_{12}$alkyl, optionally substituted $C_2$-$C_{10}$heteroalkyl, optionally substituted $C_1$-$C_{12}$haloalkyl, optionally substituted $C_3$-$C_{12}$cycloalkyl, optionally substituted $C_6$-$C_{18}$aryl, and optionally substituted $C_1$-$C_{18}$heteroaryl;

$R^4$ is selected from the group consisting of O, S, and $NR^5$;

$R^5$ is selected from the group consisting of H, $OR^6$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_1$-$C_{12}$alkyloxy, optionally substituted $C_1$-$C_{12}$haloalkyloxy, optionally substituted $C_2$-$C_{10}$heteroalkyl, optionally substituted $C_3$-$C_{12}$cycloalkyl, optionally substituted $C_3$-$C_{12}$cycloalkenyl, optionally substituted $C_2$-$C_{12}$ heterocycloalkyl, optionally substituted $C_2$-$C_{12}$ heterocycloalkenyl, optionally substituted $C_6$-$C_{18}$aryl, and optionally substituted $C_1$-$C_{18}$heteroaryl, $R^6$ is selected from the group consisting of H, optionally substituted $C_1$-$C_{12}$alkyl, optionally substituted $C_2$-$C_{10}$heteroalkyl, optionally substituted $C_3$-$C_{12}$cycloalkyl, optionally substituted $C_6$-$C_{18}$aryl, and optionally substituted $C_1$-$C_{18}$heteroaryl, or any two or more $R^a$, $R^b$, $R^c$ and $R^d$ may join together to form a multiple bond between adjacent carbon atoms such as a double or triple bond, or a cyclic moiety connecting the carbon atoms to which they are attached;

$W^1$ and $W^2$ are selected such that one is N and the other is $(CR^1_2)$;

the bond from the carbonyl carbon is joined to whichever of $W^1$ or $W^2$ is N;

D is O or $(CR^1_2)$;

n is an integer selected from the group consisting of 0, 1, 2, 3, and 4;

a is an integer selected from the group consisting of 0, 1, and 2;

b is an integer selected from the group consisting of 0, 1, 2, 3, 4, 5, 6, 7, and 8, c is an integer selected from 0, 1, and 2;

or a pharmaceutically acceptable salt, N-oxide, or prodrug thereof.

As with any group of structurally related compounds which possess a particular utility, certain embodiments of variables of the compounds of the Formula (I), are particularly useful in their end use application.

In some embodiments A is S. In some embodiments A is SO. In some embodiments A is $SO_2$. In some embodiments A is O. In some embodiments A is $CR^aR^b$.

In some embodiments $R^a$ and $R^b$ are each independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, CN, $SO_3H$, $OCH_3$, $OCH_2CH_2CH_3$, $CF_3$, and $OCF_3$. In some embodiments $R^a$ is H. In some embodiments $R^b$ is H. In some embodiments $R^a$ and $R^b$ are different such that the carbon is a chiral carbon. In some embodiments one of $R^a$ and $R^b$ is H and the other is an optionally substituted alkyl.

B is a group of the formula $-(CR^cR^d)_n-$. In some embodiments n is 0. In some embodiments n is 1. In some embodiments n is 2.

In some embodiments $R^c$ and $R^d$ are each independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, CN, $SO_3H$, $OCH_3$, $OCH_2CH_2CH_3$, $CF_3$, and $OCF_3$. In some embodiments both $R^c$ and $R^d$ are H such that B is $CH_2$.

In some embodiments any two or more $R^a$, $R^b$, $R^c$ and $R^d$ may join together to form a multiple bond between adjacent carbon atoms such as a double or triple bond, or a cyclic moiety connecting the carbon atoms to which they are attached.

In some embodiments two of $R^a$, $R^b$, $R^c$ and $R^d$ on adjacent carbon atoms are joined to form a double bond. In some embodiments four of $R^a$, $R^b$, $R^c$ and $R^d$ on adjacent carbon atoms are joined to form a triple bond.

In some embodiments one of $R^a$ and $R^b$ and one or $R^c$ and $R^d$ when taken together with the carbon atoms to which they are attached form a cyclic moiety. Examples of cyclic moieties that may be formed include cyclopropyl, cyclobutyl, cyclopentyl and cyclohexyl.

In some embodiments n=2 and one of $R^a$ and $R^b$ and one or $R^c$ and $R^d$ on the carbon atom two carbons removed (on the beta carbon) when taken together with the carbon atoms to which they are attached and the alpha carbon atom form a cyclic moiety. Examples of cyclic moieties that may be formed include cyclobutyl, cyclopentyl and cyclohexyl.

In some embodiments A is $CR^aR^b$ and B is $CH_2$, this provides compounds of formula

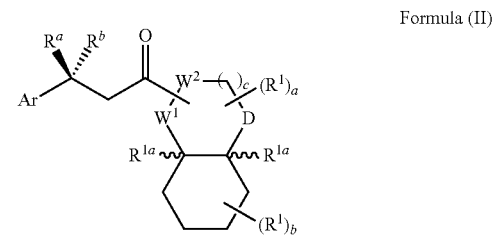

Formula (II)

wherein $R^1$, $R^{1a}$, $R^a$, $R^b$, Ar, $W^1$, $W^2$, D, a, b and c are as defined above.

In some embodiments D is O. In some embodiments D is $(CR^1_2)$.

In some embodiments A is $CR^aR^b$, B is $CH_2$ and D is O, this provides compounds of formula (IIIa):

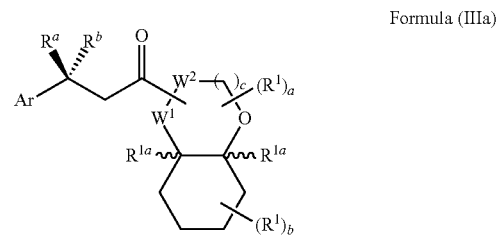

Formula (IIIa)

wherein $R^1$, $R^{1a}$, $R^a$, $R^b$, Ar, $W^1$, $W^2$, a, b and c are as defined above.

In some embodiments A is $CR^aR^b$, B is $CH_2$ and D is $(CR^1_2)$, this provides compounds of formula (IIIb):

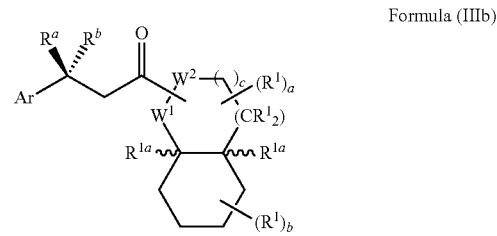

Formula (IIIb)

wherein $R^1$, $R^{1a}$, $R^a$, $R^b$, Ar, $W^1$, $W^2$, a, b and c are as defined above.

In some embodiments c is 0 and the ring containing $W^1$ and $W^2$ is a 5 membered ring. In some embodiments c is 1 and the ring containing $W^1$ and $W^2$ is a 6 membered ring. In some embodiments c is 2 and the ring containing $W^1$ and $W^2$ is a 7 membered ring.

In some embodiments A is $CR^aR^b$, B is $CH_2$, D is O and c is 1, this provides compounds of formula (IVa):

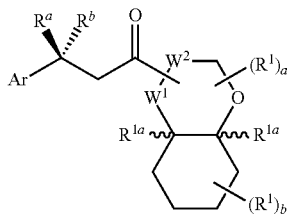

Formula (IVa)

wherein $R^1$, $R^{1a}$, $R^a$, Ar, $W^1$, $W^2$, a, and b are as defined above.

In some embodiments A is $CR^aR^b$, B is $CH_2$, D is $(CR^1_2)$ and c is 1, this provides compounds of formula (IVb):

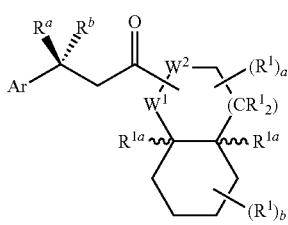

Formula (IVb)

wherein $R^1$, $R^{1a}$, $R^a$, $R^b$, $W^1$, $W^2$, a and b are as defined above.

In some embodiments $W^1$ is N and $W^2$ is $(CR^1_2)$. In some embodiments $W^1$ is $(CR^1_2)$, and $W^2$ is N.

In some embodiments A is $CR^aR^b$, B is $CH_2$, D is O, c is 1, $W^1$ is N and $W^2$ is $(CR^1_2)$. This provides compounds of formula (Va):

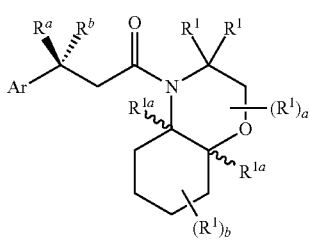

Formula (Va)

wherein $R^1$, $R^{1a}$, $R^a$, $R^b$, Ar, a, and b are as defined above.

In some embodiments A is $CR^aR^b$, B is $CH_2$, D is $(CR^1_2)$, c is 1, $W^1$ is N and $W^2$ is $(CR^1_2)$, this provides compounds of formula (Vb).

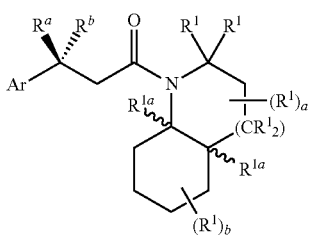

Formula (Vb)

wherein $R^1$, $R^{1a}$, $R^a$, $R^b$, Ar, a and b are as defined above.

In some embodiments A is $CR^aR^b$, B is $CH_2$, D is O, c is 1, $W^1$ is $(CR^1_2)$, and $W^2$ is N this provides compounds of formula (Vc):

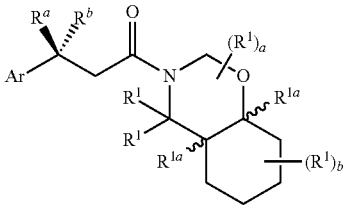

Formula (Vc)

wherein $R^1$, $R^{1a}$, $R^a$, $R^b$, Ar, a, and b are as defined above.

In some embodiments A is $CR^aR^b$, B is $CH_2$, D is $(CR^1_2)$, c is 1, $W^1$ is N and $W^2$ is $(CR^1_2)$, this provides compounds of formula (Vd).

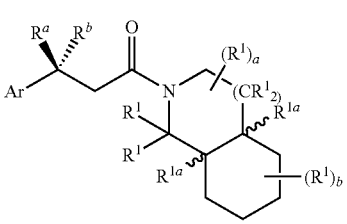

Formula (Vd)

wherein $R^1$, $R^{1a}$, $R^a$, $R^b$, Ar, a and b are as defined above.

The group Ar may be any optionally substituted $C_1$-$C_{18}$ heteroaryl moiety. Suitable heteroaryl groups include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, pyridyl, quinolyl, isoquinolinyl, indolyl, and thienyl. In each instance where there is the possibility of multiple sites of substitution on the heteroaryl ring all possible attachment points are contemplated. Merely by way of example if the heteroaryl is a pyridyl moiety it may be a 2-pyridyly, a 3-pyridyl or a 4 pyridyl.

In some embodiments Ar is a group of the formula VI:

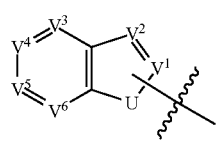

(VI)

wherein each $V^1$, $V^2$, $V^3$, $V^4$, $V^5$ and $V^6$ is independently selected from the group consisting of N and $CR^7$;

U is selected from the group consisting of $NR^8$, O, S and $CR^8_2$, wherein each $R^7$ is independently selected from the group consisting of each $R^3$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl, optionally substituted $C_2$-$C_{12}$alkenyl, optionally substituted $C_2$-$C_{12}$alkynyl, optionally substituted $C_2$-$C_{12}$heteroalkyl, optionally substituted C$_3$-C$_{12}$cycloalkyl, optionally substituted C$_3$-C$_{12}$cycloalkenyl, optionally substituted C$_2$-C$_{12}$heterocycloalkyl, optionally substituted C$_2$-C$_{12}$ heterocycloalkenyl, optionally substituted C$_6$-C$_{18}$aryl, optionally substituted C$_1$-C$_{18}$heteroaryl, optionally substituted C$_1$-C$_{12}$alkyloxy, optionally substituted C$_2$-C$_{12}$alkenyloxy, optionally substituted C$_2$-C$_{12}$alkynyloxy, optionally substituted C$_2$-C$_{10}$heteroalkyloxy, optionally substituted C$_3$-C$_{12}$cycloalkyloxy, optionally substituted C$_3$-C$_{12}$cycloalkenyloxy, optionally substituted C$_2$-C$_{12}$ heterocycloalkyloxy, optionally substituted C$_2$-C$_{12}$ heterocycloalkenyloxy, optionally substituted C$_6$-C$_{18}$aryloxy, optionally substituted C$_1$-C$_1$ heteroaryloxy, optionally substituted C$_1$-C$_{12}$alkylamino, SR$^9$, SO$_3$H, SO$_2$NR$^9$R$^{10}$, SO$_2$R$^9$, SONR$^9$R$^{10}$, SOR$^9$, COR$^9$, COOH, COOR$^9$, CONR$^9$R$^{10}$, NR$^9$COR$^{10}$, NR$^9$COOR$^{10}$, NR$^9$SO$_2$R$^{10}$, NR$^9$CONR$^9$R$^{10}$, NR$^9$R$^{10}$, and acyl;

wherein R$^8$ is selected from the group consisting of H, optionally substituted C$_1$-C$_{12}$alkyl, optionally substituted C$_2$-C$_{12}$alkenyl, optionally substituted C$_2$-C$_{12}$alkynyl, optionally substituted C$_2$-C$_{12}$ heteroalkyl, optionally substituted C$_3$-C$_{12}$cycloalkyl, optionally substituted C$_2$-C$_{12}$heterocycloalkyl, optionally substituted C$_6$-C$_{18}$aryl, optionally substituted C$_1$-C$_{18}$heteroaryl, SO$_3$H, SO$_2$NR$^9$R$^{10}$, SO$_2$R$^9$, SONR$^9$R$^{10}$, SOR$^9$, COR$^9$, COOH, COOR$^9$, and CONR$^9$R$^{10}$;

wherein each R$^9$ and R$^{10}$ is independently selected from the group consisting of H, optionally substituted C$_1$-C$_{12}$alkyl, optionally substituted C$_2$-C$_{10}$heteroalkyl, optionally substituted C$_1$-C$_{12}$haloalkyl, optionally substituted C$_3$-C$_{12}$cycloalkyl, optionally substituted C$_6$-C$_{18}$aryl, and optionally substituted C$_1$-C$_{18}$heteroaryl.

In some embodiments Ar is selected from the group consisting of:

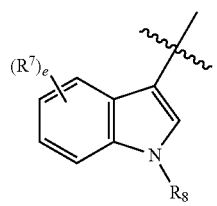
VIa

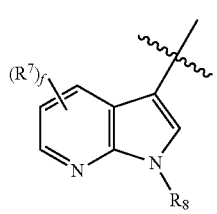
VIb

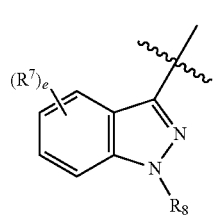
VIc

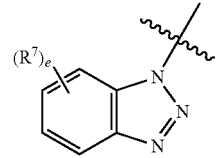
VId

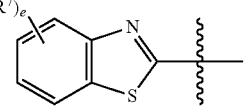
VIe

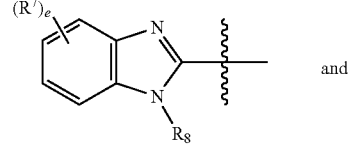
VIf and

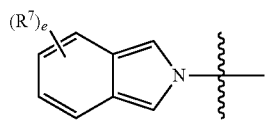
VIg wherein R$^7$ is as defined above;

e is an integer selected from the group consisting of 0, 1, 2, 3 and 4;

f is an integer selected the group consisting of 0, 1, 2, and 3.

In some embodiments A is CR$^a$R$^b$, B is CH$_2$, D is (CR$^1_2$), c is 1, W$^1$ is N, W$^2$ is (CR$^1_2$) and Ar is a group of formula VIa, this provides compounds of formula (VIIa):

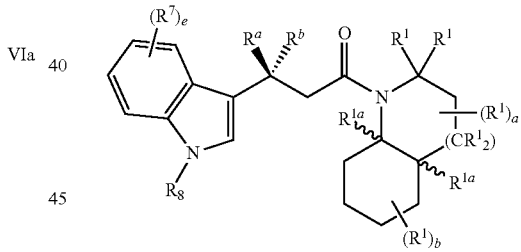
Formula (VIIa)

wherein R$^1$, R$^{1a}$, R$^a$, R$^b$, R$^7$, R$^8$, a, b and e are as defined above.

In some embodiments A is CR$^a$R$^b$, B is CH$_2$, D is (CR$^1_2$), c is 1, W$^1$ is N, W$^2$ is (CR$^1_2$) and Ar is a group of formula VIb, this provides compounds of formula (VIIb):

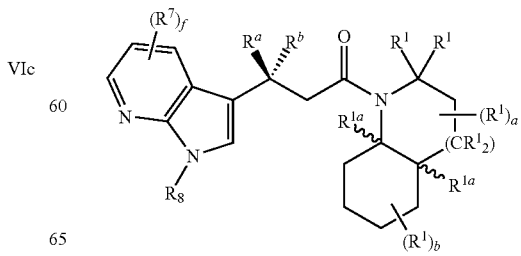
Formula (VIIb)

wherein $R^1$, $R^{1a}$, $R^a$, $R^b$, $R^7$, $R^8$, a, b and f are as defined above.

In some embodiments A is $CR^aR^b$, B is $CH_2$, D is $(CR^1_2)$, c is 1, $W^1$ is N, $W^2$ is $(CR^1_2)$ and Ar is a group of formula VIc, this provides compounds of formula (VIIc):

Formula (VIIc)

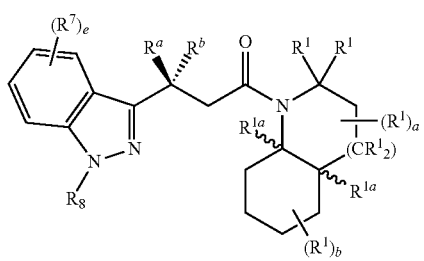

wherein $R^1$, $R^{1a}$, $R^a$, $R^b$, $R^7$, $R^8$, a, b and e are as defined above.

In some embodiments A is $CR^aR^b$, B is $CH_2$, D is $(CR^1_2)$, c is 1, $W^1$ is N, $W^2$ is $(CR^1_2)$ and Ar is a group of formula VId, this provides compounds of formula (VIId):

Formula (VIId)

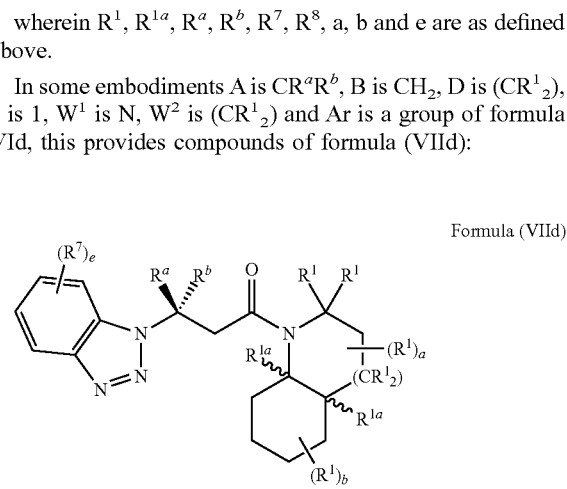

wherein $R^1$, $R^{1a}$, $R^a$, $R^b$, $R^7$, a, b and e are as defined above.

In some embodiments A is $CR^aR^b$, B is $CH_2$, D is $(CR^1_2)$, c is 1, $W^1$ is N, $W^2$ is $(CR^1_2)$ and Ar is a group of formula VIe, this provides compounds of formula (VIIe):

Formula (VIIe)

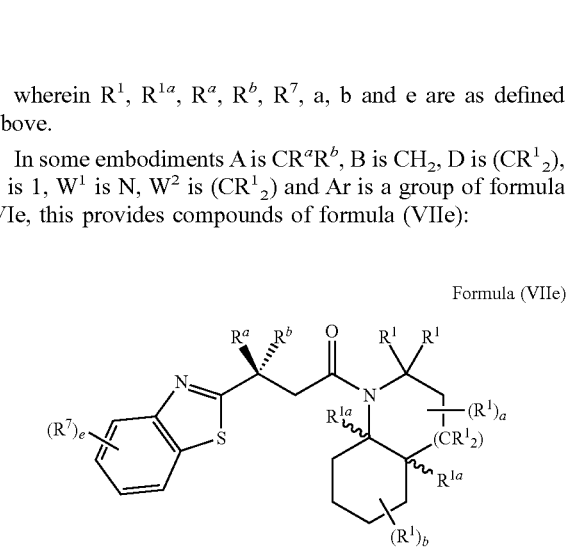

wherein $R^1$, $R^{1a}$, $R^a$, $R^b$, $R^7$, a, b and e are as defined above.

In some embodiments A is $CR^aR^b$, B is $CH_2$, D is $(CR^1_2)$, c is 1, $W^1$ is N, $W^2$ is $(CR^1_2)$ and Ar is a group of formula VIf, this provides compounds of formula (VIIf):

Formula (VIIf)

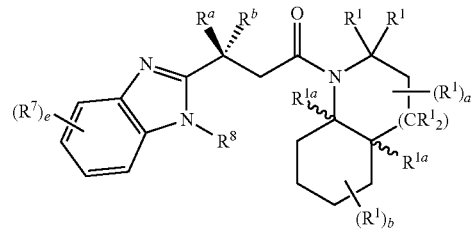

wherein $R^1$, $R^{1a}$, $R^a$, $R^b$, $R^7$, $R^8$, a, b and e are as defined above.

In some embodiments A is $CR^aR^b$, B is $CH_2$, D is $(CR^1_2)$, c is 1, $W^1$ is N, $W^2$ is $(CR^1_2)$ and Ar is a group of formula VIg, this provides compounds of formula (VIIg):

Formula (VIIg)

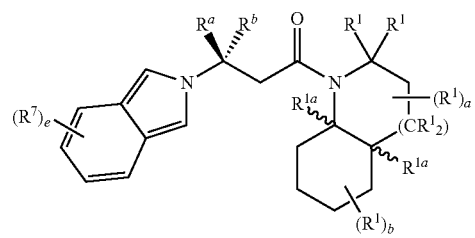

wherein $R^1$, $R^{1a}$, $R^a$, $R^b$, $R^7$, a, b and e are as defined above.

As can be seen many of the compounds of the present invention contain a quinoline or isoquinoline moiety as shown below. In order to assist the reader in determining substitution patterns on these moieties the accepted ring atom numbering is shown below.

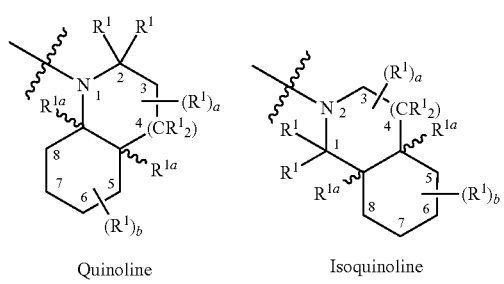

Quinoline    Isoquinoline

In some embodiments of the compounds described above $R^1$ is selected from the group consisting of H, methyl, $CONHC(CH_3)_3$, OH, $CO_2H$, $CO_2CH_3$, $CO_2CH_2CH_3$, phenyl, $CH_2OH$, $CH_2CO_2H$, CN and $OCH_3$. In some embodiments $R^1$ is $CO_2H$.

In some embodiments a is 0. In some embodiments a is 1. In some embodiments a is 2. In some embodiments a is 3.

In some embodiments b is 0. In some embodiments b is 1. In some embodiments b is 2. In some embodiments b is 3. In some embodiments b is 4. In some embodiments b is 5. In some embodiments b is 6. In some embodiments b is 7. In some embodiments b is 8.

In the compounds of the invention where there is a non H value for $R^1$, the substituent may be present on any available carbon atom. In some embodiments the substituent is located at the 4 position of the isoquinoline or quinoline ring. In some embodiments the substituent is located at the 5 position of the the isoquinoline or quinoline ring.

In some embodiments of the compounds described above $R^{1a}$ is selected from the group consisting of H, methyl, $CONHC(CH_3)_3$, OH, $CO_2H$, $CO_2CH_3$, $CO_2CH_2CH_3$, phenyl, $CH_2OH$, CN and $OCH_3$.

In some embodiments of the compounds of the invention containing an $R^2$ group, the $R^2$ group is selected from H and $C_1$-$C_{12}$alkyl. In some embodiments $R^2$ is H. in some embodiments $R^2$ is methyl.

In some embodiments of the compounds of the invention containing an $R^3$ group, the $R^3$ group is selected from H and $C_1$-$C_{12}$alkyl. In some embodiments $R^3$ is H. in some embodiments $R^3$ is methyl.

In some embodiments of the compounds of the invention containing an $R^4$ group, the $R^4$ group is selected from O and S. In some embodiments $R^4$ is O. in some embodiments $R^4$ is S.

In some embodiments of the compounds of the invention containing an $R^5$ group, the $R^5$ group is selected from H and $C_1$-$C_{12}$alkyl. In some embodiments $R^5$ is H. in some embodiments $R^5$ is methyl.

In some embodiments e is 1. In some embodiments e is 2. In some embodiments e is 3. In some embodiments e is 4. In circumstances where e is 1 the $R^7$ group may be located at either the 4, 5, 6, or 7 position on the six membered ring. In some embodiments where e is 1 the $R^7$ substituent is located at the 4 position on the ring. In some embodiments where e is 1 the $R^7$ substituent is located at the 5 position on the ring. In some embodiments where e is 1 the $R^7$ substituent is located at the 6 position on the ring. In some embodiments where e is 1 the $R^7$ substituent is located at the 7 position on the ring.

In some embodiments f is 1. In some embodiments f is 2. In some embodiments fi is 3. In some embodiments where f is 1 the $R^7$ substituent is located at the 4 position on the ring. In some embodiments where f is 1 the $R^7$ substituent is located at the 5 position on the ring. In some embodiments where f is 1 the $R^7$ substituent is located at the 6 position on the ring. In some embodiments where f is 1 the $R^7$ substituent is located at the 7 position on the ring.

$R^7$ may be selected from a wide range of possible substituents as discussed above. In some embodiments each $R^7$ is independently selected from the group consisting of H, halogen, OH, $NO_2$, CN, optionally substituted $C_1$-$C_{12}$alkyl, optionally substituted $C_3$-$C_{12}$cycloalkyl $C_1$-$C_{12}$haloalkyl, optionally substituted, optionally substituted $C_6$-$C_{18}$aryl, optionally substituted $C_1$-$C_{18}$heteroaryl, optionally substituted $C_2$-$C_{12}$heterocycloalkyloxy, $C_1$-$C_{12}$alkoxyl, and $C_1$-$C_{12}$haloalkoxyl. Exemplary $R^7$ substituents include $CH_3$, $CH_2CH_3$, $CH_2CH_2CH_3$, $CH(CH_3)_2$, $(CH_2)_3CH_3$, cyclopropyl, isopropoxy, I, Br, F, Cl, OH, $NO_2$, $NH_2$, CN, $SO_3H$, $OCH_3$, $OCH_2CH_3$, $CF_3$, $OCF_3$, thiophen-2-yl, 5-fluoro-thiophen-2-yl, furan-2-yl, 5-methyl-furan-2-yl, pyridine-2-yl, 3-fluoropyridine-2-yl, 3-methyl-isoxazol-5-yl, 3-fluoro-phenyl, 4-fluoro-phenyl, 1-methyl pyroll-2-yl, 5-fluoro-furan-2-yl, 5-cyano-furan-2-yl, and 5-carboxy-furan-2-yl.

$R^8$ may be selected from a wide range of possible substituents as discussed above. In some embodiments each $R^8$ is independently selected from the group consisting of H, halogen, OH, $NO_2$, CN, $C_1$-$C_{12}$alkyl, $C_1$-$C_{12}$haloalkyl, $C_1$-$C_{12}$alkoxyl, and $C_1$-$C_{12}$haloalkoxyl. Exemplary $R^8$ substituents include $CH_3$, $CH_2CH_3$, $CH_2CH_2CH_3$, $CH(CH_3)_2$, $(CH_2)_3CH_3$, I, Br, F, I, OH, $NO_2$, $NH_2$, CN, $SO_3H$, $OCH_3$, $OCH_2CH_3$, $CF_3$, and $OCF_3$.

Many if not all of the variables discussed above may be optionally substituted. If the variable is optionally substituted then in some embodiments each optional substituent is independently selected from the group consisting of halogen, $=O$, $=S$, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)$R^e$, —C(=O)$OR^e$, C(=O)$NR^eR^f$, C(=NOH)$R^e$, C(=$NR^e$)$NR^fR^g$, $NR^eR^f$, $NR^eC(=O)R^f$, $NR^eC(=O)OR^f$, $NR^eC(=O)NR^fR^g$, $NR^eC(=NR^f)NR^gR^h$, $NR^eSO_2R^f$, —$SR^e$, $SO_2NR^eR^f$, —$OR^e$, $OC(=O)NR^eR^f$, $OC(=O)R^e$ and acyl, wherein $R^e$, $R^g$ and $R^h$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, heteroalkyl, $C_3$-$C_{12}$cycloalkyl, $C_3$-$C_{12}$cycloalkenyl, $C_1$-$C_{12}$heterocycloalkyl, heterocycloalkenyl, $C_6$-$C_{12}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments each optional substituent is independently selected from the group consisting of: F, Cl, Br, =O, =S, —CN, —$NO_2$, alkyl, alkenyl, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, —C(O)$OR^a$, COOH, SH, and acyl.

In some embodiments each optional substituent is independently selected from the group consisting of: F, Br, Cl, =O, =S, —CN methyl, trifluoro-methyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, —$NO_2$, phenoxy, hydroxy, methoxy, trifluoro-methoxy, ethoxy, and methylenedioxy.

Alternatively, two optional substituents on the same moiety when taken together may be joined to form a fused cyclic substituent attached to the moiety that is optionally substituted. Accordingly the term optionally substituted includes a fused ring such as a cycloalkyl ring, a heterocycloalkyl ring, an aryl ring or a heteroaryl ring.

In addition to compounds of formula I, the embodiments disclosed are also directed to pharmaceutically acceptable salts, pharmaceutically acceptable N-oxides, pharmaceutically acceptable prodrugs, and pharmaceutically active metabolites of such compounds, and pharmaceutically acceptable salts of such metabolites.

The invention also relates to pharmaceutical compositions including a compound of the invention and a pharmaceutically acceptable carrier, diluent or excipient.

In a further aspect the present invention provides a method of prevention or treatment of a condition in a mammal, the method comprising administering an effective amount of a compound of the invention. In one embodiment the condition is a condition that can be treated by inhibition of 11β-HSD1.

In yet an even further aspect the invention provides the use of a compound of the invention in the preparation of a medicament for the treatment of a condition in a mammal. In one embodiment the condition is a condition that can be treated by inhibition of 11β-HSD1.

In yet an even further aspect the invention provides the use of a compound of the invention in the treatment of a condition in a mammal. In one embodiment the condition is a condition that can be treated by inhibition of 11β-HSD1.

In some embodiments the condition is selected from the group consisting of is selected from the group consisting of diabetes, hyperglycemia, low glucose tolerance, hyperinsulinemia, hyperlipidemia, hypertriglyceridemia, hypercholesterolemia, dyslipidemia, obesity, abdominal obesity, glaucoma, hypertension, atherosclerosis and its sequelae, retinopathy and other ocular disorders, nephropathy, neuropathy, myopathy, osteoporosis, osteoarthritis, dementia, depression, neurodegenerative disease, psychiatric disorders, Polycystic ovaries syndrome, infertility, Cushing's Disease, Cushing's syndrome, viral diseases, and inflammatory diseases.

In some embodiments the condition is diabetes. In some embodiments the condition is type II diabetes.

In some embodiments the compound is administered in combination with an adjuvant. In some embodiments the adjuvant is selected from the group consisting of dipeptidyl peptidase-IV (DP-IV) inhibitors; (b) insulin sensitizing agents; (c) insulin and insulin mimetics; (d) sulfonylureas and other insulin secretagogues; (e) alpha.-glucosidase inhibitors; (f) GLP-1, GLP-1 analogs, and GLP-1 receptor agonists; and combinations thereof.

In one other embodiment the compound is administered as a substitute for monotherapy or combination therapy, in an event of failure of treatment by agent selected from the group consisting of dipeptidyl peptidase-IV (DP-IV) inhibitors; (b) insulin sensitizing agents; (c) insulin and insulin mimetics; (d) sulfonylureas and other insulin secretagogues; (e) alpha.-glucosidase inhibitors; (f) GLP-1, GLP-1 analogs, and GLP-1 receptor agonists; and combinations thereof.

In one embodiment the insulin sensitizing agent is selected from the group consisting of (i) PPAR-gamma-agonists, (ii) PPAR-alpha-agonists, (iii) PPAR-alpha/gamma-dual agonists, (iv) biguanides, and combinations thereof.

These and other teachings of the invention are set forth herein.

DETAILED DESCRIPTION OF THE INVENTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, $=O$, $=S$, $-CN$, $-NO_2$, $-CF_3$, $-OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, $-C(=O)OH$, $-C(=O)R^e$, $-C(=O)OR^e$, $C(=O)NR^eR^f$, $C(=NOH)R^e$, $C(=NR^e)NR^fR^g$, $NR^eR^f$, $NR^eC(=O)R^f$, $NR^eC(=O)OR^f$, $NR^eC(=O)NR^fR^g$, $NR^eC(=NR^f)NR^gR^h$, $NR^eSO_2R^1$, $-SR^e$, $SO_2NR^eR^f$, $-OR^e$, $OC(=O)NR^eR^f$, $OC(=O)R^e$ and acyl, wherein $R^e$, $R^f$, $R^g$ and $R^h$ are each independently selected from the group consisting of H, $C_1$-$C_{12}$haloalkyl, $C_2$-$C_{12}$alkenyl, $C_2$-$C_{12}$alkynyl, $C_1$-$C_{10}$heteroalkyl, $C_3$-$C_{12}$cycloalkyl, $C_3$-$C_{12}$cycloalkenyl, $C_1$-$C_{12}$heterocycloalkyl, $C_1$-$C_{12}$heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments each optional substituent is independently selected from the group consisting of: halogen, $=O$, $=S$, $-CN$, $-NO_2$, $-CF_3$, $-OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, $-COOH$, $-SH$, and acyl.

Examples of particularly suitable optional substituents include F, Cl, Br, I, $CH_3$, $CH_2CH_3$, OH, $OCH_3$, $CF_3$, $OCF_3$, $NO_2$, $NH_2$, and CN.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Acyl" means an $R-C(=O)-$ group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Acylamino" means an $R-C(=O)-NH-$ group in which the R group may be an alkyl, cycloalkyl, heterocycloalkyl, aryl or heteroaryl group as defined herein. The group may be a terminal group or a bridging group. If the group is a terminal group it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. The alkenyl group is preferably a 1-alkenyl group. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are $C_1$-$C_6$alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a $C_1$-$C_{12}$alkyl, more preferably a $C_1$-$C_{10}$alkyl, most preferably $C_1$-$C_6$ unless otherwise noted. Examples of suitable straight and branched $C_1$-$C_6$alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means an Alkyl-NH— group, in which alkyl is as defined herein. "Dialkylamino" means a $(alkyl)_2$N— group, in which each alkyl may be the same or different and are each as defined herein for alkyl. The alkyl group is preferably a $C_1$-$C_6$alkyl group. The group may be a terminal group or a bridging group. If the group is a terminal group it is bonded to the remainder of the molecule through the nitrogen atom.

"Alkylaminocarbonyl" refers to a group of the formula $(Alkyl)_x(H)_yNC(=O)$— in which alkyl is as defined herein, x is 1 or 2, and the sum of X+Y=2. The group may be a terminal group or a bridging group. If the group is a terminal group it is bonded to the remainder of the molecule through the carbonyl carbon.

"Alkyloxy" refers to an alkyl-O— group in which alkyl is as defined herein. Preferably the alkyloxy is a $C_1$-$C_6$alkyloxy. Examples include, but are not limited to, methoxy and ethoxy. The group may be a terminal group or a bridging group.

"Alkyloxyalkyl" refers to an alkyloxy-alkyl- group in which the alkyloxy and alkyl moieties are as defined herein. The group may be a terminal group or a bridging group. If the group is a terminal group it is bonded to the remainder of the molecule through the alkyl group.

"Alkyloxyaryl" refers to an alkyloxy-aryl- group in which the alkyloxy and aryl moieties are as defined herein. The group may be a terminal group or a bridging group. If the group is a terminal group it is bonded to the remainder of the molecule through the aryl group.

"Alkyloxycarbonyl" refers to an alkyl-O—C(=O)— group in which alkyl is as defined herein. The alkyl group is preferably a $C_1$-$C_6$ alkyl group. Examples include, but are not limited to, methoxycarbonyl and ethoxycarbonyl. The group may be a terminal group or a bridging group. If the group is a terminal group it is bonded to the remainder of the molecule through the carbonyl carbon.

"Alkyloxycycloalkyl" refers to an alkyloxy-cycloalkyl- group in which the alkyloxy and cycloalkyl moieties are as defined herein. The group may be a terminal group or a bridging group. If the group is a terminal group it is bonded to the remainder of the molecule through the cycloalkyl group.

"Alkyloxyheteroaryl" refers to an alkyloxy-heteroaryl- group in which the alkyloxy and heteroaryl moieties are as defined herein. The group may be a terminal group or a bridging group. If the group is a terminal group it is bonded to the remainder of the molecule through the heteroaryl group.

"Alkyloxyheterocycloalkyl" refers to an alkyloxy-heterocycloalkyl- group in which the alkyloxy and heterocycloalkyl moieties are as defined herein. The group may be a terminal group or a bridging group. If the group is a terminal group it is bonded to the remainder of the molecule through the heterocycloalkyl group.

"Alkylsulfinyl" means an alkyl-S—(=O)— group in which alkyl is as defined herein. The alkyl group is preferably a $C_1$-$C_6$ alkyl group. Exemplary alkylsulfinyl groups include, but not limited to, methylsulfinyl and ethylsulfinyl. The group may be a terminal group or a bridging group. If the group is a terminal group it is bonded to the remainder of the molecule through the sulfur atom.

"Alkylsulfonyl" refers to an alkyl-S$(=O)_2$— group in which alkyl is as defined above. The alkyl group is preferably a $C_1$-$C_6$alkyl group. Examples include, but not limited to methylsulfonyl and ethylsulfonyl. The group may be a terminal group or a bridging group. If the group is a terminal group it is bonded to the remainder of the molecule through the sulfur atom.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$alkynyloxy groups. The group may be a terminal group or a bridging group. If the group is a terminal group it is bonded to the remainder of the molecule through the oxygen atom.

"Aminoalkyl" means an $NH_2$-alkyl- group in which the alkyl group is as defined herein. The group may be a terminal group or a bridging group. If the group is a terminal group it is bonded to the remainder of the molecule through the alkyl group.

"Aminosulfonyl" means an $NH_2$—S$(=O)_2$— group. The group may be a terminal group or a bridging group. If the group is a terminal group it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal or a bridging group. Typically an aryl group is a $C_6$-$C_{18}$ aryl group.

"Arylalkenyl" means an aryl-alkenyl- group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl- group in which the aryl and alkyl moieties are as defined herein. Preferred arylalkyl groups contain a $C_{1-5}$alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono-arylamino means a group of formula arylNH—, in which aryl is as defined herein. Di-arylamino means a group of formula $(aryl)_2N$— where each aryl may be the same or different and are each as defined herein for aryl. The group may be a terminal group or a bridging group. If the group is a terminal group it is bonded to the remainder of the molecule through the nitrogen atom.

"Arylheteroalkyl" means an aryl-heteroalkyl- group in which the aryl and heteroalkyl moieties are as defined herein. The group may be a terminal group or a bridging group. If the group is a terminal group it is bonded to the remainder of the molecule through the heteroalkyl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

"Arylsulfonyl" means an aryl-S(=O)$_2$— group in which the aryl group is as defined herein. The group may be a terminal group or a bridging group. If the group is a terminal group it is bonded to the remainder of the molecule through the sulfur atom.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or Spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Cycloalkylalkyl" means a cycloalkyl-alkyl- group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl- group in which the cycloalkyl and alkenyl moieties are as defined herein. The group may be a terminal group or a bridging group. If the group is a terminal group it is bonded to the remainder of the molecule through the alkenyl group.

"Cycloalkylheteroalkyl" means a cycloalkyl-heteroalkyl-group in which the cycloalkyl and heteroalkyl moieties are as defined herein. The group may be a terminal group or a bridging group. If the group is a terminal group it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

Failure of treatment can be defined as condition in which a non-fasting blood glucose level of less than 200 mg/di and a blood glucose level during fasting (deprived of food for at least 8 hr) of less than 126 mg/dl are retained after administration of the agent in its recommended dose.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-

$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroalkyloxy" refers to a heteroalkyl-O— group in which heteroalkyl is as defined herein. Preferably the heteroalkyloxy is a $C_2$-$C_6$heteroalkyloxy. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$ heteroaryl group. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl- group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl- group in which the heteroaryl and heteroalkyl moieties are as defined herein. The group may be a terminal group or a bridging group. If the group is a terminal group it is bonded to the remainder of the molecule through the heteroalkyl group.

"Heteroaryloxy" refers to a heteroaryl-O— group in which the heteroaryl is as defined herein. Preferably the heteroaryloxy is a $C_1$-$C_{18}$heteroaryloxy. The group may be a terminal group or a bridging group. If the group is a terminal group it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl group as defined herein but containing at least one double bond. A heterocycloalkenyl group typically is a $C_2$-$C_{12}$ heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazapane, and 1,4-oxathiapane. A heterocycloalkyl group typically is a $C_2$-$C_{12}$heterocycloalkyl group. The group may be a terminal group or a bridging group.

"Heterocycloalkylalkyl" refers to a heterocycloalkyl-alkyl- group in which the heterocycloalkyl and alkyl moieties are as defined herein. Exemplary heterocycloalkylalkyl groups include (2-tetrahydrofuryl)methyl, (2-tetrahydrothiofuranyl) methyl. The group may be a terminal group or a bridging group. If the group is a terminal group it is bonded to the remainder of the molecule through the alkyl group.

"Heterocycloalkylalkenyl" refers to a heterocycloalkyl-alkenyl- group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl- group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the Heterocycloalkenyloxy is a $C_1$-$C_6$ Heterocycloalkenyloxy. The group may be a terminal group or a bridging group. If the group is a terminal group it is bonded to the remainder of the molecule through the oxygen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$. In groups of this type n is typically from 1 to 10, more preferably from 1 to 6, most preferably 1 to 3. x is typically 1 to 6, more preferably 1 to 3.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfonylamino" means an R—S(=O)$_2$—NH— group. The group may be a terminal group or a bridging group. If the group is a terminal group it is bonded to the remainder of the molecule through the nitrogen atom.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art. For those compounds where there is the possibility of geometric isomerism the applicant has drawn the isomer that the compound is thought to be although it will be appreciated that the other isomer may be the correct structural assignment.

Some of the compounds of the disclosed embodiments may exist as single stereoisomers, racemates, and/or mixtures of enantiomers and for diastereomers. All such single stereoisomers, racemates and mixtures thereof, are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propanoic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-p-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987). Similarly, an acyl prodrug of a compound of formula (I) containing an amino group may be convertible by hydrolysis in vivo to the parent molecule (Many examples of prodrugs for these and other functional groups, including amines, are described in Prodrugs: Challenges and Rewards (Parts 1 and 2); Ed V. Stella, R. Borchardt, M. Hageman, R. Oliyai, H. Maag and J Tilley; Springer, 2007).

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Specific compounds of the invention include the following:

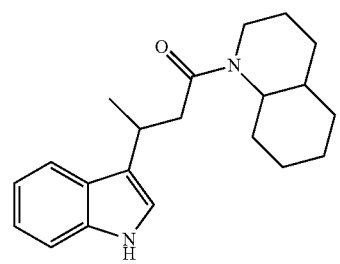

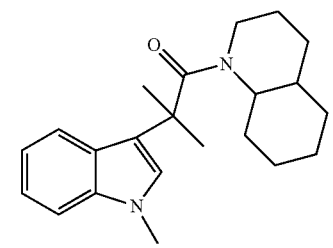

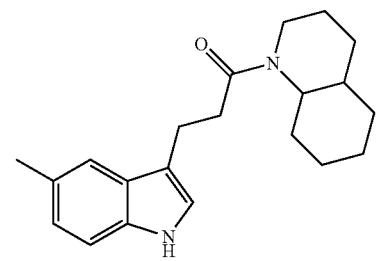

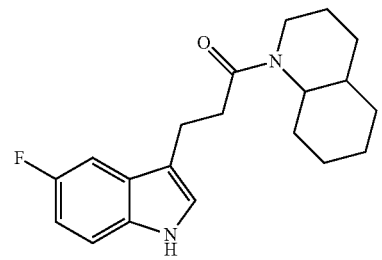

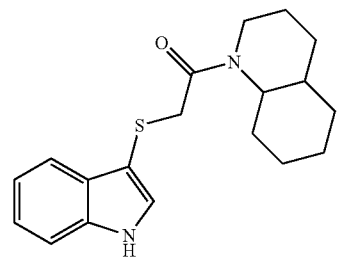

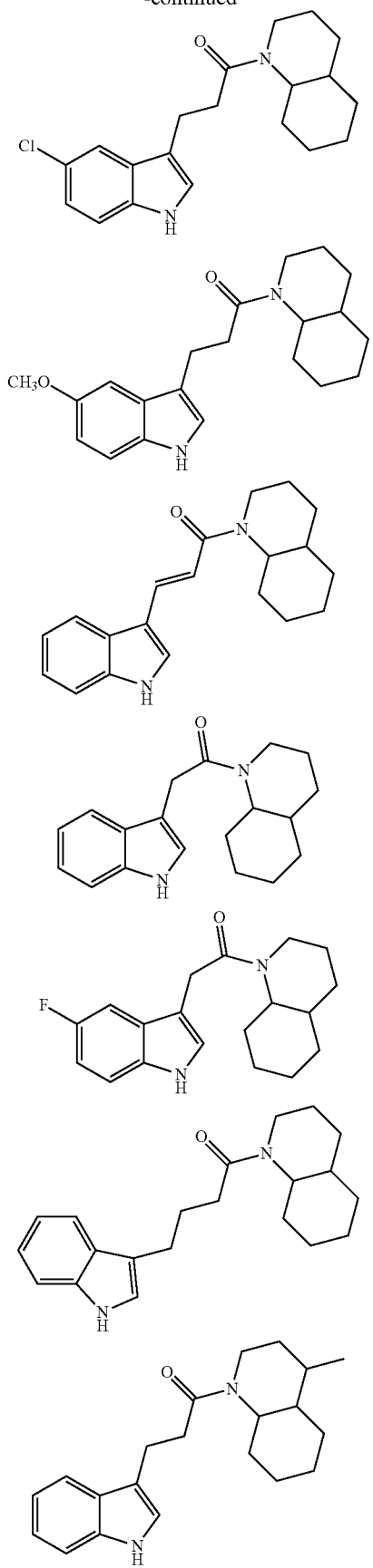
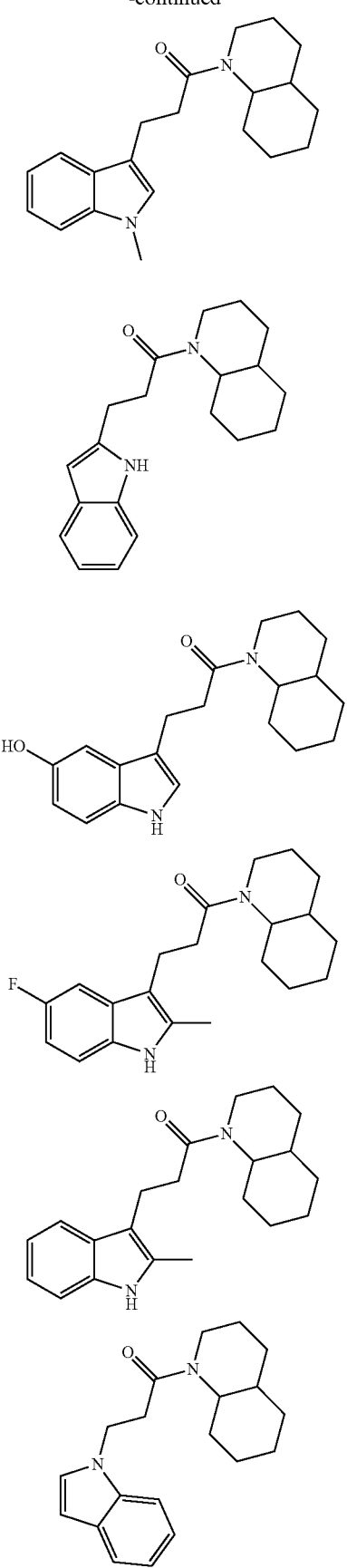

29
-continued
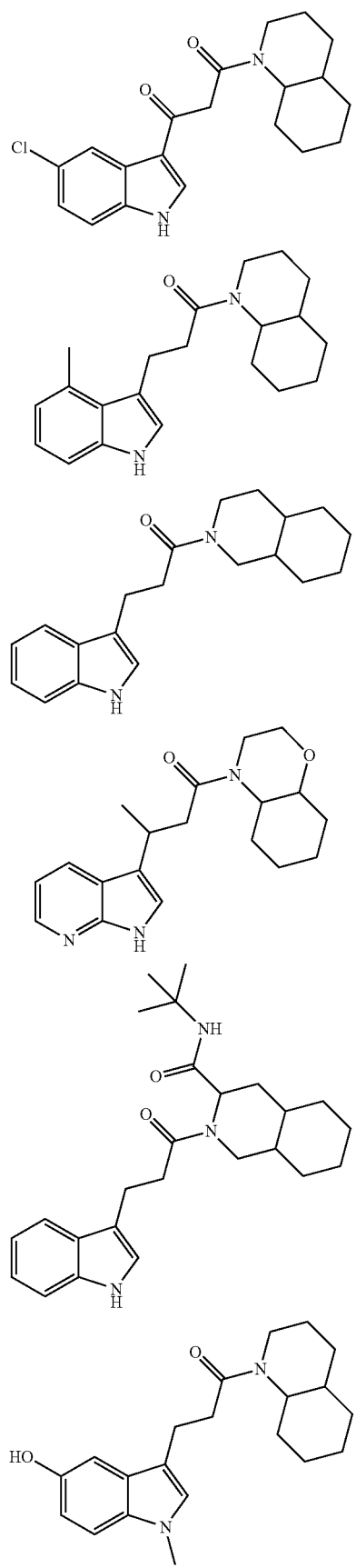
30
-continued
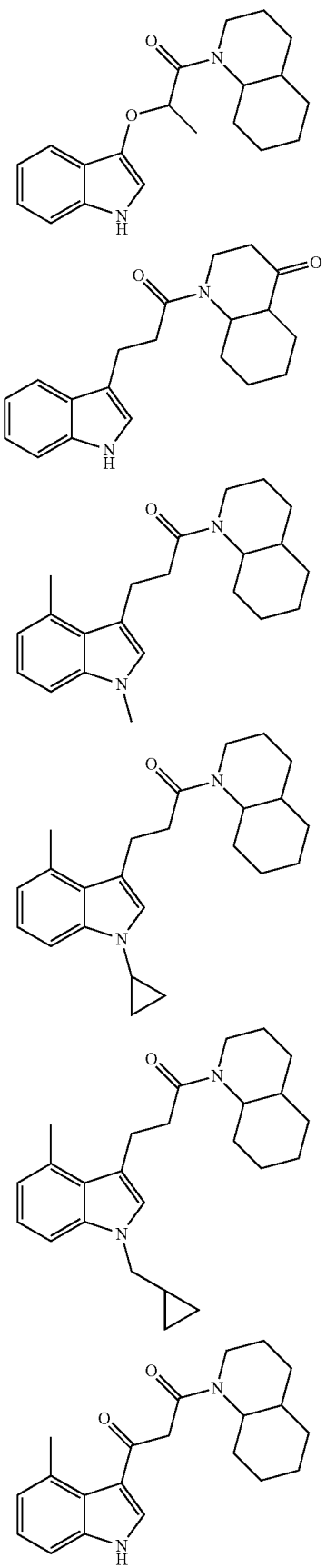

31
-continued
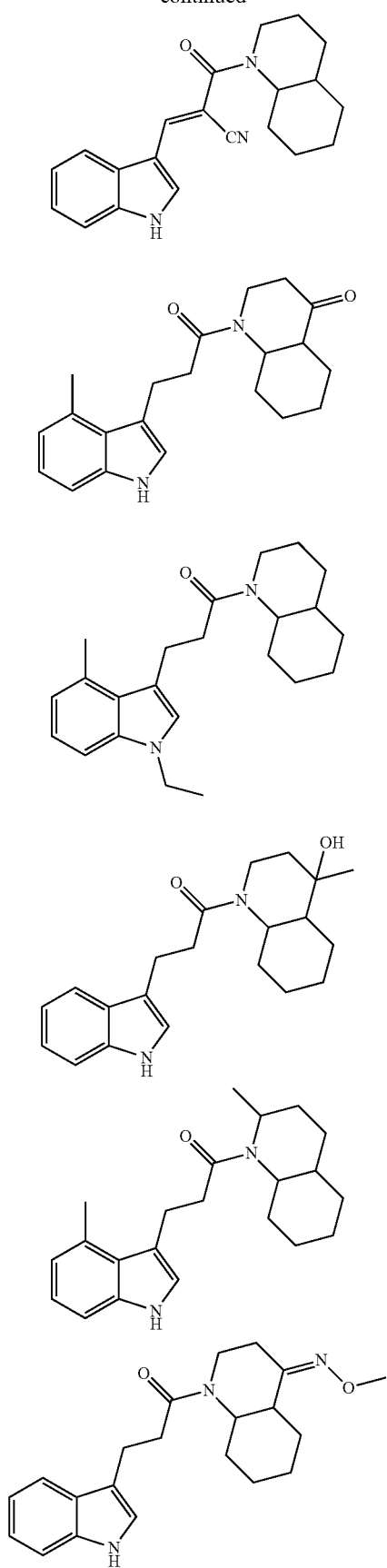
32
-continued
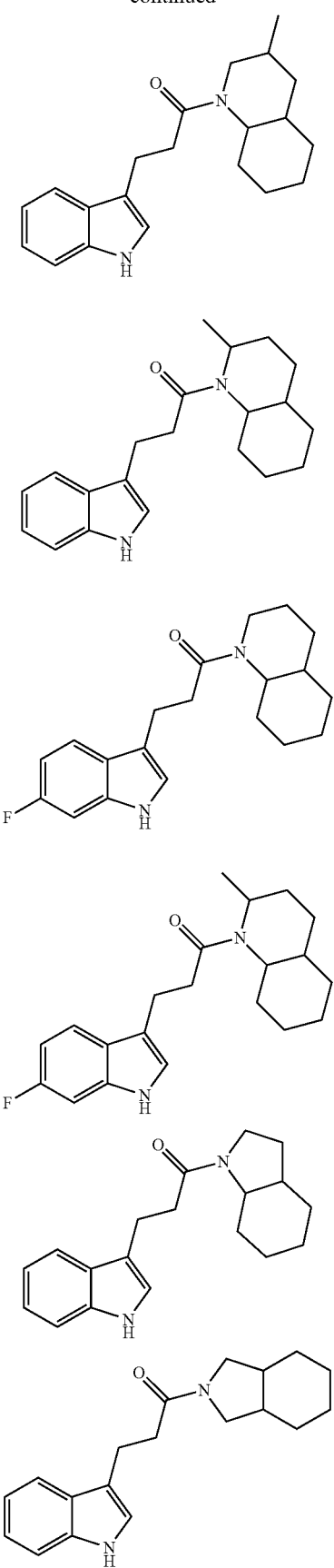

33
-continued
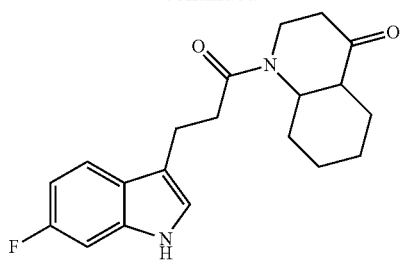
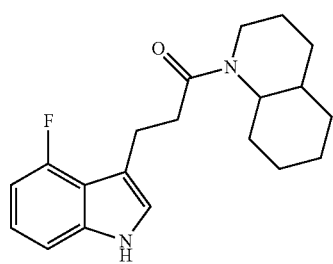
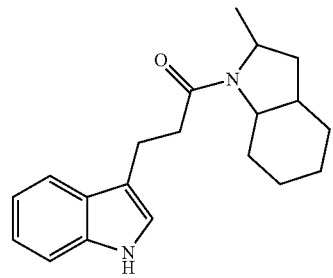
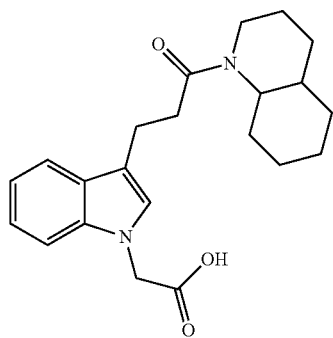
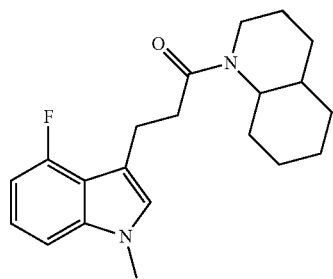
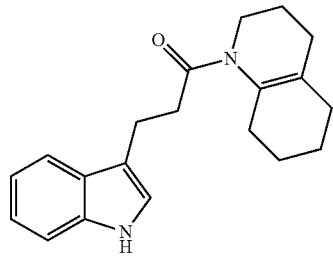
34
-continued
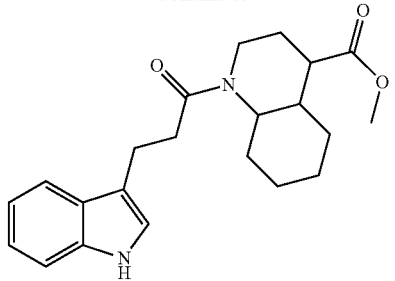
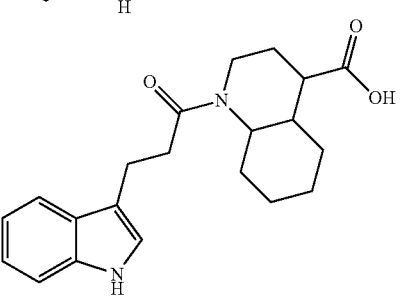
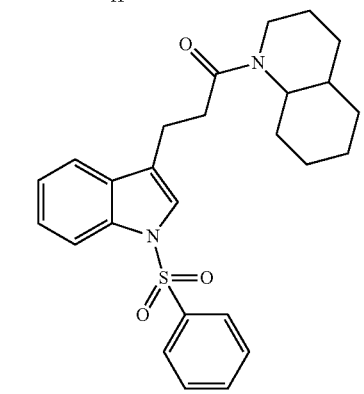
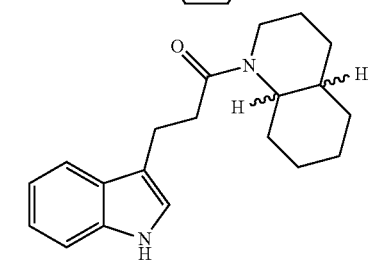
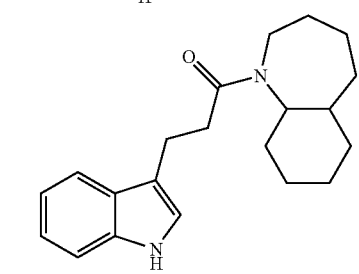
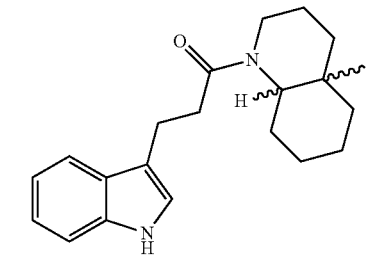

-continued
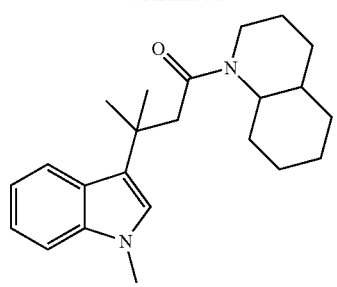
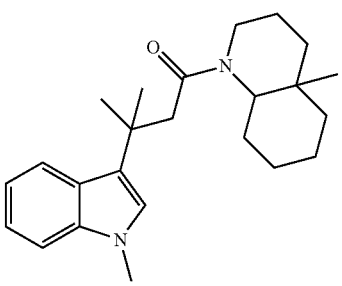
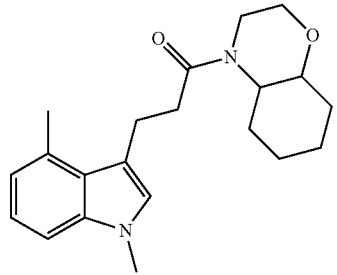
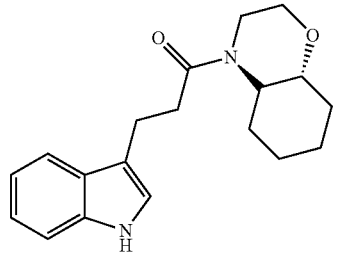
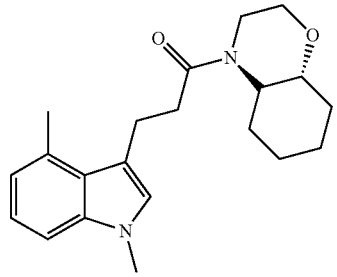
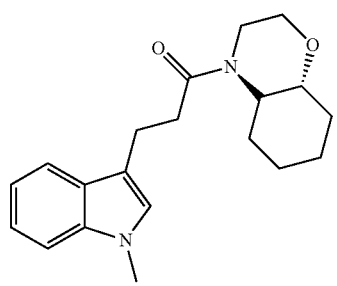
-continued
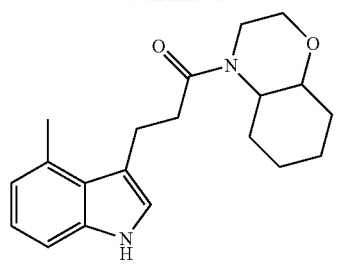
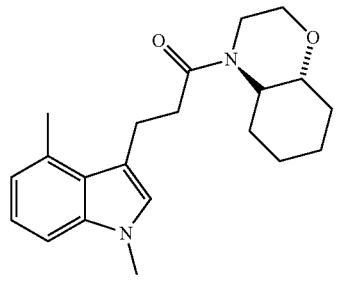
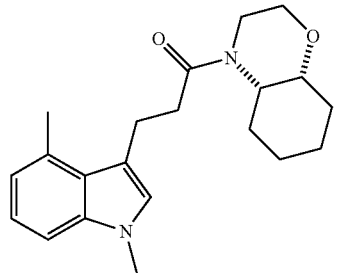
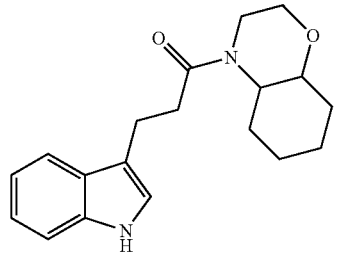
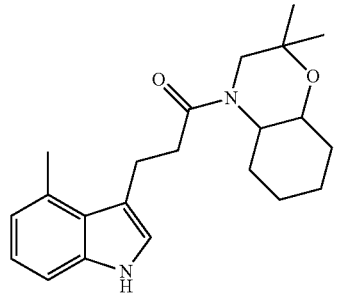
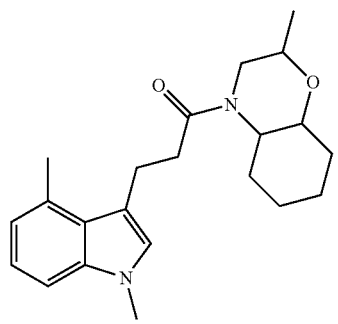

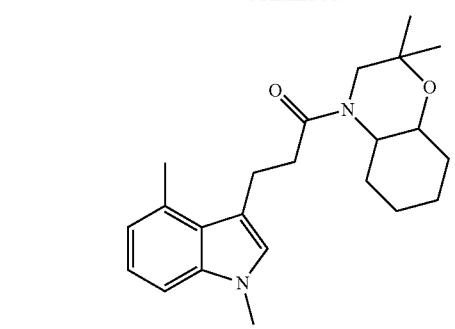
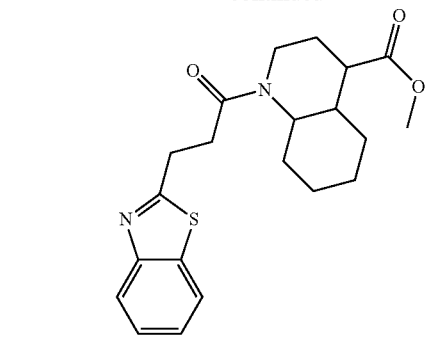
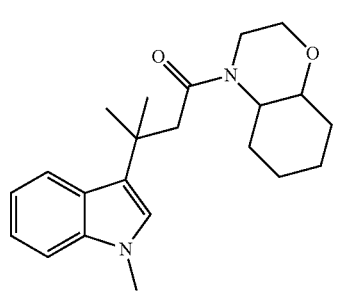
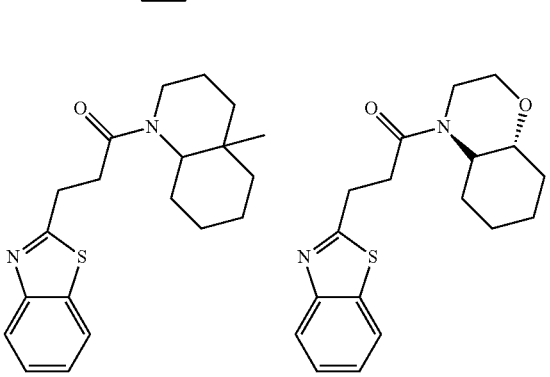
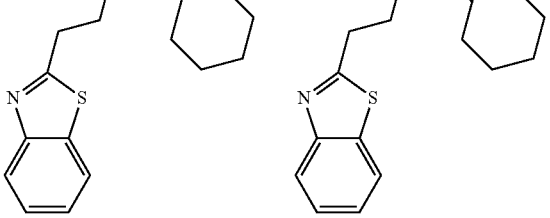
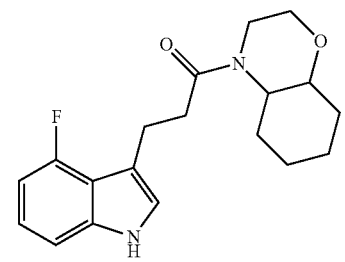
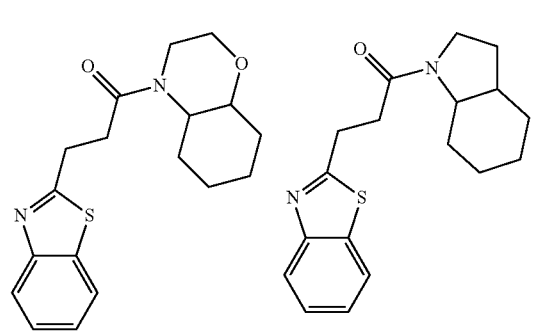

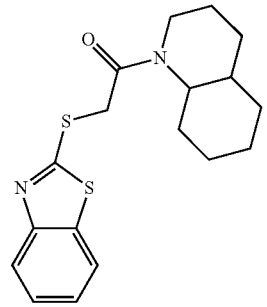
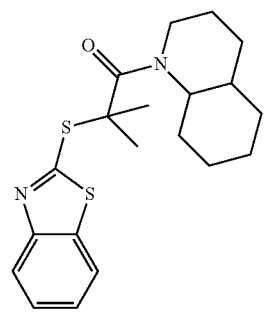
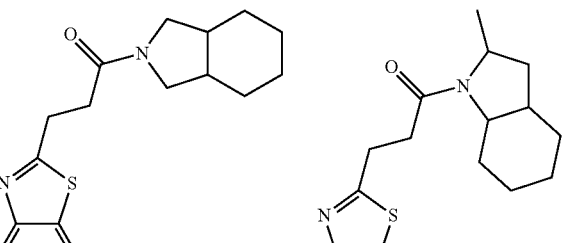
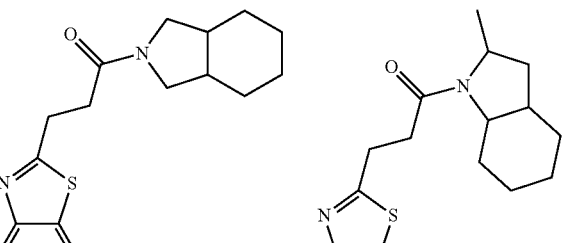
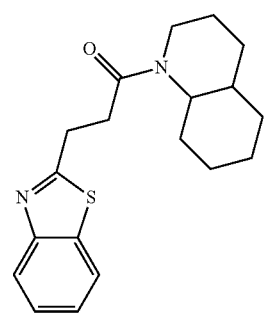
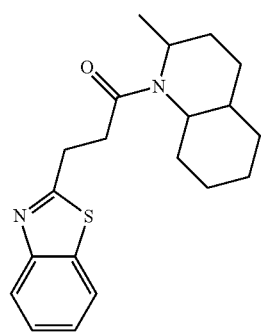
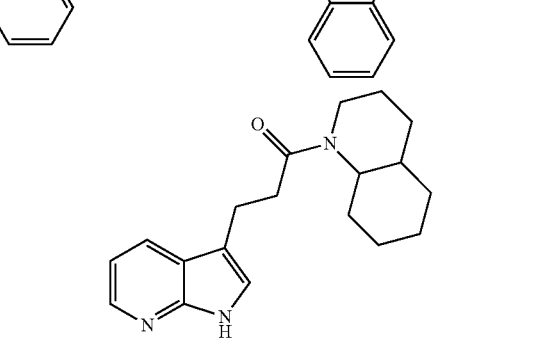
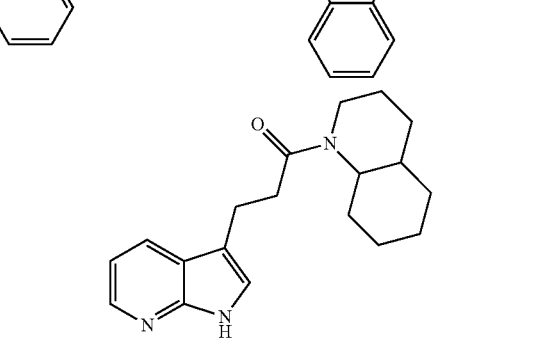
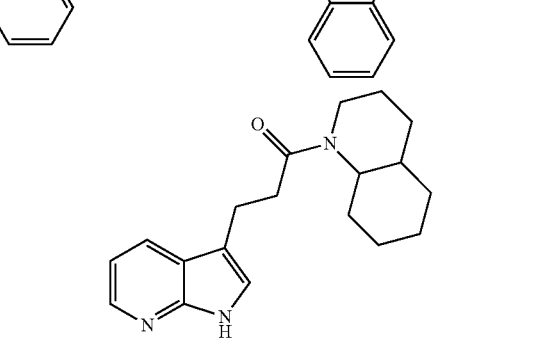
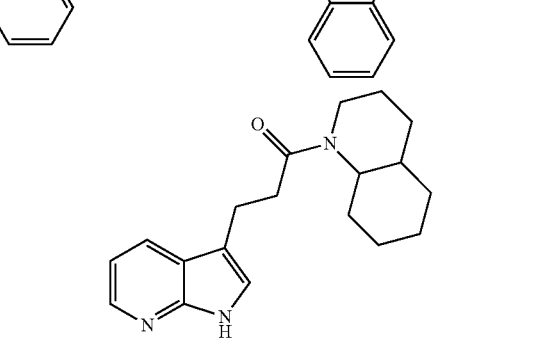

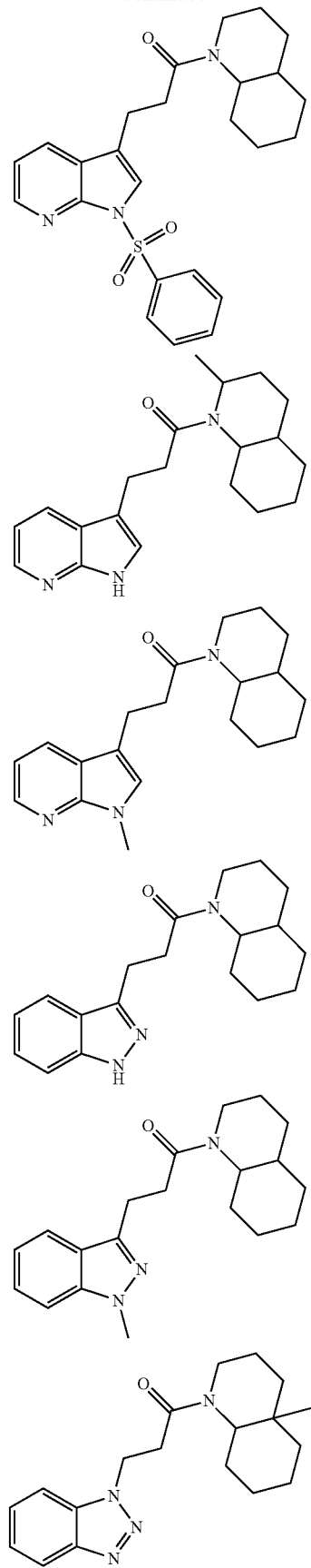
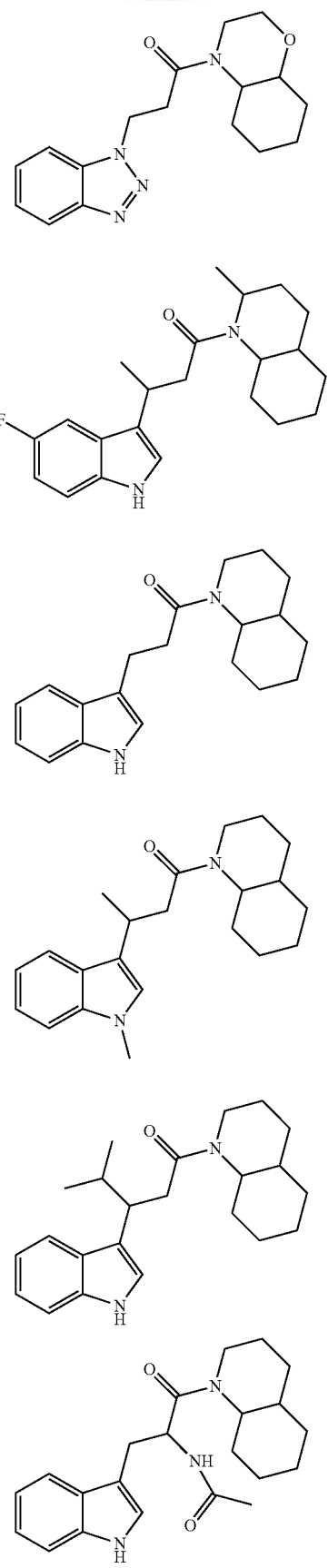

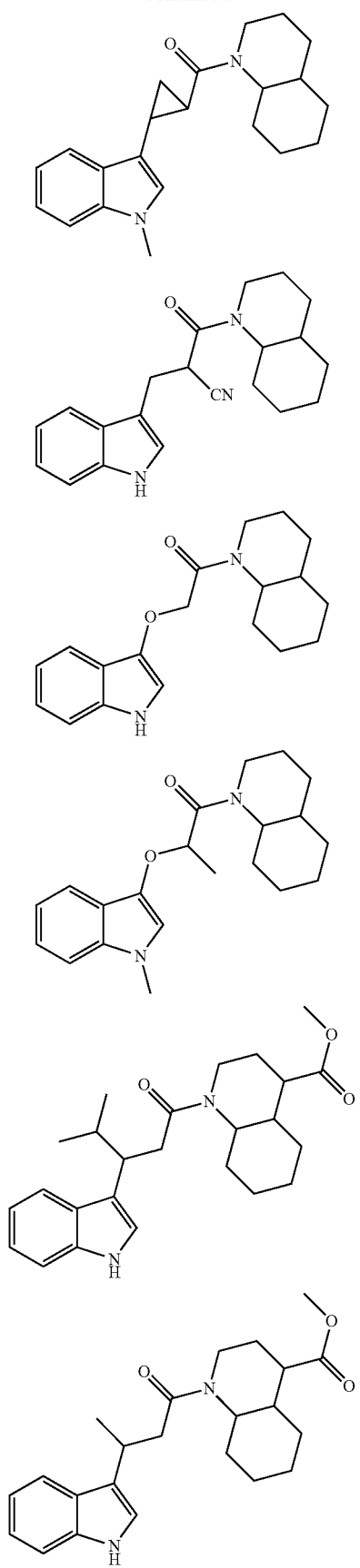 [SMILES: Cn1cc(C2CC2C(=O)N2CCCC3CCCCC32)c2ccccc21 ; N#CC(Cc1c[nH]c2ccccc12)C(=O)N1CCCC2CCCCC21 ; O=C(COc1c[nH]c2ccccc12)N1CCCC2CCCCC21 ; CC(Oc1cn(C)c2ccccc12)C(=O)N1CCCC2CCCCC21 ; COC(=O)C1CCN(C(=O)CC(c2c[nH]c3ccccc23)C(C)C)C2CCCCC12 ; COC(=O)C1CCN(C(=O)CC(C)c2c[nH]c3ccccc23)C2CCCCC12]
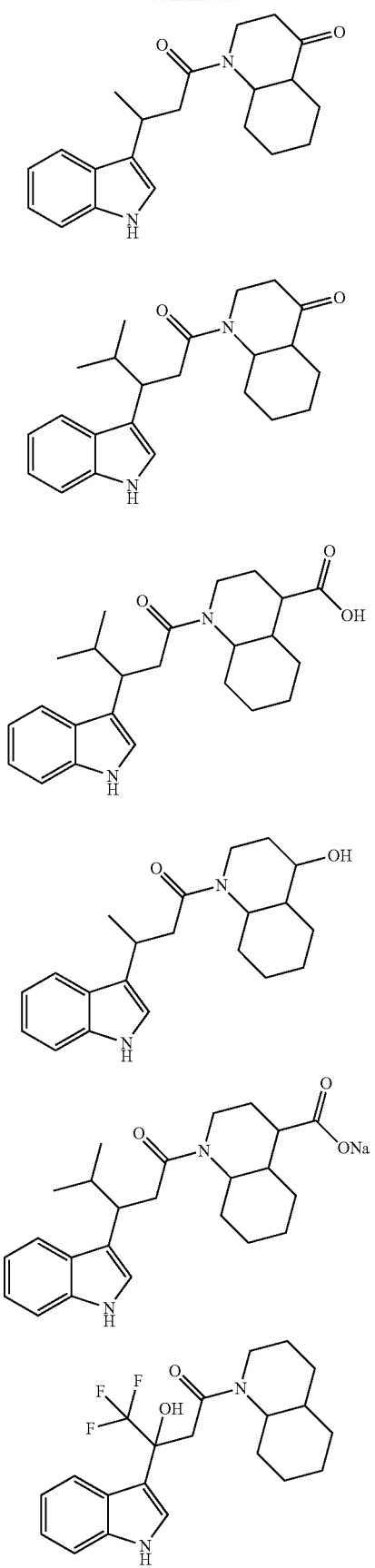

43
-continued
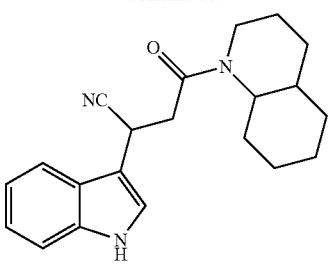
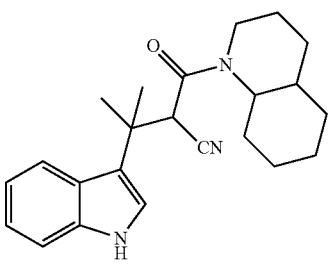
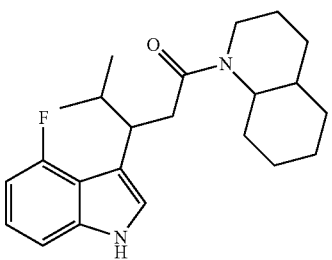
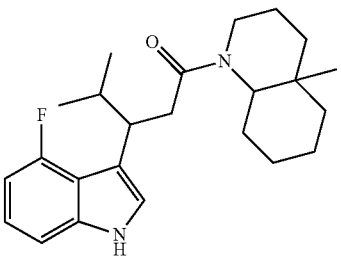
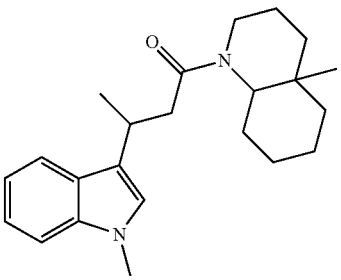
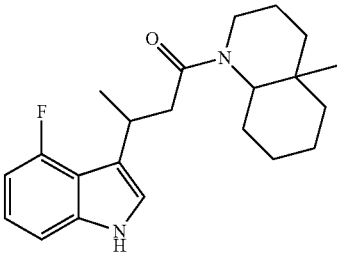
44
-continued
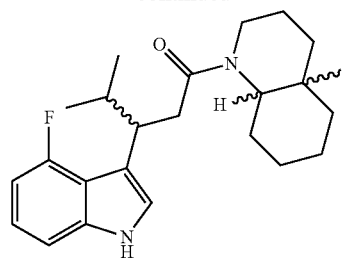
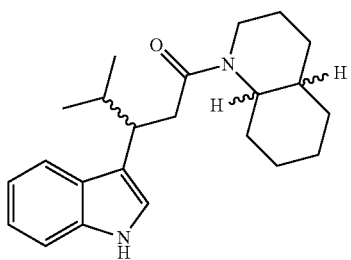
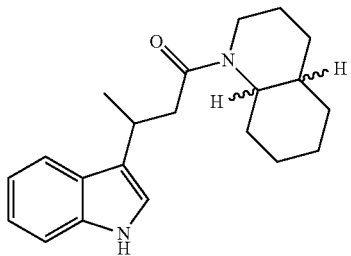
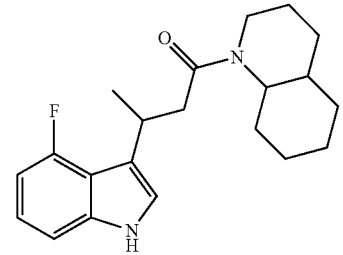
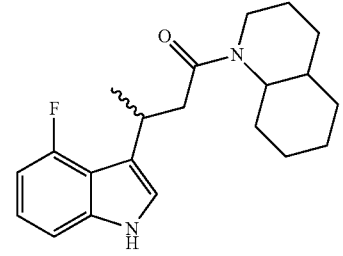
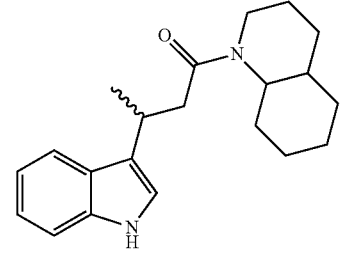

45
-continued
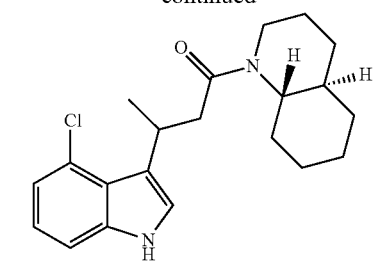
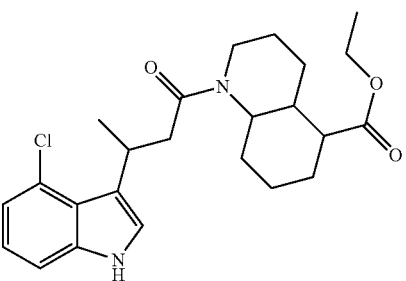
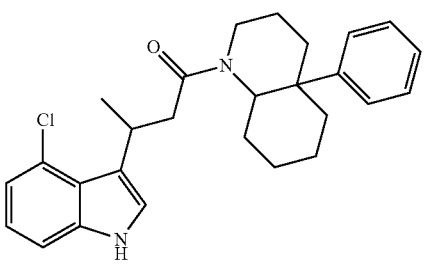
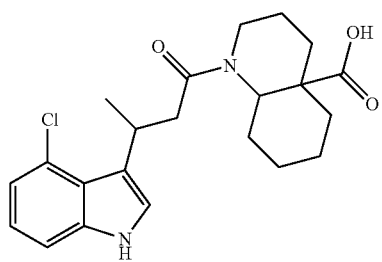
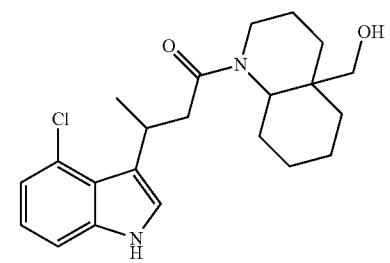
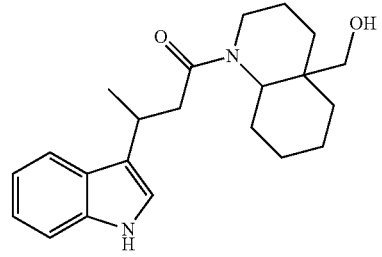
46
-continued
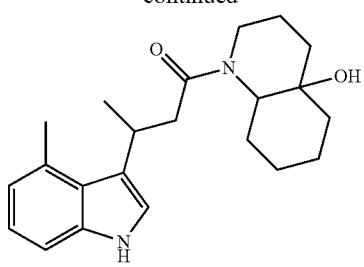
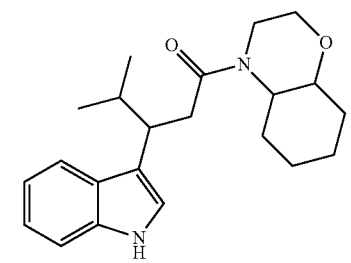
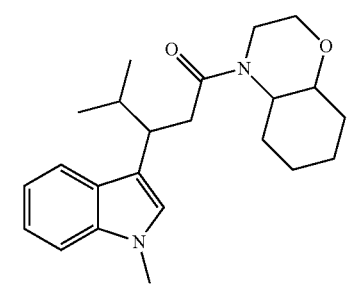
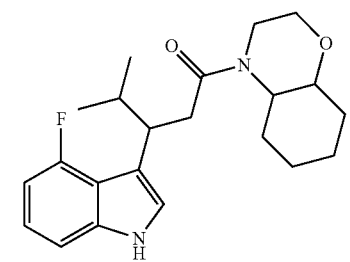
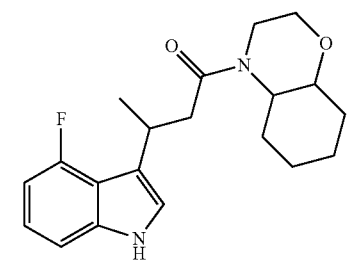
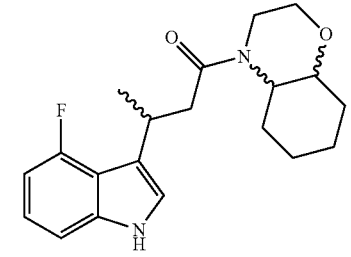

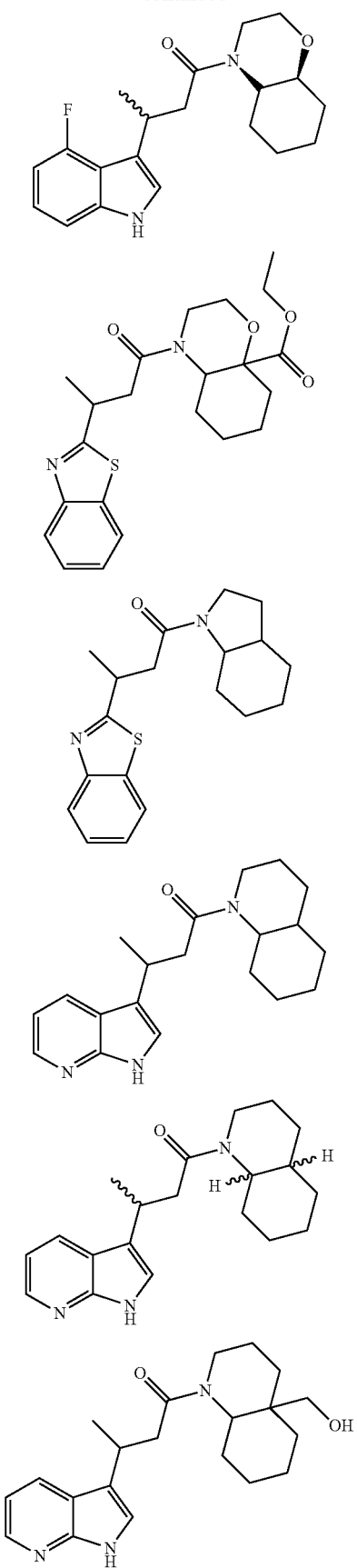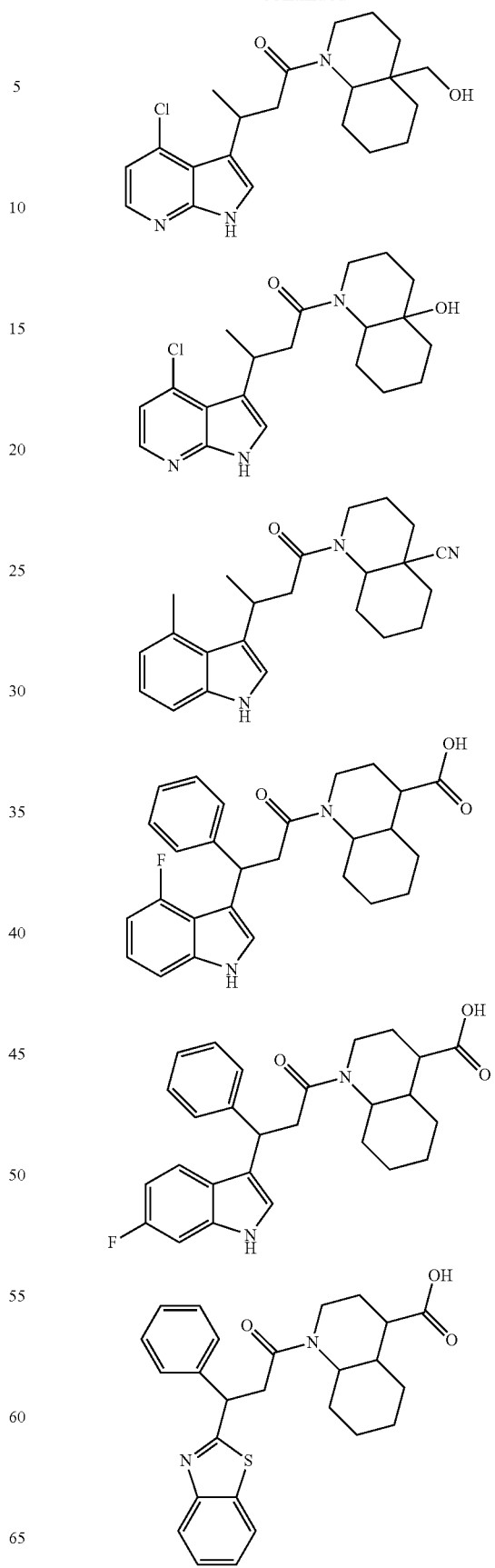

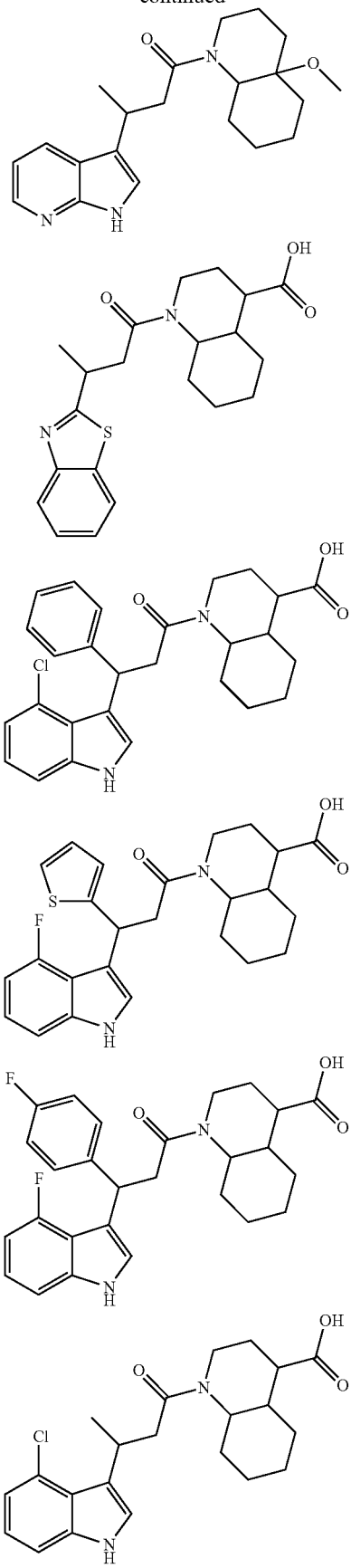
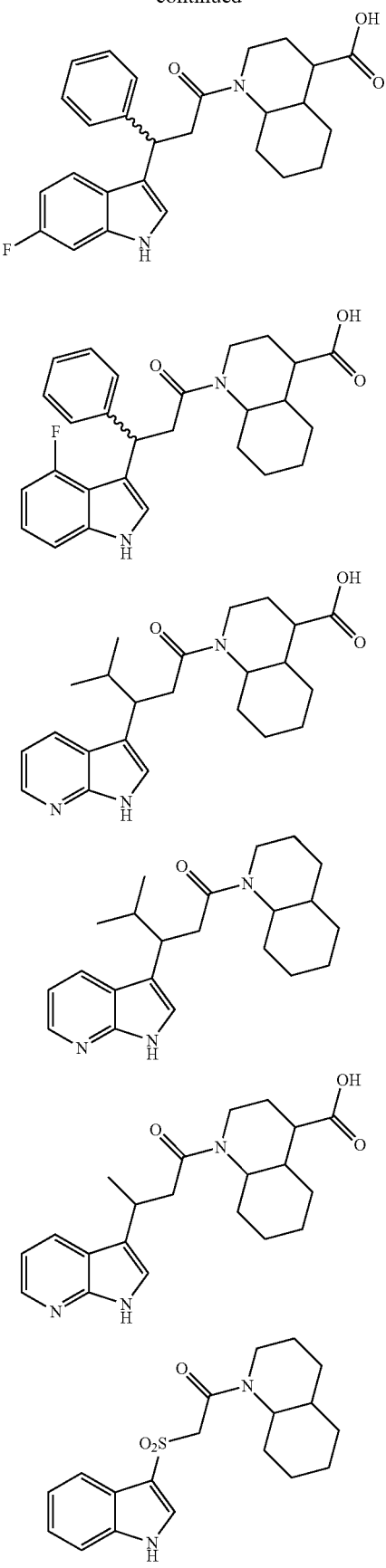

51
-continued
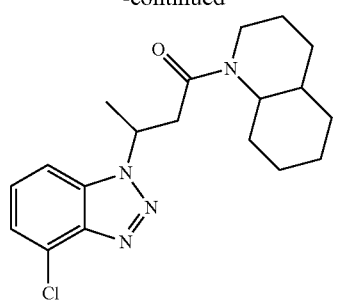
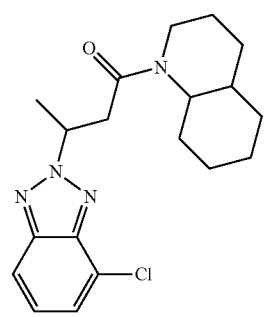
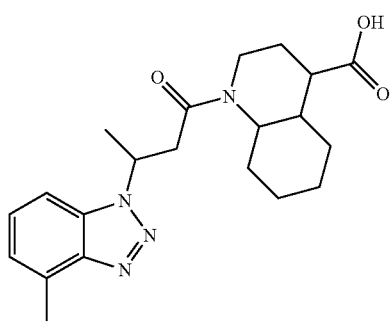
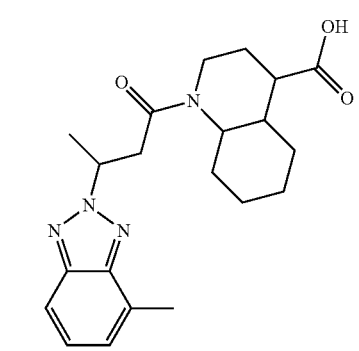
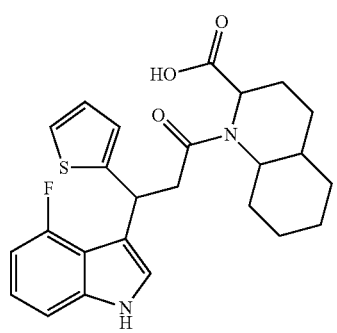
52
-continued
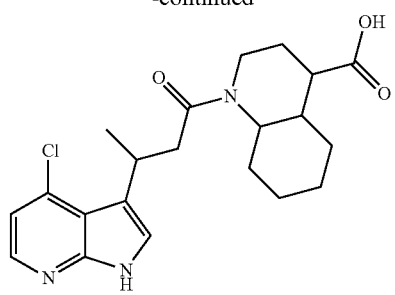
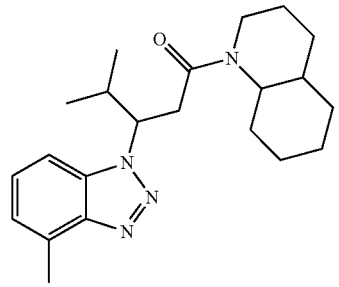
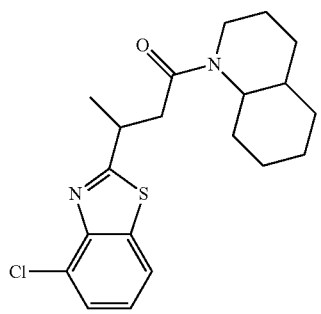
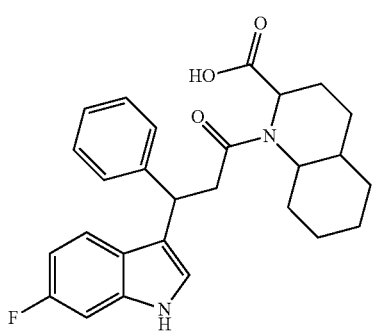
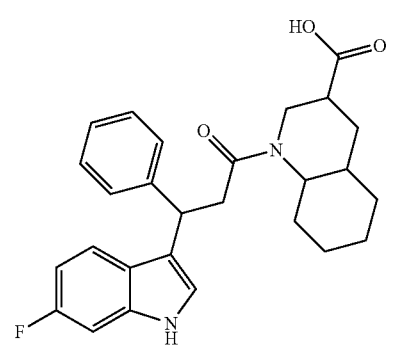

53
-continued
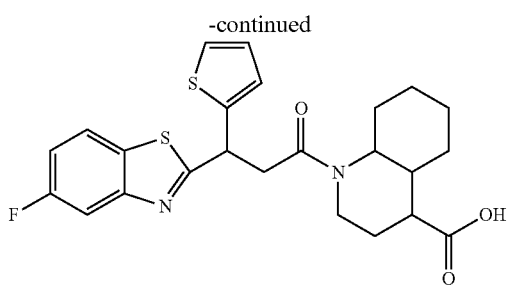
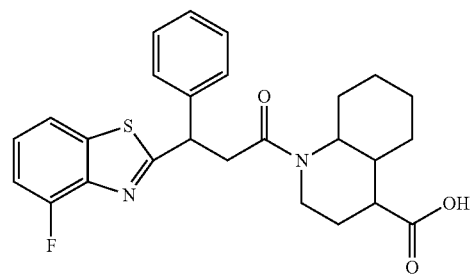
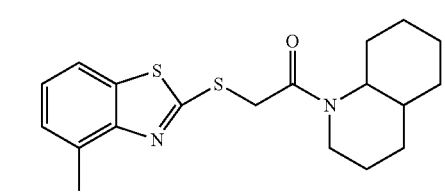
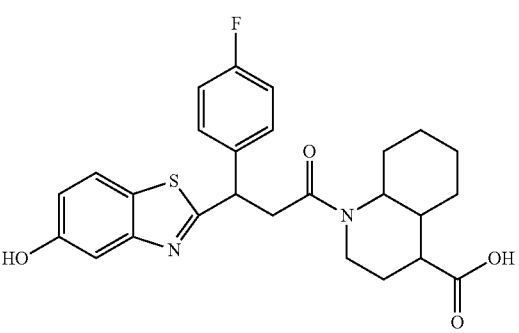
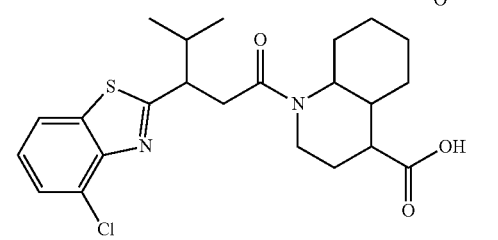
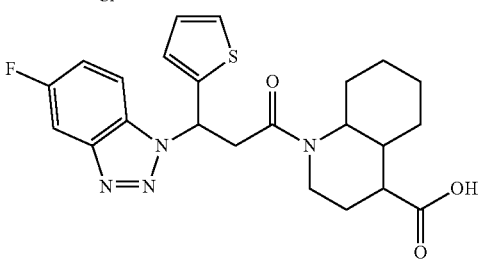
54
-continued
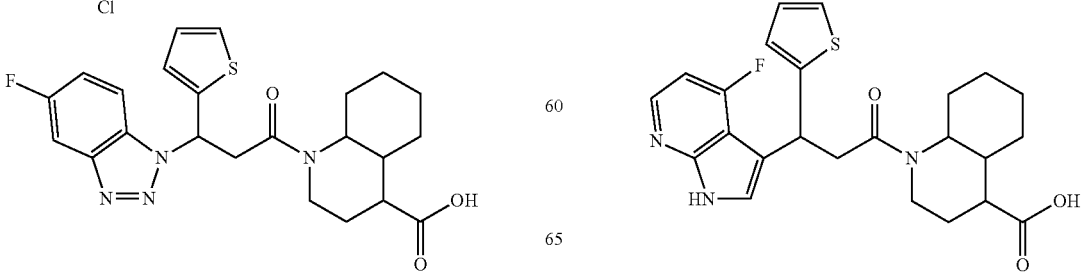
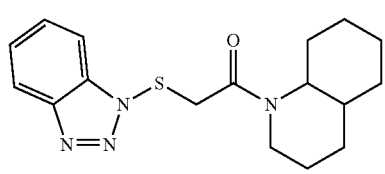
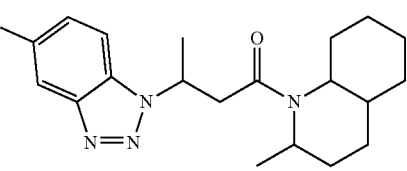
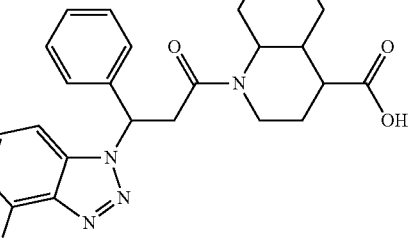
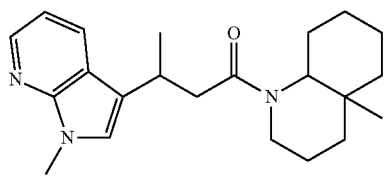
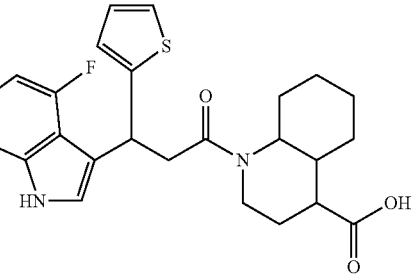

55
-continued
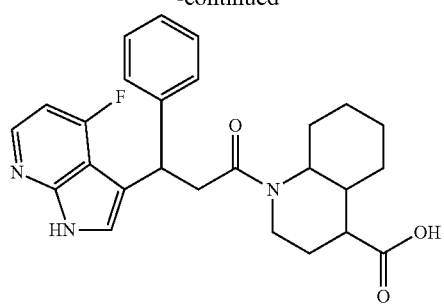
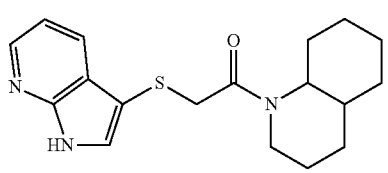
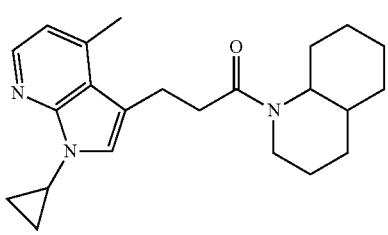
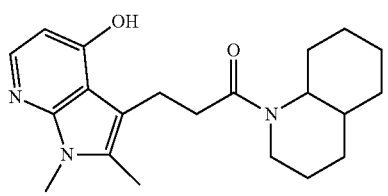
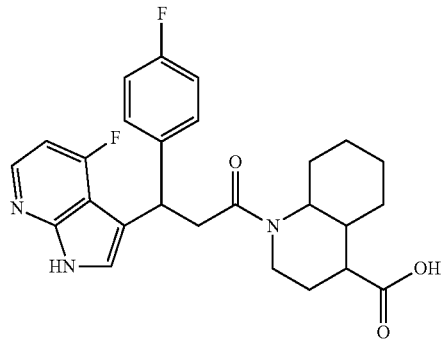
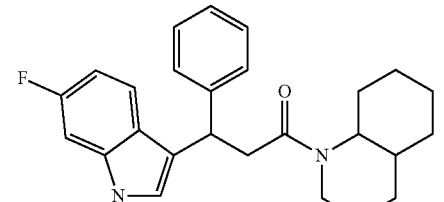
56
-continued
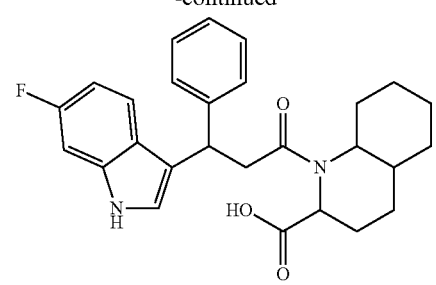
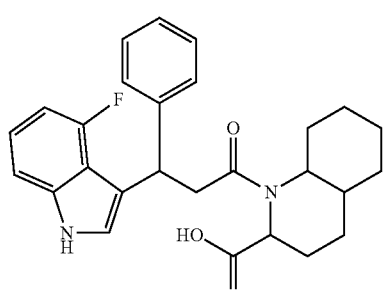
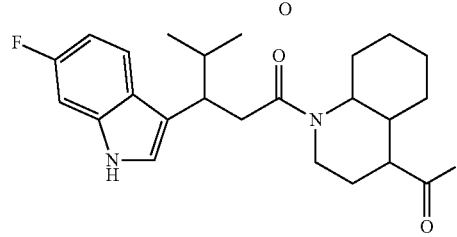
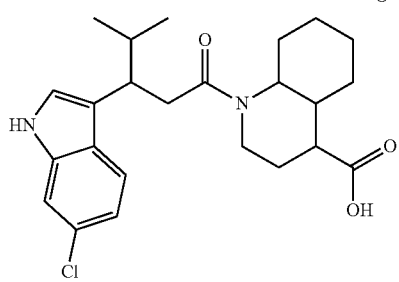
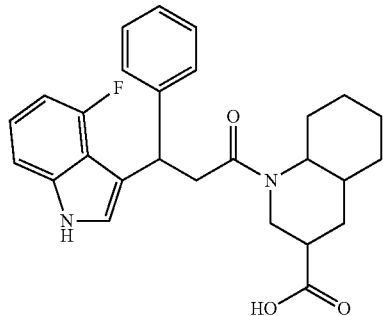
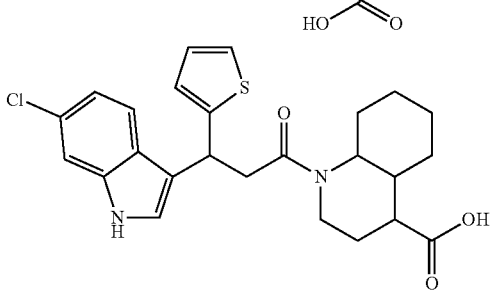

57
-continued
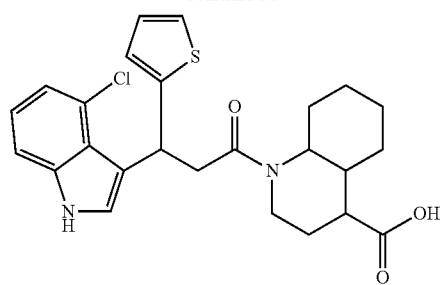
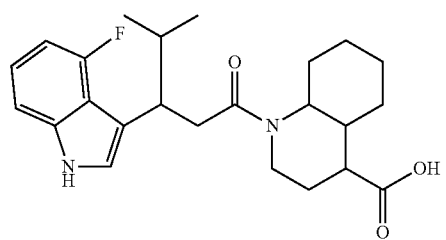
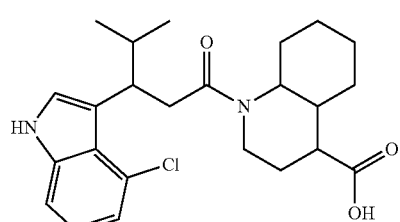
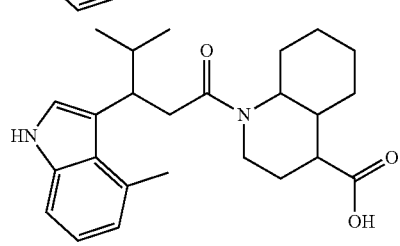
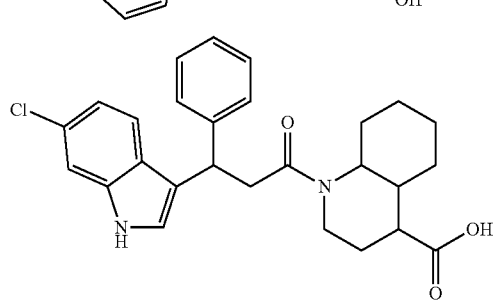
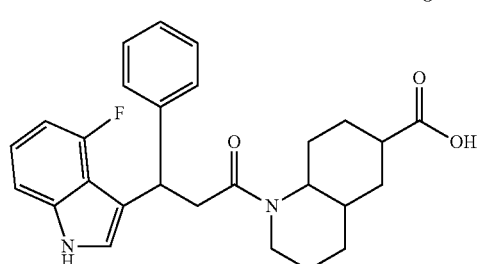
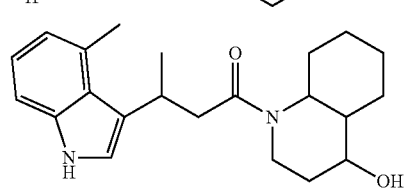
58
-continued
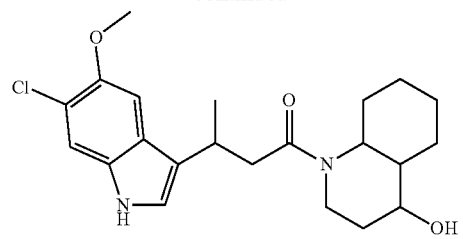
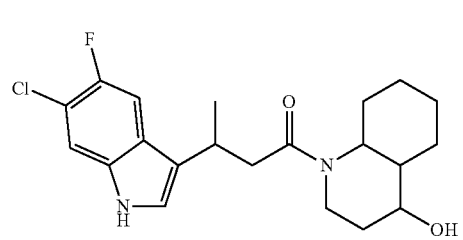
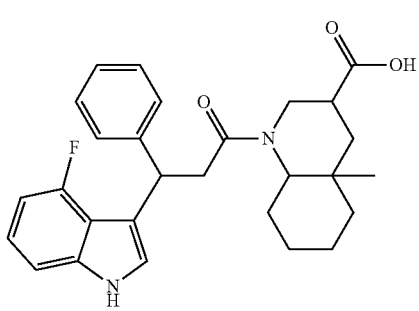
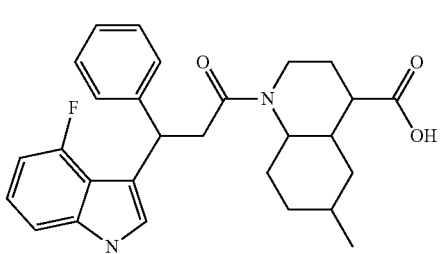
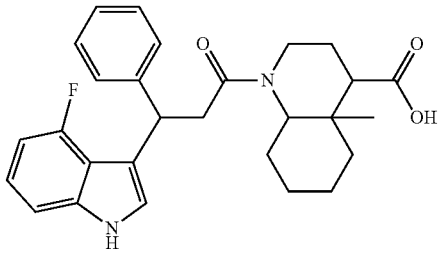
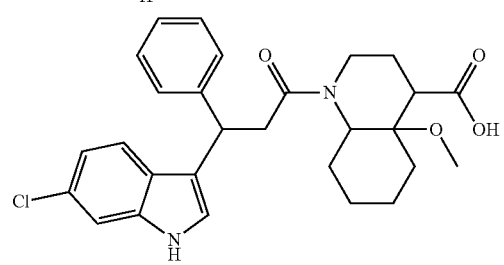

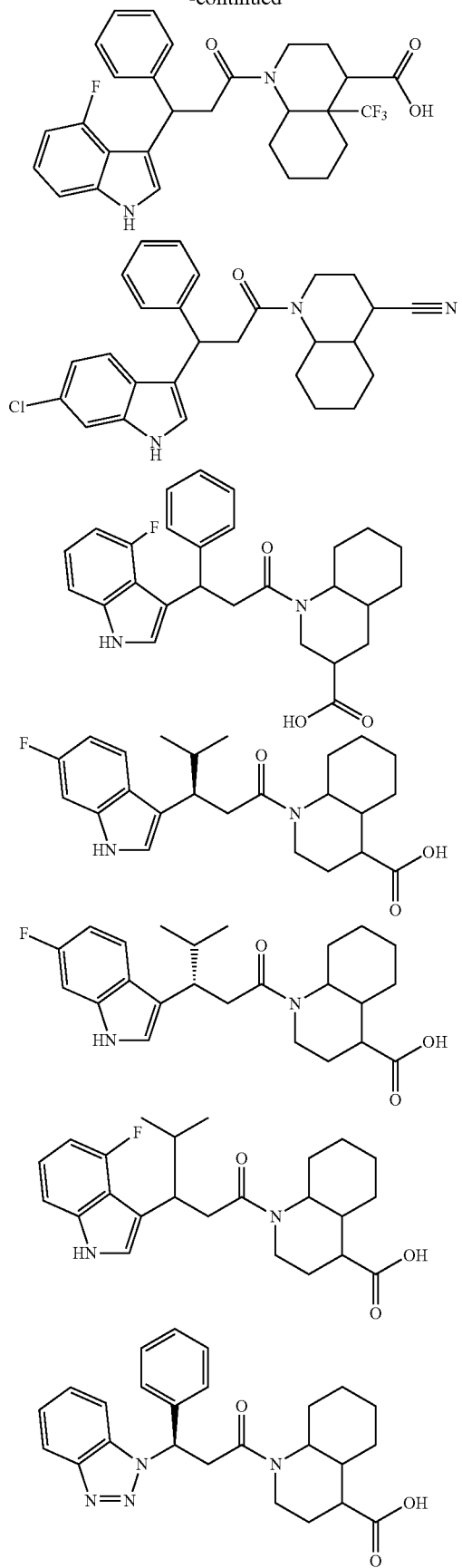

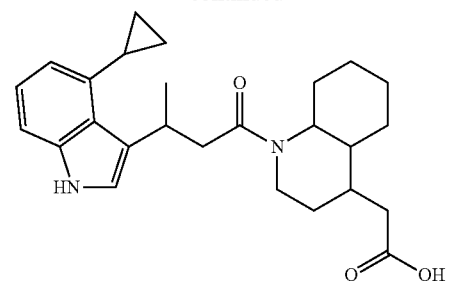
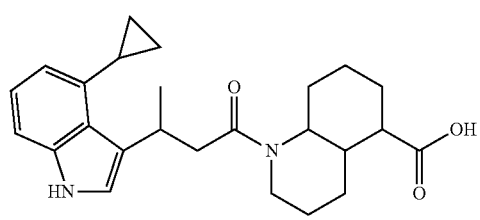
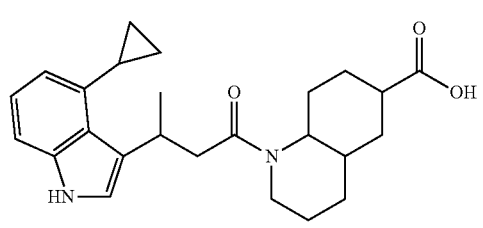
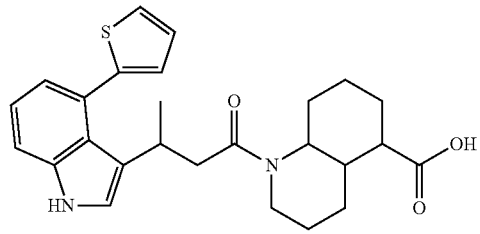
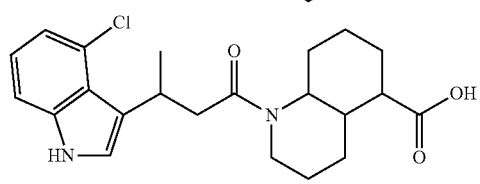
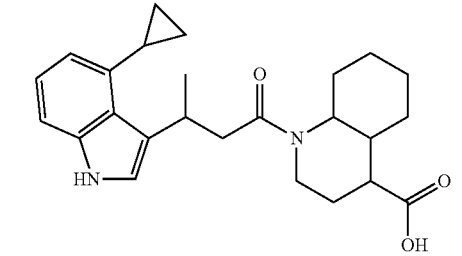
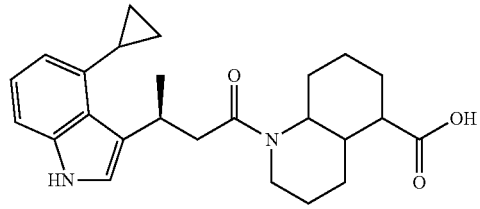
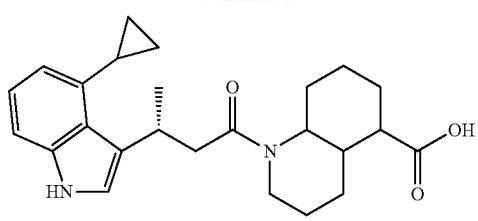
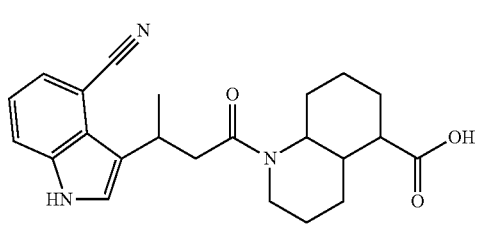
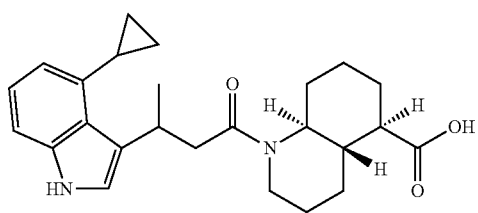
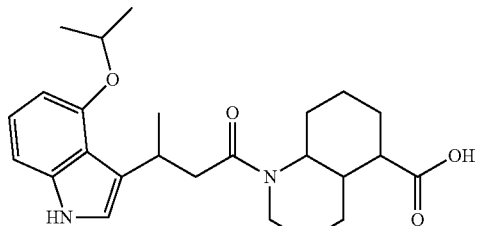
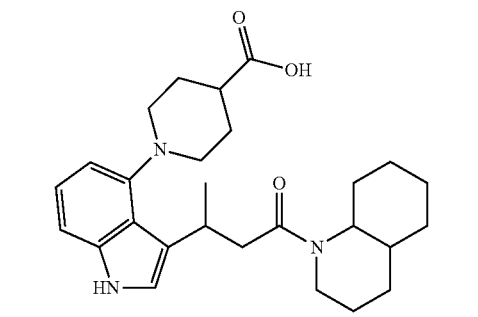
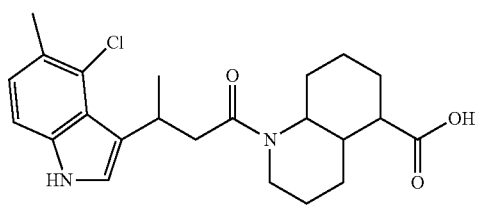
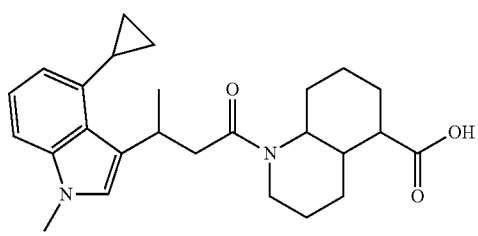

63
-continued
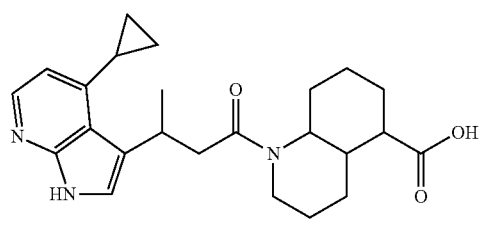
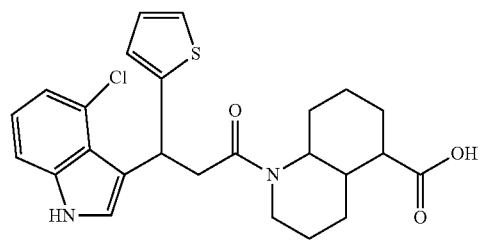
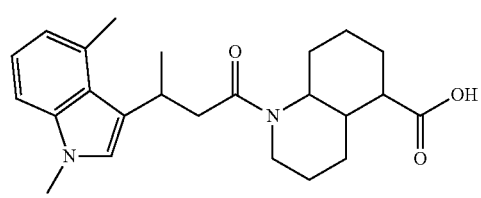
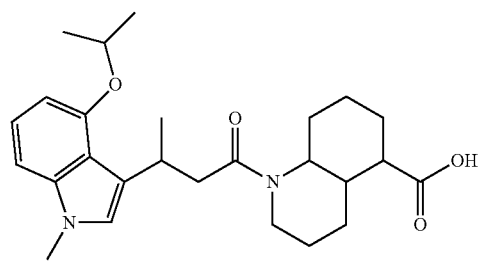
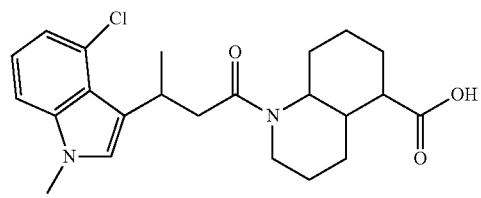
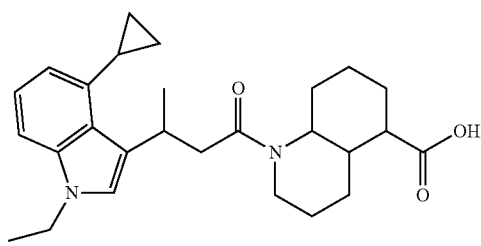
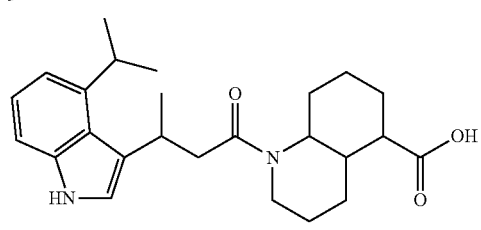
64
-continued
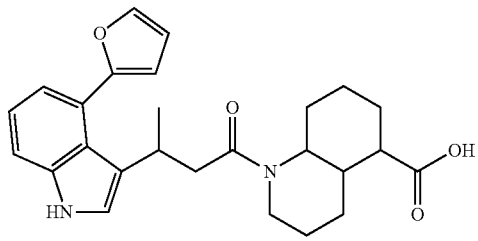
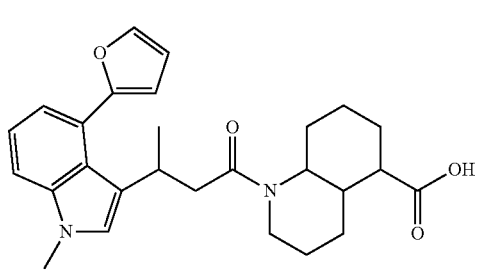
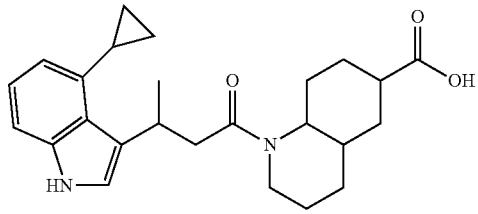
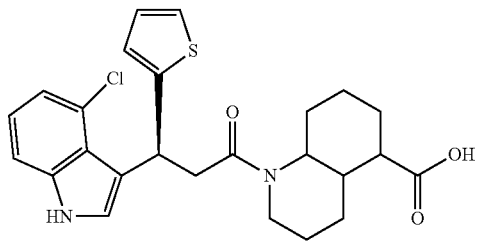
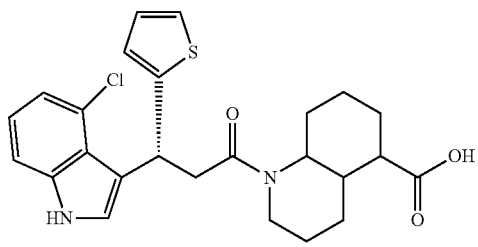
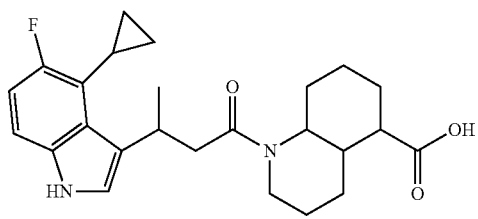
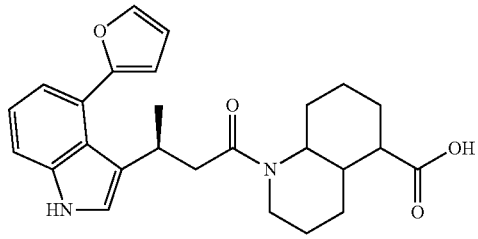

65
-continued
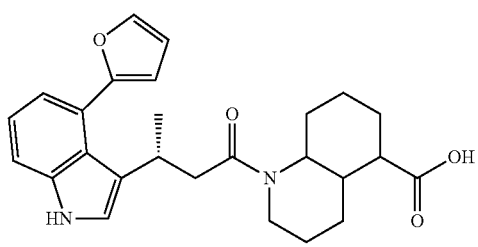
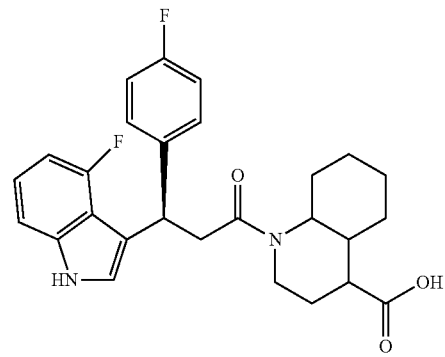
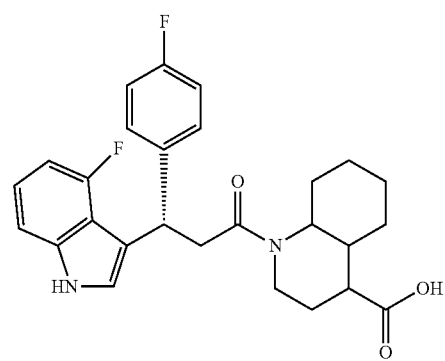
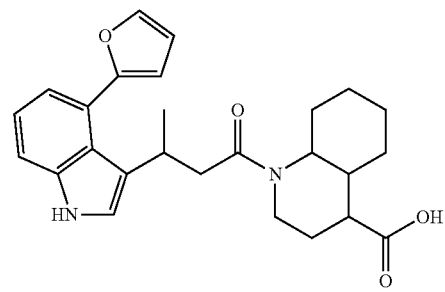
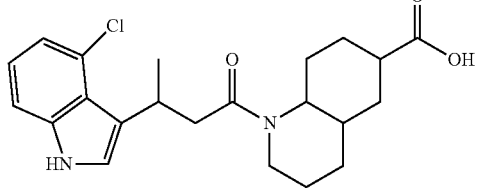
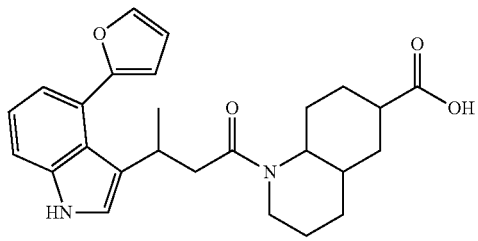
66
-continued
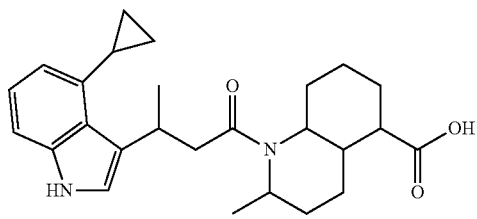
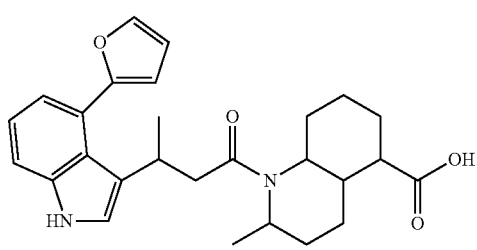
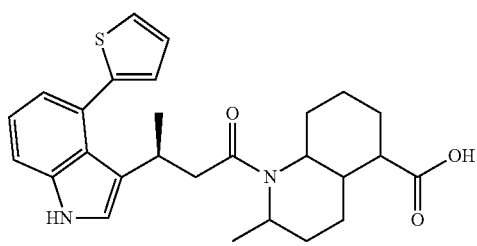
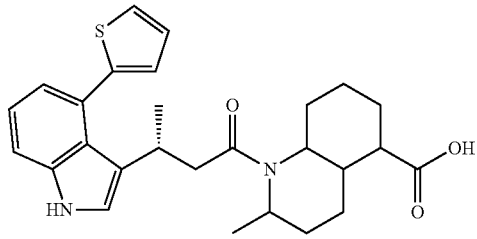
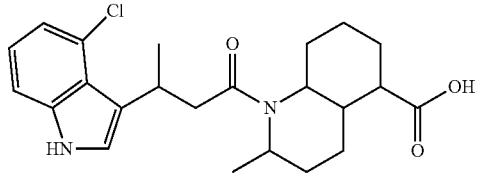
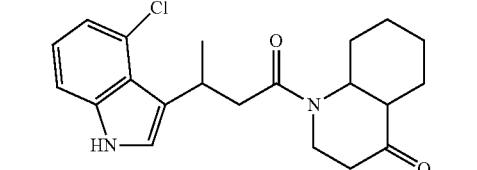
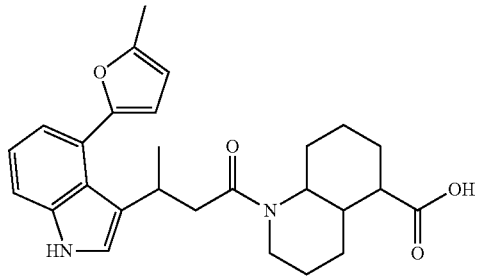

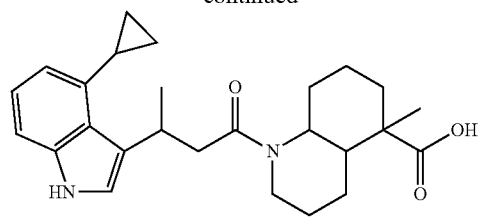
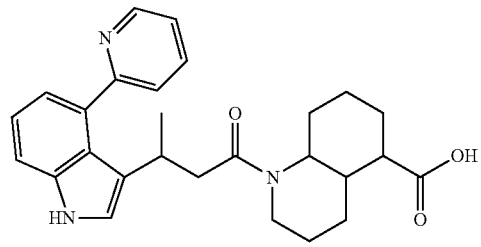
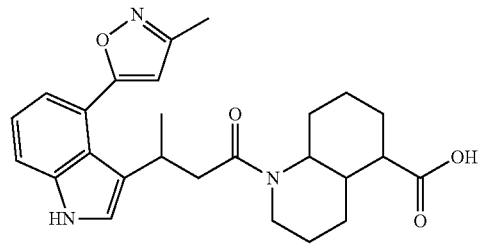
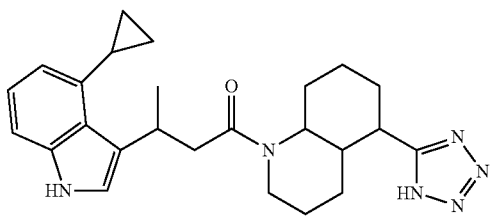
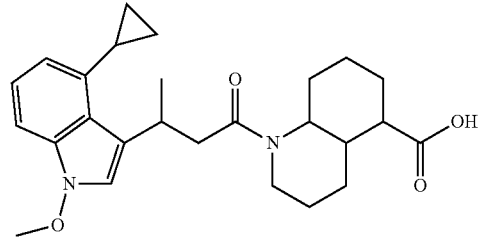
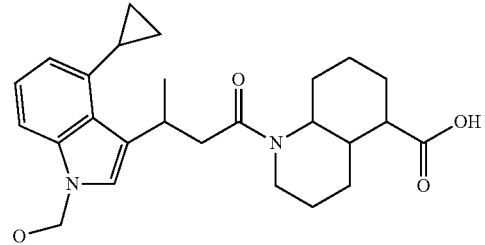
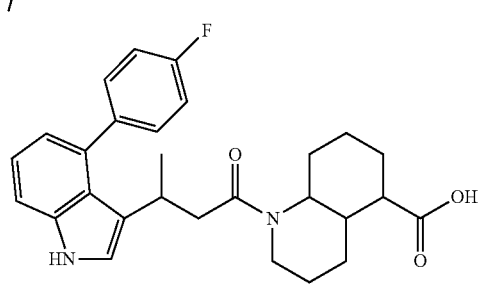
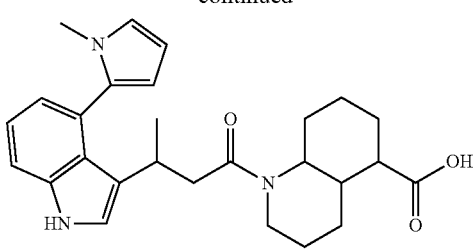
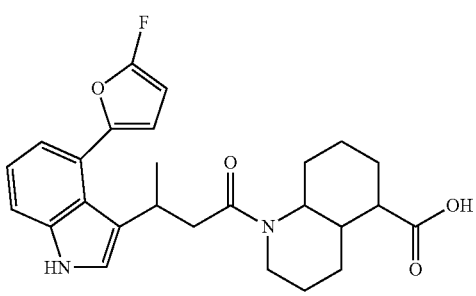
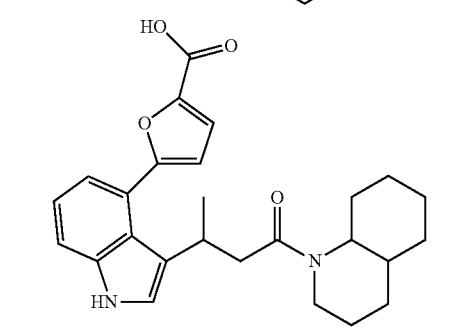
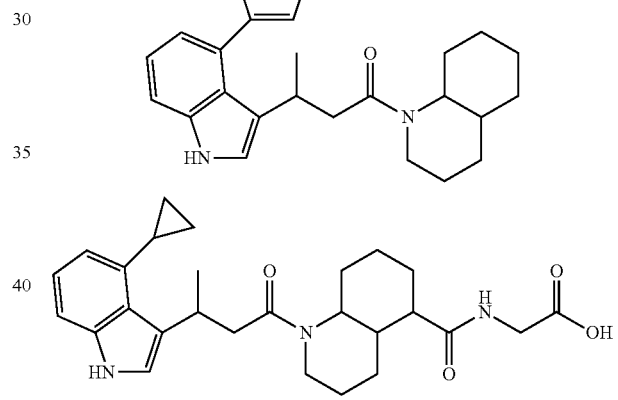
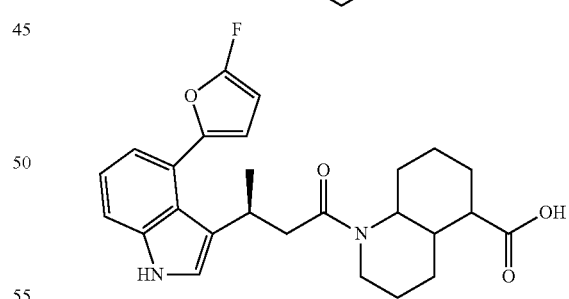
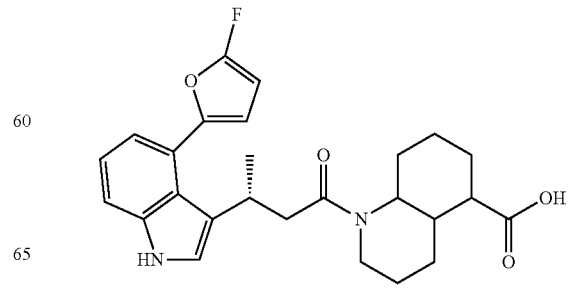

-continued
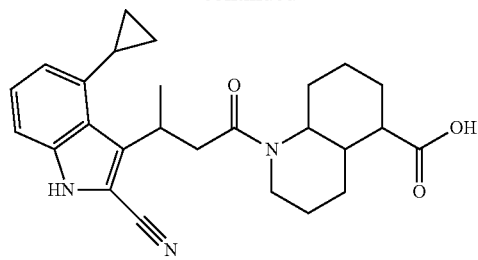
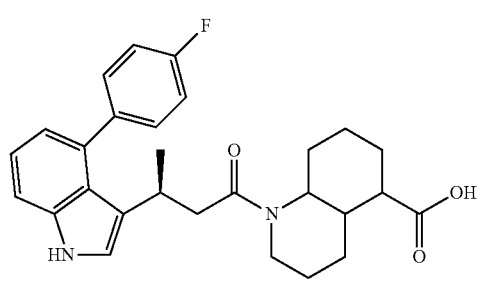
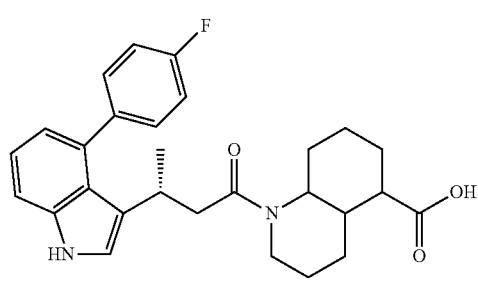
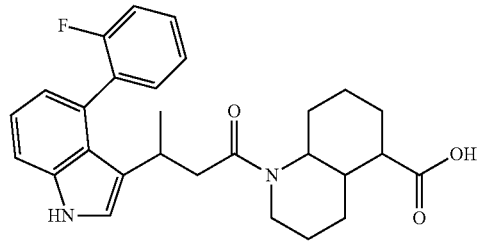
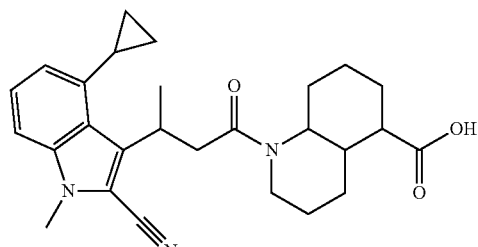
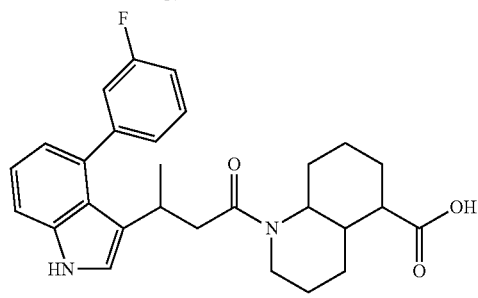
-continued
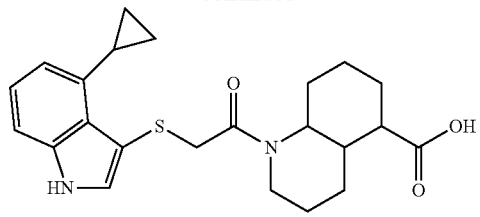
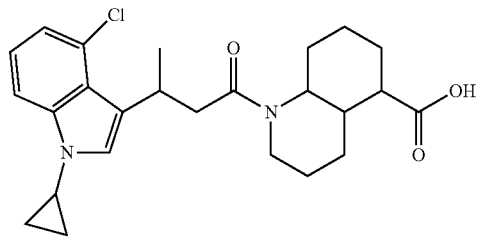
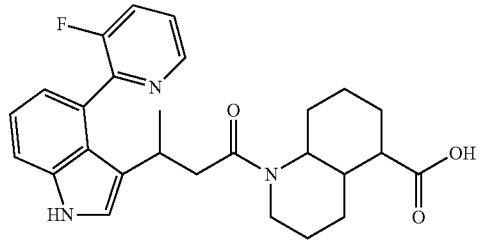
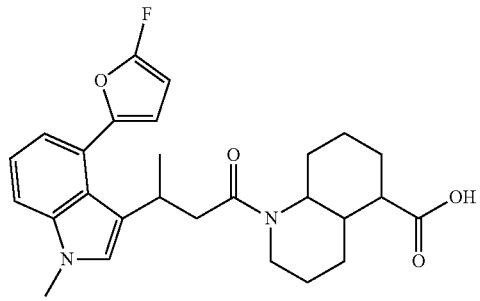
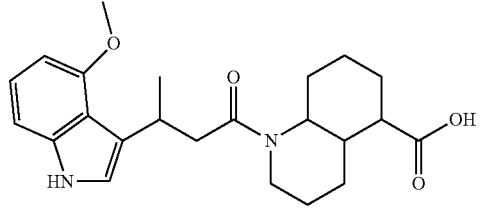
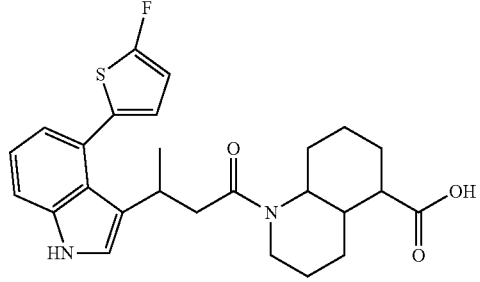
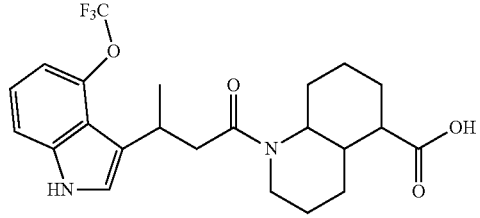

71
-continued
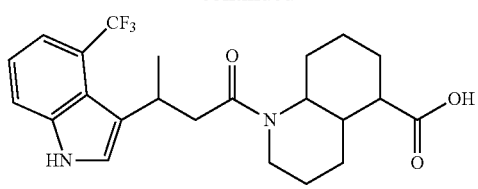
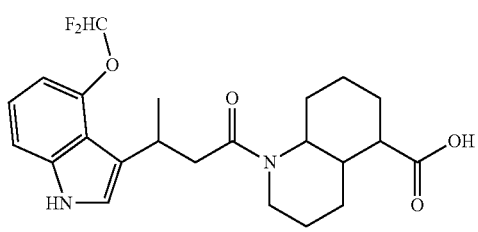
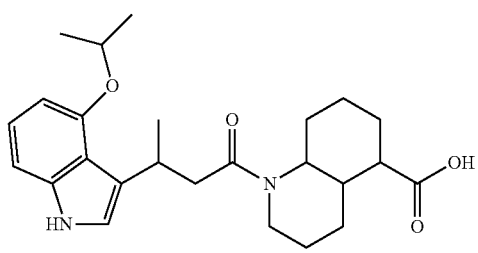
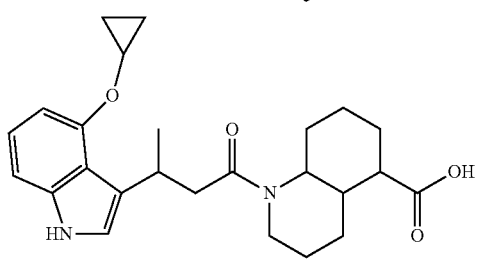
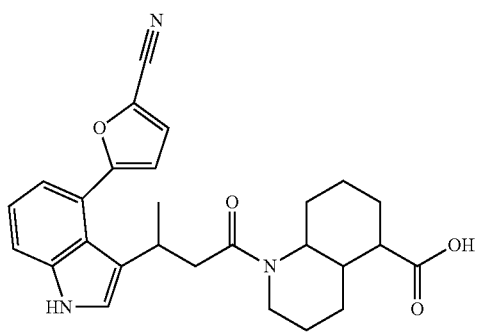
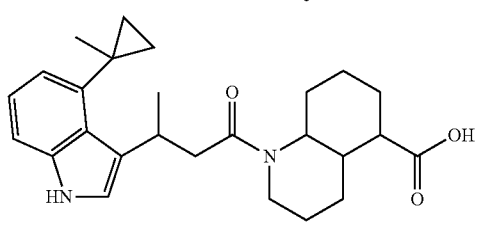
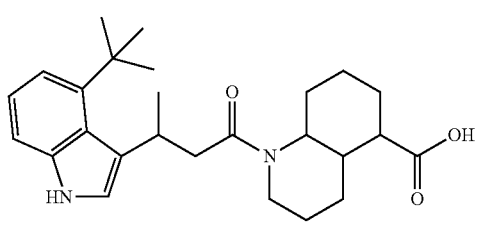
72
-continued
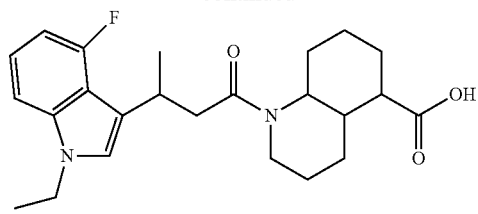
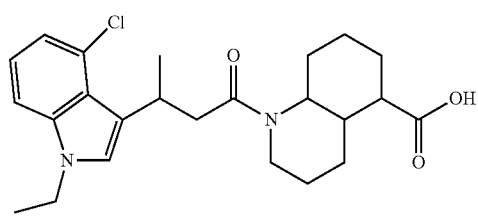
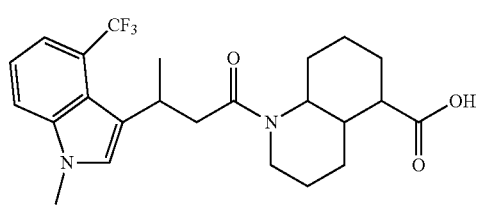
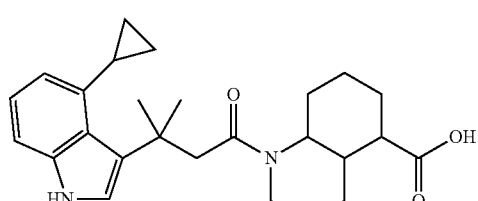
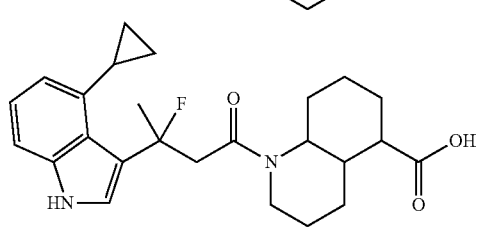
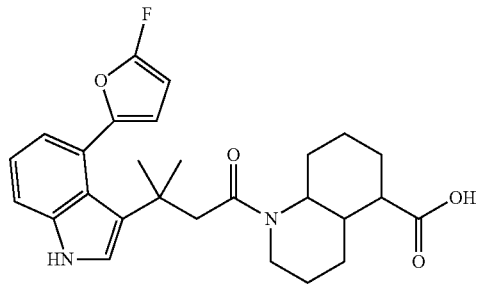
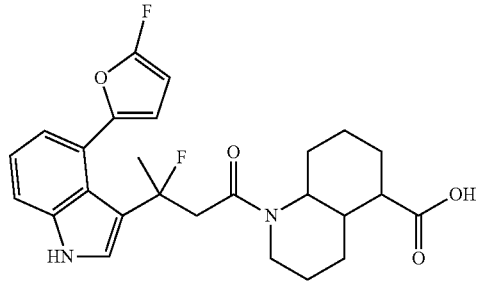

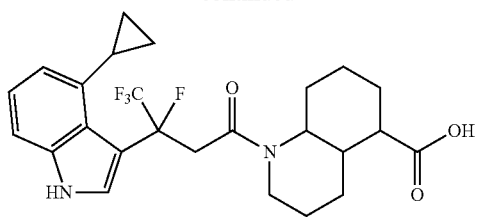
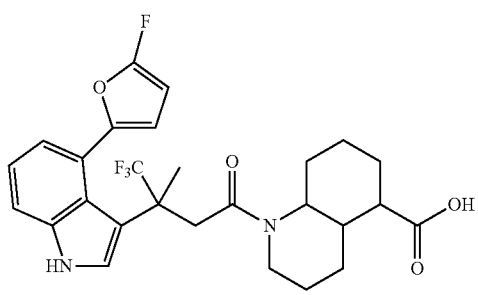
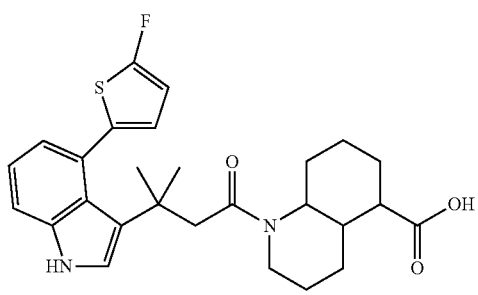
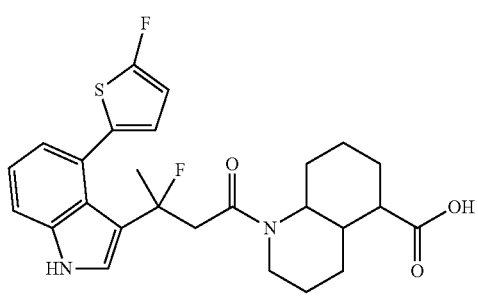
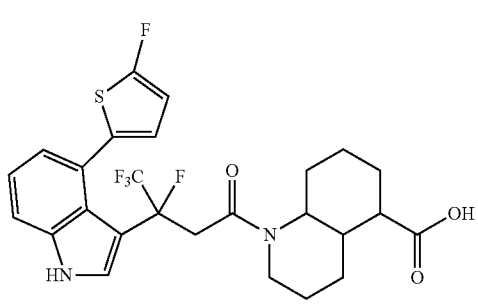
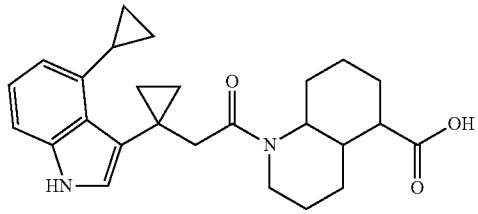
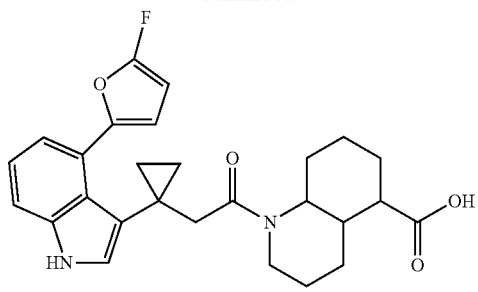
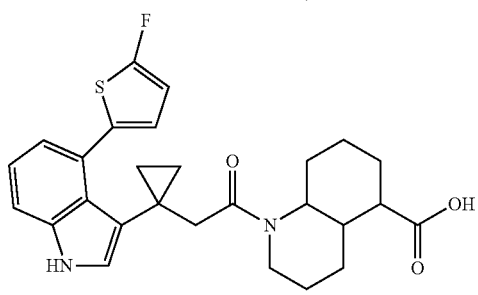
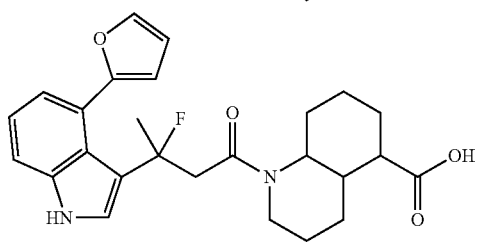
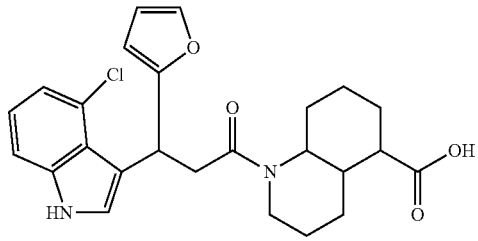
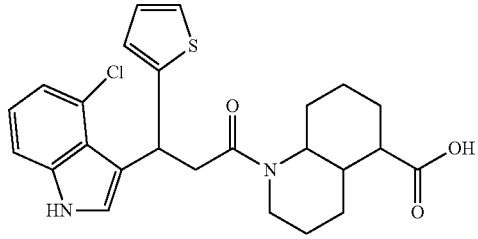
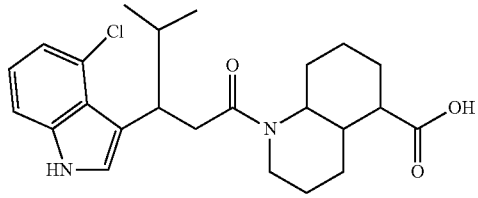
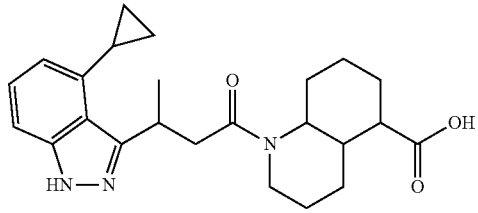

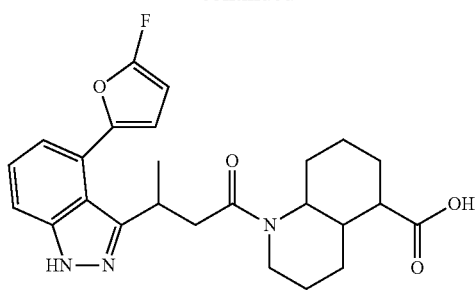
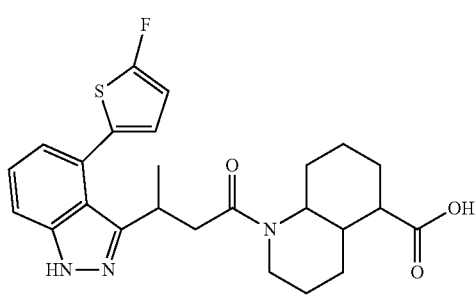
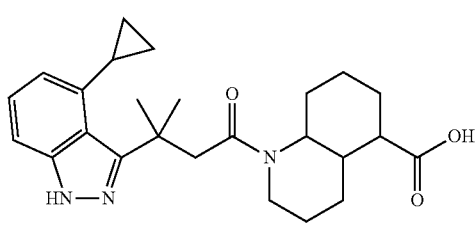
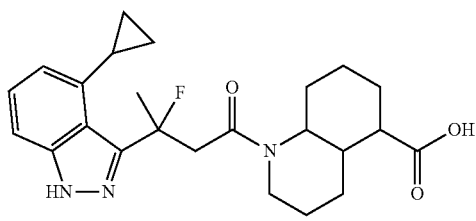
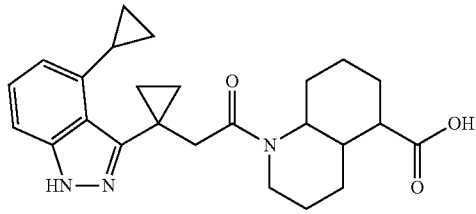
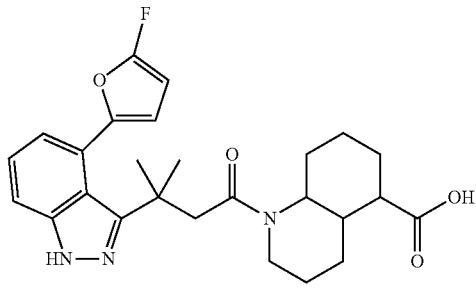
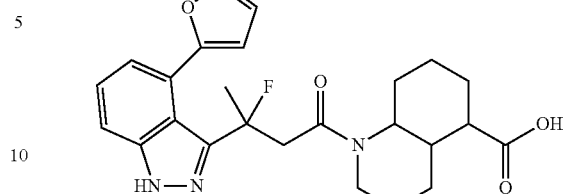
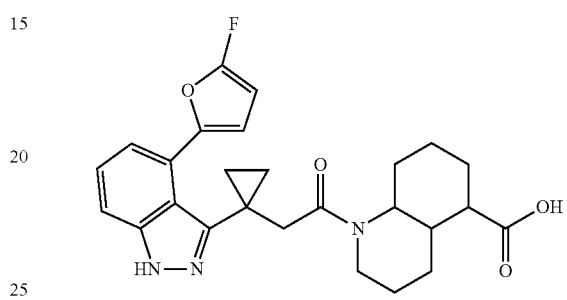
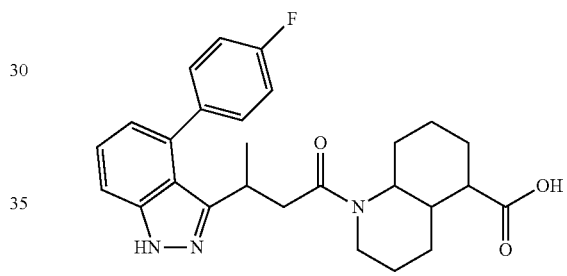
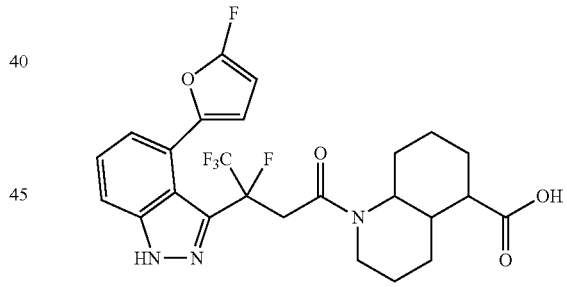
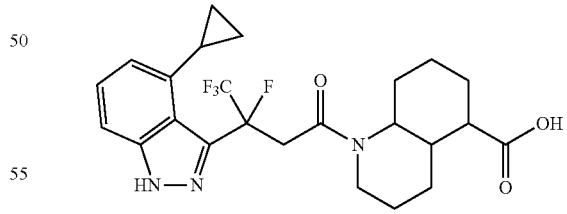
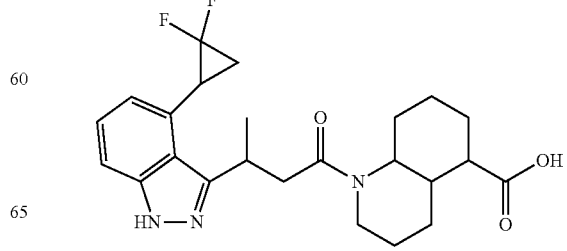

77
-continued
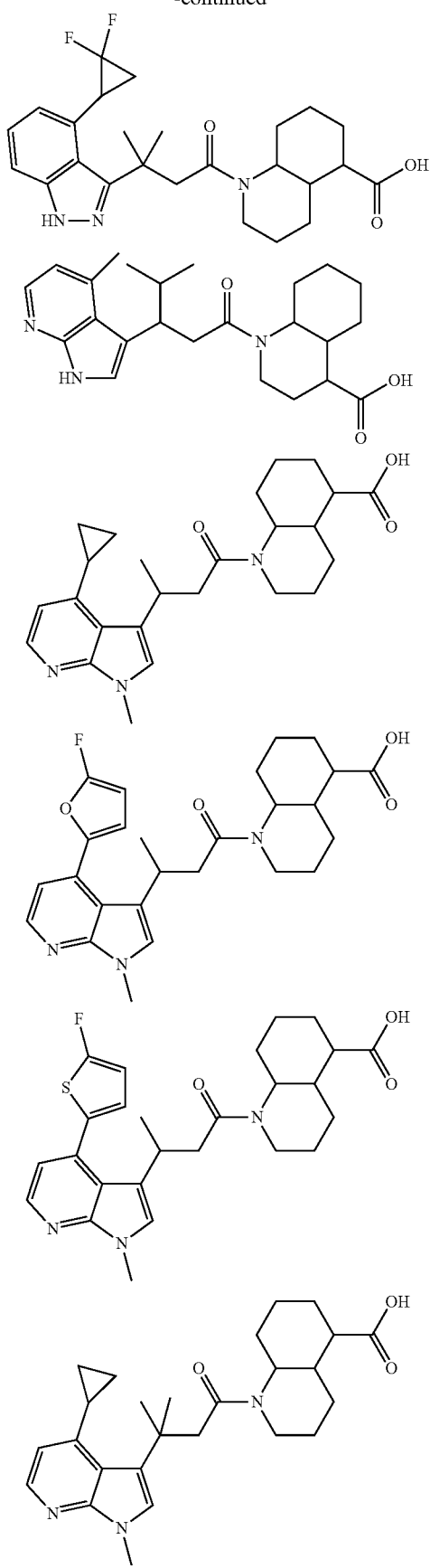
78
-continued
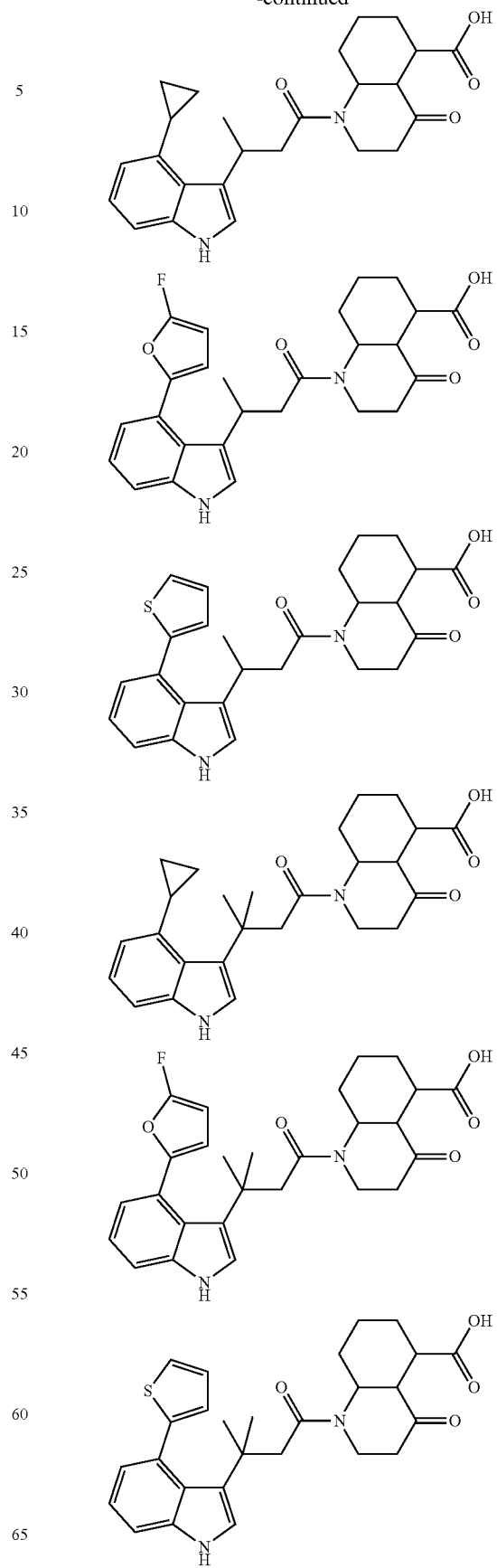

79
-continued
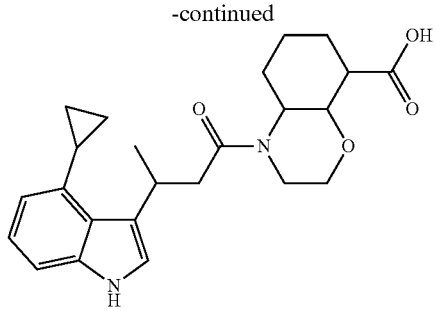
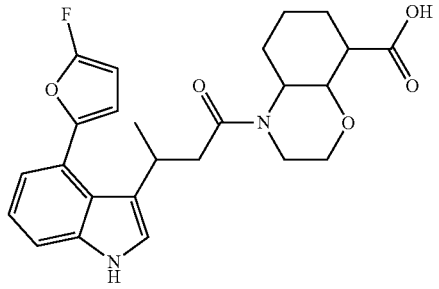
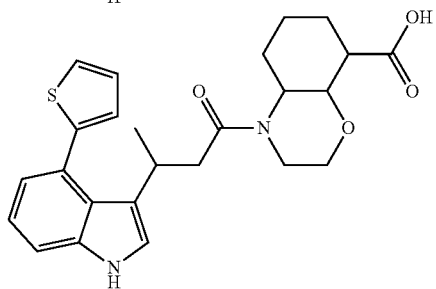
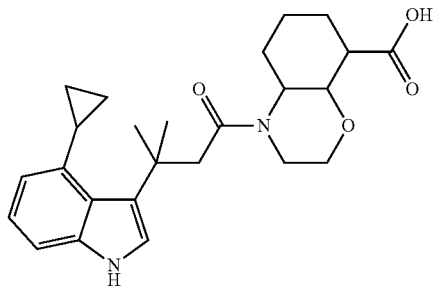
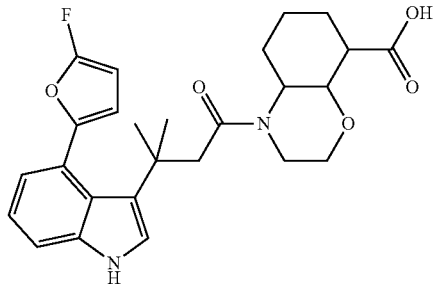
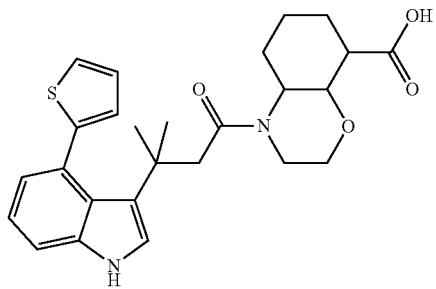
80
-continued
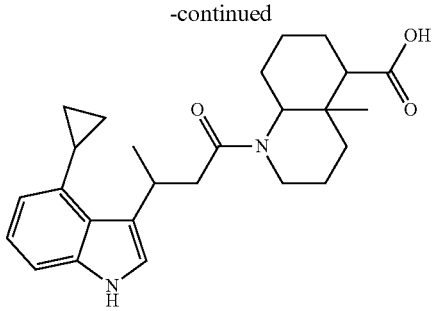
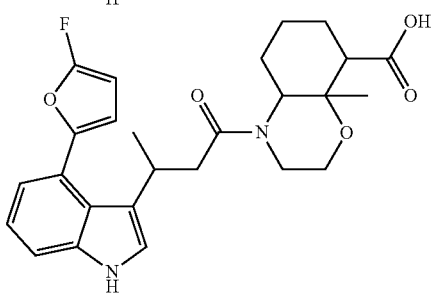
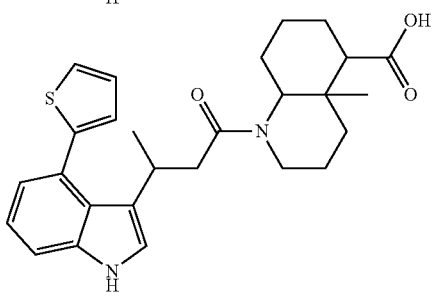
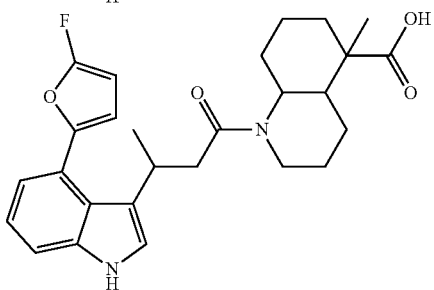
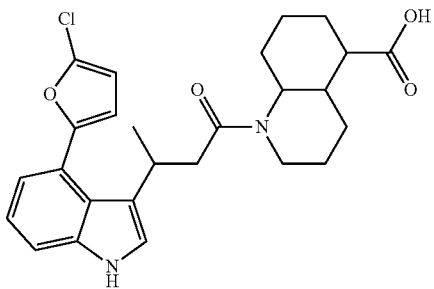
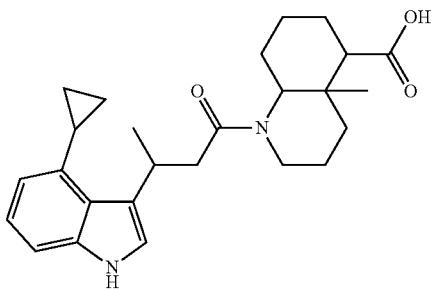

-continued
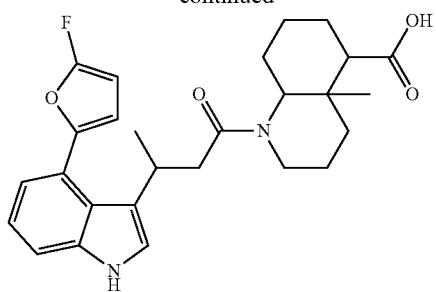
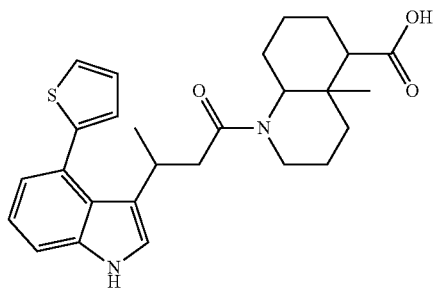
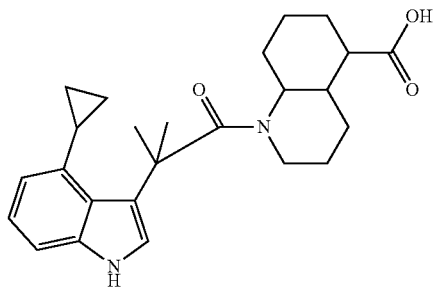
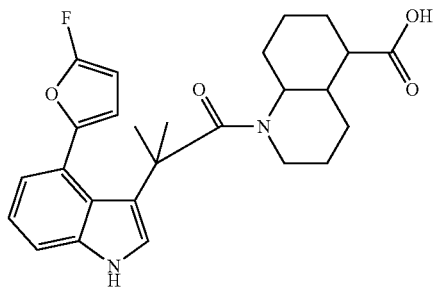
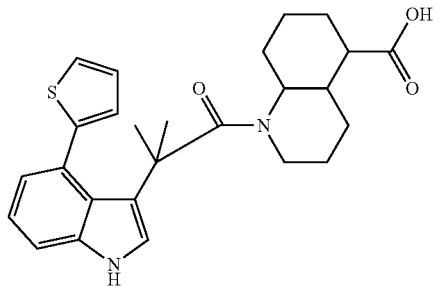
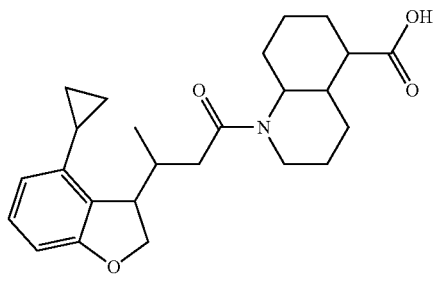
-continued
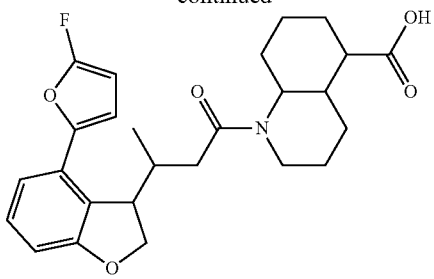
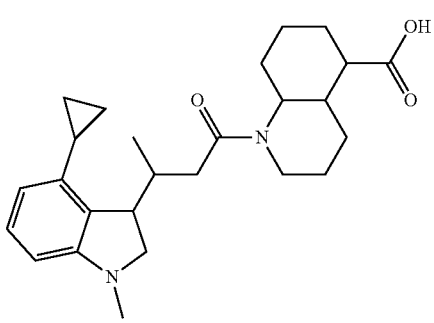
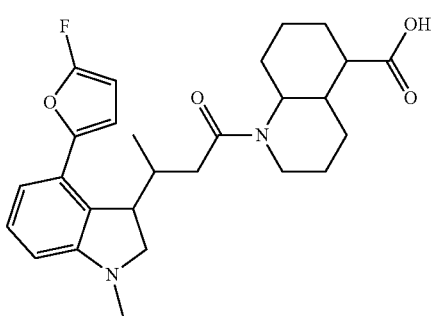
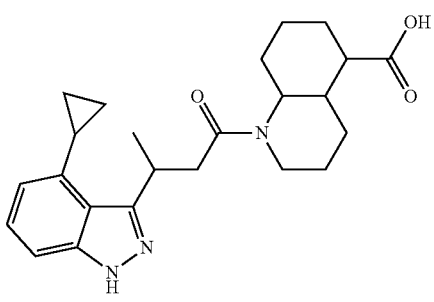
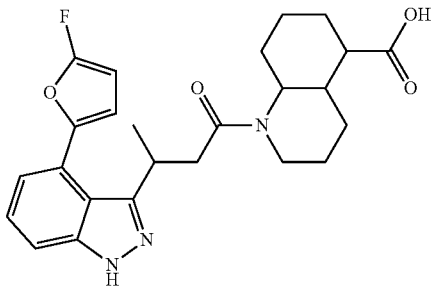

83
-continued
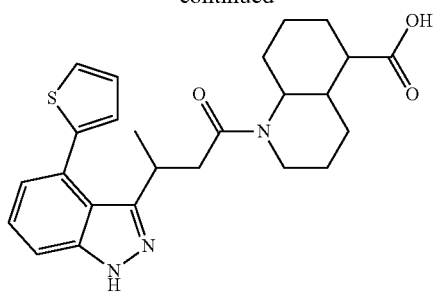
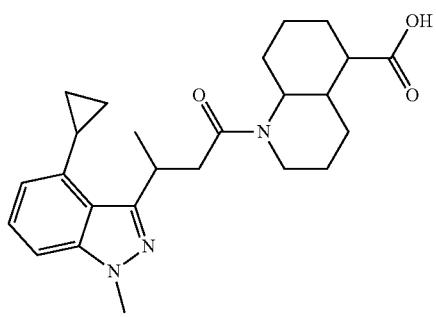
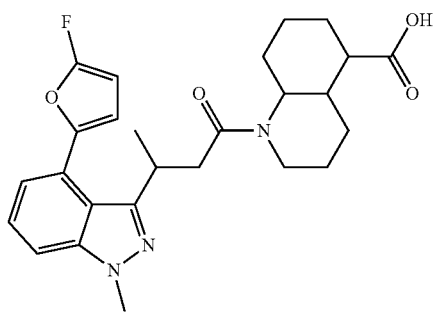
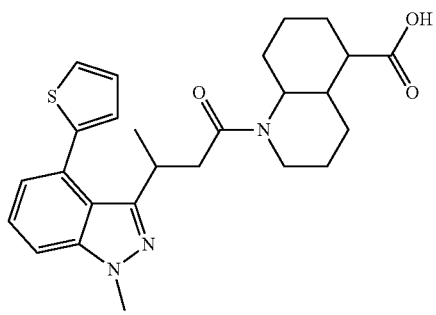
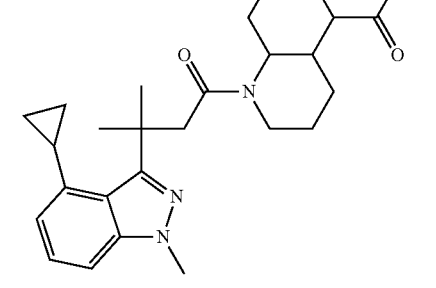
84
-continued
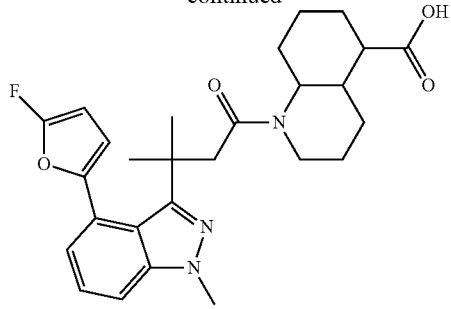
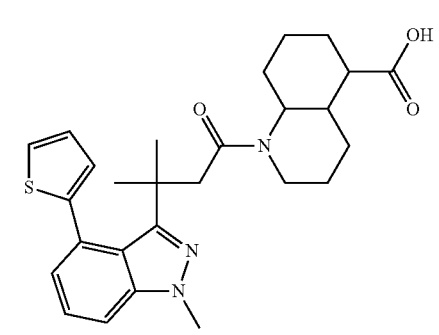
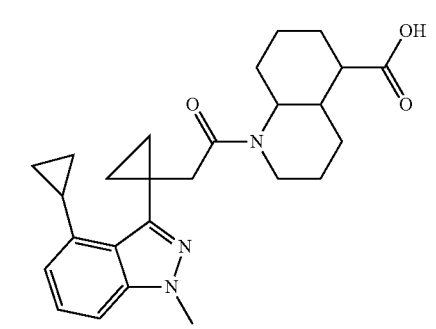
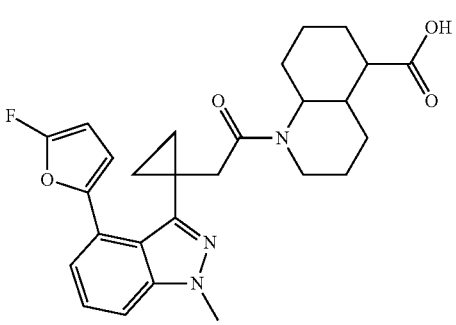
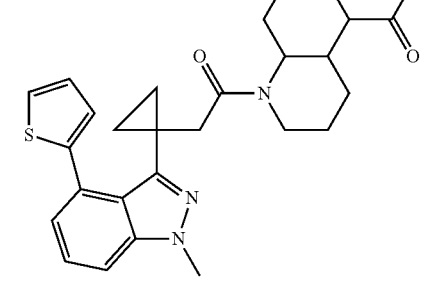

85
-continued
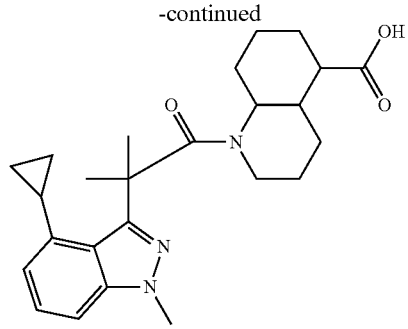
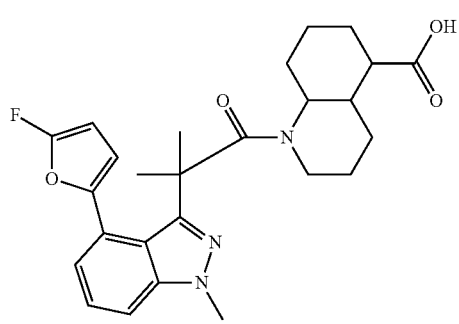
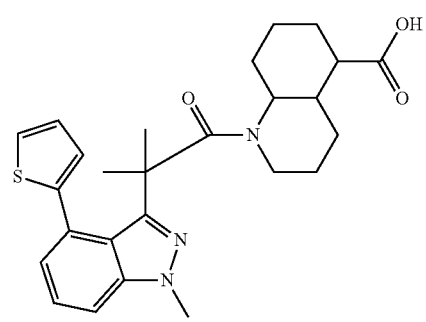
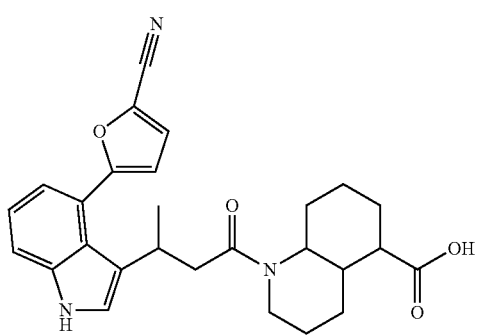
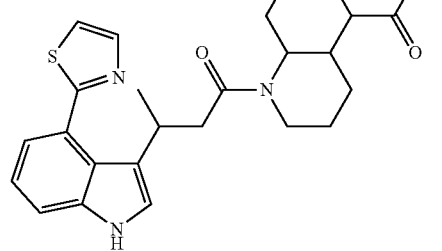
86
-continued
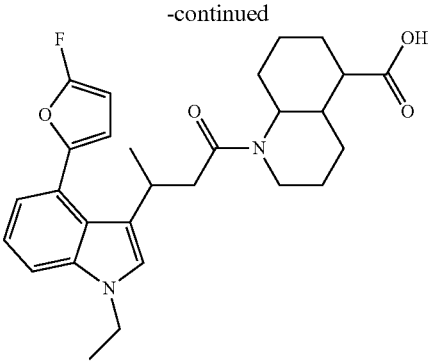
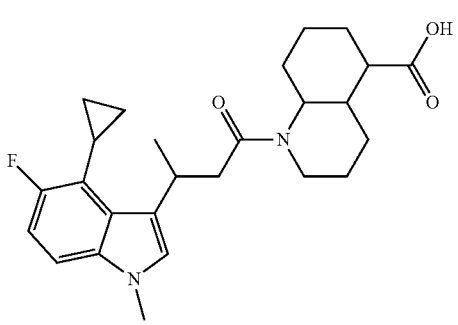
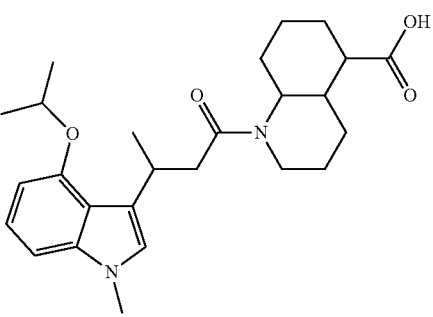
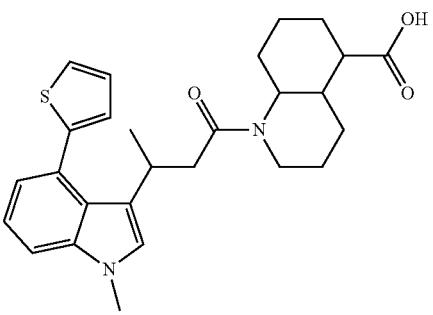
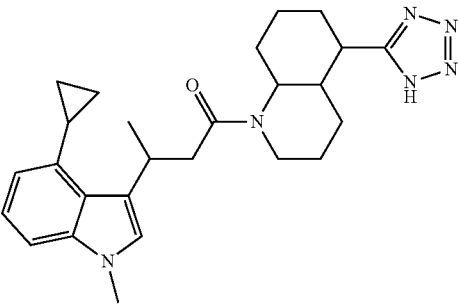

87
-continued
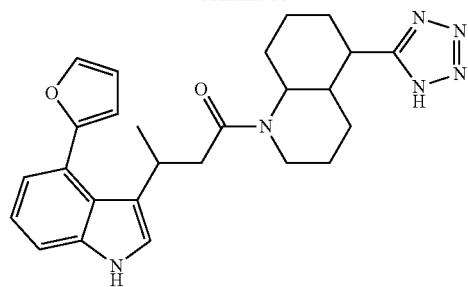
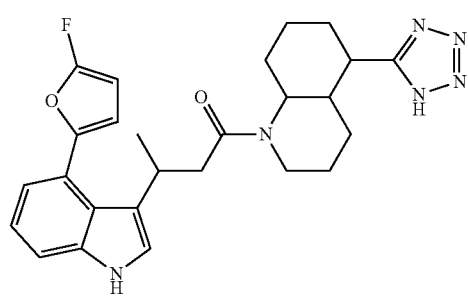
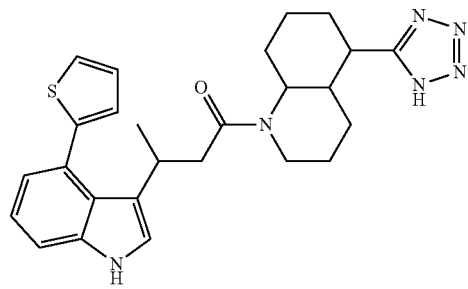
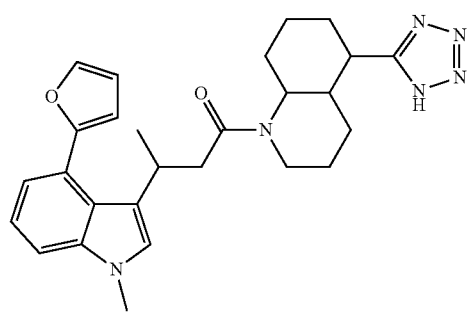
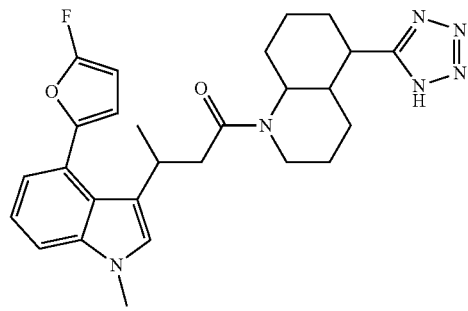
88
-continued
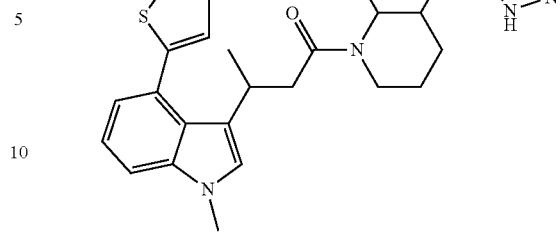
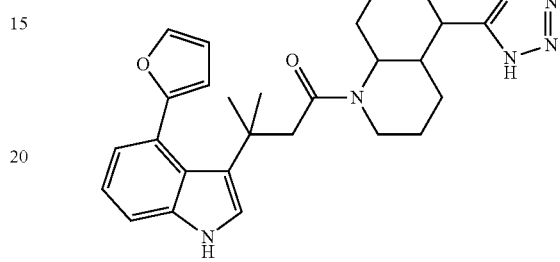
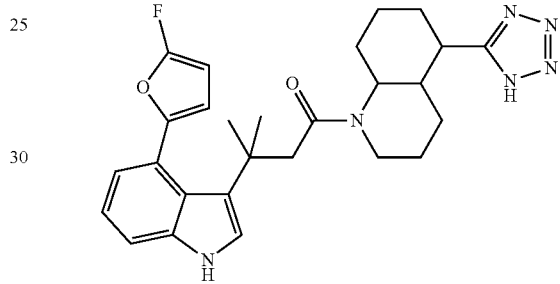
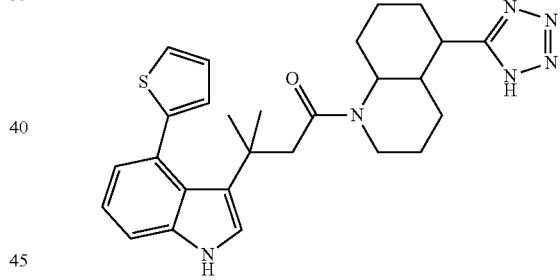
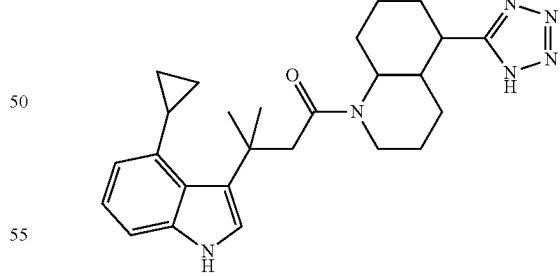
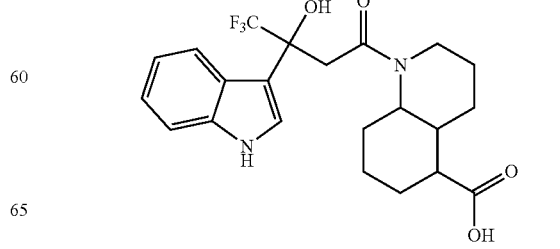

-continued
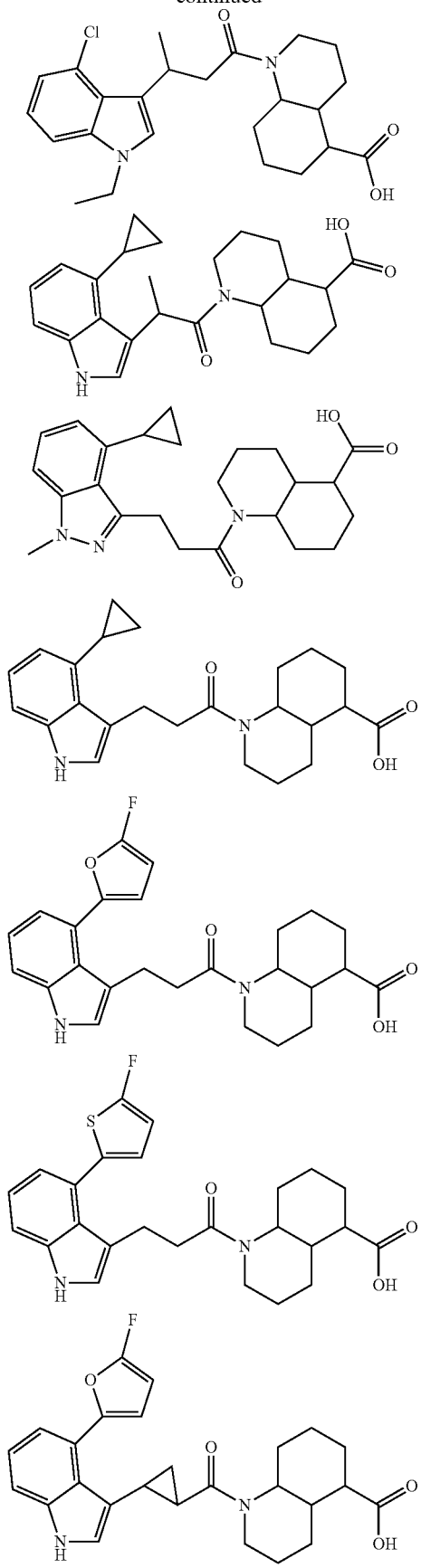
-continued
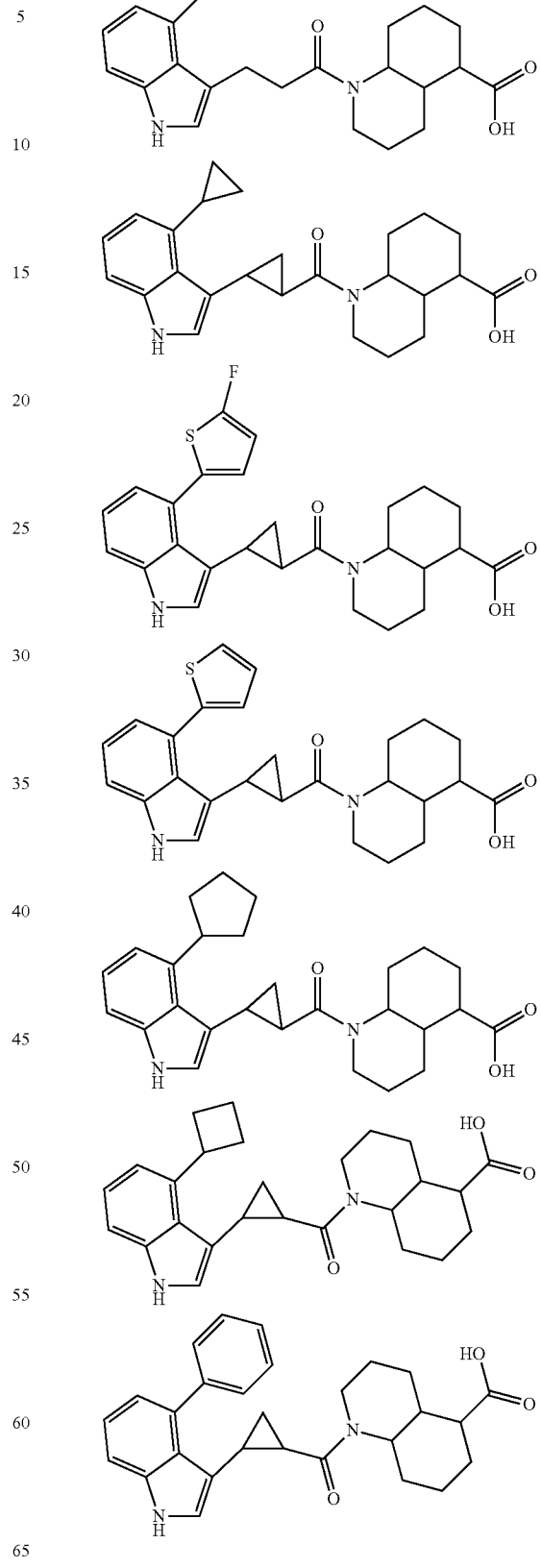
or pharmaceutically acceptable salt or prodrug thereof.

The compounds have the ability to inhibit 11β-HSD1. The ability to inhibit 11β-HSD1 may be a result of the compounds acting directly and solely on the 11β-HSD1 to modulate/potentiate biological activity. However, it is understood that the compounds may also act at least partially on other factors associated with 11β-HSD1 activity.

The inhibition of 11β-HSD1 may be carried out in any of a number of ways known in the art. For example if inhibition of 11β-HSD1 in vitro is desired an appropriate amount of the compound may be added to a solution containing the 11β-HSD1. In circumstances where it is desired to inhibit 11β-HSD1 in a mammal, the inhibition of the 11β-HSD1 typically involves administering the compound to a mammal containing the 11β-HSD1.

Accordingly the compounds may find a multiple number of applications in which their ability to inhibit 11β-HSD1 enzyme of the type mentioned above can be utilised.

Accordingly compounds of the invention would be expected to have useful therapeutic properties especially in relation to diabetes, hyperglycemia, low glucose tolerance, hyperinsulinemia, hyperlipidemia, hypertriglyceridemia, hypercholesterolemia, dyslipidemia, obesity, abdominal obesity, glaucoma, hypertension, atherosclerosis and its sequelae, retinopathy and other ocular disorders, nephropathy, neuropathy, myopathy, osteoporosis, osteoarthritis, dementia, depression, neurodegenerative disease, psychiatric disorders, Polycystic ovaries syndrome, infertility, Cushing's Disease, Cushing's syndrome, virus diseases, and inflammatory diseases.

Administration of compounds within Formula (I) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the activator compound may be selectively toxic or more toxic to rapidly proliferating cells, e.g. cancerous tumours, than to normal cells.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, 19$^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in some embodiments the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug(s) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs, the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

The compound of the invention may also be administered in combination with (or simultaneously or sequentially with) an adjuvant to increase compound performance. Suitable adjuvants may include (a) dipeptidyl peptidase-IV (DP-IV) inhibitors; (b) insulin sensitizing agents; (iv) biguanides; (c) insulin and insulin mimetics; (d) sulfonylureas and other insulin secretagogues; (e) alpha-glucosidase inhibitors; and (f) GLP-1, GLP-1 analogs, and GLP-1 receptor agonists. The adjuvants may be part of the same composition, or the adjuvants may be administered separately (either simultaneously or sequentially). The order of the administration of the composition and the adjuvant will generally be known to the medical practitioner involved and may be varied.

Synthesis of Compounds of the Invention

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, 3$^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

The symbols, abbreviations and conventions in the processes, schemes, and examples are consistent with those used in the contemporary scientific literature. Specifically but not meant as limiting, the following abbreviations may be used in the examples and throughout the specification.

g (grams)
L (liters)
Hz (Hertz)
mol (moles)
RT (room temperature)
min (minutes)
MeOH (methanol)
$CHCl_3$ (chloroform)
DCM (dichloromethane)
DMSO (dimethylsulfoxide)
EtOAc (ethyl acetate)
mg (milligrams)
mL (milliliters)
psi (pounds per square inch)
mM (millimolar)
MHz (megahertz)
h (hours)
TLC (thin layer chromatography)
EtOH (ethanol)
$CDCl_3$ (deuterated chloroform)
HCl (hydrochloric acid)
DMF (N, N-dimethylformamide)
THF (tetrahydrofuran)
$K_2CO_3$ (potassium carbonate)
$Na_2SO_4$ (sodium sulfate)
RM (Reaction Mixture)

Unless otherwise indicated, all temperatures are expressed in ° C. (degree centigrade). All reactions conducted at room temperature unless otherwise mentioned.

All the solvents and reagents used are commercially available and purchased from Sigma Aldrich, Fluka, Acros, Spectrochem, Alfa Aesar, Avra, Qualigens, Merck, Rankem and Leonid Chemicals.

$^1$H NMR spectra were recorded on a Bruker A V 300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad).

Mass spectra were obtained on single quadruple 6120 LCMS from Agilent technologies, using either atmospheric chemical ionization (APCI) or Electrospray ionization (ESI) or in the combination of these two sources.

All samples were run on SHIMADZU system with an LC-20 AD pump, SPD-M20A diode array detector, SIL-20A auto sampler.

Synthetic Scheme 1

One scheme for making certain compounds of the invention is shown in scheme 1 below.

Synthetic Scheme-1

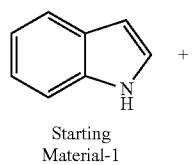

Starting Material-1

-continued

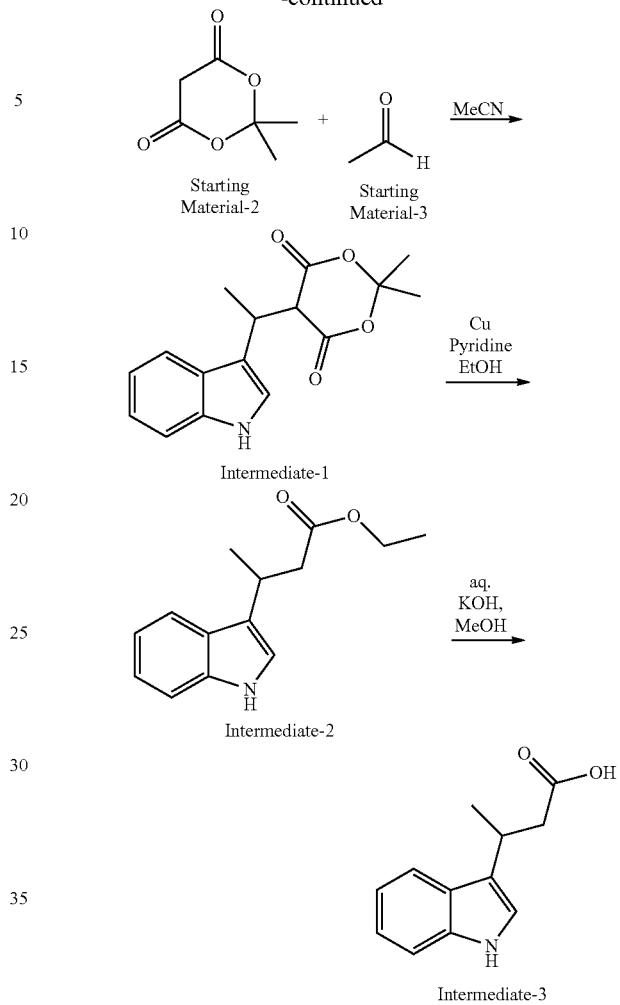

Synthesis of 5-[1-(1H-indol-3-yl)ethyl]-2,2-dimethyl-1,3-dioxane-4,6-dione (Intermediate-1)

A 100 mL RB flask fitted with magnetic stirrer was charged with Starting Material 1 (4.0 g, 34 mmol), Starting Material 2 (4.92, 34 mmol) and Starting Material 3 (3 g, 68 mmol) in 75 mL of acetonitrile. The resulting solution was stirred at room temperature overnight. After completion of the reaction (reaction monitored by TLC), the Solvent was removed under reduced pressure, and the resulting crude compound was purified by column chromatography on silica gel (230-400 mesh) using Petroleum ether (60-80) and ethyl acetate as eluent. The product (intermediate 1) was obtained as a brown liquid (2.51 g). LC-MS (M–H)$^+$=286.

Synthesis of ethyl 3-(1H-indol-3-yl)butanoate (Intermediate-2)

A 100 mL RB flask fitted with magnetic stirrer was charged with intermediate-1 (2.5 g, 8.7 mmol) in 50 mL of pyridine and 8 ml of ethanol. To this mixture copper powder (0.4 g, 5 mol %) was added. Then the resulting reaction mass was refluxed at 110° C. for 3 hours. After completion of the reaction (reaction monitored by TLC), solvent was removed from the reaction mass and the reaction mass was diluted with 100 mL of ethyl acetate, washed with 50 mL 1.5N HCl (2×25 mL) and brine solution. Then the organic layer was dried over anhydrous MgSO$_4$. The solvent was removed under reduced pressure, and the resulting crude compound was purified by column chromatography on silica gel (230-400 mesh) using Petroleum ether (60-80) and ethyl acetate as eluent. The product (intermediate 2) was obtained as a brown liquid. (0.380 g). LC-MS (M+H)$^+$=232.

Synthesis of ethyl 3-(1H-indol-3-yl)butanoic acid (Intermediate-3)

A 50 mL RB flask fitted with magnetic stirrer was charged with 6 mL of methanol and 2 mL of water. To the stirred solvent intermediate-2 (0.145 g, 0.62 mmol) and KOH (0.098 g, 2.54 mmol) was added. Then the resulting reaction mass was refluxed at 70° C. for 3 hours. After completion of the reaction (reaction monitored by TLC), solvent was removed from the reaction mass and the reaction mass was diluted with 20 mL of water. The resulting aqueous layer was then washed with 20 mL of diethylether. The aqueous layer was acidified by 1 NHCl to pH 5.5 and product was extracted with ethyl acetate and the solvent was removed under reduced pressure. The product (intermediate 3) was obtained as a brown liquid (0.115 g). The product obtained above was directly taken for next step without any purification.

Example 1

Compound (1): 3-(1H-indol-3-yl)-1-(octahydroquinolin-1(2H)-yl)butan-1-one

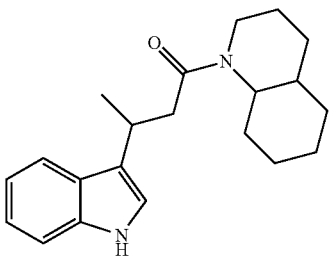

(1)

Synthetic Scheme-2

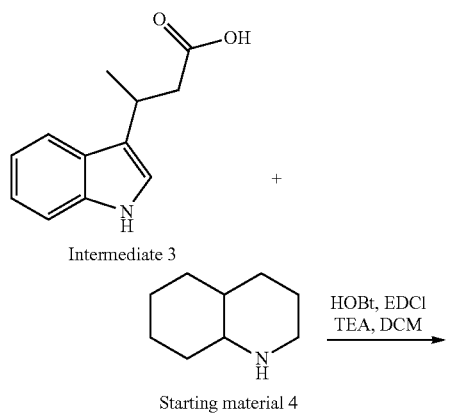

Synthesis of Compound (1)

A 100 mL RB flask fitted with magnetic stirrer was charged with intermediate-3 (0.115 g, 0.56 mmol), Starting Material 4 (0.078 g, 0.56 mmol), EDCI (0.162 g, 0.84 mmol), HOBt (0.104 g, 0.69 mmol) in 8 mL of dichloromethane and it was cooled to 0° C. Then to the stirred solution triethylamine (0.301 mL, 2.0 mmol) was added. The resulting solution was stirred at room temperature overnight. After completion of the reaction (reaction monitored by TLC), the reaction mass was diluted with 20 mL of water and organic layer was separated. The Solvent was removed under reduced pressure, and the resulting crude compound was purified by 60-120 silical-gel chromatography by using petether ethylacetate as eluent. The final product obtained was pale yellow gummy solid (0.110 g). $^1$H NMR (300 MHz, CDCl3): δ 7.89 (s, 1H), 7.59-7.61 (m, 1H), 7.27-7.30 (d, 1H), 7.00-7.13 (m, 2H), 6.94-6.95 (d, 1H), 4.41-4.60 (m, 1H), 3.49-3.61 (m, 2H), 2.46-2.91 (m, 3H), 0.98-1.71 (m, 16H). LC-MS (M+H)$^+$=325.2; HPLC purity: 92.84%.

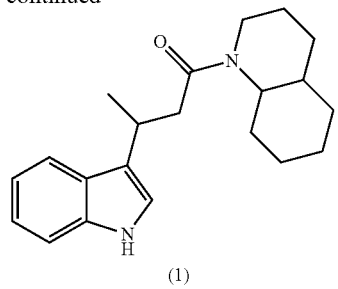

(1)

Example 2

Compound (2): 2-methyl-2-(1-methyl-1H-indol-3-yl)-1-(octahydroquinolin-1(2H)-yl)propan-1-one

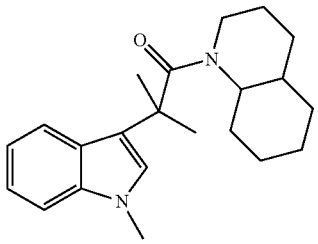

(2)

Synthetic Scheme-2

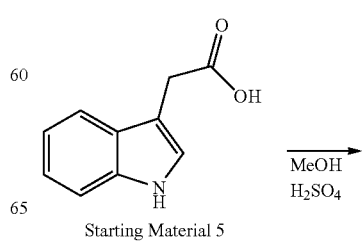

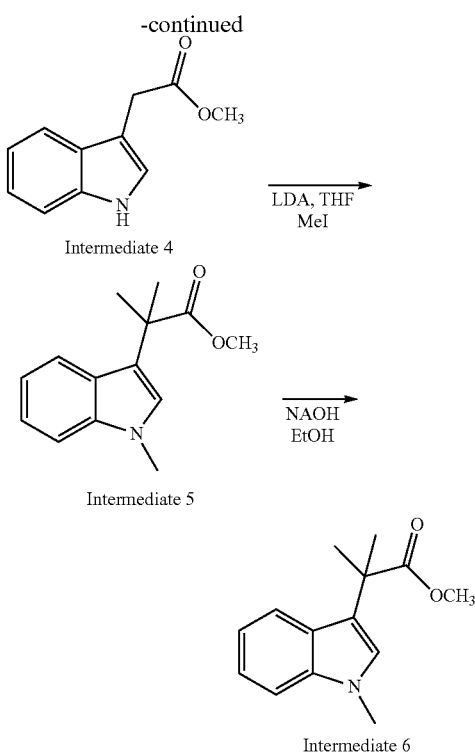

Synthesis of methyl 1H-indol-3-ylacetate (Intermediate-4)

A 100 mL RB flask fitted with magnetic stirrer was charged with 15 mL of Methanol. To the stirred solvent Starting Material-5 (2.0 g, 11.41 mmol) was added. The resulting mixture was cooled to zero degrees to which concentrated $H_2SO_4$ (0.5 mL) was added. The mixture was then stirred at ambient temperatures for 1 hour. After completion of the reaction (reaction monitored by TLC), the solvent from the reaction mass was removed under reduced pressure. The resulting crude mass was taken in Ethyl acetate (100 mL) and was washed with water (50 mL), Sodium bicarbonate solution (100 mL×2) saturated brine solution (50 mL) and the organic layer dried over anhydrous sodium sulphate. Then the solvent Was removed under reduced pressure. The product was obtained as brown syrup. (2.1 g). LC-MS $(M+H)^+=190.2$.

Synthesis of methyl 2-methyl-2-(1-methyl-1H-indol-3-yl)propanoate (Intermediate-5)

A 100 mL 3 neck RB flask fitted with magnetic stirrer was charged with 10 mL of dry THF. To the stirred solvent, diisopropyl amine (401.12 mg, 3.964 mmol) was added and the resulting solution was cooled to −78 degrees. Further n-BuLi (2.5 mL, 3.964 mmol) was added to it and stirred for 1 hour at 0° C. Once again the resulting solution was cooled to −78 degrees to which Intermediate-4 (150 mg, 0.7928 mmol) was added and stirred for 1 hour. Then Methyl Iodide was added and the resulting mass was stirred at ambient temperature for 15 hours. After completion of the reaction (reaction monitored by TLC), the reaction mass was quenched with saturated ammonium chloride and was extracted using EtOAc (100 mL×3). The combined organic layer washed with brine was dried and the solvent was removed under reduced pressure. The resulting crude compound was purified by column chromatography on silica gel (120 meshes) using Petroleum ether (60-80) and ethyl acetate as eluent. The product was obtained as brown syrup. (150 mg). LC-MS $(M+H)^+=232.2$.

Synthesis of 2-methyl-2-(1-methyl-1H-indol-3-yl)propanoic acid (Intermediate-6)

A 100 mL RB flask fitted with magnetic stirrer was charged with THF 5 mL. To the stirred solvent Intermediate-5 (150 mg, 0.6485 mmol) was added which was followed by the addition of NaOH (77.82 mg; 1.945 mmol), and water-methanol mixture (1 mL, 1:1). The resulting mass was heated at 70° C. for 4 hours. After completion of the reaction, the solvent from the reaction mass was removed under reduced pressure. The crude mass was treated with water and washed with ether (50 mL×3). The resulting aqueous solution was acidified to pH=1 to 2 by using 1N HCl and extracted with DCM (50 mL×3). The combined DCM layers were washed with brine, dried over anhydrous $Na_2SO_4$ and the solvent was removed under reduced pressure to give Intermediate-6 as brown solid (85 mg). LC-MS $(M+H)^+=218.2$.

Synthesis of Compound (2)

Compound (2) was synthesized by following the procedure used to make compound (1) (Scheme 2). The crude product was obtained by evaporating the organic layer under reduced pressure and was purified using silica gel column where Petroleum ether: Ethyl acetate was used as an eluent to obtain Compound (2). $^1$H NMR (300 MHz, CDCl3): δ 7.43-7.48 (m, 1H), 7.18-7.21 (d, 1H), 7.09-7.14 (t, 1H), 6.92-6.97 (t, 1H), 6.75-6.80 (d, 1H), 4.50-4.75 (m, 1H), 3.57-3.98 (m, 4H), 2.28-2.45 (m, 1H), 1.47-1.58 (m, 8H), 1.37-1.40 (m, 6H), 0.94-1.09 (m, 5H). LC-MS $(M+H)^+=339.2$; HPLC purity: 98.09%.

Example 3

3-(5-methyl-1H-indol-3-yl)-1-(octahydroquinolin-1(2H)-yl)propan-1-one (3)

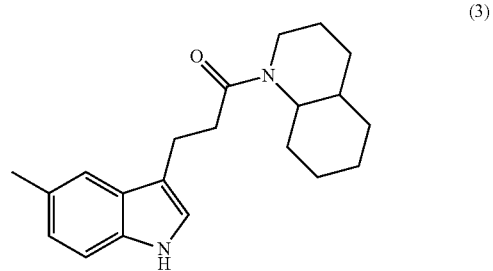 [SMILES: Cc1ccc2[nH]cc(CCC(=O)N3CCCC4CCCCC43)c2c1]

(3)

Synthetic Scheme-4

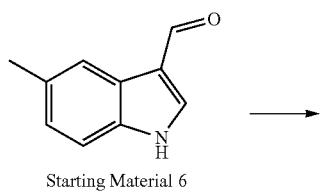

Starting Material 6

Synthesis of 3-(5-methyl-1H-indol-3-yl)propanoic acid (Intermediate-9)

Intermediate-8 (600 mg, 2.5 mmol) was taken in MeOH (8 mL) to which KOH (500 mg, 9.0 mmol) and 1 mL of water was added. Resulting reaction mixture was refluxed for 3 hours. The reaction mixture was concentrated and then diluted with water. The resulting mixture was acidified (pH=1 to 2) with 1N HCl, extracted with EtOAc and then concentrated to give Intermediate-9 (430 mg). LC-MS $(M+H)^+=204$.

Synthesis of (3)

Compound (3) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (3). $^1$H NMR (300 MHz, CDCl3): δ 7.90 (s, 1H), 7.31-7.34 (d, 1H), 7.15-7.18 (m, 1H), 6.92-6.95 (m, 2H), 4.30-4.40 (m, 1H), 3.30-3.60 (m, 1H), 2.45-3.06 (m, 5H), 2.38-2.39 (d, 3H), 1.18-1.77 (m, 13H). LC-MS $(M+H)^+=325.2$; HPLC purity: 95.93%.

Example 4

3-(5-fluoro-1H-indol-3-yl)-1-(octahydroquinolin-1(2H)-yl)propan-1-one ((4))

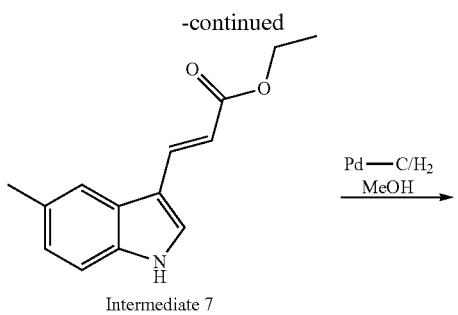
Intermediate 7

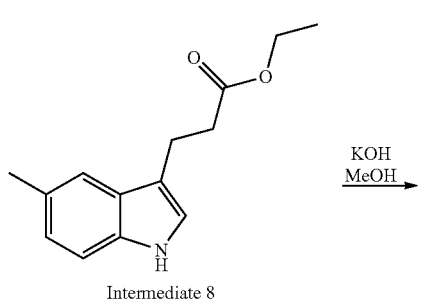
Intermediate 8

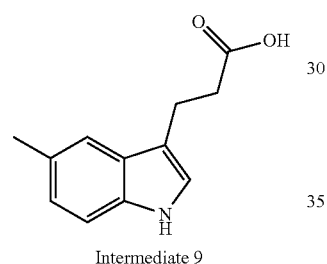
Intermediate 9

Synthesis of ethyl (2E)-3-(5-methyl-1H-indol-3-yl)prop-2-enoate (Intermediate-7)

Triethylphosphenoacetate (9.4 mmol) was taken in THF (20 mL) to which NaH (60%) was added portion wise at −5° C. The reaction mass thus obtained was maintained at same temperature for 45 min. To this the Starting Material-6 (750 mg, 4.7 mmol) was added and the resulting reaction mass was stirred at RT for 24 hours. Then reaction mass was diluted with ethyl acetate and the organic layer was separated and the separated organic layer was washed with saturated NaHCO₃, dried over anhydrous Na₂SO₄ and concentrated. The crude product thus obtained was purified by 60-120 silica gel by using hexanes: EtOAc as eluent to give Intermediate 7 (490 mg). LC-MS $(M+H)^+=230$.

Synthesis of ethyl 3-(5-methyl-1H-indol-3-yl)propanoate (Intermediate-8)

Intermediate-7 (1.31 g, 5.6 mmol) was taken in MeOH (25 mL) to which 10% Pd/C (150 mg) was added. The resulting reaction mass was stirred under H₂ atmosphere (25 psi) for 10 hours. Further the reaction mass thus obtained was filtered through celite bed and concentrated to give Intermediate-8 (820 mg). LC-MS $(M+H)^+=232$.

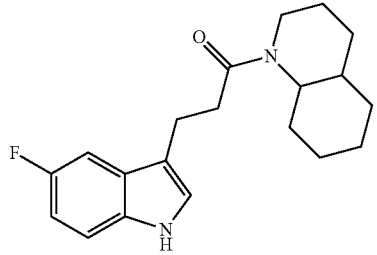
(4)

Synthetic Scheme-5

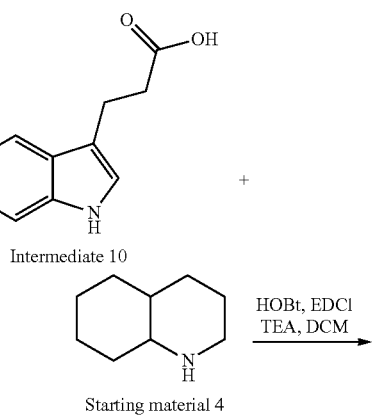
Intermediate 10
Starting material 4

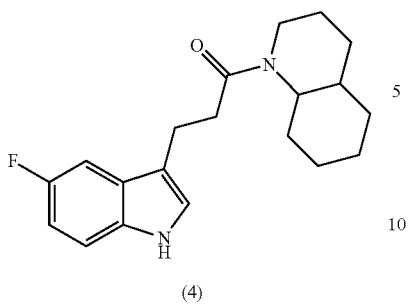

(4)

Synthesis of 3-(5-fluoro-1H-indol-3-yl)propanoic acid (Intermediate-10)

Intermediate-10 was synthesized by following the procedure used to make Intermediate-9 (Scheme 4).

Synthesis of Compound (4)

Compound (4) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (4). $^1$H NMR (300 MHz, CDCl3): δ 8.55 (s, 1H), 7.17-7.18 (d, 2H), 6.96 (s, 1H), 6.80-6.85 (t, 1H), 4.43-4.57 (m, 1H), 3.41-3.58 (m, 1H), 2.44-3.03 (m, 5H), 0.99-1.94 (m, 13H). LC-MS (M+H)$^+$=329.1; HPLC purity: 96.44%.

Example 5

2-(1H-indol-3-ylsulfanyl)-1-(octahydroquinolin-1(2H)-yl)ethanone (5)

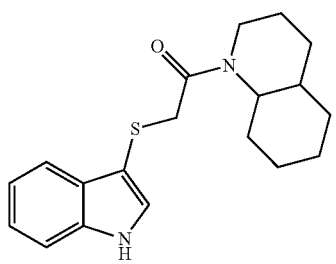

(5)

Synthetic Scheme-6

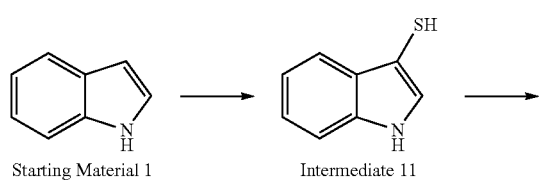

Starting Material 1   Intermediate 11

Intermediate 12

Intermediate 13

Synthesis of 1H-indole-3-thiol (Intermediate-11)

A stirred solution of Starting Material-1 (2.93 g, 25.0 mmol) and thiourea (1.9 g, 25.0 mmol) in methanol (50 ml) was treated with a mixture of iodine (6.35 g, 25.0 mmol) and KI (4.17 g, 25.0 mmol) in water (25 ml), stirred for 1 hour, filtered through a cotton plug, concentrated in vacuo to remove methanol and ⅓ of water, and filtered concentrated solution again. The tan solid filter cake is heated with 2M NaOH (50 ml) at 85° C. for 30 min, cooled and filtered. The filtrate is acidified with conc. HCl to pH=1 and filtered. This filter cake is dried under a nitrogen stream to obtain the Intermediate-11 as cream-colored solid (900 mg).

Synthesis of methyl (1H-indol-3-ylsulfanyl)acetate (Intermediate-12)

Anhydrous potassium carbonate (2.1 g, 15.9 mmol) was added to a solution of Intermediate-11 (0.8 g, 5.3 mmol) and ethyl 2-chlortoacetate (0.96 ml, 5.3 mmol) in acetonitrile (30 mL). The resulting mixture was heated to reflux under argon for 18 hours. The cooled mixture was filtered and concentrated under vacuo. Water was added to the reaction mass and extracted with ethyl acetate. Combined organic extracts were dried over (MgSO$_4$) and concentrated to a crude gummy material, which was purified by column chromatography using hexane: ethyl acetate (1:9) to give Intermediate-12 (300 mg).

Synthesis of (1H-indol-3-ylsulfanyl)acetic acid (Intermediate-13)

A mixture of (1H-Intermediate-12 (0.30 g, 1.27 mmol), 10% aqueous sodium hydroxide solution (5 ml) and methanol (8 mL) were stirred at room temperature over-night. Reaction was monitored by TLC and LC-MS. Then reaction mixture was concentrated under reduced pressure. Aqueous layer was washed twice with DCM to remove organic impurities and was then acidified with concentrated HCl. A white solid thus formed was isolated by extraction and the solvent was removed under high vacuum. The crude reaction mass was purified by column chromatography using ethylacetate:hexane (1:1) as eluent to give Intermediate-13 (170 mg).

Synthetic Scheme-7

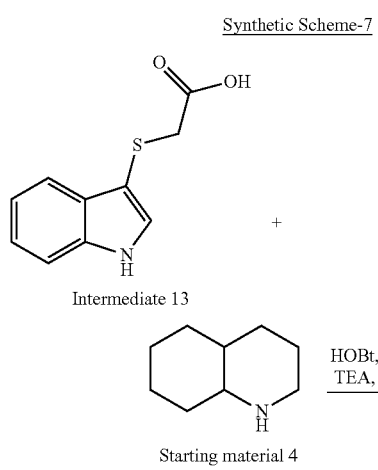

Intermediate 13

Starting material 4

Synthetic Scheme-8

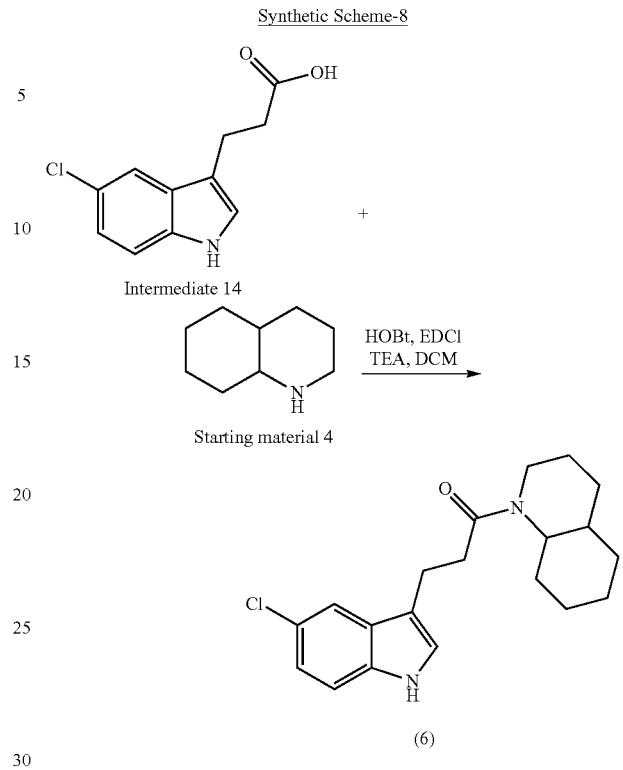

Intermediate 14

Starting material 4

Synthesis of Compounds (5)

Compound (5) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (5). $^1$H NMR (300 MHz, CDCl3): δ 8.78-8.96 (d, 1H), 7.73-7.76 (m, 1H), 7.37 (s, 2H), 7.00-7.06 (m, 2H), 4.23-4.64 (m, 1H), 3.41-3.85 (m, 3H), 2.26-3.41 (m, 3H), 1.25-1.72 (m, 11H). LC-MS (M+H)+=329.1; HPLC purity: 98.84%.

Example 6

3-(5-chloro-1H-indol-3-yl)-1-(octahydroquinolin-1(2H)-yl)propan-1-one (6)

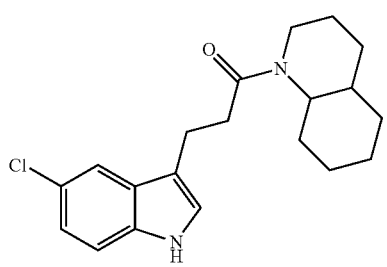

(6)

Synthesis of 3-(5-chloro-1H-indol-3-yl)propanoic acid (Intermediate-14)

Intermediate-14 was synthesized by following the procedure used to make Intermediate-9 (Scheme 4).

Synthesis of Compound (6)

Compound (6) was synthesized by following the procedure used to make Compound(1) (Scheme 2). The crude product was obtained by evaporating the organic layer under reduced pressure and was purified by silica gel column using Petroleum ether: Ethyl acetate as eluent to obtain Compound (6). $^1$H NMR (300 MHz, CDCl3): δ 8.05 (s, 1H), 7.48-7.51 (m, 1H), 7.17-7.21 (m, 1H), 7.03-7.08 (m, 1H), 6.99 (s, 1H), 4.43-4.61 (m, 1H), 3.45-3.59 (m, 1H), 2.96-3.04 (m, 2H), 2.45-2.93 (m, 3H), 1.21-1.66 (m, 13H). LC-MS (M+H)$^+$=345.2; HPLC purity: 89.78%.

Example 7

3-(5-methoxy-1fi-indol-3-yl)-1-(octahydroquinolin-1(2H)-yl)propan-1-one (7)

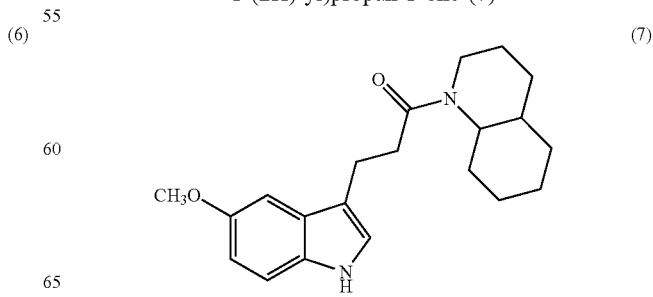

(7)

Synthetic Scheme-9

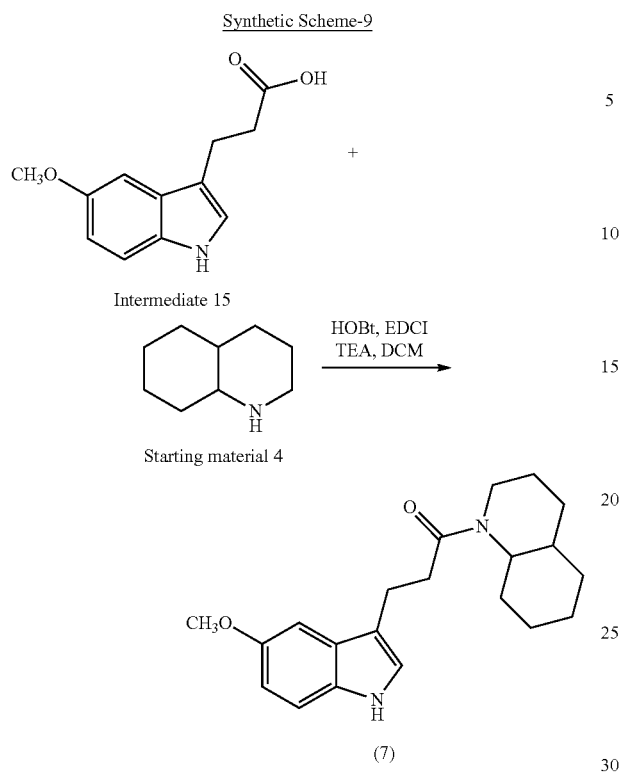

Intermediate 15

Starting material 4

(7)

Synthesis of 3-(5-methoxy-1H-indol-3-yl)propanoic acid (Intermediate-15)

Intermediate-15 was synthesized by following the procedure used to make Intermediate-9 (Scheme 4).

Synthesis of Compound (7)

Compound (7) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (7). $^1$H NMR (300 MHz, CDCl3): 8.19 (s, 1H), 7.22-7.25 (m, 1H), 7.04-7.05 (d, 1H), 6.98 (s, 1H), 6.82-6.86 (m, 1H), 4.48-4.75 (m, 1H), 3.82 (s, 3H), 3.48-3.72 (m, 1H), 3.04-3.13 (m, 2H), 2.74-2.95 (m, 1H), 2.56-2.72 (m, 3H), 1.55-1.79 (m, 6H), 1.20-1.49 (m, 6H). LC-MS (M+H)$^+$=341.2; HPLC purity: 98.01%.

Example 8

(2E)-3-(1H-indol-3-yl)-1-(octahydroquinolin-1(2H)-yl)prop-2-en-1-one (8)

(8)

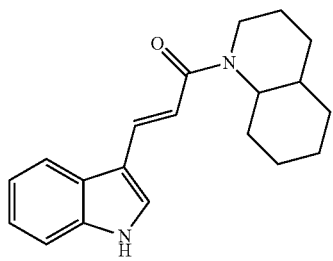

Synthetic Scheme-10

Intermediate 16

Intermediate 17

(8)

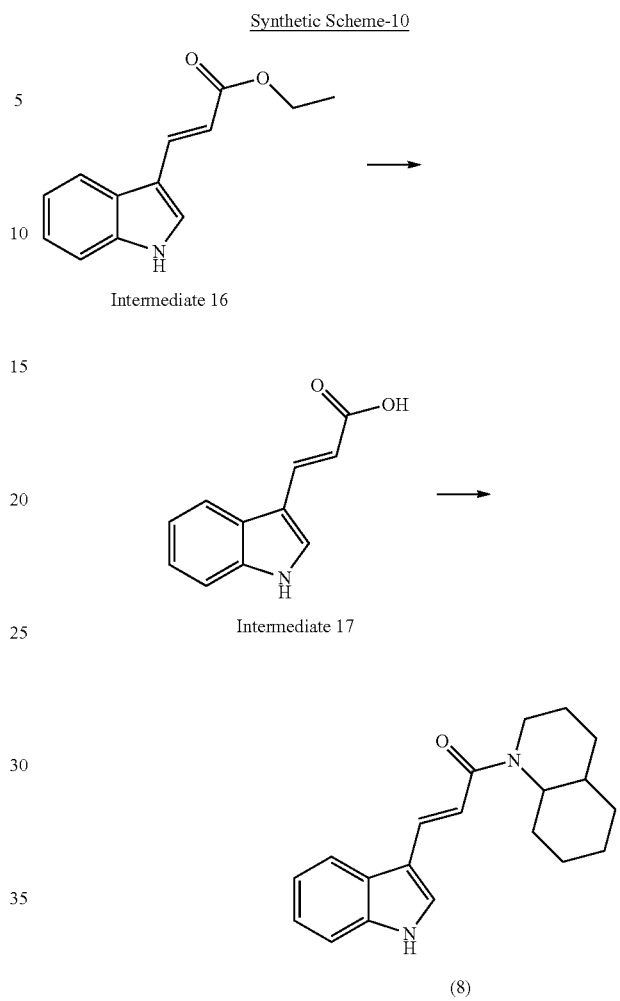

Synthesis of ethyl (2E)-3-(1H-indol-3-yl)prop-2-enoate (Intermediate-16)

Intermediate-16 was synthesized by following the procedure used to make Intermediate-7 (Scheme 4).

Synthesis of (2E)-3-(1H-indol-3-yl)prop-2-enoic acid (Intermediate-17)

Intermediate-17 was synthesized by following the procedure used to make Intermediate-9 (Scheme 4).

Synthesis of Compound (8)

Compound (8) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (8). $^1$H NMR (300 MHz, CDCl3): δ 8.50 (s, 1H), 7.80-7.88 (m, 3H), 7.34-7.38 (m, 2H), 6.78-6.89 (m, 2H), 4.55-4.76 (m, 1H), 3.89-4.18 (m, 1H), 3.05-3.48 (m, 1H), 2.06-2.71 (m, 1H), 1.29-1.81 (m, 12H). LC-MS (M+H)$^+$=309.1; HPLC purity: 98.83%.

Example 9

2-(1H-indol-3-yl)-1-(octahydroquinolin-1(2H)-yl)ethanone (9)

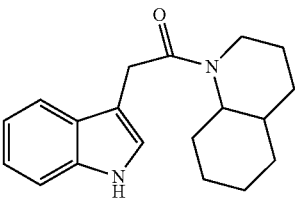
(9)

Synthetic Scheme-11

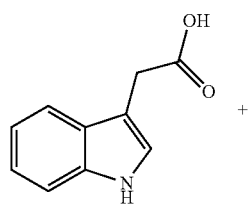

Intermediate 7

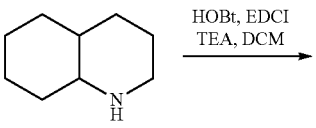

Starting material 4

HOBt, EDCI
TEA, DCM
→

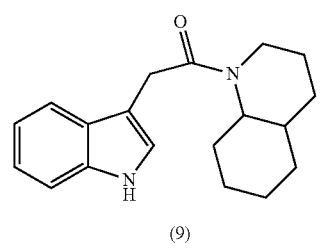
(9)

Synthesis of Compound (9)

Compound (9) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (9). $^1$H NMR (300 MHz, CDCl3): δ 8.20 (s, 1H), 7.61-7.63 (d, 1H), 7.34-7.36 (d, 1H), 7.05-7.21 (m, 3H), 4.57-4.73 (m, 1H), 3.69-3.88 (m, 3H), 3.10-3.50 (m, 1H), 2.60-3.00 (m, 1H), 1.01-1.90 (m, 12H). LC-MS (M+H)$^+$=297.3; HPLC purity: 98.39%.

Example 10

2-(5-fluoro-1H-indol-3-yl)-1-(octahydroquinolin-1(2H)-yl)ethanone (10)

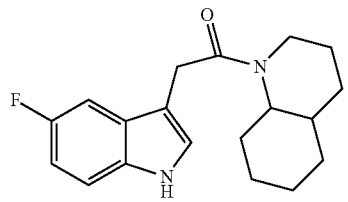
(10)

Synthesis of Compound (10)

Compound (10) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (10). $^1$H NMR (300 MHz, CDCl3): δ 8.45 (s, 1H), 7.20-7.30 (m, 2H), 7.00-7.15 (d, 1H), 6.95 (m, 1H), 4.53-4.73 (m, 1H), 3.64-3.91 (m, 2H), 2.60-3.03 (m, 1H), 1.29-1.84 (m, 14H). LC-MS (M+H)$^+$=315.1; HPLC purity: 89.32%.

Example 11

4-(1H-indol-3-yl)-1-(octahydroquinolin-1(2H)-yl)butan-1-one (11)

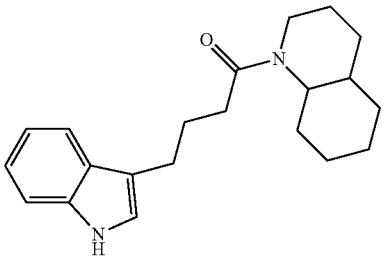
(11)

Synthetic Scheme-12

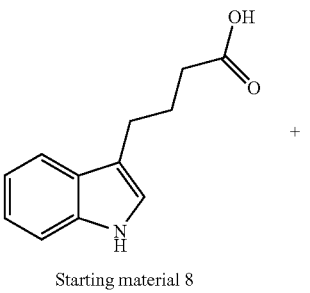

Starting material 8

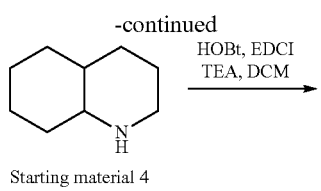

Starting material 4

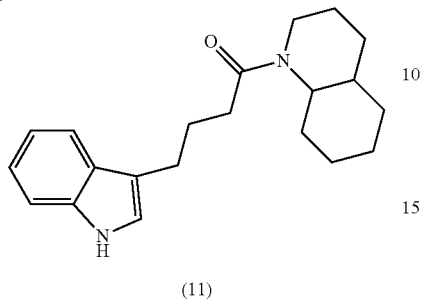

(11)

Synthesis of Compound (11)

Compound (11) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (11). $^1$H NMR (300 MHz, CDCl3): δ 8.04 (s, 1H), 7.59-7.62 (d, 1H), 7.34-7.36 (d, 1H), 7.07-7.20 (m, 2H), 7.00 (s, 1H), 4.48-4.75 (m, 1H), 3.48-3.62 (m, 1H), 2.88-3.15 (m, 1H), 2.80-2.85 (m, 2H), 2.31-2.52 (m, 2H), 2.02-2.11 (m, 2H), 1.51-1.80 (m, 7H), 1.23-1.38 (m, 6H). LC-MS (M+H)$^+$ =325.2; HPLC purity: 91.10%.

Example 12

3-(1H-indol-3-yl)-1-(4-methyloctahydroquinolin-1(2H)-yl)propan-1-one (HS_A_287) (12)

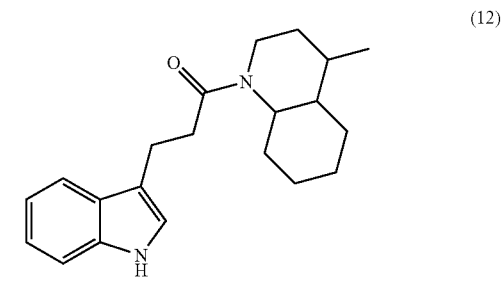 [SMILES: CC1CCN(C(=O)CCc2c[nH]c3ccccc23)C2CCCCC12]

Synthetic Scheme-13

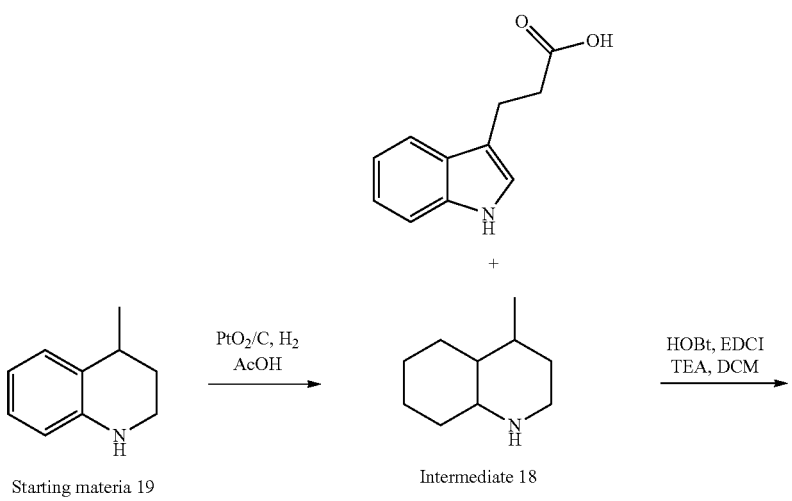

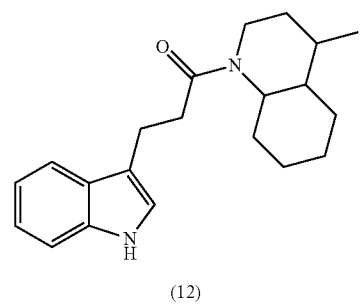

(12)

Synthesis of 4-methyldecahydroquinoline (Intermediate-18)

To a solution of Starting Material-9 (1 g, 6.9 mmol) in 15 mL of acetic acid, PtO$_2$ (0.793 g, 3.5 mmol) was added under N$_2$ atmosphere. N$_2$ gas was purged for 5 min and then was degassed (two times). This reaction mixture as then kept under hydrogen atmosphere at 60 psi for 12 hours. The mixture was filtered and basified with 10% NaOH solution, extracted with EtOAc and concentrated to give Intermediate-18 (700 mg).

Synthesis of Compound (12)

Compound (12) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (12). $^1$H NMR (300 MHz, CDCl3): δ 8.03 (s, 1H), 7.61-7.63 (d, 1H), 7.34-7.37 (d, 1H), 7.09-7.21 (m, 2H), 7.04 (s, 1H), 4.00 (m, 1H), 3.11-3.16 (t, 2H), 2.97 (m, 1H), 2.61-2.81 (m, 2H), 1.28-1.84 (m, 13H), 1.11-1.13 (d, 3H). LC-MS (M+H)+=325.2; HPLC purity: 99.15%.

Example 13

3-(1-methyl-1H-indol-3-yl)-1-(octahydroquinolin-1(2H)-yl)propan-1-one (13)

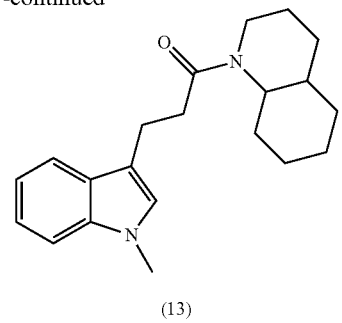

(13)

Synthesis of (13)

18-crown-6 ether (30 mg) and potassium tertiary butyl oxide (108 mg, 0.9 mmol) was taken in benzene at 4° C. To this mixture (96) (250 mg, 0.8 mmol) was added. The reaction mass was then stirred at room temperature for 15 minutes and was further cooled to 0° C. To this, Methyl iodide (171 mg, 1.2 mmol) dissolved in benzene was added. This reaction mixture was then stirred at room temperature for 15 hours. The mixture was filtered through celite and concentrated. Resulted crude material was purified by using silica gel column chromatography eluting with hexanes: EtOAc to give (13) (156 mg). $^1$H NMR (300 MHz, CDCl3): δ 7.48-7.52 (m, 1H), 6.97-7.18 (m, 3H), 6.78 (s, 1H), 4.42-4.60 (m, 1H), 3.60 (s, 3H), 3.37-3.54 (m, 1H), 2.99-3.05 (m, 2H), 2.49-2.74 (m, 3H), 0.99-1.52 (m, 13H). LC-MS (M+H)$^+$=325.2; HPLC purity: 98.37%.

Example 14

3-(1H-indol-2-yl)-1-(octahydroquinolin-1(2H)-yl) propan-1-one (14)

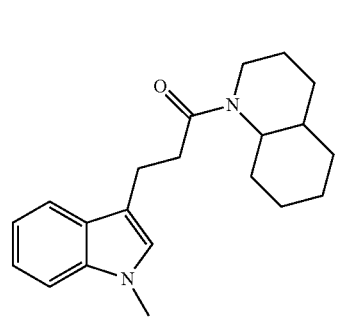

(13)

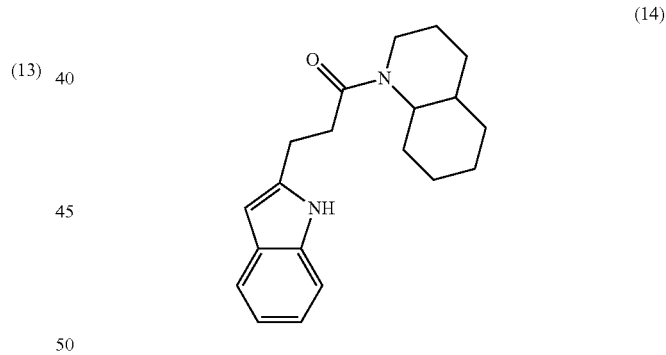

(14)

Synthetic Scheme-14

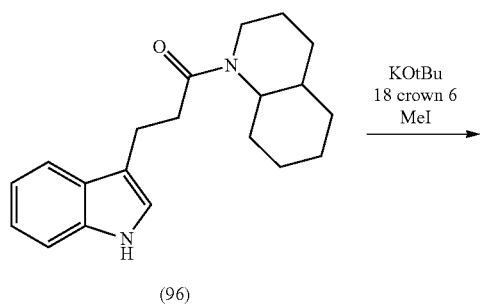

(96)

Synthetic Scheme-15

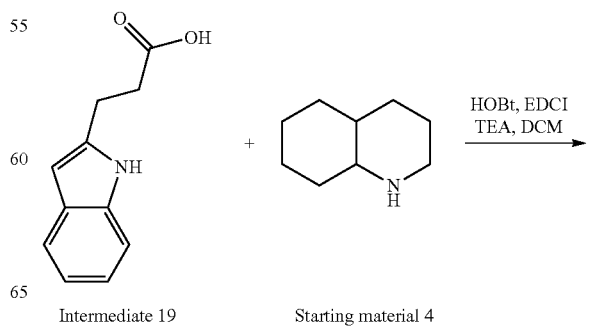

Intermediate 19      Starting material 4

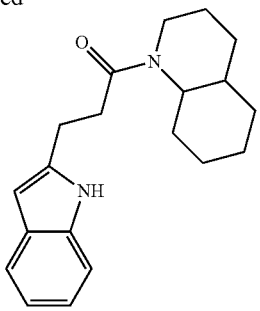

(14)

Synthesis of 3-(1H-indol-2-yl)propanoic acid (Intermediate-19)

Intermediate-19 was synthesized by following the procedure used to make Intermediate-9 (Scheme 4).

Synthesis of Compound (14)

Compound (14) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (14). $^1$H NMR (300 MHz, CDCl3) δ 9.28 (s, 1H), 7.41-7.43 (d, 1H), 7.21-7.24 (d, 1H), 6.92-7.03 (m, 2H), 6.11 (s, 1H), 4.50-4.63 (m, 1H), 3.43-3.63 (m, 1H), 2.50-3.02 (m, 5H), 1.16-1.67 (m, 13H). LC-MS (M+H)$^+$=311.2; HPLC purity: 99.23%.

Example 15

3-(5-hydroxy-1H-indol-3-yl)-1-(octahydroquinolin-1 (2H)-yl)propan-1-one (15)

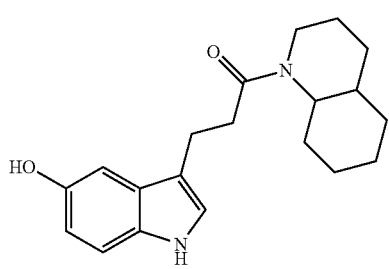

(15)

Synthetic Scheme-16

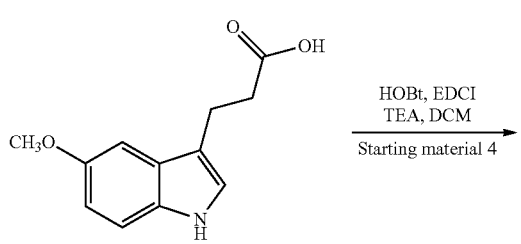

Synthesis of 3-(5-methoxy-1H-indol-3-yl)propanoic acid (Intermediate-20)

Intermediate-20 was synthesized by following the procedure used to make Intermediate-9 (Scheme 4).

Synthesis of 3-(5-methoxy-1H-indol-3-yl)-1-(octahydroquinolin-1(2H)-yl)propan-1-one (Intermediate-21)

Intermediate-21 was synthesized by following the procedure used to make Compound (1) (Scheme 2). The crude product was obtained by evaporating the organic layer under reduced pressure and was purified by silica gel column using Petroleum ether: Ethyl acetate as eluent to obtain Intermediate-21.

Synthesis of Compound (15)

A 100 mL RB flask fitted with magnetic stirrer was charged with 5 mL of DCM. Intermediate-21 (80 mg, 0.23 mmol) was then added to the stirred solvent. The resulting solution was cooled to −78° C. to which 1M solution of BBr$_3$ (188.6 mg, 0.74 mmol) in DCM was added. The reaction mass was further stirred at room temperature for 20 hours. After completion of the reaction (reaction monitored by TLC), reaction mass was diluted with 10 mL of water and extracted with DCM (2×10 mL). The DCM layer was dried over of anhydrous Na$_2$SO$_4$. Solvent was removed under reduced pressure. Crude material was purified by silica gel column chromatography eluting with hexanes: EtOAc to give Compound (15) (55 mg). $^1$H NMR (300 MHz, CDCl3): δ 7.79 (s, 1H), 7.11-7.15 (m, 1H), 6.93-6.97 (m, 2H), 6.68-6.73 (m, 1H), 5.21 (s, 1H), 4.44-4.62 (m, 1H), 3.45-3.59 (m, 1H), 2.94-3.03 (m, 2H), 2.66-2.91 (m, 1H), 2.53-2.63 (m, 2H), 1.63-1.76 (m, 6H), 1.25-1.35 (m, 7H). LC-MS (M+H)$^+$=327.2; HPLC purity: 87.98%.

Example 16

3-(5-fluoro-2-methyl-1H-indol-3-yl)-1-(octahydro-quinolin-1(2H)-yl)propan-1-one (16)

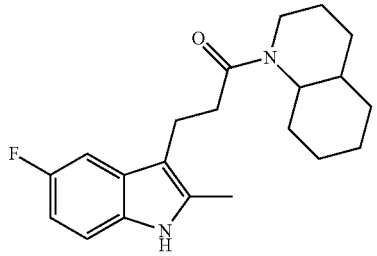
(16)

Synthetic Scheme-17

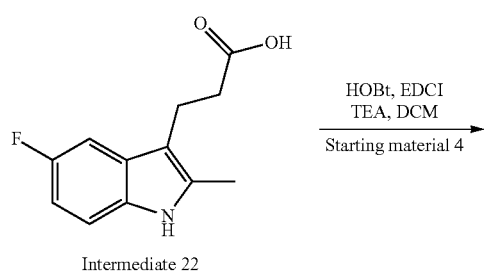

Intermediate 22

Synthesis of 3-(5-fluoro-2-methyl-1H-Indol-3-yl) propanoic acid (Intermediate-22)

Intermediate-22 was synthesized by following the procedure used to make Intermediate-9 (Scheme 4).

Synthesis of Compound (16)

Compound (16) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (16). $^1$H NMR (300 MHz, CDCl3): δ 7.81 (s, 1H), 7.10-7.18 (m, 2H), 6.81-6.88 (m, 1H), 4.49-4.68 (m, 1H), 3.47-3.53 (m, 1H), 2.94-3.11 (m, 2H), 2.48-3.11 (m, 3H), 2.37 (s, 3H), 1.30-1.78 (m, 13H). LC-MS (M+H)$^+$=343.2; HPLC purity: 90.88%.

Example 17

3-(2-methyl-1H-indol-3-yl)-1-(octahydroquinolin-1 (2H)-yl)propan-1-one (17)

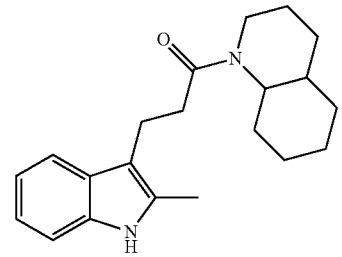
(17)

Synthetic Scheme-18

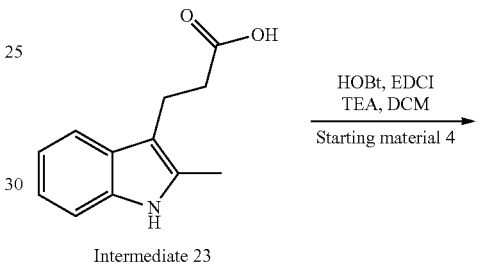

Intermediate 23

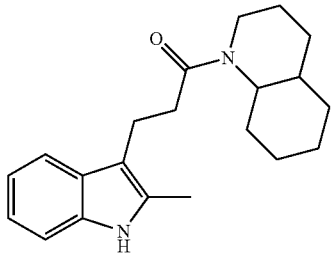
(17)

Synthesis of 3-(2-methyl-1H-indol-3-yl)propanoic acid (Intermediate-23)

Intermediate-23 was synthesized by following the procedure used to make Intermediate-9 (Scheme 4).

Synthesis of Compound (17)

Compound (17) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (17). $^1$H NMR (300 MHz, CDCl3): δ 7.89 (s, 1H), 7.40-7.44 (m, 1H), 7.17-7.19 (t, 1H), 6.98-7.05 (m, 2H), 4.43-4.62 (m, 1H), 3.38-3.47 (m, 1H), 2.94-3.04 (m, 2H), 2.68-2.86 (m, 1H), 2.51-2.66 (m, 2H), 2.29 (s, 3H), 1.52-1.70 (m, 6H), 1.21-1.34 (m, 7H). LC-MS (M+H)$^+$=325.2; HPLC purity: 94.48%.

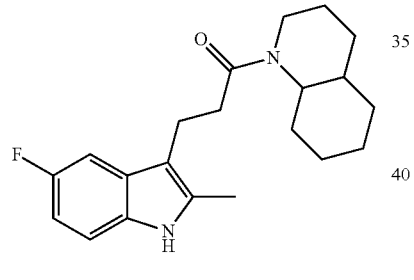
(16)

Example 18

3-(1H-indol-1-yl)-1-(octahydroquinolin-1(2H)-yl)propan-1-one (18)

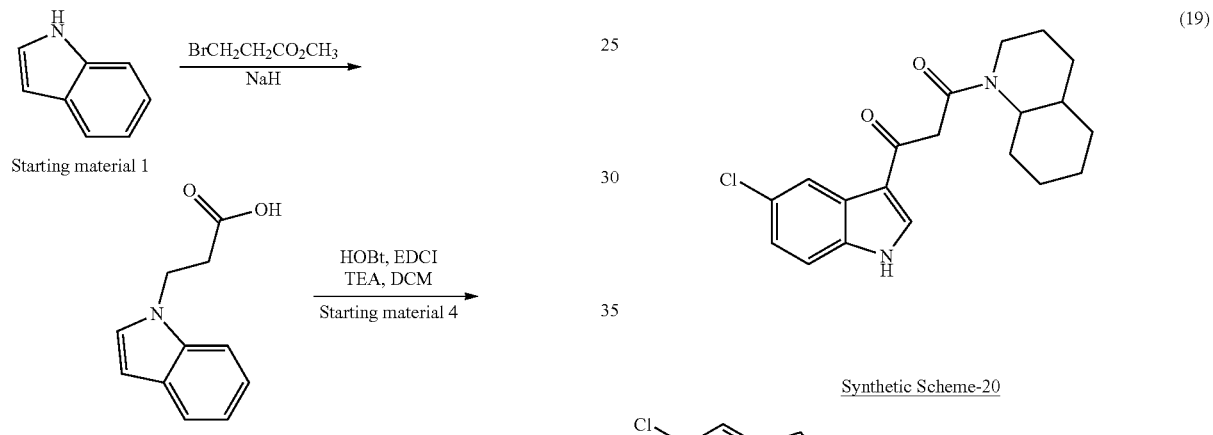

Synthesis of 3-(1H-indol-1-yl)propanoic acid (Intermediate-25)

A 100 ml RB flask fitted with magnetic stirrer was charged with 10 ml of DMF. To the stirred solvent Starting Material-1 (1.0 g, 8.53 mmol) followed by Sodium hydride (400 mg, 10.24 mmol) were added. The resulting solution was stirred at room temperature for 1 hour. To the above solution methyl-3-bromo-propionate (2.13 g, 12.79 mmol) was added and stirred at room temperature for 24 hours. After completion of the reaction (reaction monitored by TLC), reaction mass was diluted with 30 mL of ice cold water and washed with ether. Aqueous portion was acidified with 1N HCl (pH=2) and was then extracted with EtOAc and concentrated to give Intermediate-24 (900 mg).

Synthesis of Compound (18)

Compound (18) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (18). $^1$H NMR (300 MHz, CDCl3): δ 7.38-7.43 (t, 1H), 7.16-7.28 (m, 1H), 7.01-7.10 (m, 1H), 6.84-6.90 (m, 2H), 6.43-6.52 (m, 1H), 4.40-4.77 (m, 1H), 4.30-4.35 (t, 2H), 3.14-3.35 (m, 3H), 2.42-2.78 (m, 2H), 1.57-1.61 (t, 4H), 1.28-1.49 (m, 3H), 1.06-1.16 (m, 5H). LC-MS $(M+H)^+$=311.1; HPLC purity: 98.08%.

Example 19

1-(5-chloro-1H-indol-3-yl)-3-(octahydroquinolin-1(2H)-yl)propane-1,3-dione (19)

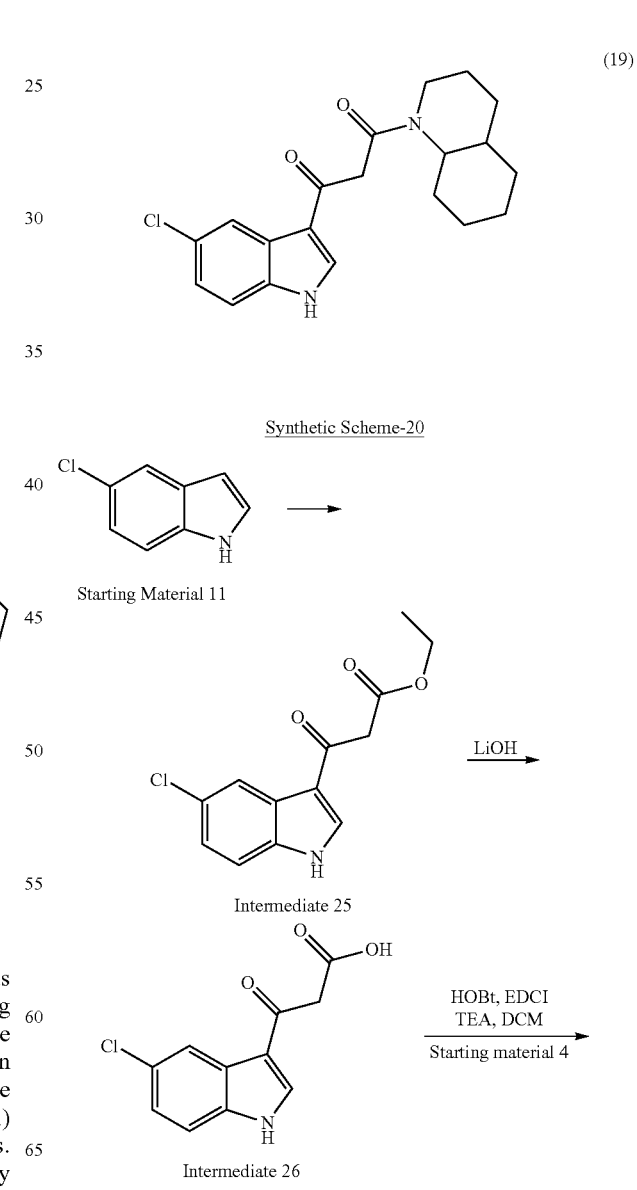

121

-continued

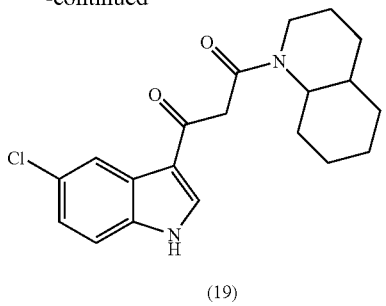

(19)

Synthesis of ethyl 3-(5-chloro-1H-indol-3-yl)-3-oxopropanoate (Intermediate-25)

To a 50 mL two neck RB 10 mL of dichloromethane was added. To this solvent, ethylmalonylchloride (1.0 mL, 8.24 mmol) was added and the reaction mixture thus obtained was cooled to 0° C. To the cooled reaction mixture, TiCl$_4$ (0.9 ml, 8.24 mmol) was slowly added and the mixture was stirred at room temperature for 20 min. The reaction mixture was once again cooled to 0° C. and to the cooled mixture Starting Material-11 (0.5 g, 3.29 mmol) dissolved in 2 mL of dichloroethane was added and stirred at room temperature for 3 hours. The reaction mass was quenched with 1N HCl solution and extracted with ethyl acetate. Organic layers were concentrated, purified by silica-gel column chromatography eluting with hexanes: EtOAc to give Intermediate-25 (566 mg).

Synthesis of ethyl 3-(5-chloro-1H-indol-3-yl)-3-oxopropanoic acid (Intermediate-26)

Intermediate-26 was synthesized by following the procedure used to make intermediate-3 (1) (Scheme 1).

Synthesis of Compound (19)

Compound (19) was synthesized by following the procedure used to make Compound (1) (Scheme 2). The crude product was obtained by evaporating the organic layer under reduced pressure and was purified by silica gel column using Petroleum ether: Ethyl acetate (1:4) as eluent to obtain Compound (19). $^1$H NMR (300 MHz, CDCl3): δ 10.58 (s, 1H), 8.22 (s, 1H), 7.96 (s, 1H), 7.10 (m, 2H), 4.00-4.58 (m, 1H), 3.31-3.84 (m, 3H), 2.50-3.10 (m, 1H), 1.16-1.82 (m, 13H). LC-MS (M+H)$^+$=359.1; HPLC purity: 90.09%.

Example 20

3-(4-methyl-1H-indol-3-yl)-1-(octahydroquinolin-1(2H)-yl)propan-1-one (20)

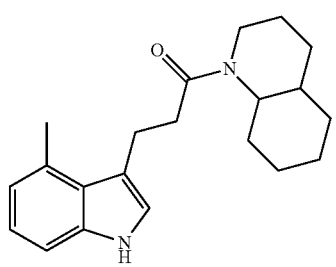

(20)

122

Synthetic Scheme-21

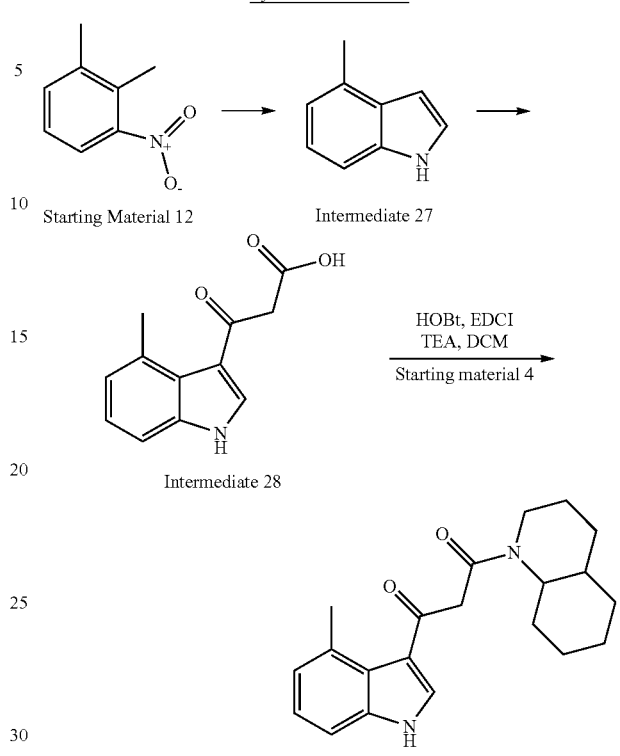

Synthesis of 4-methyl-1H-indole (Intermediate-27)

A 100 mL RB flask fitted with magnetic stirrer and reflux condenser was charged with 60 mL of DMF. To the stirred solvent Starting Material-12 (5 g, 33 mmol) was added followed by addition of Dimethyl formamide dimethyl acetal (13.1 mL, 99.2 mmol). To this reaction mixture Pyrrolidine (3.2 mL, 39.6 mmol) was added and it was heated at 120° C. under Nitrogen atmosphere for 21 hours. After completion of the reaction the mixture was cooled to room temperature and solvent was removed under reduced pressure. The resulting crude mass was taken in ether (250 mL) and was washed with water (50 mL×3) and saturated brine solution (50 mL) and the organic layer was dried over anhydrous sodium sulphate and concentrated. Resulted crude material was taken in Ethyl acetate (50 mL). To this 10% Pd/C (1.0 g, 10% w/w) was added and hydrogenated in a parr shaker for 2 hours. After completion of the reaction (reaction monitored by TLC), the mixture was filtered through celite bed. Filtrate was concentrated to give crude product, which was purified by column chromatography on silica gel (120 meshe) using Petroleum ether (60-80) and ethyl acetate as eluent to give Intermediate-27 (1.2 g).

Synthesis of 3-(4-methyl-1H-Indo)-3-yl)propanoic acid (Intermediate-28)

A 100 mL RB flask fitted with magnetic stirrer was charged with 2.5 mL of acetic acid. To the stirred solvent acetic anhydride 2.0 mL was added followed by addition of acrylic acid (1.8 mL, 27.4 mmol). To this stirred mixture, Intermediate-27 (1.2 g, 9.15 mmol) was added and the reaction mixture was further stirred at room temperature for 1 week. After completion of the reaction (reaction was monitored by TLC), reaction mass was basified using 5N NaOH (5 mL) and washed with Ethyl acetate (100 mL×2). The aqueous layer was acidified with Concentrated HCl (3 ML) and was extracted using Ethyl acetate (100 mL×3). The combined ethyl acetate layer was washed with brine solution and concentrated to give Intermediate-28 (350 mg).

Synthesis of Compound (20)

Compound (20) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (20). $^1$H NMR (300 MHz, CDCl3): δ 8.23 (s, 1H), 7.08-7.11 (t, 1H), 6.93-6.99 (m, 1H), 6.88-6.89 (d, 1H), 6.73-6.77 (t, 1H), 4.46-4.50 (m, 1H), 3.53-3.60 (m, 1H), 3.46-3.51 (m, 2H), 2.71-2.92 (m, 1H), 2.45-2.87 (m, 6H), 1.71-1.77 (m, 5H), 1.29-1.39 (m, 7H). LC-MS (M+H)$^+$=325.2; HPLC purity: 96.28%.

Example 21

3-(1H-indol-3-yl)-1-(octahydroisoquinolin-2(1H)-yl)propan-1-one (21)

(21)

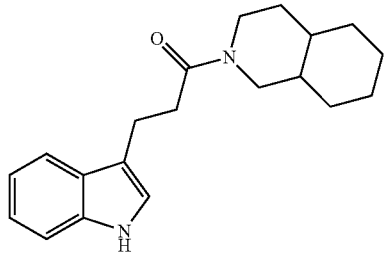

Synthesis of Compound (21)

Compound (21) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (21). $^1$H NMR (300 MHz, CDCl3): δ 8.59 (s, 1H), 7.49-7.52 (d, 1H), 7.24-7.26 (d, 1H), 6.98-7.10 (m, 2H), 6.90 (s, 1H), 4.44-4.66 (m, 1H), 3.40-3.70 (m, 1H), 3.01-3.06 (m, 2H), 1.99-2.81 (m, 4H), 0.44-1.63 (m, 12H). LC-MS (M+H)$^+$=311.0; HPLC purity: 96.03%.

Example 22

1-(octahydro-4H-1,4-benzoxazin-4-yl)-3-(1H-pyrrolo[2,3-b]pyridin-3-yl)butan-1-one (22)

(22)

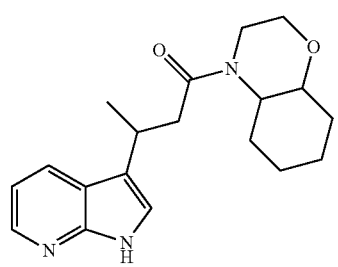

Synthetic Scheme-22

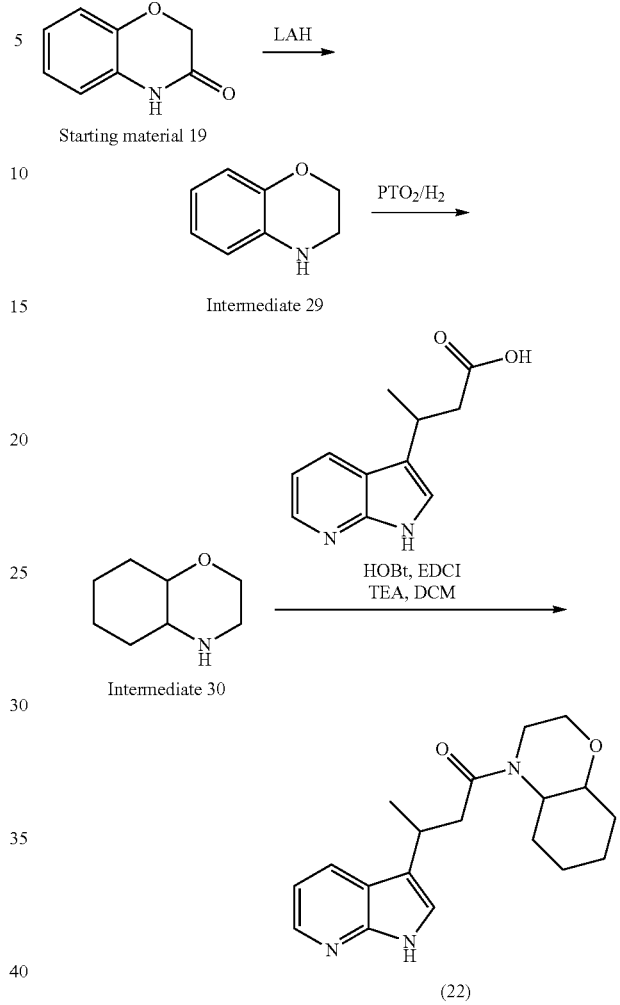

Synthesis of 3,4-dihydro-2H-1,4-benzoxazine (Intermediate-29)

A solution of Starting Material-13 (5 g, 33.5 mmol) in tetrahydrofuran (50 mL) was slowly added to a suspension of lithium aluminum hydride (3.18 g, 83.8 mmol) under N$_2$ atmosphere at 0° C. The reaction mixture was refluxed for 16 h. The reaction mixture was diluted with EtOAc, quenched with 15% aqueous sodium hydroxide solution at 0° C., and extracted with ether, and concentrated to give Intermediate-29 as brown liquid (4.3 g).

Synthesis of octahydro-2H-1,4-benzoxazine (Intermediate-30

To a solution of Intermediate-29 (1.5 g, 11.1 mmol) in 20 mL of acetic acid, 10% PtO$_2$ (252 mg) was added, and hydrogenated at 60 psi for 5 h. The mixture was filtered and basified with 10% NaOH solution, extracted with diethyl ether, dried over sodium sulphate and concentrated to give Intermediate-30 as brown liquid (520 mg).

Synthesis of 3-(1H-pyrrolo[2,3-b]pyridin-3-yl)butanoic acid (Intermediate-31)

Intermediate-31 was synthesized by following the procedure used to make Intermediate-3 (Scheme 1).

Synthesis of Compound (22)

Compound (22) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (22). $^1$H NMR (300 MHz, DMSO-d6): δ 11.31 (s, 1H), 8.15-8.17 (m, 1H), 7.95-7.99 (m, 1H), 7.25-7.29 (d, 1H), 6.98-7.04 (m, 1H), 3.99-4.10 (m, 1H), 3.43-3.74 (m, 4H), 2.63-3.10 (m, 3H), 1.15-1.99 (m, 12H). LC-MS (M+H)$^+$=328.2; HPLC purity: 95.42%.

Example 23

N-tert-butyl-2-[3-(1H-indol-3-yl)propanoyl]decahydroisoquinoline-3-carboxamide (23)

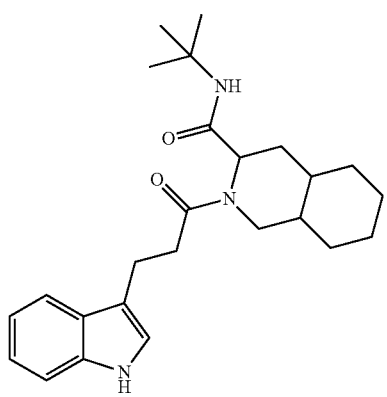

(23)

Synthetic Scheme-23

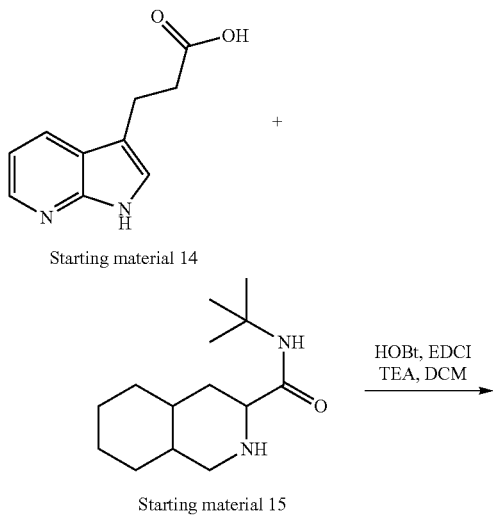

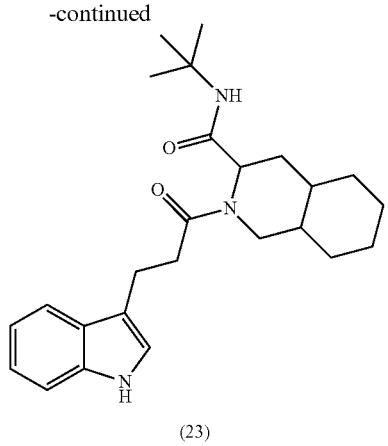

(23)

Synthesis of Compound (23)

Compound (23) was synthesized by following the procedure used to make Compound (1) (Scheme 2). The crude product was obtained by evaporating the organic layer under reduced pressure and was purified by silica gel column using Petroleum ether: Ethyl acetate (1:4) as eluent to obtain Compound (23). $^1$H NMR (300 MHz, CDCl3): 7.99 (s, 1H), 7.48-7.55 (m, 1H), 7.28-7.30 (d, 1H), 7.03-7.15 (m, 2H), 6.97 (s, 1H), 5.57-5.72 (d, 1H), 4.95 (s, 1H), 3.24-4.33 (m, 3H), 3.05-3.37 (m, 1H), 2.09-2.86 (m, 3H), 1.15-1.56 (m, 20H). LC-MS (M–H)$^+$=408.2; HPLC purity: 98.47%.

Example 24

3-(5-hydroxy-1-methyl-1H-indol-3-yl)-1-(octahydroquinolin-1(2H)-yl)propan-1-one (24)

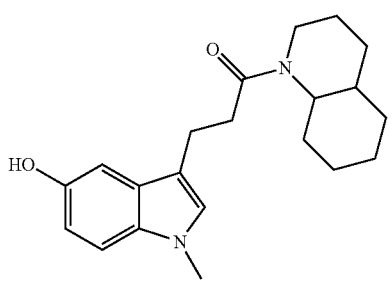

(24)

Synthesis of Compound (24)

Compound (24) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (24). $^1$H NMR (300 MHz, CDCl3) δ 6.95-7.02 (m, 2H), 6.76-6.79 (d, 1H), 6.70-6.79 (d, 1H), 4.44-4.62 (m, 1H), 3.56-3.57 (d, 3H), 3.41-3.50 (m, 1H), 2.91-3.06 (m, 2H), 2.67-2.84 (m, 1H), 2.48-2.65 (m, 2H), 1.57-1.71 (m, 4H), 1.46-1.47 (d, 2H), 1.18-1.34 (m, 7H). LC-MS (M+H)$^+$=341.2; HPLC purity: 97.31%.

Example 25

2-(1H-indol-3-yloxy)-1-(octahydroquinolin-1(2H)-yl)propan-1-one (25)

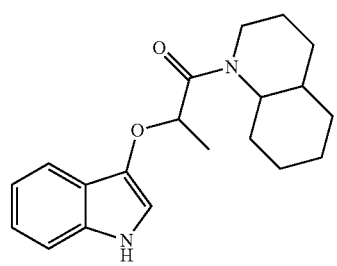
(25)

Synthetic Scheme-24

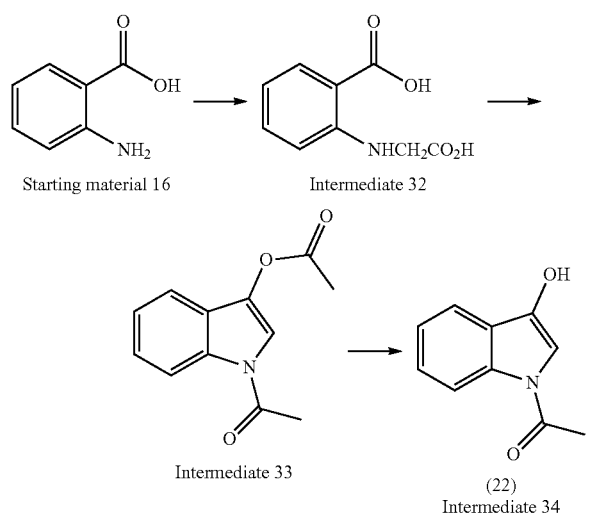

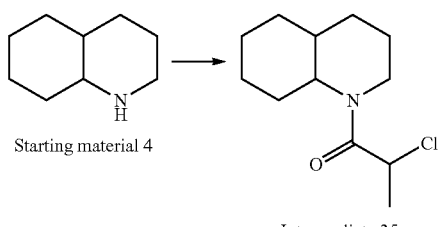

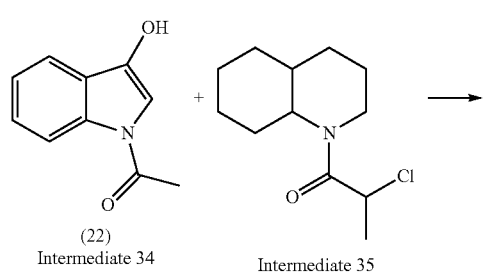

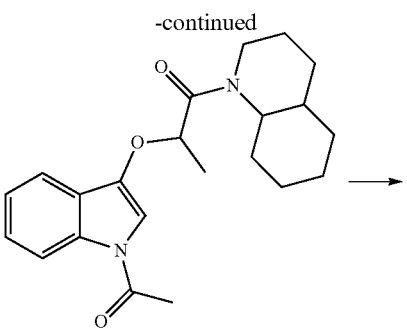
Intermediate 36

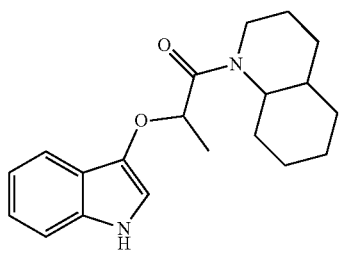
(25)

Synthesis of 2-[(carboxymethyl)amino]benzoic acid (Intermediate-32)

To a 500 mL 2 neck RB flask fitted with magnetic stirrer, Starting Material-16 (20 g, 145 mmol) was added lot wise to a stirred solution of $K_2CO_3$ (83 g, 602 mmol) in water (140 mL) followed by chloroacetic acid (13.7 g, 145 mmol) under $N_2$ atmosphere at room temperature for about 30 minutes. Then reaction mass was heated at 90° C. for 16 hours. After the reaction was cooled to room temperature the reaction mass pH was adjusted to 4-5 using citric acid. The solid material was then filtered and dried under vacuum oven at 70° C. for 12 hours to give Intermediate-32 (23 g) as brownish solid.

Synthesis of 1-acetyl-1H-indol-3-yl acetate (Intermediate-33)

To a 500 mL 2 neck RB flask fitted with magnetic stirrer, acetic anhydride (110 mL, 1200 mmol) was added slowly at 0° C. to a stirred solution of triethylamine (170 mL, 1242 mmol) and Intermediate-32 (23 g, 117 mmol) under $N_2$ atmosphere. Reaction mass was stirred at room temperature for 5 hours and was further heated at 80° C. for 16 hours. Then the reaction was cooled to 0° C. and was extracted with ethyl acetate (4×150 mL). Organic layer was washed with brine solution, dried over $Na_2SO_4$ and concentrated. Crude material was purified by silica gel column eluting with hexanes: EtOAc to give Intermediate-33 (5.5 g) as brown solid.

Synthesis of 1-(3-hydroxy-1H-indol-1-yl)ethanone (Intermediate-34)

To a 50 mL 2 neck RB flask fitted with magnetic stirrer, ethanol and water was added. To the solvent, the stirred mixture of Intermediate-33 (5 g, 23 mmol), $Na_2SO_3$ (11.6 g, 426 mmol) was added. The reaction mixture was heated at 80° C. for 12 hours. After completion of reaction (reaction monitored by TLC), reaction mass was quenched with water and extracted with Ethyl Acetate (3×100 mL). The organic layer was washed with saturated brine solution (15 mL), dried over anhydrous Na$_2$SO$_4$, and concentrated. The crude product was purified by silica gel column eluting with hexanes: EtOAc to give Intermediate-34 (1.5 g) as pink solid.

Synthesis of 2-chloro-1-(octahydroquinolin-1(2H)-yl)propan-1-one (Intermediate-35)

To a 50 mL 2 neck RB flask fitted with magnetic stirrer containing reaction mixture of Starting Material-4 (0.7 g, 5 mmol), EDCI (1.17 g, 6.3 mmol) and 1-hydroxy benzothioazole (0.762 g, 5.6 mmol) in DCM at 0° C., triethylamine (1.3 mL, 9.9 mmol), was added followed by addition of 2-chloropropanoic acid (0.543 g, 5 mmol). Resulted reaction mixture was stirred at room temperature for 16 hours. After completion of reaction (reaction monitored by TLC), reaction mass was quenched with water and extracted with DCM (3×25 mL). The organic layer was washed with saturated brine solution (15 mL), dried over anhydrous Na$_2$SO$_4$, and concentrated. The crude product was purified by silica gel column eluting with hexanes: EtOAc to give Intermediate-35 (0.5 g) as liquid material.

Synthesis of 2-[(1-acetyl-1H-Indol-3-yl)oxy]-1-(octahydroquinolin-1(2H)-yl)propan-1-one (Intermediate-36)

To a 50 mL 2 neck RB flask fitted with magnetic stirrer Intermediate-34 (0.05 g, 0.28 mmol) and DMSO (3 ml) were added at 0° C. under nitrogen atmosphere. To this Potassium t-Butoxide (0.05 g, 0.46 mmol) was added and stirred for 1 hour, then Intermediate-35 (0.065 g, 0.28 mmol) was added. Resulting mixture stirred at room temperature for 16 hours. After reaction (reaction monitored by TLC), quenched with water and extracted with ethyl acetate (3×10 mL). The organic layer was washed with saturated brine solution (10 mL), dried over anhydrous Na$_2$SO$_4$, and concentrated to give Intermediate-36 (100 mg).

Synthesis of Compound (25)

To a stirred solution of Intermediate-36 (0.1 g, 0.27 mmol) in methanol and water was added K$_2$CO$_3$ (0.15 g, 1.0 mmol), and stirred at room temperature for 3 hours. After completion of the reaction (reaction monitored by TLC), quenched with water and extracted with ethyl acetate (3×10 mL). The organic layer was washed with saturated brine solution (15 mL), and concentrated. The crude product was purified by silica gel column eluting with hexanes: EtOAc to give Compound (25) (6 mg) as a sticky solid. $^1$H NMR (300 MHz, CDCl3): δ 7.55-7.58 (d, 2H), 7.19-7.22 (d, 1H), 7.08-7.013 (t, 1H), 6.98-7.02 (t, 1H), 6.67-6.68 (d, 1H), 4.75-4.85 (m, 1H), 4.10-4.56 (m, 2H), 2.52-2.96 (m, 1H), 1.18-1.60 (m, 16H). LC-MS (M+H)$^+$=327.2; HPLC purity: 99.99%.

Example 26

1-[3-(1H-indol-3-yl)propanoyl]octahydroquinolin-4(1H)-one (26)

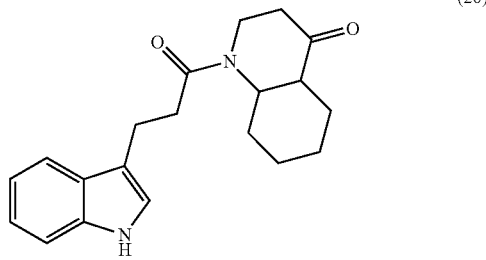

(26)

Synthetic Scheme-25

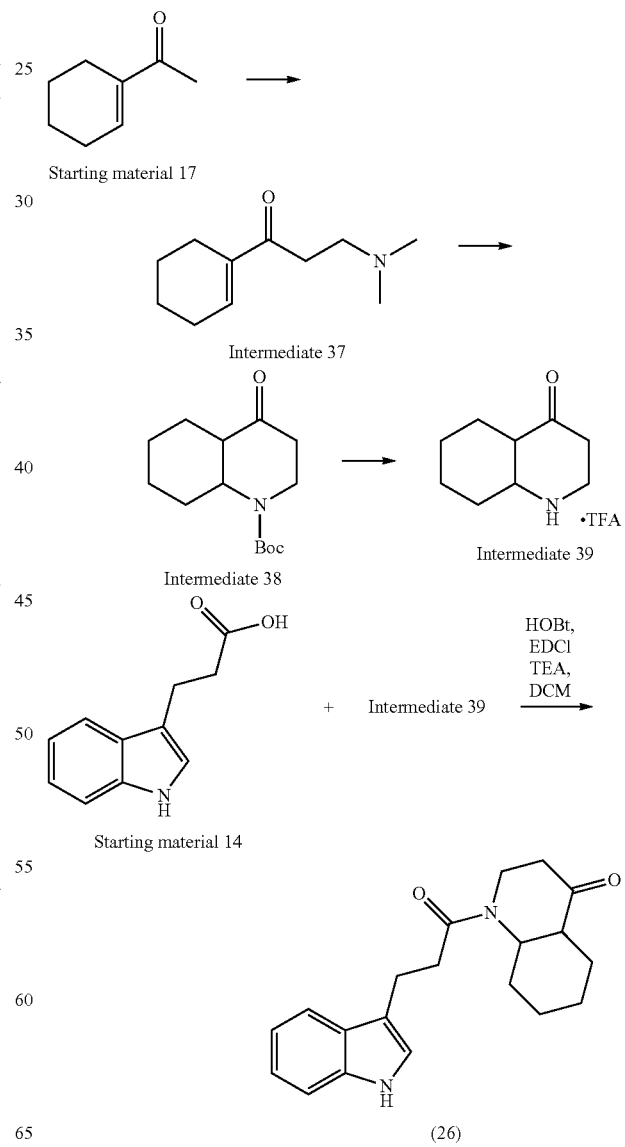

Synthesis of 1-(cyclohex-1-en-1-yl)-3-(dimethyl-amino)propan-1-one (Intermediate-37)

Starting Material-17 (5 g, 40.3 mmol), dimethyl amine hydrochloride (3.62 g, 44.3 mmol), paraformaldehyde (2.42 g, 80.5 mmol), 37% aqueous HCl (0.2 mL, 40.3 mmol) were combined in ethanol (5 mL). The resultant mixture was heated to reflux in a sealed tube for 20 hours. The reaction was then concentrated, basified with aq. NaOH and extracted with CHCl3. The combined organic layers were dried over $Na_2SO_4$, concentrated to give Intermediate-37 (4.78 g) as light orange oily material.

Synthesis of tert-butyl 4-oxooctahydroquinolin-1(2H)-carboxylate (Intermediate-38)

Intermediate-37 (4.2 g, 23.2 mmol), was taken in 1,4-dioxane (3 mL), and concentrated $NH_4OH$ (5 mL) in a sealed tube. The vessel was sealed and then heated in an oil bath at 120° C. for 18 hours. Then reaction mixture was cooled to room temperature, and concentrated. The residue was taken up in $CHCl_3$, dried over $Na_2SO_4$ and concentrated to give crude material (3.35 g). This crude material was treated with $Boc_2O$ (4.8 g, 29.8 mmol), in presence of TEA (9 mL, 64.5 mmol), in THF (10 mL) at room temperature for 16 hours. After completion of reaction, the reaction mixture was diluted with water, extracted with EtOAc and concentrated to give crude material, which is purified by silica gel column chromatography eluting with hexanes: EtOAc to give Intermediate-38 (1.34 g).

Synthesis of octahydroquinolin-4(1H)-one trifluoroacetic acid salt (Intermediate-39)

At 0° C., Trifluoro acetic acid (0.162 g, 1.42 mmol) was added drop wise to a solution of Intermediate-38 (0.3 g, 1.18 mmol) in DCM (3 mL), under nitrogen atmosphere. Resultant mixture was stirred at RT for 16 h. After completion the reaction mixture was concentrated to give Intermediate-39 (352 mg).

Synthesis of Compound (26)

Compound (26) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (26). $^1$H NMR (300 MHz, CDCl3): δ 8.05 (s, 1H), 7.53-7.58 (t, 1H), 7.27-7.29 (d, 1H), 7.02-7.19 (m, 2H), 6.98 (s, 1H), 4.60-4.92 (m, 1H), 3.69-3.83 (m, 1H), 306-3.37 (m, 3H), 2.63-2.92 (m, 2H), 1.35-2.25 (m, 11H). LC-MS $(M+H)^+$=325.2; HPLC purity: 93.87%.

Example 27

3-(1,4-dimethyl-1H-indol-3-yl)-1-(octahydroquinolin-1(2H)-yl)propan-1-one (27)

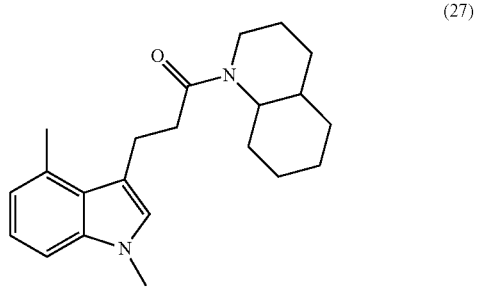

(27)

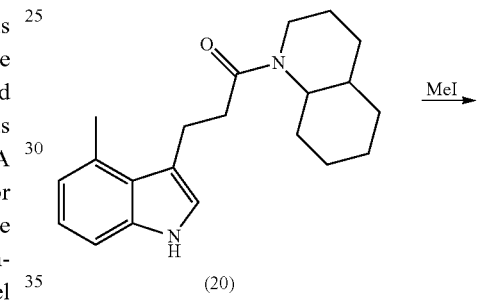

Synthetic Scheme-26

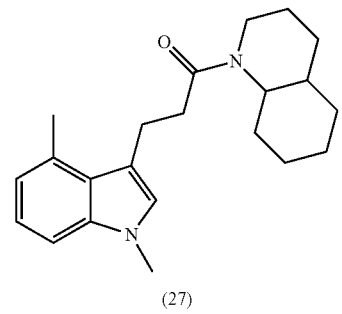

Synthesis of Compound (27)

Under $N_2$ atmosphere to a stirred solution of (20) (70 mg 0.2157 mmol) in 5 mL of dry THF, sodium hydride (22 mg, 0.5394 mmol) was added, and stirred for 30 minutes at room temperature. To this reaction mixture methyl iodide (77 mg, 0.5394 mmol) was added at 0° C. The mixture was stirred at room temperature for 3 hours. The mixture was quenched with crushed ice and extracted with ethyl acetate, and concentrated. Resulting crude material was purified by silica-gel column chromatography eluting with hexanes: EtOAc to give Compound (27) (55 mg). $^1$H NMR (300 MHz, CDCl3): δ 6.98-7.03 (m, 2H), 6.76-6.78 (m, 2H), 3.47-4.63 (m, 1H), 3.62-3.63 (d, 3H), 3.15-3.20 (m, 2H), 2.63-2.92 (m, 4H), 2.46-2.60 (m, 2H), 1.23-1.93 (m, 14H). LC-MS $(M+H)^+$=339.2; HPLC purity: 99.79%.

Example 28

3-(1-cyclopropyl-4-methyl-1H-indol-3-yl)-1-(octahydroquinolin-1(2H)-yl)propan-1-one (28)

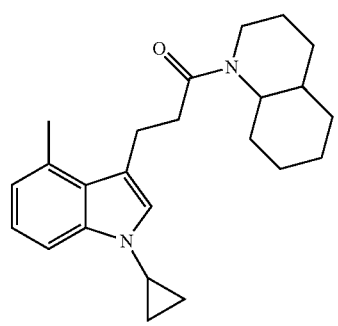

(28)

Synthesis of Compound (28)

Compound (28) was synthesized by following the procedure used to make Compound (27) (Scheme 26). The crude product was obtained by evaporating the organic layer under reduced pressure and was purified by silica gel column using Petroleum ether: Ethyl acetate as eluent to obtain Compound (28). $^1$H NMR (300 MHz, CDCl3): δ 6.96-7.04 (m, 2H), 6.80-6.81 (m, 1H), 6.64-6.67 (m, 1H), 5.34-5.41 (m, 1H), 4.49-4.63 (m, 1H), 3.49-3.63 (m, 1H), 3.18-3.22 (m, 2H), 2.64-2.74 (m, 4H), 2.46-2.60 (m, 2H), 1.23-1.80 (m, 17H). LC-MS (M+H)$^+$=365.3; HPLC purity: 98.79%.

Example 29

3-[1-(cyclopropylmethyl)-4-methyl-1H-indol-3-yl]-1-(octahydroquinolin-1(2H)-yl)propan-1-one (29)

(29)

Synthesis of Compound (29)

Compound (29) was synthesized by following the procedure used to make Compound (27) (Scheme 26). The crude product was obtained by evaporating the organic layer under reduced pressure and was purified by silica gel column using Petroleum ether: Ethyl acetate as eluent to obtain Compound (29). $^1$H NMR (300 MHz, CDCl3): δ 7.08-7.10 (d, 1H), 6.97-7.02 (m, 1H), 6.91-6.93 (d, 1H), 6.75 (m, 1H), 4.45-4.63 (m, 1H), 3.81-3.83 (d, 2H), 3.45-3.58 (m, 1H), 3.16-3.21 (m, 2H), 2.49-2.77 (m, 6H), 1.23-1.97 (m, 14H), 0.51-0.54 (m, 2H), 0.26-0.27 (m, 2H). LC-MS (M+H)$^+$=379.3; HPLC purity: 99.43%.

Example 30

1-(4-methyl-1H-indol-3-yl)-3-(octahydroquinolin-1(2H)-yl)propane-1,3-dione (30)

(30)

Synthesis of Compound (30)

Compound (30) was synthesized by following the procedure used to make Compound (19) (Scheme 20). The crude product was obtained by evaporating the organic layer under reduced pressure and was purified by silica gel column using Petroleum ether: Ethyl acetate as eluent to obtain Compound (30). $^1$H NMR (300 MHz, CDCl3): δ 9.25-9.31 (d, 1H), 8.26-8.30 (m, 1H), 7.06-7.15 (m, 2H), 6.95-6.97 (d, 1H), 4.12-4.60 (m, 1H), 3.90 (s, 2H), 3.59-4.16 (m, 1H), 2.52-3.06 (m, 1H), 2.75-2.76 (d, 3H), 1.93-2.30 (m, 1H), 1.26-1.98 (m, 12H). LC-MS (M+H)$^+$=339.2; HPLC purity: 98.52%.

Example 31

(2E)-3-(1H-indol-3-yl)-2-(octahydroquinolin-1(2H)-ylcarbonyl)prop-2-enenitrile (31)

(31)

Synthetic Scheme-27

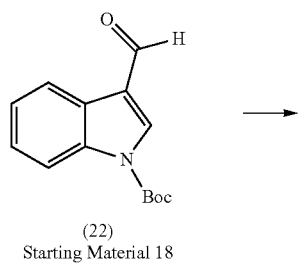

(22)
Starting Material 18

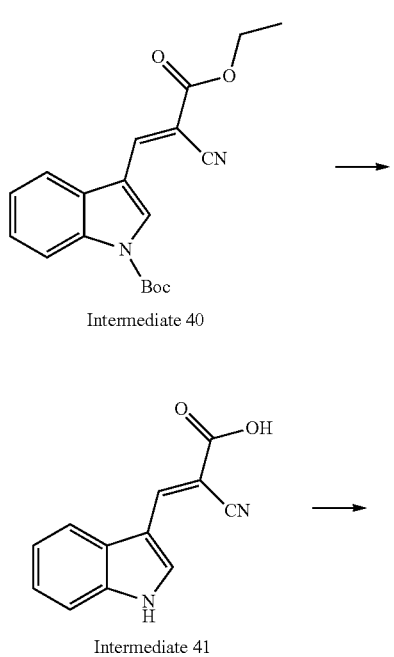

Intermediate 40

Intermediate 41

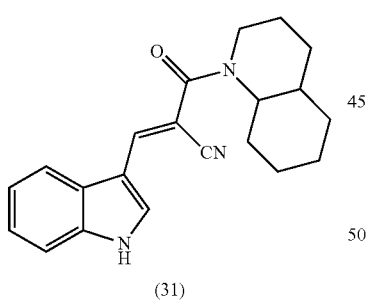

(31)

Synthesis of tert-butyl 3-[(1Z)-2-cyano-3-ethoxy-3-oxoprop-1-en-1-yl]-1H-indole-1-carboxylate (Intermediate-40)

A 50 mL RB flask fitted with magnetic stirrer was charged with isoproponol (10 mL) and Starting Material-18. To this ethyl cyano acetate (0.255 g, 2.2 mmol) and potassium hydroxide (0.12 g, 2.2 mmol) were added at 0° C. and was stirred for 1 hour. After completion of the reaction (reaction monitored by TLC), reaction mixture was quenched with Ice-Water 350 mL and extracted with ethyl acetate. The organic layer washed with brine solution and dried by anhydrous sodium sulphate and concentrated to give Intermediate-40 (600 mg).

Synthesis of (2Z)-2-cyano-3-(1H-indol-3-yl)prop-2-enoic acid (Intermediate-41)

A 100 mL RB flask fitted with magnetic stirrer was charged with 5 mL of Ethanol and Intermediate-40 (0.6 g, 1.7 mmol). To this NaOH (0.20 g, 2.4 mmol) in 0.5 mL of water was added and the reaction mixture was stirred at room temperature for 3 hours. After completion of the reaction (reaction monitored by TLC), the reaction mixture was concentrated. The resulted crude was acidified with 1N HCl (pH 1-2), and extracted with ethyl acetate. Organic layers were washed with brine solution and dried by anhydrous sodium sulphate and concentrated to give Intermediate-41(400 mg).

Synthesis of Compound (31)

Compound (31) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (31). $^1$H NMR (300 MHz, CDCl3): δ 8.94 (s, 1H), 8.44 (s, 1H), 8.13 (s, 1H), 7.68-7.71 (d, 1H), 7.37-7.40 (d, 1H), 7.21-7.26 (m, 2H), 4.30-4.48 (m, 1H), 3.90-4.08 (m, 1H), 2.75-3.18 (m, 1H), 1.30-1.86 (m, 13H). LC-MS (M+H)$^+$=334.2; HPLC purity: 94.91%.

Example 32

1-[3-(4-methyl-1H-indol-3-yl)propanoyl]octahydroquinolin-4(1H)-one (32)

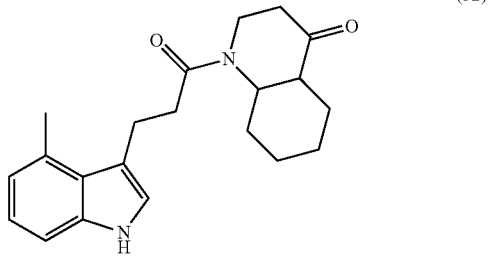

Synthesis of Compound (32)

Compound (32) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (32). $^1$H NMR (300 MHz, CDCl3): δ 7.92 (s, 1H), 7.11-7.14 (d, 1H), 6.95-6.99 (m, 2H), 6.79 (s, 1H), 4.62-4.94 (m, 1H), 4.04-4.06 (d, 3H), 3.57-3.87 (m, 1H), 3.25-3.39 (m, 2H), 2.57-2.66 (m, 4H), 1.43-2.26 (m, 10H). LC-MS (M+H)$^+$=339.2; HPLC purity: 92.86%.

Example 33

3-(1-ethyl-4-methyl-1H-indol-3-yl)-1-(octahydroquinolin-1(2H)-yl)propan-1-one (33)

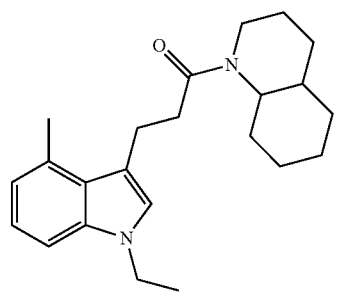

(33)

Synthesis of Compound (33)

Compound (33) was synthesized by following the procedure used to make Compound (27) (Scheme 26). The crude product was obtained by evaporating the organic layer under reduced pressure and was purified by silica gel column using Petroleum ether: Ethyl acetate as eluent to obtain Compound (33). $^1$H NMR (300 MHz, CDCl3): δ 6.98-7.08 (m, 2H), 6.83-6.84 (d, 1H), 6.75-6.77 (m, 1H), 4.45-4.63 (m, 1H), 3.98-4.05 (m, 2H), 3.47-3.57 (m, 1H), 3.16-3.20 (t, 2H), 2.50-2.92 (m, 6H), 1.23-1.76 (m, 16H). LC-MS (M+H)$^+$ =353.3

Example 34

1-(4-hydroxy-4-methyloctahydroquinolin-1(2H)-yl)-3-(1H-indol-3-yl)propan-1-one (34)

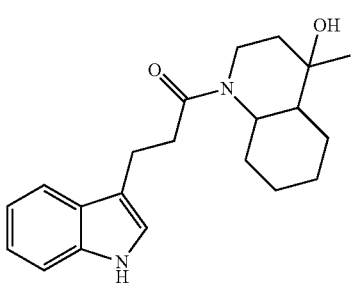

(34)

Synthetic Scheme-28

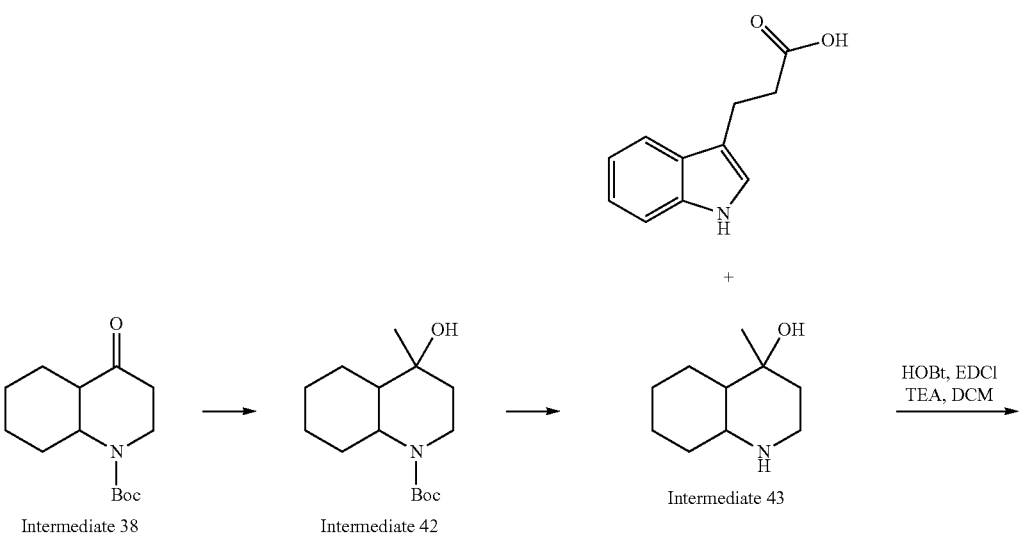

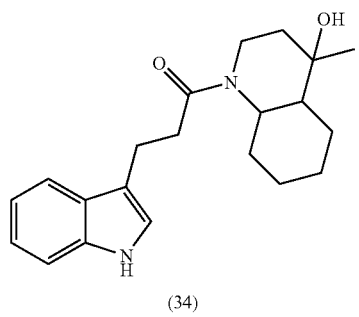

(34)

Synthesis of tert-butyl 4-hydroxy-4-methyloctahydroquinoline-1(2H)-carboxylate (Intermediate-42)

In a 50 mL-2 neck-RB flask fitted with magnetic sitter, a 3.0 M solution of methyl magnesium iodide in ether (1.45 mL, 4.4 mmol) was added drop wise at −20° C. to a stirred solution of Intermediate-38 (0.55 g, 2.2 mmol) in 5 ml of dry THF under $N_2$ atmosphere. Resulting mixture was stirred at room temperature for 16 hours. After completion of the reaction (monitored by TLC), the reaction mixture was quenched with ice water and extracted with ethyl acetate (3×15 ml). Organic layer was washed with brine solution and dried over $Na_2SO_4$ and concentrated. Crude material was purified by silica-gel column chromatography eluting with hexanes: EtOAc to give Intermediate-42 (82 mg) as gummy solid. LC-MS (M+H)+=270.1.

Synthesis of -methyldecahydroquinolin-4-ol trifluoroacetic acid salt (Intermediate-43)

Intermediate-43 was synthesized by following the procedure used to make Intermediate-39 (Scheme 25).

Synthesis of Compound (34)

Compound (34) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (34). $^1$H NMR (300 MHz, CDCl3): δ 7.95 (s, 1H), 7.54-7.56 (d, 1H), 7.27-7.29 (d, 1H), 7.02-7.14 (m, 2H), 6.97 (s, 1H), 4.38-4.53 (m, 1H), 3.39-3.42 (m, 1H), 3.06-3.08 (m, 2H), 2.51-2.77 (m, 2H), 0.86-2.10 (m, 16H). LC-MS (M+H)$^+$=341.2; HPLC purity: 80.53%.

Example 35

3-(4-methyl-1H-indol-3-yl)-1-(2-methyloctahydroquinolin-1(2H)-yl)propan-1-one (35)

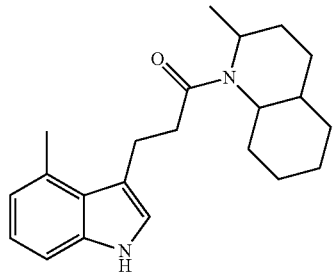

(35)

Synthesis of Compound (35)

Compound (35) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (35). $^1$H NMR (300 MHz, CDCl3): δ 7.90 (s, 1H), 7.10-7.13 (d, 1H), 6.92-7.01 (m, 2H), 6.79 (m, 1H), 4.48-4.71 (m, 1H), 3.48-3.94 (m, 1H), 3.19-3.24 (t, 2H), 2.48-2.79 (m, 6H), 1.09-1.77 (m, 15H). LC-MS (M+H)$^+$=339.3; HPLC purity: 98.23%.

Example 36

3-(1H-indol-3-yl)-1-[(4E)-4-(methoxyimino)decahydronaphthalen-1-yl]propan-1-one (36)

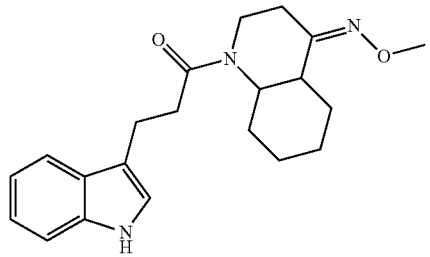

(36)

Synthetic Scheme-29

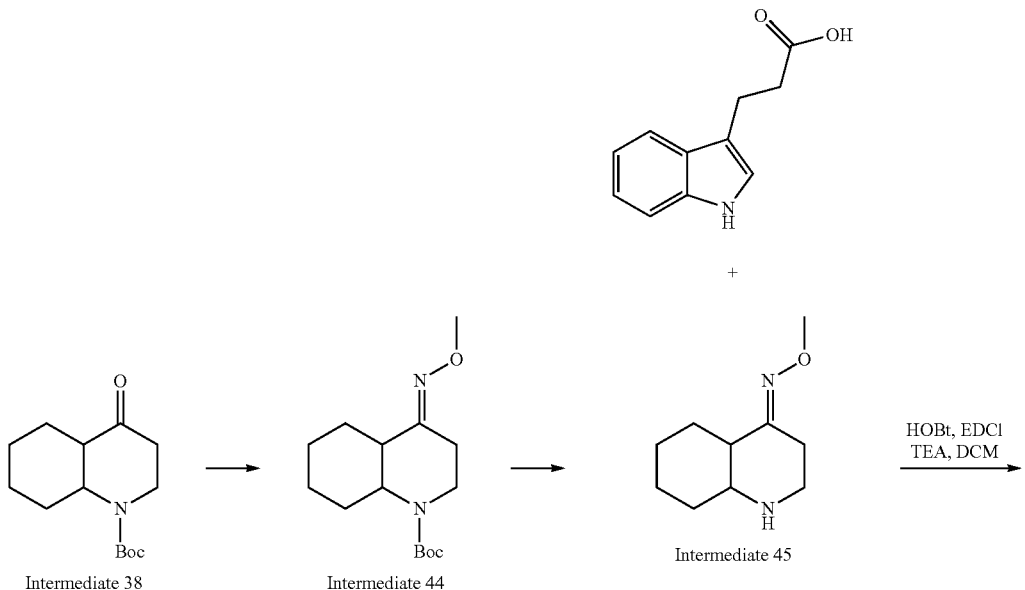

-continued

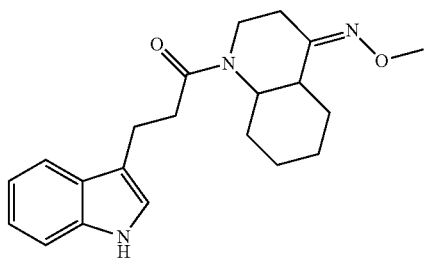

(36)

Synthesis of tert-butyl (4E)-4-(methoxyimino)octahydroquinoline-1(2H)-carboxylate (Intermediate-44)

In a 50 mL-2 neck-RB flask fitted with magnetic sitter, pyridine (0.45 mL, 3 vol) was added to a stirred solution of Intermediate-38 (150 mg, 0.596 mmol) in ethanol (1.5 ml, 8 vol). To this O-methoxylamine hydrochloride (250 mg, 2.96 mmol) was added. The resulting mass was refluxed at 90° C. for 3 hours. After completion of reaction (monitored by TLC), the solvent was completely removed from the reaction mass under vacuum. Crude was portioned between water and ethyl acetate. The organic layer was separated and the aqueous layer thus obtained was washed with ethyl acetate and concentrated. Resulted crude material was purified by silica-gel column chromatography eluted with hexanes: EtOAc to give Intermediate-44 (150 mg) as pale greenish liquid material.

Synthesis of (4E)-N-methoxyoctahydroquinolin-4(1H)-imine trifluoroacetic acid salt (Intermediate-45)

Intermediate-45 was synthesized by following the procedure used to make Intermediate-39 (Scheme 25).

Synthesis of Compound (36)

Compound (36) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (36). $^1$H NMR (300 MHz, CDCl3): δ 7.95 (s, 1H), 7.52-7.54 (m, 1H), 7.27-7.30 (m, 1H), 7.02-7.15 (m, 2H), 6.97 (s, 1H), 4.10-4.67 (m, 1H), 3.76 (d, 3H), 3.18-3.59 (m, 1H), 3.04-3.17 (m, 2H), 2.54-2.86 (m, 3H), 1.35-2.26 (m, 11H). LC-MS (M+H)$^+$=354.2; HPLC purity: 88.00%.

Example 37

3-(1H-indol-3-yl)-1-(3-methyloctahydroquinolin-1(2H)-yl)propan-1-one (37)

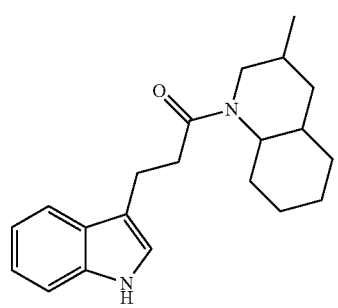

(37)

Synthesis of Compound (37)

Compound (37) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (37). $^1$H NMR (300 MHz, DMSO-d6): δ 10.76 (s, 1H), 7.49-7.52 (d, 1H), 7.30-7.33 (d, 1H), 7.02-7.12 (m, 2H), 6.94-6.99 (t, 1H), 4.00-4.60 (m, 1H), 3.37-3.66 (m, 1H), 3.01-3.19 (m, 1H), 2.87-2.95 (m, 2H), 2.54-2.78 (m, 2H), 0.30-1.98 (m, 15H). LC-MS (M+H)$^+$=325.2; HPLC purity: 97.66%.

Example 38

3-(1H-indol-3-yl)-1-(2-methyloctahydroquinolin-1(2H)-yl)propan-1-one (38)

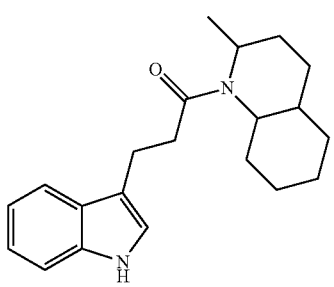

(38)

Synthesis of Compound (38)

Compound (38) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (38). $^1$H NMR (300 MHz, CDCl3): δ 8.05 (s, 1H), 7.54-7.57 (m, 1H), 7.27-7.30 (d, 1H), 7.04-7.18 (m, 2H), 6.96 (s, 1H), 4.48-4.87 (m, 1H), 3.26-4.09 (m, 1H), 3.05-3.10 (m, 2H), 2.50-2.81 (m, 2H), 0.90-1.80 (m, 16H). LC-MS (M+H)$^+$=325.2; HPLC purity: 98.14%.

Example 39

3-(6-fluoro-1H-indol-3-yl)-1-(octahydroquinolin-1(2H)-yl)propan-1-one (39)

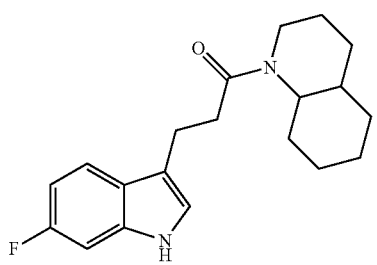

(39)

Synthesis of Compound (39)

Compound (39) was synthesized by following the procedure used to make Compound (1) (Scheme 2). The crude product was obtained by evaporating the organic layer under reduced pressure and was purified by silica gel column using Petroleum ether: Ethyl acetate (1:4) as eluent to obtain Compound (39). $^1$H NMR (300 MHz, CDCl3): δ 7.92 (s, 1H), 7.41-7.47 (m, 1H), 6.94-6.98 (m, 2H), 6.78-6.84 (m, 1H), 4.30-4.60 (m, 1H), 3.30-3.60 (m, 1H), 3.10-3.30 (m, 3H), 2.49-2.68 (m, 2H), 1.16-1.66 (m, 13H). LC-MS (M+H)$^+$=329.2

Example 40

3-(6-fluoro-1H-indol-3-yl)-1-(2-methyloctahydroquinolin-1(2H)-yl)propan-1-one (40)

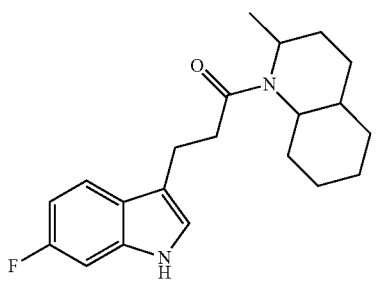

(40)

Synthesis of Compound (40)

Compound (40) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (40). $^1$H NMR (300 MHz, CDCl3): δ 7.98 (s, 1H), 7.41-7.47 (m, 1H), 6.94-6.98 (d, 2H), 6.78-6.84 (m, 1H), 4.47-4.71 (m, 1H), 3.37-3.90 (m, 1H), 3.02-3.07 (t, 2H), 2.46-2.77 (m, 2H), 0.91-1.82 (m, 16H). LC-MS (M+H)$^+$=343.22; HPLC purity: 97.64%.

Example 41

3-(1H-indol-3-yl)-1-(octahydro-1H-Indol-1-yl)propan-1-one (41)

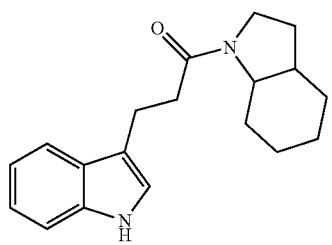

(41)

Synthetic Scheme-30

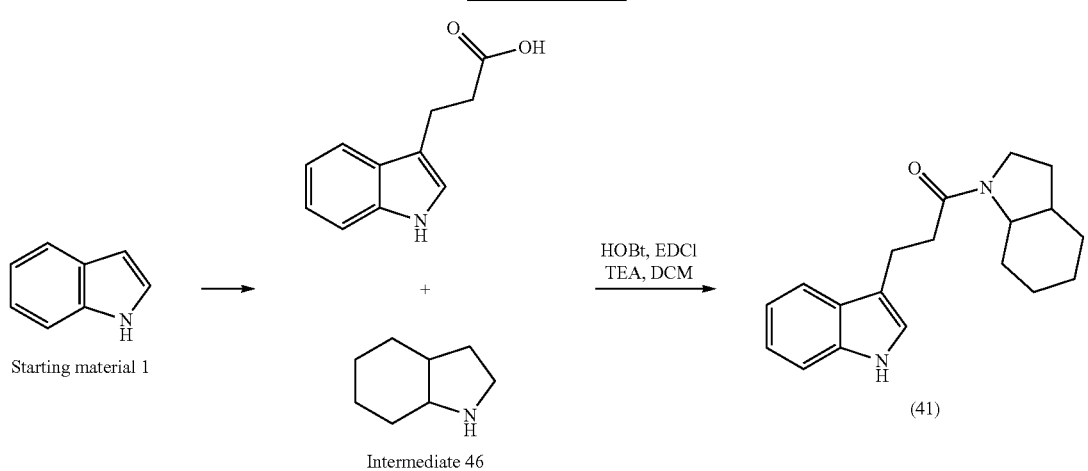

Synthesis of octahydro-1H-indole (Intermediate-46)

Intermediate-46 was synthesized by following the procedure used to make Intermediate-18 (Scheme 13).

Synthesis of Compound (41)

Compound (41) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (41). $^1$H NMR (300 MHz, CDCl3): δ 8.02 (s, 1H), 7.53-7.56 (d, 1H), 7.27-7.30 (d, 1H), 7.02-7.14 (m, 2H), 6.96 (s, 1H), 3.29-4.03 (m, 3H), 3.03-3.23 (m, 2H), 2.49-2.70 (m, 2H), 0.88-2.07 (m, 11H). LC-MS (M+H)$^+$=297.22; HPLC purity: 99.0%.

Example 42

3-(1H-indol-3-yl)-1-(octahydro-2H-isoindol-2-yl)propan-1-one (42)

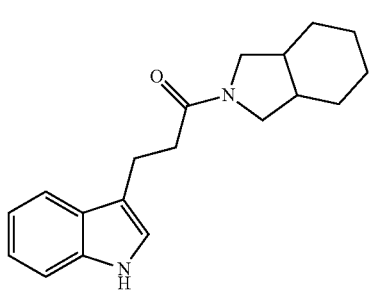

(42)

Synthesis of Compound (42)

Compound (42) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (42). $^1$H NMR (300 MHz, CDCl3): δ 7.98 (s, 1H), 7.53-7.56 (d, 1H), 7.27-7.30 (d, 1H), 6.99-7.13 (m, 3H), 3.28 (s, 2H), 3.13 (m, 3H), 2.94 (s, 1H), 2.63-2.68 (t, 2H), 2.24 (s, 3H), 2.02 (s, 2H), 1.31 (m, 5H). LC-MS (M+H)$^+$=297.2; HPLC purity: 97.66%.

Example 43

1-[3-(6-fluoro-1H-indol-3-yl)propanoyl]octahydroquinolin-4(1H)-one (43)

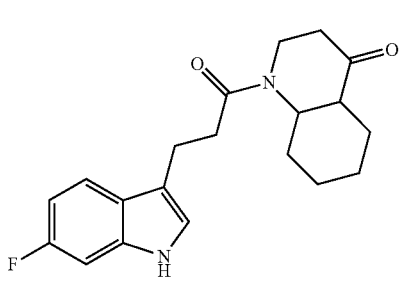

(43)

Synthesis of Compound (43)

Compound (43) was synthesized by following the procedure used to make Compound (1) (Scheme 2). The crude product was obtained by evaporating the organic layer under reduced pressure and was purified by silica gel column using Petroleum ether: Ethyl acetate (1:4) as eluent to obtain Compound (43). $^1$H NMR (300 MHz, CDCl3): δ 8.14 (s, 1H), 7.42-7.43 (m, 1H), 6.95 (s, 1H), 6.67-6.84 (m, 2H), 4.62-4.91 (m, 1H), 3.71-3.81 (m, 1H), 2.78-3.42 (m, 4H), 2.69 (m, 2H), 1.28-2.47 (m, 10H). LC-MS (M+H)$^+$=343.2; HPLC purity: 96.03%.

Example 44

3-(4-fluoro-1H-indol-3-yl)-1-(octahydroquinolin-1(2H)-yl)propan-1-one (44)

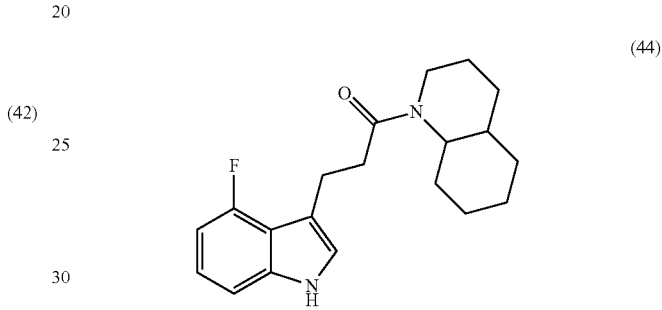

(44)

Synthesis of Compound (44)

Compound (44) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (44). $^1$H NMR (300 MHz, DMSO-d6): δ 11.07 (s, 1H), 7.14-7.17 (m, 2H), 6.99-7.01 (m, 1H), 6.66-6.75 (m, 1H), 4.29-4.48 (m, 1H), 3.63-3.76 (m, 1H), 2.95-2.97 (m, 2H), 2.56-2.76 (m, 3H), 1.66-1.75 (m, 5H), 1.52-1.61 (m, 2H), 1.28-1.45 (m, 6H). LC-MS (M+H)$^+$=329.3; HPLC purity: 97.26%.

Example 45

3-(1H-indol-3-O-1-(2-methyloctahydro-1H-indol-1-yl)propan-1-one (45)

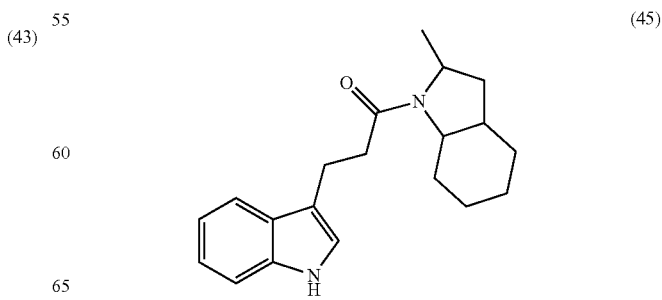

(45)

Synthesis of Compound (45)

Compound (45) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (45). $^1$H NMR (300 MHz, CDCl3): δ 8.00 (s, 1H), 7.54-7.56 (d, 1H), 7.28-7.30 (d, 1H), 7.02-7.14 (m, 2H), 6.97 (s, 1H), 3.86-4.10 (m, 1H), 3.29-3.65 (m, 1H), 3.01-3.20 (m, 2H), 2.57-2.72 (m, 2H), 2.04 (s, 3H), 1.72-1.86 (m, 2H), 1.55-1.66 (m, 3H), 1.03-1.35 (m, 6H). LC-MS (M+H)$^+$=311.2; HPLC purity: 99.27%.

Example 46

{3-[3-(octahydroquinolin-1(2H)-yl)-3-oxopropyl]-1H-indol-1-yl}acetic acid (46)

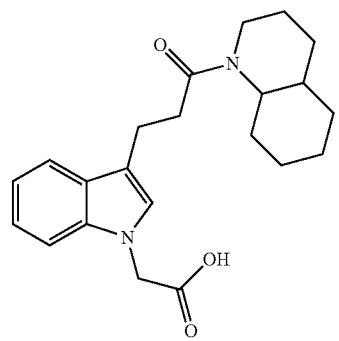

(46)

Synthetic Scheme-31

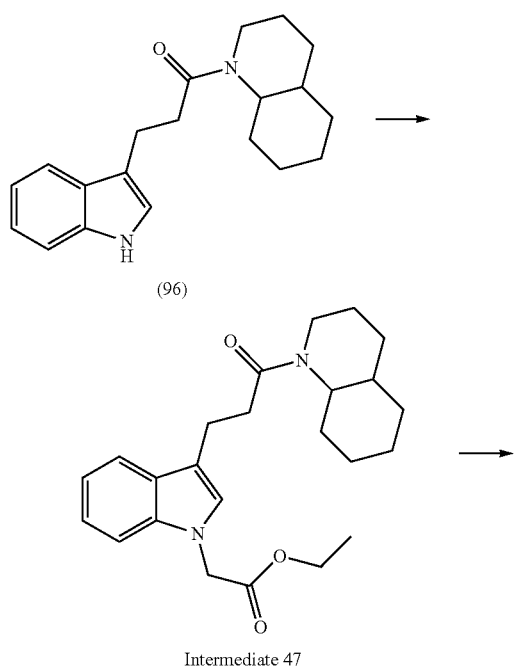

Synthesis of ethyl {3-[3-(octahydroquinolin-1(2H)-yl)-3-oxopropyl]-1H-Indol-1-yl}acetate (Intermediate-47)

Intermediate-47 was synthesized by following the procedure used to make Intermediate-24 (Scheme 19).

Synthesis of Compound (46)

Compound (46) was synthesized by following the procedure used to make Intermediate-3 (Scheme 1). The crude product was obtained by evaporating the organic layer under reduced pressure and was purified by silica gel column using Petroleum ether: Ethyl acetate as eluent to obtain Compound (46). $^1$H NMR (300 MHz, CDCl3): δ 7.46-7.50 (t, 1H), 7.02-7.18 (m, 3H), 6.80 (s, 1H), 4.66 (s, 2H), 4.39-4.58 (m, 1H), 3.47-3.60 (m, 1H), 2.93-3.01 (m, 2H), 2.44-2.85 (m, 4H), 1.25-1.65 (m, 13H). LC-MS (M+H)$^+$=369.22; HPLC purity: 93.09%.

Example 47

3-(4-fluoro-1-methyl-1H-Indol-3-yl)-1-(octahydroquinolin-1(2H)-yl)propan-1-one (47)

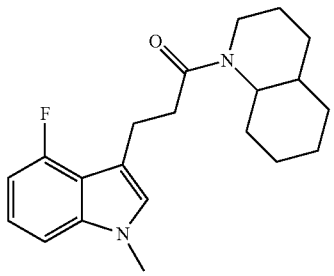

Synthesis of Compound (47)

Compound (47) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (47). $^1$H NMR (300 MHz, CDCl3): δ 7.20-7.23 (d, 1H), 7.14 (s, 1H), 7.05-7.11 (m, 1H), 6.71-6.79 (1H), 4.29-4.48 (m, 1H), 3.62-3.79 (m, 4H), 2.92-2.98 (m, 2H), 2.61-2.72 (m, 3H), 1.35-1.75 (m, 13H). LC-MS (M+H)$^+$=343.3; HPLC purity: 98.84%.

Example 48

1-(3,4,5,6,7,8-hexahydroquinolin-1(2H)-yl)-3-(1H-indol-3-yl)propan-1-one (48)

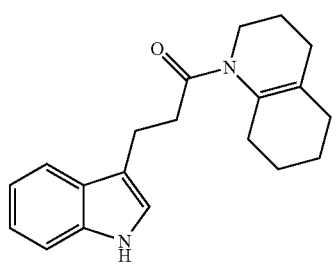

(48)

Synthesis of Compound (48)

Compound (48) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (48). $^1$H NMR (300 MHz, CDCl3): 8.00 (s, 1H), 7.51-7.54 (d, 1H), 7.26-7.29 (d, 1H), 7.01-7.18 (m, 2H), 6.94 (s, 1H), 3.37 (s, 2H), 3.03-3.08 (t, 2H), 2.65-2.70 (t, 2H), 2.30-2.39 (m, 1H), 1.87 (s, 3H), 1.79 (s, 2H), 1.53-1.59 (m, 6H). LC-MS (M+H)$^+$=309.25; HPLC purity: 85.06%.

Example 49 methyl 1-[3-(1H-indol-3-yl)propanoyl]decahydro-quinoline-4-carboxylate (49)

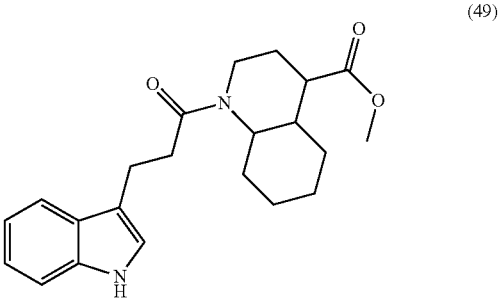 [SMILES: COC(=O)C1CCN(C(=O)CCc2c[nH]c3ccccc23)C2CCCCC12]

(49)

Synthetic Scheme-32

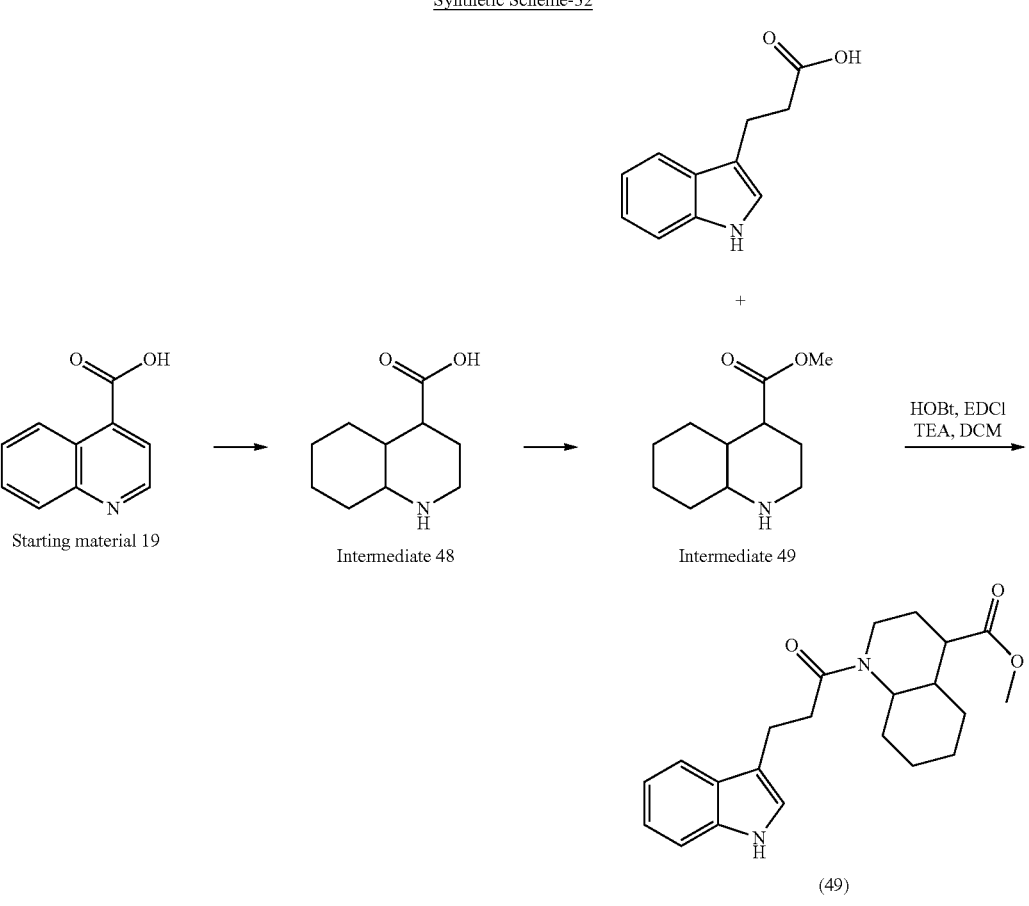

Synthesis of decahydroquinoline-4-carboxylic acid (Intermediate-48)

Intermediate- was synthesized by following the procedure used to make Intermediate-18 (Scheme 13).

Synthesis of methyl decahydroquinoline-4-carboxylate (Intermediate-49)

To a stirred solution of Intermediate-48 (800 mg g, 4.3656 mmol) in methanol (30 mL) thionyl chloride (0.48 mL, 6.5483 mmol) was added under nitrogen atmosphere at 0° C. The mixture was stirred at room temperature for 16 hours. After completion of the reaction, the reaction mixture was concentrated to give Intermediate-49 (775 mg).

Synthesis of Compound (49)

Compound (49) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (49). $^1$H NMR (300 MHz, CDCl3): δ 7.97 (s, 1H), 7.54-7.56 (d, 1H), 7.27-7.30 (d, 1H), 7.02-7.14 (m, 2H), 6.97 (s, 1H), 3.73-4.08 (m, 1H), 3.59 (s, 3H), 3.28-3.53 (m, 1H), 3.04-3.09 (t, 2H), 2.46-2.74 (m, 3H), 0.91-2.03 (m, 12H). LC-MS $(M+H)^+$=369.2; HPLC purity: 96.44%.

Example 50

1-[3-(1H-indol-3-yl)propanoyl]decahydroquinoline-4-carboxylic acid (50)

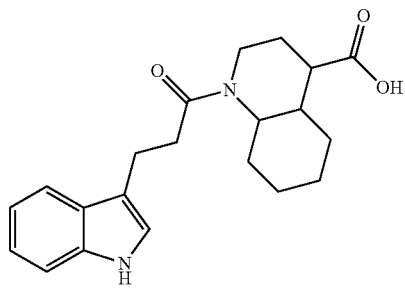

(50)

Synthesis of Compound (50)

Compound (50) was synthesized by following the procedure used to make Intermediate-3 (Scheme 1). The crude product was obtained by evaporating the organic layer under reduced pressure and was purified by silica gel column using Petroleum ether: Ethyl acetate as eluent to obtain Compound (50). $^1$H NMR (300 MHz, DMSO-d6): δ 12.26 (s, 1H), 10.77 (s, 1H), 7.50-7.52 (d, 1H), 7.30-7.33 (d, 1H), 7.13 (s, 1H), 6.94-7.07 (m, 2H), 3.69-4.53 (m, 1H), 2.89-2.94 (t, 2H), 2.42-2.74 (m, 3H), 1.27-1.91 (m, 13H). LC-MS $(M+H)^+$=355.2.

Example 51

1-(octahydroquinolin-1(2H)-yl)-3-[1-(phenylsulfonyl)-1H-indol-3-yl]propan-1-one (51)

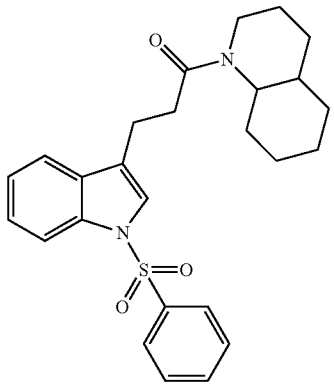

(51)

Synthetic Scheme-33

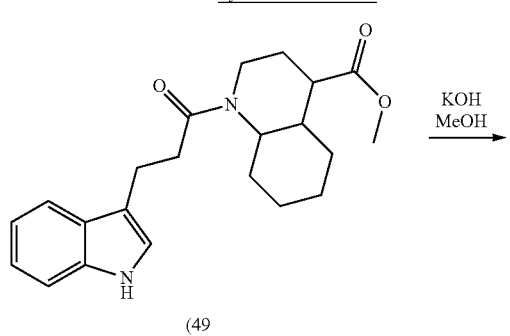

Synthetic Scheme-34

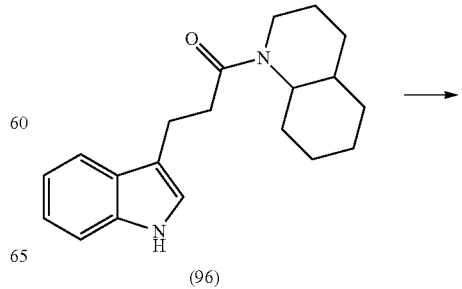

-continued

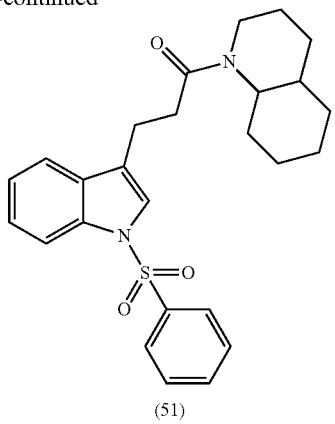

(51)

Synthesis of Compound (51)

A 100 mL RB flask fitted with magnetic stirrer was charged with 60% NaH (77.26 mg, 1.932 mmol). To this 10 mL of THF was added at 0° C. under nitrogen atmosphere. (96) (200 mg, 0.644 mmol) in THF was then added to the solvent and stirred at this temperature for 30 minutes. Phenyl sulfonyl chloride (170.61 mg, 0.966 mmol) was added and stirred at room temperature for 15 hours. After completion of reaction (reaction monitored by TLC), the reaction mass was quenched with crushed ice, extracted with ether (100 mL×3). The combined ether layer was washed with water (100 mL×3), brine, dried over anhydrous $Na_2SO_4$, and concentrated. Crude material was purified by silica-gel column chromatography eluting with hexanes: EtOAc to give (170 mg) as yellow sticky solid. $^1H$ NMR (300 MHz, CDCl3): δ 7.89-7.92 (d, 1H), 7.77-7.81 (m, 2H), 7.42-7.46 (m, 2H), 7.13-7.36 (m, 5H), 4.42-4.60 (m, 1H), 3.45-3.57 (m, 1H), 2.22-2.43 (m, 5H), 1.54-1.76 (m, 6H), 1.49 (s, 2H), 1.27-1.34 (m, 5H). LC-MS $(M+H)^+$=451.2; HPLC purity: 93.06%.

Example 52

3-(1H-indol-3-yl)-1-(octahydroquinolin-1(2H)-yl)propan-1-one (Peak-1) (52)

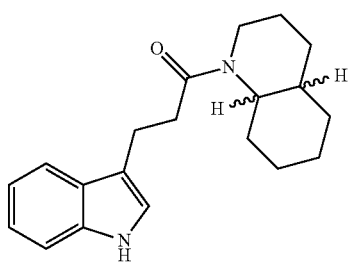

Synthesis of Compound (52) (Peak-1

Compound (96) mixture of isomers was separated by reverse phase column to give Compound (52) (Peak-1). $^1H$ NMR (300 MHz, CDCl3): δ 8.13 (s, 1H), 7.52-7.55 (d, 1H), 7.26-7.28 (d, 1H), 7.01-7.12 (m, 2H), 6.92-6.93 (d, 1H) m, 3.66-3.68 (m, 1H), 2.73-3.09 (m, 5H), 1.94 (s, 2H), 1.21-1.66 (m, 12H). LC-MS $(M+H)^+$=311.2; HPLC purity: 99.86% (Column: Zorbax eclipse XDB-C18, RT=16.83 min, mobile phase: $H_2O$:MeCN=55:45).

Example 53

3-(1H-indol-3-yl)-1-(octahydroquinolin-1(2H)-yl)propan-1-one (Peak-2) (53)

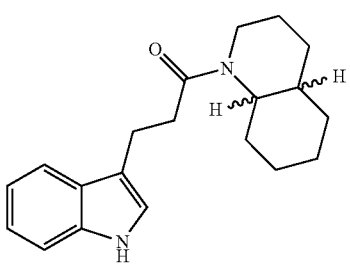

Synthesis of Compound (53) (Peak 2

Compound (96) mixture of isomers was separated by reverse phase column to give compound, Compound (53) (peak 2). $^1H$ NMR (300 MHz, CDCl3): δ 7.89 (s, 1H), 7.53-7.58 (t, 1H), 7.26-7.31 (t, 1H), 7.02-7.14 (m, 2H), 6.98 (s, 1H), 4.45-4.62 (m, 1H), 3.47-3.58 (m, 1H), 3.01-3.09 (m, 2H), 2.50-2.91 (m, 3H), 1.27-1.67 (m, 13H). LC-MS $(M+H)^+$=311.1; HPLC purity: 99.80% (Column: Zorbax eclipse XDB-C18, RT=17.87 min, mobile phase: $H_2O$:MeCN=55:45).

Example 54

1-(decahydro-1H-1-benzazepin-1-yl)-3-(1H-indol-3-yl)propan-1-one (54)

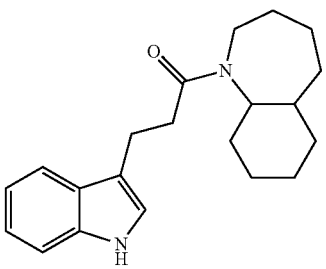

Synthesis of Compound (54)

Compound (54) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (54). $^1H$ NMR (300 MHz, CDCl3): δ 7.93 (s, 1H), 7.53-7.57 (t, 1H), 7.27-7.30 (d, 1H), 7.02-7.14 (m, 2H), 6.97 (s, 1H), 4.13-4.70 (m, 1H), 3.35-3.62 (m, 1H), 3.05-3.17 (m, 2H), 2.53-2.81 (m, 3H), 1.29-1.81 (m, 15H). LC-MS (M+H)+=325.2; HPLC purity: 98.41%.

Example 55

3-(1H-indol-3-yl)-1-(4a-methyloctahydroquinolin-1 (2H)-yl)propan-1-one Peak-1 (55)

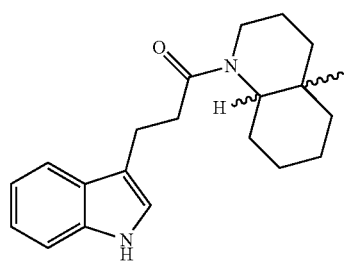

(55)

Synthesis of Compound (55) (Peak 1

Mixture of isomers were separated by silica gel column chromatography eluting with hexanes: EtOAc to give Compound (55) (peak 1). $^1$H NMR (300 MHz, CDCl3): δ 7.92 (s, 1H), 7.53-7.55 (d, 1H), 7.28-7.31 (d, 1H), 7.04-7.15 (m, 2H), 6.97 (s, 1H), 4.25-4.54 (m, 1H), 3.24-3.52 (m, 1H), 3.03-3.08 (m, 2H), 2.58-2.76 (m, 3H), 0.83-1.94 (m, 15H). LC-MS (M+H)+=325.2; HPLC purity: 91.22%; Column: Zorbax eclipse XDB-C18, RT=17.43 min, mobile phase: H$_2$O: MeCN: TFA (0.01%) gradient.

Example 56

3-(1H-indol-3-yl)-1-(4a-methyloctahydroquinolin-1 (2H)-yl)propan-1-one Peak-2 (56)

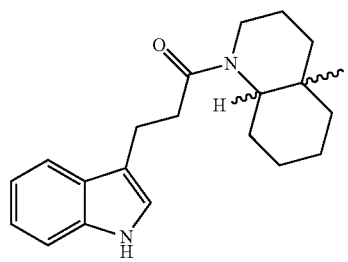

(56)

Synthesis of Compound (56) (Peak 2

Mixture of isomers were separated by silica gel column chromatography eluting with hexanes: EtOAc to give Compound (56) (Peak-2). $^1$H NMR (300 MHz, CDCl3): δ 7.93 (s, 1H), 7.53-7.55 (d, 1H), 7.27-7.30 (d, 1H), 7.01-7.14 (m, 2H), 6.96 (s, 1H), 3.80-4.61 (m, 1H), 3.25-3.60 (m, 1H), 2.99-3.05 (m, 2H), 2.59-2.78 (m, 4H), 0.83-1.93 (m, 14H). LC-MS (M+H)+=325.2; HPLC purity: 97.45%; Zorbax eclipse XDB-C18, RT=18.36 min, mobile phase: H2O: MeCN: TFA (0.01%) gradient.

Example 57

2-(1H-indol-3-ylsulfonyl)-1-(octahydroquinolin-1 (2H)-yl)ethanone (57)

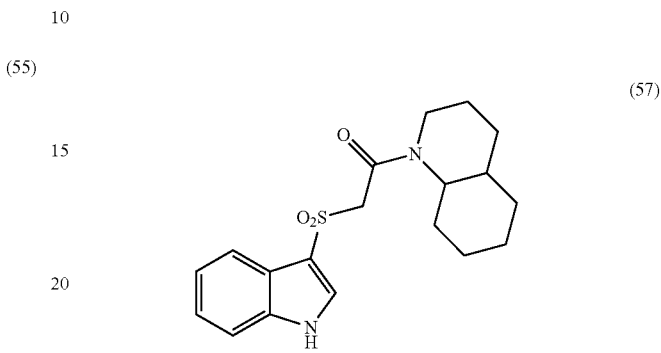

(57)

Synthetic Scheme-35

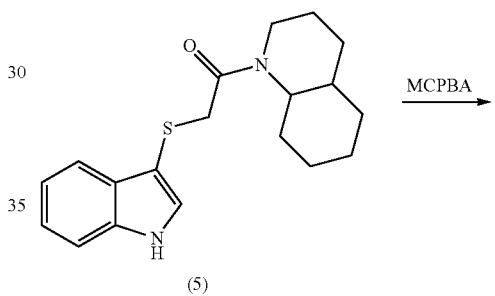

(5)

MCPBA

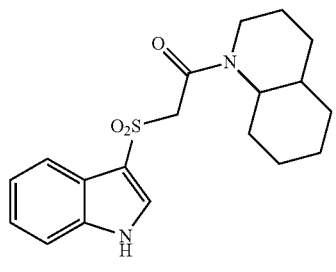

(57)

Synthesis of Compound (57)

To a stirred solution of (5) (100 mg, 0.30 mmol) in DCM (5 mL) was added m-CPBA (78 mg, 0.45 mmol) and stirred at rt for 16 hours. After completion of reaction (reaction monitored by TLC), the reaction mixture was quenched with saturated NaHCO$_3$ solution, extracted with DCM and concentrated. The crude product was purified by silica gel column using Petroleum ether: Ethyl acetate as eluent to obtain Compound (57) (50 mg) as yellow solid. $^1$H NMR (300 MHz, CDCl3): δ 9.95 (s, 1H), 7.81-7.84 (d, 1H), 7.49 (s, 1H), 7.10-7.15 (m, 3H), 3.85-4.43 (m, 3H), 2.56-3.28 (m, 1H), 1.16-1.86 (m, 14H). LC-MS (M+H)+=361.1; HPLC purity: 98.60%.

Example 58

3-methyl-3-(1-methyl-1H-indol-3-yl)-1-(octahydro-quinolin-1(2H)-yl)butan-1-one (58)

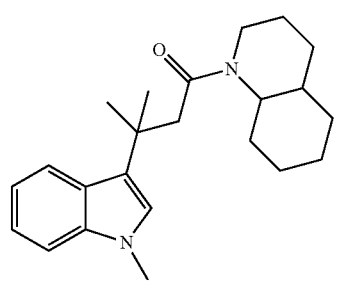

(58)

Synthetic Scheme-36

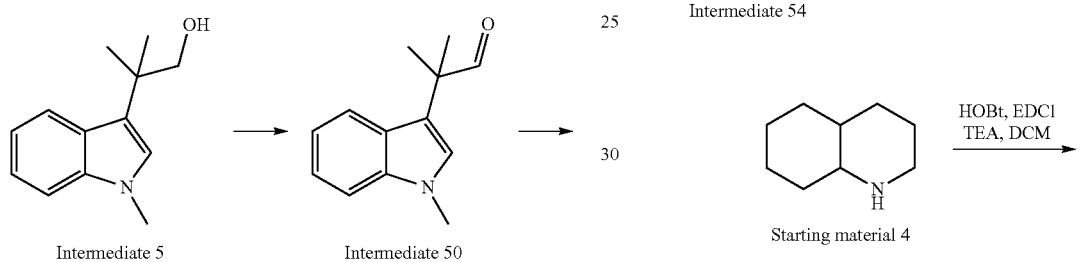

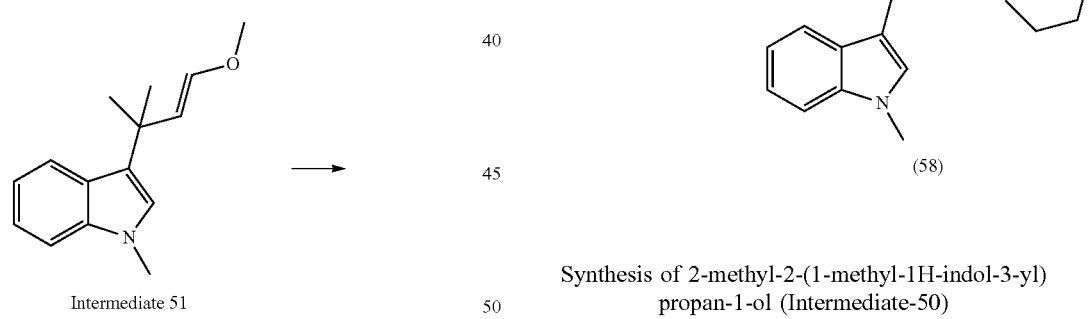

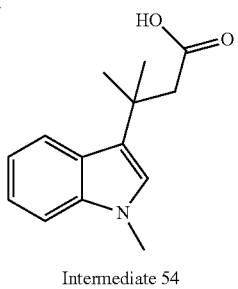

Intermediate 54

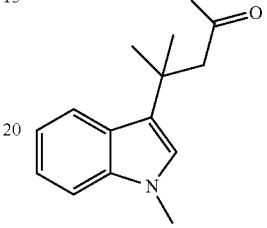

Intermediate 54

+

Starting material 4 → HOBt, EDCl, TEA, DCM →

(58)

Synthesis of 2-methyl-2-(1-methyl-1H-indol-3-yl)propan-1-ol (Intermediate-50)

A 250 mL RB flask fitted with magnetic stirrer was charged with Lithium aluminum hydride (0.983 g, 25.951 mmol) and THF (20 mL) was added to it at 0° C. To this resulting suspension Intermediate-5 (2.0 g, 8.65 mmol) in THF (20 mL) was added and the resulting mixture was stirred at room temperature for 2 hours. After completion of the reaction, the reaction mixture was diluted with EtOAc (50 mL) and was quenched with $Na_2SO_4$ (5 g) and the resulting slurry was stirred at room temperature for 1 hour, filtered through celite washed with ethyl acetate. The resulting filtrate was concentrated to give Intermediate-50 (0.9 g). $^1$H NMR (300 MHz, DMSO-d6): δ 7.65-7.68 (d, 1H), 7.34-7.36 (d, 1H), 7.07-7.12 (0H), 7.03 (s, 1H), 6.94-6.99 (t, 1H), 4.53-4.57 (t, 1H), 3.71 (s, 3H), 3.54-3.56 (d, 2H), 1.31 (s, 6H).

Synthesis of 2-methyl-2-(1-methyl-1H-indol-3-yl) propanal (Intermediate-51)

A 100 mL RB flask fitted with magnetic stirrer was charged with 30 mL DCM and Pyridinium chloro chromate (2.466 g, 11.4419 mmol) was added followed by the addition of Intermediate-50 (1.55 g, 7.627 mmol) in 10 mL of DCM. The resulting mixture was stirred at room temperature for 2 hours. After completion of the reaction, the solvent from the reaction mass was removed under reduced pressure to yield the crude compound. Crude mass was purified by column chromatography using 60-120 silica gel and 9:1 Pet ether/ethyl acetate as eluent to give Intermediate-51 (0.79 g). $^1$H NMR (300 MHz, DMSO-d6): δ 9.39 (s, 1H), 7.40-7.44 (t, 1H), 7.32 (s, 1H), 7.13-7.18 (t, 1H), 6.98-7.03 (t, 1H), 3.77 (s, 3H), 1.46 (s, H).

Synthesis of 3-[(3E)-4-methoxy-2-methylbut-3-en-2-yl]-1-methyl-1H-Indole (Intermediate-52)

A 100 mL RB flask fitted with magnetic stirrer was charged with 20 mL of dry THF and Methoxy methyl triphenyl phosphonium chloride (2.566 g, 7.487 mmol) was added followed by addition of Pot tea butoxide (2.295 g, 20.451 mmol). The resulting mass was stirred at room temperature for 2 hours and then cooled to 0° C. Intermediate-51 (1.37 g, 6.807 mmol) in 10 mL of THF was added to the above reaction mass and was stirred at room temperature for 2 hours. After completion of the reaction (by TLC) reaction mass was diluted with 10 mL of water and was extracted with ethyl acetate (100 mL×3) and the combined organic layers were washed with brine solution and was dried over anhydrous sodium sulfate concentrated. Crude product was purified by column chromatography using 60-120 silica gel and 6% of ethyl acetate in Pet ether as eluent to give Intermediate-52. Yield: 1.12 g (71.8%). $^1$H NMR (300 MHz, CDCl3): δ 7.73-7.80 (m 1H), 7.33 (s, 1H), 7.16-7.21 (t, 1H), 7.03-7.08 (t, 1H), 6.81 (s, 1H), 5.79-6.34 (m, 1H), 4.58-5.15 (m, 1H), 3.73-3.74 (d, 3H), 3.49-3.53 (d, 3H), 1.55 (s, 6H).

Synthesis of 3-methyl-3-(1-methyl-1H-indol-3-yl) butanal (Intermediate-53)

A 100 mL RB flask fitted with magnetic stirrer was charged with 50.4 mL of 1,4 dioxane and 12.76 mL of water. To this Intermediate-52 (1.12 g, 4.884 mmol) followed by p-toluene sulphonic acid (0.0424 g, 0.2232 mmol) was added. The resulting mass was heated at 60° C. for 16 hours. After completion of the reaction, the reaction mixture was quenched with 10 mL of water and extracted with ethyl acetate (100 mL×3) and the combine organic layer was washed with saturated sodium bicarbonate solution followed by brine solution and was dried over anhydrous sodium sulfate and concentrated. Crude product was purified by column chromatography using 60-120 silica gel and 8% of ethyl acetate in Pet ether as eluent to give Intermediate-53. $^1$H NMR (300 MHz, DMSO-d6): δ 9.47-9.49 (t, 1H), 7.73-7.76 (d, 1H), 7.37-7.40 (d, 1H), 7.11-7.16 (t, 1H), 7.10 (s, 1H), 6.99-7.04 (t, 1H) 3.72 (s, 3H), 2.78 (s, 2H), 1.49 (s, 6H).

Synthesis of 3-methyl-3-(1-methyl-1H-indol-3-yl) butanoic acid (Intermediate-54)

A 50 mL RB flask fitted with magnetic stirrer was charged with 10 mL of THF and was cooled to −78° C. to which 2-methyl 2 butene (3 mL) was added and stirred for 15 minutes. Another 100 mL RB flask fitted with magnetic stirrer was charged with Intermediate-53 (557 mg, 2.59 mmol) and tert butanol (15 mL) and was stirred at RT and the above prepared THF solution was added to it. Then the resulting mass was cooled to 0° C. to which NaH$_2$PO$_4$ (1.42 g) in water was added followed by addition of NaClO$_2$ (0.35 g) in water. The resulting mixture was stirred at 0° C. for 20 minutes and quenched with water and pH adjusted to 1-2 using 1N HCl and extracted with ethyl acetate and concentrated to give Intermediate-54 (480 mg). $^1$H NMR (300 MHz, DMSO-d6): δ 11.82 (s, 1H), 7.69-7.71 (d, 1H), 7.35-7.38 (d, 1H), 7.09-7.14 (t, 1H), 7.05 (s, 1H), 6.96-7.01 (t, 1H), 3.71 (s, 3H), 2.66 (s, 2H), 1.48 (s, 6H).

Synthesis of Compound (58)

Compound (58) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (58). $^1$H NMR (300 MHz, CDCl3): δ 7.72-7.74 (d, 1H), 7.20-7.23 (d, 1H), 7.11-7.16 (t, 1H), 7.03 (s, 1H), 6.76 (s, 1H), 4.34-4.53 (m, 1H), 3.65 (s, 1H), 3.07-3.29 (2H), 2.75-2.84 (m, 2H), 2.75-2.84 (m, 2H), 2.27-2.39 (m, 4H), 1.54-1.56 (d, 6H), 1.38-1.43 (m, 3H), 1.07 (m, 2H), 0.09 (m, 2H), 0.37-0.65 (m, 2H). LC-MS (M+H)$^+$=353.3; HPLC purity: 92.52%.

Example 59

3-methyl-3-(1-methyl-1H-indol-3-yl)-1-(4a-methyl-octahydroquinolin-1 (2H)-yl)butan-1-one (59)

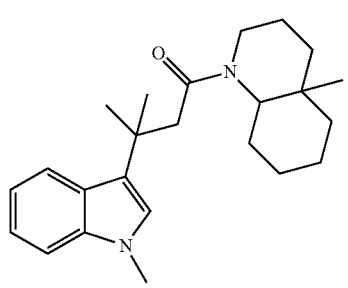

(59)

Synthetic Scheme-37

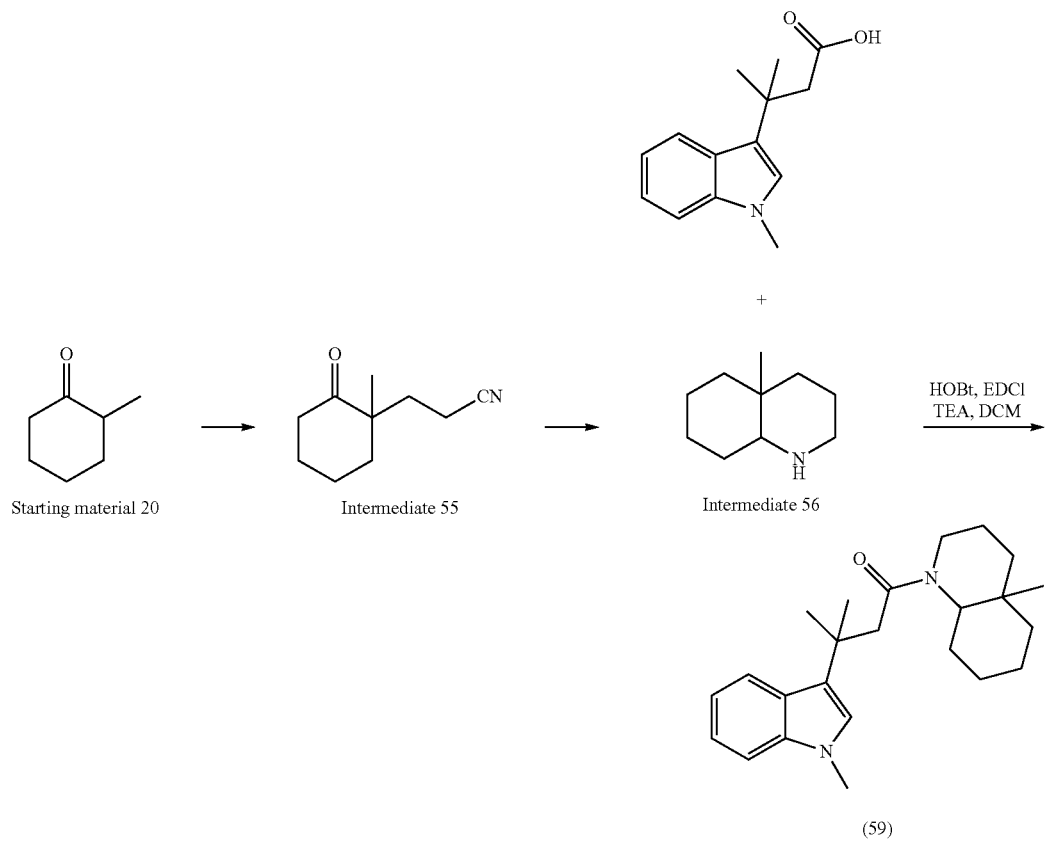

Starting material 20     Intermediate 55     Intermediate 56

Synthesis of 3-(1-methyl-2-oxocyclohexyl)propanenitrile (Intermediate-55)

To a stirred solution of Starting Material-20 (5 g, 44.6 mmol) in 15 mL of DMF, Triton-B (40% solution of Binzyl trimethylammonium hydroxide) (20.5 mL, 49.0 mmol) was added in 10 mL of DMF drop wise at 0° C. under nitrogen atmosphere. The mixture was stirred at RT for 30 minutes. To this acrylonitrile (2.6 g, 49.0 mmol) in 15 mL of DMF was added and stirred for 16 hours. Then reaction mixture was poured in water and extracted with ethyl acetate, and concentrated. The crude material was purified by column chromatography using hexanes: ethyl acetate as eluent to give Intermediate-55 (975 mg).

Synthesis of 4a-methyldecahydroquinoline (Intermediate-56)

A solution of Intermediate-55 (500 mg, 3.0261 mmol) in 25 mL of methanol was added to 10% of Pd/C (100 mg, 20% W/W) under $N_2$ atmosphere. $N_2$ gas was purged 5 min and then the reaction mixture was kept under hydrogen atmosphere at 60 psi for 16 h. After reaction, the catalyst was filtered and the solvent was concentrated to give Intermediate-56 (287 mg).

Synthesis of Compound (59)

Compound (59) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (59). $^1$H NMR (300 MHz, CDCl3): δ 7.70-7.73 (m, 1H), 7.18-7.21 (m, 1H), 7.02-7.14 (m, 1H), 7.00-7.02 (m, 1H), 6.75-6.76 (m, 1H), 4.10-4.40 (m, 1H), 3.63-3.64 (d, 3H), 2.62-3.00 (m, 5H), 1.64-1.66 (m, 3H), 1.52-1.55 (m, 6H), 0.62-1.46 (m, 11H). LC-MS (M+H)$^+$=367.3; HPLC purity: 96.39%.

Example 60

3-(1,4-dimethyl-1H-indol-3-yl)-1-(octahydro-4H-1,4-benzoxazin-4-yl)propan-1-one (60)

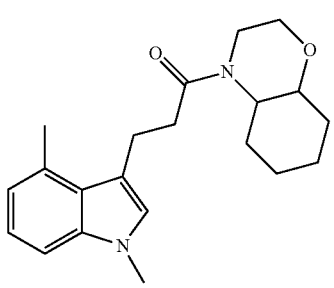

(60)

Synthesis of Compound (60)

Compound (60) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (60). $^1$H NMR (300 MHz, CDCl3): δ 6.99-7.05 (m, 2H), 6.76-6.78 (m, 2H), 4.16-4.34 (m, 1H), 3.70-3.88 (m, 1H), 3.63-3.64 (d, 3H), 3.16-3.43 (m, 5H), 2.83-2.97 (m, 1H), 2.47-2.73 (m, 4H), 0.90-1.90 (m, 9H). LC-MS (M+H)$^+$=341.2; HPLC purity: 98.03%.

Example 61

3-(1H-indol-3-yl)-1-[(trans-4a,8a)-octahydro-4H-1,4-benzoxazin-4-yl]propan-1-one (61)

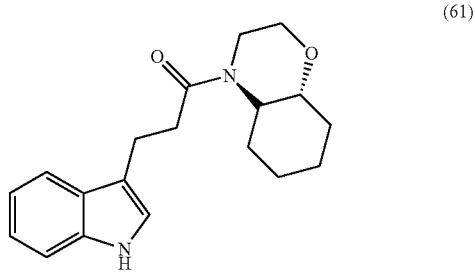

(61)

Synthesis of 2-chloro-N-[trans-(1,2)-2-hydroxycyclohexyl]acetamide (Intermediate-57)

Starting Material (1 g, 6.6 mmol) was suspended in DCM (10 mL) and triethylamine (1.94 mL, 13.9 mmol) was added at −10° C. To this chloroacetyl chloride (0.53 mL, 6.6 mmol) was added slowly and the mixture was stirred at RT for 16 hours. After reaction was completed the reaction mixture was diluted with saturated aqueous sodium hydrogen carbonate and extracted with 5 percent IPA in ethyl acetate, and concentrated to give Intermediate-57 (570 mg) as brown oil.

Synthesis of (trans-4a,8a)-hexahydro-2H-1,4-benzoxazin-3(4M-one (Intermediate-58)

To a stirred solution of Intermediate-57 (570 mg, 2.974 mmol) in THF (10 mL) at 0° C. under N$_2$ atmosphere, sodium hydride (60 percent in mineral oil) (131 mg, 3.2714 mmol) was added carefully and the mixture was stirred for 16 h at room temperature. After completion of the reaction, the reaction mixture was quenched with 1N HCl and extracted with DCM and concentrated. The crude material was purified by chromatography on a silica gel column chromatography eluting with DCM: MeOH afforded Intermediate-58 (300 mg).

Synthesis of (trans-4a,8a)-octahydro-2H-1,4-benzoxazine (Intermediate-59)

Intermediate-58 (250 mg, 1.6114 mmol) in tetrahydrofuran (10 mL) was slowly added to a suspension of lithium aluminum hydride (153 mg, 4.0286 mmol) at 0° C. Then reaction mixture was refluxed for 16 hours. After completion of the reaction, the reaction mixture was quenched with 15%

Synthetic Scheme-38

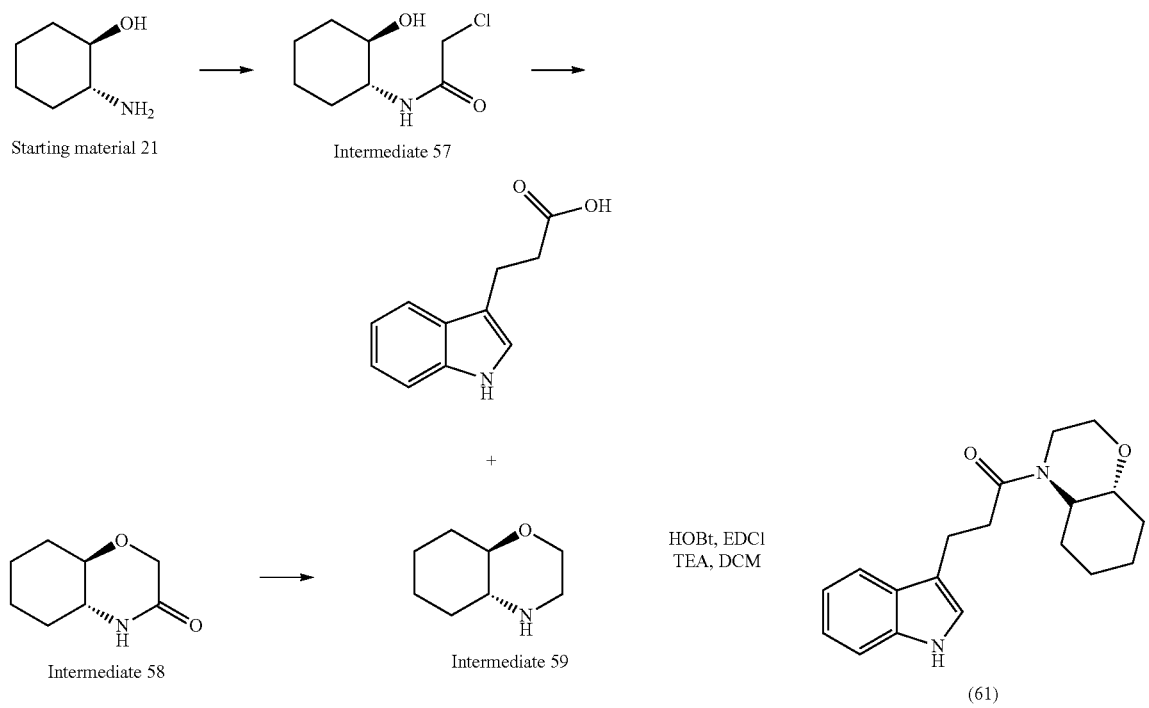

Synthesis of Compound (61)

Compound (61) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (61). $^1$H NMR (300 MHz, CDCl3): δ 8.00 (s, 1H), 7.52-7.55 (d, 1H), 7.27-7.30 (d, 1H), 7.02-7.14 (m, 2H), 6.95 (s, 1H), 3.67-3.73 (m, 3H), 3.32-3.44 (m, 3H), 3.05-3.10 (m, 2H), 2.87-2.90 (m, 1H), 2.45-2.66 (m, 4H), 2.15 (s, 1H), 1.81-1.84 (m, 2H), 1.60-1.64 (m, 2H). LC-MS (M+H)$^+$=313.2; HPLC purity: 94.77%.

Example 62

3-(1,4-di methyl-1H-indol-3-yl)-1-[(trans-4a,8a)-octahydro-4H-1,4-benzoxazin-4-yl]propan-1-one (62)

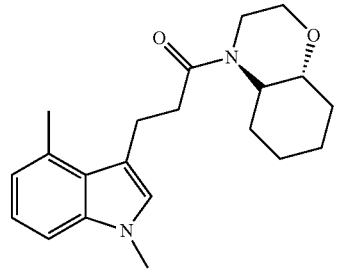

(62)

Synthesis of (62)

Compound (62) was synthesized by following the procedure used to make (Scheme 2). The crude product was obtained by evaporating the organic layer under reduced pressure and was purified by silica gel column using Petroleum ether: Ethyl acetate as eluent to obtain. $^1$H NMR (300 MHz, CDCl3): δ 6.99-7.06 (m, 2H), 6.75-6.77 (d, 2H), 3.68-3.86 (m, 3H), 3.63 (s, 3H), 3.35-3.48 (m, 2H), 3.12-3.29 (m, 3H), 2.64 (s, 3H), 2.50-2.61 (m, 2H), 1.05-2.14 (m, 8H). LC-MS (M+H)$^+$=341.2; HPLC purity: 94.06%.

Example 63

3-(1-methyl-1H-indol-3-yl)-1-[(trans-4a,8a)-octahydro-4H-1,4-benzoxazin-4-yl]propan-1-one (63)

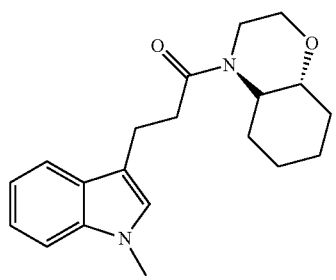

(63)

Synthesis of Compound (63)

Compound (63) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (63). $^1$H NMR (300 MHz, CDCl3): δ 7.51-7.53 (d, 1H), 7.12-7.23 (m, 2H), 7.01-7.06 (t, 1H), 6.81 (s, 1H), 3.68-3.76 (m, 3H), 3.67 (s, 3H), 3.22-3.48 (m, 4H), 3.03-3.08 (t, 2H), 2.51-2.69 (m, 2H), 1.05-2.12 (m, 7H). LC-MS (M+H)$^+$=327.2; HPLC purity: 96.13%.

Example 64

3-(4-methyl-1H-indol-3-yl)-1-(octahydro-4H-1,4-benzoxazin-4-yl)propan-1-one (64)

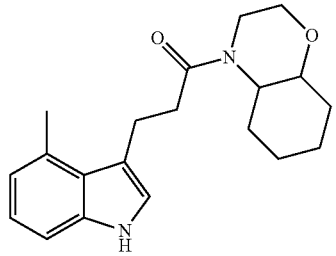

(64)

Synthesis of Compound (64)

Compound (64) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (64). $^1$H NMR (300 MHz, CDCl3): δ 7.94 (s, 1H), 7.10-7.14 (m, 1H), 6.90-7.02 (m, 2H), 6.76-6.80 (t, 1H), 4.11-4.35 (m, 1H), 3.66-3.87 (m, 1H), 3.13-3.49 (m, 5H), 2.47-2.99 (m, 6H), 0.91-1.97 (m, 8H). LC-MS (M+H)$^+$=327.2; HPLC purity: 98.86%.

Example 65

3-(1,4-dimethyl-1H-Indol-3-yl)-1-[trans-(4a,8a)-octahydro-4H-1,4-benzoxazin-4-yl]propan-1-one (Peak-1) (65)

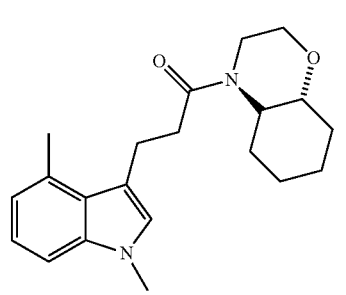

(65)

Synthesis of Compound (65) (Peak-1)

Mixture of isomers of Compound (60) was separated by reverse phase column chromatography to give Compound (65) (Peak-1). $^1$H NMR (300 MHz, CDCl3): δ 6.99-7.06 (m, 2H), 6.75-6.77 (d, 2H), 3.68-3.76 (m, 3H), 3.63 (s, 3H), 3.40-3.48 (m, 2H), 3.08-3.35 (m, 3H), 2.64 (s, 3H), 2.45-2.61 (m, 2H), 1.05-2.14 (m, 8H). LC-MS (M+H)$^+$=341.2; HPLC purity: 97.63% % (column: Zorbax eclipse XDB-C18, RT=15.84 min, mobile phase: 0.01% TFA:MeCN gradient).

Example 66

3-(1,4-dimethyl-1H-indol-3-yl)-1-[cis-(4a,8a)-octahydro-4H-1,4-benzoxazin-4-yl]propan-1-one Peak-2 (66)

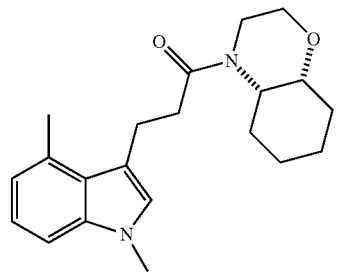

(66)

Synthesis of Compound (66) (Peak-2)

Mixture of isomers of Compound (60) was separated by reverse phase column chromatography to give Compound (66) (Peak-2). $^1$H NMR (300 MHz, CDCl3): δ 6.98-7.06 (m, 2H), 6.76-6.78 (m, 2H), 4.16-4.34 (m, 1H), 3.69-3.87 (m, 1H), 3.63 (d, 3H), 3.07-3.43 (m, 5H), 2.81-2.97 (m, 1H), 2.43-2.73 (m, 5H), 0.91-1.94 (m, 8H). LC-MS (M+H)$^+$=341.2; HPLC purity: 96.84% (column: Zorbax eclipse XDB-C18, RT=16.19 min, mobile phase: 0.01% TFA:MeCN gradient).

Example 67

3-(1H-indol-3-yl)-1-(octahydro-4H-1,4-benzoxazin-4-yl)propan-1-one (67)

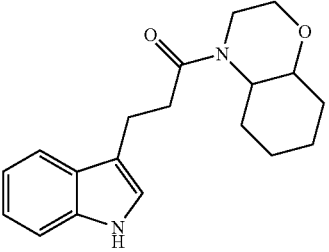

(67)

Synthesis of Compound (67)

Compound (67) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (66). $^1$H NMR (300 MHz, CDCl3): δ 8.02 (s, 1H), 7.53-7.56 (m, 1H), 7.27-7.30 (m, 1H), 7.02-7.15 (m, 2H), 6.96 (s, 1H), 4.13-4.32 (m, 1H), 3.61-3.84 (m, 1H), 3.03-3.47 (m, 5H), 2.47-2.93 (m, 3H), 0.94-2.12 (m, 8). LC-MS (M+H)$^+$=313.2; HPLC purity: 98.01%.

Example 68

1-(2,2-dimethyloctahydro-4H-1,4-benzoxazin-4-yl)-3-(4-methyl-1H-indol-3-yl)propan-1-one (68)

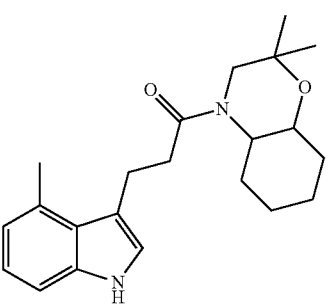

(68)

Synthetic Scheme-39

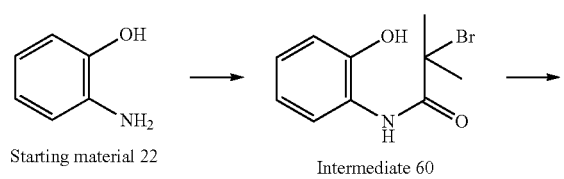

Starting material 22     Intermediate 60

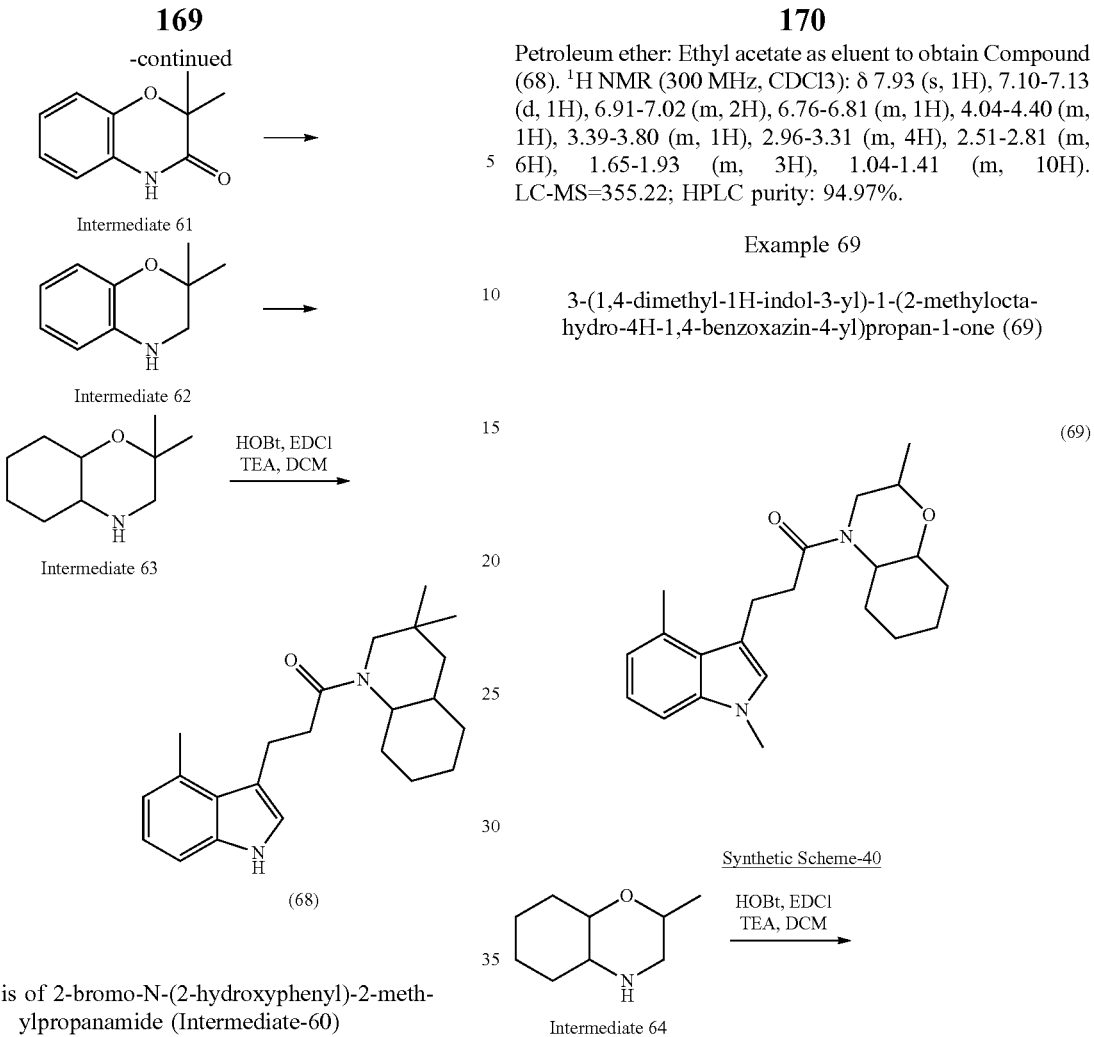

Petroleum ether: Ethyl acetate as eluent to obtain Compound (68). $^1$H NMR (300 MHz, CDCl3): δ 7.93 (s, 1H), 7.10-7.13 (d, 1H), 6.91-7.02 (m, 2H), 6.76-6.81 (m, 1H), 4.04-4.40 (m, 1H), 3.39-3.80 (m, 1H), 2.96-3.31 (m, 4H), 2.51-2.81 (m, 6H), 1.65-1.93 (m, 3H), 1.04-1.41 (m, 10H). LC-MS=355.22; HPLC purity: 94.97%.

Example 69

3-(1,4-dimethyl-1H-indol-3-yl)-1-(2-methyloctahydro-4H-1,4-benzoxazin-4-yl)propan-1-one (69)

Synthesis of 2-bromo-N-(2-hydroxyphenyl)-2-methylpropanamide (Intermediate-60)

Intermediate-60 was synthesized by following the procedure used to make Intermediate-57 (Scheme 38).

Synthesis of 2,2-dimethyl-2H-1,4-benzoxazin-3(4H)-one (Intermediate-61)

Intermediate-61 was synthesized by following the procedure used to make Intermediate-58 (Scheme 38).

Synthesis of 2,2-dimethyl-3,4-dihydro-2H-1,4-benzoxazine (Intermediate-62)

Intermediate-62 was synthesized by following the procedure used to make Intermediate-29 (Scheme 22).

Synthesis of 2,2-dimethyloctahydro-2H-1,4-benzoxazine (Intermediate-63)

Intermediate-63 was synthesized by following the procedure used to make Intermediate-30 (Scheme 22).

Synthesis of Compound (68)

Compound (68) was synthesized by following the procedure used to make Compound (1) (Scheme 2). The crude product was obtained by evaporating the organic layer under reduced pressure and was purified by silica gel column using Synthesis of Intermediate-64 (2-methyloctahydro-2H-1,4-benzoxazine)

Intermediate-64 was synthesized by following the procedure used to make Intermediate-63 (Scheme 39).

Synthesis of Compound (69)

Compound (69) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (69). $^1$H NMR (300 MHz, CDCl3): δ 6.99-7.06 (m, 2H), 6.77-6.77 (d, 2H), 3.86-4.31 (m, 1H), 3.63 (s, 3H), 3.29-3.44 (m, 2H), 3.16-3.13 (m, 3H), 3.04-3.12 (m, 1H), 2.68-2.75 (m, 1H), 2.64 (s, 3H), 2.42-2.61 (m, 2H), 1.80-2.24 (m, 1H), 1.63-1.76 (m, 3H), 1.29-1.43 (m, 2H), 1.11-1.13 (d, 1H), 1.01-1.07 (m, 2H), 0.92-0.98 (m, 1H). LC-MS (M+H)$^+$=355.2; HPLC purity: 95.0%.

Example 70

3-(1,4-dimethyl-1H-indol-3-yl)-1-(2,2-dimethyloctahydro-4H-1,4-benzoxazin-4-yl)propan-1-one (70)

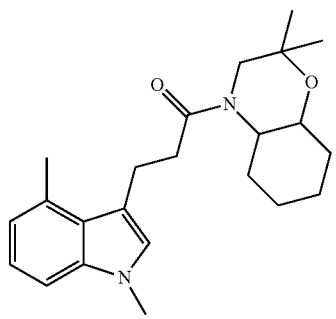

(70)

Synthesis of Compound (70)

Compound (70) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (70). $^1$H NMR (300 MHz, CDCl3): δ 6.99-7.06 (m, 2H), 6.76-6.78 (m, 2H), 4.03-4.39 (m, 1H), 3.62-3.63 (d, 3H), 3.41 (m, 1H), 2.95-3.29 (m, 4H), 2.47-2.80 (m, 5H), 0.99-1.93 (m, 14H). LC-MS (M+H)$^+$=369.2; HPLC purity: 98.90%.

Example 71

3-methyl-3-(1-methyl-1H-indol-3-yl)-1-(octahydro-4H-1,4-benzoxazin-4-yl)butan-1-one (71)

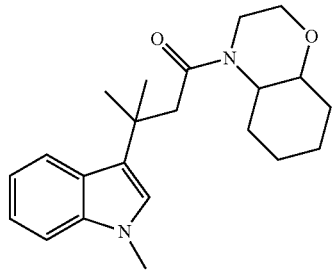

(71)

Synthesis of Compound (71)

Compound (71) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (71). $^1$H NMR (300 MHz, CDCl3) δ 7.70-7.79 (m, 1H), 7.35-7.40 (t, 1H), 7.03-7.11 (m, 3H), 4.04-4.11 (m, 1H), 3.70 (m, 3H), 3.50 (m, 3H), 2.00-3.40 (m, 5H), 0.83-1.70 (m, 14H). LC-MS (M+H)$^+$=355.3; HPLC purity: 88.82%.

Example 72

3-(4-fluoro-1H-indol-3-yl)-1-(octahydro-4H-1,4-benzoxazin-4-yl)propan-1-one (72)

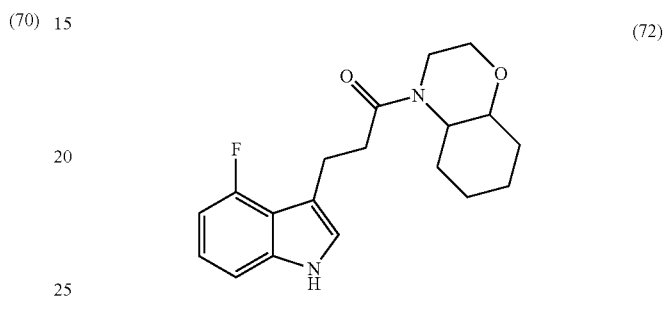

(72)

Synthetic Scheme-41

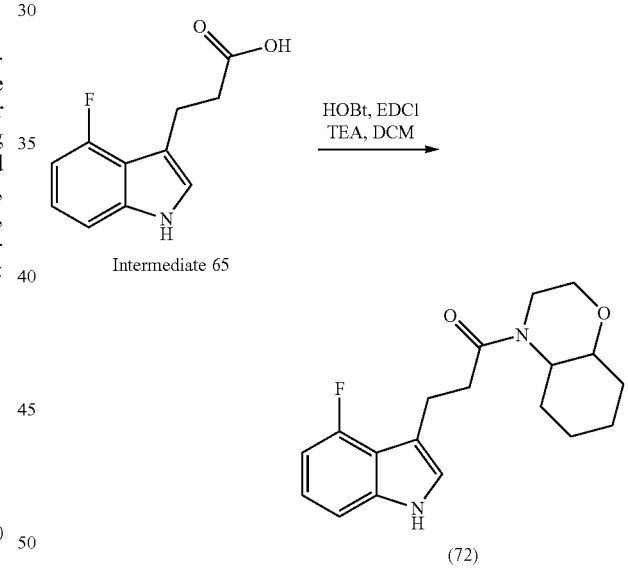

Synthesis of 3-(4-fluoro-1H-indol-3-yl)propanoic acid (Intermediate-65)

Intermediate-65 was synthesized by following the procedure used to make Intermediate-28 (Scheme 21).

Synthesis of Compound (72)

Compound (72) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (72). $^1$H NMR (300 MHz, CDCl3): 8.12 (s, 1H), 6.99-7.08

(m, 2H), 6.95 (s, 1H), 6.64-6.74 (m, 1H), 4.15-4.20 (m, 1H), 3.66-3.85 (m, 1H), 3.12-3.43 (m, 4H), 2.65-2.97 (m, 3H), 1.18-2.10 (m, 9H). LC-MS (M+H)$^+$=331.2; HPLC purity: 97.15%.

Example 73

2-(1,3-benzothiazol-2-ylsulfanyl)-1-(octahydroquinolin-1(2H)-yl)ethanone (73)

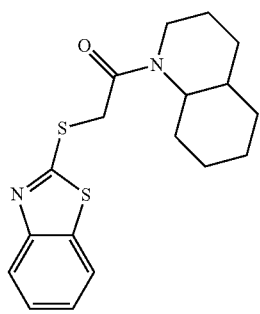

Synthetic Scheme-42

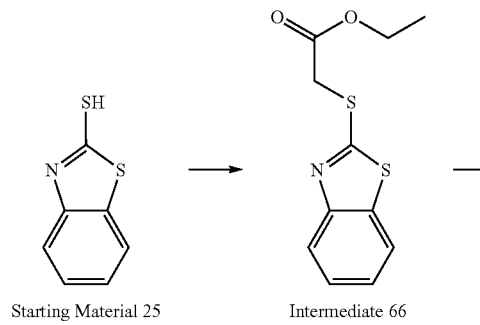

Starting Material 25        Intermediate 66

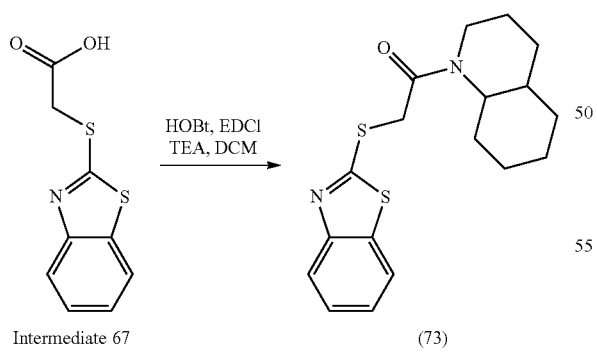

Intermediate 67        (73)

Synthesis of ethyl (1,3-benzothiazol-2-ylsulfanyl)acetate (Intermediate-66)

To a 100 mL RB flask fitted with magnetic stirrer was charged 10 mL of dimethylformamide. To this Starting Material-25 (1.0 g, 5.979 mmol) followed by potassium carbonate (2.477 g, 17.925 mmol) were added and stirred at room temperature for 30 minutes. Then ethylbromoacetate (1.997 g, 11.958 mmol) was added. The resulting solution was stirred at room temperature for 15 hours. After completion of the reaction (reaction monitored by TLC), the reaction mixture was concentrated. The resulting crude was taken in ethyl acetate (100 mL) and washed with water (100 mL×3), brine (100 mL) and concentrated to give Intermediate-66 (2.6 g).

Synthesis of (1,3-benzothiazol-2-ylsulfanyl)acetic acid (Intermediate-67)

To a 100 mL RB flask fitted with magnetic stirrer was charged 15 mL of tetrahydrofuran, 0.5 mL water, 0.5 mL methanol. To this Intermediate-66 (2.6 g, 10.262 mmol), followed by lithium hydroxide (738.9 mg, 30.788 mmol) were added at 0° C. Then the reaction mixture was stirred at room temperature for 7 hours. After completion of the reaction (reaction monitored by TLC), reaction mass was diluted with 10 mL of water and washed with 20 mL dichloro methane DCM (2×10 mL). Then aqueous layer was acidified with 1N HCl (pH=2), and the resulted solids were filtered and dried to give Intermediate-67 (1.17 g).

Synthesis of Compound (73)

Compound (73) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (73). $^1$H NMR (300 MHz, CDCl3): δ 7.69-7.73 (m, 1H), 7.58-7.60 (d, 1H), 7.21-7.28 (m, 1H), 7.11-7.16 (t, 1H), 4.33-4.40 (m, 1H), 4.19-4.29 (m, 2H), 3.78-3.82 (m, 1H), 2.47-3.05 (m, 1H), 1.56-1.77 (m, 5H), 1.42 (s, 2H), 1.14-1.33 (m, 6H). LC-MS (M+H)$^+$=347.1; HPLC purity: 97.01%.

Example 74

2-(1,3-benzothiazol-2-ylsulfanyl)-2-methyl-1-(octahydroquinolin-1(2H)-yl)propan-1-one (74)

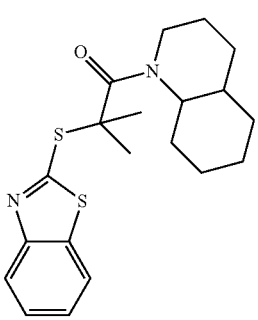

Synthetic Scheme-43

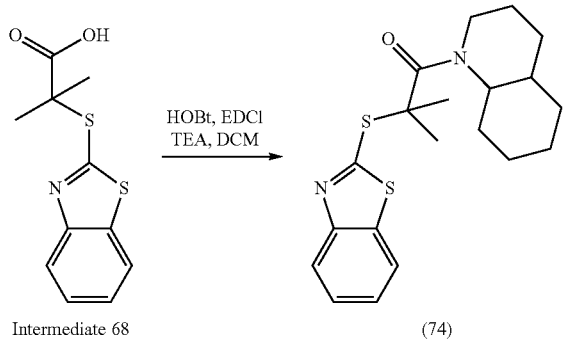

Intermediate 68 (74)

Synthesis of 2-(1,3-benzothiazol-2-ylsulfanyl)-2-methylpropanoic acid (Intermediate-68)

Intermediate-68 was synthesized by following the procedure used to make Intermediate-67 (Scheme 42).

Synthesis of Compound (74)

Compound (74) was synthesized by following the procedure used to make 1) (Scheme 2). The crude product was obtained by evaporating the organic layer under reduced pressure and was purified by silica gel column using Petroleum ether: Ethyl acetate as eluent to obtain Compound (77). $^1$H NMR (300 MHz, CDCl3): δ 7.86-7.89 (d, 1H), 7.68-7.71 (m, 1H), 7.33-7.38 (m, 1H), 7.23-7.29 (m, 1H), 4.58-4.62 (m, 2H), 2.69-3.05 (m, 1H), 1.63-1.72 (m, 12H), 1.42-1.45 (m, 1H), 1.22-1.40 (m, 6H). LC-MS (M+H)$^+$=375.1; HPLC purity: 91.48%.

Example 75

3-(1,3-benzothiazol-2-yl)-1-(octahydroquinolin-1(2H)-yl)propan-1-one (75)

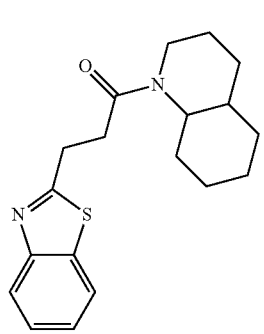

(75)

Synthetic Scheme-44

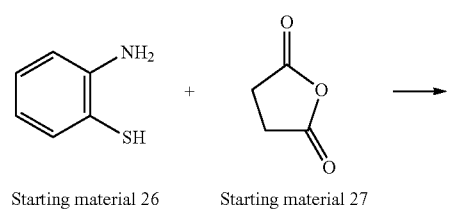

Starting material 26    Starting material 27

-continued

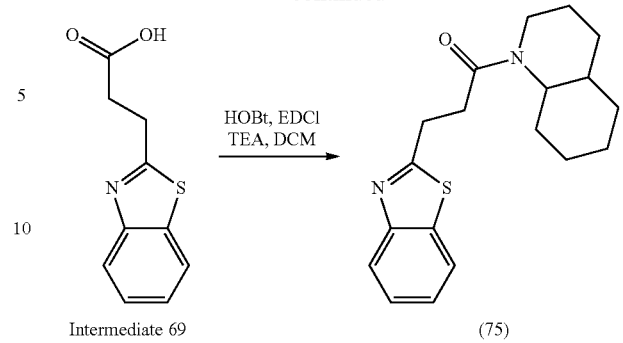

Intermediate 69 (75)

Synthesis of 3-(1,3-benzothiazol-2-yl)propanoic acid (Intermediate-69)

Starting material-27 (3.97 mmol) in benzene was added drop wise to the solution of Starting Material-26 (3.97 mmol) in benzene. The resulting solution was heated to reflux for 2 hours. After 2 hours the reaction mass was cooled to room temperature and extracted with 10% sodium hydroxide solution. The aqueous layer was acidified using Conc.HCl (3 ml) at 0° C. The resulting solids were filtered and dried at room temperature to get Intermediate-69 (660 mg).

Synthesis of Compound (75)

Compound (75) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (75). $^1$H NMR (300 MHz, CDCl3): δ 7.93-7.97 (m, 1H), 7.81-7.84 (d, 1H), 7.41-7.46 (m, 1H), 7.31-7.36 (m, 1H), 4.49-4.67 (m, 1H), 3.65-3.83 (m, 1H), 3.44-3.51 (m, 2H), 2.61-3.10 (m, 3H), 1.71-1.78 (m, 6H), 1.30-1.42 (m, 7H). LC-MS (M+H)$^+$=329.1; HPLC purity: 98.13%.

Example 76

3-(1,3-benzothiazol-2-yl)-1-(2-methyloctahydroquinolin-1(2H)-yl)propan-1-one (76)

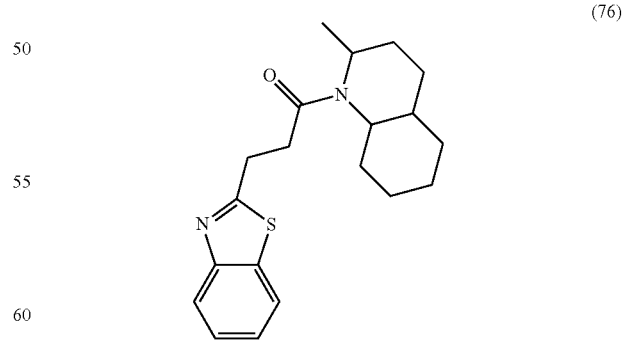

(76)

Synthesis of Compound (76)

Compound (76) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (76). $^1$H NMR (300 MHz, CDCl3): δ 7.86-7.89 (d, 1H), 7.75-7.77 (d, 1H), 7.34-7.39 (t, 1H), 7.24-7.29 (t, 1H), 4.45-4.70 (m, 1H), 3.67-4.08 (m, 1H), 3.40-3.45 (t, 2H), 2.94-3.05 (m, 1H), 2.77-2.85 (m, 1H), 1.58-1.76 (m, 9H), 1.20-1.23 (d, 7H). LC-MS (M+H)$^+$=343.1; HPLC purity: 95.24%.

Example 77 methyl 1-[3-(1,3-benzothiazol-2-yl)propanoyl]decahydroquinoline-4-carboxylate (80)

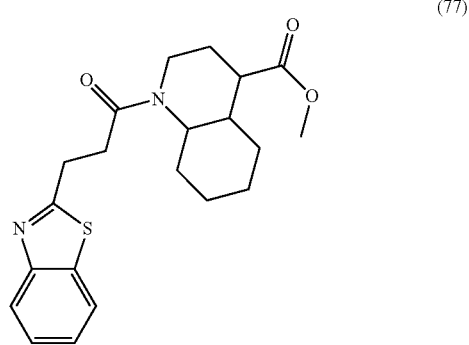 [SMILES: COC(=O)C1CCN(C(=O)CCc2nc3ccccc3s2)C2CCCCC12]

(77)

Synthesis of Compound (77)

Compound (77) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (77). $^1$H NMR (300 MHz, CDCl3): δ 7.86-7.89 (d, 1H), 7.75-7.77 (d, 1H), 7.35-7.39 (t, 1H), 7.25-7.30 (t, 1H), 3.86-4.32 (m, 1H), 3.61 (d, 3H), 3.39-3.44 (t, 2H), 2.55-3.01 (m, 2H), 0.90-2.24 (m, 14H). LC-MS (M+H)$^+$=387.2; HPLC purity: 95.28%.

Example 78

3-(1,3-benzothiazol-2-yl)-1-(4a-methyloctahydroquinolin-1(2H)-yl)propan-1-one (78)

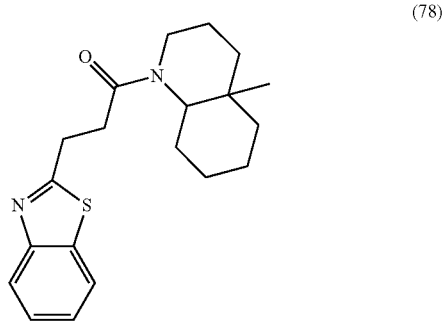 [SMILES: CC12CCCCC1N(C(=O)CCc1nc3ccccc3s1)CCC2]

(78)

Synthesis of Compound (78)

Compound (78) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (78). $^1$H NMR (300 MHz, CDCl3): δ 7.85-7.89 (m, 1H), 7.74-7.77 (d, 1H), 7.34-7.39 (t, 1H), 7.24-7.29 (t, 1H), 4.23-4.50 (m, 1H), 3.31-3.64 (m, 3H), 2.54-3.09 (m, 3H), 0.84-1.96 (m, 15H). LC-MS (M+H)$^+$=343.2; HPLC purity: 97.13%.

Example 79

3-(1,3-benzothiazol-2-yl)-1-[trans-(4a,8a)-octahydro-4H-1,4-benzoxazin-4-yl]propan-1-one (79)

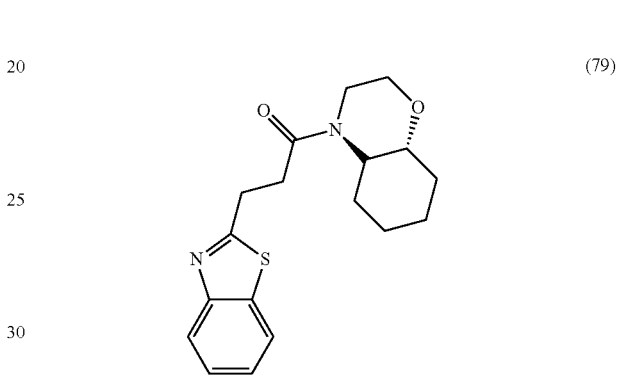

(79)

Synthesis of Compound (79)

Compound (79) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (79). $^1$H NMR (300 MHz, CDCl3): δ 7.86-7.89 (d, 1H), 7.75-7.77 (d, 1H), 7.35-7.39 (t, 1H), 7.25-7.30 (t, 1H), 3.80-3.93 (m, 2H), 3.39-3.55 (m, 5H), 2.78-2.96 (m, 2H), 1.18-2.22 (m, 9H). LC-MS (M+H)$^+$=331.22; HPLC purity: 96.52%.

Example 80

3-(1,3-benzothiazol-2-yl)-1-(octahydro-4H-1,4-benzoxazin-4-yl)propan-1-one (80)

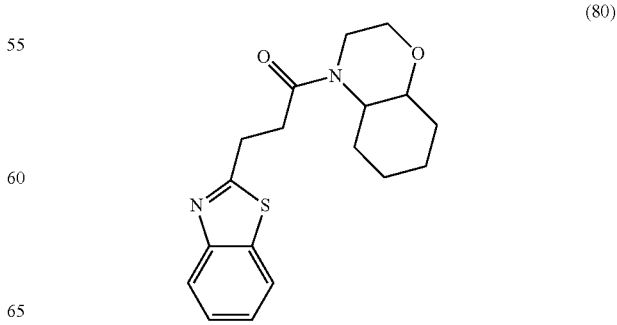

(80)

Synthesis of Compound (80)

Compound (80) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (80). $^1$H NMR (300 MHz, CDCl3): δ 7.85-7.89 (m, 1H), 7.75-7.77 (d, 1H), 7.34-7.40 (m, 1H), 7.25-7.30 (m, 1H), 4.11-4.31 (m, 1H), 3.80-3.91 (m, 1H), 3.31-3.57 (m, 5H), 2.68-3.04 (m, 2H), 1.66-2.24 (m, 6H), 1.32-1.44 (m, 3H). LC-MS (M+H)$^+$=331.2; HPLC purity: 94.03%.

Example 81

3-(1,3-benzothiazol-2-yl)-1-(octahydro-1H-indol-1-yl)propan-1-one (81)

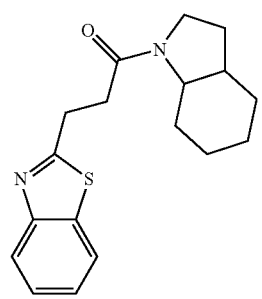

(81)

Synthesis of Compound (81)

Compound (81) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (81). $^1$H NMR (300 MHz, CDCl3): δ 7.89-7.91 (d, 1H), 7.75-7.77 (d, 1H), 7.36-7.41 (t, 1H), 7.26-7.31 (t, 1H), 3.64-4.03 (m, 1H), 3.32-3.52 (m, 3H), 2.71-2.97 (m, 2H), 0.95-2.24 (m, 12H). LC-MS (M+H)$^+$=315.1; HPLC purity: 95.99%.

Example 82

3-(1,3-benzothiazol-2-yl)-1-(octahydro-2H-isoindol-2-yl)propan-1-one (82)

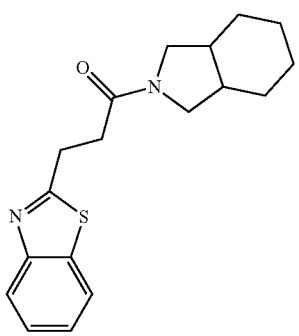

(82)

Synthesis of Compound (82)

Compound (82) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (82). $^1$H NMR (300 MHz, CDCl3): δ 7.91-7.94 (d, 1H), 7.75-718 (d, 1H), 7.37-7.42 (t, 1H), 7.27-7.32 (t, 1H), 3.22-3.47 (m, 6H), 2.81-2.91 (m, 2H), 2.10-2.21 (m, 2H), 1.89 (s, 1H), 1.30-1.40 (m, 7H). LC-MS (M+H)$^+$=315.2; HPLC purity: 98.47%.

Example 83

3-(1,3-benzothiazol-2-yl)-1-(2-methyloctahydro-1H-indol-1-yl)propan-1-one (83)

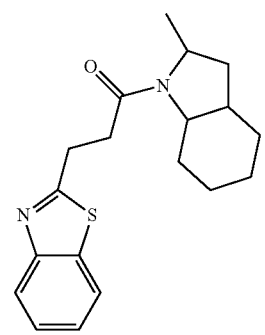

(83)

Synthesis of Compound (83)

Compound (83) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (83). $^1$H NMR (300 MHz, CDCl3): δ 7.87-7.90 (d, 1H), 7.75-7.77 (d, 1H), 7.35-7.40 (t, 1H), 7.25-7.30 (t, 1H), 3.86-4.13 (m, 1H), 3.62-3.69 (m, 1H), 3.34-3.52 (m, 2H), 2.68-2.97 (m, 2H), 1.80-2.14 (m, 4H), 1.00-1.67 (m, 10H). LC-MS (M+H)$^+$=329.2; HPLC purity: 97.23%.

Example 84

1-(octahydroquinolin-1(2H)-yl)-3-(1H-pyrrolo[2,3-b]pyridin-3-yl)propan-1-one (84)

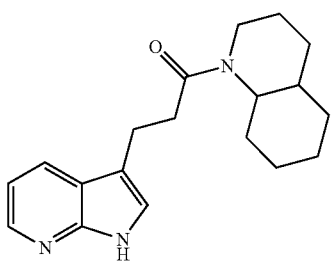

(84)

Synthetic Scheme-45

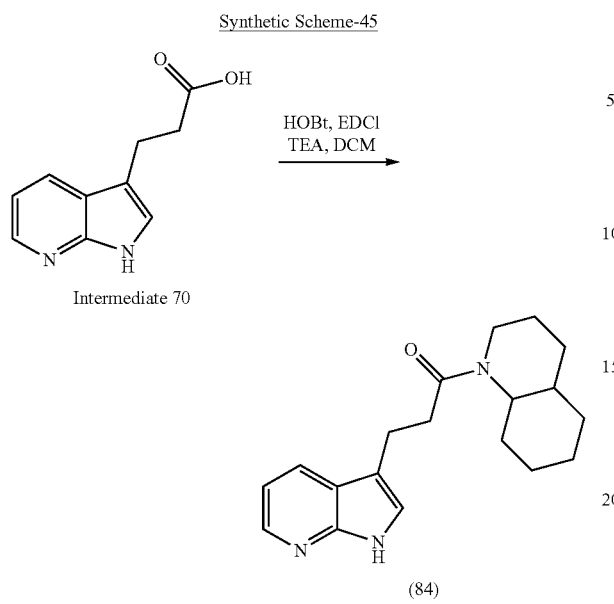

Synthesis of 3-(1H-pyrrolo[2,3-b]pyridin-3-yl)propanoic acid (Intermediate-70)

Intermediate-70 was synthesized by following the procedure used to make Intermediate-9 (Scheme 4).

Synthesis of Compound (84)

Compound (84) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (84). $^1$H NMR (300 MHz, CDCl3): δ 9.77-9.80 (d, 1H), 8.29-8.30 (d, 1H), 7.93-7.96 (m, 1H), 7.16-7.18 (d, 1H), 7.05-7.11 (m, 1H), 4.50-4.68 (m, 1H), 3.57-3.65 (m, 1H), 3.07-3.15 (m, 2H), 2.56-2.95 (m, 4H), 1.25-1.87 (m, 12H). LC-MS (M+H)$^+$=312.3; HPLC purity: 95.95%.

Example 85

1-(octahydroquinolin-1(2H)-yl)-3-[1-(phenylsulfonyl)-1H-pyrrolo[2,3-b]pyridin-3-yl]propan-1-one (85)

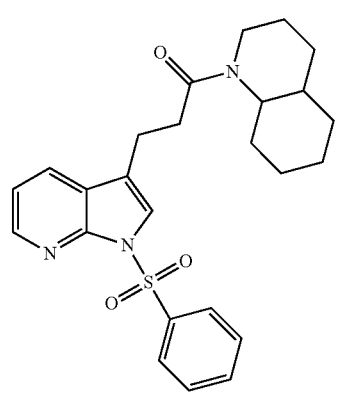

Synthetic Scheme-46

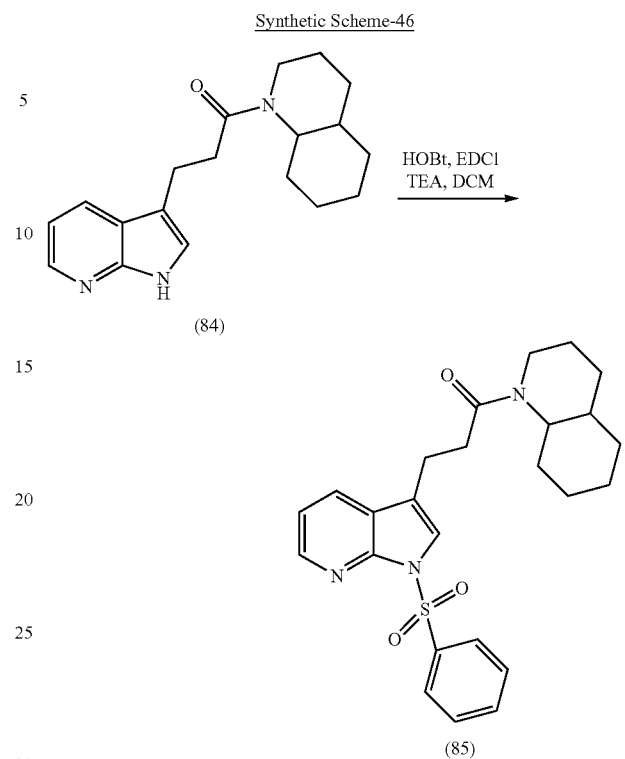

Synthesis of Compound (85)

Compound (85) was synthesized by following the procedure used to make (51) (Scheme 34). The crude product was obtained by evaporating the organic layer under reduced pressure and was purified by silica gel column using Petroleum ether: Ethyl acetate as eluent to obtain Compound (85). $^1$H NMR (300 MHz, CDCl3): δ 8.34-8.36 (t, 1H), 8.09-8.13 (t, 2H), 7.78-7.81 (d, 1H), 7.37-7.49 (m, 4H), 7.08-7.14 (m, 1H), 4.42-4.59 (m, 1H), 3.48-3.60 (m, 1H), 2.89-2.97 (m, 2H), 2.47-2.75 (m, 3H), 1.25-1.74 (m, 13H). LC-MS (M+H)$^+$=452.2; HPLC purity: 99.87%.

Example 86

1-(2-methyloctahydroquinolin-1(2H)-yl)-3-(1H-pyrrolo[2,3-b]pyridin-3-yl)propan-1-one (86)

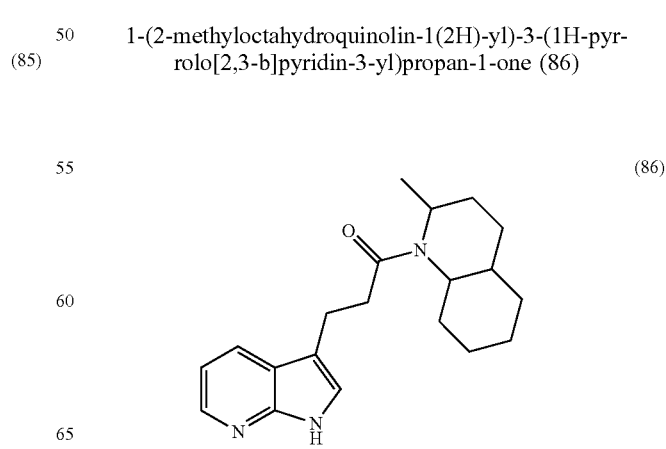

Synthesis of Compound (86)

Compound (86) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (86). $^1$H NMR (300 MHz, CDCl3): δ 9.48 (s, 1H), 8.21-8.23 (d, 1H), 7.86-7.90 (m, 1H), 6.98-7.09 (m, 2H), 4.46-4.70 (m, 1H), 3.47-3.90 (m, 1H), 3.03-3.08 (m, 2H), 2.49-2.77 (m, 2H), 1.07-1.86 (m, 16H). LC-MS (M+H)$^+$=326.2; HPLC purity: 97.13%.

Example 87

3-(1-methyl-1H-pyrrolo[2,3-b]pyridin-3-yl)-1-(octahydroquinolin-1 (2H)-yl)propan-1-one (87)

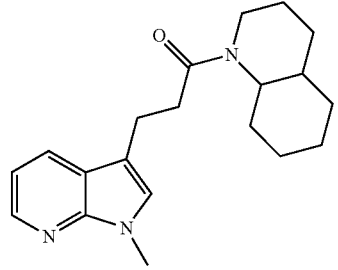

(87)

Synthesis of Compound (87)

Compound (87) was synthesized by following the procedure used to make Compound (27) (Scheme 26). The crude product was obtained by evaporating the organic layer under reduced pressure and was purified by silica gel column using Petroleum ether: Ethyl acetate as eluent to obtain Compound (87). $^1$H NMR (300 MHz, CDCl3): δ 8.25 (s, 1H), 7.82-7.84 (m, 1H), 6.94-7.00 (m, 2H), 4.43-4.61 (m, 1H), 3.77 (s, 1H), 3.38-3.62 (m, 1H), 2.98-3.05 (m, 2H), 2.45-2.92 (m, 4H), 1.18-1.66 (m, 14H). LC-MS (M+H)$^+$=326.3; HPLC purity: 98.68%.

Example 88

3-(1H-indazol-3-yl)-1-(octahydroquinolin-1(2H)-yl)propan-1-one (88)

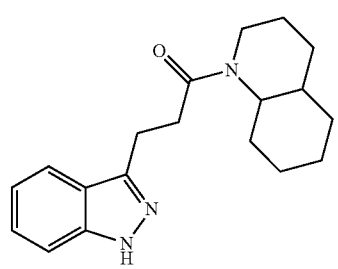

(88)

Synthetic Scheme-47

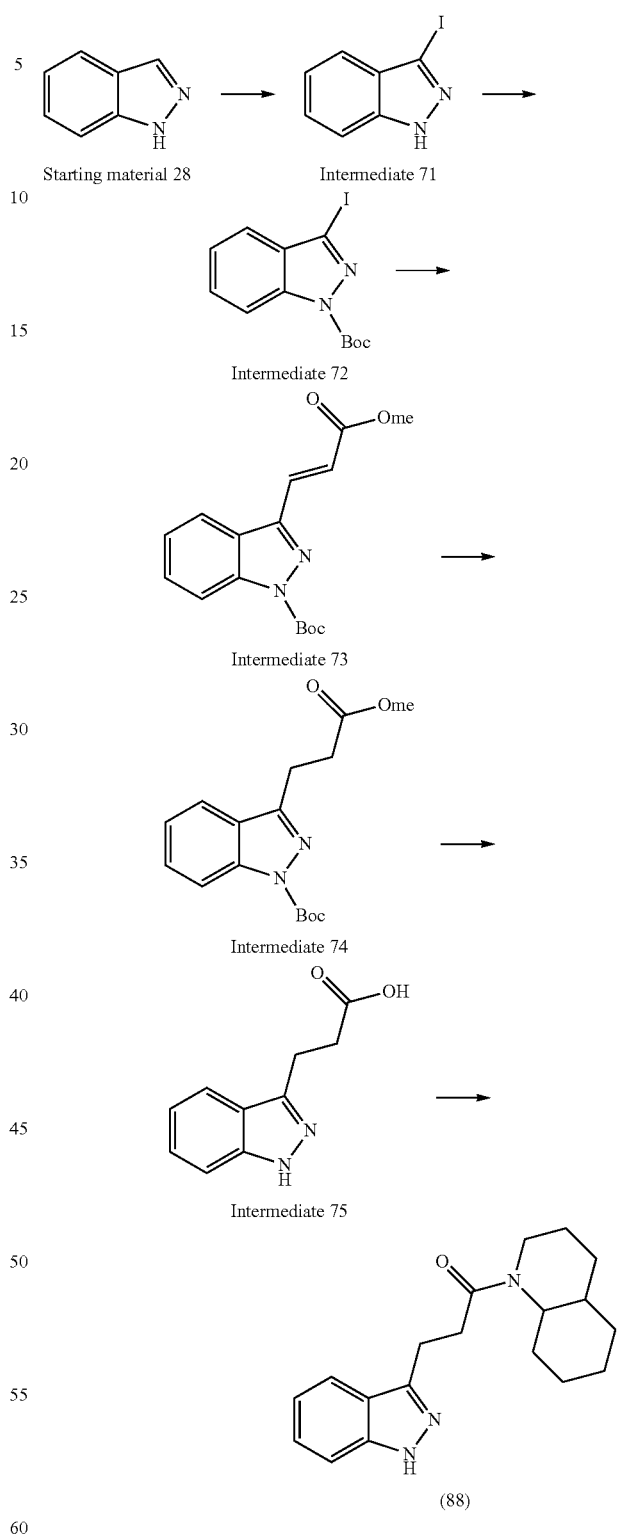

Synthesis of 3-iodo-1H-indazole (Intermediate-71)

Starting Material-28 (42 mmol) in DMF (50 ml) was cooled to 0° C. Then potassium hydroxide (84.6 mmol) was added which was followed by the addition of Iodine (42 mmol). The reaction mixture was maintained at room temperature for 2 hours. Then the reaction mixture was diluted with ice cooled water and extracted with ethyl acetate. The organic layer was dried over anhydrous MgSO4, and evaporated to give Intermediate-71 (8 g, pale yellow solid).

Synthesis of tert-butyl 3-iodo-1H-indazole-1-carboxylate (Intermediate-72)

DMAP (16.37 mmol) was added to Intermediate-71(39 mmol) in acetonitrile (50 ml). The reaction mixture was then cooled to 0° C. BOC anhydride (39.9 mmol) was added to the cooled reaction mixture. The reaction was carried out at room temperature for 16 hours. Then the reaction mixture was diluted with water (100 ml) and extracted with ethyl acetate. The organic layer was dried over anhydrous $Na_2SO_4$ and evaporated to obtain Intermediate-72 (7 g, pale yellow solid).

Synthesis of tert-butyl 3-[(1E)-3-ethoxy-3-oxoprop-1-en-1-yl]-1H-indazole-1-carboxylate (Intermediate-73)

To Triethylamine (3 ml), Intermediate-72 (5.8 mmol) was added to which methyl acrylate (5.8 mmol) was further added. The reaction mixture was purged with argon for 10 minutes. The Pd (II) acetate (0.5 mmol) and tri-o-tolyl phosphine (0.5 mmol) was added to the reaction mixture. The reaction was carried out for 16 hours at room temperature. Then the reaction mixture was filtered through celite, the filtrate was diluted with ethyl acetate (250 ml) and washed with $NaHCO_3$ (50 ml) and brine solution. The organic layer was dried over anhydrous $MgSO_4$, and obtained the crude product by evaporating the organic layer under reduced pressure. The crude product was purified using silica gel column using Hexane and Ethyl acetate as the eluent, to obtain Intermediate-73 (500 mg, pale yellow liquid). $^1$H NMR (300 MHz, DMSO-$d_6$): δ 8.24-8.27 (d, 1H), 8.13-8.16 (d, 1H), 7.85-7.90 (d, 1H), 7.65-7.71 (t, 1H), 7.45-7.50 (t, 1H), 6.96-7.02 (d, 1H), 3.80 (s, 3H), 1.67 (s, 9H).

Synthesis of tert-butyl 3-(3-ethoxy-3-oxopropyl)-1H-indazole-1-carboxylate (Intermediate-74)

Intermediate-73 (1.58 mmol) dissolved in EtOAc (10 ml) was taken in a par shaker flask. To this reaction mixture 10% Pd—C (20% W/W) was added. The resulting reaction mixture was stirred under hydrogen atmosphere (50 psi) for 5 hours at room temperature. After 5 hours the reaction mixture was filtered through celite. The filtrate was further concentrated to give Intermediate-74 (200 mg, pale yellow liquid). $^1$H NMR (300 MHz, DMSO-$d_6$): δ 7.99-8.02 (d, 1H), 7.62-7.65 (d, 1H), 7.44-7.47 (t, 1H), 7.21-7.26 (t, 1H), 3.63 (s, 3H), 3.21-3.26 (t, 2H), 2.84-2.89 (t, 2H), 1.65 (s, 9H).

Synthesis of 3-(1H-indazol-3-yl) propanoic acid (Intermediate-75)

Intermediate 74 (0.6 mmol) is added to a solvent (equal ratio of the solvents THF (2 ml) and MeOH (2 ml)) to which LION (3.4 mmol) solution in 1 ml water is further added. The reaction was allowed for 16 hours at room temperature. After 16 hours the reaction mixture was concentrated, and acidified with 1N HCl (pH=2). The reaction mixture was then extracted with ethyl acetate. The organic layer was dried over anhydrous $MgSO_4$, and evaporated to obtain Intermediate-75(100 mg, pale yellow liquid).

Synthesis of Compound (88)

Compound (88) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (88). $^1$H NMR (300 MHz, CDCl3): δ 7.72-7.74 (d, 1H), 7.36-7.47 (m, 2H), 7.11-7.16 (m, 1H), 4.42-4.61 (m, 1H), 3.57-3.74 (m, 1H), 3.10-3.35 (m, 3H), 2.22-3.00 (m, 3H), 1.56-1.67 (m, 12H). LC-MS (M+H)$^+$=312.2; HPLC purity: 90.23%.

Example 89

3-(1-methyl-1H-indazol-3-yl)-1-(octahydroquinolin-1(2H)-yl)propan-1-one (89)

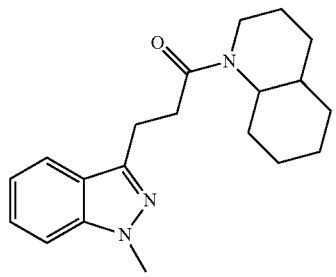

(89)

Synthetic Scheme-48

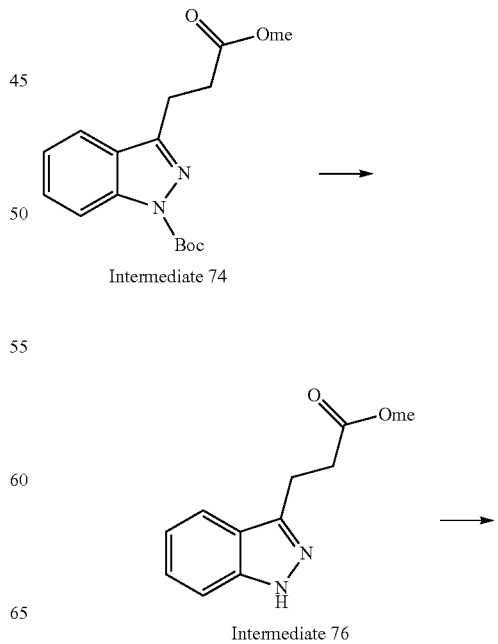

Intermediate 74

Intermediate 76

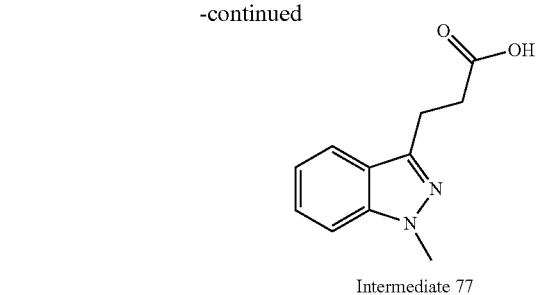

Intermediate 77

Synthesis of ethyl 3-(1H-indazol-3-yl)propanoate (Intermediate-76)

Intermediate-74 (1.7 mmol) in DCM (5 ml) was cooled to 0° C., followed by the addition of TFA (5.1 mmol). The reaction was allowed for 3 hours at room temperature. After 3 hours the reaction mixture was concentrated and diluted with ethyl acetate (50 ml). Further washed with NaHCO$_3$ solution (20 ml), the organic layer was dried over anhydrous MgSO$_4$, and evaporated to obtain Intermediate-76 (250 mg, pale yellow liquid).

Synthesis of 3-(1-methyl-1H-Indazol-3-yl)propanoic acid (Intermediate-77)

Intermediate-76 (1.2 mmol) was added to dry THF (5 ml) and was cooled to 0° C. Then to the reaction mixture, NaH (2.4 mmol) was added. After 15 minutes, MeI (1.8 mmol) was added to the reaction mixture. The reaction was allowed for 3 hours at room temperature. After 3 hours the reaction mixture was quenched with 1N HCl and extracted with ethyl acetate. The organic layer was dried over anhydrous MgSO$_4$, and evaporated to obtain Intermediate-77 (100 mg, pale yellow liquid).

Synthesis of Compound (89)

Compound (89) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (89). $^1$H NMR (300 MHz, CDCl3): δ 7.64-7.67 (d, 1H), 7.24-7.33 (m, 2H), 7.03-7.11 (m, 1H), 4.44-4.62 (m, 1H), 3.93-3.95 (d, 3H), 3.57-3.70 (m, 1H), 3.21-3.26 (m, 2H), 2.42-2.93 (m, 3H), 1.21-1.68 (m, 13H). LC-MS (M+H)$^+$=326.3; HPLC purity: 96.80%.

Example 90

3-(1H-benzotriazol-1-yl)-1-(4a-methyloctahydroquinolin-1(2H)-yl)propan-1-one (90)

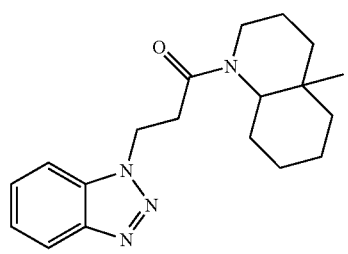

(90)

Synthetic Scheme-49

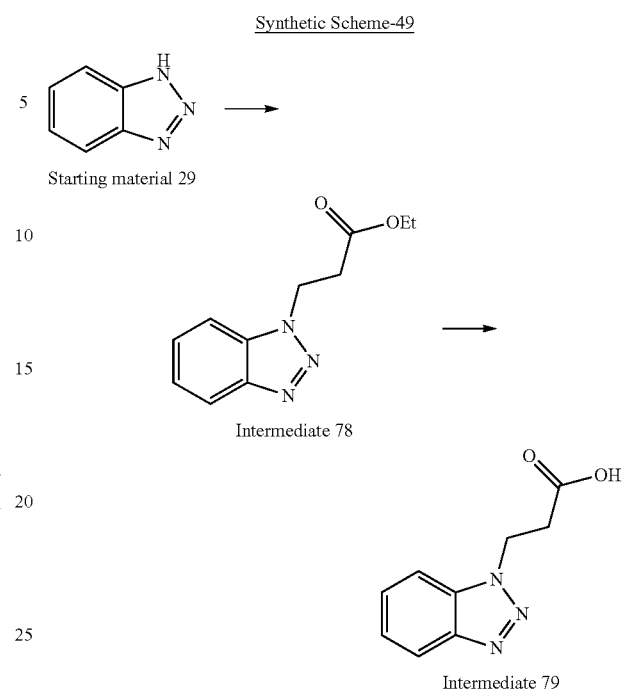

Synthesis of ethyl 3-(1H-benzotriazol-1-yl)propanoate (Intermediate-78)

The starting material-29 (4.1 mmol) in dry THF (5 ml) was cooled to 0° C., followed by the addition of NaH (6.0 mmol). The reaction mixture was gradually warmed to room temperature and allowed to react for 20 minutes. The reaction mixture was again cooled to 0° C., followed by the drop wise addition of ethyl 3-bromopropanoate (4.6 mmol) in THF (2.5 ml). The reaction was allowed for 12 hours at room temperature. After 12 hours the reaction mixture was quenched with ice cooled water and extracted with ethyl acetate. The organic layer was dried over anhydrous MgSO$_4$, and concentrated to obtain Intermediate-78 (70 mg). 1H NMR (300 MHz, CDCl3): δ 7.98-8.01 (1H, d), 7.55-7.58 (d, 1H), 7.41-7.46 (t, 1H), 7.28-7.33 (t, 1H), 4.82-4.87 (t, 2H), 4.00-4.07 (t, 2H), 3.00-3.05 (t, 2H), 1.08-1.1 (t, 3H).

Synthesis of 3-(1H-benzotriazol-1-yl)propanoic acid (Intermediate-79)

At 0° C., LiOH (1.5 mmol) in water (1 ml) was added to Intermediate-78 in the solvent THF: MeOH (1:1, 3 ml each). The reaction was allowed for 12 hours at room temperature. After 12 hours the reaction mixture was concentrated, further acidified with 1N HCl (pH=2). The reaction mixture was extracted with ethyl acetate. The organic layer was dried over anhydrous MgSO$_4$, and evaporated under reduced pressure to obtain Intermediate-79 (60 mg). 1H NMR (300 MHz, CDCl3): δ 7.29-8.00 (4H, m), 4.82-4.87 (t, 2H), 3.09-3.14 (t, 2H).

Synthesis of Compound (90)

Compound (90) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (90). $^1$H NMR (300 MHz, CDCl3): δ 7.96-7.99 (m, 1H), 7.60-7.62 (m, 1H), 7.42-7.47 (m, 1H), 7.28-7.33 (m, 1H), 4.88-4.94 (m, 2H), 4.10-4.50 (m, 1H), 3.20-3.30 (m, 1H), 2.40-3.20 (m, 3H), 0.70-1.94 (m, 15H). LC-MS (M+H)$^+$=327.2; HPLC purity: 99.10%.

Example 91

3-(1H-benzotriazol-1-yl)-1-(octahydro-4H-1,4-benzoxazin-4-yl)propan-1-one (91)

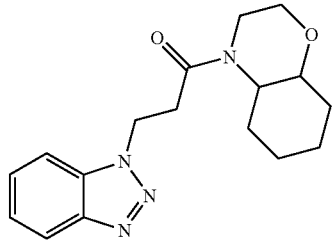
(91)

Synthesis of Compound (91)

Compound (91) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (91). $^1$H NMR (300 MHz, CDCl3): δ 7.96-7.99 (m, 1H), 7.57-7.61 (m, 1H), 7.41-7.46 (t, 1H), 7.27-7.33 (t, 1H), 4.89-4.94 (m, 2H), 3.77-4.11 (m, 2H), 2.90-3.31 (m, 5H), 1.18-1.88 (m, 9H). LC-MS (M+H)$^+$=315.2; HPLC purity: 92.32%.

Example 92

3-(5-fluoro-1H-indol-3-yl)-1-(2-methyloctahydroquinolin-1(2H)-yl)butan-1-one (92)

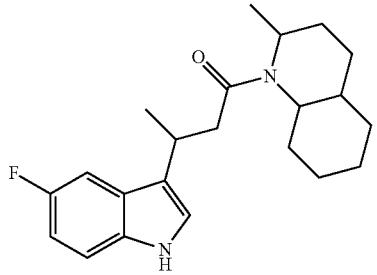
(92)

Synthesis of Compound (92)

Compound (92) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (92). $^1$H NMR (300 MHz, CDCl3): δ 8.00 (s, 1H), 7.29 (m, 2H), 6.98 (s, 1H), 6.82 (t, 1H), 4.40-4.70 (m, 1H), 2.61-3.58 (m, 5H), 1.59 (m, 9H), 1.35-1.43 (t, 6H), 1.02 (m, 3H). LC-MS (M+H)$^+$=357.2; HPLC purity: 82.80%.

Example 93

3-(1H-indol-3-yl)-1-(octahydroquinolin-1(2H)-yl)propan-1-one (93)

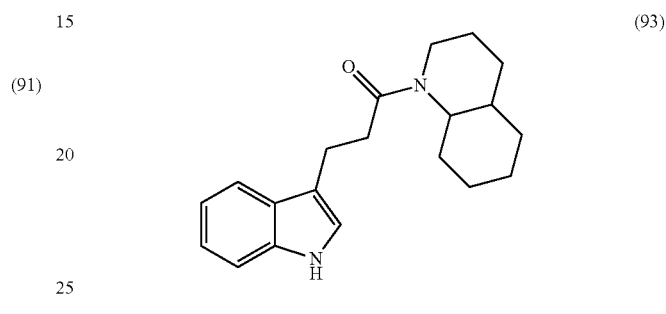
(93)

Synthesis of Compound (93)

Compound (93) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (93). $^1$H NMR (300 MHz, DMSO-d6): δ 10.75 (s, 1H), 7.48-7.52 (t, 1H), 7.30-7.33 (m, 1H), 7.12 (s, 1H), 6.93-7.07 (m, 2H), 4.29-4.48 (m, 1H), 3.60-3.71 (m, 1H), 2.43-2.96 (m, 5H), 1.23-1.70 (m, 13H). LC-MS (M+H)$^+$=311.1; HPLC purity: 97.67%.

Example 94

3-(1-methyl-1H-indol-3-yl)-1-(octahydroquinolin-1(2H)-yl)butan-1-one (94)

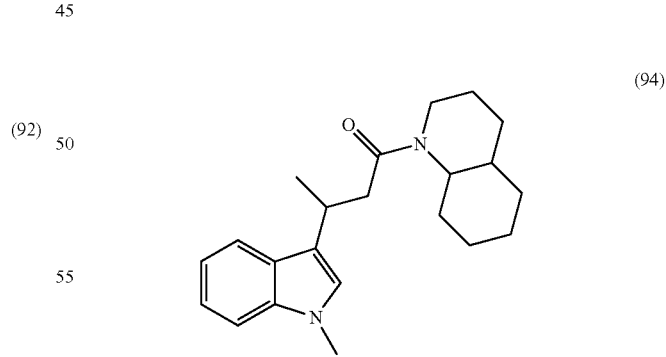
(94)

Synthesis of Compound (94)

Compound (94) was synthesized by following the procedure used to make Compound (27) (Scheme 26). The crude product was obtained by evaporating the organic layer under reduced pressure and was purified by silica gel column using Petroleum ether: Ethyl acetate as eluent to obtain Compound (94). ¹H NMR (300 MHz, CDCl3): δ 7.57 (m, 1H), 7.10-7.28 (m, 2H), 6.98-7.03 (m, 1H), 6.78-6.80 (d, 1H), 4.43-4.60 (m, 1H), 3.65 (m, 3H), 3.51-3.59 (m, 2H), 2.37-2.87 (m, 3H), 0.90-1.63 (m, 16H). LC-MS (M+H)⁺=339.2; HPLC purity: 91.90%.

Example 95

3-(1H-indol-3-yl)-4-methyl-1-(octahydroquinolin-1(2H)-yl)pentan-1-one (95)

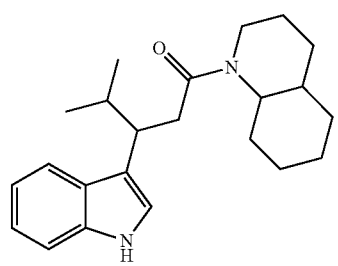

(95)

Synthesis of Compound (95)

Compound (95) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (95). ¹H NMR (300 MHz, CDCl3): δ 8.51-8.55 (d, 1H), 7.53-7.61 (m, 1H), 7.22-7.25 (d, 1H), 6.94-7.06 (m, 2H), 6.84 (d, 1H), 4.32-4.47 (m, 1H), 3.35-3.65 (m, 1H), 3.02-3.20 (m, 1H), 2.28-2.92 (m, 3H), 0.78-1.99 (m, 20H). LC-MS (M+H)⁺=353.3; HPLC purity: 88.81%.

Example 96

N-[3-(1H-indol-3-yl)-1-(octahydroquinolin-1(2H)-yl)-1-oxopropan-2-yl]acetamide (96)

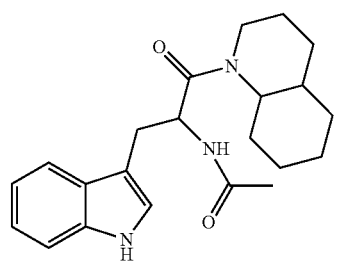

(96)

Synthesis of Compound (96)

Compound (96) was synthesized by following the procedure used to make Compound (1) (Scheme 1). The crude product was obtained by evaporating the organic layer under reduced pressure and was purified by silica gel column using Petroleum ether: Ethyl acetate as eluent to obtain Compound (96). ¹H NMR (300 MHz, DMSO-d6): δ 10.78-10.85 (m, 1H), 8.19-8.22 (m, 1H), 7.52-7.58 (m, 1H), 7.30-7.33 (m, 1H), 6.97-7.11 (m, 3H), 5.06 (m, 1H), 4.20 (m, 1H), 2.86-3.07 (m, 3H), 0.96-1.83 (m, 17H). LC-MS (M+H)⁺=368.1; HPLC purity: 94.46%.

Example 97

[2-(1-methyl-1H-indol-3-yl)cyclopropyl](octahydroquinolin-1(2H)-yl)methanone (97)

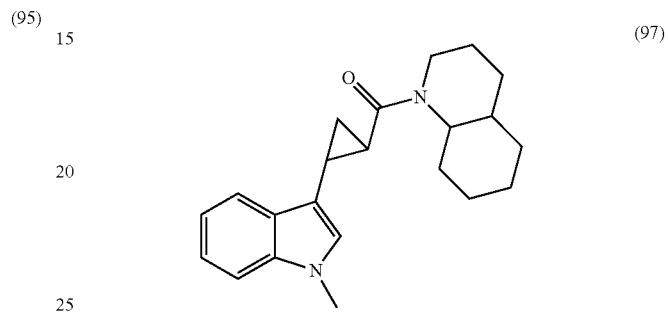

(97)

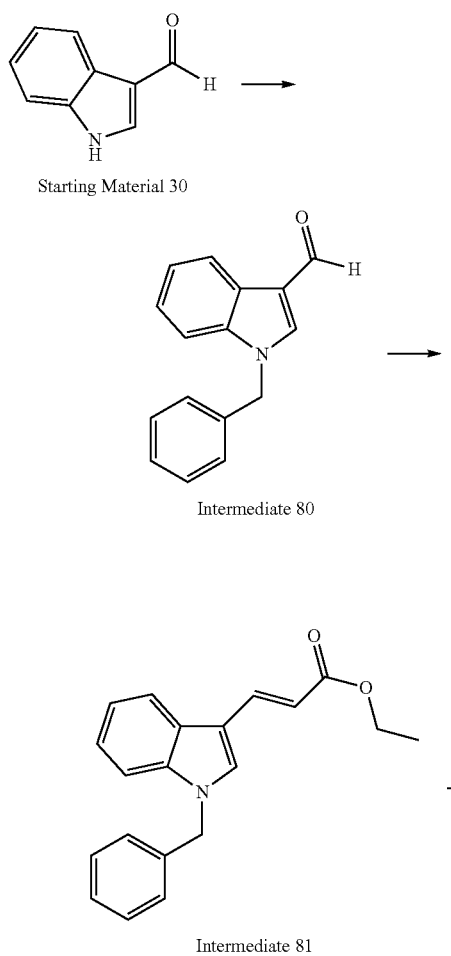

Synthetic Scheme-50

Starting Material 30

Intermediate 80

Intermediate 81

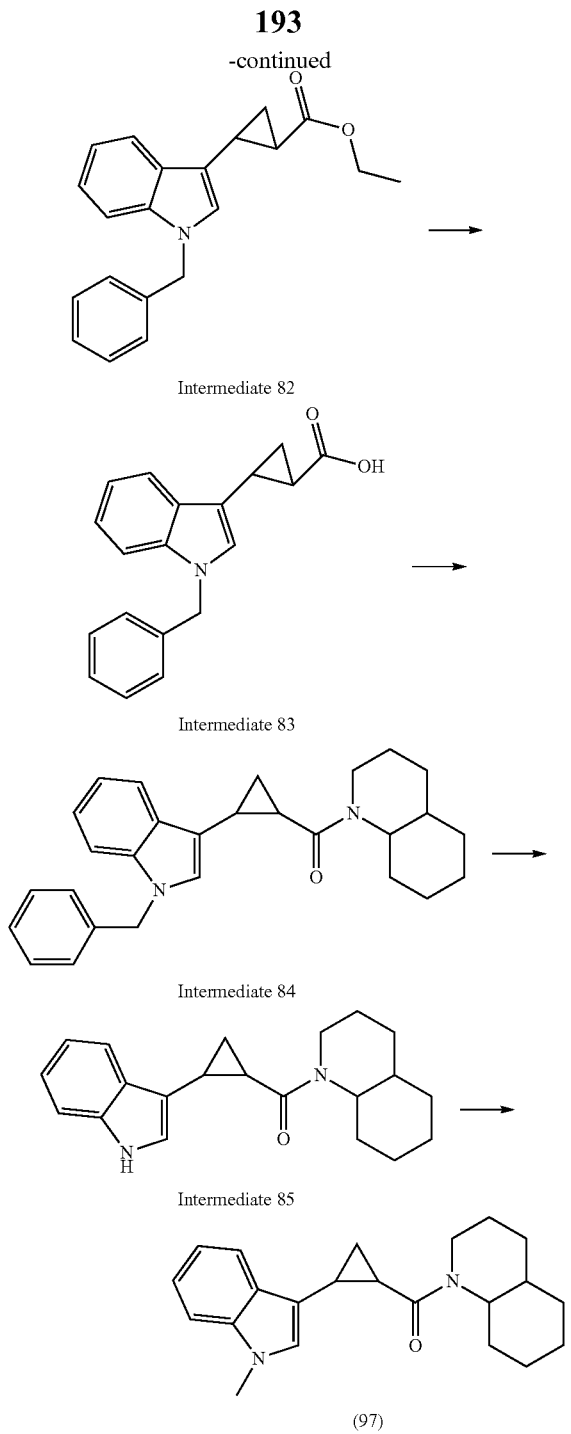

Intermediate 82

Intermediate 83

Intermediate 84

Intermediate 85

(97)

Synthesis of 1-benzyl-1H-indole-3-carbaldehyde (Intermediate-80)

To a 250 ml 3 neck RBF was charged 40 ml of THF. To the stirred solution NaH (1.24 g, 31.0 mmol) was added followed by addition of Starting Material-30 (3 g, 20.6 mmol). The reaction mixture was stirred at RT for 30 min. Then benzyl bromide (2.7 ml, 22.6 mmol) was added to the mixture at 0° C. Resulted reaction mixture was stirred at RT for 12 h. After completion of reaction, the reaction mixture was quenched with ice and extracted with ethylacetate and concentrated. Crude Material was purified by silica gel column chromatography eluting with hexanes: EtOAc to give Intermediate-80 (4.25 g).

Synthesis of ethyl (2E)-3-(1-benzyl-1H-indol-3-yl) prop-2-enoate (Intermediate-81)

Intermediate-81 was synthesized by following the procedure used to make Intermediate-7 (Scheme 4). The crude product was obtained by evaporating the organic layer under reduced pressure and was purified by silica gel column using Petroleum ether: Ethyl acetate as eluent to obtain Intermediate-81 (3.85 g)

Synthesis of ethyl 2-(1-benzyl-1H-Indol-3-yl)cyclopropanecarboxylate Intermediate-82)

To a 250 ml 3neck RB was charged 40 ml of DMSO. To this Intermediate-81 (3.5 g, 11.4 mmol), TMSOI (2.7 g, 12.6 mmol), and then KOH (55 mg, 0.98 mmol) was added. Resulting reaction mixture was stirred at RT for 12 hours. After reaction was completed (monitored by TLC) the reaction mixture was quenched with water and extracted with ethyl acetate, and concentrated. Crude material was purified by silica gel column chromatography eluting with hexanes: EtOAc to give Intermediate-82 (655 mg).

Synthesis of 2-(1-benzyl-1H-indol-3-yl)cyclopropanecarboxylic acid (Intermediate-83)

Intermediate-83 was synthesized by following the procedure used to make Intermediate-79 (Scheme 49).

Synthesis of [2-(1-benzyl-1H-indol-3-yl)cyclopropyl] (octahydroquinol in-1(2H)-yl)methanone (Intermediate-84)

Intermediate-84 was synthesized by following the procedure used to make Compound (1) (Scheme 2). The crude product was obtained by evaporating the organic layer under reduced pressure and was purified by silica gel column using Petroleum ether: Ethyl acetate as eluent to obtain Intermediate-84 (275 mg).

Synthesis of [2-(1H-indol-3-yl)cyclopropyl](octahydroquinolin-1 (2H)-yl)methanone (Intermediate-85)

5 ml of DMSO was taken in a 25 ml single neck RB. To this Intermediate-84 (275 mg, 0.66 mmol) followed by potassium-t-butoxide (525 mg, 4.66 mmol) in THF was added and stirred at rt for 3 hours. After reaction quenched with NH4Cl solution and extracted with ethyl acetate. The combined organic layers were washed with DM water and brine solution and concentrated. The crude product was obtained purified by silica gel column using Petroleum ether: Ethyl acetate as eluent to obtain Intermediate-85 (18 mg).

Synthesis of Compound (97)

Compound (97) was synthesized by following the procedure used to make Intermediate-77 (Scheme 48). The crude product was obtained by evaporating the organic layer under reduced pressure and was purified by silica gel column using Petroleum ether: Ethyl acetate as eluent to obtain Compound (97). $^1$H NMR (300 MHz, CDCl3): δ 7.52-7.58 (m, 1H), 7.13-7.22 (m, 2H), 7.01-7.06 (m, 1H), 6.65-6.78 (m, 1H), 4.41-4.66 (m, 1H), 3.84-4.06 (m, 1H), 3.70 (s, 3H), 2.98-3.33 (m, 1H), 2.42-2.76 (m, 2H), 1.52-1.86 (m, 9H), 1.26-1.45 (m, 6H). LC-MS (M+H)$^+$=337.2; HPLC purity: 96.48%.

Example 98

2-(1H-indol-3-ylmethyl)-3-(octahydroquinolin-1(2H)-yl)-3-oxopropanenitrile (98)

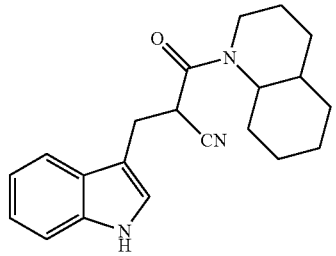

(98)

Synthesis of Compound (98)

Compound (98) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (98). $^1$H NMR (300 MHz, CDCl3): δ 8.11 (s, 1H), 7.48-7.55 (m, 1H), 7.31-7.34 (d, 1H), 7.09-7.13 (m, 3H), 4.36-4.59 (m, 1H), 3.82-4.03 (m, 1H), 3.26-3.48 (m, 3H), 2.51-2.85 (m, 1H), 2.15-2.30 (m, 1H), 1.93-2.01 (m, 1H), 1.52-1.64 (m, 11H). LC-MS (M+H)$^+$=336.2; HPLC purity: 92.84%.

Example 99

2-(1H-indol-3-yloxy)-1-(octahydroquinolin-1(2H)-yl)ethanone (99)

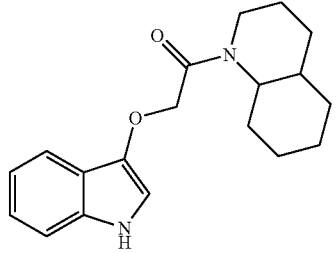

(99)

Synthesis of Compound (99)

Compound (99) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (99). $^1$H NMR (300 MHz, CDCl3): δ 7.53-7.58 (t, 1H), 7.50 (s, 1H), 7.20-7.23 (d, 1H), 7.09-7.14 (t, 1H), 6.98-7.03 (t, 1H), 6.76-6.77 (t, 1H), 4.57-4.72 (m, 2H), 4.35-4.52 (m, 1H), 3.82-4.02 (m, 1H), 2.54-3.07 (m, 1H), 1.26-1.78 (m, 13H). LC-MS (M+H)$^+$=313.2; HPLC purity: 96.80%.

Example 100

2-[(1-methyl-1H-indol-3-yl)oxy]-1-(octahydroquinolin-1(2H)-yl)propan-1-one (100)

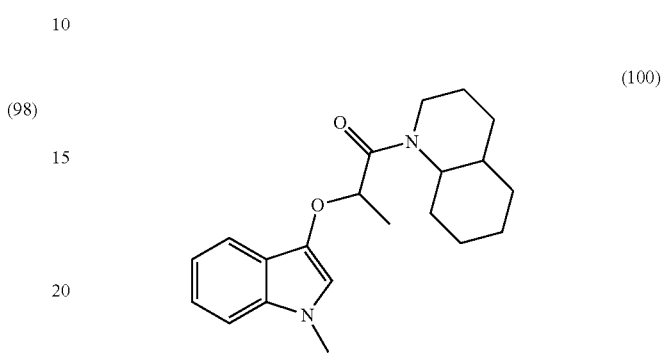

(100)

Synthesis of Compound (100)

Compound (100) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (100). $^1$H NMR (300 MHz, CDCl3): δ 7.53-7.55 (m, 1H), 7.14-7.18 (m, 2H), 6.97-6.99 (m, 1H), 6.53-6.55 (t, 1H), 4.71-4.79 (m, 1H), 4.08-4.58 (m, 2H), 3.58 (d, 3H), 2.47-2.95 (m, 1H), 1.18-1.68 (m, 16H). LC-MS (M+H)$^+$=341.2; HPLC purity: 98.96%.

Example 101 methyl 1-[3-(1H-indol-3-yl)-4-methylpentanoyl]decahydroquinoline-4-carboxylate (101)

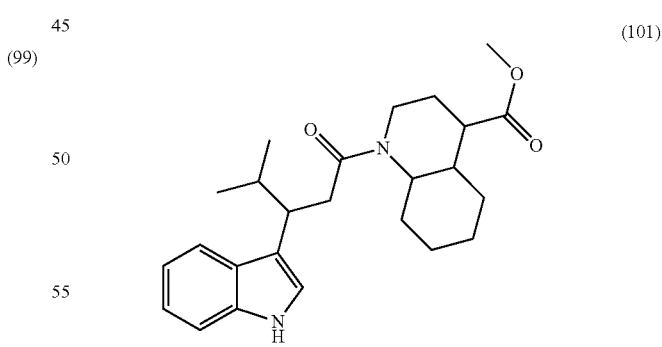

(101)

Synthesis of Compound (101)

Compound (101) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (101). $^1$H NMR (300 MHz, CDCl3): δ 8.02 (s, 1H), 7.56-

7.59 (d, 1H), 7.23-7.26 (m, 1H), 7.06-7.11 (t, 1H), 6.97-7.04 (t, 1H), 6.91-6.92 (d, 1H), 4.00-4.09 (m, 1H), 3.66-3.67 (d, 1H), 3.56 (s, 3H), 3.45-3.49 (d, 1H), 3.17-3.24 (m, 1H), 2.66-2.81 (m, 2H), 2.24-2.28 (m, 1H), 1.97-2.15 (m, 1H), 1.07-1.78 (m, 11H), 0.93-0.96 (d, 3H), 0.77-0.80 (d, 3H). LC-MS (M+H)+=411.3; HPLC purity: 94.17%.

Example 102 methyl 1-[3-(1H-indol-3-yl)butanoyl]decahydroquinoline-4-carboxylate (102)

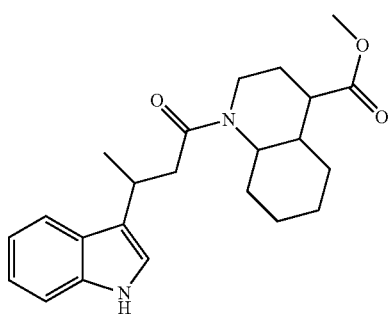

(102)

Synthesis of Compound (102)

Compound (102) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (102). ¹H NMR (300 MHz, CDCl3): δ 7.99 (s, 1H), 7.59-7.65 (m, 1H), 7.25-7.28 (d, 1H), 6.97-7.12 (m, 2H), 6.94-6.95 (d, 1H), 4.00-4.23 (m, 1H), 3.52-3.65 (m, 4H), 2.69-2.79 (m, 1H), 2.43-2.57 (m, 1H), 2.37 (s, 1H), 0.95-2.01 (m, 16H). LC-MS (M+H)+=383.3; HPLC purity: 95.38%.

Example 103

1-[3-(1H-indol-3-yl)butanoyl]octahydroquinolin-4(1H)-one (103)

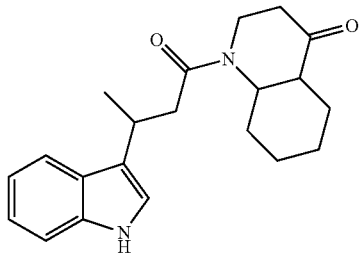

(103)

Synthesis of Compound (103)

Compound (103) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (103). ¹H NMR (300 MHz, CDCl3): δ 8.08 (s, 1H), 7.57-7.67 (m, 1H), 7.24-7.30 (m, 1H), 6.97-7.11 (m, 3H), 4.45-4.85 (m, 1H), 3.62-3.67 (m, 3H), 1.11-3.31 (m, 16H). LC-MS (M+H)+=339.2; HPLC purity: 81.37%.

Example 104

1-[3-(1H-indol-3-yl)-4-methylpentanoyl]octahydroquinolin-4(1H)-one (104)

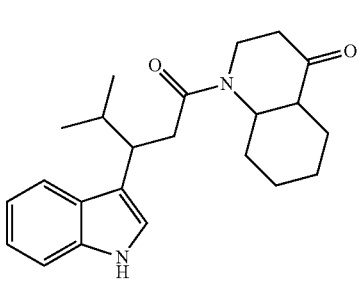

(104)

Synthesis of Compound (104)

Compound (104) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (104). ¹H NMR (300 MHz, CDCl3): δ 7.94 (s, 1H), 7.55-7.61 (m, 1H), 7.23-7.25 (m, 1H), 6.95-7.09 (m, 3H), 4.44-4.84 (m, 1H), 3.63-3.70 (m, 1H), 3.14-3.24 (m, 1H), 1.94-2.98 (m, 15H), 1.06-1.08 (d, 3H), 1.00-1.01 (d, 3H). LC-MS (M+H)+=367.3; HPLC purity: 96.24%.

Example 105

1-[3-(1H-indol-3-yl)-4-methylpentanoyl]decahydroquinoline-4-carboxylic acid (105)

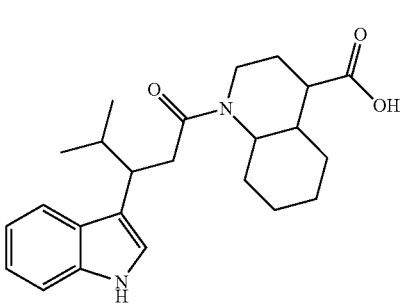

(105)

Synthetic Scheme-51

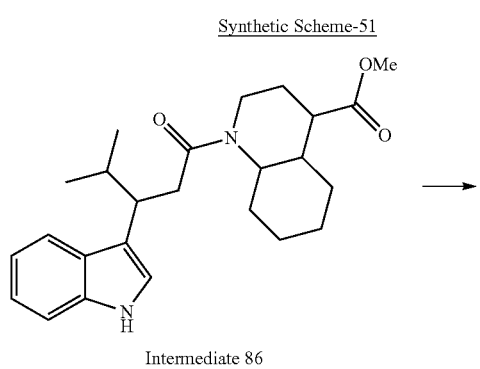

Intermediate 86

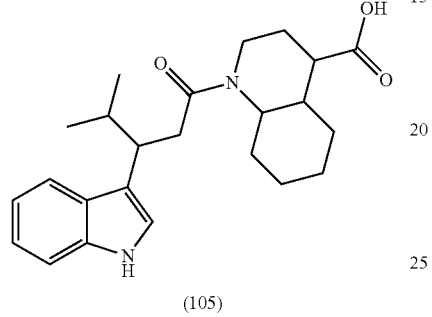

(105)

Synthesis of methyl 1-[3-(1H-indol-3-yl)-4-methyl-pentanoyl]decahydroquinoline-4-carboxylate (Intermediate-86)

Intermediate-86 was synthesized by following the procedure used to make (49) (Scheme 32).

Synthesis of Compound (105)

Compound (105) was synthesized by following the procedure used to make Intermediate-3 (Scheme 1). $^1$H NMR (300 MHz, CDCl3): δ 7.97-8.00 (d, 1H), 7.56-7.59 (d, 1H), 7.23-7.25 (d, 1H), 6.97-7.11 (m, 2H), 6.92-6.93 (d, 1H), 4.04-4.21 (m, 1H), 3.37-3.64 (m, 1H), 3.07-3.19 (m, 1H), 2.63-2.90 (m, 2H), 1.34-2.28 (m, 14H), 0.94-0.96 (3H), 0.75-0.80 (d, 3H) LC-MS (M+H)$^+$=397.2; HPLC purity: 97.21%.

Example 106

1-(4-hydroxyoctahydroquinolin-1(2H)-yl)-3-(1H-indol-3-yl)butan-1-one (106)

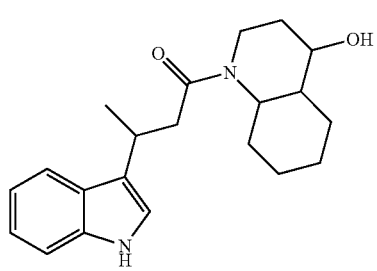

(106)

Synthesis of Compound (106)

Compound (106) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (106). $^1$H NMR (300 MHz, CDCl3): δ 7.91 (s, 1H), 7.60-7.62 (d, 1H), 7.27 (m, 1H), 7.01-7.13 (m, 2H), 6.95 (s, 1H), 3.89-4.51 (m, 1H), 3.56-3.61 (m, 2H), 3.12-3.29 (m, 2H), 1.53-2.76 (m, 13H), 1.36-1.40 (m, 3H). LC-MS (M+H)$^+$=341.3; HPLC purity: 89.75%.

Example 107

1-[3-(1H-indol-3-yl)-4-methylpentanoyl]decahydroquinoline-4-carboxylic acid sodium salt (107)

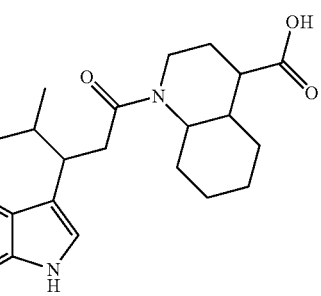

(107)

Synthetic Scheme-52

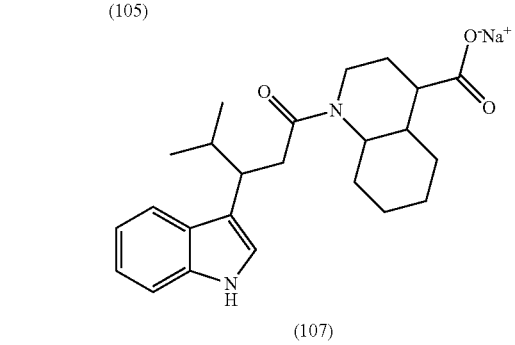

Synthesis of Compound (107)

To the stirred solution of Compound (105) (25 mg, 0.063 mmol) in THF, MeOH and water, NaHCO$_3$ (0.063 mmol)

was added at 0° C. The reaction mixture was stirred at RT for 30 minutes. After completion of the reaction, the reaction mixture was concentrated. Resulted crude material was triturated with ether to give Compound (107) (24 mg) as white solid. $^1$H NMR (300 MHz, DMSO-d6): δ 10.90 (s, 1H), 7.44-7.52 (m, 1H), 7.28-7.31 (d, 1H), 6.92-7.05 (m, 3H), 4.17 (m, 1H), 3.70-3.90 (m, 1H), 3.165-3.21 (m, 4H), 2.64-2.67 (m, 2H), 1.40-2.31 (m, 11H), 0.80-0.90 (m, 6H). LC-MS (M+H)$^+$=397.2; HPLC purity: 89.15%.

Example 108

4,4,4-trifluoro-3-hydroxy-3-(1H-indol-3-yl)-1-(octahydroquinolin-1(2H)-yl)butan-1-one (108)

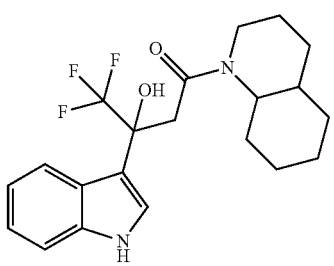

(108)

Synthesis of Compound (108)

Compound (108) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (108). $^1$H NMR (300 MHz, CDCl3): δ 8.15 (s, 1H), 7.70 (m, 1H), 7.29-7.37 (m, 3H), 7.08-7.12 (m, 1H), 4.25-4.43 (m, 1H), 3.51-3.62 (m, 1H), 3.29-3.37 (m, 1H), 2.76-3.05 (m, 1H), 1.30-1.82 (m, 14H). LC-MS (M+H)$^+$=395.1; HPLC purity: 97.32%.

Example 109

2-(1H-indol-3-yl)-4-(octahydroquinolin-1(2H)-yl)-4-oxobutanenitrile (109)

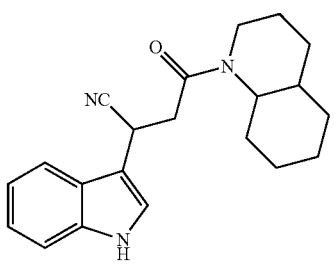

(109)

Synthesis of Compound (109)

Compound 109) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (109). $^1$H NMR (300 MHz, CDCl3): δ 8.15 (s, 1H), 7.61-7.66 (t, 1H), 7.32-7.36 (m, 1H), 7.20-7.25 (m, 2H), 7.08-7.17 (m, 1H), 4.66-4.72 (m, 1H), 4.40-4.62 (m, 1H), 3.37-3.48 (m, 1H), 2.48-3.13 (m, 3H), 1.30-1.84 (m, 13H). LC-MS (M+11)÷=336.1; HPLC purity: 98.95%.

Example 110

3-(1H-indol-3-yl)-3-methyl-2-(octahydroquinolin-1(2H)-ylcarbonyl)butanenitrile (110)

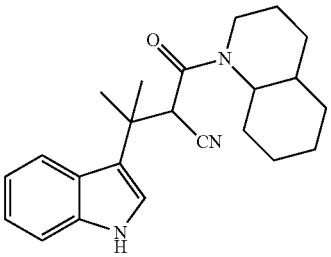

(110)

Synthesis of Compound (110)

Compound (110) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (110). $^1$H NMR (300 MHz, CDCl3): δ 8.08 (s, 1H), 7.61-7.72 (m, 1H), 7.30-7.33 (m, 1H), 7.01-7.16 (m, 3H), 4.35-4.40 (m, 1H), 3.00-3.20 (m, 1H), 2.25-2.41 (m, 2H), 1.07-1.78 (m, 19H). LC-MS (M–H)$^+$=362.4; HPLC purity: 95.88%.

Example 111

3-(4-fluoro-1H-indol-3-yl)-4-methyl-1-(octahydroquinolin-1(2H)-yl)pentan-1-one (111)

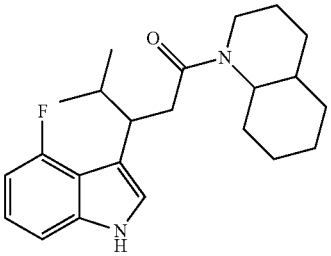

(111)

Synthesis of Compound (111)

Compound (111) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (111). ¹H NMR (300 MHz, CDCl3): δ 8.19-8.23 (d, 1H), 7.09-7.12 (d, 1H), 7.05 (m, 1H), 6.97 (m, 1H), 6.73-6.81 (m, 1H), 4.36-4.50 (m, 1H), 3.59-3.79 (m, 1H), 3.00-3.30 (m, 1H), 2.60-2.96 (m, 2H), 2.10-2.45 (m, 1H), 1.00-1.48 (m, 14H), 0.75-0.88 (m, 6H). LC-MS (M+H)$^+$=371.2; HPLC purity: 99.54%.

Example 112

3-(4-fluoro-1H-indol-3-yl)-4-methyl-1-(4a-methyl-octahydroquinolin-1(2H)-yl)pentan-1-one (112)

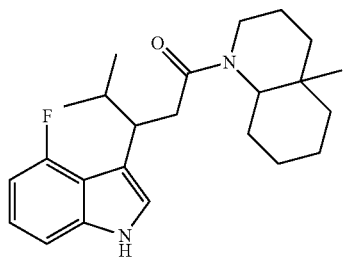

(112)

Synthesis of Compound (112)

Compound (112) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (112). ¹H NMR (300 MHz, CDCl3): δ 8.28-8.34 (d, 1H), 7.07-7.12 (m, 1H), 6.95-7.04 (m, 2H), 6.68-6.76 (m, 1H), 4.12-4.43 (m, 1H), 3.58-3.67 (m, 1H), 3.25-3.39 (m, 1H), 2.92-3.00 (m, 1H), 2.68-2.87 (m, 2H), 2.43-2.56 (m, 1H), 1.21-2.03 (m, 12H), 0.77-1.04 (m, 9H). LC-MS (M+H)$^+$=385.3; HPLC purity: 98.01%.

Example 113

3-(1-methyl-1H-Indol-3-yl)-1-(4a-methyloctahydro-quinolin-1(2H)-yl)butan-1-one (113)

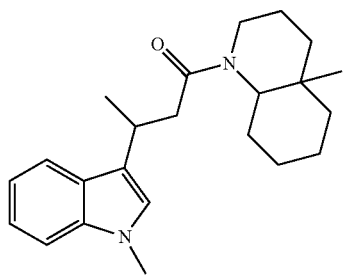

(113)

Synthesis of Compound (113)

Compound (113) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (113). ¹H NMR (300 MHz, CDCl3): δ 7.56-7.60 (m, 1H), 7.20-7.22 (m, 1H), 7.11-7.16 (t, 1H), 6.99-7.04 (t, 1H), 6.80-6.82 (d, 1H), 3.80-3.83 (m, 1H), 3.66-3.73 (m, 3H), 3.53-3.62 (m, 1H), 2.64-2.82 (m, 4H), 2.49-2.59 (m, 2H), 1.52-2.15 (m, 10H), 1.34-1.42 (m, 6H). LC-MS (M+H)$^+$=353.3; HPLC purity: 88.48%.

Example 114

3-(4-fluoro-1H-indol-3-yl)-1-(4a-methyloctahydro-quinolin-1(2H)-yl)butan-1-one (114)

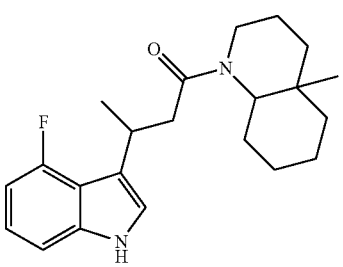

(114)

Synthesis of Compound (114)

Compound (114) was synthesized by following the procedure used to make Compound (1) (Scheme 2). The crude product was obtained by evaporating the organic layer under reduced pressure and was purified by silica gel column using Petroleum ether: Ethyl acetate as eluent to obtain (114). ¹H NMR (300 MHz, CDCl3): δ 8.13 (s, 1H), 6.96-7.07 (m, 2H), 6.92-6.93 (m, 1H), 6.65-6.73 (m, 1H), 4.20-4.48 (m, 1H), 3.38-3.65 (m, 2H), 2.80-2.97 (m, 1H), 2.37-2.59 (m, 1H), 1.14-1.97 (m, 16H), 0.76-0.79 (m, 3H). LC-MS (M+H)$^+$=357.3; HPLC purity: 98.46%.

Example 115

3-(4-fluoro-1H-indol-3-yl)-4-methyl-1-(4a-methyl-octahydroquinolin-1(2H)-yl)pentan-1-one, peak-1) (115)

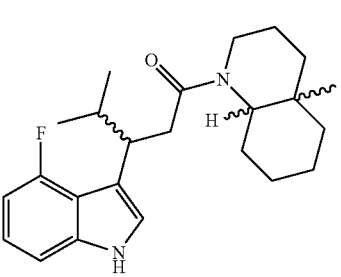

(115 peak 1)

Synthesis of Compound (115) (Peak-1)

Mixture of isomers of compound (112) was separated by reverse phase HPLC to give Compound (115) (peak 1). ¹H NMR (300 MHz, CDCl3): δ 8.31 (d, 1H), 7.02-7.05 (d, 1H), 6.92-6.99 (m, 1H), 6.85 (s, 1H), 6.62-6.68 (t, 1H), 4.05-4.36 (m, 1H), 3.17-3.57 (m, 2H), 2.85-2.95 (m, 2H), 2.66-2.68 (m, 1H), 1.58-2.63 (m, 13H), 0.69-0.96 (m, 9H). LC-MS (M+H)⁺=385.3; HPLC purity: 99.62%. Column: Zorbax eclipse XDB-C18, 4.6×150 mm, 5 μM; RT=16.97 min; Mobile phase: MeCN:H2O (6:4).

Example 116

3-(4-fluoro-1H-indol-3-yl)-4-methyl-1-(4a-methyl-octahydroquinolin-1(2H)-yl)pentan-1-one peak-2) (116)

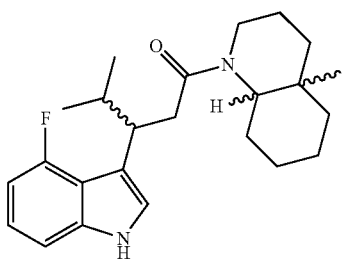

(116 peak 2)

Synthesis of Compound (116) (Peak-2)

Mixture of isomers of compound (112) was separated by reverse phase HPLC to give Compound (116) (peak-2). ¹H NMR (300 MHz, CDCl3): δ 8.47 (s, 1H), 7.02-7.05 (d, 1H), 6.87-6.98 (m, 2H), 6.85 (s, 1H), 6.60-6.88 (t, 1H), 4.04-4.37 (m, 1H), 3.24-3.60 (m, 1H), 2.85-2.95 (m, 1H), 2.65-2.76 (m, 2H), 1.58-2.46 (m, 13H), 0.69-0.96 (m, 9H). LC-MS (M+H)⁺=385.3; HPLC purity: 98.53%. Column: Zorbax eclipse XDB-C18, 4.6×150 mm, 51.1M; RT=17.70 min; Mobile phase: MeCN:H2O (6:4).

Example 117

3-(1H-indol-3-yl)-4-methyl-1-(octahydroquinolin-1(2H)-yl)pentan-1-one (120)

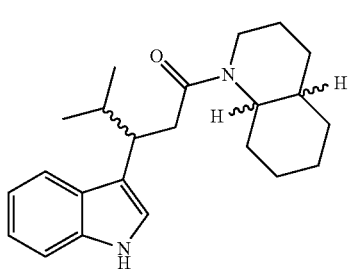

(117 peak 1)

Synthesis of Compound (117) (peak-1)

Mixture of isomers of compound (95) was separated by using reverse phase preparative HPLC to give Compound (117) (peak-1). ¹H NMR (300 MHz, CDCl3): δ 7.92 (s, 1H), 7.55-7.63 (m, 1H), 7.25-7.28 (d, 1H), 7.00-7.10 (m, 2H), 6.91-6.93 (m, 1H), 4.31-4.47 (m, 1H), 3.34-3.49 (m, 1H), 3.04-3.22 (m, 1H), 2.52-2.86 (m, 1H), 2.33-2.37 (m, 2H), 1.08-2.28 (m, 14H), 0.90-1.00 (m, 6H). LC-MS (M+H)⁺=353.3; HPLC purity: 97.76%. Column: Zorbax eclipse XDB-C18, 4.6×150 mm, 5 μM; RT=18.77 min; Mobile phase: MeCN: 0.01% TFA in H2O, runtime: 30 minutes.

Example 118

3-(1H-indol-3-yl)-4-methyl-1-(octahydroquinolin-1(2H)-yl)pentan-1-one (peak-2) (118)

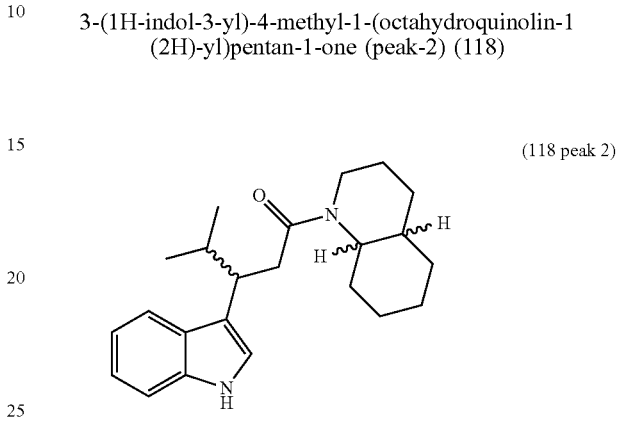

(118 peak 2)

Synthesis of Compound (118) (peak-2)

Mixture of isomers of compound (95) was separated by using reverse phase preparative HPLC to give Compound (118) (peak-2). ¹H NMR (300 MHz, CDCl3): δ 7.91 (s, 1H), 7.56-7.59 (m, 1H), 7.24-7.27 (d, 1H), 6.97-7.09 (m, 2H), 6.92-6.94 (m, 1H), 4.31-4.46 (m, 1H), 3.34-3.64 (m, 1H), 3.17-3.26 (m, 1H), 2.67-2.87 (m, 2H), 2.03-2.41 (m, 1H), 1.08-2.28 (m, 14H), 0.91-0.94 (m, 6H). LC-MS (M+H)⁺=353.3; HPLC purity: 97.40%. Column: Zorbax eclipse XDB-C18, 4.6×150 mm, 5 μM; RT=19.07 min; Mobile phase: MeCN: 0.01% TFA in H2O, runtime: 30 minutes.

Example 119

3-(1H-indol-3-yl)-1-(octahydroquinolin-1(2H)-yl)butan-1-one (peak-1) (119)

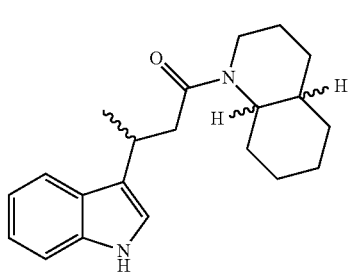

(119 peak 1)

Synthesis of Compound (119) (Peak-1)

Mixture of isomers of compound (1) was separated by using reverse phase preparative HPLC to give Compound (119) (peak-1). δ 7.92 (s, 1H), 7.58-7.65 (m, 1H), 7.27-7.30 (d, 1H), 7.00-7.13 (m, 2H), 6.93-6.96 (m, 1H), 4.30-4.60 (m, 1H), 3.50-3.58 (m, 1H), 2.60-2.90 (m, 1H), 2.30-2.55 (m, 2H), 0.78-1.67 (m, 17H). LC-MS (M+H)⁺=325.3; HPLC purity: 99.59%. Column: Zorbax eclipse XDB-C18, 4.6×150 mm, 5 μM; RT=13.37 min; Mobile phase: MeCN:H2O (50:50).

Example 120

3-(1H-indol-3-yl)-1-(octahydroquinolin-1(2H)-yl)butan-1-one (peak-2) (120)

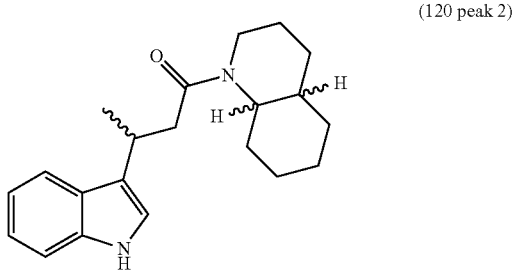 [SMILES: CC(CC(=O)N1CCCC2CCCCC21)c1c[nH]c2ccccc12]

(120 peak 2)

Synthesis of Compound (120) (peak-2)

Mixture of isomers of compound (1) was separated by using reverse phase preparative HPLC to give Compound (120) (peak-2). ¹H NMR (300 MHz, CDCl3): δ 7.90 (s, 1H), 7.59-7.63 (m, 1H), 7.26-7.30 (d, 1H), 7.00-7.13 (m, 2H), 6.94-6.95 (m, 1H), 4.30-4.60 (m, 1H), 3.56-3.65 (m, 1H), 2.43-2.89 (m, 3H), 0.79-1.64 (m, 17H). LC-MS (M+H)⁺=325.2; HPLC purity: 98.57%. Column: Zorbax eclipse XDB-C18, 4.6×150 mm, 5 μM; RT=14.37 min; Mobile phase: MeCN:H2O (50:50).

Example 121

3-(4-fluoro-1H-indol-3-yl)-1-(octahydroquinolin-1(2H)-yl)butan-1-one (121)

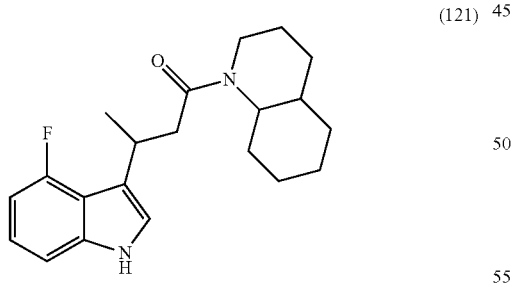

(121)

Synthesis of Compound (121)

Compound (121) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (121). ¹H NMR (300 MHz, CDCl3): δ 8.85-8.88 (d, 1H), 6.98-7.08 (m, 1H), 6.92-6.97 (m, 1H), 6.85 (s, 1H), 6.62-6.72 (m, 1H), 4.41-4.59 (m, 1H), 3.54-3.79 (m, 2H), 2.37-3.04 (m, 3H), 1.52-1.63 (m, 6H), 1.46-1.47 (m, 2H), 1.37 (s, 5H), 1.32-1.34 (m, 3H). LC-MS (M+H)⁺=343.2; HPLC purity: 96.57%.

Example 122

3-(4-fluoro-1H-indol-3-yl)-1-(octahydroquinolin-1(2H)-yl)butan-1-one (peak-1) (122)

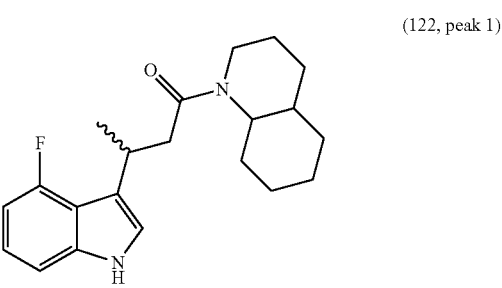 [SMILES: CC(CC(=O)N1CCCC2CCCCC21)c1c[nH]c2cccc(F)c12]

(122, peak 1)

Synthesis of Compound (122) (peak-1)

Compound (122) (peak-1) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (122) (peak-1). ¹H NMR (300 MHz, CDCl3): δ 8.10 (s, 1H), 6.96-7.07 (m, 2H), 6.93 (d, 1H), 6.67-6.75 (m, 1H), 4.45-4.59 (m, 1H), 3.55-3.69 (m, 2H), 2.41-2.96 (m, 3H), 0.76-1.60 (m, 16H). LC-MS (M+H)⁺=343.2; HPLC purity: 97.18%.

Example 123

3-(4-fluoro-1H-indol-3-yl)-1-(octahydroquinolin-1(2H)-yl)butan-1-one (peak-2) (123)

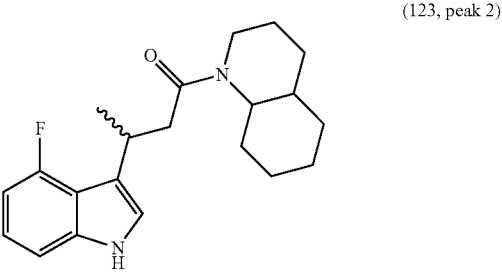 [SMILES: CC(CC(=O)N1CCCC2CCCCC21)c1c[nH]c2cccc(F)c12]

(123, peak 2)

Synthesis of Compound (123) (peak-2)

Compound (123) (peak-2) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (123) (peak-2). ¹H NMR (300 MHz, CDCl3): δ 8.08 (s, 1H), 6.96-7.07 (m, 2H), 6.93-6.94 (d, 1H), 6.65-6.75 (m, 1H), 4.40-4.59 (m, 1H), 3.55-3.69 (m, 2H), 2.41-2.96 (m, 3H), 0.76-1.60 (m, 16H). LC-MS (M+H)⁺=343.2; HPLC purity: 95.41%.

Example 124

3-(1H-indol-3-yl)-1-(octahydroquinolin-1(2H)-yl)butan-1-one (peak-1) (124)

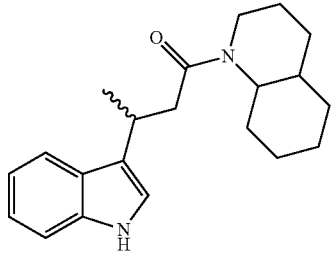
(124, peak 1)

Synthesis of Compound (124) (peak-1)

Compound (124) (peak-1) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (124) (peak-1). ¹H NMR (300 MHz, CDCl3): δ 7.93 (s, 1H), 7.59-7.65 (m, 1H), 7.27-7.30 (d, 1H), 7.00-7.13 (m, 2H), 6.95 (s, 1H), 4.40-4.61 (m, 1H), 3.46-3.65 (m, 2H), 2.37-2.92 (m, 4H), 1.61-1.64 (m, 6H), 1.36-1.47 (m, 5H), 1.26-1.29 (m, 4H). LC-MS (M+H)⁺=325.2; HPLC purity: 93.69%.

Example 125

3-(1H-indol-3-yl)-1-(octahydroquinolin-1(2H)-yl)butan-1-one (peak-2) (125)

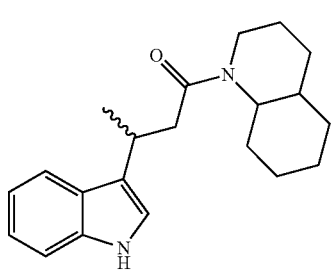
(125, peak 2)

Synthesis of (125) (peak-2)

Compound (125) (peak-2) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (125) (peak-2). ¹H NMR (300 MHz, CDCl3): δ 7.94 (s, 1H), 7.59-7.65 (m, 1H), 7.27-7.30 (d, 1H), 7.02-7.13 (m, 2H), 7.00 (s, 1H), 4.40-4.61 (m, 1H), 3.46-3.64 (m, 2H), 2.42-2.97 (m, 4H), 1.64-1.91 (m, 6H), 1.41-1.47 (m, 5H), 1.36 (m, 4H). LC-MS (M+H)⁺=325.2; HPLC purity: 94.79%.

Example 126

3-(4-chloro-1H-indol-3-yl)-1-[trans-(4a,8a)-octahydroquinolin-1(2H)-yl]butan-1-one (126)

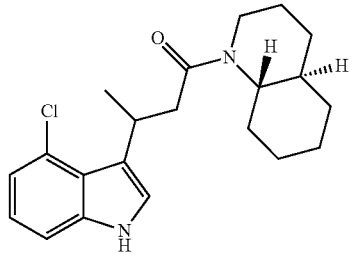
(126)

Synthesis of Compound (126)

Compound (126) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (126). ¹H NMR (300 MHz, CDCl3): δ 8.32 (s, 1H), 7.12 (s, 1H), 6.99-7.04 (m, 3H), 3.68-4.16 (m, 1H), 2.98-3.22 (m, 2H), 2.25-2.85 (m, 1H), 0.65-1.85 (m, 18H). LC-MS (M+H)⁺=359.2; HPLC purity: 84.27%.

Example 127 ethyl 1-[3-(4-chloro-1H-indol-3-yl)butanoyl]octahydroquinoline-4a(2H)-carboxylate (127)

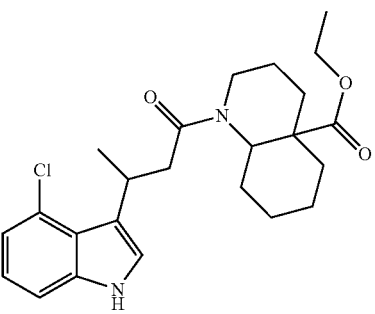
(127)

Synthesis of Compound (127)

Compound (127) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (127). ¹H NMR (300 MHz, CDCl3): δ 8.06 (s, 1H), 6.99-

7.02 (m, 4H), 3.99-4.10 (m, 5H), 2.66-3.08 (m, 2H), 1.74-2.50 (m, 13H), 1.33-1.36 (m, 6H). LC-MS (M+H)+=431.2; HPLC purity: 94.82%.

Example 128

3-(4-chloro-1H-indol-3-yl)-1-(4a-phenyloctahydroquinolin-1(2H)-yl)butan-1-one (128)

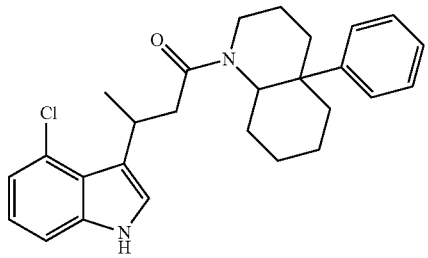

Synthesis of (128)

Compound (128) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (128). $^1$H NMR (300 MHz, CDCl3): δ 8.01 (s, 1H), 7.60-7.62 (d, 2H), 7.11-7.19 (m, 3H), 7.02 (m, 1H), 6.98 (d, 3H), 3.80-4.21 (m, 2H), 3.17-3.23 (m, 1H), 2.80-2.92 (m, 2H), 2.41-2.49 (m, 2H), 0.78-2.15 (m, 14H). LC-MS (M+H)+=435.2; HPLC purity: 88.09%.

Example 129

1-[3-(4-chloro-1H-indol-3-yl)butanoyl]octahydroquinoline-4a(2H)-carboxylic acid (129)

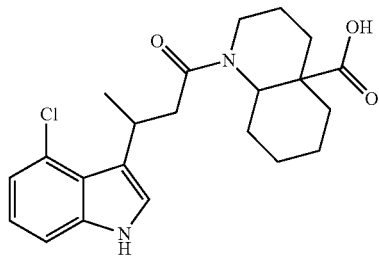

Synthesis of (129)

Compound (129) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (129). $^1$H NMR (300 MHz, DMSO-d6): 12.24 (s, 1H), 11.15 (s, 1H), 7.24-7.31 (m, 2H), 6.97-7.01 (m, 2H), 3.92-3.95 (m, 1H), 3.26 (m, 2H), 2.72-2.76 (m, 2H), 1.21-2.40 (m, 16H). LC-MS (M+H)+=403.2; HPLC purity: 99.09%.

Example 130

3-(4-chloro-1H-indol-3-yl)-1-[4a-(hydroxymethyl)octahydroquinolin-1(2H)-yl]butan-1-one (130)

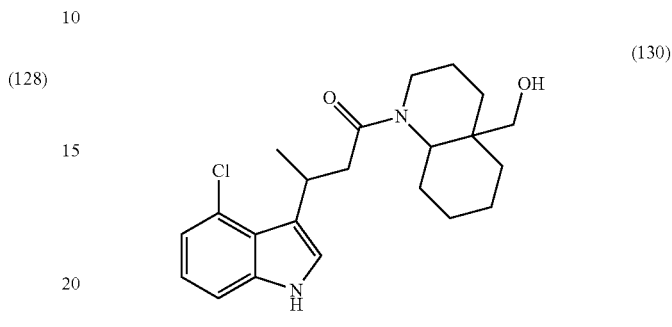

Synthesis of (130)

Compound (130) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (130). $^1$H NMR (300 MHz, CDCl3): δ 8.10 (s, 1H), 7.16 (m, 1H), 7.02-7.03 (d, 1H), 6.98-7.00 (m, 2H), 3.87-4.00 (m, 1H), 3.46-3.71 (m, 1H), 2.79-2.98 (m, 3H), 2.44-2.52 (m, 1H), 1.37-1.81 (m, 17H). LC-MS (M+H)+=389.2; HPLC purity: 93.28%.

Example 131

1-[4a-(hydroxymethyl)octahydroquinolin-1(2H)-yl]-3-(1H-indol-3-yl)butan-1-one (131)

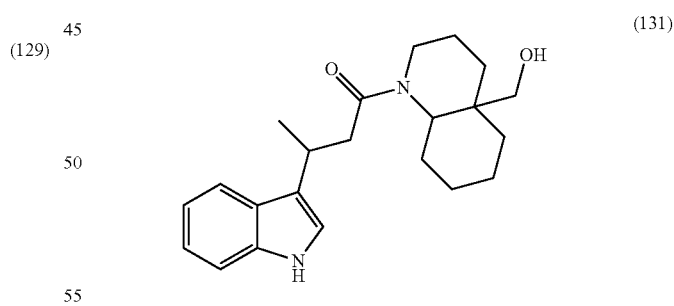

Synthesis of (131)

Compound (131) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (131). $^1$H NMR (300 MHz, CDCl3): δ 7.94 (s, 1H), 7.60-7.63 (d, 1H), 7.27-7.30 (d, 1H), 7.01-7.13 (m, 2H), 6.96-6.97 (m, 1H), 3.32-3.76 (m, 3H), 2.79-2.84 (m, 3H), 2.44-2.62

(m, 2H), 1.62-1.96 (m, 12H), 1.36-1.38 (d, 3H). LC-MS (M+H)⁺=355.2; HPLC purity: 97.69%.

Example 132

1-(4a-hydroxyoctahydroquinolin-1(2H)-yl)-3-(4-methyl-1H-indol-3-yl)butan-1-one (132)

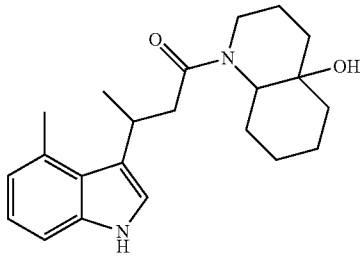

(132)

Synthesis of Compound (132)

Compound (132) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (132). ¹H NMR (300 MHz, CDCl3): δ 7.96 (s, 1H), 7.10-7.13 (m, 1H), 6.94-7.01 (m, 2H), 6.76-6.78 (d, 1H), 4.40-4.53 (m, 1H), 3.86-3.95 (m, 1H), 3.41-3.66 (m, 1H), 2.71-3.01 (m, 2H), 2.66-2.68 (m, 3H), 2.28-2.60 (m, 2H), 1.31-1.99 (m, 14H). LC-MS (M+H)⁺=355.2; HPLC purity: 91.85%.

Example 133

3-(1H-indol-3-yl)-4-methyl-1-(octahydro-4H-1,4-benzoxazin-4-yl)pentan-1-one (133)

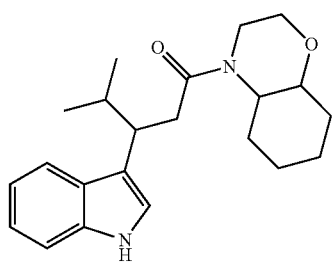

(133)

Synthesis of Compound (133)

Compound (133) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (133). ¹H NMR (300 MHz, CDCl3): δ 7.98 (s, 1H), 7.56-7.58 (d, 1H), 7.26-7.28 (d, 1H), 6.97-7.11 (m, 2H), 6.92-6.93 (d, 1H), 4.01-4.22 (m, 1H), 3.29-3.57 (m, 3H), 3.10-3.25 (m, 2H), 2.64-2.94 (m, 2H), 1.99-2.39 (m, 1H), 1.67-1.84 (m, 1H), 1.15-1.21 (m, 5H), 0.95-0.99 (m, 4H), 0.76-0.83 (m, 5H). LC-MS (M+H)⁺=355.2; HPLC purity: 98.87%.

Example 134

4-methyl-3-(1-methyl-1H-indol-3-yl)-1-(octahydro-4H-1,4-benzoxazin-4-yl)pentan-1-one (134)

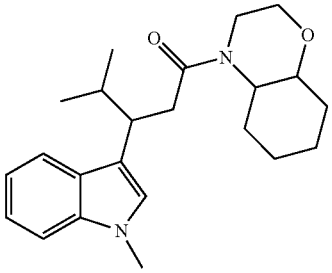

(134)

Synthesis of Compound (134)

Compound (134) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (134). ¹H NMR (300 MHz, CDCl3): δ 7.53-7.56 (d, 1H), 7.19-7.21 (d, 1H), 7.08-7.13 (t, 1H), 6.95-7.02 (m, 1H), 6.77 (s, 1H), 3.76-4.16 (m, 1H), 3.66 (s, 3H), 3.47-3.55 (m, 1H), 3.27-3.42 (m, 2H), 3.09-3.20 (m, 2H), 2.62-2.92 (m, 3H), 2.24-2.35 (m, 1H), 1.94-2.17 (m, 2H), 1.51-1.80 (m, 6H), 0.93-0.97 (m, 3H), 0.76-0.80 (m, 3H). LC-MS (M+H)⁺=369.3; HPLC purity: 91.33%.

Example 135

3-(4-fluoro-1H-indol-3-yl)-4-methyl-1-(octahydro-4H-1,4-benzoxazin-4-yl)pentan-1-one (135)

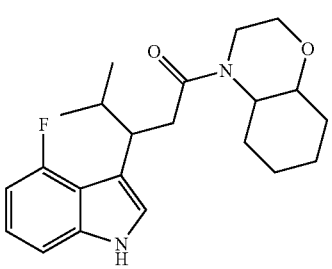

(135)

Synthesis of Compound (135)

Compound (135) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (135). ¹H NMR (300 MHz, CDCl3): δ 8.22 (s, 1H), 6.98-

7.13 (m, 3H), 6.70-6.76 (m, 1H), 4.07-4.22 (m, 1H), 3.10-3.83 (m, 3H), 2.70-2.88 (m, 2H), 2.04-2.13 (m, 1H), 1.66-1.86 (m, 3H), 0.77-1.33 (m, 14H). LC-MS (M+H)$^+$=373.2; HPLC purity: 94.76%.

Example 136

3-(4-fluoro-1H-indol-3-yl)-1-(octahydro-4H-1,4-benzoxazin-4-yl)butan-1-one (136)

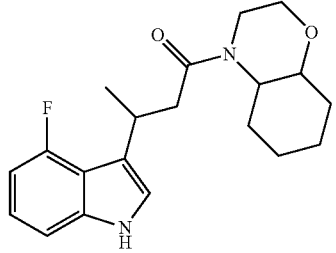

(136)

Synthesis of Compound (136)

Compound (136) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (136). $^1$H NMR (300 MHz, CDCl3): δ 8.08 (s, 1H), 6.96-7.12 (m, 3H), 6.68-6.77 (m, 1H), 3.87-4.28 (m, 1H), 3.24-3.87 (m, 2H), 2.64-2.96 (m, 2H), 2.42-2.56 (m, 1H), 2.21-2.30 (m, 1H), 1.32-2.02 (m, 13H). LC-MS (M+H)$^+$=345.2; HPLC purity: 94.02%.

Example 137

3-(4-fluoro-1H-indol-3-yl)-1-(octahydro-4H-1,4-benzoxazin-4-yl)butan-1-one (peak-1) (137)

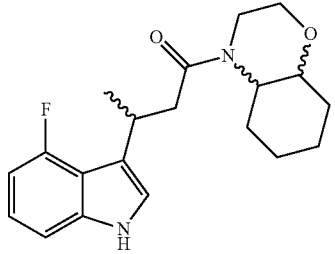

(137, peak 1)

Synthesis of Compound (137) (peak-1)

Mixture of isomers of Compound (136) was separated by using preparative reverse phase HPLC column to give Compound (137) (peak-1). $^1$H NMR (300 MHz, CDCl3): δ 8.26-8.33 (d, 1H), 6.91-7.10 (m, 3H), 6.65-6.76 (m, 1H), 4.11-4.29 (m, 1H), 3.58-3.78 (m, 1H), 3.54-3.58 (m, 1H), 3.29-3.42 (m, 2H), 3.08-3.15 (m, 1H), 2.77-3.03 (m, 2H), 2.34-2.55 (m, 2H), 1.78-1.91 (m, 1H), 1.52-1.67 (m, 3H), 1.32-1.41 (m, 6H). LC-MS (M+H)$^+$=345.2; HPLC purity: 97.60%; Column: Zorbax eclipse XDB-C18, Mobile phase: MeCN:H2O, 40:60, RT=14.93 min.

Example 138

3-(4-fluoro-1H-indol-3-yl)-1-(octahydro-4H-1,4-benzoxazin-4-yl)butan-1-one (peak-2) (138)

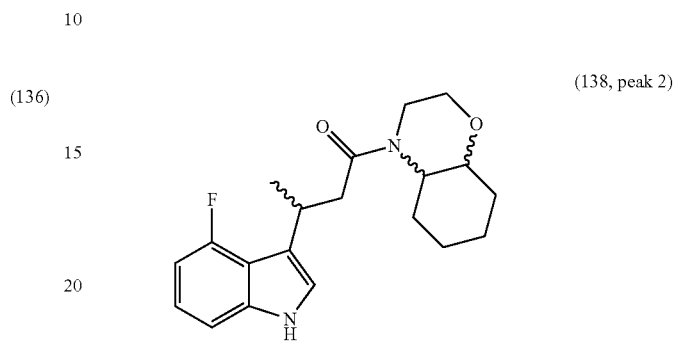

(138, peak 2)

Synthesis of Compound (138) (peak-2)

Mixture of isomers of Compound (136) was separated by using preparative reverse phase HPLC column to give Compound (138) (peak-2). $^1$H NMR (300 MHz, CDCl3): δ 8.14 (s, 1H), 6.93-7.12 (m, 3H), 6.65-6.74 (m, 1H), 4.13-4.28 (m, 1H), 3.44-3.86 (m, 2H), 3.18-3.38 (m, 2H), 2.57-2.88 (m, 2H), 2.43-2.52 (m, 1H), 1.84-2.33 (m, 2H), 1.56-1.88 (m, 4H), 1.33-1.40 (m, 6H). LC-MS (M+H)$^+$=345.2; HPLC purity: 96.43%; column: Zorbax eclipse XDB-C18, Mobile phase: MeCN:H2O, 40:60, RT=15.46 min.

Example 139

3-(4-fluoro-1H-indol-3-yl)-1-[cis-(4a,8a)-octahydro-4H-1,4-benzoxazin-4-yl]butan-1-one (peak-1) (139)

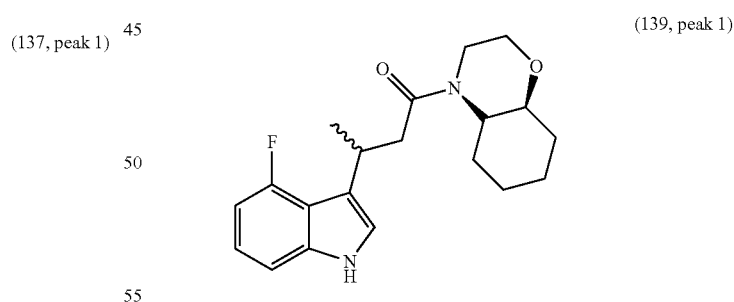

(139, peak 1)

Synthesis of Compound (139) (peak-1)

Compound (139) (peak-1) was synthesized by following the procedure used to make Compound (1) (Scheme 2). The crude product was obtained by evaporating the organic layer under reduced pressure and was purified by silica gel column using Petroleum ether: Ethyl acetate as eluent to obtain, Compound (139) (peak-1). $^1$H NMR (300 MHz, CDCl3): δ 8.03 (s, 1H), 6.92-7.10 (m, 3H), 6.72-6.77 (m, 1H), 4.10-4.30 (m, 1H), 3.54-3.76 (m, 2H), 2.46-3.27 (m, 7H), 1.67-1.79 (m, 4H), 1.33-1.41 (m, 6H). LC-MS (M+H)+=345.2; HPLC purity: 96.25%.

Example 140

3-(4-fluoro-1H-indol-3-yl)-1-[cis-(4a,8a)-octahydro-4H-1,4-benzoxazin-4-yl]butan-1-one (peak-2) (140)

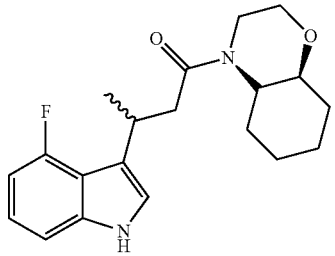

(140, peak 2)

Synthesis of Compound (140)

Compound (140) (peak-2) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (140) (peak-2). $^1$H NMR (300 MHz, CDCl3): δ 8.03 (s, 1H), 6.92-7.07 (m, 3H), 6.7-6.77 (m, 1H), 4.10-4.30 (m, 1H), 3.54-3.76 (m, 2H), 2.-3.27 (m, 7H), 1.67-1.83 (m, 4H), 1.33-1.41 (m, 6H). LC-MS (M+H)+=345.2; HPLC purity: 97.10%.

Example 141 ethyl 1-[3-(1,3-benzothiazol-2-yl)butanoyl]octahydroquinoline-4a(2H)-carboxylate (141)

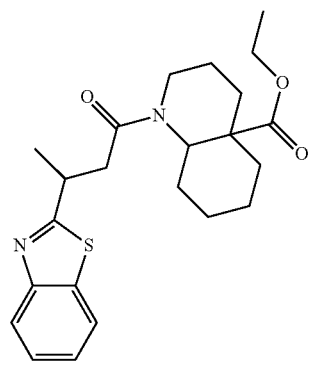

(141)

Synthesis of Compound (141)

Compound (141) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (141). $^1$H NMR (300 MHz, CDCl3): δ 7.75-7.89 (m, 2H), 7.23-7.38 (m, 2H), 3.81-4.13 (m, 3H), 2.99-3.09 (m, 1H), 2.53-2.87 (m, 1H), 2.01-2.19 (m, 3H), 1.22-1.78 (m, 18H). LC-MS (M+H)+=415.2; HPLC purity: 93.99%.

Example 142

3-(1,3-benzothiazol-2-yl)-1-(octahydro-1H-indol-1-yl)butan-1-one (142)

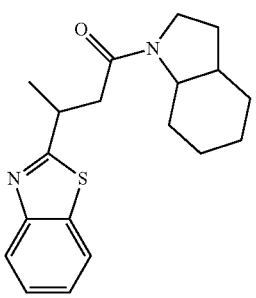

(142)

Synthesis of Compound (142)

Compound (142) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (142). $^1$H NMR (300 MHz, CDCl3): δ 7.88-7.91 (d, 1H), 7.75-7.78 (d, 1H), 7.35-7.40 (t, 1H), 7.25-7.30 (t, 1H), 3.86-4.10 (m, 2H), 3.38-3.50 (m, 2H), 2.91 (m, 1H), 2.56 (m, 1H), 1.05-2.06 (m, 14H). LC-MS (M+H)+329.2; HPLC purity: 97.29%.

Example 143

1-(octahydroquinolin-1(2H)-yl)-3-(1H-pyrrolo[2,3-b]pyridin-3-yl)butan-1-one (143)

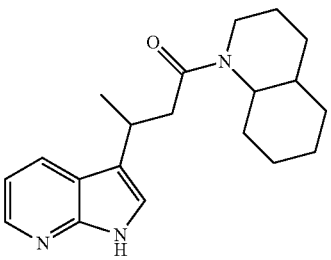

(143)

Synthesis of Compound (143)

Compound (143) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (143). $^1$H NMR (300 MHz, CDCl3): δ 9.63 (s, 1H), 7.94-

8.14 (m, 2H), 6.97-7.07 (m, 2H), 4.40-4.60 (m, 1H), 3.40-3.65 (m, 2H), 2.41-2.88 (m, 5H), 1.18-1.48 (m, 14H). LC-MS (M+H)⁺=326.1; HPLC purity: 94.48%.

Example 144

1-(octahydroquinolin-1(2H)-yl)-3-(1H-pyrrolo[2,3-b]pyridin-3-yl)butan-1-one (peak-1) (144)

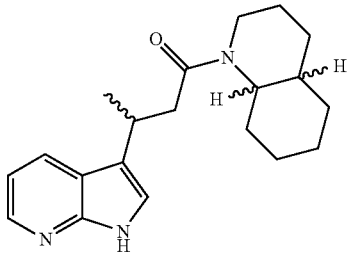

(144, peak 1)

Synthesis of Compound (144) (Peak-1)

Mixture of isomers of Compound (143) was separated by using preparative reverse phase HPLC column to give Compound (144) (peak-1). ¹H NMR (300 MHz, CDCl3): δ 12.04 (s, 1H), 8.55-8.57 (d, 1H), 8.14-8.16 (d, 1H), 7.30-7.34 (m, 2H), 4.32-4.67 (m, 1H), 3.47-3.85 (m, 2H), 2.51-2.98 (m, 5H), 1.32-1.73 (m, 14H). LC-MS (M+H)⁺=326.2; HPLC purity: 99.85%; Column: Zorbax eclipse XDB-C-18, mobile phase: MeCN:H2O 50:50, RT=4.77 min.

Example 145

1-(octahydroquinolin-1(2H)-yl)-3-(1H-pyrrolo[2,3-b]pyridin-3-yl)butan-1-one (peak-2) (145)

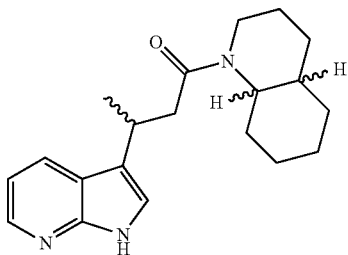

(145, peak 2)

Synthesis of Compound (145) (Peak-2)

Mixture of isomers of Compound (143) was separated by using preparative reverse phase HPLC column to give Compound (145) (peak-2). ¹H NMR (300 MHz, CDCl3): δ 11.84 (s, 1H), 8.51-8.54 (d, 1H), 8.16 (d, 1H), 7.30 (m, 2H), 4.32-4.67 (m, 1H), 3.45-3.76 (m, 2H), 2.51-2.98 (m, 5H), 1.32-1.73 (m, 14H). LC-MS (M+H)⁺=326.2; HPLC purity: 98.76%; Column: Zorbax eclipse XDB-C-18, mobile phase: MeCN:H2O 50:50, RT=5.24 min.

Example 146

1-[4a-(hydroxymethyl)octahydroquinolin-1(2H)-yl]-3-(1H-pyrrolo[2,3-b]pyridin-3-yl)butan-1-one (146)

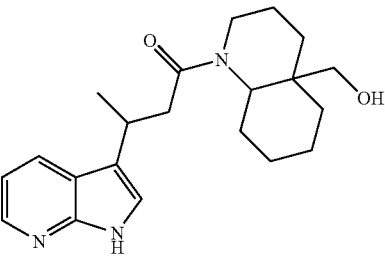

(146)

Synthesis of Compound (146)

Compound (146) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (146). ¹H NMR (300 MHz, DMSO-d6): δ 11.28 (s, 1H), 8.15-8.17 (d, 1H), 7.93-7.96 (d, 1H), 6.99-7.25 (m, 2H), 3.90-4.25 (m, 1H), 3.39-3.70 (m, 3H), 2.84-2.93 (m, 2H), 2.58-2.75 (m, 4H), 1.24-2.03 (m, 14H). LC-MS (M+H)⁺=356.2; HPLC purity: 96.35%.

Example 147

3-(4-chloro-1H-pyrrolo[2,3-b]pyridin-3-yl)-1-[4a-(hydroxymethyl) octahydroquinolin-1(2H)-yl]butan-1-one (147)

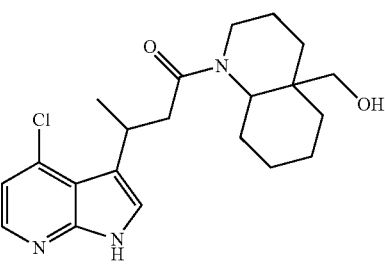

(147)

Synthesis of Compound (147)

Compound (147) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (147). ¹H NMR (300 MHz, CDCl3): δ 9.07 (s, 1H), 8.05-8.07 (d, 1H), 6.99-7.10 (m, 2H), 3.51-3.92 (m, 4H), 2.78-2.94 (m, 4H), 2.14-2.32 (m, 2H), 1.35-1.96 (m, 13H). LC-MS (M+H)⁺=390.2; HPLC purity: 91.09%.

Example 148

1-(4a-hydroxyoctahydroquinolin-1(2H)-yl)-3-(1H-pyrrolo[2,3-b]pyridin-3-yl)butan-1-one (148)

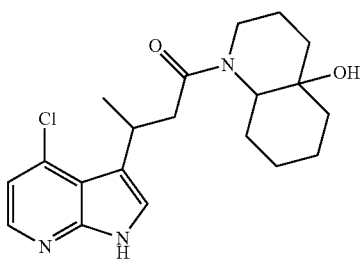

(148)

Synthesis of Compound (148)

Compound (148) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (148). $^1$H NMR (300 MHz, DMSO-d6): δ 11.28 (s, 1H), 8.16 (d, 1H), 7.95-7.99 (m, 1H), 7.20-7.24 (m, 1H), 6.99-7.03 (m, 1H), 4.35 (s, 1H), 4.15-4.29 (m, 1H), 3.63-3.72 (m, 1H), 3.42-3.51 (m, 2H), 2.62-2.83 (m, 3H), 1.20-1.98 (m, 14H). LC-MS (M+H)$^+$=342.2; HPLC purity: 98.98%.

Example 149

1-[3-(4-methyl-1H-indol-3-yl)butanoyl]octahydroquinoline-4a(2H)-carbonitrile (149)

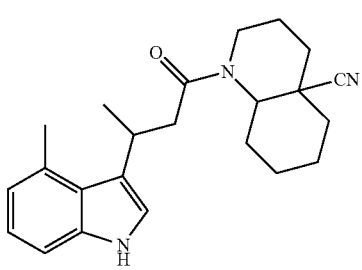

(149)

Synthesis of Compound (149)

Compound (149) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (149). $^1$H NMR (300 MHz, CDCl3): δ 6.98-7.05 (m, 2H), 6.75-6.78 (m, 2H), 4.82 (s, 1H), 3.93 (s, 1H), 3.63 (s, 3H), 3.16-3.22 (m, 2H), 2.64 (s, 3H), 2.55-2.61 (m, 2H), 1.97-2.01 (m, 2H), 1.75-1.79 (m, 2H), 1.70-1.72 (m, 3H), 1.59-1.65 (m, 7H). LC-MS (M+H)$^+$=364.2; HPLC purity: 93.73%.

Example 150

1-[3-(4-fluoro-1H-indol-3-yl)-3-phenylpropanoyl]decahydroquinoline-4-carboxylic acid (150)

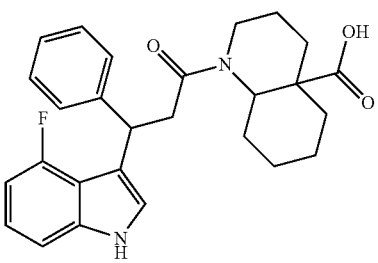

(150)

Synthesis of Compound (150)

Compound (150) was synthesized by following the procedure used to make Compound (105) (Scheme 51). $^1$H NMR (300 MHz, DMSO-d6): δ 12.23 (s, 1H), 11.17 (s, 1H), 7.34-7.36 (d, 1H), 7.18-7.27 (m, 4H), 7.09-7.15 (m, 2H), 6.93-7.00 (m, 1H), 6.58-6.64 (m, 1H), 4.83 (m, 1H), 3.91-4.06 (m, 1H), 3.00-3.18 (m, 3H), 1.09-1.88 (m, 13H). LC-MS (M+H)$^+$=449.2; HPLC purity: 96.20%.

Example 151

1-[3-(6-fluoro-1H-indol-3-yl)-3-phenylpropanoyl]decahydroquinoline-4-carboxylic acid (151)

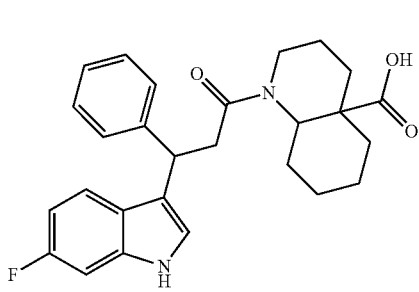

(151)

Synthesis of Compound (151)

Compound (151) was synthesized by following the procedure used to make Compound (105) (Scheme 51). $^1$H NMR (300 MHz, DMSO-d6): δ 12.21 (s, 1H), 10.94 (s, 1H), 7.27-7.30 (m, 4H), 7.19-7.24 (t, 2H), 7.05-7.13 (m, 2H), 6.69-6.75 (m, 1H), 4.63-4.65 (m, 1H), 3.90-3.98 (m, 2H), 2.98-3.26 (m, 3H), 2.27-2.43 (m, 2H), 1.10-1.84 (m, 10H). LC-MS (M+H)$^+$=449.22; HPLC purity: 96.21%.

Example 152

1-[3-(1,3-benzothiazol-2-yl)-3-phenylpropanoyl]decahydroquinoline-4-carboxylic acid (152)

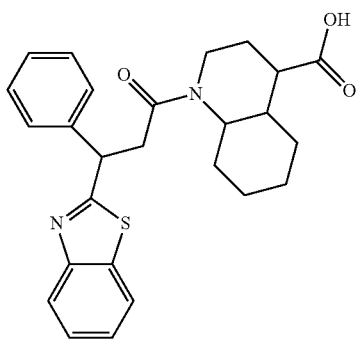

(152)

Synthesis of Compound (152)

Compound (152) was synthesized by following the procedure used to make Compound (105) (Scheme 51). $^1$H NMR (300 MHz, DMSO-d6): δ 12.26 (s, 1H), 7.92-8.00 (m, 2H), 7.24-7.49 (m, 7H), 4.96-4.98 (m, 1H), 3.50-4.23 (m, 3H), 2.90-3.21 (m, 1H), 1.47-2.27 (m, 13H). LC-MS (M+H)$^+$=449.1; HPLC purity: 99.48%.

Example 153

1-(4a-methoxyoctahydroquinolin-1(2H)-yl)-3-(1H-pyrrolo[2,3-b]pyridin-3-yl)butan-1-one (153)

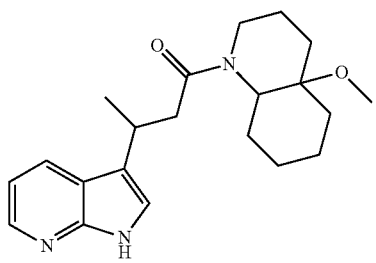

(153)

Synthesis of Compound (153)

Compound (153) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (153). $^1$H NMR (300 MHz, CDCl3): δ 9.14 (s, 1H), 8.20-8.21 (d, 1H), 7.93-7.96 (m, 1H), 6.96-7.08 (m, 2H) 3.44-3.64 (m, 3H), 303-3.06 (m, 3H), 2.42-2.75 (m, 2H), 1.27-1.83 (m, 16H). LC-MS (M+H)$^+$=356.2; HPLC purity: 94.26%.

Example 154

1-[3-(1,3-benzothiazol-2-yl)butanoyl]decahydroquinoline-4-carboxylic acid (154)

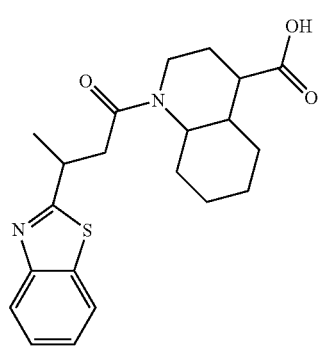

(154)

Synthesis of Compound (154)

Compound (154) was synthesized by following the procedure used to make Compound (105) (Scheme 51). $^1$H NMR (300 MHz, CD3OD): δ 7.88-7.94 (m, 2H), 7.44-7.50 (m, 1H), 7.35-7.41 (m, 1H), 4.17 (s, 1H), 3.79-3.97 (m, 2H), 3.52-3.63 (m, 1H), 3.07-3.22 (m, 1H), 2.69-2.86 (m, 1H), 2.56 (m, 1H) 2.04-2.11 (m, 2H), 1.88-1.92 (m, 2H), 1.61 (m, 4H), 1.45-1.51 (m, 3H), 1.35-1.38 (m, 4H). LC-MS (M+H)$^+$=387.2; HPLC purity: 93.02%.

Example 155

1-[3-(4-chloro-1H-indol-3-yl)-3-phenylpropanoyl]decahydroquinoline-4-carboxylic acid (155)

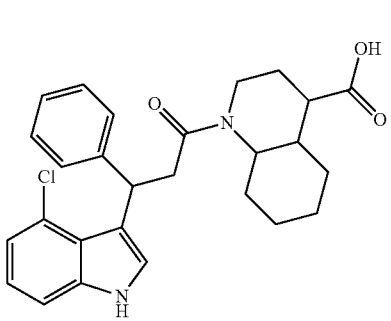

(155)

Synthesis of (155)

Compound (155) was synthesized by following the procedure used to make Compound (105) (Scheme 51). 1H NMR (300 MHz, DMSO-d6): δ 12.19 (brs, 1H), 11.31 (s, 1H), 7.49, brs, 1H), 7.20-7.31 (m, 5H), 7.09-7.11 (m, 1H), 6.96-7.01 (t, 1H), 6.85-6.87 (d, 1H), 5.27-5.30 (m, 1H), 3.81-3.91 (2H, m), 2.60-2.95 (m, 3H), 2.25 (brs, 1H), 1.39-1.95 (m, 11H). LC-MS (M+H)$^+$=465.2; HPLC purity: 99.0%.

Example 156

1-[3-(4-fluoro-1H-indol-3-yl)-3-(thiophen-2-yl)propanoyl]decahydroquinoline-4-carboxylic acid (160)

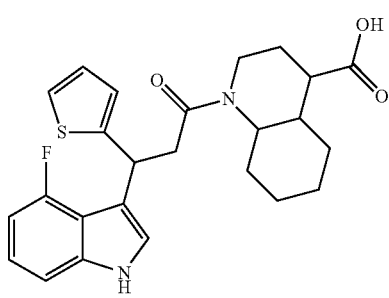

(156)

Synthesis of (156):

Compound (156) was synthesized by following the procedure used to make Compound (105) (Scheme 51). 1H NMR (300 MHz, CDCl3): δ 8.28 (brs, 1H), 6.98-7.06 (m, 4H), 6.80-6.82 (m, 2H), 6.62-6.68 (m, 1H), 5.06-5.20 (m, 1H), 4.46-4.59 (m, 1H), 3.94-4.06 (m, 1H) 3.54-3.64 (1H), 3.30-3.42 (m, 1H), 3.04-3.16 (m, 2H), 2.27-2.55 (m, 1H), 1.59-1.87 (m, 6H), 1.35-1.40 (m, 4H). LC-MS (M+H)+=455.2; HPLC purity: 98.58%.

Example 157

1-[3-(4-fluoro-1H-indol-3-yl)-3-(4-fluorophenyl)propanoyl]decahydroquinoline-4-carboxylic acid (157)

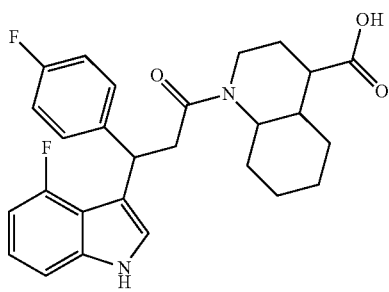

(157)

Synthesis of (157)

Compound (157) was synthesized by following the procedure used to make Compound (105) (Scheme 51). 1H NMR (300 MHz, DMSO-d6): δ 12.23 (brs, 1H), 11.19 (brs, 1H), 7.24-7.53 (m, 3H), 7.12-7.15 (d, 1H), 6.94-7.06 (m, 3H), 6.61-6.65 (m, 1H), 4.83 (brs, 1H), 3.87-4.06 (m, 1H), 2.92-3.20 (4H), 2.45-2.60 (m, 2H), 1.47-1.86 (m, 10H). LC-MS (M+H)+=467.2; HPLC purity: 97.74%.

Example 158

1-[3-(4-chloro-1H-indol-3-yl)butanoyl]decahydroquinoline-4-carboxylic acid (158)

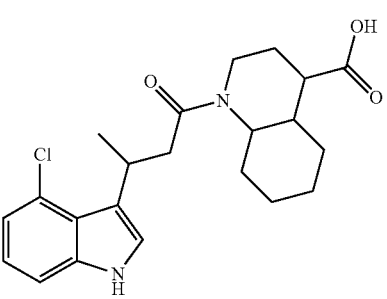

(158)

Synthesis of (158)

Compound (158) was synthesized by following the procedure used to make Compound (105) (Scheme 51). 1H NMR (300 MHz, DMSO-d6): δ 12.25 (brs, 1H), 11.19 (brs, 1H), 7.28-7.32 (m, 2H), 6.96-7.04 (m, 2H), 3.96-4.01 (m, 2H), 3.45-3.50 (m, 1H), 2.63-2.79 (4H), 1.91-1.95 (m, 1H), 1.23-1.70 (m, 13H). LC-MS (M+H)+=403.2; HPLC purity: 93.16%.

Example 159

1-[3-(6-fluoro-1H-indol-3-yl)-3-phenylpropanoyl]decahydroquinoline-4-carboxylic acid (peak-1) (159)

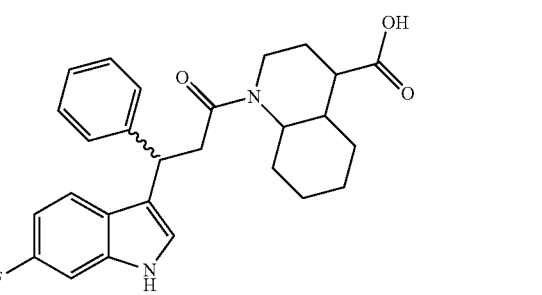

(159, peak 1)

Synthetic Scheme-53

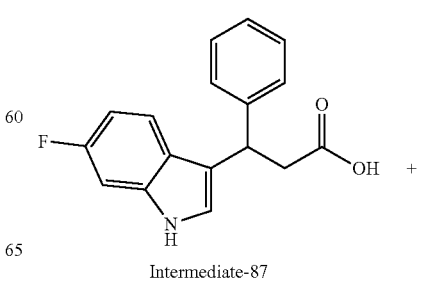

Intermediate-87

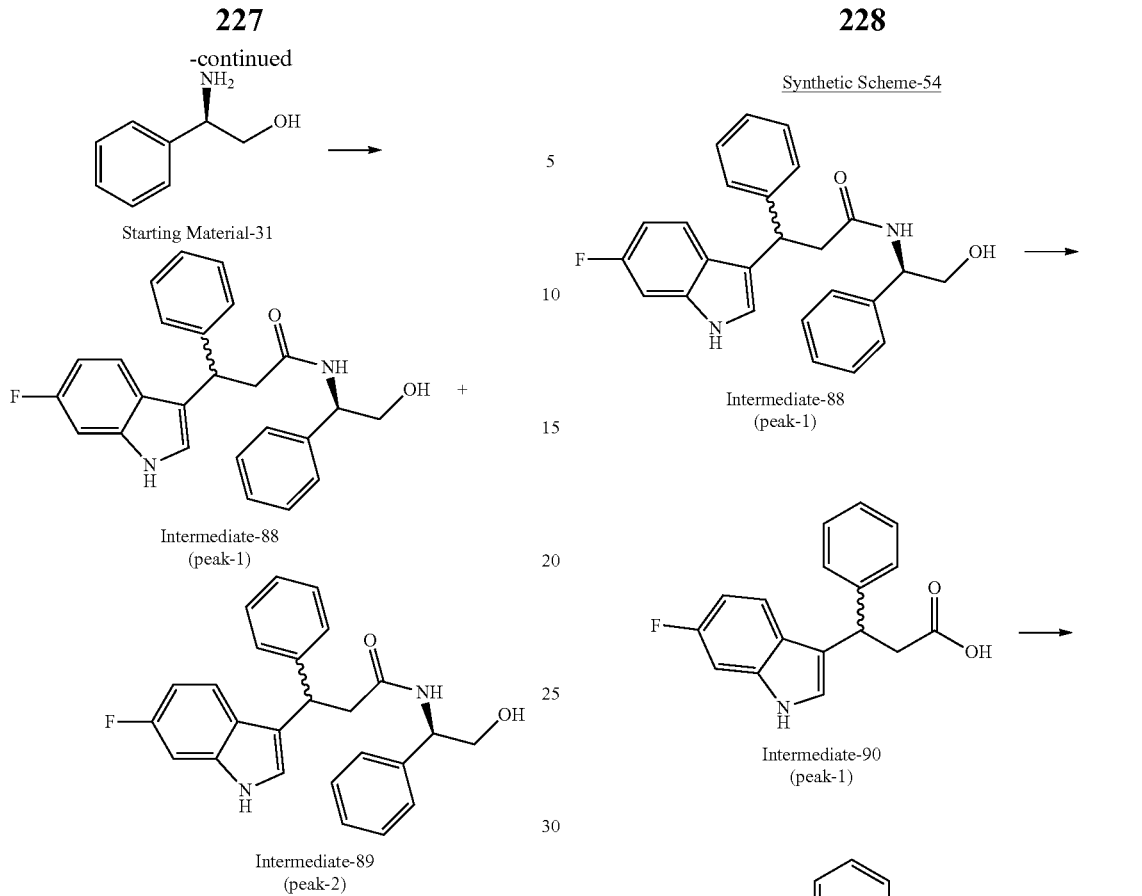

Synthesis of 3-(6-fluoro-1H-indol-3-yl)-N-[(1R)-2-hydroxy-1-phenylethyl]-3-phenylpropanamide (Intermediate-88, peak-1 and Intermediate-89 peak-2)

At 0° C., to a stirred solution of Intermediate-87 (0.800 g, 2.8 mmol) and Starting Material-31 (0.387 g, 2.8 mmol) in THF: DMF (10 mL: 0.5 mL), HBTU (1.28 g, 3.3 mmol) was added followed by addition of isopropyl ethylamine (1.09 g, 8.4 mmol). The resulted reaction mixture was stirred at room temperature for 2 hours. After completion of the reaction (reaction monitored by TLC), the reaction mass was quenched with water and extracted with Ethyl acetate (3×50 mL). The organic layer was washed with saturated brine solution (50 mL) and concentrated. Crude product was purified by combi flash chromatography eluting with hexanes:EtOAc (1:1) to give Intermediate-88 (200 mg) and Intermediate-89 (280 mg) as pink solid.

Intermediate-88, peak-1

LC-MS (M+H)$^+$=403.2; HPLC purity: 91.08%; Column: Zorbax eclipse XDB-C18, 4.6×50 mm, 5 μm; RT=13.58 minutes, Mobile phase: MeCN: 0.01% TFA gradient.

Intermediate-89, peak-2

LC-MS (M+H)$^+$=403.2; HPLC purity: 91.62%; Column: Zorbax eclipse XDB-C18, 4.6×50 mm, 5 μm; RT=13.82 minutes, Mobile phase: MeCN: 0.01% TFA gradient.

Synthesis of 3-(6-fluoro-1H-indol-3-yl)-3-phenyl-propanoic acid (Intermediate-90, peak-1)

To a stirred solution of Intermediate-88, peak-1 (0.200 g, 0.49 mmol) in 1,4 dioxane: H$_2$O (2 mL: 2 mL) Conc. H$_2$SO$_4$ (0.6 mL) was added and the resultant mixture was heated at 90° C. for 6 hours. After completion of the reaction (reaction monitored by TLC), the reaction mass was quenched with ice and extracted with Ethyl acetate (3×50 mL). The organic layer was washed with saturated brine solution (50 mL) and dried over anhydrous Na$_2$SO$_4$ and concentrated to give Intermediate-90 (130 mg) as a pink oily material.

Synthesis of methyl 1-[3-(6-fluoro-1H-indol-3-yl)-3-phenylpropanoyl]decahydroquinoline-4-carboxylate (Intermediate-91, peak-1)

Intermediate-91, peak-1 was synthesized by following the procedure used to make Compound (1) (Scheme 2).

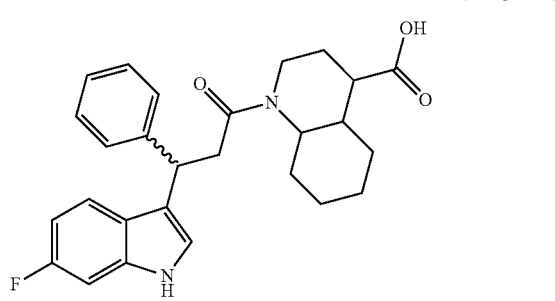

(159, peak 1)

Synthesis of Compound (159) (peak-1)

Compound (159) (peak-1) was synthesized by following the procedure used to make Compound (105) (Scheme 51). 1H NMR (300 MHz, DMSO-d6): δ 12.21 (brs, 1H), 10.93 (brs, 1H), 7.22-7.29 (m, 3H), 7.05-7.13 (m, 3H), 6.93-6.97 (m, 2H), 6.75-6.80 (m, 1H), 4.56-4.64 (m, 1H), 3.50-3.60 (m, 2H), 2.99-3.1 (m, 3H), 2.27-2.32 (m, 1H), 1.15-1.83 (m, 11H). LC-MS (M+H)$^+$=449.2; HPLC purity: 96.66%.

Example 160

1-[3-(6-fluoro-1H-indol-3-yl)-3-phenylpropanoyl]decahydroquinoline-4-carboxylic acid (peak-2) (160)

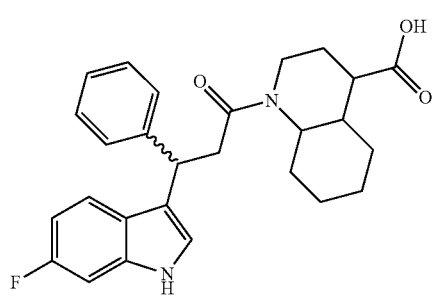

(160, peak 2)

Synthetic Scheme-55

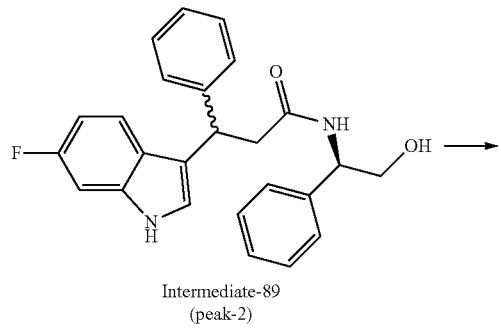

Intermediate-89 (peak-2)

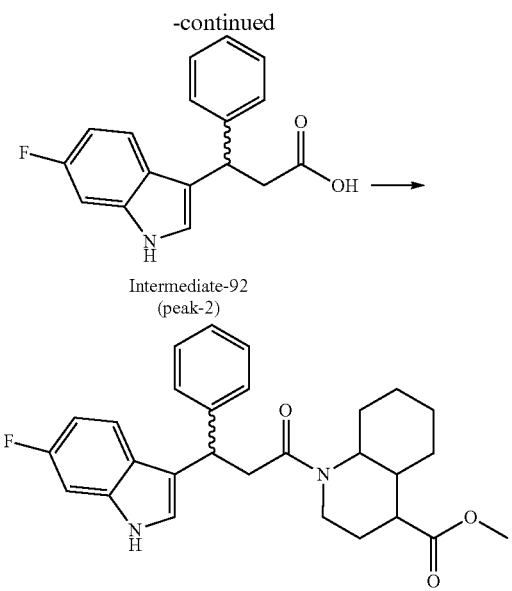

Intermediate-92 (peak-2)

Intermediate-93 (peak-2)

Synthesis of 3-(6-fluoro-1H-indol-3-yl)-3-phenyl-propanoic acid (Intermediate-92, peak-2)

Intermediate-92 (peak-2) was synthesized by following the procedure used to make Intermediate-90 (peak-1) (Scheme 54).

Synthesis of methyl 1-[3-(6-fluoro-1H-indol-3-yl)-3-phenylpropanoyl]decahydroquinoline-4-carboxylate (Intermediate-93, peak-2)

Intermediate-93 (peak-2) was synthesized by following the procedure used to make Compound (1) (Scheme 2).

Synthesis of Compound (160) (peak-2)

Compound (160) (peak-2) was synthesized by following the procedure used to make Compound (105) (Scheme 51). 1H NMR (300 MHz, DMSO-d6): δ 12.22 (brs, 1H), 10.94 (brs, 1H), 7.19-7.31 (m, 3H), 7.05-7.13 (m, 3H), 7.05-7.11 (m, 2H), 6.69-6.75 (m 1H), 4.62-4.65 (m, 1H), 3.78-3.93 (m, 1H), 2.97-3.18 (m, 4H), 2.41-2.45 (m, 1H), 1.46-1.90 (m, 11H). LC-MS (M+H)$^+$=449.2; HPLC purity: 97.44%.

Example 161

1-[3-(4-fluoro-1H-indol-3-yl)-3-phenylpropanoyl]decahydroquinoline-4-carboxylic acid (peak-1) (161)

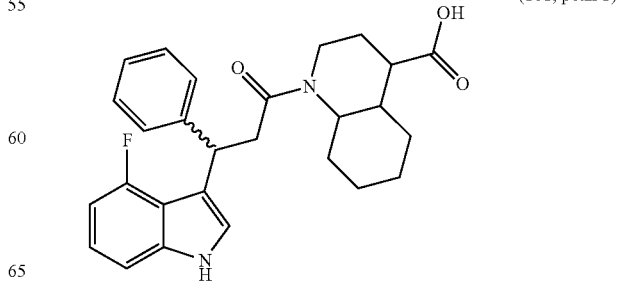

(161, peak 1)

Synthesis of Compound (161) (Peak-1)

Compound (161) (peak-1) was synthesized by following the procedure used to make Compound (159) (peak-2) (Scheme 53, & 54). 1H NMR (300 MHz, CDCl3): δ 8.38 (brs, 1H), 6.90-7.35 (m, 8H), 6.55-6.61 (m, 1H), 4.86-4.93 (m, 1H), 3.73-3.93 (m, 1H), 3.31-3.36 (m, 1H), 2.98-3.08 (m, 3H), 2.22-2.35 (m, 1H), 1.31-1.69 (m, 11H). LC-MS (M+H)$^+$=449.2; HPLC purity: 97.90%.

Example 162

1-[3-(4-fluoro-1H-indol-3-yl)-3-phenylpropanoyl] decahydroquinoline-4-carboxylic acid (peak-2) (162)

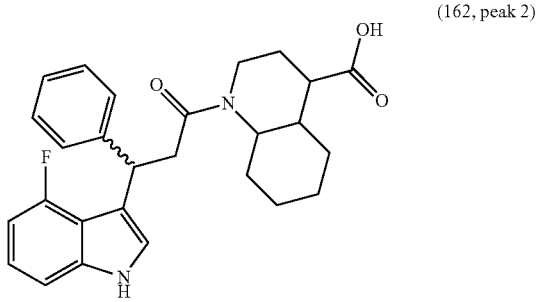 [SMILES: O=C(O)C1CCN(C(=O)CC(c2ccccc2)c2c[nH]c3cccc(F)c23)C2CCCCC12]

(162, peak 2)

Synthesis of Compound (162) (peak-2)

Compound (162) (peak-2) was synthesized by following the procedure used to make Compound (160) (peak-2) (Scheme 55). 1H NMR (300 MHz, DMSO-d6): δ 12.23 (brs, 1H), 11.18 (brs, 1H), 7.35-7.36 (m, 1H), 7.07-7.27 (m, 6H), 6.93-7.00 (m, 1H), 6.51-6.71 (dd, 1H), 4.83 (brs, 1H), 3.91-3.99 (m, 1H), 2.92-3.20 (m, 3H), 2.41-2.45 (m, 2H), 1.45-1.88 (m, 11H). LC-MS (M+H)$^+$=449.2; HPLC purity: 98.50%.

Example 163

1-[4-methyl-3-(1H-pyrrolo[2,3-b]pyridin-3-yl)pentanoyl]decahydro quinoline-4-carboxylic acid (163)

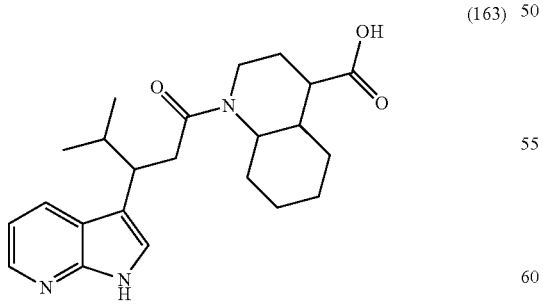

(163)

Synthesis of Compound (163)

Compound (163) was synthesized by following the procedure used to make Compound (105) (Scheme 51). 1H NMR (300 MHz, DMSO-d6): 12.22 (brs, 1H), 11.30 (brs, 1H), 8.13-8.14 (d, H), 7.94-7.96 (d, 1H), 7.19-7.20 (m, 1H), 6.97-7.01 (m, 1H), 3.82-4.04 (m, 1H), 3.16-3.21 (m, 2H), 2.71-2.84 (m, 5H), 2.20-2.25 (m, 1H), 1.40-2.03 (m, 6H), 1.17-1.23 (4H), 0.90-0.92 (d, 3H), 0.56-0.58 (d, 3H). LC-MS (M+H)$^+$=396.2; HPLC purity: 95.12%.

Example 164

4-methyl-1-(octahydroquinolin-1(2H)-yl)-3-(1H-pyrrolo[2,3-b]pyridin-3-yl)pentan-1-one (164)

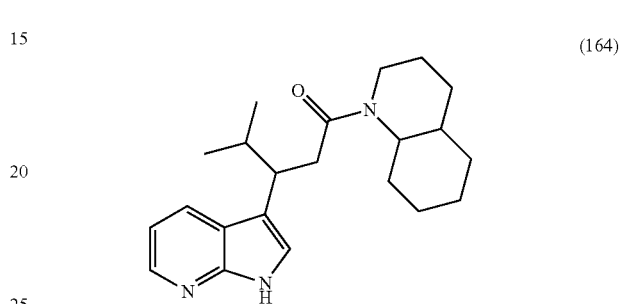

(164)

Synthesis of Compound (164)

Compound (164) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (164). 1H NMR (300 MHz, CDCl3): δ 9.46 (brs, 1H), 8.17-8.21 (m, 1H), 7.89-7.95 (m, 1H), 6.95-7.05 (m, 2H), 4.29-4.45 (m, 1H), 3.35-3.65 (m, 2H), 3.09-3.25 (m, 1H), 2.69-2.89 (m, 3H), 2.29-2.37 (m, 1H), 1.95-2.12 (m, 3H0, 1.55-1.70 (m, 3H), 1.37-1.49 (m, 6H), 0.90-0.92 (d, 3H), 0.76-0.78 (d, 3H). LC-MS (M+H)$^+$=354.3; HPLC purity: 96.20%.

Example 165

1-[3-(1H-pyrrolo[2,3-b]pyridin-3-yl)butanoyl]decahydroquinoline-4-carboxylic acid (165)

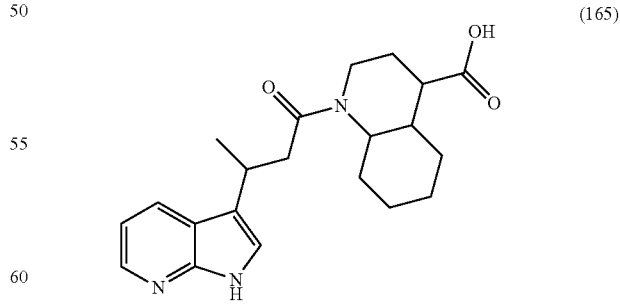

(165)

Synthesis of Compound (165)

Compound (165) was synthesized by following the procedure used to make Compound (105) (Scheme 51). 1H NMR (300 MHz, DMSO-d6): δ 12.22 (brs, 1H), 11.31 1H), 8.15-8.16 (m, H), 7.95-7.98 (d, 1H), 7.25-7.26 (m, 1H), 6.98-7.02 (m, 1H), 4.05-4.06 (m, 1H), 3.74-3.87 (m, 1H), 3.48-3.52 (m, 2H), 2.63-2.81 (m, 3H), 2.27-2.34 (m, 1H), 1.60-1.98 (m, 8H), 1.45-1.49 (m, 2H), 1.25-1.28, m, 3H). LC-MS (M+H)$^+$=370.2; HPLC purity: 91.67%.

Example 166

3-(4-chloro-1H-benzotriazol-1-yl)-1-(octahydroquinolin-1(2H)-yl)butan-1-one (166)

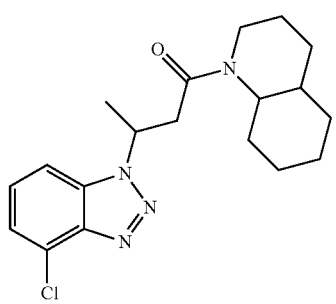
(166)

Synthesis of Compound (166)

Compound (166) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (166). $^1$H NMR (300 MHz, CD3OD) 1H NMR (300 MHz, CDCl3): δ 7.49-7.54 (t, 1H), 7.26-7.35 (m, 2H), 5.40-5.44 (m, 1H), 4.23-4.38 (m, 1H), 3.30-3.76 (m, 2H0, 2.71-3.02 (m, 1.5H), 2.41-2.51 (m, 0.5H), 1.18-1.75 (m, 16H): LC-MS: (M+H)+=361.1; HPLC purity=89.09%.

Example 167

3-(4-chloro-2H-benzotriazol-2-yl)-1-(octahydroquinolin-1(2H)-yl)butan-1-one (167)

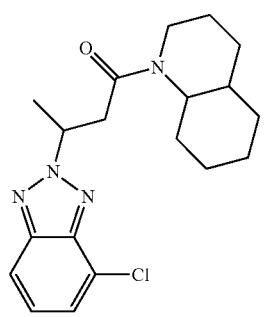
(167)

Synthesis of Compound (167)

Compound (167) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (167). 1H NMR (300 MHz, CDCl3): δ 7.67-7.71 (m, 1H), 7.28-7.31 (M, 1H), 7.19-7.24 (m, 1H), 5.55-5.64 (m, 1H), 4.38-4.55 (m, 1H), 3.50-3.62 (m, 1H), 3.20-3.45 (m, 1H), 2.75-3.05 (m, 2H), 2.46-2.50 (m, 1H), 1.70 (d, 3H), 1.17-1.68 (m, 12H). LC-MS: (M+H)+=361.2; HPLC purity=95.89%.

Example 168

1-[3-(4-methyl-1H-benzotriazol-1-yl)butanoyl]decahydroquinoline-4-carboxylic acid (168)

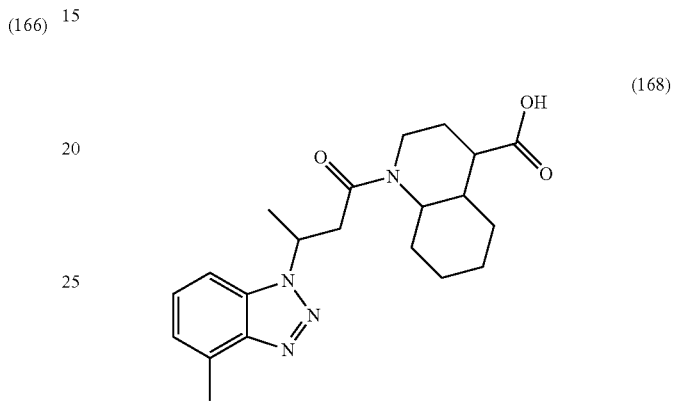
(168)

Synthesis of Compound (168)

Compound (168) was synthesized by following the procedure used to make Compound (105) (Scheme 51). 1H NMR (300 MHz, DMSO-d6): δ 7.66-7.69 (d, 1H), 7.37-7.42 (t, 1H), 7.14-7.16 (d, 1H), 5.41 (brs, 1H), 3.70-3.86 (m, 3H), 2.66 (s, 3H), 2.45-2.51 (m, 2H), 2.27 (brs, 1H), 1.19-1.83 (m, 14H). LC-MS: (M+H)+=385.2; HPLC purity=83.84%.

Example 169

1-[3-(4-methyl-2H-benzotriazol-2-yl)butanoyl]decahydroquinoline-4-carboxylic acid (169)

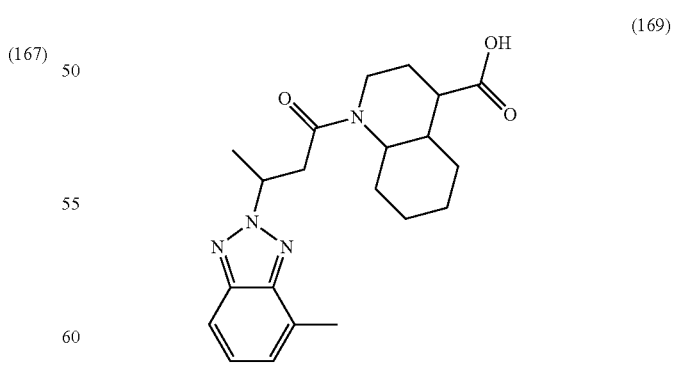
(169)

Synthesis of Compound (169)

Compound (169) was synthesized by following the procedure used to make Compound (105) (Scheme 51). 1H NMR (300 MHz, DMSO-d6): 12.26 (brs, 1H), 7.65-7.70 (1H, m), 7.37-7.42 (t, 1H), 7.14-7.16 (d, 1H), 5.41-5.43 (m, 1H), 3.88-3.96 (m, 2H), 2.85-3.12 (m, 3H0, 2.69 (s, 3H), 2.27 (brs, 1H), 1.70-2.0 (m, 11H), 1.61 (d, 3H). LC-MS: (M+H)+=385.2; HPLC purity=84.25%.

Example 170

1-[3-(4-fluoro-1H-indol-3-yl)-3-(thiophen-2-yl)propanoyl]decahydroquinoline-2-carboxylic acid (170)

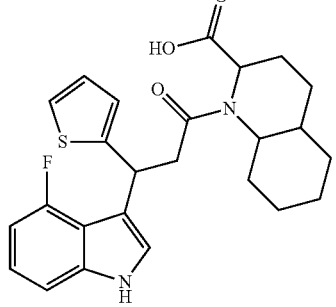

(170)

Synthesis of Compound (170)

Compound (170) was synthesized by following the procedure used to make (105) (Scheme 51). 1H NMR (300 MHz, DMSO-d6): δ 11.18 (brs, 1H), 7.35-7.40 (m, 1H), 7.13-7.28 (m, 2H), 6.98-7.02 (m, 1H), 6.80-6.88 (m, 2H), 6.65-6.71 (m, 1H), 5.00-5.12 (m, 1H), 4.59-4.66 (m, 0.5H), (4.26-4.34 (m, 0.5H), 3.80-3.86 (m, 1H), 2.92-3.05 (m, 2H), 2.20-2.22 (m, 1H), 1.33-1.75 (m, 10H). LC-MS: (M+H)+=455.1; HPLC purity=97.36%.

Example 171

1-[3-(4-chloro-1H-pyrrolo[2,3-b]pyridin-3-yl)butanoyl]decahydroquinoline-4-carboxylic acid (171)

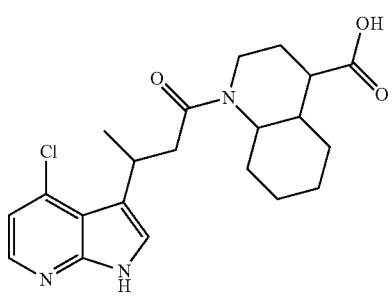

(171)

Synthesis of (171)

Compound (171) was synthesized by following the procedure used to make Compound (105) (Scheme 51). 1H NMR (300 MHz, DMSO-d6): δ 12.26 (brs, 1H), 11.77 (s, 1H), 8.09-8.11 (d, 1H), 7.42 (s, 1H), 7.10-7.12 (d, 1H), 4.05 (brs, 1H), 3.85-3.87 (m, 2H), 3.45-3.51 (m, 2H), 2.66-2.76 m, 2H), 1.62-1.97 (m, 11H), 1.40-1.43 (d, 3H). LC-MS: (M+H)+=404.2; HPLC purity=90.05%

Example 172

4-methyl-3-(4-methyl-1H-benzotriazol-1-yl)-1-(octahydroquinolin-1(2H)-yl)pentan-1-one (172)

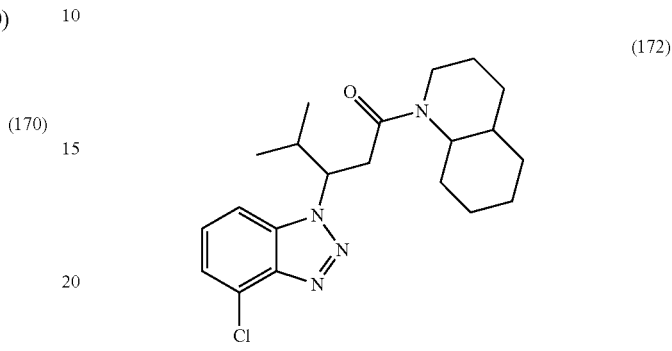

(172)

Synthesis of Compound (172)

Compound (172) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (172) 1H NMR (300 MHz, CDCl3): δ 7.34-7.39 (m, 1H), 7.25-7.30 (m, 1H), 7.00-7.02 (m, 1H), 5.00-5.03 (m, 1H), 4.61 (brs, 0.5H), 4.15-4.30 (m, 0.5H), 3.41-3.61 (m, 2H), 2.78-3.01 (m, 1H), 2.70 (s, 3H), 2.15-2.42 (m, 1H), 1.32-1.95 (m, 14H), 0.70-0.81 (m, 6H). LC-MS: (M+H)+=369.3; HPLC purity=82.9%

Example 173

3-(4-chloro-1,3-benzothiazol-2-yl)-1-(octahydroquinolin-1(2H)-yl)butan-1-one (173)

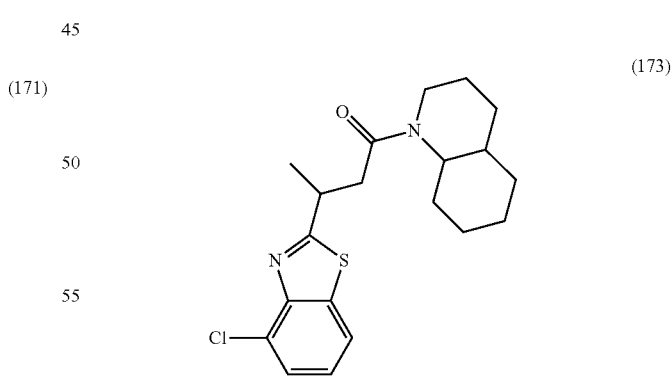

(173)

Synthesis of Compound (173)

Compound (173) was synthesized by following the procedure used to make Compound (1) (Scheme 2). The crude product was obtained by evaporating the organic layer under reduced pressure and was purified by silica gel column using Petroleum ether: Ethyl acetate as eluent to obtain Compound (173) 1H NMR (300 MHz, CDCl3): δ 7.64-7.67 (d, 1H), 7.36-7.39 (d, 1H), 7.16-7.21 (m, 1H), 4.39-4.56 (m, 1H), 3.64-3.94 (m, 2H), 3.01-3.23 (m, 2H), 2.48-2.65 (m, 2H), 1.52-1.78 (m, 8H), 1.46 (d, 3H), 1.31-142 (m, 6H). LC-MS: (M+H)+=377.1; HPLC purity=98.83%

Example 174

1-[3-(6-fluoro-1H-indol-3-yl)-3-phenylpropanoyl] decahydroquinoline-2-carboxylic acid (174)

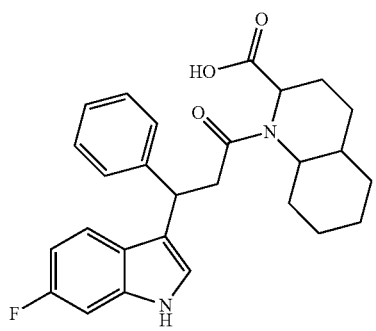

(174)

Synthesis of Compound (174)

Compound (174) was synthesized by following the procedure used to make Compound (105) (Scheme 51) 1H NMR (300 MHz, CDCl3): δ 8.06 (brs, 0.5H), 7.98 (brs, 0.5H), 7.22-7.24 (m, 2H), 6.91-6.98 (m, 5H), 6.60-6.75 (m, 2H), 4.85-4.87 (m, 1H), 4.78-4.83 (m, 2H), 3.54-3.66 (m, 2H), 3.24-3.32 (dd, 1H), 3.03-3.10 (dd, 1H), 2.12-2.30 (m, 2H), 1.85-2.00 (m, 5H), 1.41-1.58 (m, 4H). LC-MS: (M+H)+=449.2; HPLC purity=93.61%.

Example 175

1-[3-(6-fluoro-1H-indol-3-yl)-3-phenylpropanoyl] decahydroquinoline-3-carboxylic acid (175)

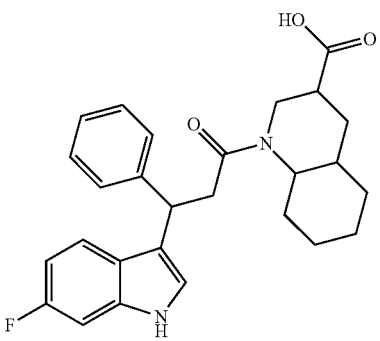

(175)

Synthesis of Compound (175)

Compound (175) was synthesized by following the procedure used to make Compound (105) (Scheme 51) 1H NMR (300 MHz, DMSO-d6): 12.35 (brs, 1H), 10.99 (brs, 1H), 7.20-7.31 (m, 6H), 7.05-7.12 (m, 2H), 6.69-6.75 (t, 1H), 4.62-4.66 (m, 1H), 4.30-4.45 (m, 0.5H), 3.81-4.10 (m, 0.5H), 2.93-3.22 (m, 2H), 2.45-2.51 (m, 2H), 2.24-2.30 (m, 1H), 1.17-1.75 (m, 11H). LC-MS: (M+H)+=449.2.

Example 176

1-[3-(4-fluoro-1H-indol-3-yl)-3-phenylpropanoyl] decahydroquinoline-3-carboxylic acid (176)

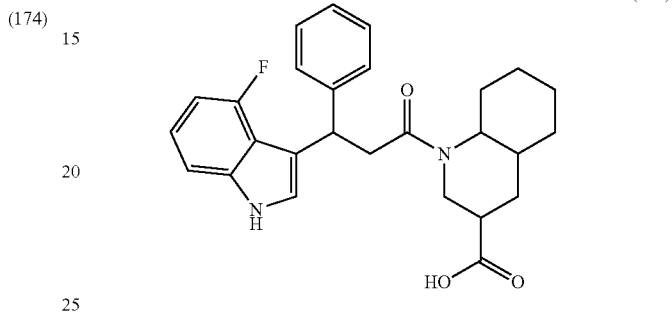

(176)

Synthesis of Compound (176)

Compound (176) was synthesized by following the procedure used to make Compound (105) (Scheme 51). 1H NMR (300 MHz, CDCl3): δ 8.19 (brs, 1H), 7.19-7.23 (m, 1H), 6.92-7.12 (m, 7H), 6.54-6.65 (m, 1H), 4.88-4.90 (m, 1H), 4.51-4.64 (m, 1H), 3.66-3.79 (m, 1H), 2.94-3.09 (m, 2H), 2.48-2.74 (m, 2H), 2.12-2.30 (m, 1H), 1.95-2.02 (m, 1H), 1.31-1.85 (m, 10H). LC-MS: (M+H)+=449.2; HPLC purity=99.50%.

Example 177

1-[3-(6-fluoro-1H-indol-3-yl)-4-methylpentanoyl] decahydroquinoline-4-carboxylic acid (peak-1) (177)

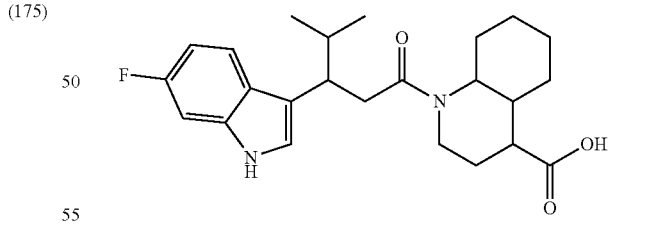

(177)

Synthesis of Compound (177)

Compound (177) was synthesized by following the procedure used to make Compound (105) (Scheme 51). 1H NMR (300 MHz, DMSO-d6): δ 10.87 (brs, 1H), 7.48-7.53 (dd, 1H), 7.04-7.07 (m, 2H), 6.75-6.82 (m, 1H), 3.75-3.96 (m, 2H), 3.17-3.24 (q, 2H), 2.67-2.69 (d, 2H), 2.23-2.30 (m, 1H), 1.94-2.02 (m, 2H), 1.01-1.84 (m, 10H), 0.86-0.88 (d, 3H), 0.76-0.78 (d, 3H). LC-MS: (M+H)+=415.2; HPLC purity=99.75%.

Example 178

1-[3-(6-fluoro-1H-indol-3-yl)-4-methylpentanoyl]decahydroquinoline-4-carboxylic acid (peak-2) (178)

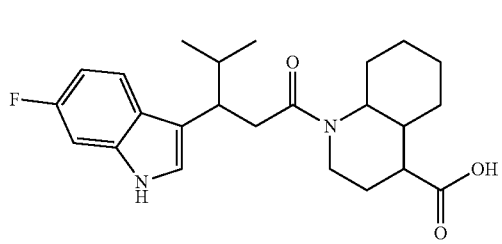

(178)

Synthesis of Compound (178)

Compound (178) was synthesized by following the procedure used to make Compound (105) (Scheme 51). 1H NMR (300 MHz, CDCl3): δ 8.81 (brs, 0.5H), 8.45 (brs, 0.5H), 7.43-7.47 (dd, 1H), 6.84-6.90 (m, 1H), 6.79 (brs, 1H), 6.70-6.76 (m, 1H), 4.35-4.50 (m, 1H), 3.45-3.53 (m, 1H), 3.02-3.15 (m, 2H), 2.63-2.77 (m, 2H), 2.00-2.10 (m, 1H), 1.75-1.95 (m, 2H), 1.23-1.65 (m, 10H), 0.94-0.96 (d, 3H), 0.78-0.80 (d, 3H). LC-MS: (M+H)+=415.2; HPLC purity=88.97%.

Example 179

1-[3-(4-fluoro-1H-Indol-3-yl)-4-methylpentanoyl]decahydroquinoline-4-carboxylic acid (179)

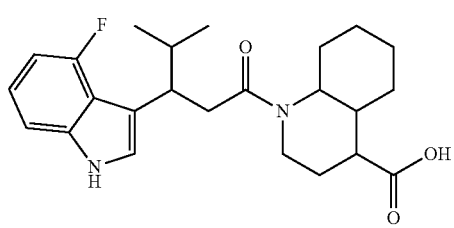

(179)

Synthesis of Compound (179)

Compound (179) was synthesized by following the procedure used to make Compound (105) (Scheme 51). 1H NMR (300 MHz, CDCl3): δ 8.44 (brs, 0.5H), 8.37 (brs, 1H), 6.88-7.05 (m, 3H), 6.62-6.70 (m, 1H), 4.37-4.50 (m, 1H), 3.61 (t, 1H), 3.51-3.58 (m, 1H), 3.10-3.20 (m, 1H), 2.60-2.80 (m, 2H), 2.34-2.45 (m, 1H), 1.99-2.04 (m, 1H), 1.79-1.87 (m, 1H), 1.15-1.80 (m, 10H), 0.93-0.95 (d, 3H), 0.70-0.72 (d, 3H). LC-MS: (M+H)+=415.3; HPLC purity=96.54%.

Example 180

1-[4-methyl-3-(4-methyl-1H-pyrrolo[2,3-b]pyridin-3-yl)pentanoyl]decahydroquinoline-4-carboxylic acid (180)

(180)

Synthesis of Compound (180)

Compound (180) was synthesized by following the procedure used to make Compound (105) (Scheme 51). 1H NMR (300 MHz, CDCl3): δ 11.71 (brs, 0.5H), 11.32 (brs, 0.5H), 7.88-8.01 (m, 1H), 7.07 (s, 1H), 6.81-6.84 (m, 1H), 3.92-3.94 (m, 1H), 3.73-3.75 (m, 1H), 3.45-3.50 (m, 1H), 2.86 (s, 2H), 2.84 (s, 1H), 2.45-2.70 (m, 4H), 1.95-2.10 (m, 2H), 1.12-1.75 (m, 10H), 0.95-1.05 (m, 6H). LC-MS: (M+H)+=412.3; HPLC purity=97.39%.

Example 181

1-[3-(1H-benzotriazol-1-yl)-3-phenylpropanoyl]decahydroquinoline-4-carboxylic acid (peak-1) (181)

(181)

Synthesis of Compound (181)

Compound (181) was synthesized by following the procedure used to make Compound (105) (Scheme 51). 1H NMR (300 MHz, DMSO-d6): δ 7.67-7.73 (m, 3H), 7.45-7.50 (m, 1H), 7.37-7.42 (m, 4H), 7.21-7.28 (dd, 1H), 7.08-7.13 (d, 1H), 4.55-4.65 (m, 1H), 4.25-4.41 (m, 1H), 4.00-4.13 (m, 1H)<3.02-3.09 (m, 1H), 3.02-3.09 (m, 1H), 2.72-2.79 (m, 1H), 2.27-2.32 (m, 1H), 1.30-2.15 (m, 10H). LC-MS: (M+H)+=433.2; HPLC purity=98.45%.

Example 182

1-[3-(1H-benzotriazol-1-yl)-3-phenylpropanoyl]
decahydroquinoline-4-carboxylic acid (Peak-2)
(182)

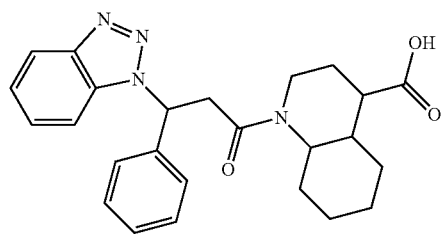

Synthesis of Compound (182)

Compound (182) was synthesized by following the procedure used to make Compound (105) (Scheme 51). 1H NMR (300 MHz, DMSO-d6): 12.36 (brs, 1H), 7.69-7.71 (d, 2H), 7.36-7.48 (m, 7H), 7.19-7.24 (d, 1H), 4.26-4.30 (m, 1H), 4.11-4.15 (m, 1H), 3.52-3.59 (m, 2H), 2.39-2.45 (m, 2H), 2.25-2.28 (m, 1H), 1.35-2.16 (m, 10H). LC-MS: (M+H)+=433.2; HPLC purity=97.16%.

Example 183

1-[4-methyl-3-(4-methyl-1H-benzotriazol-1-yl)pentanoyl]decahydroquinoline-4-carboxylic acid (183)

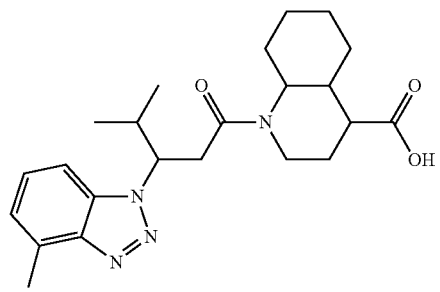

Synthesis of Compound (183)

Compound (183) was synthesized by following the procedure used to make Compound (105) (Scheme 51). 1H NMR (300 MHz, CDCl3): δ 7.38-7.41 (d, 1H), 7.25-7.30 (t, 1H), 7.00-7.03 (d, 1H), 5.02-5.05 (m, 1H), 3.95-4.10 (m, 1H), 3.46-3.68 (m, 2H), 2.84-2.90 (m, 1H), 2.75 (s, 3H), 2.21-2.39 (m, 4H), 1.25-1.95 (m, 10H), 0.96-0.98 (d, 3H), 0.75-0.77 (d, 3H). LC-MS: (M+H)+=413.2; HPLC purity=95.52%.

Example 184

1-[3-(4-chloro-1H-indol-3-yl)-3-(thiophen-2-yl)propanoyl]decahydroquinoline-4-carboxylic acid (184)

(184)

Synthesis of Compound (184)

Compound (184) was synthesized by following the procedure used to make Compound (105) (Scheme 51). 1H NMR (300 MHz, CDCl3): δ 8.36 (br s, 1H), 7.16-7.21 (m, 2H), 7.11-7.14 (d, 1H), 7.06-7.09 (m, 1H), 6.95-6.97 (m, 1H), 6.83-6.78 (m, 2H), 5.58-5.64 (m, 1H), 4.40-4.60 (m, 1H), 3.60-3.65 (m, 1H), 3.34-3.42 (M, 1H), 2.99-3.19 (m, 1H), 2.43-2.71 (m, 1H), 2.12-2.15 (m, 1H), 1.23-1.84 (m, 11H). LC-MS: (M+H)+=471.2; HPLC purity=98.02%.

Example 185

1-[3-(6-chloro-1H-indol-3-yl)-4-methylpentanoyl]
decahydroquinoline-4-carboxylic acid (185)

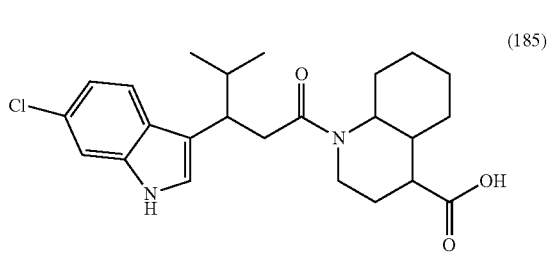 [SMILES: CC(C)C(CC(=O)N1CCC(C(=O)O)C2CCCCC21)c1c[nH]c2cc(Cl)ccc12]

Synthesis of Compound (185)

Compound (185) was synthesized by following the procedure used to make Compound (105) (Scheme 51). 1H NMR (300 MHz, DMSO-d6): δ 10.94 (br s, 1H), 7.52-7.55 (d, 1H), 7.33 (s, 1H), 7.13 (s, 1H), 6.93-6.96 (d, 1H), 3.78-3.97 (m, 1H), 3.34-3.41 (m, 1H), 3.16-3.22 (m, 2H), 2.68-2.70 (m, 2H), 2.29-2.33 (m, 1H), 1.06-2.02 (m, 12H), 0.86-0.88 (d, 3H), 0.75-0.77 (d, 3H). LC-MS: (M+H)+=431.3; HPLC purity=96.39%.

Example 186

1-[3-(4-fluoro-1H-indol-3-yl)-3-phenylpropanoyl]decahydroquinoline-6-carboxylic acid (186)

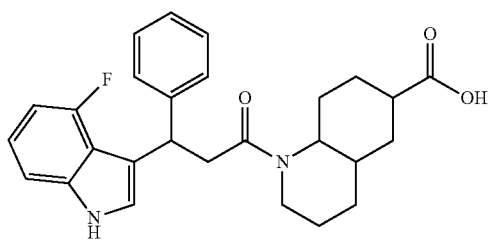

(186)

Synthesis of Compound (186)

Compound (186) was synthesized by following the procedure used to make Compound (105) (Scheme 51). 1H NMR (300 MHz, DMSO-d6): 12.07 (br s, 1H), 11.18 (brs, 1H), 7.33-7.38 (m, 1H), 7.18-7.29 (m, 4H), 7.08-7.15 (m, 2H), 6.93-7.00 (m, 1H), 6.55-6.64 (m, 1H), 4.78-4.85 (m, 1H), 4.18-4.35 (m, 1H), 3.74-4.00 (m, 1H), 2.93-3.19 (m, 2H), 2.20-2.25 (m, 2H), 1.25-1.82 (m, 11H). LC-MS: (M+H)+=449.3; HPLC purity=98.98%.

Example 187

1-[3-(4-chloro-1H-indol-3-yl)pentanoyl]decahydroquinoline-4-carboxylic acid (187)

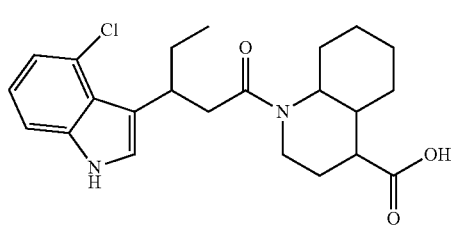

(187)

Synthesis of Compound (187)

Compound (187) was synthesized by following the procedure used to make Compound (105) (Scheme 51). 1H NMR (300 MHz, CDCl3): δ 8.31 (brs 1H), 7.16-7.18 (m, 1H), 6.97-7.01 (m, 3H), 3.65-3.87 (m, 2H), 3.39-3.53 (m, 1H), 2.44-2.73 (m, 4H0, 1.23-1.85 (m, 13H), 0.81-0.86 (t, 3H). LC-MS: (M+H)+=417.2; HPLC purity=90.53%.

Example 188

1-[3-(4-fluoro-1H-indol-3-yl)-3-phenylpropanoyl]decahydroquinoline-5-carboxylic acid (188)

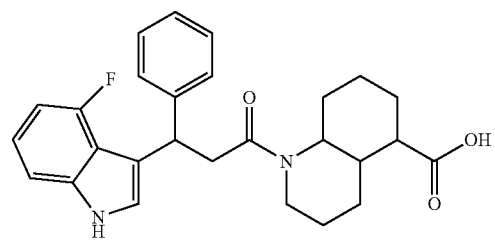

(188)

Synthesis of Compound (188)

Compound (188) was synthesized by following the procedure used to make Compound (105) (Scheme 51). 1H NMR (300 MHz, DMSO-d6): 12.26 (br s, 1H), 11.18 (br s, 1H), 7.32-7.35 (m, 1H), 7.09-7.27 (m, 6H), 6.93-7.00 (m, 1H), 6.58-6.64 (m, 1H), 4.79-4.86 (m, 1H), 4.04-4.41 (m, 1H), 3.93-4.05 (m, 1H), 3.75-3.79 (m, 1H), 2.95-3.17 (m, 2H), 2.71-2.75 (m, 1H), 1.25-1.89 (m, 11H). LC-MS: (M+H)+=449.2; HPLC purity=94.73%.

Example 189

(1-[3-(4-cyclopropyl-1H-indol-3-yl)butanoyl]decahydroquinolin-4-yl)acetic acid (189)

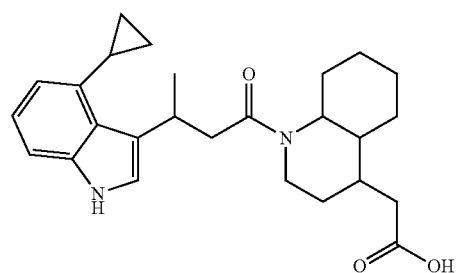

(189)

Synthesis of Compound (189)

Compound (189) was synthesized by following the procedure used to make Compound (105) (Scheme 51). 1H NMR (300 MHz, CDCl3): δ 7.99 (br s, 1H), 7.09-7.12 (d, 1H), 6.97-7.01 (m, 2H), 6.66-6.68 (d, 1H), 4.45-4.53 (m, 0.5H), 4.10-4.15 (m, 1H), 3.50-3.64 (m, 1H), 3.05-3.07 (m, 0.5H), 2.67-2.83 (m, 2H), 2.19-2.50 (m, 4H), 1.40-1.96 (m, 12H), 1.36-1.38 (d, 3H), 0.89-0.93 (m, 2H), 0.82-0.85 (m, 2H). LC-MS: (M+H)+=423.2; HPLC purity=95.52%.

Example 190

1-[3-(4-cyclopropyl-1H-Indol-3-yl)butanoyl]decahydroquinoline-5-carboxylic acid (190)

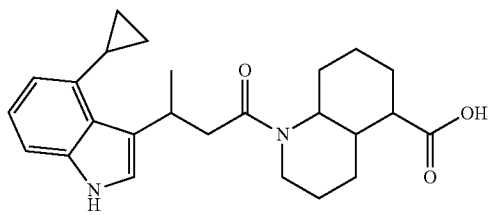
(190)

Synthetic Scheme-56

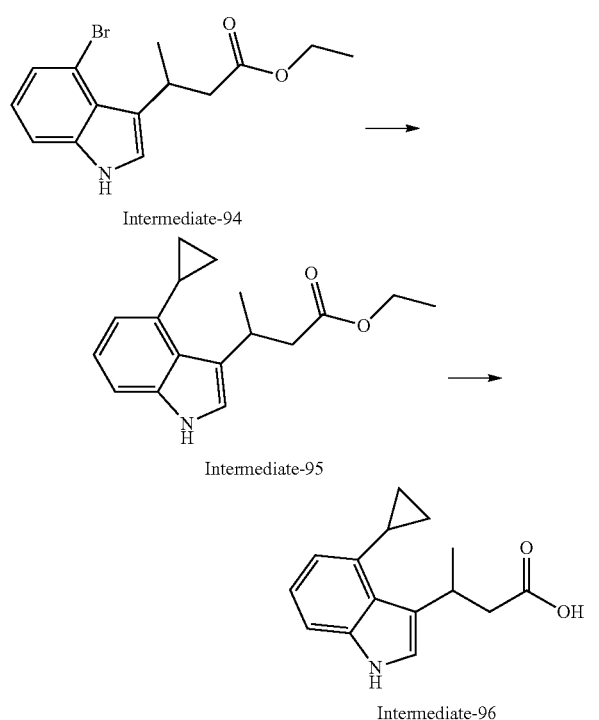

Synthesis of ethyl 3-(4-bromo-1H-indol-3-yl)butanoate (intermediate-94)

Intermediate-94 was synthesized by following the procedure used to make Intermediate-2 (Scheme-1).

Synthesis of ethyl 3-(4-cyclopropyl-1H-indol-3-yl)butanoate (intermediate-95)

A 250 mL RB flask fitted with magnetic stirrer was charged with Intermediate-94 (15.95 g, 51.47 mmol), cyclopropylboronic acid (8.8 g, 102.9 mmol), cesium carbonate (33.45 g, 102.9 mmol), in a mixture of dioxane and water (100 mL: 20 ML). Then purged with $N_2$ gas and added $PdCl_2(dppf)$ (4.2 g, 5.1 mmol). Resulting solution was stirred at 100° C. for 13 h. After completion of the reaction (reaction monitored by TLC), reaction solution was filtered through celite. Filtrate diluted with water and extracted with EtOAc and concentrated to give crude material, which is purified by silica gel column chromatography eluting with Petroleum ether (60-80) and ethyl acetate as eluent. The product (intermediate-95) was obtained as a brown liquid (12.5 g).

Synthesis of 3-(4-cyclopropyl-1H-indol-3-yl)butanoic acid (intermediate-96)

Intermediate-96 was synthesized by following the procedure used to make Intermediate-3 (Scheme-1).

Synthetic Scheme-57

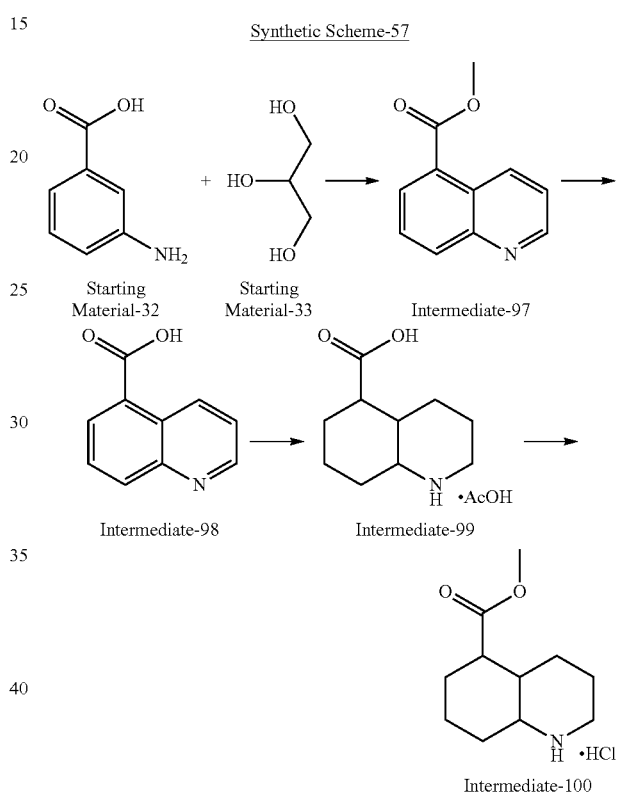

Synthesis of methyl quinoline-5-carboxylate (intermediate-97)

A 500 mL RB flask fitted with magnetic stirrer was charged with Starting Material-32 (60 g, 435 mmol), Starting material-33 (168 g, 1824 mmol), 3-nitrobenzoic acid (30 g, 179 mmol) in 90 mL of conc.$H_2SO_4$. Then reaction mixture was heated at 150° C. for 7 h. After reaction cooled to RT and added MeOH (600 mL) and refluxed for 12 hours. Then cooled to 0° C. quenched with ice and concentrated. Crude reaction mixture was basified with $NaHCO_3$, extracted with DCM and concentrated. Resulted crude material was purified by silica gel column chromatography eluting with Petroleum ether (60-80), ethyl acetate and 0.5% of triethylamine as eluent. The product (intermediate-97) was obtained as a brown liquid (21 g).

Synthesis of quinoline-5-carboxylic acid (intermediate-98)

To a stirred solution of Intermediate-97 (21 g, 112 mmol) in a mixture of THF: MeOH (25 mL: 200 mL) was added LiOH (10.75 g, 448 mmol) in water (25 mL) at 0 qC. Resulted reaction mixture was stirred at room temperature for 3 hours. After reaction (monitored by TLC), it was concentrated and acidified (PH=5) with 1N. HCl. Resisted precipitate was filtered and dried to give product Intermediate-98 (19 g).

Synthesis of decahydroquinoline-5-carboxylic acid (intermediate-99)

Intermediate-99 was synthesized by following the procedure used to make Intermediate-18 (Scheme-13).

Synthesis of methyl decahydroquinoline-5-carboxylate (intermediate-100)

A 250 mL RB flask fitted with magnetic stirrer was charged with Intermediate-99 (5.4 g, 29.5 mmol) in 50 mL MeOH. To this thionylchloride (10 mL) was slowly added at 0° C. Resulted reaction mixture was stirred at room temperature for 12 hours. After reaction (Monitered by LC-MS), it was concentrated followed by azetroped with with tolune to give product Intermediate-100 as white solid (4.4 g).

Synthesis of Compound (190)

Compound (190) was synthesized by following the procedure used to make Compound (105) (Scheme 51). 1H NMR (300 MHz, CDCl3): δ 7.94 (br s, 1H), 7.10-7.12 (m, 1H), 6.96-7.00 (m, 2H), 6.65-6.69 (m, 1H), 4.68-4.70 (m, 0.5H), 4.44-4.48 (m, 0.5H), 4.14-4.17 (m, 1H), 3.57-3.63 (m, 1H), 2.70-2.94 (m, 2H), 2.41-2.55 (m, 3H), 2.12-2.15 (m, 1H), 1.44-1.77 (m, 8H), 1.35-1.37 (d, 3H), 1.30-1.35 (m, 2H), 0.91-0.93 (m, 2H), 0.77-0.80 (m, 2H). LC-MS: (M+H)+=409.2; HPLC purity=97.56%.

Example 191

1-[3-(4-cyclopropyl-1H-Indol-3-yl)butanoyl]decahydroquinoline-6-carboxylic acid (191)

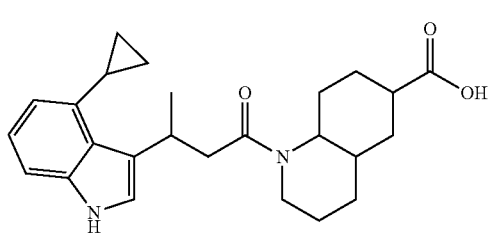
(191)

Synthesis of Compound (191)

Compound (191) was synthesized by following the procedure used to make Compound (105) (Scheme 51). 1H NMR (300 MHz, DMSO-d6): δ 12.11 (br s, 1H), 10.80 (br s, 1H), 7.16-7.19 (m, 1H), 7.12-7.14 (d, 1H), 6.88-6.93 (t, 1H), 6.55-6.58 (d, 1H), 4.05-4.10 (m, 1H), 3.70-3.73 (m, 1H), 2.90-3.01 (m, 1H), 2.61-2.70 (m, 2H), 2.30-2.39 (m, 2H), 2.25-2.28 (m, 1H), 1.31-2.06 (m, 11H), 1.27-1.29 (d, 3H), 0.89-0.91 (m, 2H), 0.72-0.73 (m, 2H). LC-MS: (M+H)+=409.2; HPLC purity=93.25%.

Example 192

1-{3-[4-(thiophen-2-yl)-1H-indol-3-yl]butanoyl}decahydroquinoline-5-carboxylic acid (192)

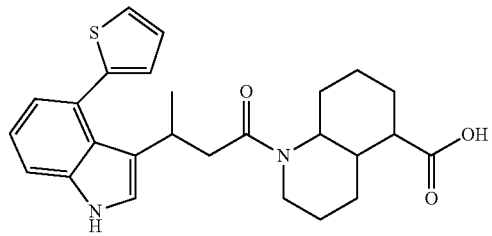
(192)

Synthesis of Compound (192)

Compound (192) was synthesized by following the procedure used to make Compound (105) (Scheme 51). 1H NMR (300 MHz, CDCl3): δ 8.30 (br s, 1H), 7.37-7.40 (d, 1H), 7.29-7.32 (m, 1H), 7.18-7.20 (d, 1H), 7.08-7.15 (m, 4H), 3.22-3.46 (m, 2H), 2.71-2.93 (m, 1H), 2.39-2.57 (m, 2H), 2.10-2.25 (m, 2H), 1.42-1.94 (m, 11H), 0.85-0.88 (d, 3H). LC-MS: (M+H)+=451.1; HPLC purity=99.67%.

Example 193

1-[3-(4-chloro-1H-indol-3-yl)butanoyl]decahydroquinoline-5-carboxylic acid (HS_A_643) (193)

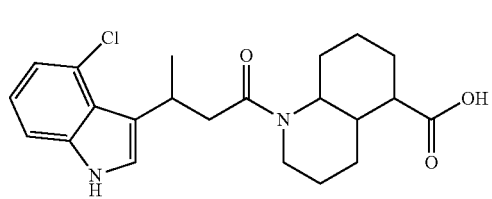
(193)

Synthesis of Compound (193)

Compound (193) was synthesized by following the procedure used to make Compound (105) (Scheme 51). 1H NMR (300 MHz, DMSO-d6): δ 12.15 (br s, 1H), 11.18 (brs, 1H), 7.28-7.31 (m, 2H), 7.01-6.98 (m, 2H), 4.47-4.49 (m, 0.5H), 4.29-4.33 (m, 0.5H), 3.72-3.95 (m, 2H), 2.62-3.02 (m, 4H), 1.30-1.94 (m, 11H), 1.25-1.27 (d, 3H). LC-MS: (M+H)+=403.1; HPLC purity=98.12%.

Example 194

1-[3-(4-cyclopropyl-1H-indol-3-yl)butanoyl]decahydroquinoline-4-carboxylic acid (194)

(194)

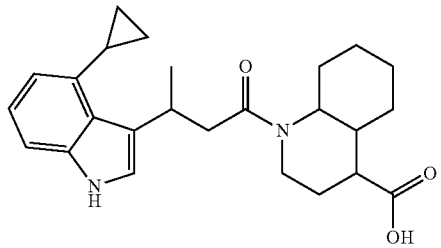

Synthesis of Compound (194)

Compound (194) was synthesized by following the procedure used to make Compound (105) (Scheme 51). 1H NMR (300 MHz, CDCl3): δ 7.95 (br s, 1H), 7.10-7.13 (d, 1H), 6.96-7.02 (m, 2H), 6.66-6.68 (d, 1H), 4.17-4.20 (m, 2H), 3.46-3.49 (m, 1H), 2.80-2.88 (m, 1H), 2.53-2.60 (m, 2H), 2.41-2.48 (m, 2H), 1.45-1.98 (m, 11H), 1.36-1.38 (d, 3H), 0.92-0.95 (m, 2H), 0.74-0.81 (m, 2H). LC-MS: (M+H)+=409.2; HPLC purity=92.83%.

Example 195

1-[3-(4-cyclopropyl-1H-indol-3-yl)butanoyl]decahydroquinoline-5-carboxylic acid (peak-1) (195)

(195)

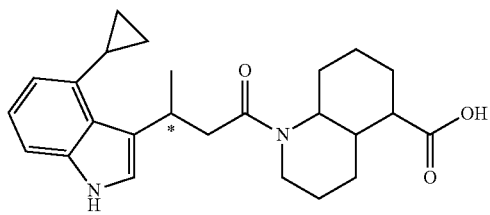

Synthetic Scheme-58

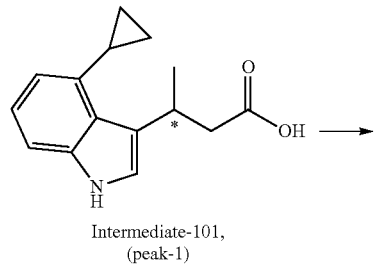

Intermediate-101,
(peak-1)

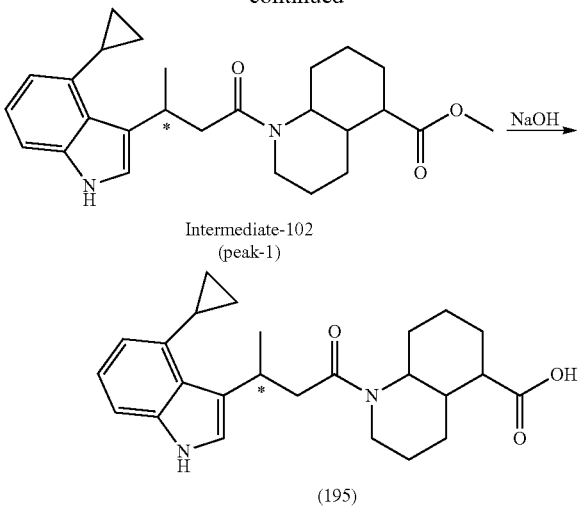

Synthesis of 3-(4-cyclopropyl-1H-indol-3-yl)butanoic acid (intermediate-101, Peak-1)

Intermediate-101, peak-1 was synthesized by following the procedure used to make Intermediate-90, peak-1 (Scheme-54). 1H NMR (300 MHz, DMSO-d6): δ 12.01 (br s, 1H), 10.83 (br s, 1H), 7.12-7.15 (m, 2H) m 6.89-6.94 (t, 1H), 6.58-6.61 (d, 1H), 3.99-4.03 (m, 1H), 2.71-2.78 (dd, 1H), 2.34-2.42 (m, 2H), 1.30-1.32 (d, 3H), 0.92-0.94 (m, 2H), 0.72-0.74 (m, 2H). LC-MS: (M+H)+=244.1; HPLC purity=96.90%; Chiral RT=7.91 min [chiral pak IA, mobile phase hexane:i-PrOH:DCM (8.5:1.0:0.5)]; $[\alpha]_D^{23}$=+10.62° (c 0.032, MeOH).

Synthesis of methyl 1-[3-(4-cyclopropyl-1H-indol-3-yl)butanoyl]decahydroquinoline-5-carboxylate (intermediate-102, Peak-1)

Intermediate-102, peak-1 was synthesized by following the procedure used to make Compound-1 (Scheme-2).

Synthesis of Compound (195)

Compound (195) was synthesized by following the procedure used to make Compound (105) (Scheme 51). 1H NMR (300 MHz, CDCl3): δ 8.04 (br s, 1H), 7.08-7.11 (d, 1H), 6.95-6.98 (m, 2H), 6.68 (s, 1H), 4.44-4.68 (m, 1H), 4.16 (br s, 1H), 3.39-3.59 (m, 1H), 2.66-2.93 (m, 2H), 2.14-2.51 (m, 3H), 1.38-1.85 (m, 11H), 1.30-0.132 (d, 3H), 0.91-0.93 (m, 2H), 0.70-0.72 (m, 2H). LC-MS: (M+H)+=409.2; HPLC purity=96.52%.

Example 196

1-[3-(4-cyclopropyl-1H-indol-3-yl)butanoyl]decahydroquinoline-5-carboxylic acid (196)

(196)

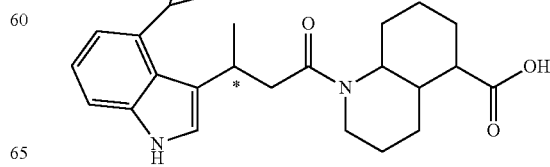

Synthetic Scheme-59

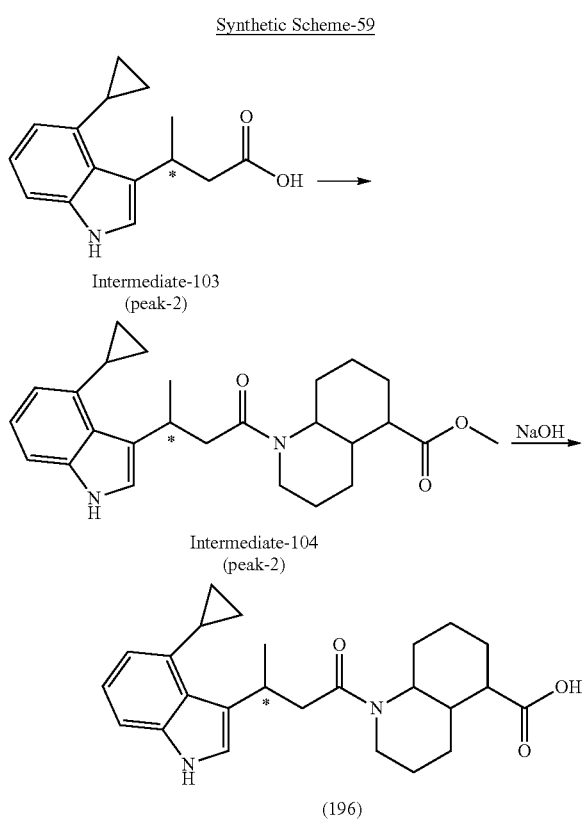

Synthesis of 3-(4-cyclopropyl-1H-indol-3-yl)butanoic acid (intermediate-103, Peak-2)

Intermediate-103, peak-2 was synthesized by following the procedure used to make Intermediate-90, peak-1 (Scheme-54). 1H NMR (300 MHz, DMSO-d6): δ 12.01 (br s, 1H), 10.83 (br s, 1H), 7.12-7.15 (m, 2H) m 6.89-6.94 (t, 1H), 6.58-6.61 (d, 1H), 3.99-4.03 (m, 1H), 2.71-2.78 (dd, 1H), 2.34-2.42 (m, 2H), 1.30-1.32 (d, 3H), 0.92-0.94 (m, 2H), 0.72-0.74 (m, 2H). LC-MS: (M+H)+=244.1; HPLC purity=89.91%; Chiral RT=9.15 min [chiral pak IA, mobile phase hexane:i-PrOH:DCM (8.5:1.0:0.5)]; $[\alpha]_D^{23}$=–6.04° (c 0.033, MeOH)

Synthesis of methyl 1-[3-(4-cyclopropyl-1H-indol-3-yl)butanoyl]decahydroquinoline-5-carboxylate (intermediate-104, Peak-2)

Intermediate-104, peak-2 was synthesized by following the procedure used to make Compound-1 (Scheme-2).

Synthesis of Compound (196)

Compound (196) was synthesized by following the procedure used to make Compound (105) (Scheme 51). 1H NMR (300 MHz, CDCl3): δ 8.08 (br s, 1H), 7.08-7.10 (d, 1H), 6.94-7.00 (m, 2H), 6.65-6.67 (m, 1H), 4.44-4.68 (m, 1H), 4.15 (br s, 1H), 3.38-3.64 (m, 1H), 2.71-2.92 (m, 2H), 2.13-2.54 (m, 3H), 1.45-1.78 (m, 11H), 1.40-1.43 (d, 3H), 0.90-0.93 (m, 2H), 0.74-0.77 (m, 2H). LC-MS: (M+H)+=409.2; HPLC purity=96.11%.

Example 197

1-[3-(4-cyano-1H-indol-3-yl)butanoyl]decahydroquinoline-5-carboxylic acid (197)

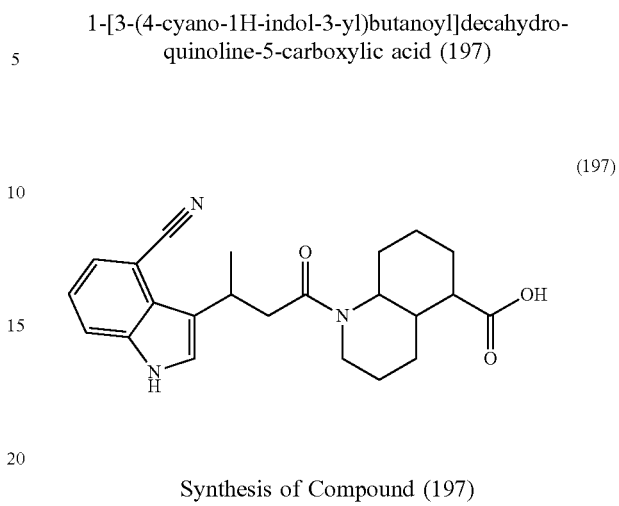

(197)

Synthesis of Compound (197)

Compound (197) was synthesized by following the procedure used to make Compound (105) (Scheme 51). 1H NMR (300 MHz, DMSO-d6): δ 12.13 (br s, 1H), 11.48 (br s, 1H), 7.67-7.70 (d, 1H), 7.46-7.48 (m, 2H), 7.17-7.22 (t, 1H), 4.45-4.49 (m, 0.5H), 4.25-4.30 (0.5H), 3.74-3.85 (m, 3H), 2.91-3.00 (m, 1H), 2.69-2.86 (m, 2H), 1.30-1.98 (m, 14H). LC-MS: (M+H)+=394.2; HPLC purity=99.0%.

Example 198

1-[3-(4-cyclopropyl-1H-indol-3-yl)butanoyl]decahydroquinoline-5-carboxylic acid (HS_A_648, peak-1a) (198)

(198)

Synthesis of Compound (198)

Mixture of isomers 195 was separated by using chiral column chromatography to give Compound 198. 1H NMR (300 MHz, CDCl3): δ 7.92 (br s, 1H), 7.10-7.13 (d, 1H), 6.97-7.02 (m, 2H), 6.67-6.69 (m, 1H), 4.67-4.72 (m, 0.5H), 4.45-4.48 (m, 0.5H), 4.16-4.18 (m, 1H), 3.00-3.62 (m, 1H), 2.69-2.96 (m, 2H), 2.37-2.48 (m, 2H), 2.13-2.24 (m, 1H), 1.37-1.92 (m, 11H), 1.33-1.35 (d, 3H), 0.92-0.95 (m, 2H), 0.83-0.88 (M, 2H). LC-MS: (M+H)+=409.2; HPLC purity=99.39%; Chiral RT=12.44 min [Column: Chiral Pak IC; mobile phase: hexane: IPA:DCM (8:1:1)].

Example 199

1-[3-(4-cyclopropyl-1H-indol-3-yl)butanoyl]decahydroquinoline-5-carboxylic acid (peak-1 b) (199)

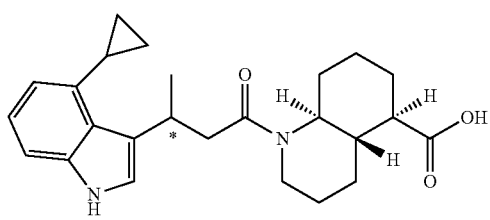

(199)

Synthesis of Compound (199)

Mixture of isomers 195 was separated by using chiral column chromatography to give Compound 199. 1H NMR (300 MHz, DMSO-d6): δ 12.11 (br s, 1H), 10.80 (br s, 1H), 7.12-7.18 (m, 2H), 6.88-6.93 (t, 1H), 6.55-6.58 (d, 1H), 4.49-4.52 (m, 0.5H), 4.31-4.35 (m, 0.5H), 3.91-4.04 (m, 2H), 3.70-3.74 (m, 1H), 2.86-2.98 (m, 1H), 2.67-2.74 (m, 2H), 2.37-2.39 (m, 1H), 1.47-2.00 (M, 11H), 1.27-1.30 (d, 3H), 0.85-0.91 (m, 2H), 0.68-0.74 (m, 2H). LC-MS: (M+H)+=409.2; HPLC purity=99.31%; Chiral RT=14.93 min [Column: Chiral Pak IC; mobile phase: hexane: IPA: DCM (8:1:1)]. [α]$_D^{24}$=+111.84° (c 0.001, MeOH).

Example 200

1-[3-(4-cyclopropyl-1H-Indol-3-yl)butanoyl]decahydroquinoline-5-carboxylic acid (peak-1c) (200)

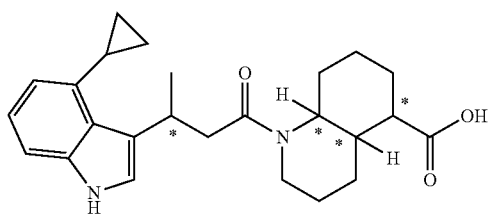

(200)

Synthesis of Compound (200)

Mixture of isomers 195 was separated by using chiral column chromatography to give Compound 200. 1H NMR (300 MHz, DMSO-d6): δ 12.23 (br s, 1H), 10.80 (br s, 1H), 7.11-7.16 (m, 2H), 6.88-6.93 (t, 1H), 6.55-6.57 (d, 1H), 4.54-4.56 (m, 0.5H), 4.30-4.34 (m, 0.5H), 3.89-4.06 (m, 2H), 3.70-3.73 (m, 1H), 2.92-3.00 (m, 1H), 2.66-2.72 (m, 2H), 2.26-2.29 (m, 1H), 1.35-1.98 (m, 11H), 1.28-1.31 (d, 3H), 0.87-0.91 (m, 2H), 0.70-0.74 (m, 2H). LC-MS: (M+H)+=409.2; HPLC purity=94.22%; Chiral RT=14.61 min [Column: Chiral Pak IC; mobile phase: hexane: IPA: DCM (8:1:1)].

Example 201

1-{3-[4-(propan-2-yloxy)-1H-indol-3-yl]butanoyl}decahydroquinoline-5-carboxylic acid (201)

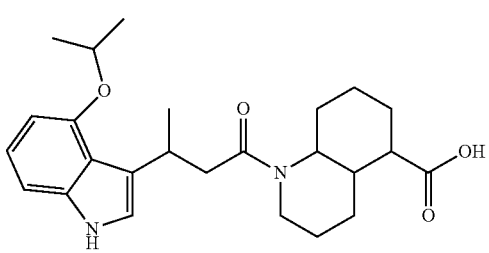

(201)

Synthesis of Compound (201)

Compound (201) was synthesized by following the procedure used to make Compound (105) (Scheme 51). 1H NMR (300 MHz, DMSO-d6): δ 12.0 (br s, 1H), 10.67 (br s, 1H), 6.83-6.92 (m, 3H), 6.40-6.43 (d, 1H), 4.69-4.72 (m, 1H), 4.53-4.55 (m, 0.5H), 4.06-4.09 (m, 0.5H), 3.58-3.75 (m, 3H), 2.63-2.98 (m, 2H), 2.18-2.22 (m, 1H), 1.45-1.98 (m, 11H), 1.27-1.31 (m, 9H). LC-MS: (M+H)+=427.2; HPLC purity=95.46%.

Example 202

1-{3-[4-(octahydroquinolin-1(2H)-yl)-4-oxobutan-2-yl]-1H-indol-4-yl}piperidine-4-carboxylic acid (202)

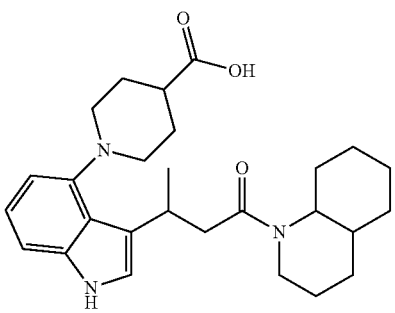

(202)

Synthetic Scheme-60

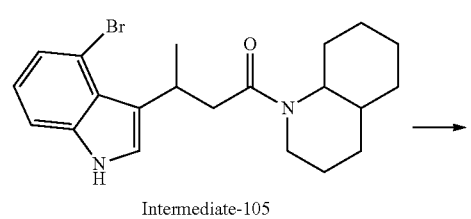

Intermediate-105

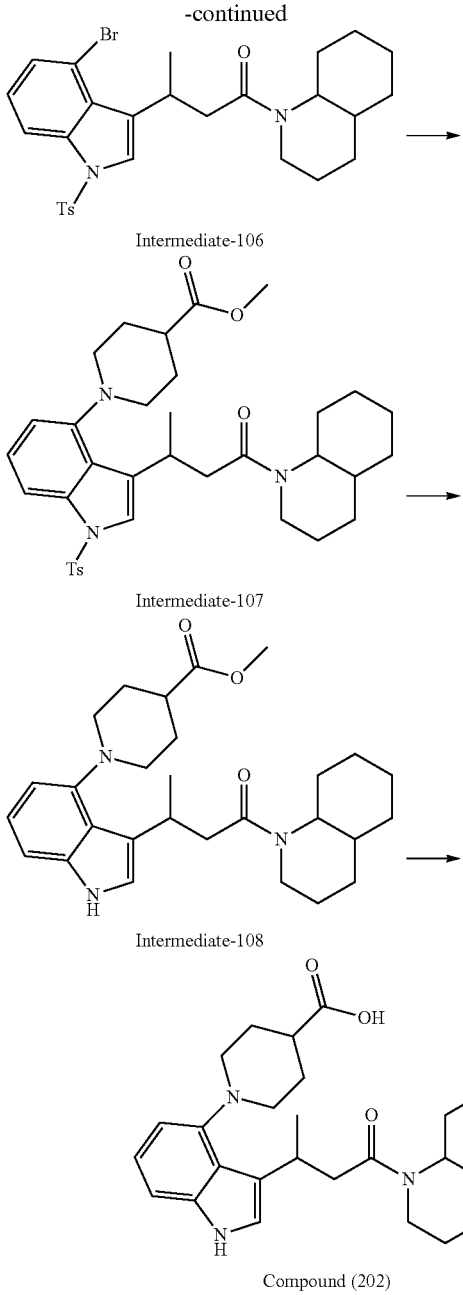

Intermediate-106

Intermediate-107

Intermediate-108

Compound (202)

Synthesis of Intermediate-105

Intermediate-105 was synthesized by following the procedure used to make Compound (1) (Scheme2).

Synthesis of Intermediate-106

To a stirred solution of Intermediates-105 (0.35 g, 1.09 mmol) in dry THF (4 mL), NaH (0.052 g, 2.1 mmol) was added at 0° C. and stirred for 10 minutes. To the stirred solution tosyl chloride (0.27 g, 1.4 mmol) was added and stirred for 30 minutes at room temperature. After completion of the reaction, the reaction mixture was quenched with H$_2$O, extracted with EtOAc to give crude material which was purified by using Silica-gel column chromatography eluting with mixture of hexanes: EtOAc to give Intermediate-106 (260 mg).

Synthesis of Intermediate-107

To a stirred solution of Intermediate-106 (0.26 g, 0.46 mmol) in dioxane (4 mL), methyl isonipecotate (0.10 mL, 0.69 mmol) and cesium carbonate (0.46 g, 1.39 mmol) were added. The resulted reaction mixture was purged with argon gas and Pd$_2$(dba)$_3$ (0.085 g, 0.009 mmol), BINAP (0.015 g, 0.023 mmol) were added, then heated at 90° C. for 12 hours. After completion of the reaction, the reaction mixture was filtered through celite and concentrated to give crude material which was purified by using Silica-gel column chromatography eluting with mixture of hexanes: EtOAc to give Intermediate-107 (150 mg).

Synthesis of Intermediate-108

To a stirred solution of magnesium (0.3 g, 12.3 mmol) in MeOH (18 mL), Intermediate-107 (0.15 g, 0.29 mol) and ammonium chloride (0.12 g, 2.1 mmol) were added, and stirred for 2 hours at room temperature. After completion of the reaction, the reaction mixture was quenched with saturated NH$_4$Cl solution, extracted with EtOAc and concentrated to give crude material which was purified by using Silica-gel column chromatography eluting with mixture of hexanes: EtOAc to give Intermediate-108 (50 mg).

Synthesis of Compound (202)

To a stirred solution of Intermediate-108 (0.05 g, 0.10 mmol) in THF: MeOH (2 mL, 1:1), aqueous NaOH (0.021 g, 0.53 mmol) was added and stirred at room temperature for 8 hours. After completion of the reaction, the reaction mixture was concentrated to give crude product, which was taken in H$_2$O, acidified with 10% aqueous KHSO$_4$ (PH=5), extracted with EtOAc, concentrated, and purified by using Silica-gel column chromatography eluting with mixture of hexanes: EtOAc to give Compound-202 (10 mg) as brown solid. 1H NMR (300 MHz, CDCl3): δ 7.95 (br s, 1H), 7.03-7.06 (m, 2H), 6.91-6.94 (m, 1H), 6.72-6.75 (m, 1H), 4.46-4.61 (m, 1H), 3.80-3.84 (m, 0.5H), 3.58-3.60 (m, 0.5H), 3.29-3.31 (m, 1H), 3.15-3.18 (m, 1H), 2.85-2.92 (m, 2H), 2.45-2.48 (m, 3H), 2.10-2.15 (m, 2H), 1.30-1.94 (m, 20H). LC-MS: (M+H)+=452.2; HPLC purity=96.62%.

Example 203

1-[3-(4-chloro-5-methyl-1H-indol-3-yl)butanoyl] decahydroquinoline-5-carboxylic acid (203)

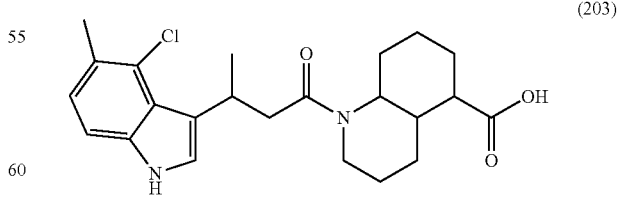

(203)

Synthesis of Compound (203)

Compound (203) was synthesized by following the procedure used to make Compound (105) (Scheme 51). 1H NMR (300 MHz, DMSO-d6): δ 11.10 (br s, 1H), 7.18-7.23 (m, 2H), 6.97-7.00 (d, 1H), 4.46-4.55 (m, 1H), 4.20-4.34 (m, 1H), 3.91-3.95 (m, 1H), 3.75-3.79 (m, 2H), 2.36 (s, 3H), 2.27-2.30 (m, 2H), 1.30-1.90 (m, 14H). LC-MS: (M+H)+=417.1; HPLC purity=99.11%.

Example 204

1-[3-(4-cyclopropyl-1-methyl-1H-indol-3-yl)bu-tanoyl]decahydroquinoline-5-carboxylic acid (204)

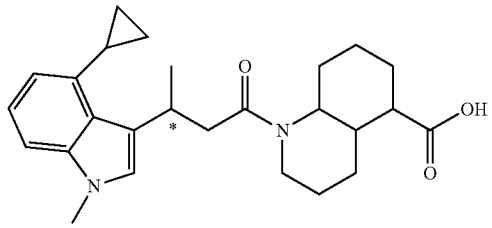

(204)

Synthetic Scheme-61

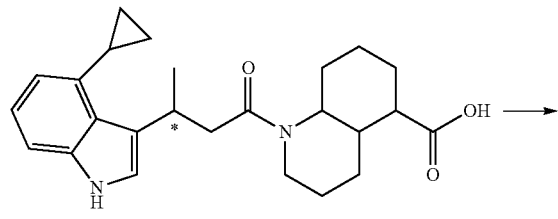

(195)

→

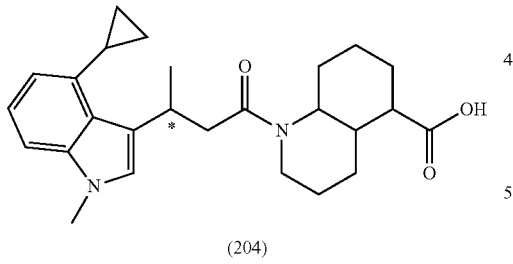

(204)

Synthesis of Compound (204)

Compound (204) was synthesized by following the procedure used to make Compound (27) (Scheme 26). 1H NMR (300 MHz, CDCl3): δ 7.10-7.12 (m, 2H), 6.88-6.91 (d, 1H), 6.72-6.75 (m, 1H), 4.77-4.82 (m, 0.5H), 4.54-4.58 (m, 0.5H), 4.23-4.25 (m, 1H), 3.72 (s, 3H), 3.68-3.70 (m, 1H), 2.74-2.92 (m, 1H), 2.54-2.62 (m, 1H), 2.46-2.49 (m, 2H), 2.20-2.23 (m, 1H), 1.30-1.90 (m, 14H0, 0.98-1.01 (m, 2H0, 0.83-0.86 (m, 2H). LC-MS: (M+H)+=423.2; HPLC purity=98.91%.

Example 205

1-[3-(4-cyclopropyl-1H-pyrrolo[2,3-b]pyridin-3-yl)butanoyl]decahydroquinoline-5-carboxylic acid (205)

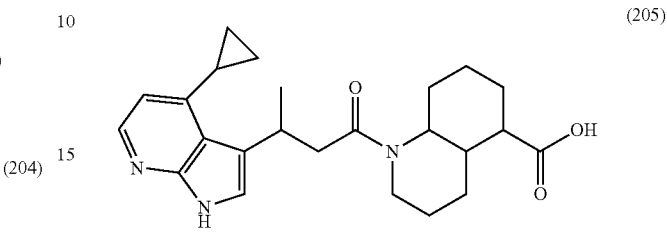

(205)

Synthesis of Compound (205)

Compound (205) was synthesized by following the procedure used to make Compound (105) (Scheme 51). 1H NMR (300 MHz, CDCl3): δ 11.01 (br s, 1H), 7.91-8.00 (m, 1H), 7.04 (s, 1H), 6.46-6.59 (m, 1H), 4.51-4.63 (m, 1H), 4.38-4.42 (m, 1H), 3.98-4.06 (m, 2H), 3.44-3.47 (0.5H), 3.15-3.19 (m, 0.5H), 2.84-2.95 (m, 1H), 2.37-2.54 (m, 2H), 1.55-1.85 (m, 6H), 1.45-1.47 (d, 3H), 1.30-1.40 (m, 5H), 0.94-0.97 (m, 2H0, 0.78-0.83 (m, 2H). LC-MS: (M+H)+=410.2; HPLC purity=98.14%.

Example 206

1-[3-(4-chloro-1H-indol-3-yl)-3-(thiophen-2-yl)propanoyl]decahydroquinoline-5-carboxylic acid (206)

(206)

Synthesis of Compound (206)

Compound (206) was synthesized by following the procedure used to make Compound (105) (Scheme 51). 1H NMR (300 MHz, DMSO-d6): δ 12.13 (br s, 1H), 11.31 (br s, 1H), 7.40-7.45 (m, 1H), 7.31-7.33 (d, 1H), 7.20-7.22 (m, 1H), 7.00-7.05 (t, 1H), 6.93-6.96 (d, 1H), 6.78-6.87 (m, 2H), 5.54-5.56 (m, 1H), 4.43-4.45 (m, 0.5H), 4.19-4.26 (m, 0.5H), 4.01-4.03 (M, 1H), 3.78-3.82 (m, 1H), 3.02-3.11 (m, 0.5H), 2.40-2.45 (m, 1H), 1.31-1.88 (m, 11H). LC-MS: (M+H)+=471.1; HPLC purity=97.94%.

Example 207

1-[3-(1,4-dimethyl-1H-indol-3-yl)butanoyl]decahydroquinoline-5-carboxylic acid (207)

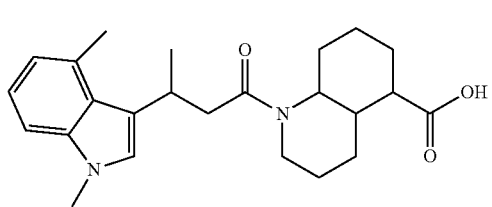

(207)

Synthesis of Compound (207)

Compound (207) was synthesized by following the procedure used to make Compound (27) (Scheme 26). 1H NMR (300 MHz, CDCl3): δ 7.05-7.12 (m, 2H), 6.80-6.89 (m, 2H), 4.73-4.77 (m, 0.5H), 4.52-4.56 (m, 0.5H), 3.91-3.95 (m, 1H), 3.71 (s, 3H), 3.60-3.63 (m, 1H), 2.86-3.06 (m, 1H), 2.72 (s, 3H), 2.41-2.57 (m, 2H), 2.21-2.24 (m, 1H), 1.49-1.90 (m, 11H), 1.39-1.41 (d, 3H). LC-MS: (M+H)+=397.2; HPLC purity=98.36%.

Example 208

1-{3-[1-methyl-4-(propan-2-yloxy)-1H-indol-3-yl]butanoyl}decahydroquinoline-5-carboxylic acid (208)

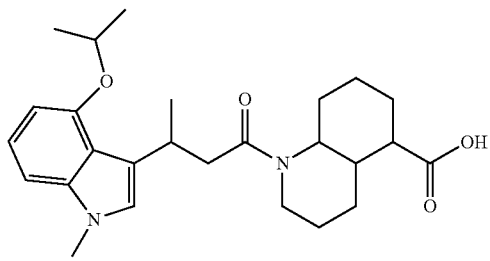

(208)

Synthesis of Compound (208)

Compound (208) was synthesized by following the procedure used to make Compound (27) (Scheme 26). 1H NMR (300 MHz, DMSO-d6: δ 12.01 (br s, 1H), 6.84-7.02 (m, 3H), 6.46-6.48 (m, 1H), 4.70-4.72 (m, 1H), 4.45-4.50 (m, 0.5H), 4.30-4.33 (m, 0.5H), 3.70-3.72 (m, 1H), 3.64 (s, 3H), 3.51-3.53 (m, 1H), 2.66-3.05 (m, 3H), 2.23-2.39 (m, 1H), 1.45-1.98 (m, 11H), 1.30-1.42 (m, 9H). LC-MS: (M+H)+=441.2; HPLC purity=99.01%.

Example 209

1-[3-(4-chloro-1-methyl-1H-indol-3-yl)butanoyl]decahydroquinoline-5-carboxylic acid (209)

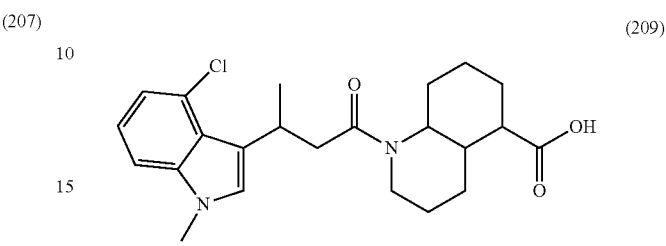

(209)

Synthesis of Compound (209)

Compound (209) was synthesized by following the procedure used to make Compound (27) (Scheme 26). 1H NMR (300 MHz, CDCl3): δ 7.09-7.11 (m, 1H), 6.97-7.05 (m, 2H), 6.85-6.91 (m, 1H), 4.664.68 (m, 0.5H), 4.47-4.49 (m, 0.5H), 3.66 (s, 3H), 2.69-3.05 (m, 2H), 2.36-2.57 (m, 1H), 2.16-2.24 (m, 1H), 1.45-1.90 (m, 11H0, 1.33-1.35 (d, 3H). LC-MS: (M+H)+=417.1; HPLC purity=98.82%.

Example 210

1-[3-(4-cyclopropyl-1-ethyl-1H-indol-3-yl)butanoyl]decahydroquinoline-5-carboxylic acid (210)

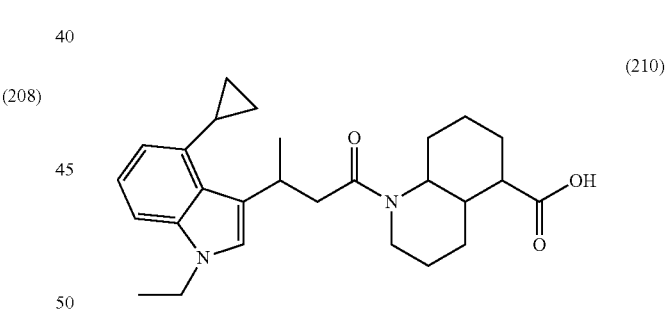

(210)

Synthesis of Compound (210)

Compound (210) was synthesized by following the procedure used to make Compound (27) (Scheme 26). 1H NMR (300 MHz, CDCl3): δ 6.98-7.09 (m, 2H0, 6.87-6.91 (m, 1H), 6.64-6.66 (d, 1H), 4.68-4.70 (m, 0.5H), 4.48-4.51 (m, 0.5H), 4.14-4.16 (m, 1H), 4.00-4.07 (q, 2H), 3.57-3.65 (m, 1H), 2.68-2.98 (m, 2H), 2.39-2.58 (m, 2H), 2.15-2.27 (m, 1H), 1.40-1.97 (m, 11H), 1.34-1.36 (d, 3H), 0.88-0.94 (m, 2H), 0.75-0.81 (m, 5H). LC-MS: (M+H)+=437.2; HPLC purity=98.31%.

Example 211

1-{3-[4-(propan-2-yl)-1H-indol-3-yl]butanoyl}decahydroquinoline-5-carboxylic acid (211)

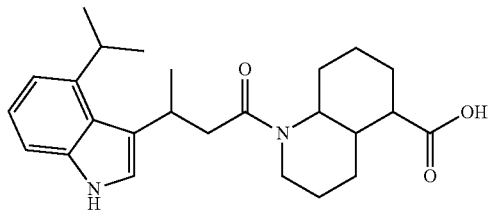

Synthesis of Compound (211)

Compound (211) was synthesized by following the procedure used to make Compound (105) (Scheme 51). 1H NMR (300 MHz, CDCl3): δ 7.99 (br s, 1H), 7.15-7.18 (m, 2H), 7.01-7.05 (m, 2H), 4.74-4.77 (m, 0.5H0, 4.53-4.56 (m, 0.5H0, 3.85-3.88 (m, 1H), 3.62-3-66 (m, 2H), 2.44-3.04 (m, 3H), 2.21-2.23 (m, 1H), 1.46-1.95 (m, 11H), 1.41-1.43 (d, 3H), 1.34-1.36 (d, 6H). LC-MS: (M+H)+=411.2; HPLC purity=93.44%.

Example 212

1-[3-(4-cyclopropyl-1-methyl-1H-indol-3-yl)butanoyl]decahydroquinoline-5-carboxylic acid (peak-1) (212)

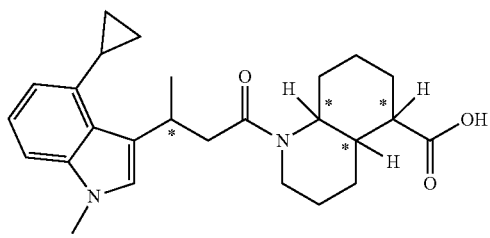

Synthesis of Compound (212)

Mixture of isomers of Compound (204) was separated by using chiral column chromatography to give compound 212. 1H NMR (300 MHz, CDCl3): δ 7.03-7.05 (m, 2H), 6.81 (s, 1H), 6.65-6.68 (m, 1H), 4.19-4.23 (m, 1H), 4.09-4.10 (m, 1H), 3.66 (s, 3H), 3.36-3.40 (m, 1H), 3.00-3.03 (m, 1H), 2.70-2.84 (m, 1H), 2.38-2.45 (m, 2H), 2.21-2.26 (m, 1H), 1.45-1.95 (m, 11H), 1.33-1.36 (d, 3H), 0.92-0.95 (m, 2H), 0.76-0.79 (m, 2H). LC-MS: (M+H)+=423.2; HPLC purity=99.14%; Chiral RT=19.99 min [Column: Chiral Pak IC; mobile phase: hexane: IPA:DCM (8.5:0.5:1.0)].

Example 213

1-[3-(4-cyclopropyl-1-methyl-1H-indol-3-yl)butanoyl]decahydroquinoline-5-carboxylic acid (peak-2) (213)

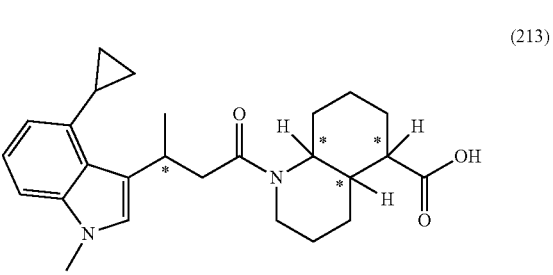 [SMILES: CC(CC(=O)N1CCCC2C(C(=O)O)CCCC21)c1cn(C)c2cccc(C3CC3)c12]

Synthesis of Compound (213)

Mixture of isomers of Compound (204) was separated by using chiral column chromatography to give compound 213. 1H NMR (300 MHz, CDCl3): δ 7.03-7.05 (m, 2H), 6.82-6.85 (d, 1H), 6.65-6.68 (m, 1H), 4.67-4.70 (m, 0.5H), 4.44-4.49 (m, 0.5H), 4.15-4.16 (m, 1H), 3.65 (s, 3H), 3.42-3.46 (m, 1H), 2.79-2.95 (m, 2H), 2.68-2.70 (m, 1H), 2.56-2.59 (m, 1H), 2.39-2.43 (m, 1H), 1.38-1.82 (m, 11H), 1.31-1.34 (d, 3H), 0.92-0.94 (m, 2H), 0.76-0.80 (m, 2H). LC-MS: (M+H)+=423.2; HPLC purity=94.30%; Chiral RT=27.35 min [Column: Chiral Pak IC; mobile phase: hexane: IPA:DCM (8.5:0.5:1.0)].

Example 214

1-[3-(4-cyclopropyl-1-methyl-1H-indol-3-yl)butanoyl]decahydroquinoline-5-carboxylic acid (peak-3) (214)

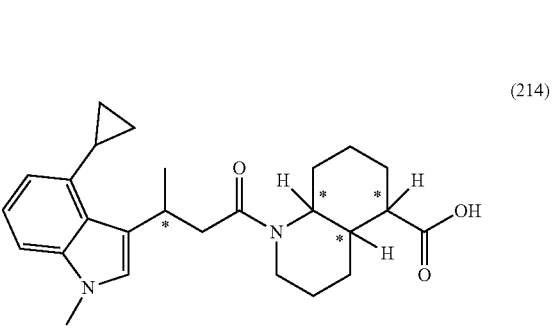 [SMILES: CC(CC(=O)N1CCCC2C(C(=O)O)CCCC21)c1cn(C)c2cccc(C3CC3)c12]

Synthesis of Compound (214)

Mixture of isomers of Compound (204) was separated by using chiral column chromatography to give compound 214. 1H NMR (300 MHz, CDCl3): δ 7.03-7.05 (m, 2H), 6.82-6.85 (d, 1H), 6.65-6.68 (m, 1H), 4.67-4.70 (m, 0.5H), 4.46-4.49 (m, 0.5H), 4.11-4.14 (m, 1H), 3.65 (s, 3H), 3.42-3.46 (m, 1H), 2.79-2.95 (m, 2H), 2.68-2.70 (m, 1H), 2.56-2.59 (m, 1H), 2.39-2.43 (m, 1H), 1.38-1.82 (m, 11H), 1.31-1.34 (d, 3H), 0.92-0.94 (m, 2H), 0.76-0.80 (m, 2H). LC-MS: (M+H)+=423.2; HPLC purity=98.00%; Chiral RT=30.61 min [Column: Chiral Pak IC; mobile phase: hexane: IPA:DCM (8.5:0.5:1.0)].

Example 215

1-{3-[4-(furan-2-yl)-1H-indol-3-yl]butanoyl}decahydroquinoline-5-carboxylic acid (215)

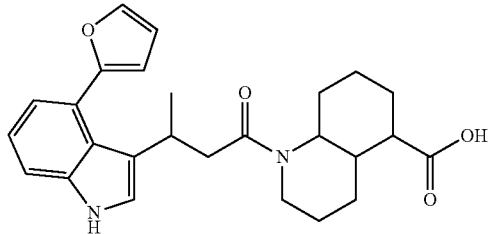
(215)

Synthesis of Compound (215)

Compound (215) was synthesized by following the procedure used to make (105) (Scheme 51). 1H NMR (300 MHz, DMSO-d6): δ 12.14 (br s, 1H), 11.08 (br s, 1H), 7.63-7.65 (m, 1H), 7.39-7.41 (d, 1H), 7.25 (s, 1H), 7.06-7.11 (t, 1H), 6.94-7.03 (m, 1H), 6.52-6.54 (m, 2H), 4.45-4.47 (m, 0.5H), 4.24-4.28 (m, 0.5H), 3.66-3.74 (m, 1H), 3.46-3.49 (m, 1H), 2.82-2.90 (m, 1H), 2.57-2.72 (m, 1H), 2.07-0.31 (m, 1H), 2.07-2.10 (m, 1H), 1.25-1.85 (m, 11H), 1.04-1.09 (d, 3H). LC-MS: (M+H)+=435.2; HPLC purity=93.62%.

Example 216

1-{3-[4-(furan-2-yl)-1-methyl-1H-indol-3-yl]butanoyl}decahydroquinoline-5-carboxylic acid (216)

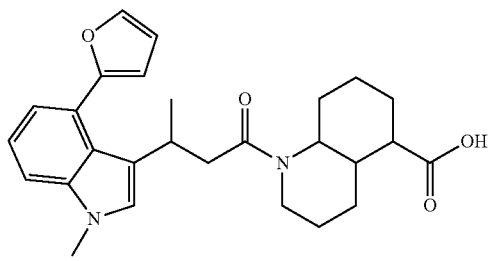
(216)

Synthesis of Compound (216)

Compound (216) was synthesized by following the procedure used to make (105) (Scheme 51). 1H NMR (300 MHz, CDCl3): δ 7.43-7.48 (m, 1H), 7.24-7.27 (m, 1H), 7.09-7.16 (m, 2H), 6.91 (s, 1H), 6.40-6.42 (m, 2H), 4.56-4.60 (m, 0.5H), 4.39-4.42 (m, 0.5H), 3.70 (s, 3H), 3.50-3.53 (m, 1H), 3.22-3.37 (m, 2H), 2.65-2.81 (m, 1H), 2.37-2.46 (m, 1H), 1.99-2.18 (m, 1H), 1.37-1.83 (m, 11H), 1.32-1.35 (d, 3H). LC-MS: (M+H)+=449.2; HPLC purity=97.01%.

Example 217

1-[3-(4-cyclopropyl-1H-indol-3-yl)butanoyl]decahydroquinoline-6-carboxylic acid (217)

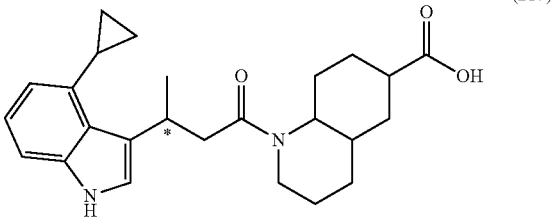
(217)

Synthesis of Compound (217)

Compound (217) was synthesized by following the procedure used to make Compound (195) (Scheme 59). 1H NMR (300 MHz, CDCl3): δ 7.95 (br s, 1H), 7.10-7.12 (d, 1H), 6.99-7.01 (d, 1H), 6.96 (s, 1H), 6.65-6.68 (d, 1H), 4.62-4.63 (m, 0.5H), 4.44-4.46 (m, 0.5H), 4.16-4.18 (m, 1H), 3.56-3.58 (m, 1H), 2.77-2.86 (m, 1H), 2.69-2.71 (m, 1H), 2.42-2.45 (m, 1H), 2.18-2.24 (m, 1H), 1.35-1.75 (m, 11H), 1.30-1.33 (d, 3H), 0.92-0.95 (m, 2H), 0.78-0.81 (m, 2H). LC-MS: (M+H)+=409.2; HPLC purity=96.63%.

Example 218

1-[3-(4-chloro-1H-indol-3-yl)-3-(thiophen-2-yl)propanoyl]decahydroquinoline-5-carboxylic acid (peak-1) (218)

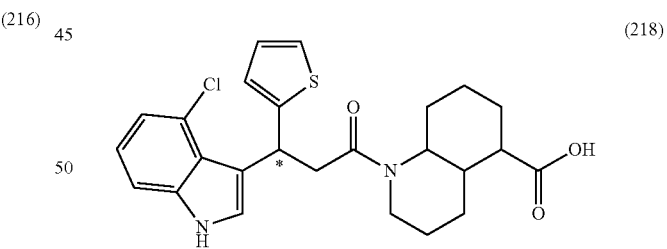
(218)

Synthesis of Compound (218)

Compound (218) was synthesized by following the procedure used to make Compound (195) (Scheme 58). 1H NMR (300 MHz, DMSO-d6): δ 12.14 (br s, 1H), 11.31 (br s, 1H), 7.40-7.45 (m, 1H), 7.31-7.33 (d, 1H), 7.20-7.22 (m, 1H), 7.00-7.05 (m, 1H), 6.89-6.96 (m, 1H), 6.78-6.86 (m, 2H), 5.48-5.55 (m, 1H), 4.42-4.44 (m, 0.5H), 4.22-4.26 (m, 0.5H), 4.00-4.04 (m, 0.5H), 3.78-3.83 (m, 0.5H), 2.95-3.16 (m, 2H), 2.45-2.55 (m, 2H), 1.32-1.92 (m, 11H). LC-MS: (M+H)+=471.1; HPLC purity=99.98%.

Example 219

1-[3-(4-chloro-1H-indol-3-yl)-3-(thiophen-2-yl)propanoyl]decahydroquinoline-5-carboxylic acid (peak-2) (219)

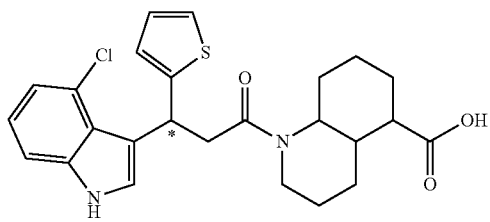

Synthesis of Compound (219)

Compound (219) was synthesized by following the procedure used to make Compound (196) (Scheme 59). 1H NMR (300 MHz, DMSO-d6): δ 12.15 (br s, 1H), 11.34 (br s, 1H), 7.41-7.45 (m, 1H), 7.31-7.33 (d, 1H), 7.22-7.24 (m, 1H), 7.00-7.05 (m, 2H), 6.94-6.96 (d, 1H), 6.86-6.89 (m, 1H), 5.56-5.58 (m, 1H), 4.41-4.51 (m, 0.5H), 4.21-4.23 (m, 0.5H), 4.00-4.04 (m, 1H), 3.78-3.82 (m, 1H), 2.95-3.11 (m, 2H), 2.08-2.15 (m, 1H), 1.33-1.80 (m, 11H). LC-MS: (M+H)+=471.1; HPLC purity=91.48%.

Example 220

1-[3-(4-cyclopropyl-5-fluoro-1H-indol-3-yl)butanoyl]decahydroquinoline-5-carboxylic acid (220)

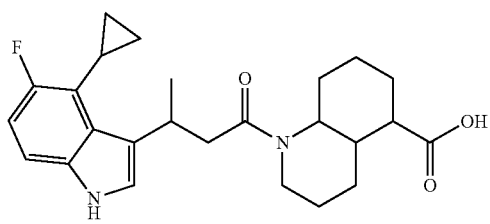

Synthesis of Compound (220)

Compound (220) was synthesized by following the procedure used to make Compound (105) (Scheme 51). 1H NMR (300 MHz, CDCl3): δ 8.02 (br s, 1H), 7.08-7.11 (m, 2H), 6.80-6.87 (t, 1H), 4.72-4.74 (m, 0.5H), 4.50-4.54 (m, 0.5H), 4.18-4.20 (m, 1H), 3.65-3.68 (m, 1H), 2.80-3.07 (m, 1H), 2.51-2.64 (m, 2H), 2.01-2.05 (m, 1H), 1.45-1.86 (11H), 1.39-1.42 (d, 3H), 1.06-1.08 (m, 2H), 0.88-0.92 (m, 2H). LC-MS: (M+H)+=427.2; HPLC purity=99.0%.

Example 221

1-{3-[4-(furan-2-yl)-1H-indol-3-yl]butanoyl}decahydroquinoline-5-carboxylic acid (221)

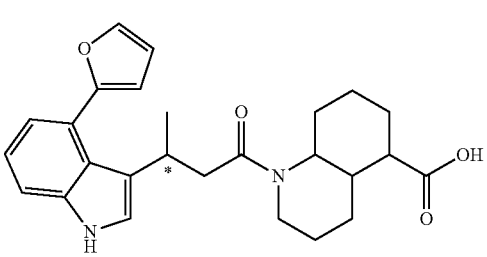

Synthesis of Compound (221)

Compound (221) was synthesized by following the procedure used to make Compound (195) (Scheme 58). 1H NMR (300 MHz, CDCl3): δ 8.20 (br s, 1H), 7.51-7.55 (m, 1H), 7.39-7.41 (m, 1H), 7.14-7.19 (m, 3H), 6.48-6.50 (m, 2H), 4.66-4.69 (m, 0.5H), 4.43-4.45 (m, 0.5H), 4.11-4.32 (m, 1H), 3.53-3.63 (m, 1H), 2.80-2.85 (m, 1H), 2.53-2.62 (m, 1H), 2.28-2.35 (m, 2H), 1.40-1.80 (m, 11H), 1.28-1.31 (d, 3H). LC-MS: (M+H)+=435.2; HPLC purity=98.74%.

Example 222

1-{3-[4-(furan-2-yl)-1H-indol-3-yl]butanoyl}decahydroquinoline-5-carboxylic acid (222)

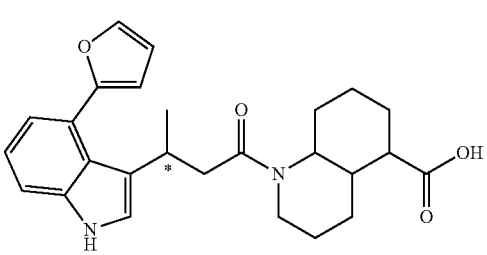

Synthesis of Compound (222)

Compound (222) was synthesized by following the procedure used to make Compound (196) (Scheme 59). 1H NMR (300 MHz, CDCl3): δ 8.27 (br s, 1H), 7.51-7.56 (m, 1H) m 7.38-7.41 (m, 1H), 7.23-7.28 (m, 1H), 7.13-7.17 (m, 3H), 6.48-6.50 (d, 1H), 4.63-4.67 (m, 0.5H), 4.46-4.49 (m, 0.5H), 3.51-3.64 (m, 1H), 3.37-3.40 (m, 1H), 2.80-2.88 (m, 1H), 2.49-2.62 (m, 1H), 2.16-2.29 (m, 2H), 1.40-1.86 (m, 11H), 1.36-1.38 (d, 3H). LC-MS: (M+H)+=435.2; HPLC purity=99.83%.

Example 223

1-{3-[4-(furan-2-yl)-1H-indol-3-yl]butanoyl}decahydroquinoline-5-carboxylic acid (223)

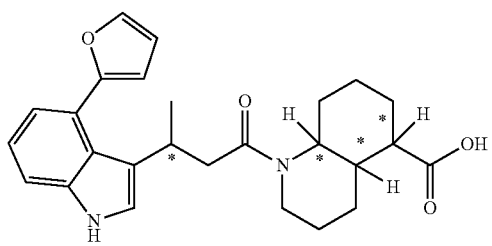

(223)

Synthesis of Compound (223)

Mixture of isomers of Compound (221) separated by preparative chiral chromatography to give Compound (223). 1H NMR (300 MHz, CD3OD): δ 7.57-7.60 (d, 1H), 7.37-7.42 (t, 1H), 7.17 (br s, 1H), 7.05-7.11 (m, 2H), 6.52-6.53 (m, 1H), 6.46-6.47 (m, 1H), 4.28-4.31 (d, 1H), 3.50-3.63 (m, 2H), 2.48-2.54 (m, 2H), 2.20-2.36 (m, 1H), 2.02-2.06 (m, 1H), 1.28-1.80 (m, 11H), 1.21-1.23 (d, 3H). LC-MS: (M+H)+=435.2; HPLC purity=100%. Chiral RT=19.31 min [Column: Chiral Pak IC; mobile phase: hexane: IPA:DCM (8.5:1:0.5)].

Example 224

1-{3-[4-(furan-2-yl)-1H-indol-3-yl]butanoyl}decahydroquinoline-5-carboxylic acid (224)

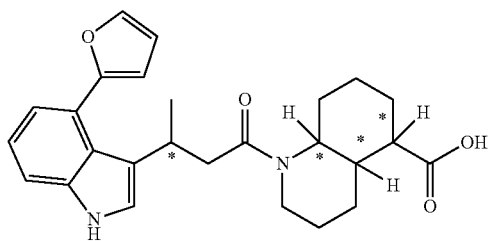

(224)

Synthesis of Compound (224)

Mixture of isomers of Compound (221) separated by preparative chiral chromatography to give Compound (224). 1H NMR (300 MHz, CDCl3): δ 8.14 (br s, 1H), 7.44-7.49 (d, 1H), 7.32-7.34 (d, 1H), 7.08-7.12 (m, 3H), 6.41-6.44 (d, 2H), 4.56-4.61 (m, 0.5H), 4.39-4.43 (m, 0.5H), 4.20 (4.25 (dd, 0.5H), 4.01-4.10 (m, 0.5H), 3.47-3.59 (m, 1H), 3.30-3.34 (m, 1H), 2.73-2.81 (m, 1H), 2.42-2.52 (m, 1H), 2.28-2.30 (m, 1H), 1.48-1.80 (m, 11H), 1.35-1.37 (d, 3H). LC-MS: (M+H)+=435.2; HPLC purity=96.72%. Chiral RT=23.19 min [Column: Chiral Pak IC; mobile phase: hexane: IPA:DCM (8.5:1:0.5)].

Example 225

1-[3-(4-fluoro-1H-indol-3-yl)-3-(4-fluorophenyl)propanoyl]decahydroquinoline-4-carboxylic acid (peak-1) (225)

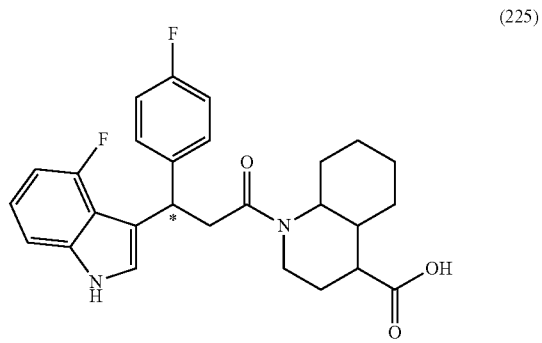 [SMILES: O=C(O)C1CCN(C(=O)CC(c2ccc(F)cc2)c2c[nH]c3cccc(F)c23)C2CCCCC12]

(225)

Synthesis of Compound (225)

Compound (225) was synthesized by following the procedure used to make Compound (195) (Scheme 58). 1H NMR (300 MHz, DMSO-d6): δ 12.23 (br s, 1H), 11.19 (br s, 1H), 7.25-7.36 (m, 3H), 7.13-7.16 (d, 1H), 7.03-7.06 (d, 1H), 6.93-6.97 (m, 2H), 6.59-6.65 (dd, 1H), 4.84 (br s, 1H), 3.88-3.94 (m, 1H), 3.30-3.32 (m, 1H), 2.94-3.21 (m, 2H), 2.38-2.40 (m, 1H), 1.40-1.90 (m, 11H). LC-MS: (M+H)+=467.1; HPLC purity=95.38%.

Example 226

1-[3-(4-fluoro-1H-indol-3-yl)-3-(4-fluorophenyl)propanoyl]decahydroquinoline-4-carboxylic acid (peak-2) (226)

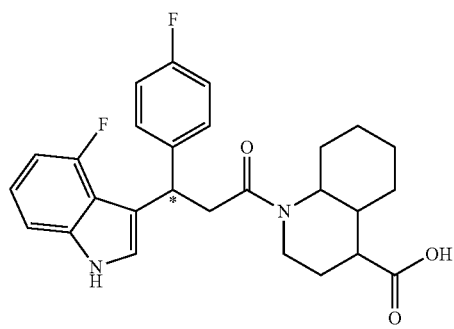

(226)

Synthesis of Compound (226)

Compound (226) was synthesized by following the procedure used to make Compound (196) (Scheme 59). 1H NMR (300 MHz, DMSO-d6): δ 12.24 (br s, 1H), 11.20 (br s, 1H), 7.36-7.37 (m, 1H), 7.25-7.29 (t, 2H), 7.13-7.16 (d, 1H), 7.03-7.06 (d, 1H), 6.94-7.00 (m, 2H), 6.59-6.66 (dd, 1H), 4.84 (br s, 1H), 3.88-3.90 (m, 1H), 3.29-3.32 (m, 1H), 2.93-3.21 (m, 2H), 2.38-2.42 (m, 2H), 1.28-1.91 (m, 11H). LC-MS: (M+H)+=467.1; HPLC purity=100%.

Example 227

1-{3-[4-(furan-2-yl)-1H-indol-3-yl]butanoyl}decahydroquinoline-4-carboxylic acid (227)

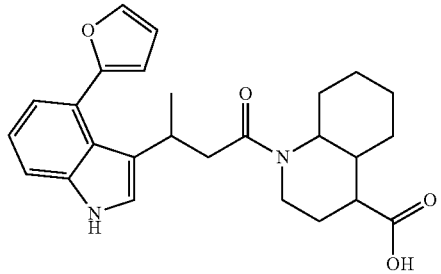

(227)

Synthesis of Compound (227)

Compound (227) was synthesized by following the procedure used to make Compound (105) (Scheme 51). 1H NMR (300 MHz, CDCl3): δ 8.39 (br s, 1H), 7.51-7.53 (m, 1H), 7.37-7.39 (m, 1H), 7.13-7.20 (m, 4H), 6.48 (s, 1H), 3.55-3.58 (m, 1H), 3.37-3.42 (m, 1H), 2.39-2.58 (m, 3H), 2.23-2.29 (m, 2H), 1.45-1.87 (m, 11H), 1.41-1.43 (d, 3H). LC-MS: (M+H)+=435.1; HPLC purity=98.43%.

Example 228

1-[3-(4-chloro-1H-indol-3-yl)butanoyl]decahydroquinoline-6-carboxylic acid (228)

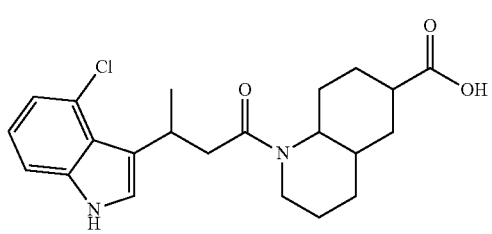

(228)

Synthesis of Compound (228)

Compound (228) was synthesized by following the procedure used to make Compound (105) (Scheme 51). 1H NMR (300 MHz, CDCl3): δ 8.19 (br s, 1H), 7.21-7.24 (m, 1H), 7.03-7.10 (m, 3H), 4.27-4.68 (m, 1H), 4.11-4.17 (m, 1H), 3.68-3.71 (m, 1H), 2.80-3.02 (m, 1H), 2.40-2.53 (m, 2H), 2.28-2.33 (m, 1H), 1.50-1.89 (m, 11H), 1.45-1.47 (d, 3H). LC-MS: (M+H)+=403.3; HPLC purity=94.02%.

Example 229

1-{3-[4-(furan-2-yl)-1H-indol-3-yl]butanoyl}decahydroquinoline-6-carboxylic acid (229)

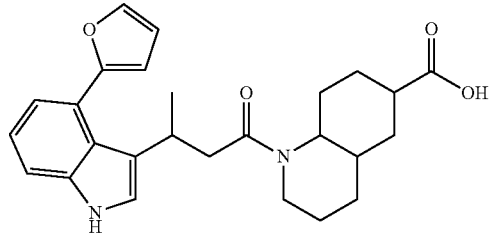

(229)

Synthesis of Compound (229)

Compound (229) was synthesized by following the procedure used to make Compound (105) (Scheme 51). 1H NMR (300 MHz, CDCl3): δ 8.19 (br s, 1H), 7.50-7.52 (m, 1H), 7.39-7.41 (m, 1H), 7.18-7.20 (m, 2H), 7.14 (s, 1H), 6.48-6.49 (d, 2H), 4.27-4.32 (dd, 0.5H), 4.11-4.17 (d, 0.5H), 3.57-3.59 (m, 1H), 3.39-3.41 (m, 1H), 2.75-2.79 (m, 1H), 2.22-2.38 (m, 3H), 1.47-1.87 (m, 14H). LC-MS: (M+H)+=435.2; HPLC purity=98.67%.

Example 230

1-[3-(4-cyclopropyl-1H-indol-3-yl)butanoyl]-2-methyldecahydroquinolin-5-carboxylic acid (230)

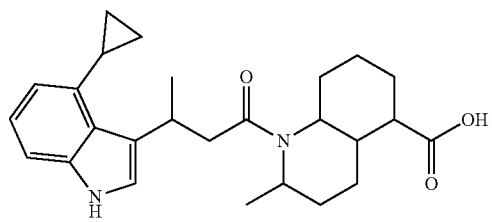

(230)

Synthesis of Compound (230)

Compound (230) was synthesized by following the procedure used to make Compound (105) (Scheme 51). 1H NMR (300 MHz, DMSO-d6): δ 12.16 (br s, 1H), 10.81 (br s, 1H), 7.17 (s, 1H), 7.13-7.15 (d, 1H), 6.88-6.94 (t, 1H), 6.55-6.58 (t, 1H), 4.58-4.62 (t, 0.5H), 4.41-4.45 (m, 0.5H), 3.99-4.11 (m, 1H), 3.81-3.85 (m, 1H), 2.58-2.93 (m, 2H), 2.31-2.43 (m, 2H), 1.33-1.99 (m, 11H), 1.27-1.30 (d, 3H), 1.06-1.08 (d, 3H), 0.90-0.96 (m, 2H), 0.65-0.72 (m, 2H). LC-MS: (M+H)+=423.4; HPLC purity=98.0%.

Example 231

1-{3-[4-(furan-2-yl)-1H-indol-3-yl]butanoyl}-2-methyldecahydroquinoline-5-carboxylic acid (231)

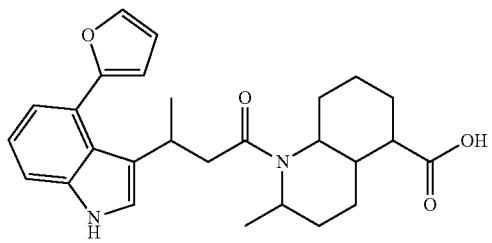

Synthesis of Compound (231)

Compound (231) was synthesized by following the procedure used to make Compound (105) (Scheme 51). 1H NMR (300 MHz, CDCl3): δ 12.11 (br s, 1H), 11.09 (br s, 1H), 7.61-7.64 (m, 1H), 7.39-7.42 (d, 1H), 7.23-7.26 (d, 1H), 7.06-7.12 (t, 1H), 7.02-7.03 (m, 1H), 6.51-6.53 (m, 2H), 4.49-4.51 (m, 0.5H), 4.33-4.45 (m, 0.5H), 3.96-3.98 (m, 1H), 2.65-2.73 (m, 2H), 2.16-2.28 (m, 2H), 1.37-1.94 (m, 11H), 1.15-1.18 (d, 3H), 1.02-1.05 (d, 3H). LC-MS: (M+H)+=449.2; HPLC purity=98.27%.

Example 232

2-methyl-1-{3-[4-(thiophen-2-yl)-1H-indol-3-yl]butanoyl}decahydroquinoline-5-carboxylic acid (232)

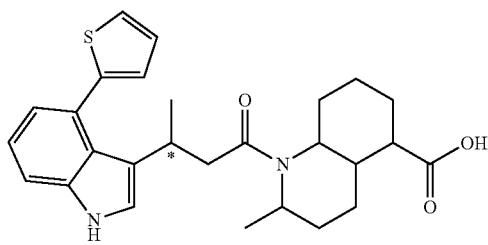

Synthesis of Compound (232)

Compound (232) was synthesized by following the procedure used to make Compound (195) (Scheme 58). 1H NMR (300 MHz, CDCl3): δ 8.23 (br s, 1H), 7.317.41 (m, 2H), 7.12-7.22 (m, 5H), 4.62-4.64 (m, 0.5H), 4.47-4.51 (m, 0.5H), 3.71-3.77 (m, 1H), 3.42-3.54 (m, 1H), 2.55-2.64 (m, 1H), 2.27-2.35 (m, 1H), 2.05-2.12 (m, 1H), 1.25-1.75 (m, 11H), 1.14-1.16 (d, 3H), 1.09-1.11 (d, 3H). LC-MS: (M+H)+=465.4; HPLC purity=96.26%.

Example 233

2-methyl-1-{3-[4-(thiophen-2-yl)-1H-indol-3-yl]butanoyl}decahydroquinoline-5-carboxylic acid (233)

Synthesis of Compound (233)

Compound (233) was synthesized by following the procedure used to make Compound (196) (Scheme 59). 1H NMR (300 MHz, CDCl3): δ 8.47 (br s, 1H), 7.21-7.29 (m, 2H), 7.00-7.11 (m, 5H), 4.56-4.57 (m, 0.5H), 4.41-4.43 (m, 0.5H), 3.63-3.68 (m, 1H), 3.42-3.44 (m, 1H), 2.51-2.59 (m, 1H), 2.25-2.27 (m, 1H), 2.02-2.10 (m, 1H), 1.34-1.68 (m, 11H), 1.00-1.03 (d, 3H), 0.98-1.00 (d, 3H). LC-MS: (M+H)+=465.4; HPLC purity=97.31%.

Example 234

1-[3-(4-chloro-1H-indol-3-yl)butanoyl]-2-methyl-decahydroquinoline-5-carboxylic acid (234)

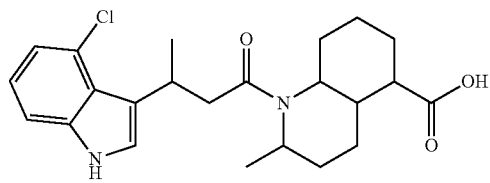

Synthesis of Compound (234)

Compound (234) was synthesized by following the procedure used to make Compound (105) (Scheme 51). 1H NMR (300 MHz, DMSO-d6): δ 12.14 (br s, 1H), 11.20 (br s, 1H), 7.25-7.32 (m, 2H), 6.96-7.02 (m, 2H), 4.58-4.60 (m, 0.5H), 4.41-4.43 (m, 0.5H), 3.99-4.01 (m, 1H), 2.72-2.93 (m, 2H), 2.25-2.27 (m, 1H), 1.92-1.97 (m, 1H), 1.30-1.72 (m, 11H), 1.15-1.17 (d, 3H), 1.07-1.09 (d, 3H). LC-MS: (M+H)+=417.1; HPLC purity=97.11%.

Example 235

1-[3-(4-chloro-1H-indol-3-yl)butanoyl]octahydroquinolin-4(1H)-one (235)

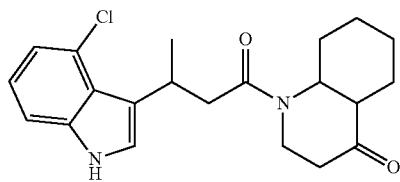
(235)

Synthesis of Compound (235)

Compound (235) was synthesized by following the procedure used to make Compound (26) (Scheme 25). 1H NMR (300 MHz, CDCl3): δ 8.18 (br s, 1H), 7.16-7.18 (m, 1H), 7.04-7.07 (m, 1H), 7.01-7.03 (d, 2H), 4.91-4.95 (m, 0.5H), 4.62-4.68 (m, 0.5H), 4.08-4.11 (m, 1H), 3.86-3.98 (m, 1H), 3.31-3.46 (m, 0.5H), 2.83-2.91 (m, 1H), 2.48-2.70 (m, 1H), 2.11-2.23 (m, 3H), 1.53-1.70 (m, 8H), 1.46-1.48 (d, 3H), 1.41-1.43 (d, 3H). LC-MS: (M+H)+=373.3; HPLC purity=97.62%.

Example 236

1-{3-[4-(5-methylfuran-2-yl)-1H-indol-3-yl]butanoyl}decahydroquinoline-5-carboxylic acid (236)

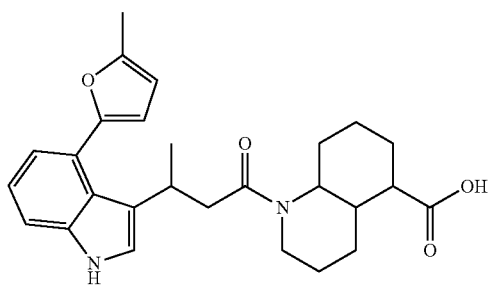
(236)

Synthesis of Compound (236)

Compound (236) was synthesized by following the procedure used to make Compound (105) (Scheme 51). 1H NMR (300 MHz, CDCl3): δ 8.19 (br s, 1H), 7.28-7.32 (m, 1H), 7.05-7.16 (m, 3H), 6.29-6.33 (m, 1H), 5.98-6.00 (m, 1H), 4.58-4.60 (m, 0.5H), 4.37-4.42 (m, 0.5H), 3.49-3.62 (m, 1H), 3.28-3.31 (m, 1H), 2.43-2.55 (m, 2H), 2.30 (s, 3H), 2.05-2.07 (m, 1H), 1.97-2.05 (m, 1H), 1.24-1.80 (m, 11H), 1.18-1.20 (d, 3H). LC-MS: (M+H)+=449.2; HPLC purity=98.32%.

Example 237

1-[3-(4-cyclopropyl-1H-indol-3-yl)butanoyl]-5-methyldecahydroquinoline-5-carboxylic acid (237)

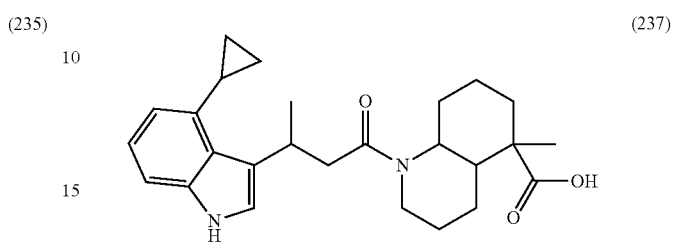
(237)

Synthesis of Compound (237)

Compound (237) was synthesized by following the procedure used to make Compound (105) (Scheme 51). 1H NMR (300 MHz, DMSO-d6): δ 12.20 (br s, 1H), 10.79 (br s, 1H), 7.12-7.15 (d, 2H), 6.88-6.92 (t, 1H), 6.55-6.58 (d, 1H), 4.01-4.03 (m, 1H), 3.69-3.87 (m, 1H), 2.90-2.95 (m, 1H), 2.65-2.78 (m, 2H), 2.35-2.41 (m, 2H), 1.49-1.98 (m, 10H), 1.28 (s, 3H), 1.24-1.26 (d, 3H). LC-MS: (M+H)+=423.2; HPLC purity=91.85%.

Example 238

1-{3-[4-(pyridin-2-yl)-1H-Indol-3-yl]butanoyl}decahydroquinoline-5-carboxylic acid (238)

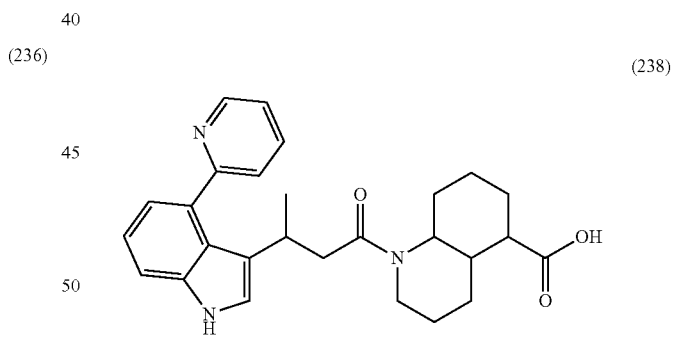
(238)

Synthesis of Compound (238)

Compound (238) was synthesized by following the procedure used to make Compound (105) (Scheme 51). 1H NMR (300 MHz, DMSO-d6): δ 12.15 (br s, 1H), 11.06 (br s, 1H), 8.59 (br s, 1H), 7.82-7.87 (t, 1H), 7.51-7.53 (d, 1H), 7.41-7.44 (d, 1H), 7.33-7.36 (m, 1H), 7.23 (s, 1H), 7.10-7.15 (t, 1H), 6.90-6.92 (d, 1H), 4.37-4.40 (m, 0.5H), 4.16-4.20 (m, 0.5H), 3.64-3.69 (m, 1H), 3.10-3.14 (m, 1H), 2.69-2.80 (m, 2H), 2.30-2.35 (m, 1H), 2.14-2.19 (m, 1H), 1.45-2.00 (m, 11H), 1.33-1.37 (d, 3H). LC-MS: (M+H)+=446.2; HPLC purity=96.69%.

Example 239

1-{3-[4-(3-methyl-1,2-oxazol-5-yl)-1H-indol-3-yl]butanoyl}decahydroquinoline-5-carboxylic acid (239)

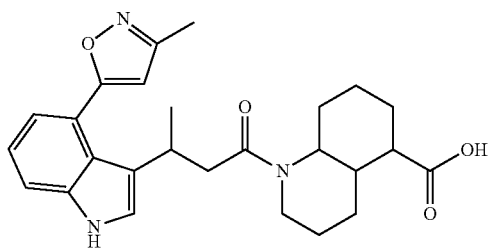

(239)

Synthesis of Compound (239)

Compound (239) was synthesized by following the procedure used to make Compound (105) (Scheme 51). 1H NMR (300 MHz, CDCl3): δ 8.28 (br s, 1H), 7.48-7.51 (d, 1H), 7.13-7.16 (m, 2H), 7.09 (s, 1H), 6.34 (s, 1H), 4.46-4.50 (m, 0.5H), 4.20-4.25 (dd, 1H), 4.04-4.08 (dd, 1H), 3.84-3.86 (m, 0.5H), 3.39-3.45 (m, 1H), 2.52-2.60 (m, 1H), 2.37 (s, 3H), 2.24-2.30 (m, 1H), 2.12-2.17 (m, 1H), 1.35-1.90 (m, 14H). LC-MS: (M+H)+=450.2; HPLC purity=99.79%.

Example 240

3-(4-cyclopropyl-1H-indol-3-yl)-1-[5-(1H-tetrazol-5-yl)octahydroquinolin-1(2H)-yl]butan-1-one (240)

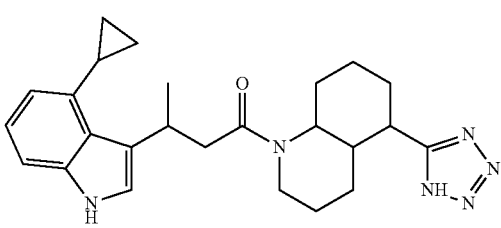

(240)

Synthetic Scheme-62

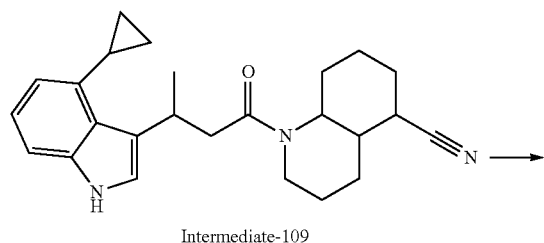

Intermediate-109

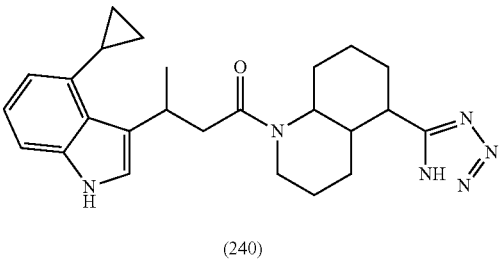

(240)

Synthesis of Compound (240)

To a stirred solution of Intermediate-109 (30 mg, 0.077 mmol) in DMF (2 mL), NaN3 (25 mg, 0.38 mmol) and ammonium chloride (15 mg, 0.22 mmol) were added. Resulted reaction mixture was heated at 110° C. for 48 hours. After completion of the reaction (monitored by TLC), the reaction mixture was quenched with water and was extracted with ethyl acetate (3×10 mL). The combined organic layer was concentrated to obtain a crude product. The resulted crude product was purified by preparative HPLC to give Compound (240) (2.5 mg) as brown gummy material. 1H NMR (300 MHz, CDCl3): δ 8.03 (br s, 1H), 7.08-7.11 (m, 1H), 6.97-7.04 (m, 2H), 6.63-6.70 (m, 1H), 5.20-5.27 (m, 1H), 4.08-4.24 (m, 2H), 3.52-3.58 (m, 1H), 2.77-2.97 (m, 2H), 2.21-2.30 (m, 2H), 1.45-1.90 (m, 11H), 1.37-1.40 (d, 3H), 0.70-0.90 (m, 4H). LC-MS: (M−H)+=431.3; HPLC purity=91.69%.

Example 241

1-[3-(4-cyclopropyl-1-methoxy-1H-indol-3-yl)butanoyl]decahydroquinoline-5-carboxylic acid (241)

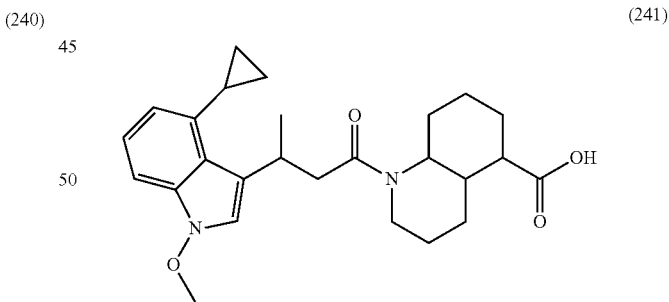

(241)

Synthesis of Compound (241)

Compound (241) was synthesized by following the procedure used to make Compound (105) (Scheme 51). 1H NMR (300 MHz, CDCl3): δ 7.10 (s, 1H), 7.02-7.07 (m, 2H), 6.65-6.68 (d, 1H), 4.20-4.25 (m, 1H), 4.04-4.10 (m, 2H), 3.98 (s, 3H), 3.52-3.65 (m, 1H), 2.61-2.82 (m, 1H), 2.38-2.47 (m, 2H), 2.21-2.24 (m, 1H), 0.7-1.90 (m, 18H). LC-MS: (M+H)+=439.3; HPLC purity=92.8%.

Example 242

1-{3-[4-cyclopropyl-1-(methoxymethyl)-1H-indol-3-yl]butanoyl}decahydroquinoline-5-carboxylic acid (242)

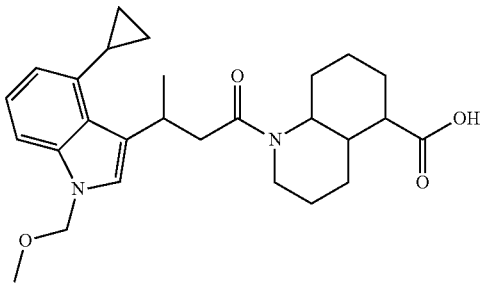

Synthesis of Compound (242)

Compound (242) was synthesized by following the procedure used to make Compound (105) (Scheme 51). 1H NMR (300 MHz, CDCl3): δ 7.23 (s, 1H), 7.02-7.07 (t, 1H), 6.94-6.97 (d, 1H), 6.70-6.72 (d, 1H), 5.31 (s, 2H), 4.62-4.69 (m, 0.5H), 4.49-4.52 (m, 0.5H), 4.17-4.25 (m, 1H), 4.04-4.10 (m, 1H), 3.52-3.62 (m, 1H), 3.18 (s, 3H), 2.75-2.81 (m, 1H), 2.39-2.43 (m, 2H), 2.15-2.30 (m, 1H), 1.39-1.80 (m, 11H), 1.32-1.35 (d, 3H), 0.94-0.96 (m, 2H), 0.73-0.77 (m, 2H). LC-MS: (M–H)+=451.2; HPLC purity=92.13%.

Example 243

1-{3-[4-(4-fluorophenyl)-1H-indol-3-yl]butanoyl}decahydroquinoline-5-carboxylic acid (243)

Synthesis of Compound (243)

Compound (243) was synthesized by following the procedure used to make Compound (105) (Scheme 51). 1H NMR (300 MHz, CDCl3): δ 8.25 (br s, 1H), 7.36-7.46 (m, 3H), 7.18-7.22 (t, 1H), 7.06-7.13 (m, 3H), 6.90-6.93 (d, 1H), 4.55-4.59 (m, 0.5H), 4.36-4.39 (m, 0.5H), 3.45-3.49 (m, 1H), 3.11-3.15 (m, 1H), 2.52-2.77 (m, 2H), 2.31-2.40 (dd, 1H), 2.07-2.16 (m, 2H), 1.36-1.96 (m, 10H), 1.13-1.15 (d, 3H). LC-MS: (M–H)+=463.3; HPLC purity=98.0%.

Example 244

1-{3-[4-(1-methyl-1H-pyrrol-2-yl)-1H-indol-3-yl]butanoyl}decahydroquinoline-5-carboxylic acid (244)

Synthesis of Compound (244)

Compound (244) was synthesized by following the procedure used to make Compound (105) (Scheme 51). LC-MS: (M–H)+=448.4; HPLC purity=84.68%.

Example 245

1-{3-[4-(5-fluorofuran-2-yl)-1H-indol-3-yl]butanoyl}decahydroquinoline-5-carboxylic acid (245)

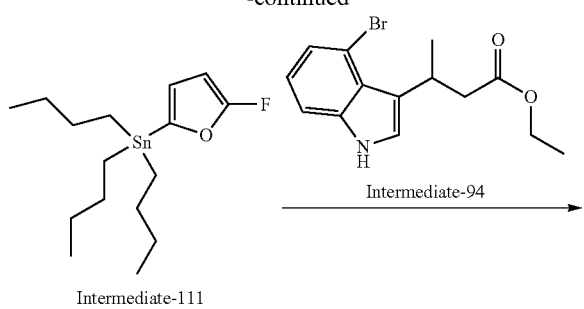

Intermediate-111  Intermediate-94

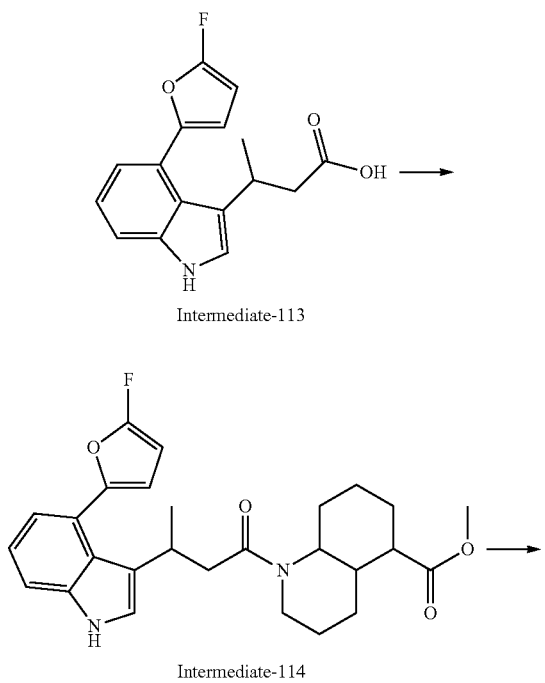

Intermediate-112

Intermediate-113

Intermediate-114

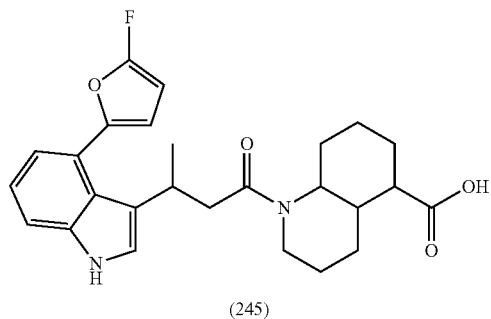

(245)

Synthesis of Intermediate-110

To a stirred solution of Starting Material-34 (1.0 g, 5.26 mmol) in water (5 mL) sodium bicarbonate (1.06 g, 12.6 mmol) was added at room temperature and stirred for 30 min. To this n-hexane (5 mL) followed by selectfluor (2.23 g, 6.31 mmol) was added at 10° C. and stirred for 2 hours at same temperature. After reaction hexane layer was separated and dried over anhydrous $MgSO_4$ to give crude intermediate-110 hexane solution, which was taken for next step without any purification.

Synthesis of Intermediate-111

To a stirred solution of Intermediate-110 hexanes solution (0.863 g, 5.26 mmol) in ether (5 mL) was added 2.5 M n-BuLi (2.52 mL, 6.31 mmol) at −78° C. and stirred for 20 minutes. To this tributyltin chloride (1.56 mL, 5.78 mmol) was added and stirred for 10 min at −78° C., then rt for 12 h. After reaction quenched with aqueous 1N NaOH solution and extracted with EtOAc and concentrated to give crude material Intermediate-111 (0.95 g) as brown liquid.

Synthesis of Intermediate-112

To a stirred solution of Intermediate-110 (0.050 g, 0.16 mmol), and Intermediate-111 (0.060 g, 0.16 mmol) in toluene purged with argon gas for 15 minutes, then added $PdCl_2$ (Dppf) catalyst (0.013 g, 0.016 mmol). Then reaction was carried out under micro wave for 30 min at 130° C. After reaction quenched with water and extracted with EtOAc and concentrated to give crude material, which was further purified by silica gel column chromatography eluting with hexanes: EtOAc to give 0.035 g of Intermediate-112 as brown liquid).

Synthesis of Intermediate-113

Intermediate-113 was synthesized by following the procedure used to make Intermediate-3 (Scheme 1).

Synthesis of Intermediate-114

Intermediate-114 was synthesized by following the procedure used to make Compound-1 (Scheme 2).

Synthesis of Compound (245)

Compound (245) was synthesized by following the procedure used to make Compound (105) (Scheme 51). 1H NMR (300 MHz, CDCl3): δ 8.24 (br s, 1H), 7.40-7.42 (m, 1H), 7.15-7.21 (m, 3H), 6.37-6.39 (m, 1H), 5.51-5.54 (m, 1H), 4.66-4.70 (m, 0.5H), 4.48-4.52 (m, 0.5H), 3.60-3.61 (m, 1H), 3.47-3.51 (m, 1H), 2.91-2.99 (m, 1H), 2.59-2.76 (m, 2H), 2.31-2.39 (m, 1H), 2.20-2.23 (m, 1H), 1.41-1.86 (m, 10H), 1.31-1.34 (d, 3H). LC-MS: (M−H)+=453.2; HPLC purity=97.87%.

Example 246

5-{3-[4-(octahydroquinolin-1(2H)-yl)-4-oxobutan-2-yl]-1H-indol-4-yl}furan-2-carboxylic acid (246)

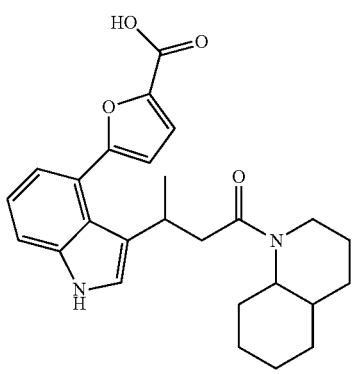

Synthetic Scheme-64

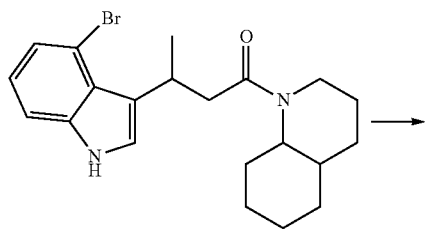

Intermediate-115

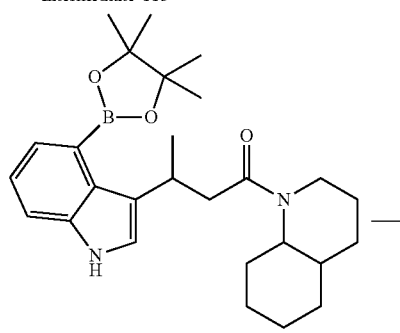

Intermediate-116

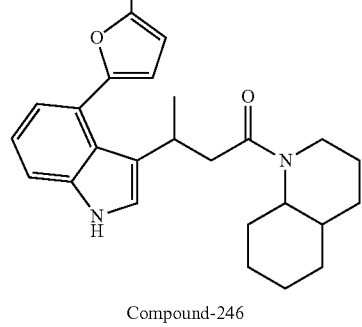

Compound-246

Synthesis of Intermediate-116

To a stirred solution of Intermediate-115 (0.2 g, 0.49 mmol) in dioxane (5 mL), bis(pinacolato)diboron (0.25 g, 0.99 mmol), and KOAc (0.145 g, 1.48 mmol) were added, and then the reaction solution was purged with argon gas. To the reaction mixture $PdCl_2$(dppf) (0.040 g, 0.049 mmol) was added and heated at 100° C. for 12 hours. After completion of the reaction, the reaction mixture was diluted with $H_2O$, extracted with EtOAc and concentrated to give crude product. The crude product was purified using Silica-gel column chromatography eluting with mixture of hexanes: EtOAc to give Intermediate-116 (100 mg) as brown gummy material.

Synthesis of Compound (246)

To a stirred solution of Intermediate-116 (0.1 g, 0.22 mmol) in dioxane: $H_2O$ (5 mL, 8:2), 2-bromofuroic acid (0.084 g, 0.44 mmol) and $Cs_2CO_3$ (0.28 g, 0.88 mmol) were added, and then reaction solution was purged with argon gas. To the reaction mixture $PdCl_2$(dppf) (0.018 g, 0.022 mmol) was added and heated at 100° C. for 12 hours. After completion of reaction, the reaction mixture was diluted with $H_2O$, extracted with EtOAc and concentrated to give crude product. The crude product was purified using Silica-gel column chromatography eluting with mixture of hexanes: EtOAc to give Compound-246 (12 mg) as white solid. 1H NMR (300 MHz, CDCl3): δ 8.59 (br s, 1H), 7.42-7.45 (m, 1H), 7.34-7.37 (m, 1H), 7.19-7.25 (m, 3H), 6.62-6.64 (m, 1H), 4.53-4.56 (m, 0.5H), 4.42-4.47 (m, 0.5H), 3.61-3.65 (m, 1H), 3.49-3.53 (m, 1H), 2.80-2.84 (m, 1H), 2.61-2.63 (m, 1H), 2.29-2.31 (m, 1H), 1.47-1.87 (m, 13H), 1.41-1.44 (d, 3H). LC-MS: (M−H)+=435.3; HPLC purity=99.33%.

Example 247

N-({1-[3-(4-cyclopropyl-1H-indol-3-yl)butanoyl]decahydroquinolin-5-yl}carbonyl)glycine (247)

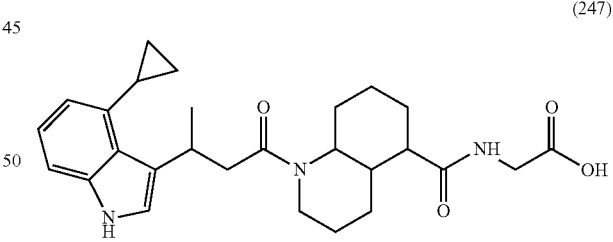

Synthesis of Compound (247)

Compound (247) was synthesized by following the procedure used to make Compound (105) (Scheme 51). 1H NMR (300 MHz, DMSO-d6): δ 12.30 (brs, 1H), 10.79 (br s, 1H), 8.02-8.04 (m, 1H), 7.12-7.15 (m, 2H), 6.88-6.93 (t, 1H), 6.55-6.59 (m, 1H), 4.49-4.52 (m, 0.5H), 4.31-4.33 (m, 0.5H), 4.02-4.05 (m, 1H), 3.68-3.70 (m, 2H), 3.10-3.13 (m, 1H), 2.93-2.98 (m, 1H), 2.62-2.78 (m, 2H), 2.31-2.35 (m, 2H), 1.90-1.95 (m, 1H), 1.37-1.75 (m, 10H), 1.31-1.34 (d, 3H), 0.84-0.88 (m, 2H), 0.72-0.76 (m, 2H). LC-MS: (M−H)+=466.4; HPLC purity=94.3%.

Example 248

1-{3-[4-(5-fluorofuran-2-yl)-1H-indol-3-yl]butanoyl}decahydroquinoline-5-carboxylic acid (248)

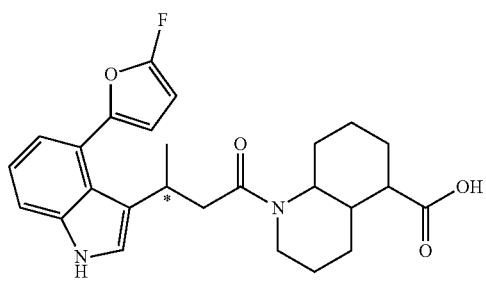
(248)

Synthetic Scheme-65

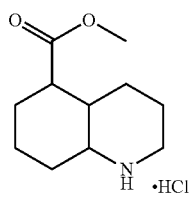
Intermediate-100

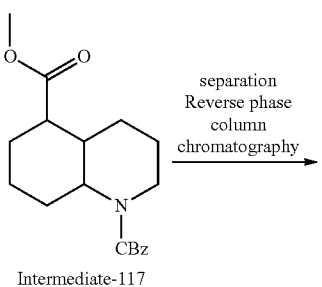
Intermediate-117

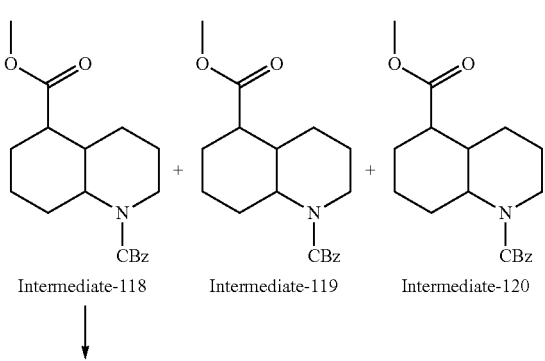
Intermediate-118  Intermediate-119  Intermediate-120

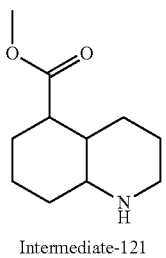
Intermediate-121

Synthesis of Intermediate-117

To a stirred solution of Intermediate-100 (14.5 g, 62.0 mmol) in DCM (250 mL), 50 mL of TEA (31.39 g, 310 mmol) was added followed by benzyl chloroformate (15.87 g, 93.1 mmol) at 0° C. Then it was stirred at room temperature for 12 hours. After completion of the reaction the reaction mixture was quenched with water and extracted with DCM. The combined organic layers were concentrated to give crude material, which was further purified by using silica gel column chromatography eluting with hexanes:EtOAc to give 20 g of Intermediate-117 as pate brown liquid.

Separation of Intermediate-118:

Mixture of isomers of Intermediate 117 (20 g) was separated by using Preparative Reverse HPLC to give 6.4 g of Intermediate-118: HPLC: [Column: Phenomenex Luna C-18, Mobile phase: 0.1% Formic acid in H2O and MeCN (1:1), RT=15.40 min].

Synthesis of Intermediate-121

A stirred solution of Intermediate-118 (6.4 g, 19.33 mmol) in MeOH (70 mL) was purged with $N_2$ gas, and then 10% Pd—C (1.2 g, 10% w/w) was added. The resulted reaction mixture was stirred under hydrogen atmosphere for 12 hours. After completion of the reaction, the reaction mixture was filtered through the celite and concentrated to give Intermediate-121 (3.79 g) as white solid.

Synthetic Scheme-66

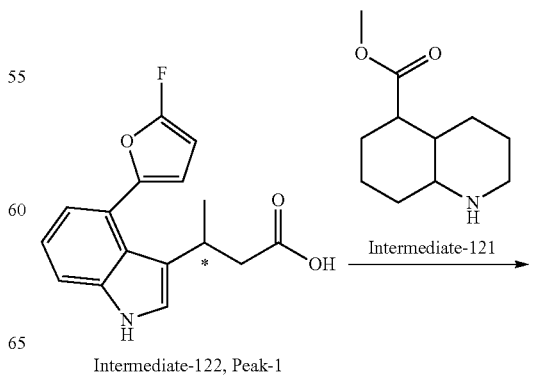
Intermediate-122, Peak-1

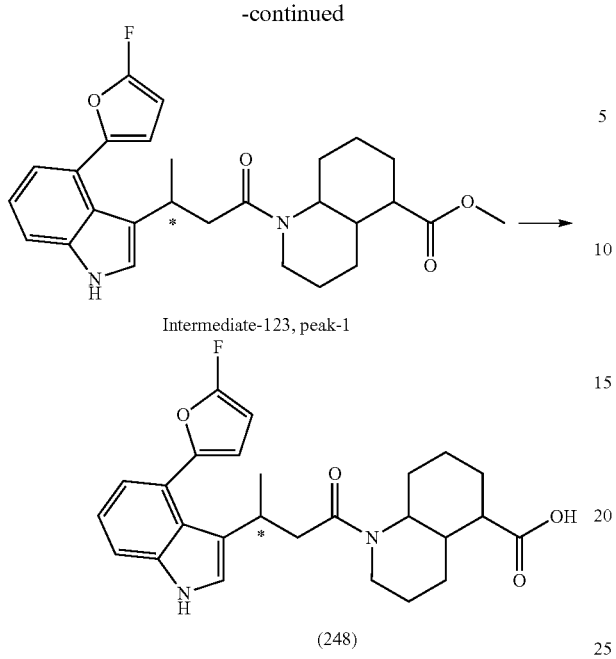

Intermediate-123, peak-1

(248)

Synthesis of Intermediate-122, Peak-1

Intermediate-122, peak-1 was synthesized by following the procedure used to make Intermediate-90 (Peak-1) (Scheme 54).

Synthesis of Intermediate-123, Peak-1

Intermediate-123, peak-1 was synthesized by following the procedure used to make Intermediate-91 (Peak-1) (Scheme 54).

Synthesis of Compound (248)

Compound (248) was synthesized by following the procedure used to make Compound (105) (Scheme 51). 1H NMR (300 MHz, CD3OD): δ 7.33-7.37 (m, 1H), 7.12-7.14 (d, 1H), 7.01-7.05 (t, 1H), 6.94-6.97 (m, 1H), 6.30-6.33 (m, 1H), 5.53-5.56 (m, 1H), 4.46-4.55 (m, 0.5H), 4.23-4.28 (m, 0.5H), 3.43-3.57 (m, 2H), 2.83-2.92 (m, 1H), 2.46-2.73 (m, 2H), 2.17-2.36 (m, 1H), 1.97-2.06 (m, 1H), 1.49-1.78 (m, 10H), 1.37-1.40 (d, 3H). LC-MS: (M−H)+=453.3; HPLC purity=93.80%.

Example 249

1-{3-[4-(5-fluorofuran-2-yl)-1H-indol-3-yl]butanoyl}decahydroquinoline-5-carboxylic acid (249)

(249)

Synthetic Scheme-67

Intermediate-121

Intermediate-124, Peak-2

Intermediate-125, peak-2

(249)

Synthesis of Intermediate-124, Peak-2

Intermediate-124, peak-2 was synthesized by following the procedure used to make Intermediate-92 (Peak-2) (Scheme 55).

Synthesis of Intermediate-125, Peak-2

Intermediate-125, peak-2 was synthesized by following the procedure used to make Intermediate-93 (Peak-2) (Scheme 55).

Synthesis of Compound (249)

Compound (249) was synthesized by following the procedure used to make Compound (105) (Scheme 51). 1H NMR (300 MHz, CDCl3): δ 8.24 (br s, 1H), 7.40-7.42 (m, 1H), 7.13-7.21 (m, 3H), 6.35-6.38 (m, 1H), 5.50-5.54 (m, 1H), 4.66-4.70 (m, 0.5H), 4.48-4.52 (0.5H), 3.60-3.62 (m, 1H), 3.47-3.51 (m, 1H), 2.91-2.99 (m, 1H), 2.60-2.73 (m, 2H), 2.32-2.39 (m, 1H), 2.25-2.28 (m, 1H), 1.48-1.87 (m, 10H), 1.41-1.43 (d, 3H). LC-MS: (M−H)+=453.3; HPLC purity=98.07%.

Example 250

1-{3-[4-(5-fluorofuran-2-yl)-1H-indol-3-yl]butanoyl}decahydroquinoline-5-carboxylic acid (250)

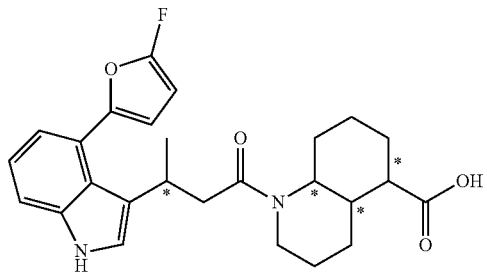

Synthesis of Compound (250)

Mixture of isomers of Compound (248) separated by using chiral column chromatography to give Compound (250). 1H NMR (300 MHz, CD3OD): δ 7.39-7.45 (t, 1H), 7.20 (s, 1H), 7.01-7.15 (m, 2H), 6.39-6.41 (m, 1H), 5.60-5.66 (m, 1H), 4.53-4.57 (d, 0.5H), 4.30-4.34 (d, 0.5H), 3.50-3.59 (m, 2H), 2.86-2.99 (m, 1H), 2.65-2.70 (m, 1H), 2.52-2.60 (m, 2H), 2.00-2.21 (m, 1H), 1.46-1.73 (m, 10H), 1.37-1.40 (d, 3H). LC-MS: (M−H)+=453.3; HPLC purity=98.29%; chiral purity=94.75% [column: Chiralpak IC; mobile phase: hexane: IPA: DCM (8.5:1.0:0.5); RT=10.88 min].

Example 251

1-{3-[4-(5-fluorofuran-2-yl)-1H-indol-3-yl]butanoyl}decahydroquinoline-5-carboxylic acid (251)

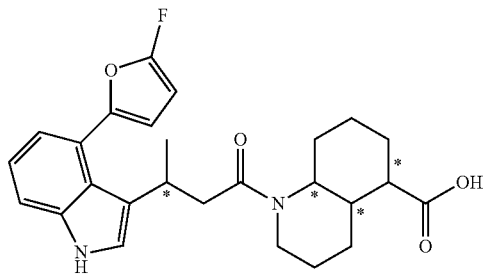

Synthesis of Compound (251)

Mixture of isomers of Compound (248) separated by using chiral column chromatography to give Compound (251). 1H NMR (300 MHz, CDCl3): δ 8.32 (br s, 1H), 7.32-7.35 (d, 1H), 7.05-7.13 (m, 3H), 6.29-6.32 (m, 1H), 5.43-5.46 (m, 1H), 4.58-4.62 (m, 0.5H), 4.39-4.44 (m, 0.5H), 3.52-3.56 (m, 2H), 2.83-2.91 (m, 1H), 2.61-2.70 (m, 1H), 2.46-2.51 (m, 1H), 2.25-2.34 (m, 1H), 2.07-2.18 (m, 1H), 1.45-1.79 (m, 10H), 1.37-1.40 (d, 3H). LC-MS: (M−H)+=453.4; HPLC purity=96.81%. chiral purity=99.52% [column: Chiralpak IC; mobile phase: hexane: IPA: DCM (8.5:1.0:0.5); RT=13.71 min].

Example 252

1-[3-(2-cyano-4-cyclopropyl-1H-indol-3-yl)butanoyl]decahydroquinoline-5-carboxylic acid (252)

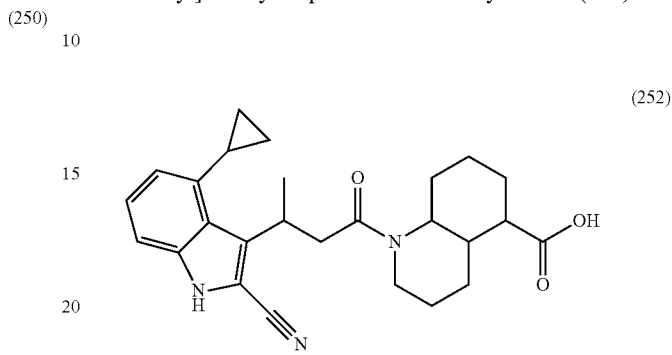

Synthesis of Compound (252)

Compound (252) was synthesized by following the procedure used to make Compound (105) (Scheme 51). 1H NMR (300 MHz, CDCl3): δ 8.75 (br s, 1H), 7.13-7.22 (m, 2H), 6.90-6.92 (d, 1H), 4.76-4.81 (m, 1H), 4.67-4.71 (m, 0.5H), 4.40-4.53 (m, 0.5H), 3.78-4.01 (m, 1H), 3.01-3.27 (m, 1H), 2.85-2.97 (m, 1H), 2.50-2.57 (m, 2H), 2.22 (2.36 (m, 1H), 2.12-2.18 (m, 1H), 1.52-1.85 (m, 10H), 1.46-1.49 (d, 3H), 1.01-1.04 (m, 2H), 0.84-0.87 (m, 2H). LC-MS: (M−H)+=434.3; HPLC purity=97.78%.

Example 253

1-{3-[4-(4-fluorophenyl)-1H-indol-3-yl]butanoyl}decahydroquinoline-5-carboxylic acid (253)

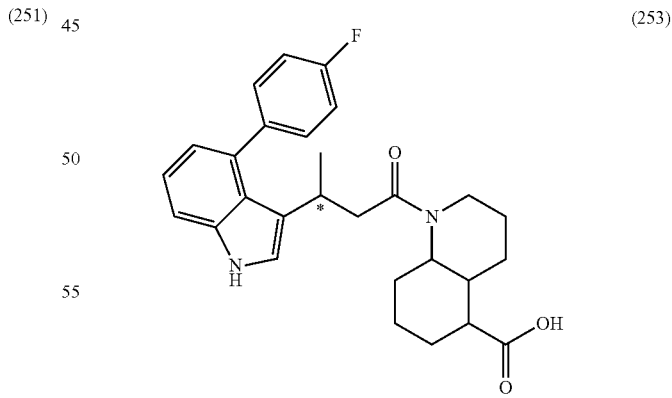

Synthesis of Compound (253)

Compound (253) was synthesized by following the procedure used to make Compound (159, peak-1) (Scheme 53-54). 1H NMR (300 MHz, CDCl3): δ 8.27 (br s, 1H), 7.42-7.46 (m, 2H), 7.36-7.39 (d, 1H), 7.14-7.20 (t, 1H), 7.08-7.14 (m, 3H), 6.90-6.97 (m, 1H), 4.55-4.59 (m, 0.5H), 4.37-4.39 (m, 0.5H), 3.06-3.32 (m, 2H), 2.73-2.82 (m, 1H), 2.59-2.64 (m, 1H), 2.41-2.48 (m, 1H), 2.32-2.38 (m, 1H), 2.10-2.15 (m, 1H), 1.39-1.93 (m, 10H), 1.13-1.15 (d, 3H). LC-MS: (M−H)+=463.3; HPLC purity=95.23%, Example 254

1-{3-[4-(4-fluorophenyl)-1H-indol-3-yl]butanoyl}decahydroquinoline-5-carboxylic acid (254)

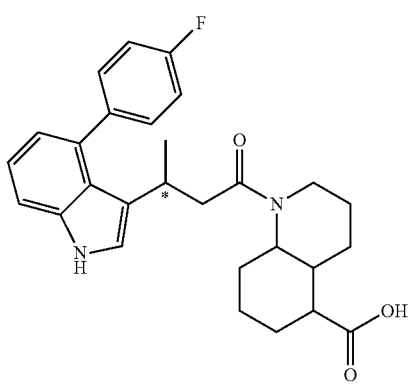

Synthesis of Compound (254)

Compound (254) was synthesized by following the procedure used to make Compound (160, peak-2) (Scheme 53 and 55). 1H NMR (300 MHz, CDCl3): δ 8.30 (br s, 1H), 7.42-7.46 (m, 2H), 7.36-7.39 (d, 1H), 7.17-7.22 (t, 1H), 7.07-7.14 (m, 3H), 6.90-6.97 (m, 1H), 4.55-4.59 (m, 0.5H), 4.37-4.39 (m, 0.5H), 3.11-3.32 (m, 2H), 2.69-2.82 (m, 1H), 2.40-2.50 (m, 2H), 2.13-2.23 (m, 2H), 1.39-1.90 (m, 10H), 1.13-1.15 (d, 3H). LC-MS: (M−H)+=463.3; HPLC purity=96.95%.

Example 255

1-{3-[4-(4-fluorophenyl)-1H-indol-3-yl]butanoyl}decahydroquinoline-5-carboxylic acid (255)

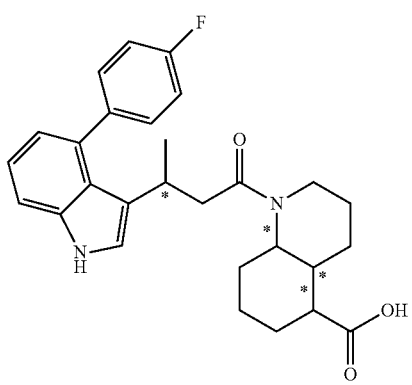

Synthesis of Compound (255)

Mixture of isomers of (253) separated by using chiral column chromatography to give Compound (255). 1H NMR (300 MHz, CDCl3): δ 8.21 (br s, 1H), 7.34-7.39 (m, 2H), 7.29-7.32 (d, 1H), 7.13-7.17 (d, 1H), 7.00-7.06 (m, 3H), 6.81-6.90 (m, 1H), 4.48-4.52 (m, 0.5H), 4.28-4.32 (m, 0.5H), 3.24-3.46 (m, 1H), 2.97-3.03 (m, 1H), 2.33-2.67 (m, 3H), 1.85-1.90 (m, 2H), 1.41-1.74 (m, 10H), 1.05-1.08 (d, 3H). LC-MS: (M−H)+=463.4; HPLC purity=99.7%; chiral purity=90.74% [column: Chiralpak IC; mobile phase: hexane: IPA: DCM (8.5:1.0:0.5); RT=16.87 min].

Example 256

1-{3-[4-(4-fluorophenyl)-1H-indol-3-yl]butanoyl}decahydroquinoline-5-carboxylic acid (256)

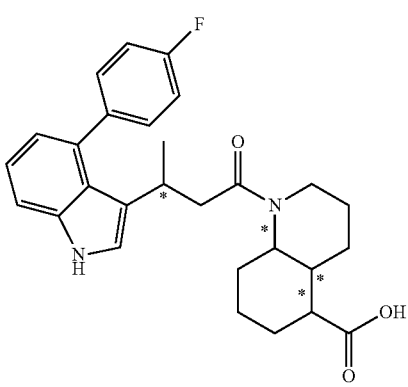

Synthesis of Compound (256)

Mixture of isomers of (253) separated by using chiral column chromatography to give Compound (256). 1H NMR (300 MHz, DMSO-d6): δ 12.15 (br s, 1H), 11.04 (br s, 1H), 7.34-7.44 (m, 3H), 7.16-7.23 (m, 3H), 7.06-7.11 (t, 1H), 6.73-6.75 (d, 1H), 4.36-4.40 (m, 0.5H), 4.17-4.21 (m, 0.5H), 3.70-3.74 (m, 1H), 3.45-3.48 (m, 1H), 3.04-3.06 (m, 1H), 2.73-2.86 (m, 1H), 2.27-2.44 (m, 2H), 2.11-2.19 (m, 1H), 1.35-1.94 (m, 10H), 1.20-1.24 (d, 3H). LC-MS: (M−H)+=463.3; HPLC purity=96.51%; chiral purity=89.64% [column: Chiralpak IC; mobile phase:hexane:IPA:DCM (8.5:1.0:0.5); RT=12.92 min].

Example 257

1-{3-[4-(2-fluorophenyl)-1H-indol-3-yl]butanoyl}decahydroquinoline-5-carboxylic acid (257)

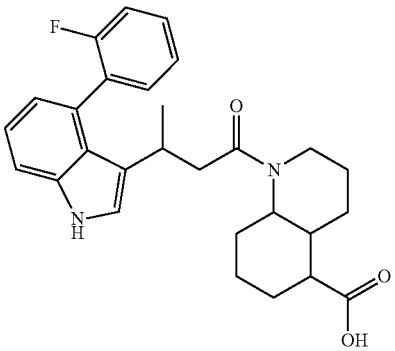

Synthesis of Compound (257)

Compound (257) was synthesized by following the procedure used to make Compound (105) (Scheme 51). 1H NMR (300 MHz, CDCl3): δ 8.22 (br s, 1H), 7.25-7.35 (m, 3H), 7.03-7.16 (m, 4H), 6.86-6.91 (m, 1H), 4.49-4.51 (m, 0.5H), 4.29-4.34 (m, 0.5H), 3.22-3.25 (m, 1H), 2.98-3.05 (m, 1H), 2.70-2.78 (m, 1H), 2.36-2.50 (m, 2H), 2.06-2.23 (m, 2H), 1.34-1.75 (m, 10H), 1.09-1.11 (d, 3H). LC-MS: (M−H)+=463.3; HPLC purity=94.78%.

Example 258

1-[3-(2-cyano-4-cyclopropyl-1-methyl-1H-indol-3-yl)butanoyl]decahydroquinoline-5-carboxylic acid (258)

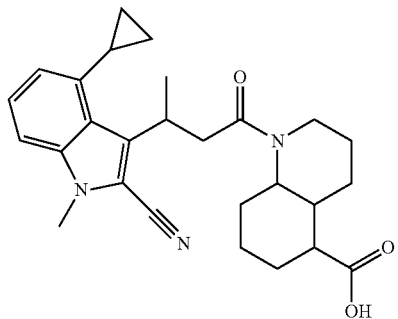

(258)

Synthesis of Compound (258)

Compound (258) was synthesized by following the procedure used to make Compound (105) (Scheme 51). 1H NMR (300 MHz, CDCl3): δ 7.16-7.21 (t, 1H), 7.04-7.07 (d, 1H), 6.85-6.87 (d, 1H), 4.70-4.75 (m, 1H), 4.60-4.65 (m, 0.1H), 4.37-4.45 (m, 1H), 3.77 (s, 3H), 2.84-3.01 (m, 2H), 2.46-2.55 (m, 2H), 2.09-2.27 (m, 2H), 1.47-1.80 (m, 10H), 1.40-1.43 (d, 3H), 0.97-1.00 (m, 2H), 0.76-0.79 (m, 2H). LC-MS: (M−H)+=448.4; HPLC purity=99.99%.

Example 259

1-{3-[4-(3-fluorophenyl)-1H-indol-3-yl]butanoyl}decahydroquinoline-5-carboxylic acid (259)

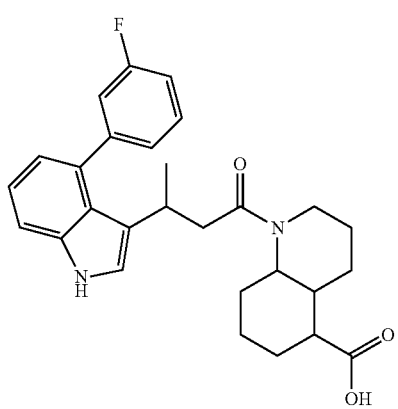

(259)

Synthesis of Compound (259)

Compound (259) was synthesized by following the procedure used to make Compound (105) (Scheme 51). 1H NMR (300 MHz, CDCl3): δ 8.50 (br s, 1H), 7.27-7.30 (m, 2H), 7.07-7.15 (m, 3H), 6.97-6.99 (m, 2H), 6.84-6.87 (m, 1H), 4.46-4.47 (m, 0.5H), 4.21-4.25 (m, 0.5H), 3.12-3.14 (m, 1H), 3.02-3.05 (m, 1H), 2.51-2.57 (m, 2H), 2.35-2.39 (m, 2H), 1.37-1.72 (m, 10H), 1.09-1.11 (d, 3H). LC-MS: (M−H)+=463.3; HPLC purity=95.6%.

Example 260

1-{[(4-cyclopropyl-1H-indol-3-yl)sulfanyl]acetyl}decahydroquinoline-5-carboxylic acid (260)

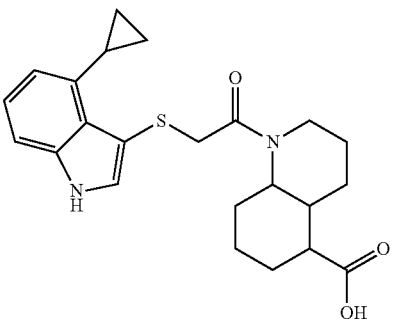

(260)

Synthesis of Compound (260)

Compound (260) was synthesized by following the procedure used to make Compound (105) (Scheme 51). 1H NMR (300 MHz, CDCl3): δ 8.33 (br s, 1H), 7.26-7.36 (m, 1H), 7.09-7.12 (m, 1H), 7.01-7.07 (m, 1H), 6.59-6.62 (d, 1H), 4.57-4.61 (m, 0.5H), 4.41-4.46 (m, 0.5H), 3.99-4.08 (m, 1H), 3.50-3.66 (m, 2H), 3.19-3.26 (m, 1H), 2.24-2.31 (m, 1H), 2.16-2.21 (m, 1H), 1.92-1.94 (m, 1H), 1.35-1.74 (m, 10H), 1.00-1.03 (m, 2H), 0.74-0.77 (m, 2H). LC-MS: (M−H)+=413.3; HPLC purity=99.65%.

Example 261

1-[3-(4-chloro-1-cyclopropyl-1H-indol-3-yl)butanoyl]decahydroquinoline-5-carboxylic acid (261)

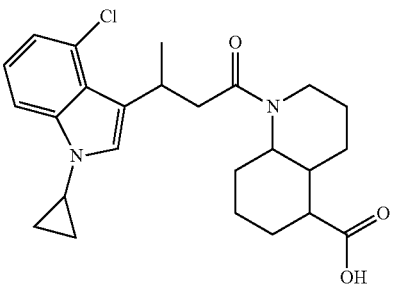

(261)

293

Synthesis of Compound (261)

Compound (261) was synthesized by following the procedure used to make Compound (105) (Scheme 51). 1H NMR (300 MHz, CDCl3): δ 7.36-7.38 (m, 1H), 6.96-7.02 (m, 3H), 4.62-4.68 (0.5H), 4.20-4.26 (m, 0.5H), 3.95-4.10 (m, 1H), 3.62-3.68 (m, 1H), 3.20-3.22 (m, 1H), 2.83-2.89 (m, 1H), 2.51-2.58 (m, 3H), 2.19-2.23 (m, 1H), 1.38-1.79 (m, 10H), 1.34-1.36 (d, 3H), 0.98-1.00 (m, 2H), 0.91-0.92 (m, 2H). LC-MS: (M−H)+=443.3; HPLC purity=97.77%.

Example 262

1-{3-[4-(3-fluoropyridin-2-yl)-1H-indol-3-yl]butanoyl}decahydroquinoline-5-carboxylic acid (262)

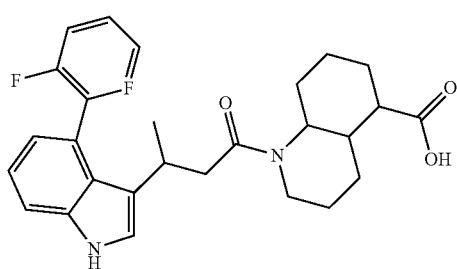

(262)

Synthesis of Compound (262)

Compound (262) was synthesized by following the procedure used to make Compound (105) (Scheme 51). 1H NMR (300 MHz, DMSO-d6): δ 12.01 (br s, 1H), 11.09 (br s, 1H), 8.45 (s, 1H), 7.72-7.81 (m, 1H), 7.47-0.50 (m, 2H), 7.24 (s, 1H), 7.12-7.17 (t, 1H), 6.88-6.90 (d, 1H), 4.14-4.38 (m, 0.5H), 3.70-3.78 (m, 0.5H), 3.40-3.48 (m, 2H), 2.72-2.78 (m, 2H), 2.30-2.35 (m, 1H), 2.22-2.26 (m, 1H), 1.91-2.05 (m, 1H), 1.33-1.70 (m, 10H), 1.13-1.17 (d, 3H). LC-MS: (M−H)+=464.3; HPLC purity=95.01%.

Example 263

1-{3-[4-(5-fluorofuran-2-yl)-1-methyl-1H-indol-3-yl]butanoyl}decahydroquinoline-5-carboxylic acid (263)

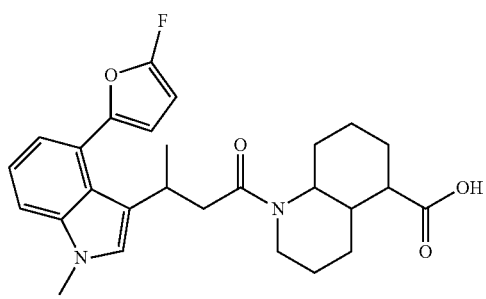

(263)

294

Synthesis of Compound (263)

Compound (263) was synthesized by following the procedure used to make Compound (105) (Scheme 51). 1H NMR (300 MHz, CDCl3): δ 7.26-7.29 (m, 1H), 7.12-7.15 (d, 1H), 7.05-7.07 (m, 1H), 6.95 (br s, 1H), 6.28-6.30 (m, 1H), 5.45-5.47 (m, 1H), 4.61-4.65 (m, 0.5H), 4.49-4.43 (m, 0.5H), 3.72 (s, 3H), 3.43-3.51 (m, 2H), 2.54-2.58 (m, 2H), 2.27-2.30 (m, 1H), 2.21-2.24 (m, 1H), 2.05-2.10 (m, 1H), 1.49-1.85 (m, 10H), 1.33-1.36 (d, 3H). LC-MS: (M−H)+=467.4; HPLC purity=98.0%.

Example 264

1-[3-(4-methoxy-1H-indol-3-yl)butanoyl]decahydroquinoline-5-carboxylic acid (264)

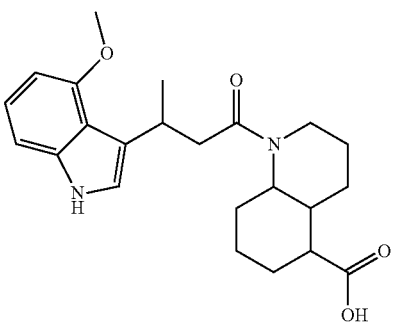

(264)

Synthesis of Compound (264)

Compound (264) was synthesized by following the procedure used to make Compound (105) (Scheme 51). 1H NMR (300 MHz, DMSO-d6): δ 12.13 (br s, 1H), 10.76 (br s, 1H), 6.95-6.98 (m, 2H), 6.92-6.93 (d, 1H), 6.43-6.46 (d, 1H), 4.52-4.56 (m, 0.5H), 4.30-4.34 (m, 0.5H), 3.82 (s, 3H), 3.61-3.63 (m, 2H), 2.96-3.05 (m, 1H), 2.74-2.90 (m, 2H), 2.16-2.39 (m, 1H), 1.44-1.90 (m, 10H), 1.37-1.40 (d, 3H). LC-MS: (M−H)+=399.2; HPLC purity=94.44%.

Example 265

1-[4,4,4-trifluoro-3-hydroxy-3-(1H-Indol-3-yl)butanoyl]-decahydroquinoline-5-carboxylic acid (265)

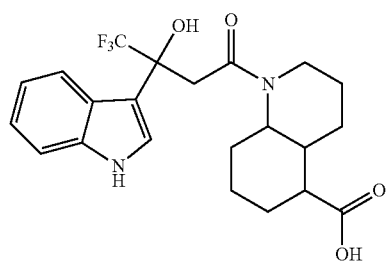

(265)

Synthetic Scheme-68

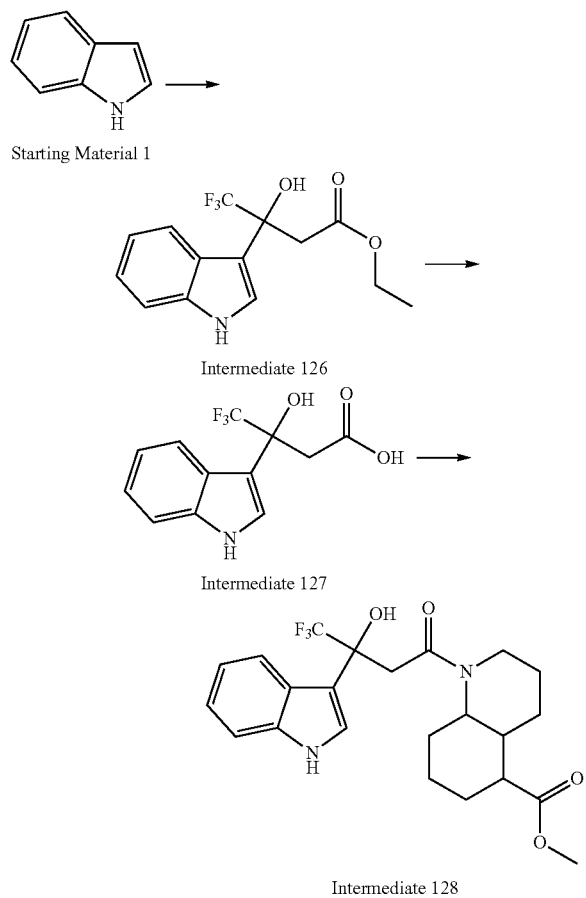

Synthesis of Intermediate-126

To a stirred solution of Starting Material-1 (3.0 g, 25.6 mmol) in toluene (50 mL), Montmorillonite K 10 (15 g) was added and heated at 80° C. for 4 hours. After completion of the reaction (LC-MS), catalyst was filtered through the sintered funnel, the filtrate diluted with H₂O and extracted with EtOAc and concentrated to give crude Intermediate 126 (5 g), which was taken for next step without any purification.

Synthesis of Intermediate-127

Intermediate-127 was synthesized by following the procedure used to make Intermediate-3 (Scheme 1).

Synthesis of Intermediate-128

Intermediate-128 was synthesized by following the procedure used to make Compound-1 (Scheme 2).

Synthesis of Compound (265)

Compound (265) was synthesized by following the procedure used to make Compound (105) (Scheme 51). 1H NMR (300 MHz, CDCl3): δ 8.25 (br s, 1H), 7.70-7.80 (m, 1H), 7.33-7.39 (m, 2H), 7.17-7.22 (m, 1H), 7.11-7.16 (m, 1H), 4.54-4.58 (m, 0.5H), 4.37-4.41 (m, 0.5H), 3.50-3.75 (m, 1H), 3.37-3.45 (d, 1H), 3.04-3.13 (d, 1H), 2.50-2.61 (m, 2H), 2.29-2.31 (m, 1H), 1.43-1.90 (m, 10H). LC-MS: (M−H)+=439.2; HPLC purity=93.26%.

Example 266

1-[3-(4-chloro-1-ethyl-1H-indol-3-yl)butanoyl]decahydroquinoline-5-carboxylic acid (266)

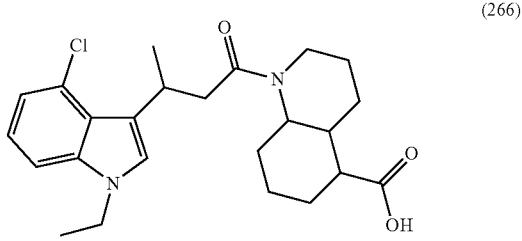 [SMILES: CCn1cc(C(C)CC(=O)N2CCCC3C(C(=O)O)CCCC32)c2c(Cl)cccc21]

Synthesis of Compound (266)

Compound (266) was synthesized by following the procedure used to make Compound (105) (Scheme 51). 1H NMR (300 MHz, DMSO-d6): δ 12.10 (br s, 1H), 7.39-7.42 (d, 3H), 7.33-7.36 (d, 3H), 7.05-7.10 (t, 1H), 7.01-7.02 (m, 1H), 4.46-4.48 (m, 0.5H), 4.27-4.29 (m, 0.5H), 4.13-4.18 (m, 2H), 3.96-3.98 (m, 1H), 3.70-3.72 (m, 1H), 1.14-1.20 (m, 2H), 2.62-2.75 (m, 2H), 2.00-2.05 (m, 1H), 1.45-1.80 (m, 10H), 1.26-1.32 (m, 6H). LC-MS: (M−H)+=431.3; HPLC purity=95.81%.

Example 267

1-(2-(4-cyclopropyl-1H-indol-3-yl)propanoyl)decahydroquinoline-5-carboxylic acid (267)

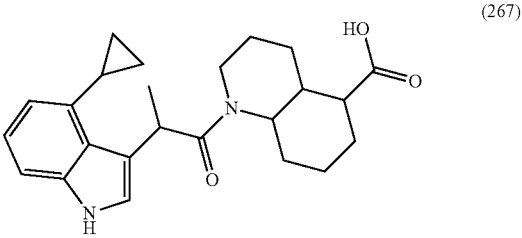 [SMILES: CC(C(=O)N1CCCC2C(C(=O)O)CCCC21)c1c[nH]c2cccc(C3CC3)c12]

Synthetic Scheme-69

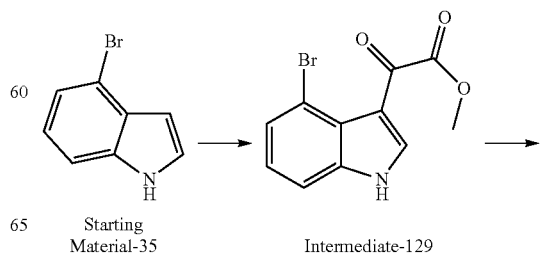

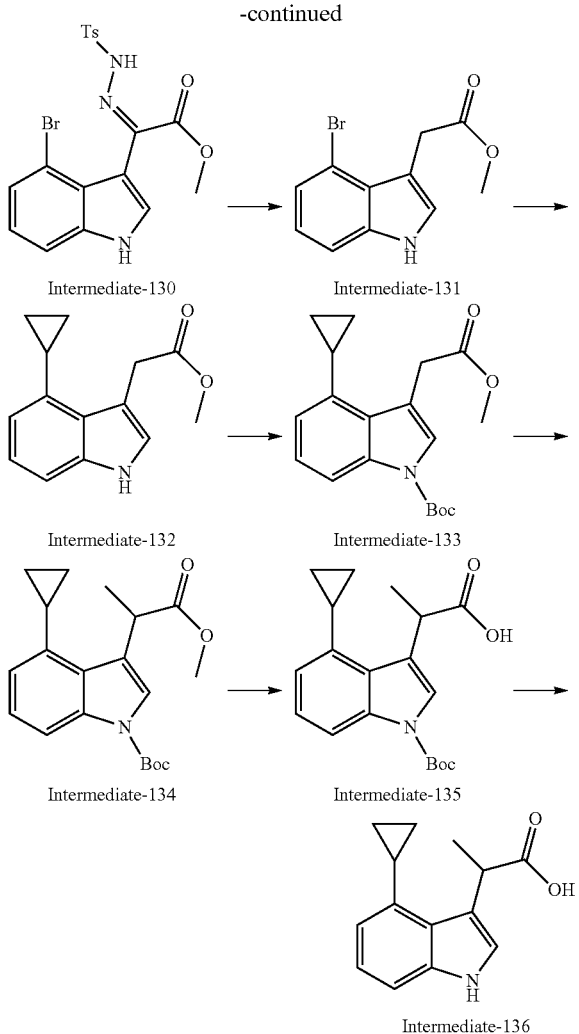

Synthesis of Intermediate 129

To a stirred solution of Starting Material-35 (40 g, 206 mmol) in ether (400 mL), oxalyl chloride (23.2 mL, 268 mmol) was added at 0° C., and stirred at room temperature for 5 hours. The reaction mixture was then filtered and washed with ether to get solid material (42 g), which was treated with MeOH (28 mL) in ether (200 mL) at 0° C. to room temperature for 5 hours. After completion of the reaction, the reaction mixture was diluted with hexanes, resulted precipitate was filtered and dried to get Intermediate-129 (35 g) as yellow solid.

Synthesis of Intermediate-130

To a stirred solution of Intermediate-129 (35 g, 129 mmol) in MeOH (350 mL), tosyl hydrazine (23.1 g, 129 mmol) was added and refluxed for 4 hours. After completion of the reaction, the reaction mixture was concentrated to give crude mixture, which was diluted with $H_2O$, extracted with DCM and concentrated to give Intermediate-130 (35 g) as pale yellow solid.

Synthesis of Intermediate-131

To a stirred solution of Intermediate-131 (14 g, 31 mmol) in THF (140 mL), NaBH$_4$ (1.8 g, 46 mmol) was added at 0° C. and continued to stir at room temperature for 6 hours. After completion of the reaction, the reaction mixture was quenched with $H_2O$, extracted with DCM and concentrated. The resulted crude product was purified by using silica gel column chromatography elusive with mixture of hexanes, EtOAc to give Intermediate-131 (3 g) as pale yellow liquid.

Synthesis of Intermediate-132

Intermediate-132 was synthesized by following the procedure used to make Intermediate-95 (Scheme 56).

Synthesis of Intermediate-133

Intermediate-133 was synthesized by following the procedure used to make Intermediate-72 (Scheme 47).

Synthesis of Intermediate-134

Intermediate-134 was synthesized by following the procedure used to make Intermediate-5 (Scheme 3).

Synthesis of Intermediate-135

Intermediate-135 was synthesized by following the procedure used to make Intermediate-3 (Scheme 1).

Synthesis of Intermediate-136

Intermediate-136 was synthesized by following the procedure used to make Intermediate-75 (Scheme 47).

Synthesis of Compound (267)

Compound (267) was synthesized by following the procedure used to make Compound (105) (Scheme 51). LC-MS: (M−H)+=395.3; HPLC purity=94.32%.

Example 268

1-(3-(4-cyclopropyl-1-methyl-1H-indazol-3-yl)propanoyl) decahydroquinoline-5-carboxylic acid (268)

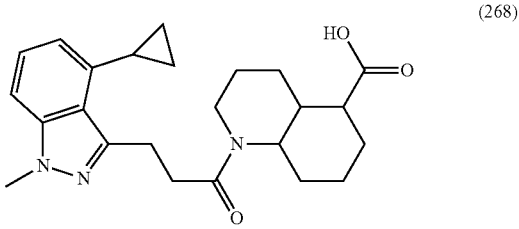 [SMILES: Cn1nc(CCC(=O)N2CCCC3C(C(=O)O)CCCC32)c2c(C3CC3)cccc21]

Synthesis of Compound (268)

Compound (268) was synthesized by following the procedure used to make Compound (88) (Scheme 47). LC-MS: (M−H)+=410.2.

Biological Activity

In Vitro HSD11β1 Inhibition Assay:

CHO cells were maintained in Dulbecco's modified Eagle's medium/nutrient mixture F-12 containing 5% fetal bovine serum (v/v) and 2 mM glutamine. Cells were cultured at 37° C. with 5% $CO_2$. For transient expression of human full length HSD11 β 1 expression vector (OriGene Technologies), cells were seeded at a density of 2×105 cells/well in a 6-well plate. Transfection was done using Turbofectin8 reagent (OriGene Technologies), according to the protocol provided with the reagent. After 24 hours post-transfection, cells were trypsinized and pooled together before they were re-seeding to 96-well plate at a density of 40000 cells/well. 24 hours after re-seeding, cells were incubated with 200 nM cortisone+500 uM NADPH (or along with small molecule inhibitors) overnight. The enzymatic activity or inhibition of enzyme activity was measured by estimating the conversion of cortisone to cortisol by LC/MS-MS method. The IC50 in nM was calculated from an 8 point log scale of concentration versus inhibition.

The results of the biological testing are shown in table 1:

TABLE 1

| Cmpd No | 11βHSD1 (IC50) |
|---|---|
| 1 | ***** |
| 2 | * |
| 3 | *** |
| 4 | **** |
| 5 | ***** |
| 6 | ** |
| 7 | * |
| 8 | **** |
| 9 | ** |
| 10 | **** |
| 11 | **** |
| 12 | * |
| 13 | ***** |
| 14 | * |
| 15 | **** |
| 16 | *** |
| 17 | ***** |
| 18 | * |
| 19 | * |
| 20 | ***** |
| 21 | * |
| 22 | * |
| 23 | * |
| 24 | * |
| 25 | * |
| 26 | * |
| 27 | ***** |
| 28 | **** |
| 29 | * |
| 30 | * |
| 31 | * |
| 32 | * |
| 33 | * |
| 34 | * |
| 35 | ***** |
| 36 | * |
| 37 | * |
| 38 | *** |
| 39 | * |
| 40 | * |
| 41 | **** |
| 42 | * |
| 43 | * |
| 44 | ***** |
| 45 | * |
| 46 | * |
| 47 | ***** |
| 48 | * |
| 49 | * |
| 50 | * |
| 51 | * |
| 52 | * |
| 53 | ***** |
| 54 | * |
| 55 | ***** |
| 56 | *** |
| 57 | * |
| 58 | * |
| 59 | *** |
| 60 | ***** |
| 61 | * |
| 62 | * |
| 63 | * |
| 64 | *** |
| 65 | * |
| 66 | ***** |
| 67 | * |
| 68 | * |
| 69 | * |
| 70 | * |
| 71 | *** |
| 72 | ***** |
| 73 | * |
| 74 | * |
| 75 | ***** |
| 76 | * |
| 77 | * |
| 78 | ***** |
| 79 | * |
| 80 | * |
| 81 | ***** |
| 82 | * |
| 83 | * |
| 84 | ***** |
| 85 | * |
| 86 | ***** |
| 87 | ***** |
| 88 | * |
| 89 | *** |
| 90 | **** |
| 91 | * |
| 92 | **** |
| 93 | ***** |
| 94 | *** |
| 95 | ***** |
| 96 | * |
| 97 | *** |
| 98 | * |
| 99 | * |
| 100 | * |
| 101 | * |
| 102 | * |
| 103 | * |
| 104 | * |
| 105 | * |
| 106 | * |
| 107 | * |
| 108 | * |
| 109 | * |
| 110 | * |
| 111 | ***** |
| 112 | ***** |
| 113 | * |
| 114 | ***** |
| 115 | * |
| 116 | * |
| 117 | ***** |
| 118 | ***** |
| 119 | ***** |
| 120 | ***** |
| 121 | ***** |
| 122 | ***** |
| 123 | ***** |
| 124 | **** |
| 125 | ***** |
| 126 | * |
| 127 | * |
| 128 | * |
| 129 | * |
| 130 | * |
| 131 | * |
| 132 | *** |
| 133 | * |
| 134 | * |

TABLE 1-continued

| Cmpd No | 11βHSD1 (IC50) |
|---|---|
| 135 | * |
| 136 | * |
| 137 | **** |
| 138 | *** |
| 139 | **** |
| 140 | ***** |
| 141 | * |
| 142 | ***** |
| 143 | ***** |
| 144 | * |
| 145 | ***** |
| 146 | * |
| 147 | * |
| 148 | * |
| 149 | * |
| 150 | **** |
| 151 | **** |
| 152 | * |
| 153 | *** |
| 154 | * |
| 155 | * |
| 156 | ***** |
| 157 | ***** |
| 158 | * |
| 159 | ***** |
| 160 | * |
| 161 | ***** |
| 162 | * |
| 163 | * |
| 164 | **** |
| 165 | * |
| 166 | * |
| 167 | ***** |
| 168 | * |
| 169 | * |
| 170 | * |
| 171 | * |
| 172 | * |
| 173 | ***** |
| 174 | * |
| 175 | * |
| 176 | *** |
| 177 | *** |
| 178 | * |
| 179 | * |
| 180 | * |
| 181 | * |
| 182 | * |
| 183 | * |
| 184 | * |
| 185 | *** |
| 186 | ***** |
| 187 | * |
| 188 | ***** |
| 189 | * |
| 190 | ***** |
| 191 | **** |
| 192 | ***** |
| 193 | **** |
| 194 | * |
| 195 | ***** |
| 196 | ***** |
| 197 | * |
| 198 | **** |
| 199 | ***** |
| 200 | ***** |
| 201 | ***** |
| 202 | * |
| 203 | * |
| 204 | ***** |
| 205 | * |
| 206 | ***** |
| 207 | * |
| 208 | **** |
| 209 | *** |
| 210 | **** |
| 211 | ***** |
| 212 | * |
| 213 | * |
| 214 | ***** |
| 215 | ***** |
| 216 | ***** |
| 217 | **** |
| 218 | ***** |
| 219 | * |
| 220 | ***** |
| 221 | ***** |
| 222 | **** |
| 223 | **** |
| 224 | ***** |
| 225 | ***** |
| 226 | * |
| 227 | * |
| 228 | * |
| 229 | **** |
| 230 | *** |
| 231 | *** |
| 232 | *** |
| 233 | * |
| 234 | * |
| 235 | ***** |
| 236 | **** |
| 237 | *** |
| 238 | * |
| 239 | * |
| 240 | * |
| 241 | * |
| 242 | * |
| 243 | ***** |
| 244 | * |
| 245 | ***** |
| 246 | * |
| 247 | * |
| 248 | ***** |
| 249 | ** |
| 250 | ***** |
| 251 | ***** |
| 252 | * |
| 253 | ***** |
| 254 | * |
| 255 | ***** |
| 256 | * |
| 257 | **** |
| 258 | * |
| 259 | *** |
| 260 | * |
| 261 | ** |
| 262 | * |
| 263 | ***** |
| 264 | * |
| 265 | * |
| 266 | * |
| 267 | * |
| 268 | * |

***** = <100 nM
**** = 100 nM< and <150 nM
*** = 150 nM< and <200 nM
** = 200 nM< and <250 nM
* = 250 nM<

The invention claimed is:
1. A compound of formula (I):

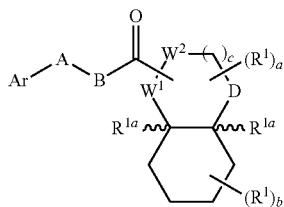

Formula (I)

wherein:
each $R^1$ and $R^{1a}$ is independently selected from the group consisting of H, methyl, $CONHC(CH_3)_3$, OH, $CO_2H$, $CO_2CH_3$, $CO_2CH_2CH_3$, phenyl, $CH_2OH$, CN, tetrazole and $OCH_3$,
or any two $R^1$ on adjacent carbon atoms may be joined to form a cyclic moiety, or any two $R^1$ on the same carbon when taken together may form a group of the formula =O,
Ar is an optionally substituted $C_1$-$C_{18}$heteroaryl group selected from the group consisting of:

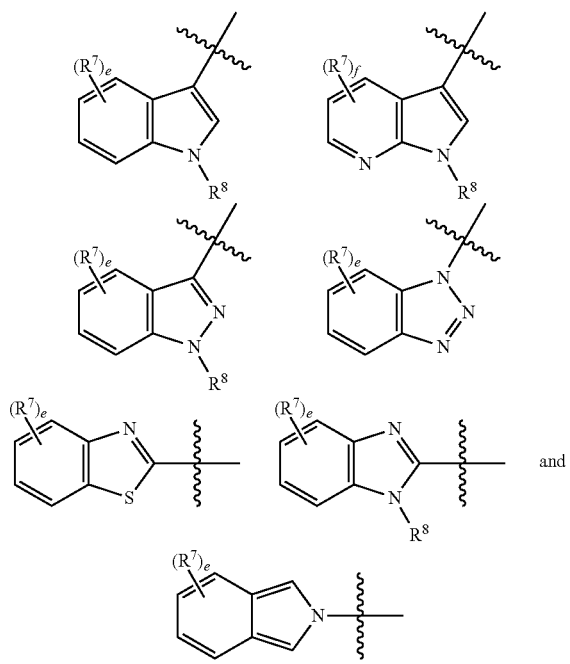

wherein each $R^7$ is independently selected from the group consisting of H, halogen, OH, $NO_2$, CN, SH, $NH_2$, $CF_3$, $OCF_3$, $C_1$-$C_{12}$alkyl, $C_1$-$C_{12}$haloalkyl, $C_2$-$C_{12}$alkenyl, $C_2$-$C_{12}$alkynyl, $C_2$-$C_{12}$heteroalkyl, $C_3$-$C_{12}$cycloalkyl, $C_3$-$C_{12}$cycloalkenyl, $C_2$-$C_{12}$heterocycloalkyl, $C_2$-$C_{12}$heterocycloalkenyl, $C_6$-$C_{18}$aryl, $C_1$-$C_{18}$heteroaryl, $C_1$-$C_{12}$alkyloxy, $C_2$-$C_{12}$alkenyloxy, $C_2$-$C_{12}$alkynyloxy, $C_2$-$C_{10}$heteroalkyloxy, $C_3$-$C_{12}$cycloalkyloxy, $C_3$-$C_{12}$cycloalkenyloxy, $C_2$-$C_{12}$heterocycloalkyloxy, $C_2$-$C_{12}$ heterocycloalkenyloxy, $C_6$-$C_{18}$aryloxy, $C_1$-$C_1$ heteroaryloxy, $C_1$-$C_{12}$alkylamino, $SR^9$, $SO_3H$, $SO_2NR^9R^{10}$, $SO_2R^9$, $SONR^9R^{10}$, $SOR^9$, $COR^9$, COOH, $COOR^9$, $CONR^9R^{10}$, $NR^9COR^{10}$, $NR^9COOR^{10}$, $NR^9SO_2R^{10}$, $NR^9CONR^9R^{10}$, $NR^9R^{10}$, and acyl;

wherein $R^8$ is selected from the group consisting of H, $C_1$-$C_{12}$alkyl, $C_2$-$C_{12}$alkenyl, $C_2$-$C_{12}$alkynyl, $C_2$-$C_{12}$heteroalkyl, $C_3$-$C_{12}$cycloalkyl, $C_2$-$C_{12}$heterocycloalkyl, $C_6$-$C_{18}$aryl, $C_1$-$C_{18}$heteroaryl, $SO_3H$, $SO_2NR^9R^{10}$, $SO_2R^9$, $SONR^9R^{10}$, $SOR^9$, $COR^9$, COOH, $COOR^9$, and $CONR^9R^{10}$;
wherein each $R^9$ and $R^{10}$ is independently selected from the group consisting of H, $C_1$-$C_{12}$alkyl, $C_2$-$C_{10}$heteroalkyl, $C_1$-$C_{12}$haloalkyl, $C_3$-$C_{12}$cycloalkyl, $C_6$-$C_{18}$aryl, and $C_1$-$C_{18}$heteroaryl;
e is an integer selected from the group consisting of 0, 1, 2, 3 and 4;
f is an integer selected the group consisting of 0, 1, 2, and 3;
A is $-CR^aR^b-$;
B is $CH_2$;
wherein each $R^a$ and $R^b$, is independently selected from the group consisting of H, halogen, OH, $NO_2$, CN, SH, $NH_2$, $CF_3$, $OCF_3$, $C_1$-$C_{12}$alkyl, $C_2$-$C_{10}$heteroalkyl, $C_1$-$C_{12}$haloalkyl, $C_3$-$C_{12}$cycloalkyl, $C_6$-$C_{18}$aryl, $C_1$-$C_{18}$heteroaryl; $SR^2$, $SO_3H$, $SO_2NR^2R^3$, $SO_2R^2$, $SONR^2R^3$, $SOR^2$, $COR^2$, COOH, $COOR^2$, $CONR^2R^3$, $NR^2COR^3$, $NR^2COOR^3$, $NR^2SO_2R^3$, $NR^2CONR^2R^2$, $NR^2R^3$, and acyl and further wherein $R^a$ and $R^b$ are different;
wherein each $R^2$ and $R^3$ is independently selected from the group consisting of H, $C_1$-$C_{12}$alkyl, $C_2$-$C_{10}$heteroalkyl, $C_1$-$C_{12}$haloalkyl, $C_3$-$C_{12}$cycloalkyl, $C_6$-$C_{18}$aryl, and $C_1$-$C_{18}$heteroaryl;
$W^1$ and $W^2$ are selected such that one is N and the other is $(CR^1_2)$,
the bond from the carbonyl carbon is joined to whichever of $W^1$ or $W^2$ is N,
D is $(CR^1_2)$,
n is an integer selected from the group consisting of 0, 1, and 2;
a is an integer selected from the group consisting of 0, 1, 2, and 3;
b is an integer selected from the group consisting of 0, 1, 2, 3, 4, 5, 6, 7, and 8,
c is 1;
or a pharmaceutically acceptable salt thereof.
2. A compound according to claim 1 having the formula:

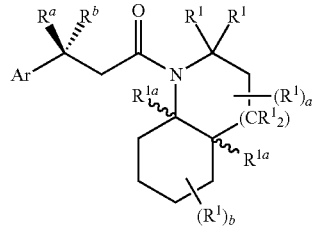

wherein Ar, $R^a$, $R^b$, $R^1$, $R^{1a}$, a and b are as defined in claim 1.
3. A compound according to claim 2 wherein one of $R^a$ and $R^b$ is H and the other is optionally substituted alkyl.
4. A compound according to claim 1 wherein the $R^7$ substituent is located in the 4 or the 5 position of the six membered ring.
5. A compound according to claim 1 wherein $R^7$ is selected from the group consisting of $CH_3$, $CH_2CH_3$, $CH_2CH_2CH_3$, $CH(CH_3)_2$, $(CH_2)_3CH_3$, Cl, Br, F, I, OH, $NO_2$, $NH_2$, CN, $SO_3H$, $OCH_3$, $OCH_2CH_2CH_3$, $CF_3$, and $OCF_3$.

6. A compound according to claim 1 selected from the group consisting of:
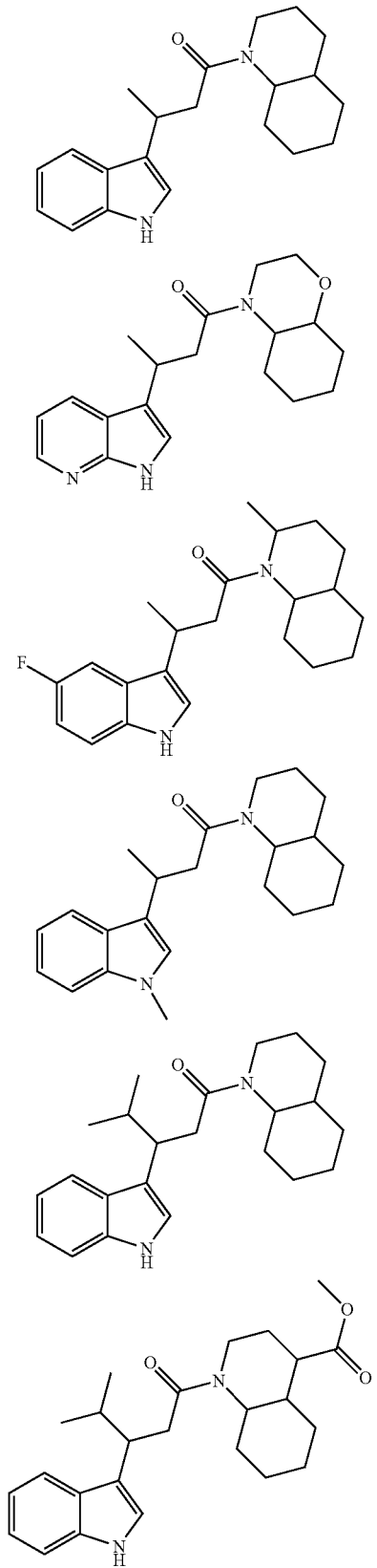
-continued
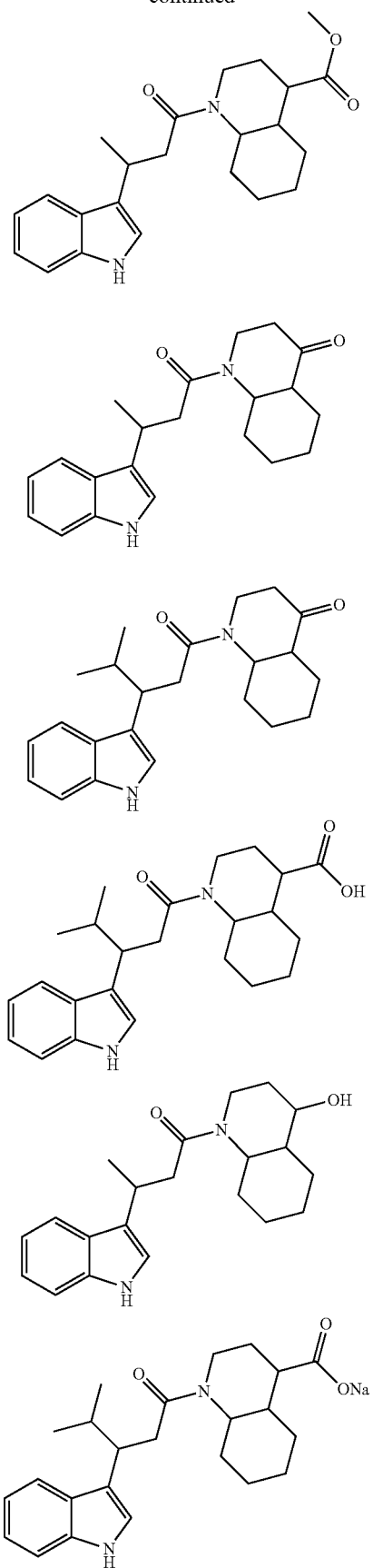

307
-continued
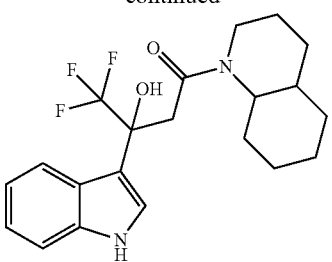
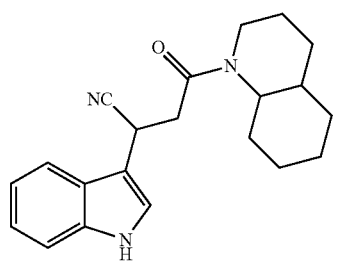
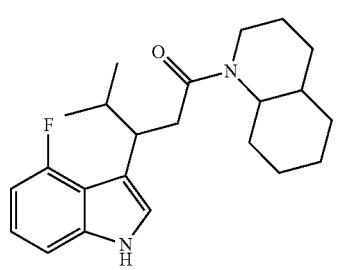
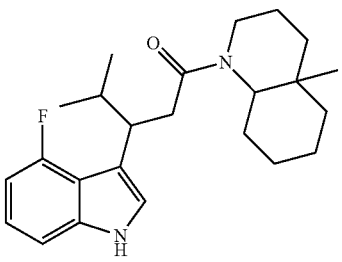
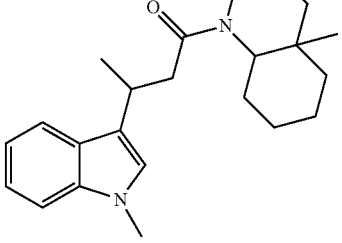
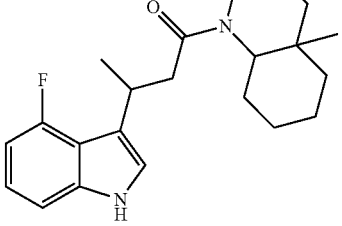
308
-continued
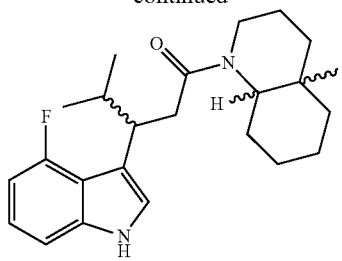
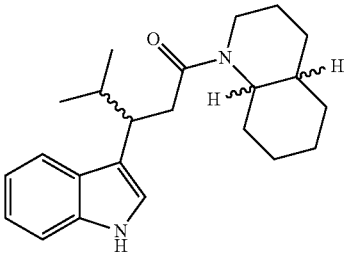
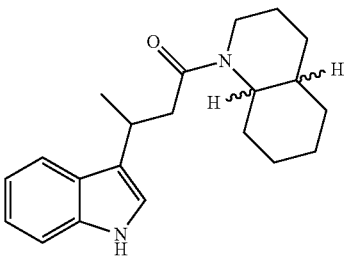
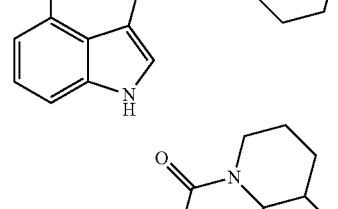
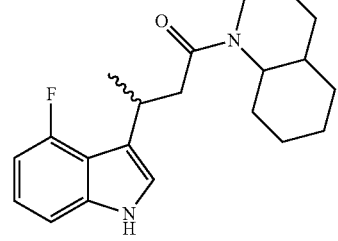
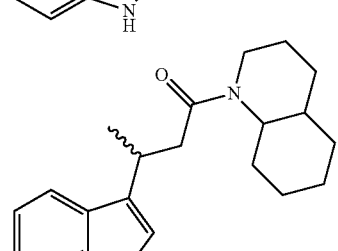

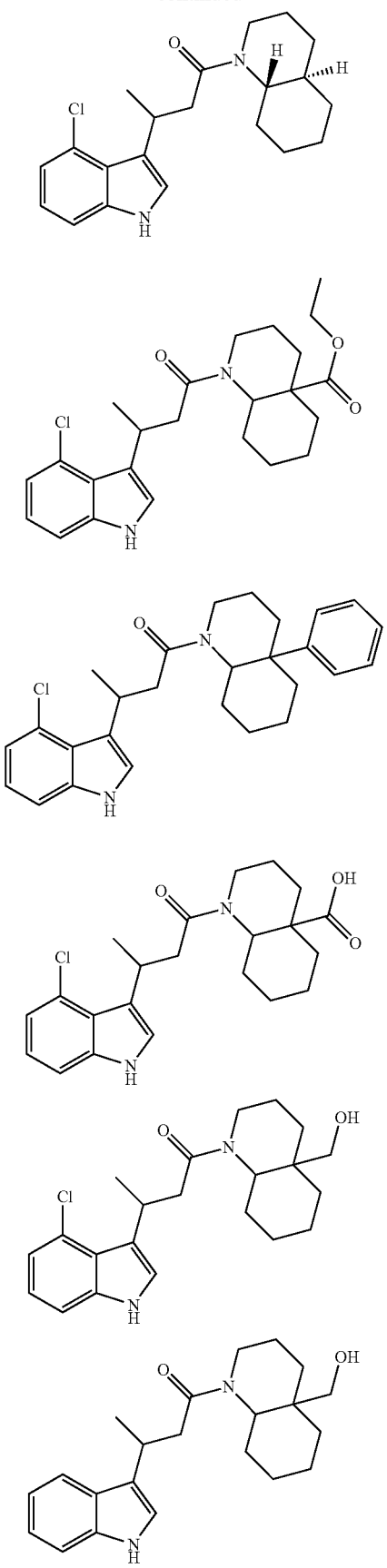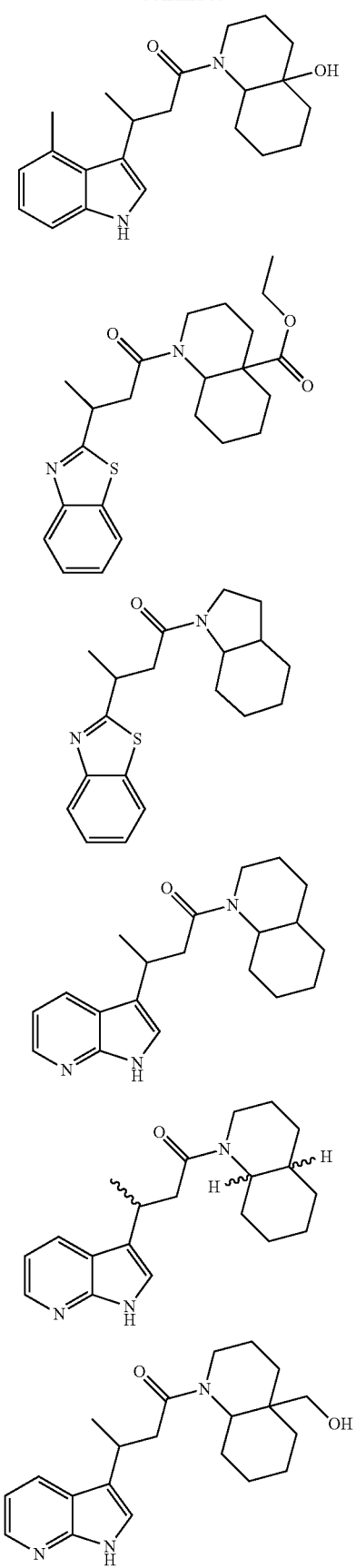

-continued
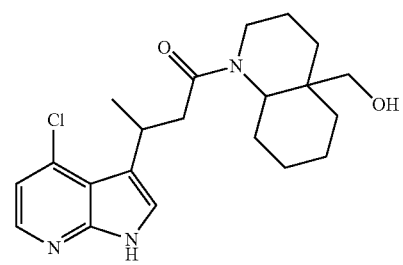
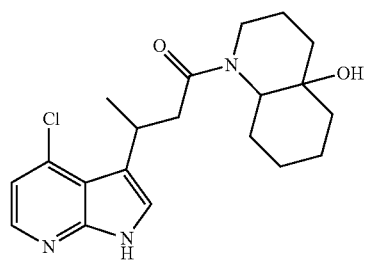
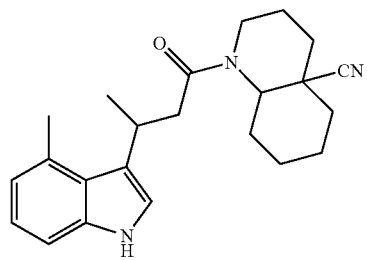
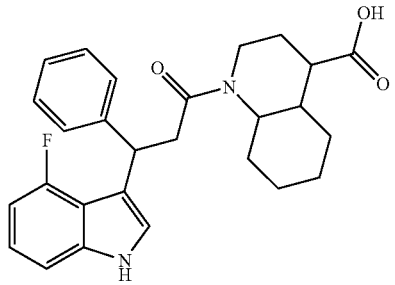
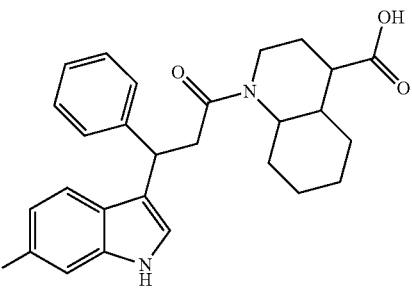
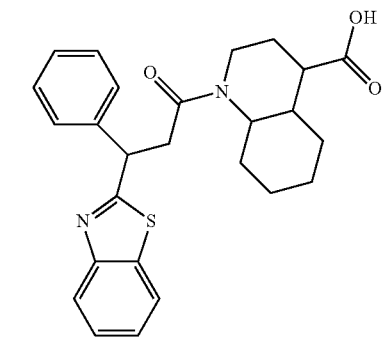
-continued
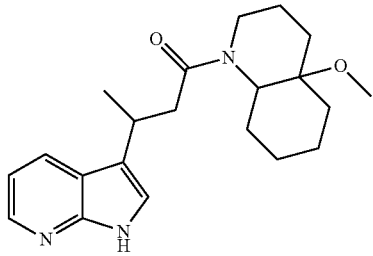
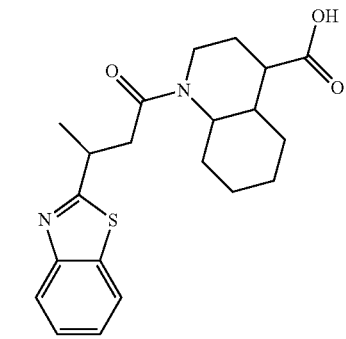
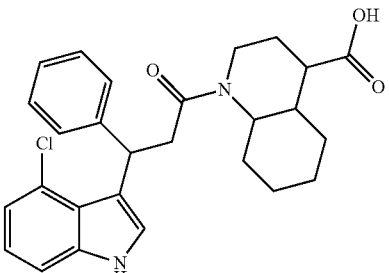
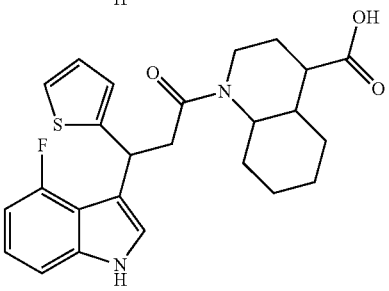
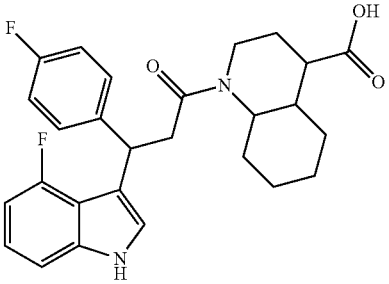
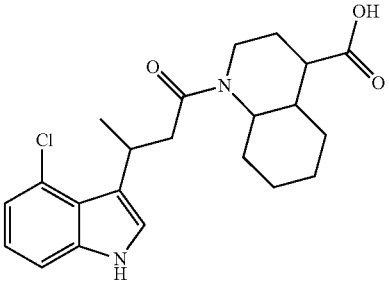

313
-continued
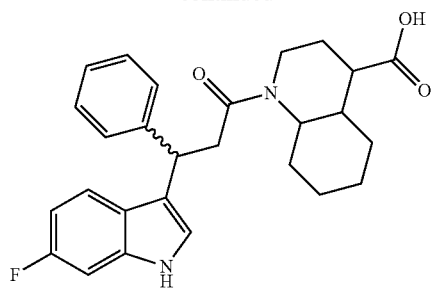
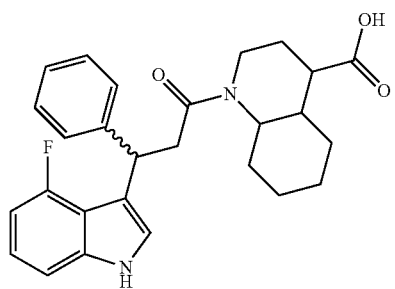
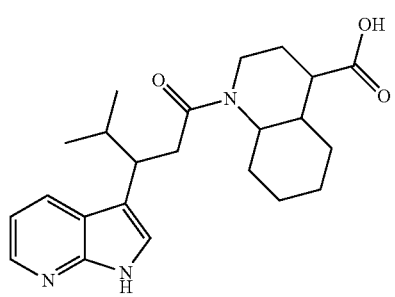
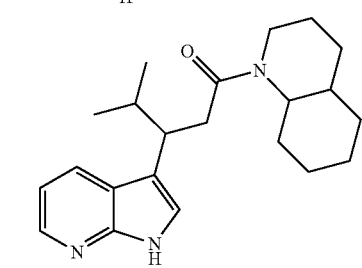
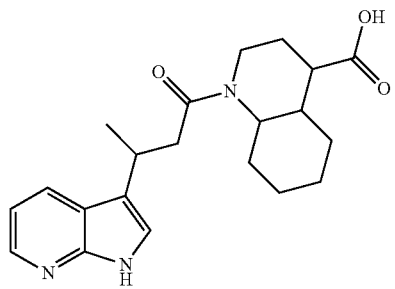
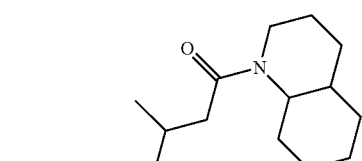
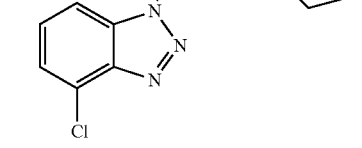
314
-continued
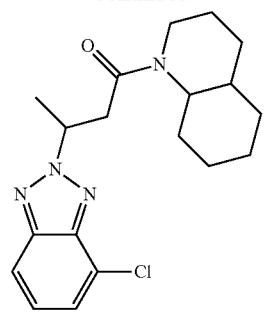
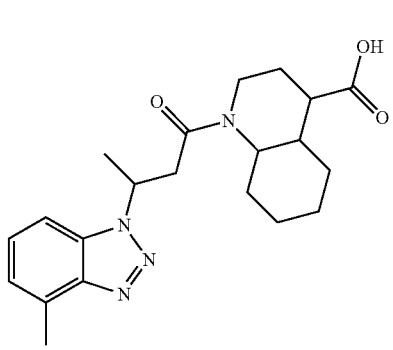
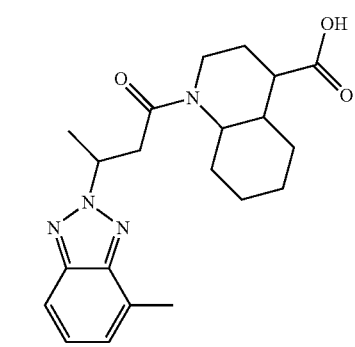
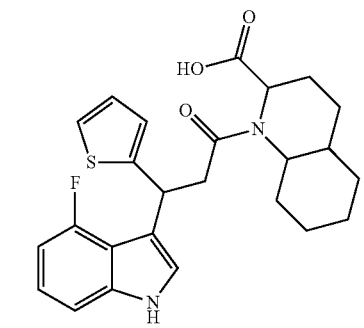
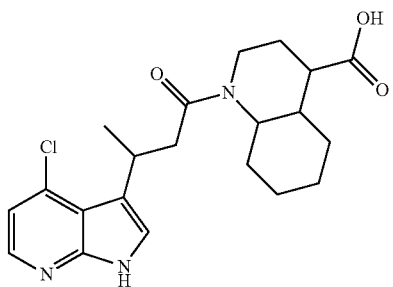

315
-continued
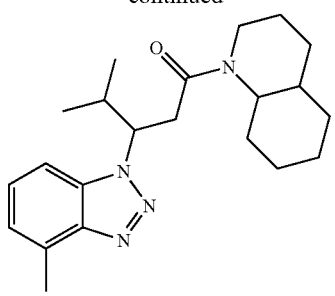
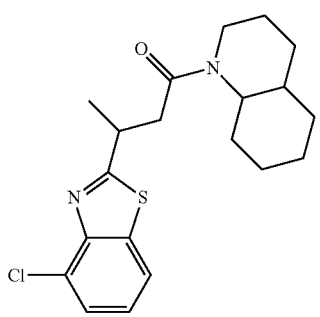
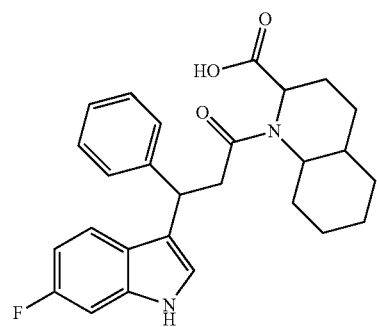
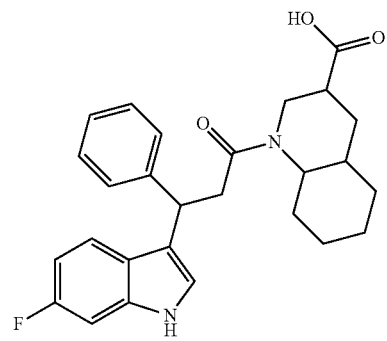
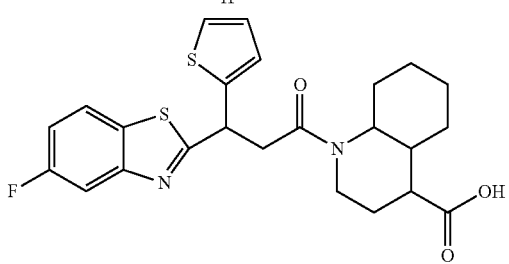
316
-continued
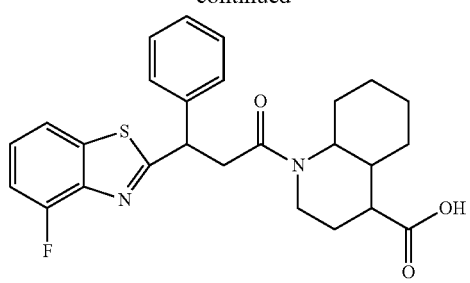
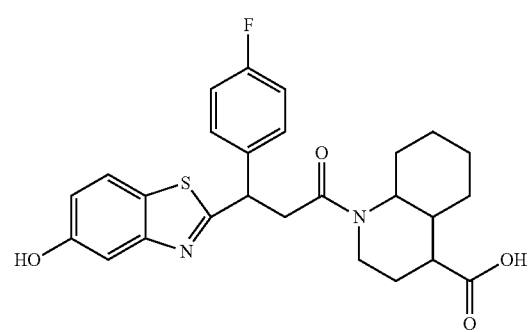
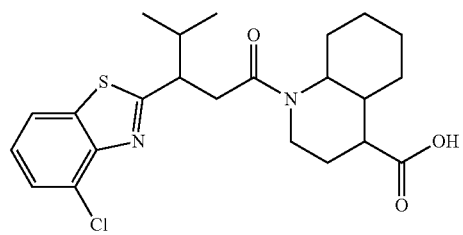
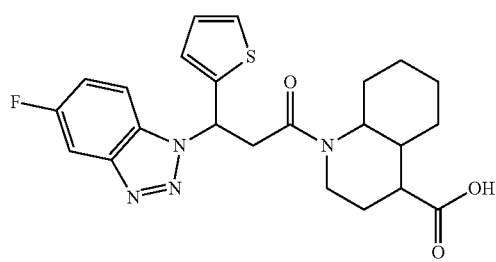
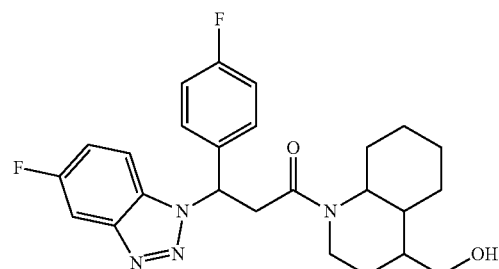
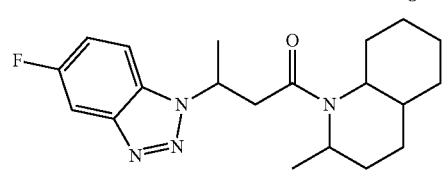

317
-continued
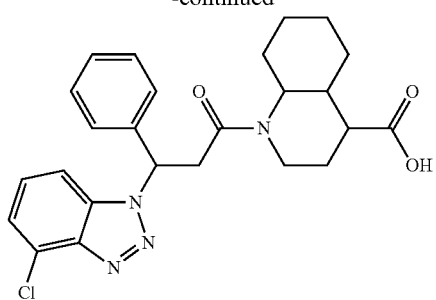
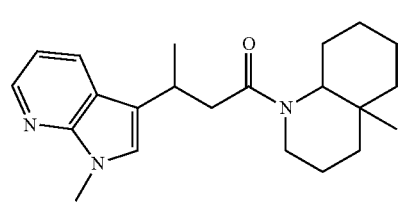
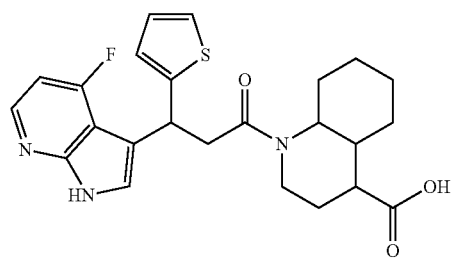
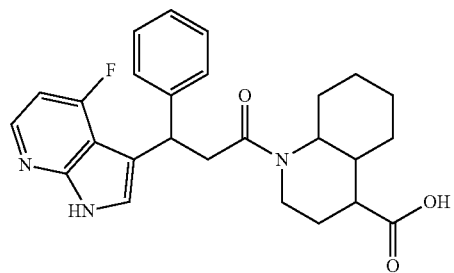
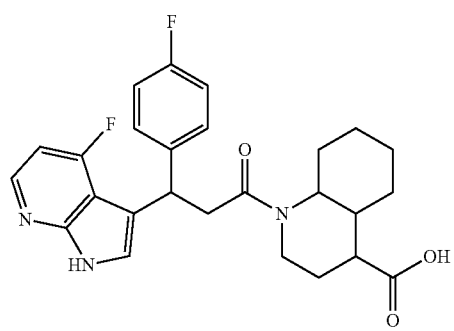
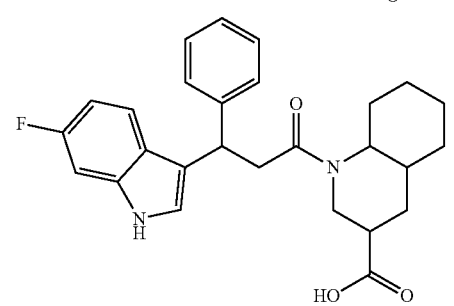
318
-continued
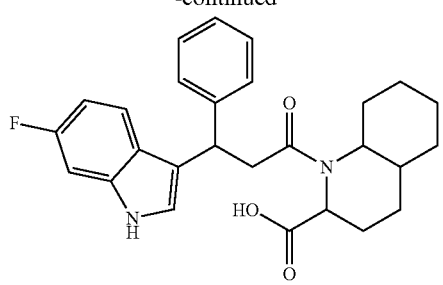
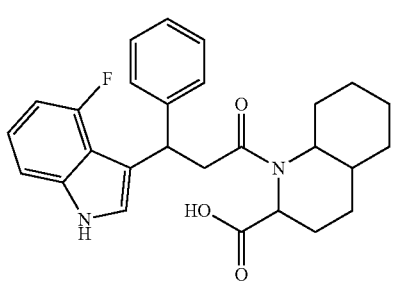
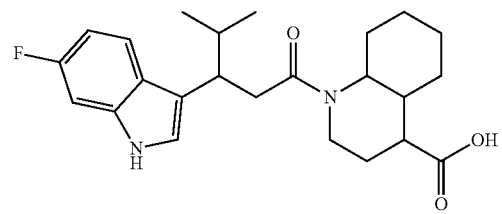
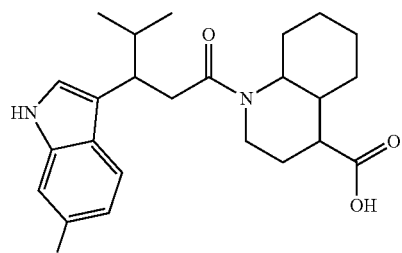
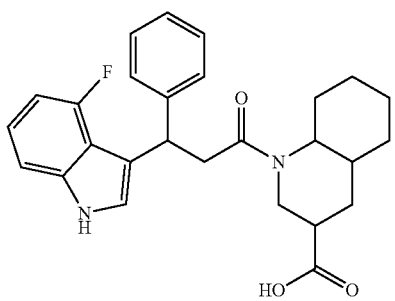
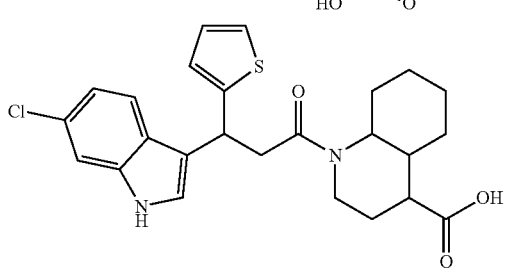

319
-continued
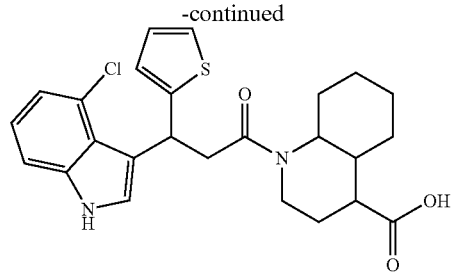
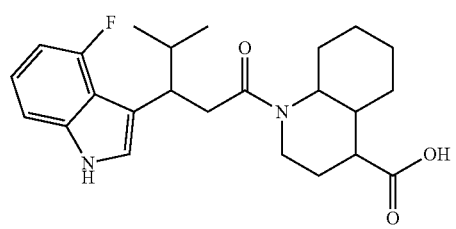
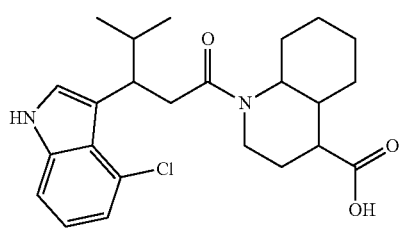
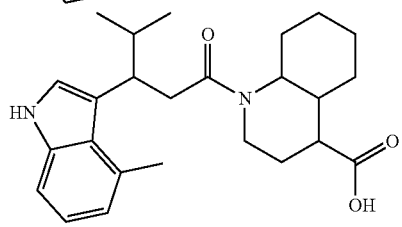
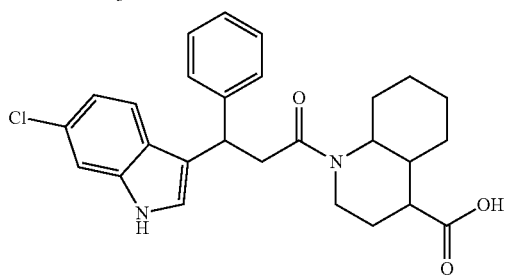
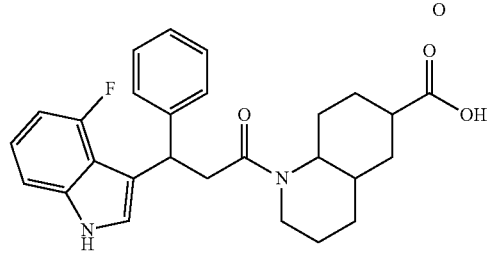
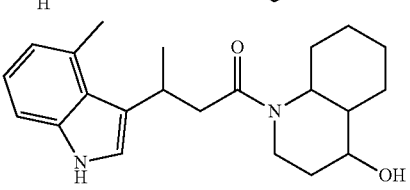
320
-continued
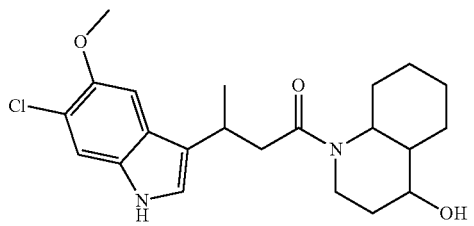
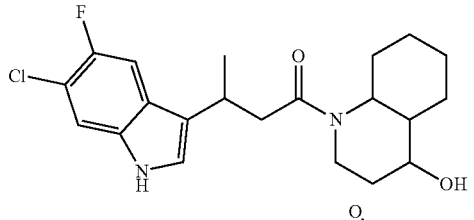
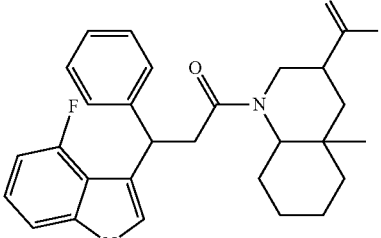
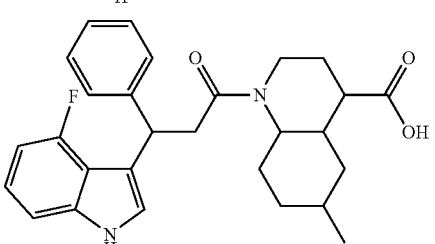
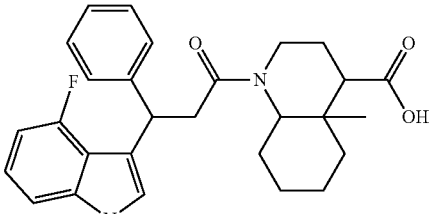
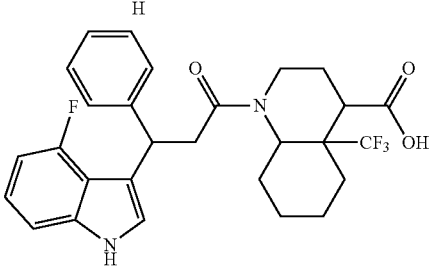

321
-continued
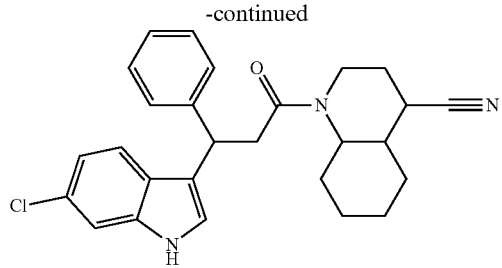
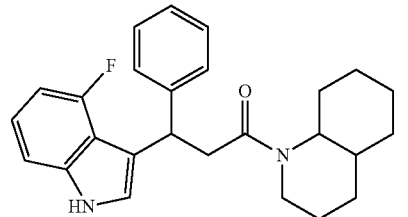
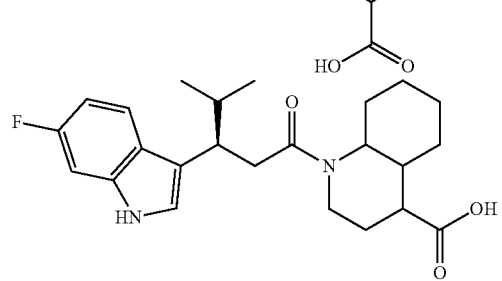
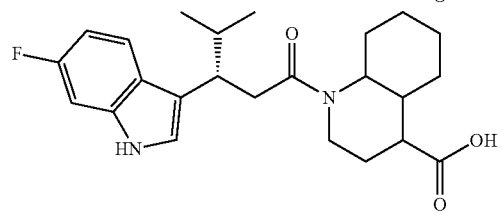
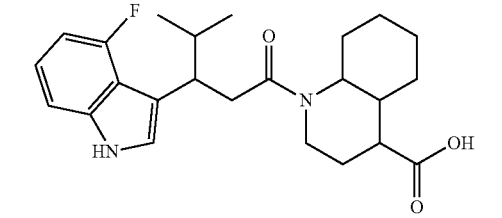
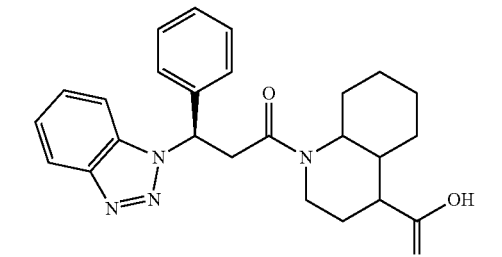
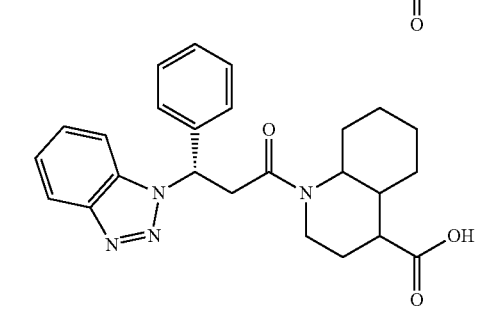
322
-continued
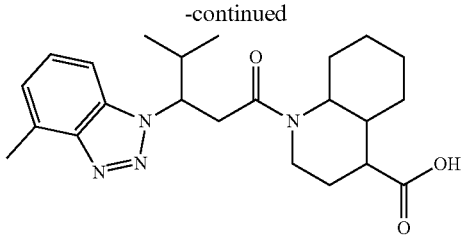
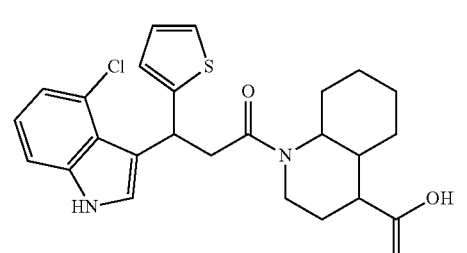
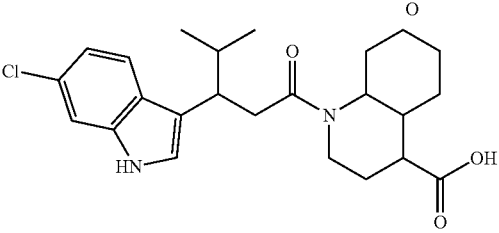
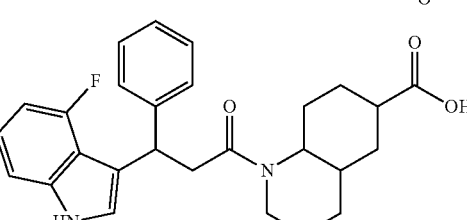
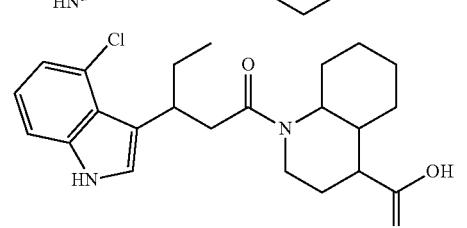
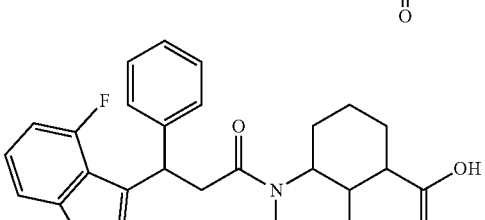
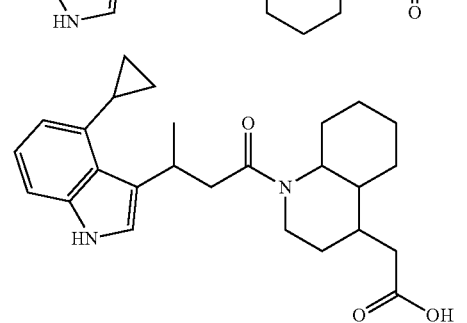

323
-continued
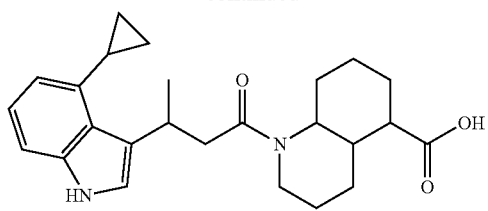
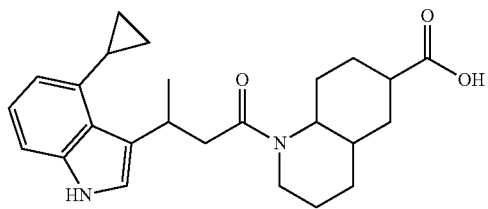
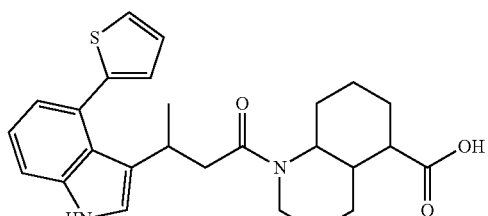
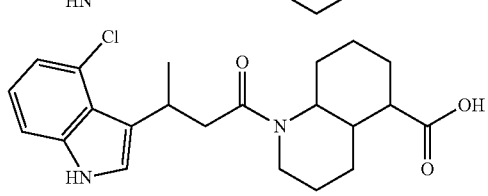
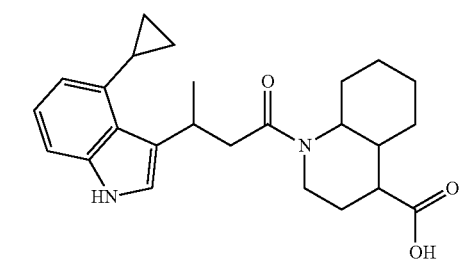
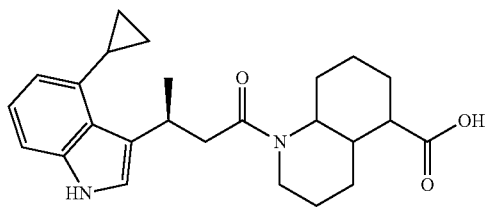
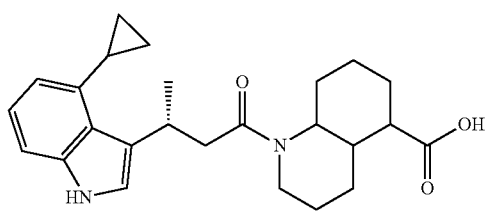
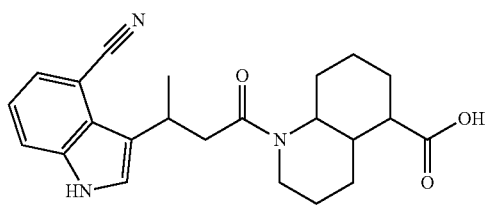
324
-continued
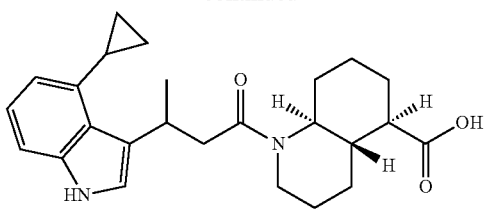
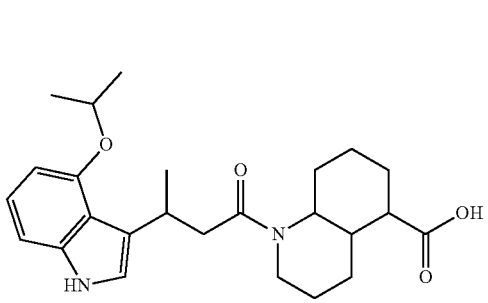
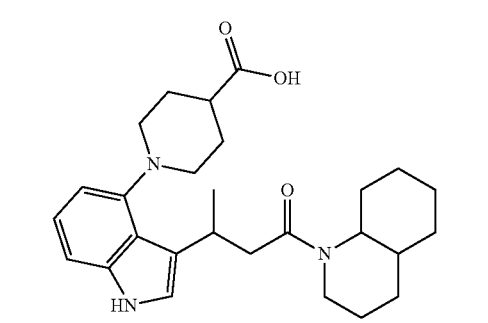
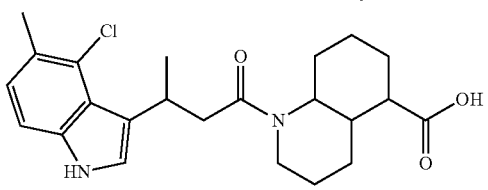
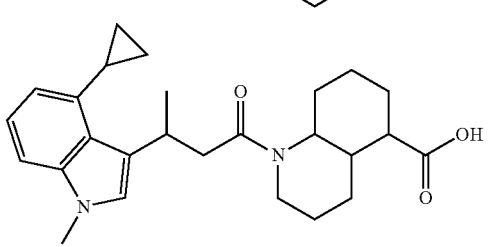
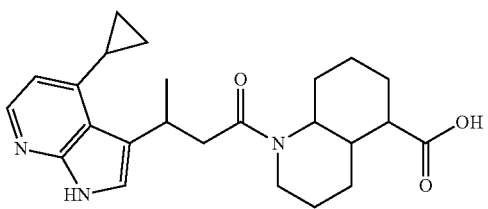
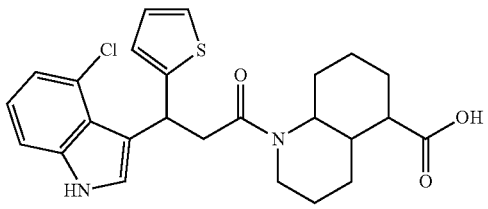

325
-continued
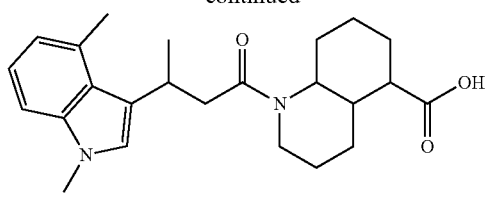
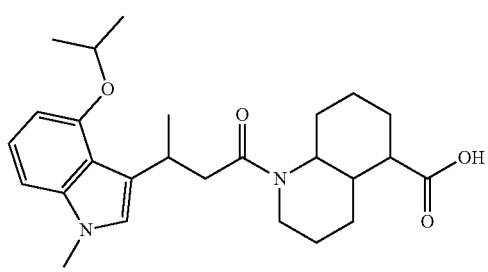
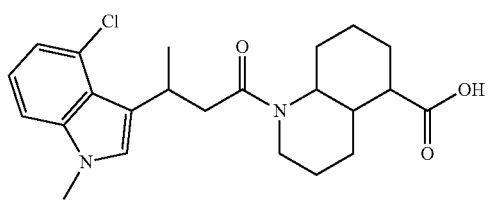
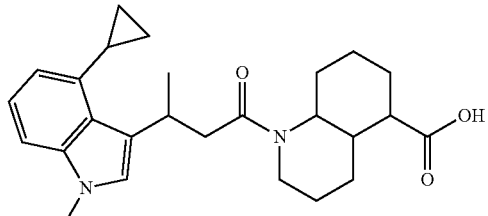
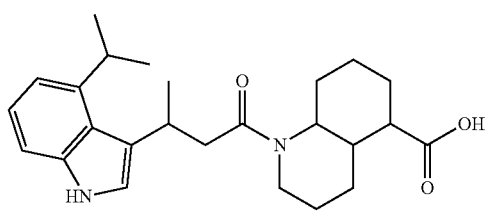
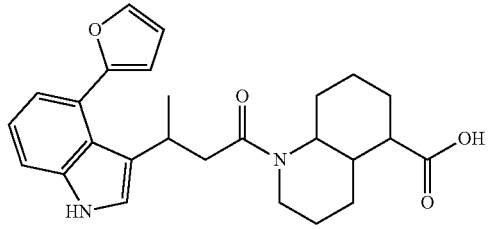
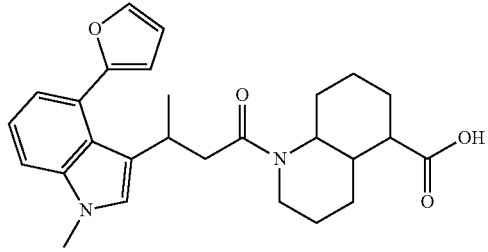
326
-continued
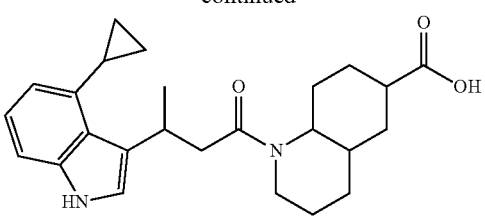
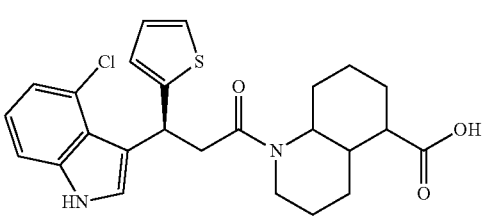
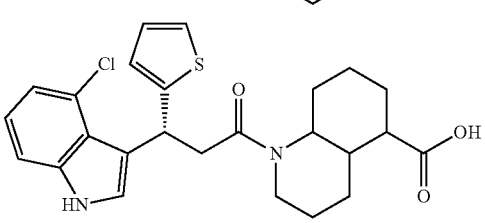
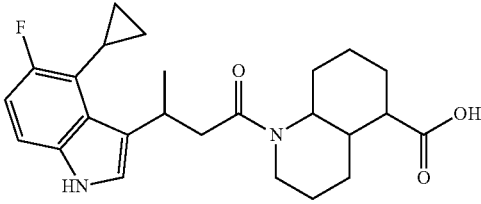
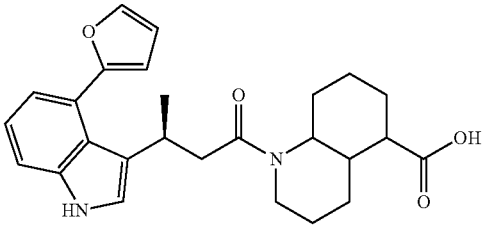
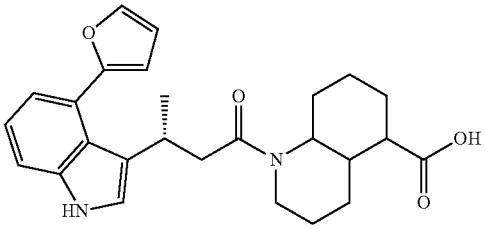
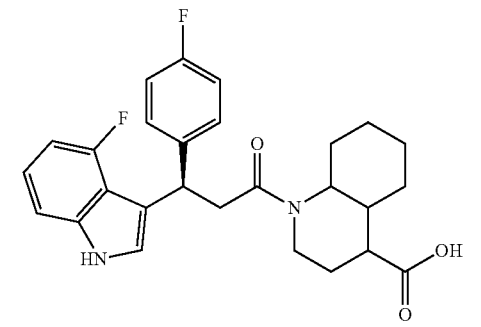

327
-continued
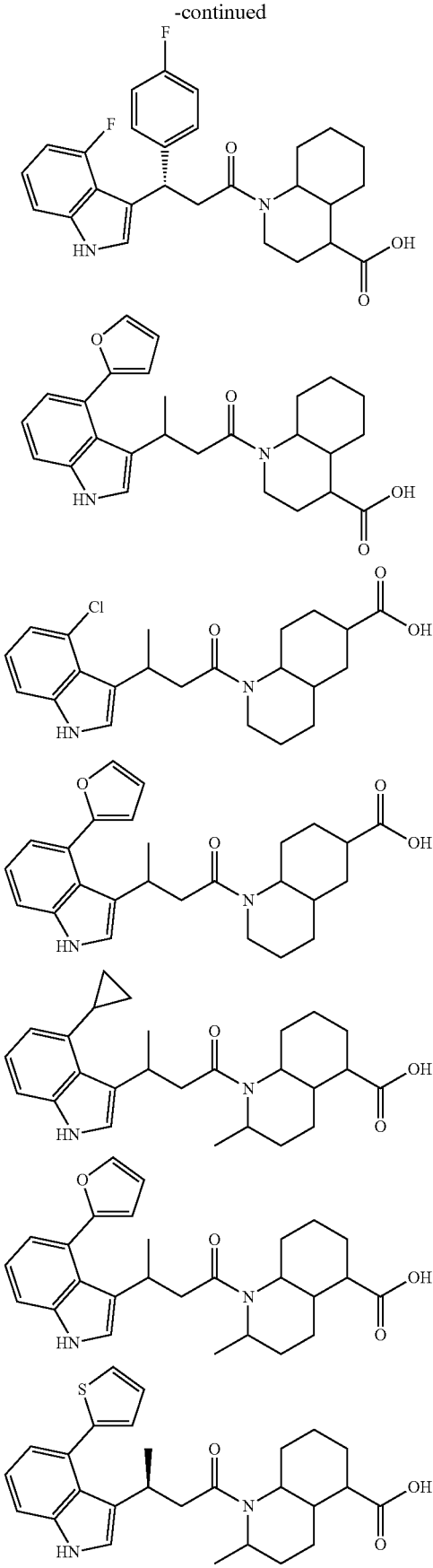
328
-continued
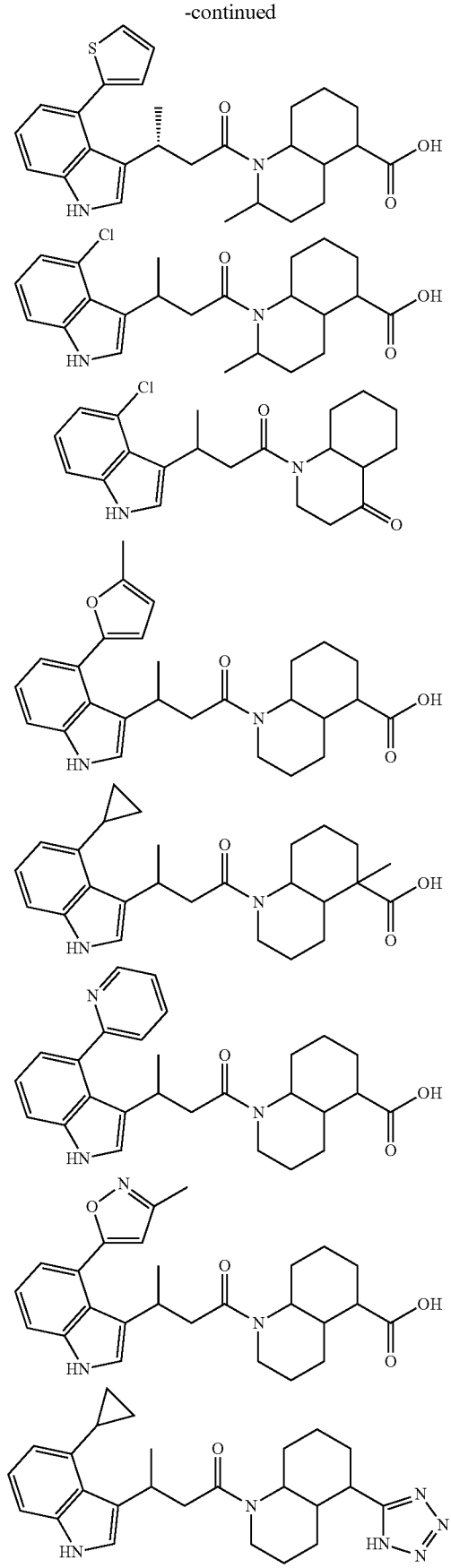

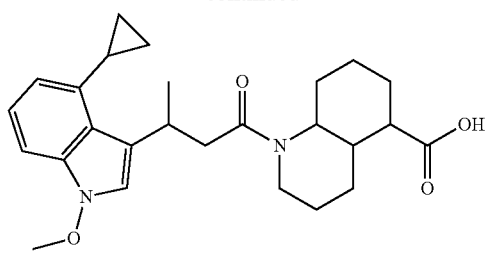
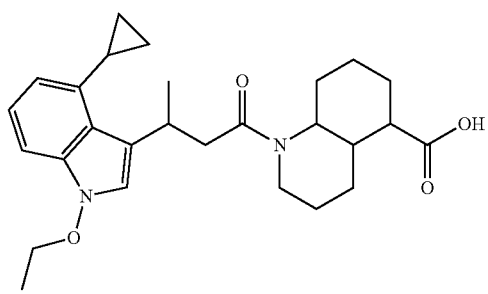
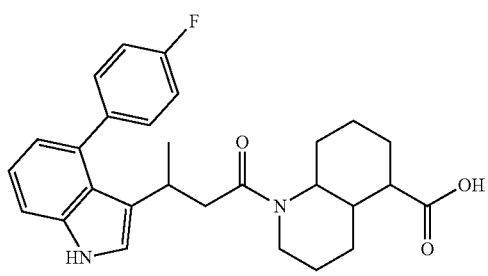
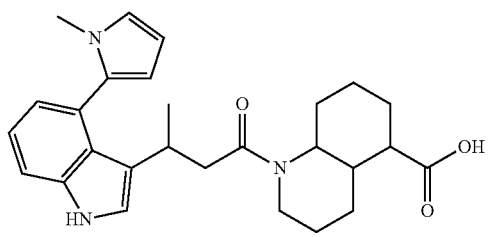
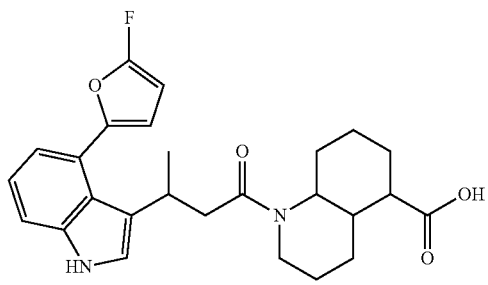
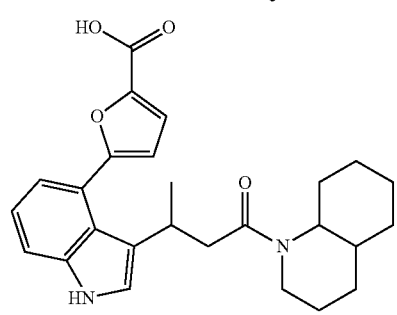
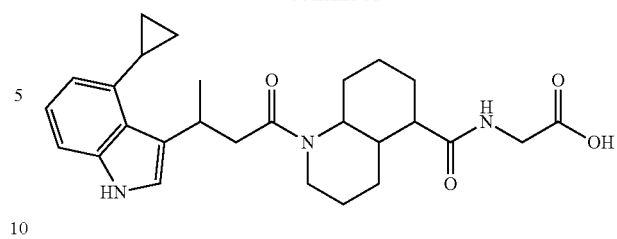
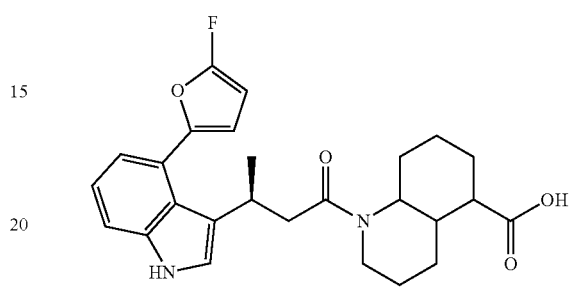
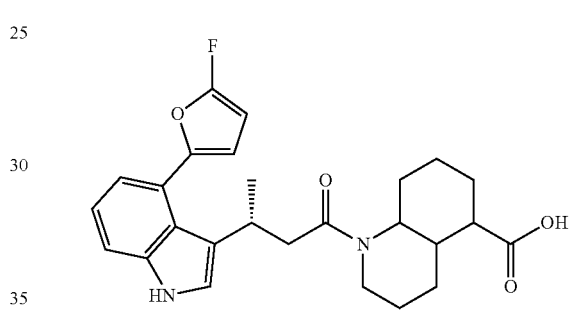
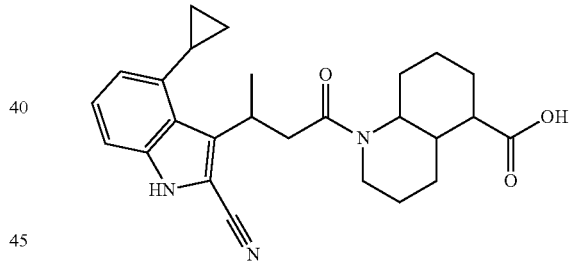
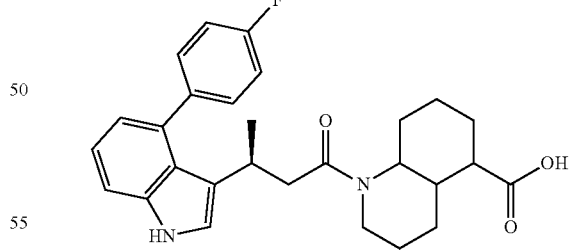
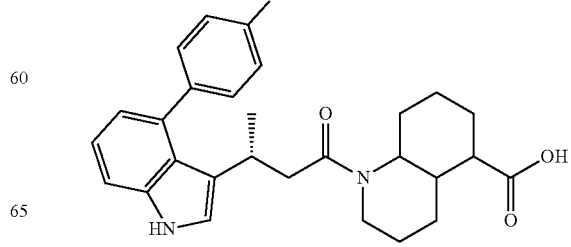

331
-continued
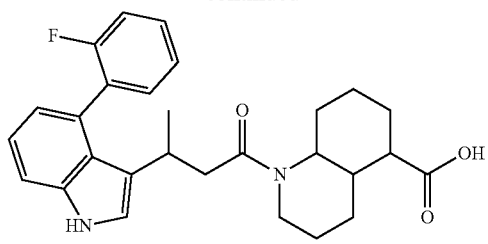
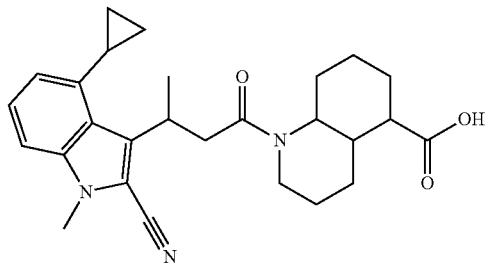
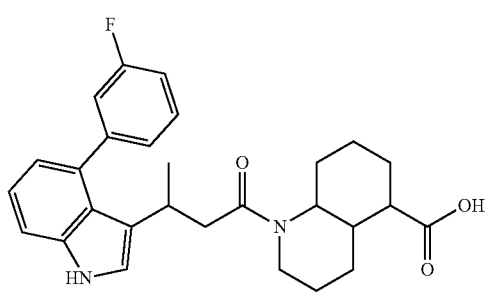
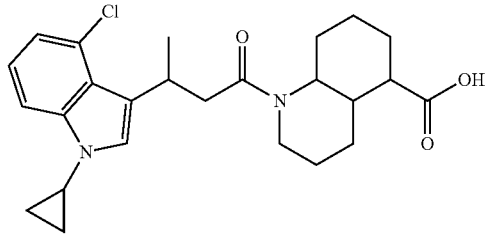
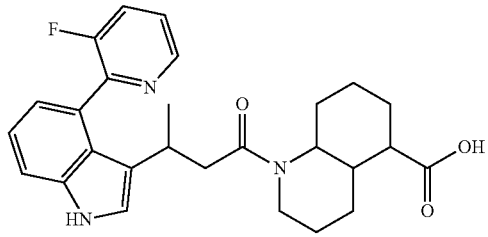
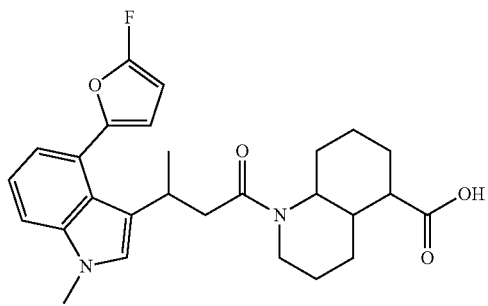
332
-continued
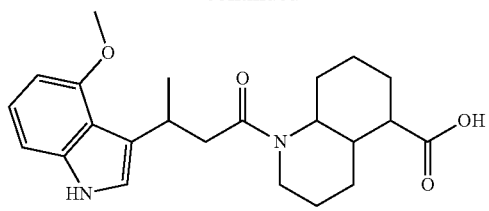
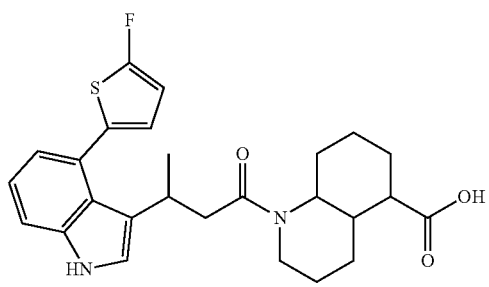
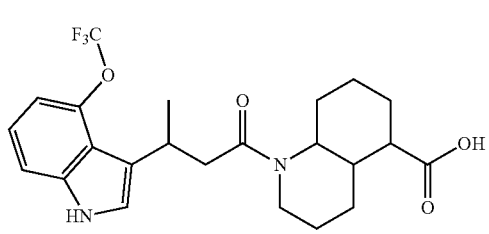
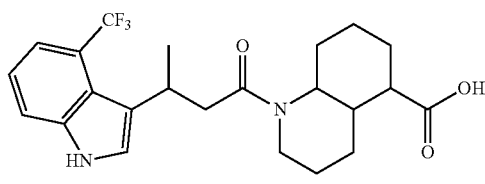
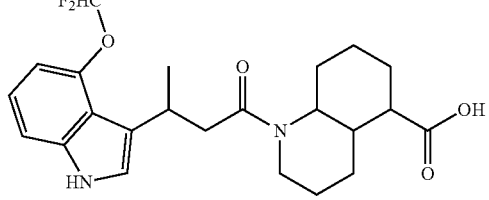
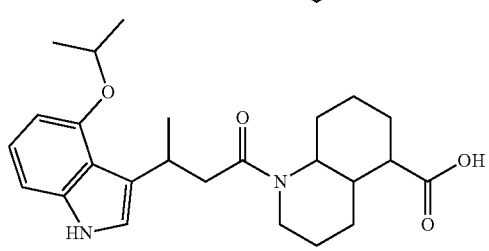
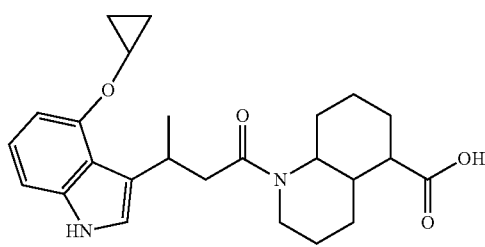

333
-continued
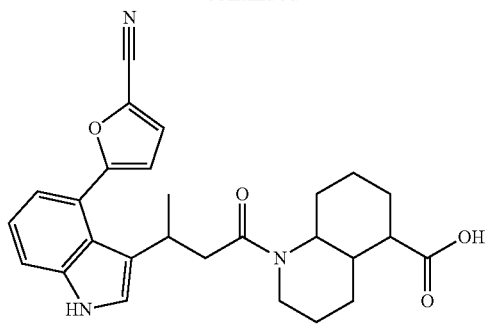
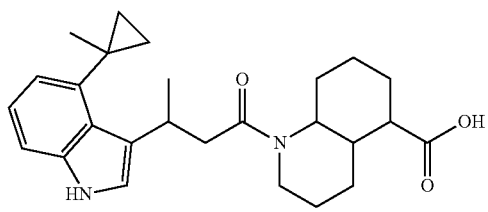
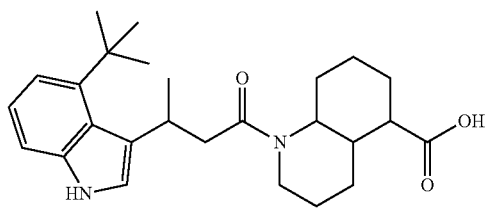
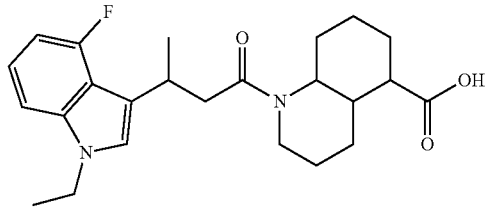
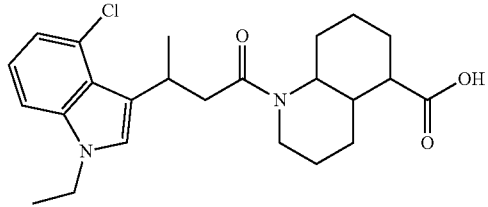
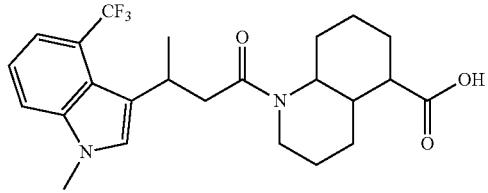
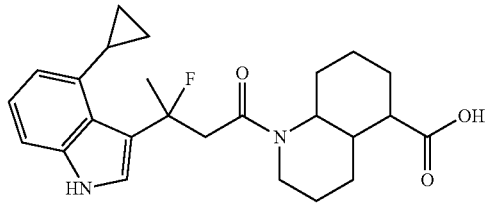
334
-continued
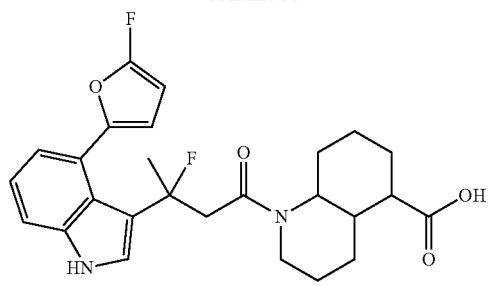
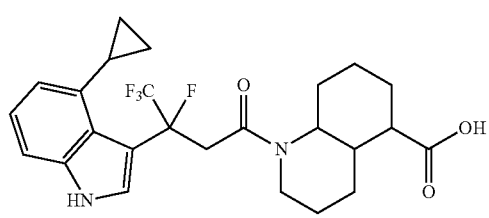
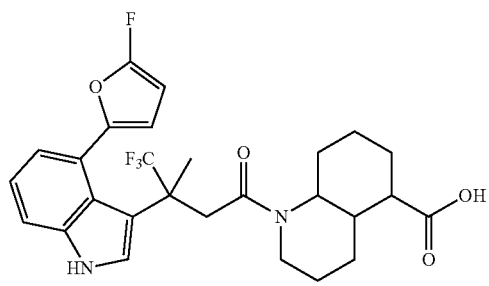
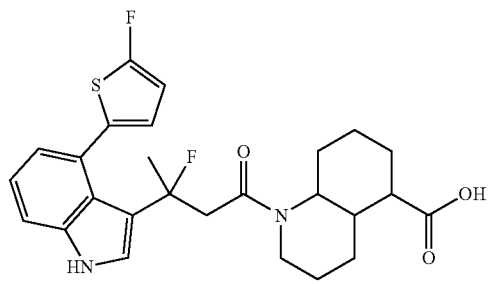
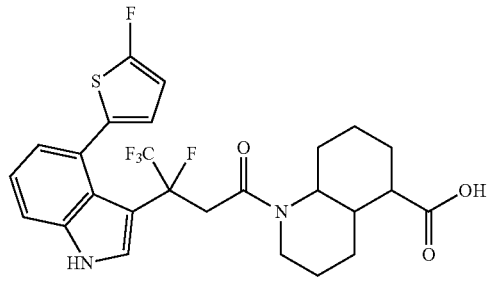
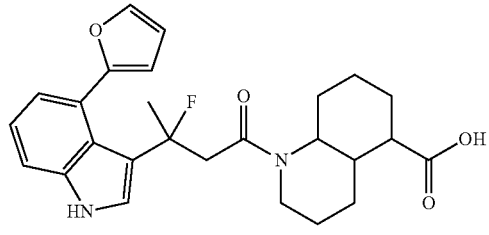

335
-continued
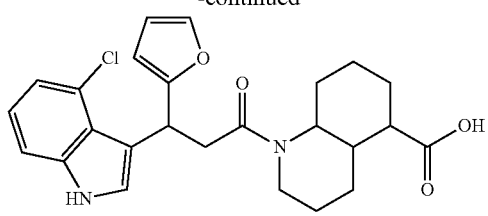
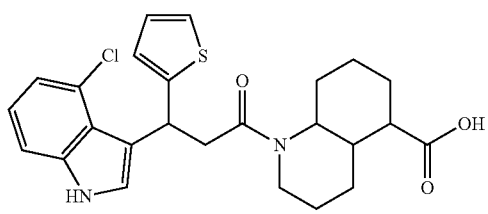
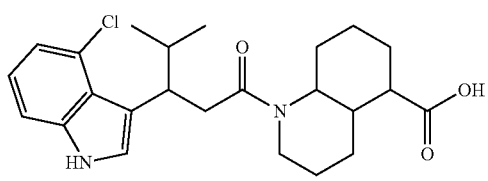
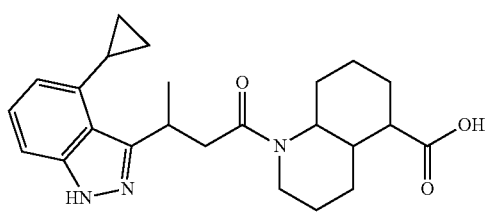
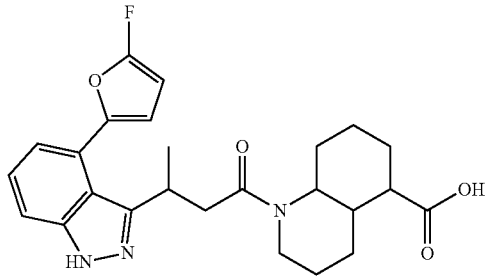
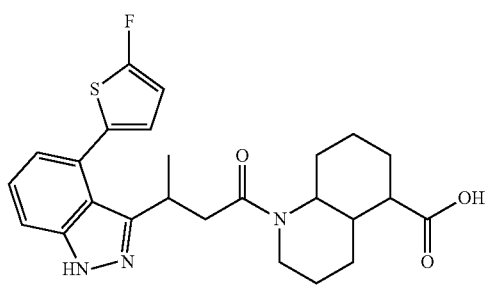
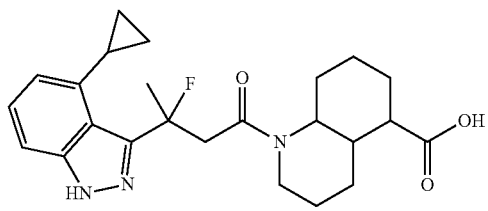
336
-continued
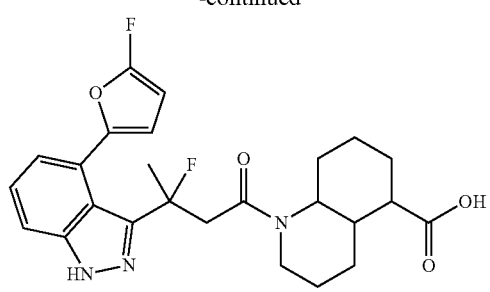
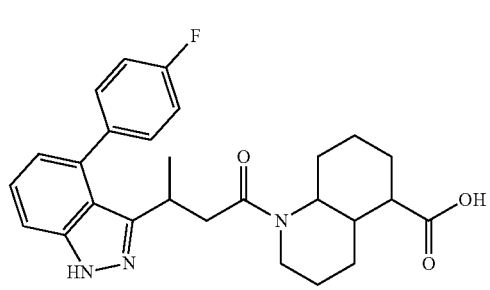
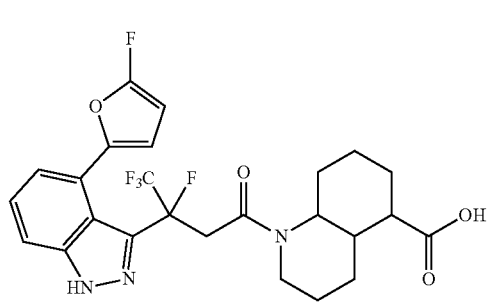
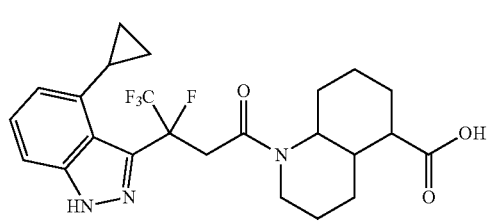
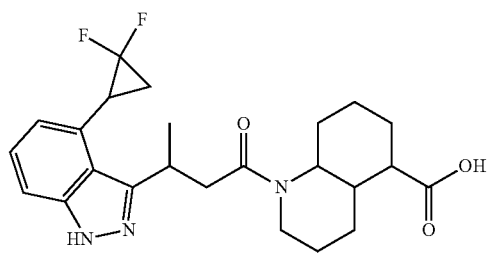
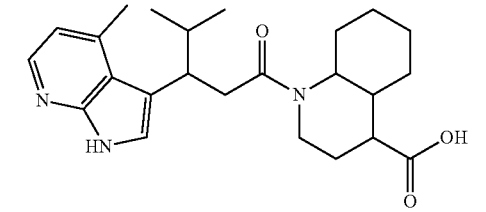

337
-continued
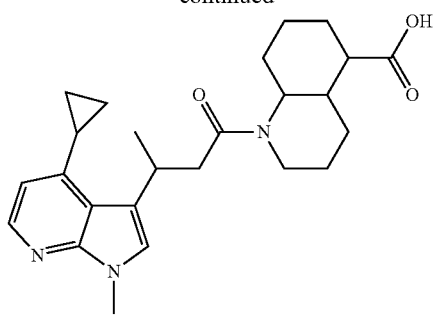
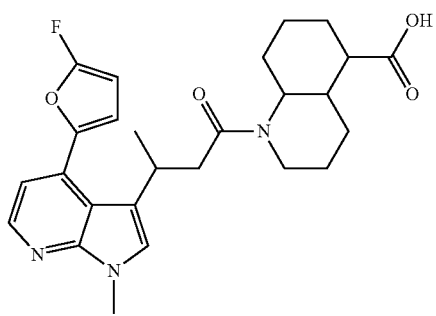
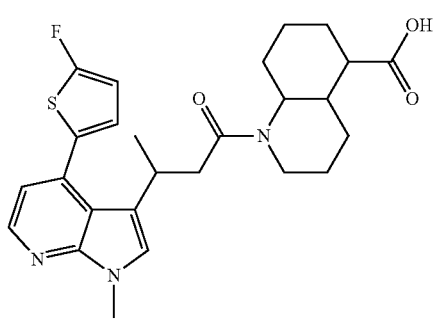
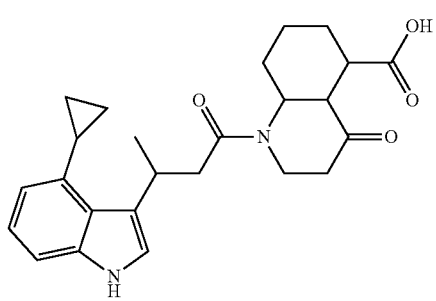
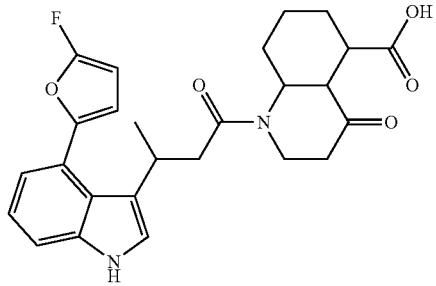
338
-continued
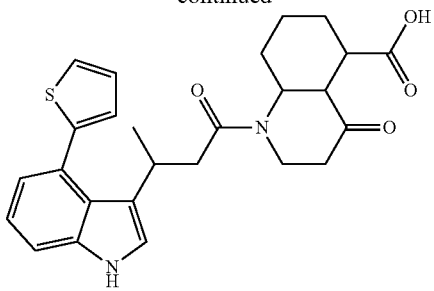
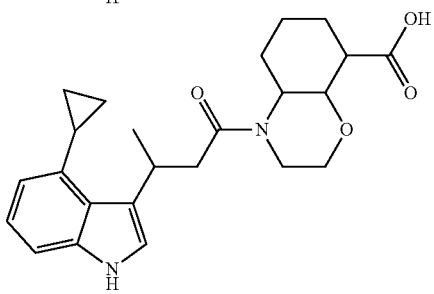
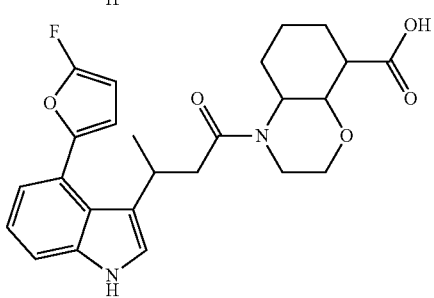
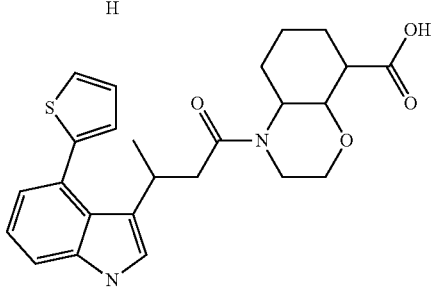
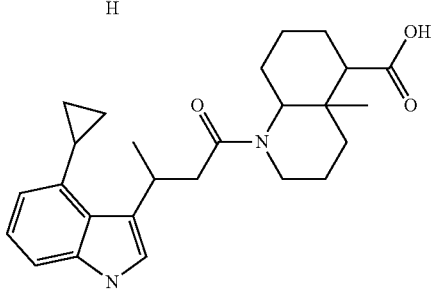
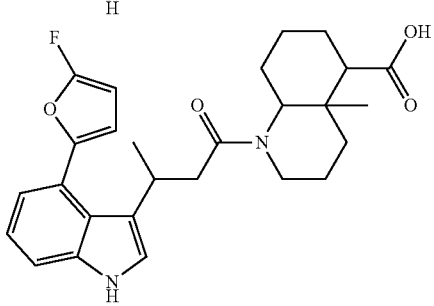

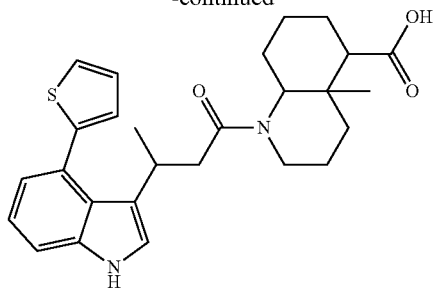
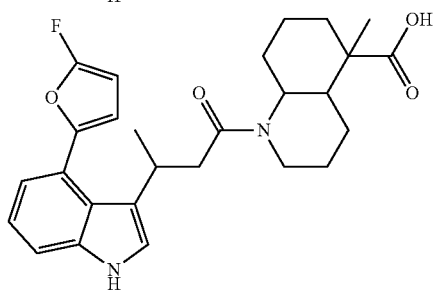
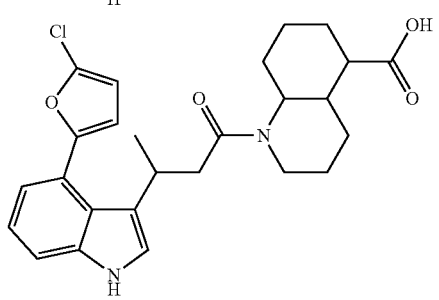
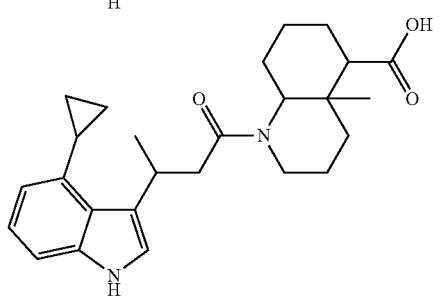
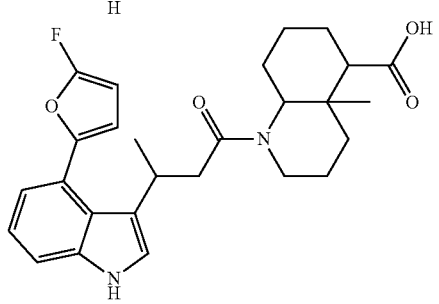
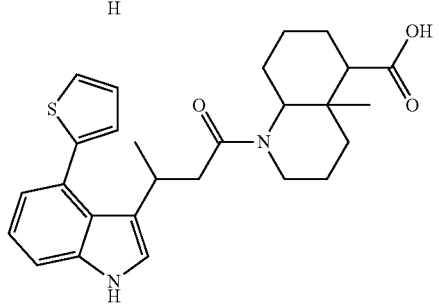
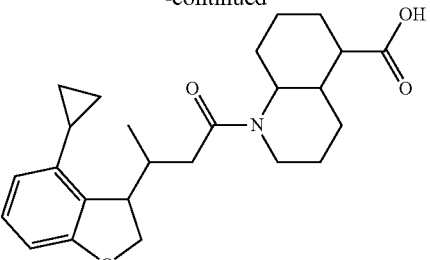
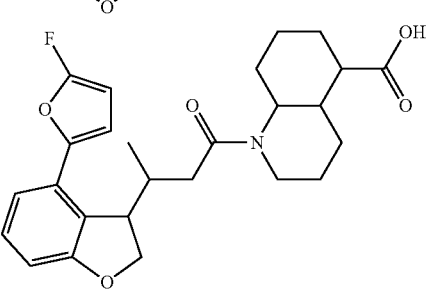
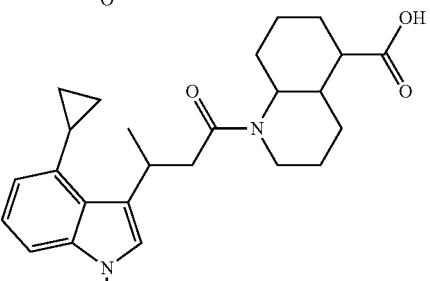
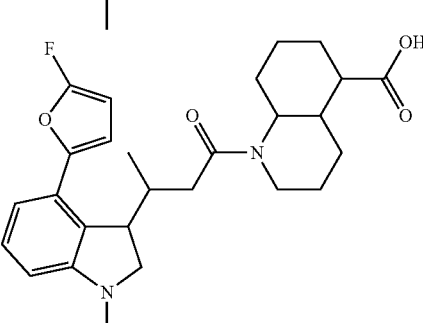
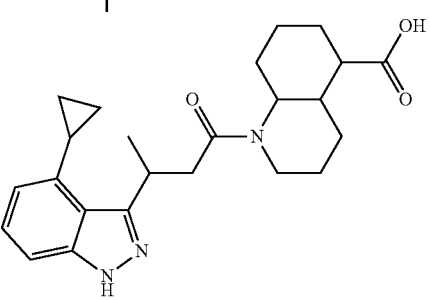
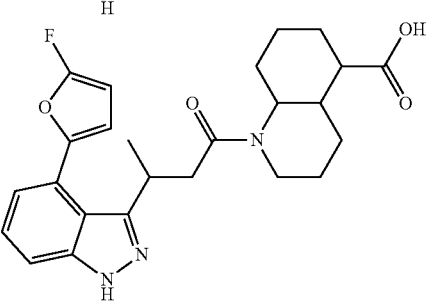

| 341 -continued | 342 -continued |
|---|---|
| 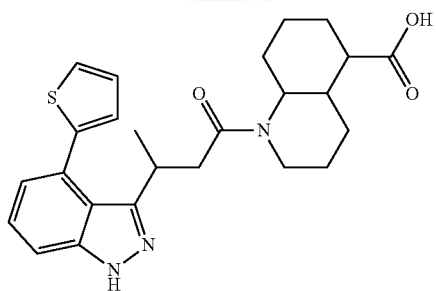 | 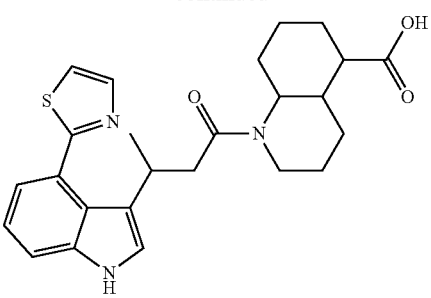 |
| 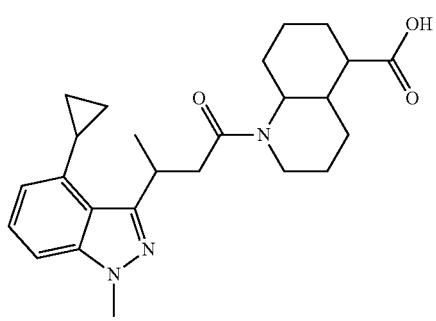 | 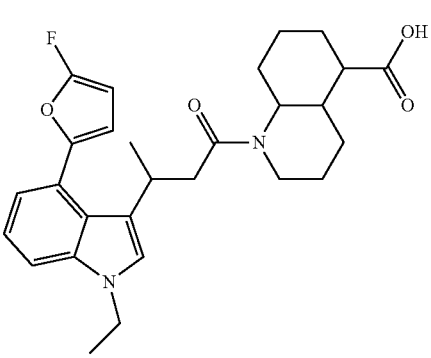 |
| 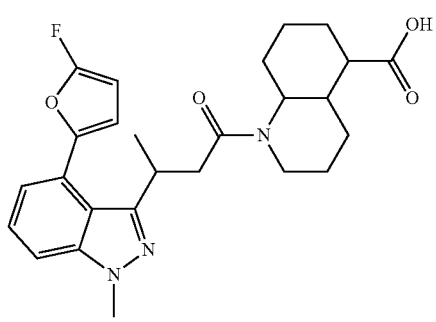 | 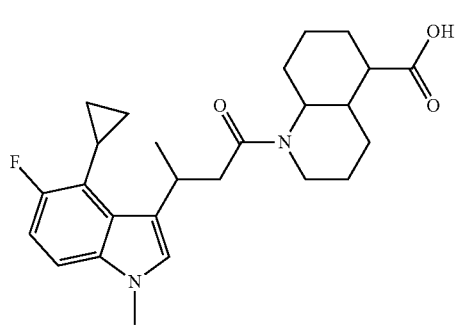 |
| 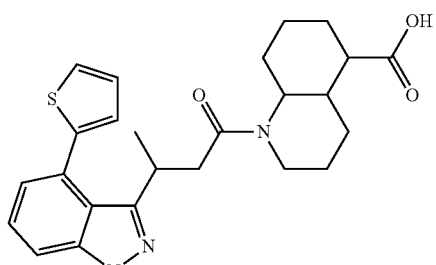 | 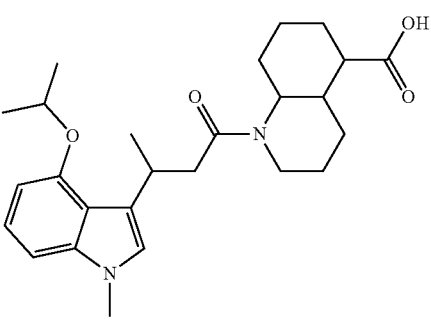 |
| 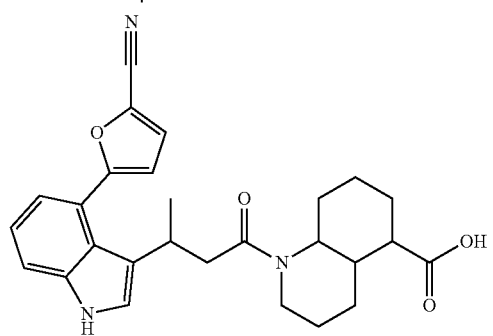 | 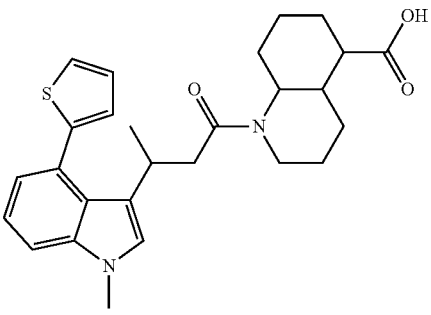 |

343
-continued

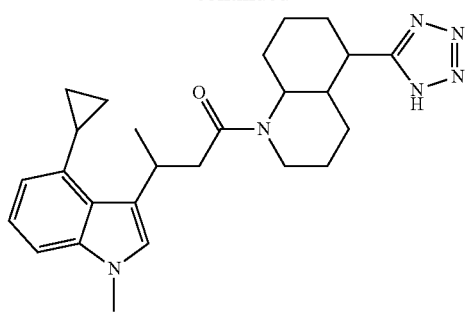

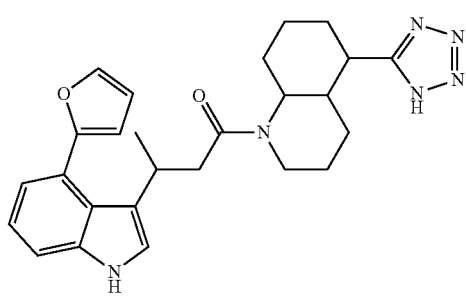

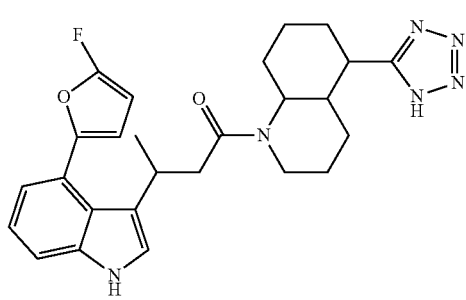

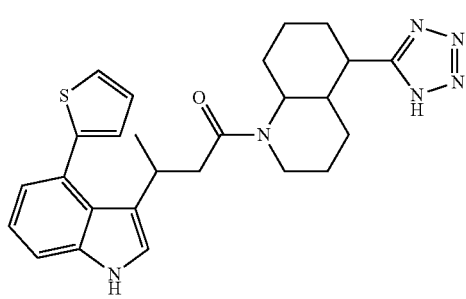

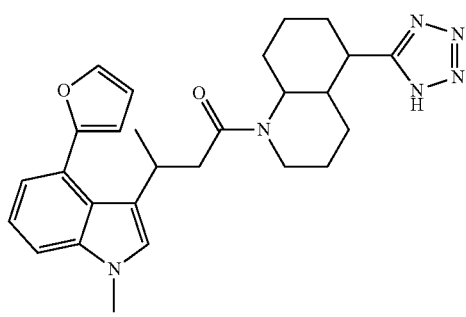

344
-continued

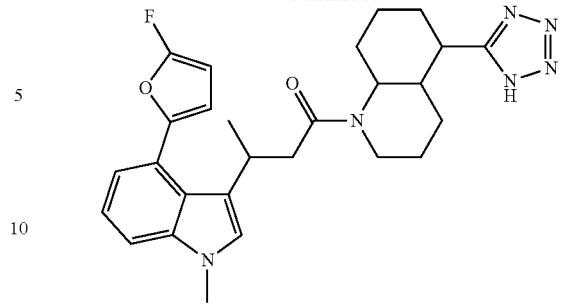

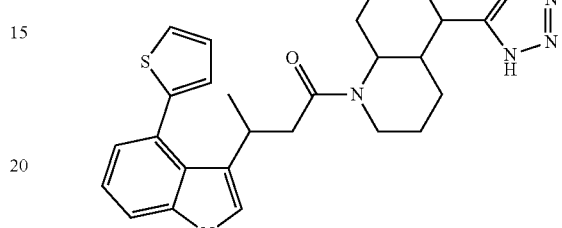

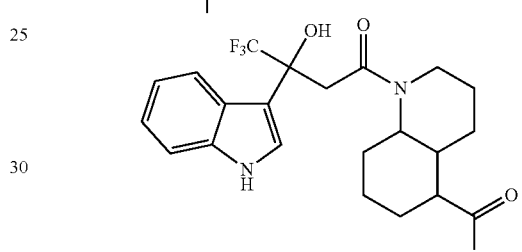

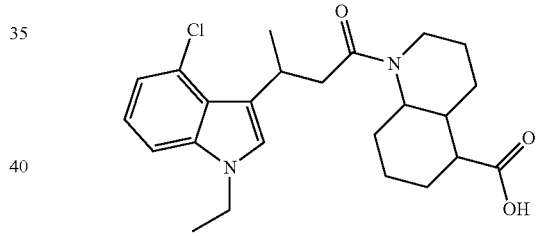

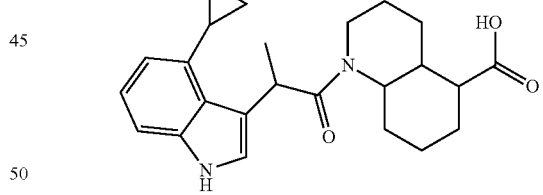

or pharmaceutically acceptable salt thereof.

7. A pharmaceutical composition including a compound according to claim 1 and a pharmaceutically acceptable diluent, excipient or carrier.

8. A method of treatment of a condition selected from the group consisting of Type I diabetes, Type II diabetes, hyperglycemia, low glucose tolerance, hyperinsulinemia, hyperlipidemia, hypertriglyceridemia, hypercholesterolemia, dyslipidemia, obesity, abdominal obesity, glaucoma, hypertension, atherosclerosis and its sequelae, retinopathy, nephropathy, neuropathy, osteoporosis, osteoarthritis, dementia, depression, psychiatric disorders, Cushing's Disease, and Cushing's syndrome, in a mammal, the method comprising administering an effective amount of a compound according to claim 1.

9. A method according to claim 8 wherein the condition is type II diabetes.

10. The method of claim 8, wherein the compound is administered in combination with an adjuvant.

11. The method of claim 10, wherein the adjuvant is selected from the group consisting of dipeptidyl peptidase-IV (DP-IV) inhibitors; (b) insulin sensitizing agents; (c) insulin and insulin mimetics; (d) sulfonylureas and other insulin secretagogues; (e) alpha-glucosidase inhibitors; (f) GLP-1, GLP-1 analogs, and GLP-1 receptor agonists; and combinations thereof.

12. The method of claim 11, wherein the insulin sensitizing agents are selected from the group consisting of (i) PPAR-gamma-agonists, (ii) PPAR-alpha-agonists, (iii) PPAR-alpha/gamma-dual agonists, (iv) biguanides, and combinations thereof.

13. A pharmaceutical composition including a compound according to claim 6 and a pharmaceutically acceptable diluent, excipient or carrier.

14. A method of treatment of a condition selected from the group consisting of Type I diabetes, Type II diabetes, hyperglycemia, low glucose tolerance, hyperinsulinemia, hyperlipidemia, hypertriglyceridemia, hypercholesterolemia, dyslipidemia, obesity, abdominal obesity, glaucoma, hypertension, atherosclerosis and its sequelae, retinopathy, nephropathy, neuropathy, osteoporosis, osteoarthritis, dementia, depression, psychiatric disorders, Cushing's Disease, and Cushing's syndrome, in a mammal, the method comprising administering an effective amount of a compound according to claim 6.

15. A method according to claim 6 wherein the condition is type II diabetes.

16. The method of claim 6, wherein the compound is administered in combination with an adjuvant.

17. The method of claim 6, wherein the adjuvant is selected from the group consisting of dipeptidyl peptidase-IV (DP-IV) inhibitors; (b) insulin sensitizing agents; (c) insulin and insulin mimetics; (d) sulfonylureas and other insulin secretagogues; (e) alpha-glucosidase inhibitors; (f) GLP-1, GLP-1 analogs, and GLP-1 receptor agonists; and combinations thereof.

18. The method of claim 6, wherein the insulin sensitizing agents are selected from the group consisting of (i) PPAR-gamma-agonists, (ii) PPAR-alpha-agonists, (iii) PPAR-alpha/gamma-dual agonists, (iv) biguanides, and combinations thereof.

* * * * *